(12) United States Patent
Roubos et al.

(10) Patent No.: US 8,812,247 B2
(45) Date of Patent: Aug. 19, 2014

(54) METHOD FOR ACHIEVING IMPROVED POLYPEPTIDE EXPRESSION

(75) Inventors: Johannes Andries Roubos, Pijnacker (NL); Noël Nicolaas Maria Elisabeth Van Peij, Delfgauw (NL)

(73) Assignee: DSM IP Assets B.V., Heerlen (NL)

( * ) Notice: Subject to any disclaimer, the term of this patent is extended or adjusted under 35 U.S.C. 154(b) by 884 days.

(21) Appl. No.: 12/306,678

(22) PCT Filed: Jun. 15, 2007

(86) PCT No.: PCT/EP2007/055943
§ 371 (c)(1),
(2), (4) Date: Dec. 24, 2008

(87) PCT Pub. No.: WO2008/000632
PCT Pub. Date: Jan. 3, 2008

(65) Prior Publication Data
US 2009/0286280 A1 Nov. 19, 2009

(30) Foreign Application Priority Data

Jun. 29, 2006 (EP) .................................... 06076328

(51) Int. Cl.
*G06F 7/00* (2006.01)
*C12N 15/81* (2006.01)
*C12N 15/80* (2006.01)
*C12N 15/67* (2006.01)

(52) U.S. Cl.
CPC .............. *C12N 15/81* (2013.01); *C12N 15/80* (2013.01); *C12N 15/67* (2013.01)
USPC .................. 702/20; 702/19; 703/11; 707/700

(58) Field of Classification Search
CPC ........... C07K 2317/21; C12N 15/8261; C12N 15/8271; C12N 15/8273; C12N 15/8286; C12N 15/67; G06F 19/22; G06F 19/16; G06F 19/20; G06F 19/24
See application file for complete search history.

(56) References Cited

U.S. PATENT DOCUMENTS

| | | | |
|---|---|---|---|
| 5,082,767 A | 1/1992 | Hatfield et al. | |
| 7,888,489 B2 | 2/2011 | Roubos et al. | |
| 2004/0005600 A1 | 1/2004 | Angov et al. | |
| 2004/0161840 A1 | 8/2004 | Contreras et al. | |

FOREIGN PATENT DOCUMENTS

| | | |
|---|---|---|
| EP | 1231272 A2 | 8/2002 |
| EP | 1231272 A3 | 11/2002 |
| WO | 99/02694 | 1/1999 |
| WO | 03070957 A2 | 8/2003 |
| WO | 03/085114 | 10/2003 |
| WO | 03085114 A1 | 10/2003 |
| WO | 03070957 A3 | 12/2003 |
| WO | 2006/077258 | 7/2006 |

OTHER PUBLICATIONS

Irwin et al. "Codon pair utilization biases influence translational elongation step times" J. Biol. Chem., vol. 270, No. 39, pp. 22801-22806 (Sep. 1995).
Boycheva et al. "Codon pairs in the genome of *Escherichia coli*" Bioinformatics, vol. 19, No. 8, pp. 987-998 (2003).
Makrides "Strategies for achieving high-level expression of genes in *Escherichia coli*" Microbiological Reviews, vol. 60, No. 3, pp. 512-538 (Sep. 1996).
International Search Report for PCT/EP2007/055943, five pages, mailed Oct. 30, 2007.
International Search Report for PCT/EP2006/050398, all pages, mailed Jun. 19, 2006.
Comeron et al. "Selective and Mutational Patterns Associated With Gene Expression in Humans: Influences on Synonymous Composition and Intron Presence". Genetics. Jul. 2004. 167(3). pp. 1293-1304.

*Primary Examiner* — Mary Zeman
(74) *Attorney, Agent, or Firm* — Miles & Stockbridge, P.C.

(57) ABSTRACT

The present invention relates to methods of optimization of a protein coding sequences for expression in a given host cell. The methods apply genetic algorithms to optimise single codon fitness and/or codon pair fitness sequences coding for a predetermined amino acid sequence. In the algorithm generation of new sequence variants and subsequent selection of fitter variants is reiterated until the variant coding sequences reach a minimum value for single codon fitness and/or codon pair fitness. The invention also relates to a computer comprising a processor and memory, the processor being arranged to read from and write into the memory, the memory comprising data and instructions arranged to provide the processor with the capacity to perform the genetic algorithms for optimization of single codon fitness and/or codon pair fitness. The invention further relates to nucleic acids comprising a coding sequence for a predetermined amino acid sequence, the coding sequence being optimised with respect to single codon fitness and/or codon pair fitness for a given host in the methods of the invention, to host cells comprising such nucleic acids and to methods for producing polypeptides and other fermentation products in which these host cells are used.

37 Claims, 31 Drawing Sheets

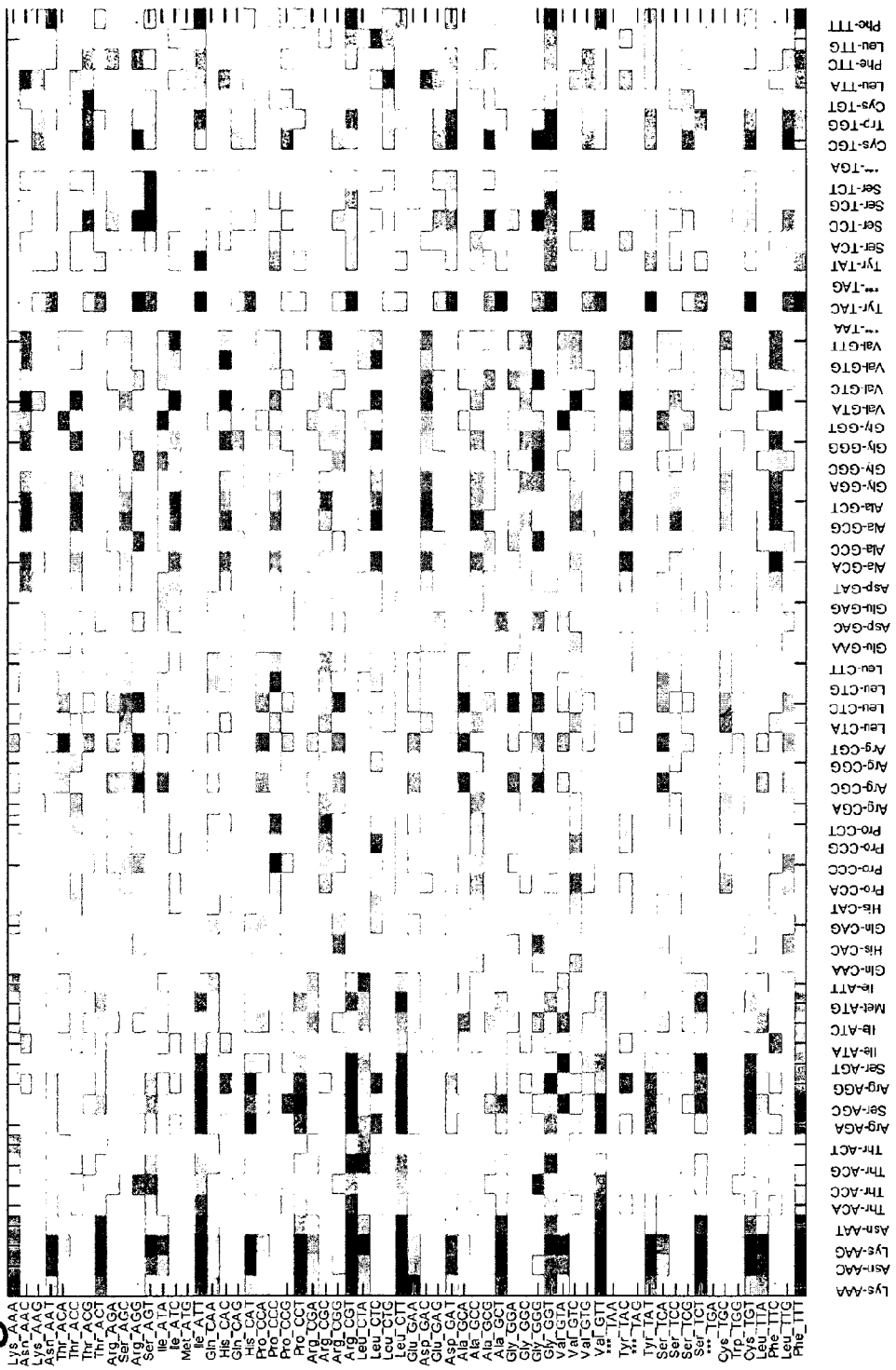
Fig 5b  NEGATIVE codon pair bias in A. niger (rows and columns sorted alphabetically)

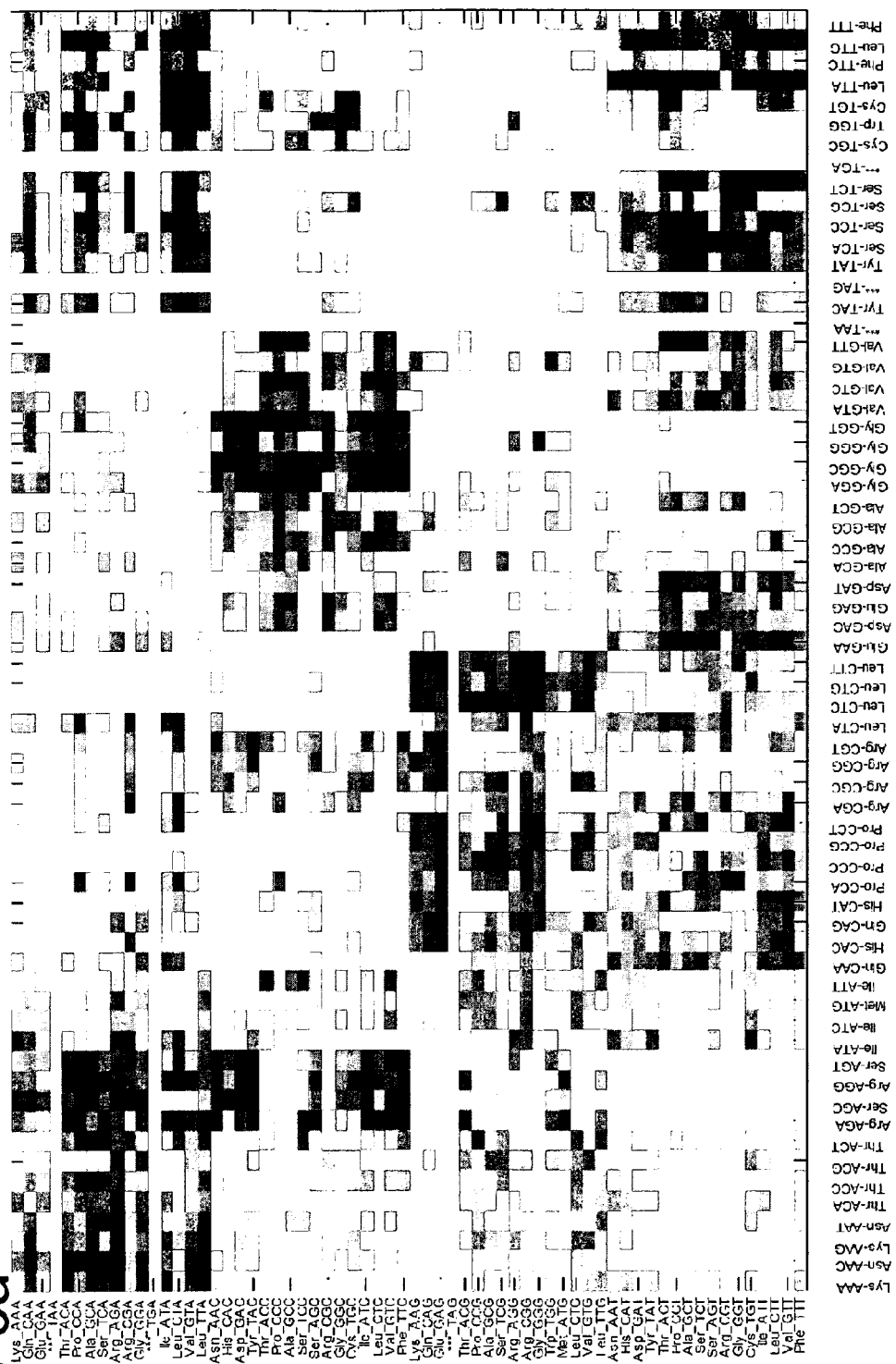

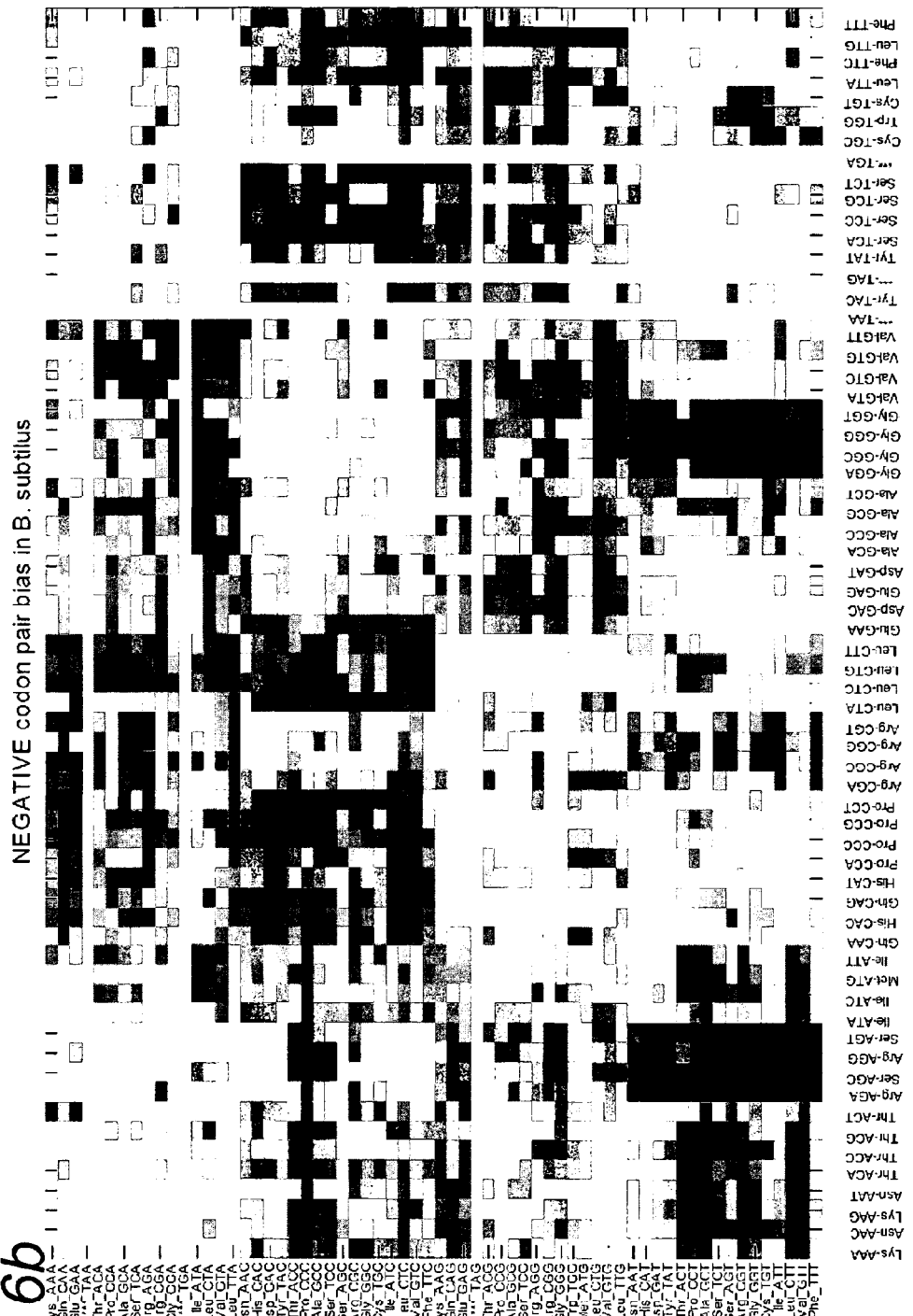

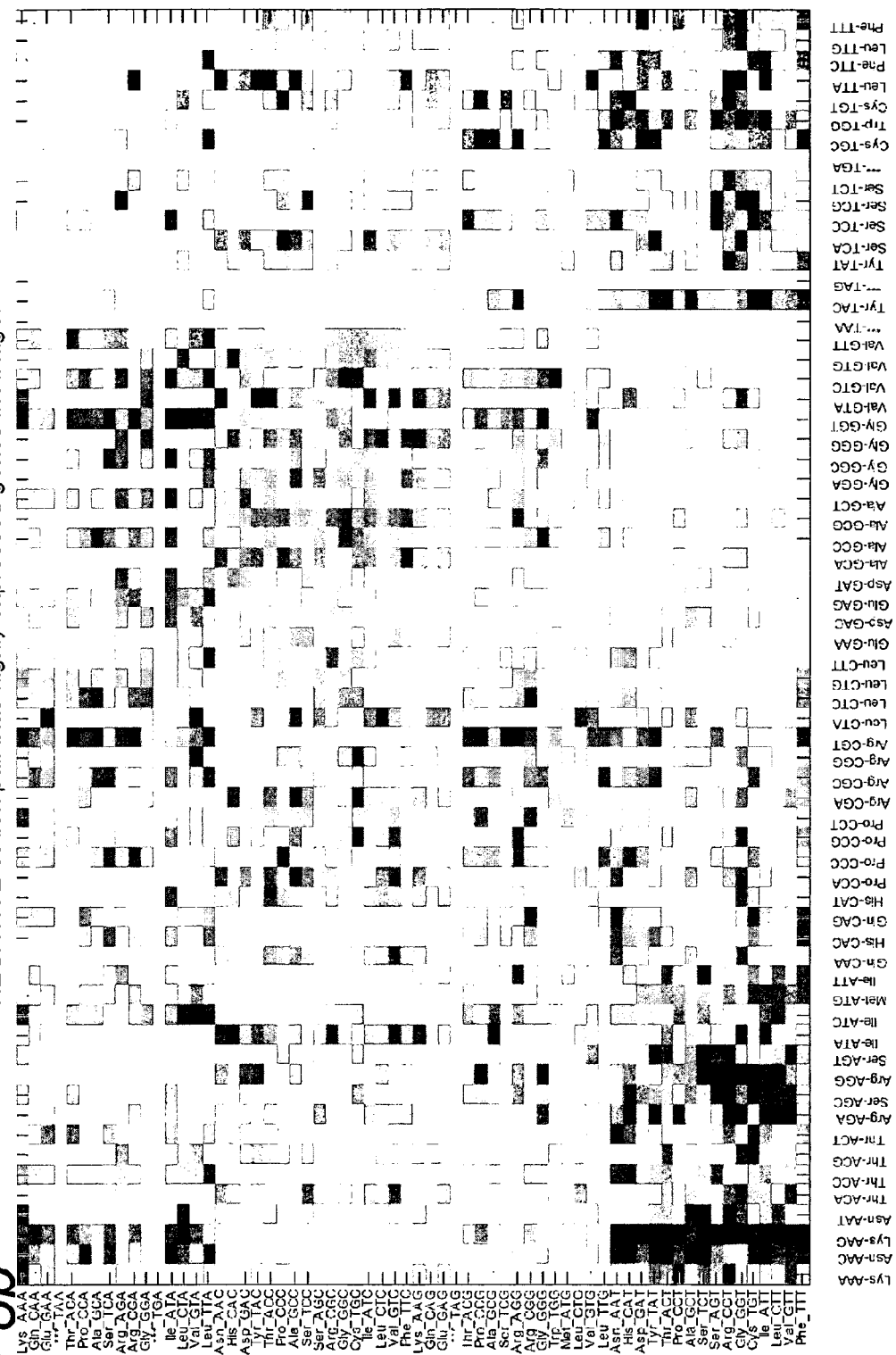

Fig 12
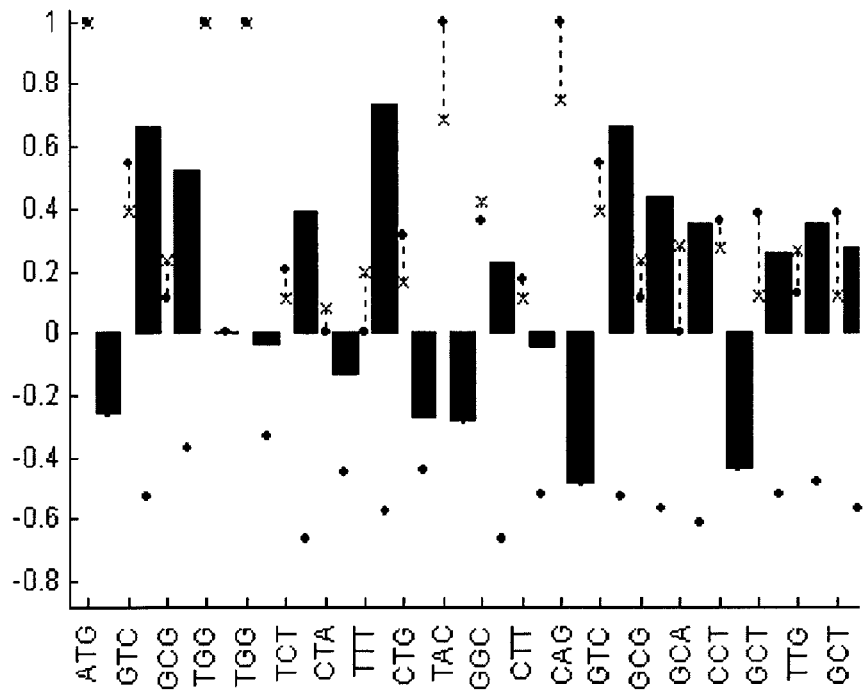
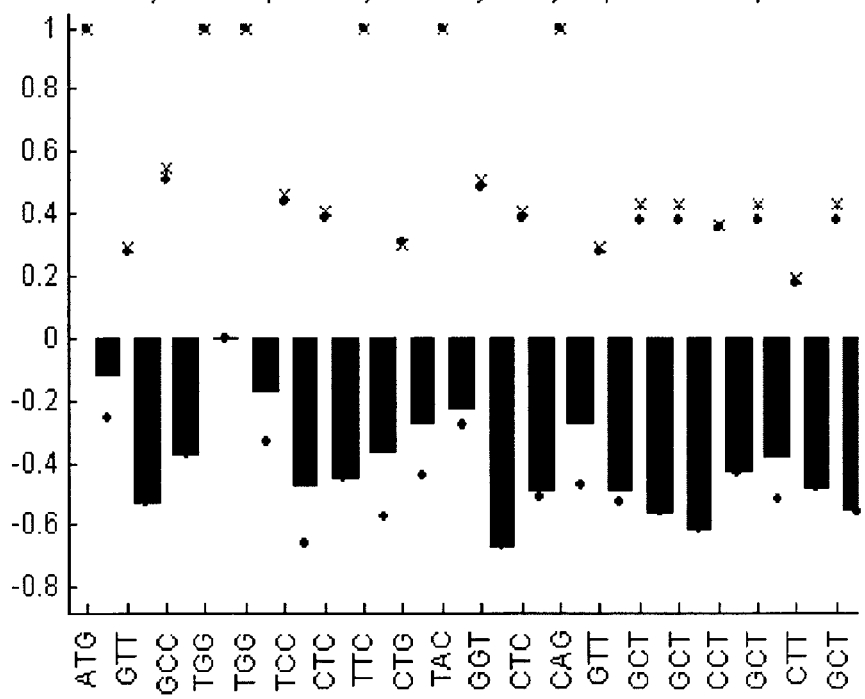

SEQUENCE LISTING

<160> NUMBER OF SEQ ID NOS: 18

<210> SEQ ID NO 1
<211> LENGTH: 3965
<212> TYPE: DNA
<213> ORGANISM: Aspergillus niger

<400> SEQUENCE: 1

```
gtttgacgcg tttgcagtgt agaagcttcc agctaccgta gattactgat acaaactcaa     60
tacactattt ctataacctt actgttcaat acagtacgat caaaatttcc ggaatattaa    120
tgttacggtt accttccata tgtagactag cgcacttggc attagggttc gaaatacgat    180
caaagagtat tggggggggt gacagcagta atgactccaa ctgtaaatcg gcttctaggc    240
gcgctccatc taaatgttct ggctgtggtg tacaggggca taaaattacg cactacccga    300
atcgatagaa ctactcattt ttatatagaa gtcagaattc atggtgtttt gatcatttta    360
aatttttata tggcgggtgg tgggcaactc gcttgcgcgg gcaactcgct taccgattac    420
gttagggctg atatttacgt aaaaatcgtc aagggatgca agaccaaagt actaaaaccc    480
cggagtcaac agcatccaag cccaagtcct tcacggagaa accccagcgt ccacatcacg    540
agcgaaggac cacctctagg catcggacgc accatccaat tagaagcagc aaagcgaaac    600
agcccaagaa aaaggtcggc ccgtcggcct tttctgcaac gctgatcacg ggcagcgatc    660
caaccaacac cctccagagt gactaggggc ggaaatttat cgggattaat ttccactcaa    720
ccacaaatca cagtcgtccc cggtattgtc ctgcagaatg caatttaaac tcttctgcga    780
atcgcttgga ttccccgccc ctggccgtag agcttaaagt atgtcccttg tcgatgcgat    840
gtatcacaac atataaatac tagcaaggga tgccatgctt ggaggatagc aaccgacaac    900
atcacatcaa gctctcccct tctgaacaa taaacccccac agaaggcatt tatgatggtc    960
gcgtggtggt ctctatttct gtacggcctt caggtcgcgg cacctgcttt ggctgcaacg   1020
cctgcggact ggcgatcgca atccatttat ttccttctca cggatcgatt tgcaaggacg   1080
gatgggtcga cgactgcgac ttgtaatact gcggatcagg tgtgttgtta cctactagct   1140
ttcagaaaga ggaatgtaaa ctgacttgat atagaaatac tgtggtggaa catggcaggg   1200
catcatcgac aaggtaaatt gccccttat caaaaaaaaa agaaggaaaa gcagaagaaa   1260
aataaaataa aaagaactct agtcctaacc atcacatagt tggactatat ccagggaatg   1320
ggcttcacag ccatctggat caccccgtt acagcccagc tgccccagac caccgcatat   1380
ggagatgcct accatggcta ctggcagcag gatatgtaag tcgatttctt taaatatcta   1440
cctgtcatct tttacatcaa tatgaactaa cttgatggtt ttagatactc tctgaacgaa   1500
aactacggca ctgcagatga cttgaaggcg ctctcttcgg cccttcatga gagggggatg   1560
tatcttatgg tcgatgtggt tgctaaccat atggttcgtg gtcctttgca actgacttcg   1620
cggatatggt tcatttcagt actgacaatg agtaatatca gggctatgat ggagcgggta   1680
```

```
gctcagtcga ttacagtgtg tttaaaccgt tcagttccca agactacttc cacccgttct    1740
gtttcattca aaactatgaa gatcagactc aggttgagga ttgctggcta ggagataaca    1800
ctgtctcctt gcctgatctc gataccacca aggatgtggt caagaatgaa tggtacgact    1860
gggtgggatc attggtatcg aactactcca gtaagatatt tctccctcat tctacaactt    1920
ggctgatcga tgatacttac gaaatcagtt gacggcctcc gtatcgacac agtaaaacac    1980
gtccagaagg acttctggcc cgggtacaac aaagccgcag gcgtgtactg tatcggcgag    2040
gtgctcgacg gtgatccggc ctacacttgt ccctaccaga acgtcatgga cggcgtactg    2100
aactatccca tgtatggttc ctccaaccat gagccttctt gcaagtctca tctcctaacg    2160
aaacggctaa aaccagttac tatccactcc tcaacgcctt caagtcaacc tccggcagca    2220
tggacgacct ctacaacatg atcaacaccg tcaaatccga ctgtccagac tcaacactcc    2280
tgggcacatt cgtcgagaac cacgacaacc cacggttcgc ttcgtaagtc ttccctttta    2340
ttttccgttc ccaatttcca cacagaaccc cacctaacaa gagcaaagtt acaccaacga    2400
catagccctc gccaagaacg tcgcagcatt catcatcctc aacgacggaa tccccatcat    2460
ctacgccggc caagaacagc actacgccgg cggaaacgac cccgcgaacc gcgaagcaac    2520
ctggctctcg ggctacccga ccgacagcga gctgtacaag ttaattgcct ccgcgaacgc    2580
aatccggaac tatgccatta gcaaagatac aggattcgtg acctacaagg taagcacaac    2640
ctctaagcat accctaatgg cctatcttca gagtatctga cacaagagac taatcactgg    2700
caatacagaa ctggcccatc tacaaagacg acacaacgat cgccatgcgc aagggcacag    2760
atgggtcgca gatcgtgact atcttgtcca acaagggtgc ttcgggtgat tcgtataccc    2820
tctccttgag tggtgcgggt tacacagccg gccagcaatt gacggaggtc attggctgca    2880
cgaccgtgac ggttggttcg gatggaaatg tgcctgttcc tatggcaggt gggctaccta    2940
gggtattgta tccgactgag aagttggcag gtagcaagat ctgtagtagc tcgtgaaggg    3000
tggagagtat atgatggtac tgctattcaa tctggcattg acagtgagt  ttgagtttga    3060
tgtacataac caaggttgtg tctgtataat atatacatgt aagatacatg agcttcggtg    3120
atataataca gaagtaccat acagtaccgc gttatgaaaa cacattaatc cggatccttt    3180
cctataatag actagcgtgc ttggcattag ggttcgaaaa acaatcgaag agtataaggg    3240
gatgacagca gtaacgactc caactgtagc ccacatcttg agttcggcaa ctactgttgg    3300
cacgtgaccc tgtgccttgt ggtagctcct taactttgtc atcattcgaa gaattttcgt    3360
cccttcccag gtaccatcca aaagacaagc atccgtcgct tcactctgag atcagatgag    3420
agtaatattg ttgactgcgt ttgtgatgcg ggtgatgtcc tctgcgatcg gccgcaagct    3480
gtttagtttg ccccggatct tctgtgccga cggttgctcc ccgaattttc ttagctagtg    3540
taatcacgct attcagaaag gcttccaaga attaggccgg tagttcggcg cgtttggtgt    3600
cgtcaagctc cagcagtgct ggggcctcgg ctatgatatg gttagaatgc tcggggtggg    3660
tcacggcagg acacccgaca ctgcaacgtc taccacattt gagcgttatt ggcagacttg    3720
cggcgagata acgaccgcta gcttgtatca accaaatcca actgaaatta ttgctttgcc    3780
atcccaacag tggatttcgg aggagggagg ggggaagata tacgatgaac ggaagactgg    3840
acaagatacg ttacataaag cagtactact tgtttcaaac tgtgtacaca ccagggctct    3900
cgcttcagcg gagagtgtcg aaagattcag taaaacatcg ccaggggtga tggaaagggg    3960
ttaag                                                                3965
```

```
<210> SEQ ID NO 2
<211> LENGTH: 1497
<212> TYPE: DNA
<213> ORGANISM: Aspergillus niger
<220> FEATURE:
<221> NAME/KEY: CDS
<222> LOCATION: (1)...(1497)

<400> SEQUENCE: 2 atg gtc gcg tgg tgg tct cta ttt ctg tac ggc ctt cag gtc gcg gca      48
Met Val Ala Trp Trp Ser Leu Phe Leu Tyr Gly Leu Gln Val Ala Ala
1               5                   10                  15 cct gct ttg gct gca acg cct gcg gac tgg cga tcg caa tcc att tat      96
Pro Ala Leu Ala Ala Thr Pro Ala Asp Trp Arg Ser Gln Ser Ile Tyr
                20                  25                  30 ttc ctt ctc acg gat cga ttt gca agg acg gat ggg tcg acg act gcg     144
Phe Leu Leu Thr Asp Arg Phe Ala Arg Thr Asp Gly Ser Thr Thr Ala
            35                  40                  45 act tgt aat act gcg gat cag aaa tac tgt ggt gga aca tgg cag ggc     192
Thr Cys Asn Thr Ala Asp Gln Lys Tyr Cys Gly Gly Thr Trp Gln Gly
        50                  55                  60 atc atc gac aag ttg gac tat atc cag gga atg ggc ttc aca gcc atc     240
Ile Ile Asp Lys Leu Asp Tyr Ile Gln Gly Met Gly Phe Thr Ala Ile
65                  70                  75                  80 tgg atc acc ccc gtt aca gcc cag ctg ccc cag acc acc gca tat gga     288
Trp Ile Thr Pro Val Thr Ala Gln Leu Pro Gln Thr Thr Ala Tyr Gly
                85                  90                  95 gat gcc tac cat ggc tac tgg cag cag gat ata tac tct ctg aac gaa     336
Asp Ala Tyr His Gly Tyr Trp Gln Gln Asp Ile Tyr Ser Leu Asn Glu
            100                 105                 110 aac tac ggc act gca gat gac ttg aag gcg ctc tct tcg gcc ctt cat     384
Asn Tyr Gly Thr Ala Asp Asp Leu Lys Ala Leu Ser Ser Ala Leu His
        115                 120                 125 gag agg ggg atg tat ctt atg gtc gat gtg gtt gct aac cat atg ggc     432
Glu Arg Gly Met Tyr Leu Met Val Asp Val Val Ala Asn His Met Gly
    130                 135                 140 tat gat gga gcg ggt agc tca gtc gat tac agt gtg ttt aaa ccg ttc     480
Tyr Asp Gly Ala Gly Ser Ser Val Asp Tyr Ser Val Phe Lys Pro Phe
145                 150                 155                 160 agt tcc caa gac tac ttc cac ccg ttc tgt ttc att caa aac tat gaa     528
Ser Ser Gln Asp Tyr Phe His Pro Phe Cys Phe Ile Gln Asn Tyr Glu
                165                 170                 175 gat cag act cag gtt gag gat tgc tgg cta gga gat aac act gtc tcc     576
Asp Gln Thr Gln Val Glu Asp Cys Trp Leu Gly Asp Asn Thr Val Ser
            180                 185                 190 ttg cct gat ctc gat acc acc aag gat gtg gtc aag aat gaa tgg tac     624
Leu Pro Asp Leu Asp Thr Thr Lys Asp Val Val Lys Asn Glu Trp Tyr
        195                 200                 205 gac tgg gtg gga tca ttg gta tcg aac tac tcc att gac ggc ctc cgt     672
Asp Trp Val Gly Ser Leu Val Ser Asn Tyr Ser Ile Asp Gly Leu Arg
    210                 215                 220 atc gac aca gta aaa cac gtc cag aag gac ttc tgg ccc ggg tac aac     720
Ile Asp Thr Val Lys His Val Gln Lys Asp Phe Trp Pro Gly Tyr Asn
225                 230                 235                 240 aaa gcc gca ggc gtg tac tgt atc ggc gag gtg ctc gac ggt gat ccg     768
Lys Ala Ala Gly Val Tyr Cys Ile Gly Glu Val Leu Asp Gly Asp Pro
                245                 250                 255 gcc tac act tgt ccc tac cag aac gtc atg gac ggc gta ctg aac tat     816
Ala Tyr Thr Cys Pro Tyr Gln Asn Val Met Asp Gly Val Leu Asn Tyr
            260                 265                 270 ccc att tac tat cca ctc ctc aac gcc ttc aag tca acc tcc ggc agc     864
Pro Ile Tyr Tyr Pro Leu Leu Asn Ala Phe Lys Ser Thr Ser Gly Ser
```

```
Pro Ile Tyr Tyr Pro Leu Leu Asn Ala Phe Lys Ser Thr Ser Gly Ser
        275                 280                 285 atg gac gac ctc tac aac atg atc aac acc gtc aaa tcc gac tgt cca      912
Met Asp Asp Leu Tyr Asn Met Ile Asn Thr Val Lys Ser Asp Cys Pro
        290                 295                 300 gac tca aca ctc ctg ggc aca ttc gtc gag aac cac gac aac cca cgg      960
Asp Ser Thr Leu Leu Gly Thr Phe Val Glu Asn His Asp Asn Pro Arg
305                 310                 315                 320 ttc gct tct tac acc aac gac ata gcc ctc gcc aag aac gtc gca gca     1008
Phe Ala Ser Tyr Thr Asn Asp Ile Ala Leu Ala Lys Asn Val Ala Ala
                325                 330                 335 ttc atc atc ctc aac gac gga atc ccc atc atc tac gcc ggc caa gaa     1056
Phe Ile Ile Leu Asn Asp Gly Ile Pro Ile Ile Tyr Ala Gly Gln Glu
            340                 345                 350 cag cac tac gcc ggc gga aac gac ccc gcg aac cgc gaa gca acc tgg     1104
Gln His Tyr Ala Gly Gly Asn Asp Pro Ala Asn Arg Glu Ala Thr Trp
            355                 360                 365 ctc tcg ggc tac ccg acc gac agc gag ctg tac aag tta att gcc tcc     1152
Leu Ser Gly Tyr Pro Thr Asp Ser Glu Leu Tyr Lys Leu Ile Ala Ser
370                 375                 380 gcg aac gca atc cgg aac tat gcc att agc aaa gat aca gga ttc gtg     1200
Ala Asn Ala Ile Arg Asn Tyr Ala Ile Ser Lys Asp Thr Gly Phe Val
385                 390                 395                 400 acc tac aag aac tgg ccc atc tac aaa gac gac aca acg atc gcc atg     1248
Thr Tyr Lys Asn Trp Pro Ile Tyr Lys Asp Asp Thr Thr Ile Ala Met
                405                 410                 415 cgc aag ggc aca gat ggg tcg cag atc gtg act atc ttg tcc aac aag     1296
Arg Lys Gly Thr Asp Gly Ser Gln Ile Val Thr Ile Leu Ser Asn Lys
            420                 425                 430 ggt gct tcg ggt gat tcg tat acc ctc tcc ttg agt ggt gcg ggt tac     1344
Gly Ala Ser Gly Asp Ser Tyr Thr Leu Ser Leu Ser Gly Ala Gly Tyr
        435                 440                 445 aca gcc ggc cag caa ttg acg gag gtc att ggc tgc acg acc gtg acg     1392
Thr Ala Gly Gln Gln Leu Thr Glu Val Ile Gly Cys Thr Thr Val Thr
450                 455                 460 gtt ggt tcg gat gga aat gtg cct gtt cct atg gca ggt ggg cta cct     1440
Val Gly Ser Asp Gly Asn Val Pro Val Pro Met Ala Gly Gly Leu Pro
465                 470                 475                 480 agg gta ttg tat ccg act gag aag ttg gca ggt agc aag atc tgt agt     1488
Arg Val Leu Tyr Pro Thr Glu Lys Leu Ala Gly Ser Lys Ile Cys Ser
                485                 490                 495 agc tcg tga                                                         1497
Ser Ser <210> SEQ ID NO 3
<211> LENGTH: 498
<212> TYPE: PRT
<213> ORGANISM: Aspergillus niger

<400> SEQUENCE: 3

Met Val Ala Trp Trp Ser Leu Phe Leu Tyr Gly Leu Gln Val Ala Ala
1               5                   10                  15

Pro Ala Leu Ala Ala Thr Pro Ala Asp Trp Arg Ser Gln Ser Ile Tyr
            20                  25                  30

Phe Leu Leu Thr Asp Arg Phe Ala Arg Thr Asp Gly Ser Thr Thr Ala
        35                  40                  45

Thr Cys Asn Thr Ala Asp Gln Lys Tyr Cys Gly Gly Thr Trp Gln Gly
    50                  55                  60

Ile Ile Asp Lys Leu Asp Tyr Ile Gln Gly Met Gly Phe Thr Ala Ile
```

```
                65                  70                  75                  80
Trp Ile Thr Pro Val Thr Ala Gln Leu Pro Gln Thr Thr Ala Tyr Gly
                    85                  90                  95
Asp Ala Tyr His Gly Tyr Trp Gln Gln Asp Ile Tyr Ser Leu Asn Glu
                    100                 105                 110
Asn Tyr Gly Thr Ala Asp Asp Leu Lys Ala Leu Ser Ser Ala Leu His
                    115                 120                 125
Glu Arg Gly Met Tyr Leu Met Val Asp Val Val Ala Asn His Met Gly
                    130                 135                 140
Tyr Asp Gly Ala Gly Ser Ser Val Asp Tyr Ser Val Phe Lys Pro Phe
145                 150                 155                 160
Ser Ser Gln Asp Tyr Phe His Pro Phe Cys Phe Ile Gln Asn Tyr Glu
                    165                 170                 175
Asp Gln Thr Gln Val Glu Asp Cys Trp Leu Gly Asp Asn Thr Val Ser
                    180                 185                 190
Leu Pro Asp Leu Asp Thr Thr Lys Asp Val Val Lys Asn Glu Trp Tyr
                    195                 200                 205
Asp Trp Val Gly Ser Leu Val Ser Asn Tyr Ser Ile Asp Gly Leu Arg
210                 215                 220
Ile Asp Thr Val Lys His Val Gln Lys Asp Phe Trp Pro Gly Tyr Asn
225                 230                 235                 240
Lys Ala Ala Gly Val Tyr Cys Ile Gly Glu Val Leu Asp Gly Asp Pro
                    245                 250                 255
Ala Tyr Thr Cys Pro Tyr Gln Asn Val Met Asp Gly Val Leu Asn Tyr
                    260                 265                 270
Pro Ile Tyr Tyr Pro Leu Leu Asn Ala Phe Lys Ser Thr Ser Gly Ser
                    275                 280                 285
Met Asp Asp Leu Tyr Asn Met Ile Asn Thr Val Lys Ser Asp Cys Pro
                    290                 295                 300
Asp Ser Thr Leu Leu Gly Thr Phe Val Glu Asn His Asp Asn Pro Arg
305                 310                 315                 320
Phe Ala Ser Tyr Thr Asn Asp Ile Ala Leu Ala Lys Asn Val Ala Ala
                    325                 330                 335
Phe Ile Ile Leu Asn Asp Gly Ile Pro Ile Ile Tyr Ala Gly Gln Glu
                    340                 345                 350
Gln His Tyr Ala Gly Gly Asn Asp Pro Ala Asn Arg Glu Ala Thr Trp
                    355                 360                 365
Leu Ser Gly Tyr Pro Thr Asp Ser Glu Leu Tyr Lys Leu Ile Ala Ser
370                 375                 380
Ala Asn Ala Ile Arg Asn Tyr Ala Ile Ser Lys Asp Thr Gly Phe Val
385                 390                 395                 400
Thr Tyr Lys Asn Trp Pro Ile Tyr Lys Asp Asp Thr Thr Ile Ala Met
                    405                 410                 415
Arg Lys Gly Thr Asp Gly Ser Gln Ile Val Thr Ile Leu Ser Asn Lys
                    420                 425                 430
Gly Ala Ser Gly Asp Ser Tyr Thr Leu Ser Leu Ser Gly Ala Gly Tyr
                    435                 440                 445
Thr Ala Gly Gln Gln Leu Thr Glu Val Ile Gly Cys Thr Thr Val Thr
                    450                 455                 460
Val Gly Ser Asp Gly Asn Val Pro Val Pro Met Ala Gly Gly Leu Pro
465                 470                 475                 480
Arg Val Leu Tyr Pro Thr Glu Lys Leu Ala Gly Ser Lys Ile Cys Ser
                    485                 490                 495
```

Ser Ser

<210> SEQ ID NO 4
<211> LENGTH: 3494
<212> TYPE: DNA
<213> ORGANISM: Artificial Sequence
<220> FEATURE:
<223> OTHER INFORMATION: optimized sequence for Aspergillus niger alpha
      amylase gene
<220> FEATURE:
<221> NAME/KEY: PROMOTER
<222> LOCATION: (1)...(1988)
<223> OTHER INFORMATION: alpha amylase promoter of Aspergillus niger
<220> FEATURE:
<221> NAME/KEY: misc_feature
<222> LOCATION: (1979)...(1988)
<223> OTHER INFORMATION: translational initiator sequence
<220> FEATURE:
<221> NAME/KEY: GENE
<222> LOCATION: (1989)...(3482)
<223> OTHER INFORMATION: optimized coding sequence for Aspergillus niger
      alpha amylase
<220> FEATURE:
<221> NAME/KEY: MISC_FEATURE
<222> LOCATION: (3483)...(3486)
<223> OTHER INFORMATION: translational terminator sequence

<400> SEQUENCE: 4

```
ctcgagggac aacgcatcgt ttgatacact tcccgccaat atggacgttg tccagaagcc    60
tgttcagcat cgatctgggc gtctcgttct gtaagcattc tcctagttac tgatgacttt   120
cctctcttat ctgtattccg tgaaagagga gggccactgt cctctatata gtttatggat   180
ataaaaagtt tgagcttctt gccaatatga aacagatttc cccacattaa gagctgtttc   240
tctataggtt tccaatcaat attagtgccg tcaaaacgtt tgttcagatc agattgtcca   300
cgttcgttta cagatactct gactgtagta tcatctgatc tcacacgttg gttgtgacgt   360 attttttcgac gcataacatt ttcagcatcc tgtgttatct tcgcccagtg tgaactgggt   420
gctacagcca agtcctgttc agtgtccttt gacacagttc ggttgttcag agttaccttc   480
cactcaatag tataatgaat acaaggcttt cctctatgtt gcctcgtagt cctttcttcg   540
ggctcctgga agaaacccag atgattgggc tgggattgat gcaagggagt ataaggttca   600
tcaagtacat gttcaggtga tgggcaaaat acggatggcg tacgatctct accgaagtca   660
ccaggggtgg gggcatacga tggagtttgt atccacggat caggtggctg aagctgagag   720
gcatcgtcat cgtagtaagg actaaacgtc atcccctcaa ggcagtagat gccactgaga   780
agcctagtgt tgggatcatc atatgttagc ctacaccata tgggtgtccc agcaagagtg   840
tccgtgaggg aagaggtgca gctaacaaaa ccagtaaaat gatcaggttc atggacaatg   900
aactaagaca ggtacagtat tgtagcccta cccgtcttgg ttaacctggt aaggtcaaaa   960
aggatcgaac cgtggctcag tacaaacaaa aggaatgtta acagtttgcg ggagatgcaa  1020
ggcacatgct ttgtcatgtt tgacgcgttt gcagtgtaga agcttccagc taccgtagat  1080
tactgataca aactcaatac actatttcta taaccttact gttcaataca gtacgatcaa  1140
aatttccgga atattaatgt tacggttacc ttccatatgt agactagcgc acttggcatt  1200
agggttcgaa atacgatcaa agagtattgg gggggtgac agcagtaatg actccaactg   1260
taaatcggct tctaggcgcg ctccatctaa atgttctggc tgtggtgtac aggggcataa  1320
aattacgcac tacccgaatc gatagaacta ctcatttta tatagaagtc agaattcatg   1380
gtgttttgat cattttaaat ttttatatgg cgggtggtgg gcaactcgct tgcgcgggca  1440
```

```
actcgcttac cgattacgtt agggctgata tttacgtaaa aatcgtcaag ggatgcaaga      1500
ccaaagtact aaaaccccgg agtcaacagc atccaagccc aagtccttca cggagaaacc      1560
ccagcgtcca catcacgagc gaaggaccac ctctaggcat cggacgcacc atccaattag      1620
aagcagcaaa gcgaaacagc caagaaaaa ggtcggcccg tcggcctttt ctgcaacgct       1680
gatcacgggc agcgatccaa ccaacaccct ccagagtgac taggggcgga aatttatcgg      1740
gattaatttc cactcaacca caaatcacag tcgtccccgg tattgtcctg cagaatgcaa      1800
tttaaactct tctgcgaatc gcttggattc cccgcccctg gccgtagagc ttaaagtatg      1860
tcccttgtcg atgcgatgta tcacaacata taaatactag caagggatgc catgcttgga      1920
ggatagcaac cgacaacatc acatcaagct ctcccttctc tgaacaataa accccacaca      1980
ccgtcaaaat ggtcgcgtgg tggtctctat ttctgtacgg ccttcaggtc gcggcacctg      2040
ctttggctgc aacgcctgcg gactggcgat cgcaatccat ttatttcctt ctcacggatc      2100
gatttgcaag gacggatggg tcgacgactg cgacttgtaa tactgcggat cagaaatact      2160
gtggtggaac atggcagggc atcatcgaca agttggacta tatccaggga atgggcttca      2220
cagccatctg gatcaccccc gttacagccc agctgcccca gaccaccgca tatggagatg      2280
cctaccatgg ctactggcag caggatatat actctctgaa cgaaaactac ggcactgcag      2340
atgacttgaa ggcgctctct tcggcccttc atgagagggg gatgtatctt atggtcgatg      2400
tggttgctaa ccatatgggc tatgatggag cgggtagctc agtcgattac agtgtgttta      2460
aaccgttcag ttcccaagac tacttccacc cgttctgttt cattcaaaac tatgaagatc      2520
agactcaggt tgaggattgc tggctaggag ataacactgt ctccttgcct gatctcgata      2580
ccaccaagga tgtggtcaag aatgaatggt acgactgggt gggatcattg gtatcgaact      2640
actccattga cggcctccgt atcgacacag taaaacacgt ccagaaggac ttctggcccg      2700
ggtacaacaa agccgcaggc gtgtactgta tcggcgaggt gctcgacggt gatccggcct      2760
acacttgtcc ctaccagaac gtcatggacg gcgtactgaa ctatcccatt tactatccac      2820
tcctcaacgc cttcaagtca acctccggca gcatggacga cctctacaac atgatcaaca      2880
ccgtcaaatc cgactgtcca gactcaacac tcctgggcac attcgtcgag aaccacgaca      2940
acccacggtt cgcttcttac accaacgaca tagccctcgc caagaacgtc gcagcattca      3000
tcatcctcaa cgacggaatc cccatcatct acgccggcca agaacagcac tacgccggcg      3060
gaaacgaccc cgcgaaccgc gaagcaacct ggctctcggg ctacccgacc gacagcgagc      3120
tgtacaagtt aattgcctcc gcgaacgcaa tccggaacta tgccattagc aaagatacag      3180
gattcgtgac ctacaagaac tggcccatct acaaagacga cacaacgatc gccatgcgca      3240
agggcacaga tgggtcgcag atcgtgacta tcttgtccaa caagggtgct tcgggtgatt      3300
cgtataccct ctccttgagt ggtgcgggtt acacagccgg ccagcaattg acggaggtca      3360
ttggctgcac gaccgtgacg gttggttcgg atgaaatgt gcctgttcct atggcaggtg      3420
ggctacctag ggtattgtat ccgactgaga agttggcagg tagcaagatc tgtagtagct      3480
cgtaaattaa ttaa                                                       3494
```

<210> SEQ ID NO 5
<211> LENGTH: 1498
<212> TYPE: DNA
<213> ORGANISM: Artificial Sequence
<220> FEATURE:
<223> OTHER INFORMATION: optimized sequence for Aspergillus niger alpha
      amylase gene
<220> FEATURE:

<220> FEATURE:
<221> NAME/KEY: GENE
<222> LOCATION: (1)...(1494)
<223> OTHER INFORMATION: optimized coding sequence for Aspergillus niger
      alpha amylase
<220> FEATURE:
<221> NAME/KEY: MISC_FEATURE
<222> LOCATION: (1495)...(1498)
<223> OTHER INFORMATION: translational terminator sequence

<400> SEQUENCE: 5

```
atggtcgcct ggtggtccct gttcctctac ggacttcagg tggctgcccc cgctctcgcc      60
gcgaccccg  ccgattggcg tagccagtcg atttacttct tgcttactga ccgcttcgct     120
cgcaccgacg gttccaccac cgccacctgc aacactgcgg accagaagta ctgcggcggc     180
acttggcagg gtatcatcga caagctggat tacatccagg gtatgggatt caccgctatc     240
tggattactc ctgttaccgc tcagctcccc cagaccaccg cctacggcga tgcctaccac     300
ggttactggc agcaggacat ctactctctg aacgaaaact acggtaccgc tgacgatctc     360
aaggccttgt cttccgccct ccacgagcgt ggcatgtacc tgatggtcga cgtcgtggct     420
aaccacatgg gttacgacgg tgcgggcagc tctgtcgatt actcggtttt caagcctttc     480
tcctcccagg attacttcca ccccttctgc ttcatccaga actacgagga ccagacccag     540
gtcgaggact gctggctggg agacaacact gtttcgcttc ccgatctcga cactaccaag     600
gacgtcgtta agaacgagtg gtacgattgg gtgggtagct tggtctccaa ctacagcatt     660
gacggcctcc gcatcgacac cgtcaagcac gtccagaagg atttctggcc tggatacaac     720
aaggccgccg tgtgtactg catcggcgaa gttctggacg tgaccctgc ttacacctgc     780
ccctaccaga acgtcatgga tggtgtcctg aactacccca tctactaccc ccttctcaac     840
gctttcaagt ctacctccgg ctccatggac gacctctaca catgattaa  cactgttaag     900
agcgattgcc ctgactcgac cctgttgggc accttcgtgg agaaccacga taacccccgt     960
ttcgcctcct acactaacga catcgcccct gcgaagaacg tcgctgcctt catcatcctc    1020
aacgacggta ttcctatcat ctacgctggt caggagcagc actacgccgg cggaaacgat    1080
cccgctaacc gcgaagccac ctggctgtcc ggttacccca ccgactctga gctctacaag    1140
ctgatcgcta gcgccaacgc gattcgtaac tacgccatct ccaaggacac tggcttcgtc    1200
acctacaaga actggcctat ctacaaggat gacaccacta tcgctatgcg taagggtacc    1260
gacggttctc agatcgttac catttttgtcc aacaagggag ccagcggtga ttcctacacc    1320
ctctctctgt ccggcgctgg ctacactgcc ggtcagcagc ttaccgaggt catcggatgc    1380
accactgtca ccgtgggttc ggacggcaac gttcccgtcc ccatggctgg tggcctccct    1440
cgcgtcctgt accccaccga gaagctcgcc ggttctaaga tctgctccag ctcctaaa     1498
```

<210> SEQ ID NO 6
<211> LENGTH: 1498
<212> TYPE: DNA
<213> ORGANISM: Artificial Sequence
<220> FEATURE:
<223> OTHER INFORMATION: optimized sequence for Aspergillus niger alpha
      amylase gene
<220> FEATURE:
<221> NAME/KEY: GENE
<222> LOCATION: (1)...(1494)
<223> OTHER INFORMATION: optimized coding sequence for Aspergillus niger
      alpha amylase
<220> FEATURE:
<221> NAME/KEY: MISC_FEATURE
<222> LOCATION: (1495)...(1498)
<223> OTHER INFORMATION: translational terminator sequence

<400> SEQUENCE: 6

```
atggttgcct ggtggtccct cttcctgtac ggtctccagg ttgctgctcc tgctcttgct    60
gccactcctg ccgactggcg ctcccagtcc atctacttcc tgctgaccga ccgcttcgct   120
cgtaccgatg aagcaccac tgccacctgc aacactgcgg accagaagta ctgcggtggt    180
acctggcagg gtatcattga caagctcgac tacatccagg catgggtttt cactgccatc   240
tggatcaccc ccgtgactgc tcagctcccc cagaccactg cctacggtga tgcctaccac   300
ggatactggc agcaggatat ctactctctg aacgagaact acggcactgc cgatgacctc   360
aaggcccttt cttctgctct gcacgagcgt ggaatgtacc tgatggtgga tgttgttgcc   420
aaccacatgg ctacgacgg tgctggcagc tctgttgact actctgtctt caagcccttc    480
tcttcccagg actacttcca ccccttctgc ttcatccaga actacgaaga ccagacccag   540
gttgaggact gctggttggg tgacaacacc gtctccctcc ccgatcttga caccaccaag   600
gatgttgtca agaacgaatg gtacgactgg gtgggatccc tggtctccaa ctactccatc   660
gatggtctcc gcattgacac cgtcaagcac gtccagaagg acttctggcc tggctacaac   720
aaggctgctg gtgtctactg cattggtgag gtcctcgatg gagatcctgc ctacacctgc   780
ccctaccaga acgtcatgga tggtgttctc aactacccca tctactaccc cttgctcaac   840
gccttcaagt ccacctccgg cagcatggat gacctctaca acatgatcaa caccgtcaag   900
tccgactgcc ccgacagcac tctccttggt accttcgtcg agaaccacga caaccctcgt   960
ttcgccagct acaccaacga cattgctctt gccaagaacg tcgctgcttt catcatcctg  1020
aacgacggta tccccatcat ctacgctggc caggagcagc actacgctgg tgcaacgac   1080
cctgccaacc gtgaggccac ctggctgtct ggctacccca ccgacagcga attgtacaag  1140
ttgattgcct ctgccaacgc catccgcaac tacgccatct ccaaggacac tggtttcgtc  1200
acctacaaga actggcccat ctacaaggat gacaccacca ttgccatgcg caagggtact  1260
gatggcagcc agatcgtcac catcctgtcc aacaagggtg cctccggtga ctcctacacc  1320
ctctcccctct ccggtgctgg ctacactgct ggccagcagc tgaccgaggt cattggctgc  1380
accaccgtca ccgttggatc ggatggcaac gtgcctgtgc ccatggccgg tggtcttcct  1440
cgtgtcctct accccactga gaagcttgct ggcagcaaga tctgctcgtc gtcgtaaa    1498
```

<210> SEQ ID NO 7
<211> LENGTH: 3494
<212> TYPE: DNA
<213> ORGANISM: Artificial Sequence
<220> FEATURE:
<223> OTHER INFORMATION: synthetic sequence for Aspergillus niger alpha
      amylase gene
<220> FEATURE:
<221> NAME/KEY: PROMOTER
<222> LOCATION: (1)...(1988)
<223> OTHER INFORMATION: alpha amylase promoter of Aspergillus niger
<220> FEATURE:
<221> NAME/KEY: MISC_FEATURE
<222> LOCATION: (1979)...(1988)
<223> OTHER INFORMATION: translational initiator sequence
<220> FEATURE:
<221> NAME/KEY: GENE
<222> LOCATION: (1989)...(3482)
<223> OTHER INFORMATION: optimized coding sequence for Aspergillus niger
      alpha amylase
<220> FEATURE:
<221> NAME/KEY: MISC_FEATURE
<222> LOCATION: (3483)...(3486)
<223> OTHER INFORMATION: translational terminator sequence

<400> SEQUENCE: 7

```
ctcgagggac aacgcatcgt ttgatacact tcccgccaat atggacgttg tccagaagcc      60
tgttcagcat cgatctgggc gtctcgttct gtaagcattc tcctagttac tgatgacttt     120
cctctcttat ctgtattccg tgaaagagga gggccactgt cctctatata gtttatggat     180
ataaaaagtt tgagcttctt gccaatatga aacagatttc cccacattaa gagctgtttc     240
tctataggtt tccaatcaat attagtgccg tcaaaacgtt tgttcagatc agattgtcca     300
cgttcgttta cagatactct gactgtagta tcatctgatc tcacacgttg gttgtgacgt     360
atttttcgac gcataacatt ttcagcatcc tgtgttatct tcgcccagtg tgaactgggt     420
gctacagcca agtcctgttc agtgtccttt gacacagttc ggttgttcag agttaccttc     480
cactcaatag tataatgaat acaaggcttt cctctatgtt gcctcgtagt cctttcttcg     540
ggctcctgga agaaacccag atgattgggc tgggattgat gcaagggagt ataaggttca     600
tcaagtacat gttcaggtga tgggcaaaat acggatggcg tacgatctct accgaagtca     660
ccaggggtgg gggcatacga tggagtttgt atccacggat caggtggctg aagctgagag     720
gcatcgtcat cgtagtaagg actaaacgtc atcccctcaa ggcagtagat gccactgaga     780
agcctagtgt tgggatcatc atatgttagc ctacaccata tgggtgtccc agcaagagtg     840
tccgtgaggg aagaggtgca gctaacaaaa ccagtaaaat gatcaggttc atggacaatg     900
aactaagaca ggtacagtat tgtagcccta cccgtcttgg ttaacctggt aaggtcaaaa     960
aggatcgaac cgtggctcag tacaaacaaa aggaatgtta acagtttgcg ggagatgcaa    1020
ggcacatgct ttgtcatgtt tgacgcgttt gcagtgtaga agcttccagc taccgtagat    1080
tactgataca aactcaatac actatttcta taaccttact gttcaataca gtacgatcaa    1140
aatttccgga atattaatgt tacggttacc ttccatatgt agactagcgc acttggcatt    1200
agggttcgaa atacgatcaa agagtattgg gggggtgac agcagtaatg actccaactg    1260
taaatcggct tctaggcgcg ctccatctaa atgttctggc tgtggtgtac aggggcataa    1320
aattacgcac tacccgaatc gatagaacta ctcattttta tatagaagtc agaattcatg    1380
gtgttttgat cattttaaat ttttatatgg cgggtggtgg gcaactcgct tgcgcgggca    1440
actcgcttac cgattacgtt agggctgata tttacgtaaa aatcgtcaag ggatgcaaga    1500
ccaaagtact aaaaccccgg agtcaacagc atccaagccc aagtccttca cggagaaacc    1560
ccagcgtcca catcacgagc gaaggaccac ctctaggcat cggacgcacc atccaattag    1620
aagcagcaaa gcgaaacagc ccaagaaaaa ggtcggcccg tcggcctttt ctgcaacgct    1680
gatcacgggc agcgatccaa ccaacaccct ccagagtgac taggggcgga aatttatcgg    1740
gattaatttc cactcaacca caaatcacag tcgtccccgg tattgtcctg cagaatgcaa    1800
tttaaactct tctgcgaatc gcttggattc cccgccctg gccgtagagc ttaaagtatg    1860
tcccttgtcg atgcgatgta tcacaacata taaatactag caagggatgc catgcttgga    1920
ggatagcaac cgacaacatc acatcaagct ctcccttctc tgaacaataa accccacaca    1980
ccgtcaaaat ggtcgcctgg tggtccctgt tcctctacgg acttcaggtg gctgcccccg    2040
ctctcgccgc gaccccgcc gattggcgta gccagtcgat ttacttcttg cttactgacc    2100
gcttcgctcg caccgacggt tccaccaccg ccacctgcaa cactgcggac cagaagtact    2160
gcggcggcac ttggcagggt atcatcgaca agctggatta catccagggt atgggattca    2220
ccgctatctg gattactcct gttaccgctc agctccccca gaccaccgcc tacggcgatg    2280
cctaccacgg ttactggcag caggacatct actctctgaa cgaaaactac ggtaccgctg    2340
```

-continued

```
acgatctcaa ggccttgtct tccgccctcc acgagcgtgg catgtacctg atggtcgacg    2400
tcgtggctaa ccacatgggt tacgacggtg cgggcagctc tgtcgattac tcggttttca    2460
agcctttctc ctcccaggat tacttccacc ccttctgctt catccagaac tacgaggacc    2520
agacccaggt cgaggactgc tggctgggag acaacactgt ttcgcttccc gatctcgaca    2580
ctaccaagga cgtcgttaag aacgagtggt acgattgggt gggtagcttg gtctccaact    2640
acagcattga cggcctccgc atcgacaccg tcaagcacgt ccagaaggat ttctggcctg    2700
gatacaacaa ggccgccggt gtgtactgca tcggcgaagt tctggacggt gaccctgctt    2760
acacctgccc ctaccagaac gtcatggatg gtgtcctgaa ctaccccatc tactaccccc    2820
ttctcaacgc tttcaagtct acctccggct ccatggacga cctctacaac atgattaaca    2880
ctgttaagag cgattgccct gactcgaccc tgttgggcac cttcgtggag aaccacgata    2940
accccgtttc cgcctcctac actaacgaca tcgcccttgc gaagaacgtc gctgccttca    3000
tcatcctcaa cgacggtatt cctatcatct acgctggtca ggagcagcac tacgccggcg    3060
gaaacgatcc cgctaaccgc gaagccacct ggctgtccgg ttaccccacc gactctgagc    3120
tctacaagct gatcgctagc gccaacgcga ttcgtaacta cgccatctcc aaggacactg    3180
gcttcgtcac ctacaagaac tggcctatct acaaggatga caccactatc gctatgcgta    3240
agggtaccga cggttctcag atcgttacca ttttgtccaa caagggagcc agcggtgatt    3300
cctacaccct ctctctgtcc ggcgctggct acactgccgg tcagcagctt accgaggtca    3360
tcggatgcac cactgtcacc gtgggttcgg acggcaacgt tcccgtcccc atggctggtg    3420
gcctccctcg cgtcctgtac cccaccgaga agctcgccgg ttctaagatc tgctccagct    3480
cctaaattaa ttaa                                                      3494
```

```
<210> SEQ ID NO 8
<211> LENGTH: 3494
<212> TYPE: DNA
<213> ORGANISM: Artificial Sequence
<220> FEATURE:
<223> OTHER INFORMATION: synthetic sequence for Aspergillus niger alpha
      amylase gene
<220> FEATURE:
<221> NAME/KEY: PROMOTER
<222> LOCATION: (1)...(1988)
<223> OTHER INFORMATION: alpha amylase promoter of Aspergillus niger
<220> FEATURE:
<221> NAME/KEY: MISC_FEATURE
<222> LOCATION: (1979)...(1988)
<223> OTHER INFORMATION: translational initiator sequence
<220> FEATURE:
<221> NAME/KEY: GENE
<222> LOCATION: (1989)...(3482)
<223> OTHER INFORMATION: optimized coding sequence for Aspergillus niger
      alpha amylase
<220> FEATURE:
<221> NAME/KEY: MISC_FEATURE
<222> LOCATION: (3483)...(3486)
<223> OTHER INFORMATION: translational terminator sequence

<400> SEQUENCE: 8
```

```
ctcgagggac aacgcatcgt ttgatacact tcccgccaat atggacgttg tccagaagcc      60
tgttcagcat cgatctgggc gtctcgttct gtaagcattc tcctagttac tgatgacttt     120
cctctcttat ctgtattccg tgaaagagga gggccactgt cctctatata gtttatggat     180
ataaaaagtt tgagcttctt gccaatatga aacagatttc cccacattaa gagctgtttc     240 tctatagtt tccaatcaat attagtgccg tcaaaacgtt tgttcagatc agattgtcca     300
cgttcgttta cagatactct gactgtagta tcatctgatc tcacacgttg gttgtgacgt     360
```

```
attttttcgac gcataacatt ttcagcatcc tgtgttatct tcgcccagtg tgaactgggt      420
gctacagcca agtcctgttc agtgtccttt gacacagttc ggttgttcag agttaccttc      480
cactcaatag tataatgaat acaaggcttt cctctatgtt gcctcgtagt cctttcttcg      540
ggctcctgga agaaacccag atgattgggc tgggattgat gcaagggagt ataaggttca      600
tcaagtacat gttcaggtga tgggcaaaat acggatggcg tacgatctct accgaagtca      660
ccaggggtgg gggcatacga tggagtttgt atccacggat caggtggctg aagctgagag      720
gcatcgtcat cgtagtaagg actaaacgtc atcccctcaa ggcagtagat gccactgaga      780
agcctagtgt tgggatcatc atatgttagc ctacaccata tgggtgtccc agcaagagtg      840
tccgtgaggg aagaggtgca gctaacaaaa ccagtaaaat gatcaggttc atggacaatg      900
aactaagaca ggtacagtat tgtagcccta cccgtcttgg ttaacctggt aaggtcaaaa      960
aggatcgaac cgtggctcag tacaaacaaa aggaatgtta acagtttgcg ggagatgcaa     1020
ggcacatgct ttgtcatgtt tgacgcgttt gcagtgtaga agcttccagc taccgtagat     1080
tactgataca aactcaatac actatttcta taaccttact gttcaataca gtacgatcaa     1140
aatttccgga atattaatgt tacggttacc ttccatatgt agactagcgc acttggcatt     1200
agggttcgaa atacgatcaa agagtattgg gggggtgac agcagtaatg actccaactg     1260
taaatcggct tctaggcgcg ctccatctaa atgttctggc tgtggtgtac aggggcataa     1320
aattacgcac tacccgaatc gatagaacta ctcatttta tatagaagtc agaattcatg     1380
gtgttttgat cattttaaat ttttatatgg cgggtggtgg gcaactcgct tgcgcgggca     1440
actcgcttac cgattacgtt agggctgata tttacgtaaa aatcgtcaag ggatgcaaga     1500
ccaaagtact aaaaccccgg agtcaacagc atccaagccc aagtccttca cggagaaacc     1560
ccagcgtcca catcacgagc gaaggaccac ctctaggcat cggacgcacc atccaattag     1620
aagcagcaaa gcgaaacagc ccaagaaaaa ggtcggcccg tcggccttt ctgcaacgct     1680
gatcacgggc agcgatccaa ccaacaccct ccagagtgac taggggcgga aatttatcgg     1740
gattaatttc cactcaacca caaatcacag tcgtccccgg tattgtcctg cagaatgcaa     1800
tttaaactct tctgcgaatc gcttggattc ccgcccctg gccgtagagc ttaaagtatg     1860
tcccttgtcg atgcgatgta tcacaacata taaatactag caagggatgc catgcttgga     1920
ggatagcaac cgacaacatc acatcaagct ctcccttctc tgaacaataa accccacaca     1980
ccgtcaaaat ggttgcctgg tggtccctct tcctgtacgg tctccaggtt gctgctcctg     2040
ctcttgctgc cactcctgcc gactggcgct cccagtccat ctacttcctg ctgaccgacc     2100
gcttcgctcg taccgatgga agcaccactg ccacctgcaa cactgcggac cagaagtact     2160
gcggtggtac ctggcagggt atcattgaca agctcgacta catccaggg atgggtttca     2220
ctgccatctg gatcaccccc gtgactgctc agctccccca gaccactgcc tacggtgatg     2280
cctaccacgg atactggcag caggatatct actctctgaa cgagaactac ggcactgccg     2340
atgacctcaa ggcccttttct tctgctctgc acgagcgtgg aatgtacctg atggtggatg     2400
ttgttgccaa ccacatgggc tacgacggtc tggcagctc tgttgactac tctgtcttca     2460
agcccttctc ttcccaggac tacttccacc ccttctgctt catccagaac tacgaagacc     2520
agacccaggt tgaggactgc tggttgggtg acaacaccgt ctccctcccc gatcttgaca     2580
ccaccaagga tgttgtcaag aacgaatggt acgactggg gggatccctg gtctccaact     2640
actccatcga tggtctccgc attgacaccg tcaagcacgt ccagaaggac ttctggcctg     2700
```

```
gctacaacaa ggctgctggt gtctactgca ttggtgaggt cctcgatgga gatcctgcct    2760
acacctgccc ctaccagaac gtcatggatg gtgttctcaa ctaccccatc tactacccct    2820
tgctcaacgc cttcaagtcc acctccggca gcatggatga cctctacaac atgatcaaca    2880
ccgtcaagtc cgactgcccc gacagcactc tccttggtac cttcgtcgag aaccacgaca    2940
accctcgttt cgccagctac accaacgaca ttgctcttgc caagaacgtc gctgctttca    3000
tcatcctgaa cgacggtatc cccatcatct acgctggcca ggagcagcac tacgctggtg    3060
gcaacgaccc tgccaaccgt gaggccacct ggctgtctgg ctaccccacc gacagcgaat    3120
tgtacaagtt gattgcctct gccaacgcca tccgcaacta cgccatctcc aaggacactg    3180
gtttcgtcac ctacaagaac tggcccatct acaaggatga caccaccatt gccatgcgca    3240
agggtactga tggcagccag atcgtcacca tcctgtccaa caagggtgcc tccggtgact    3300
cctacaccct ctccctctcc ggtgctggct acactgctgg ccagcagctg accgaggtca    3360
ttggctgcac caccgtcacc gttggatcgg atggcaacgt gcctgtgccc atggccggtg    3420
gtcttcctcg tgtcctctac cccactgaga agcttgctgg cagcaagatc tgctcgtcgt    3480
cgtaaattaa ttaa                                                      3494
```

<210> SEQ ID NO 9
<211> LENGTH: 441
<212> TYPE: PRT
<213> ORGANISM: Bacillus stearothermophilus

<400> SEQUENCE: 9

```
Met Pro Tyr Phe Asp Asn Ile Ser Thr Ile Ala Tyr Glu Gly Pro Ala
1               5                   10                  15

Ser Lys Asn Pro Leu Ala Phe Lys Phe Tyr Asn Pro Glu Glu Lys Val
            20                  25                  30

Gly Asp Lys Thr Met Glu Glu His Leu Arg Phe Ser Val Ala Tyr Trp
        35                  40                  45

His Thr Phe Thr Gly Asp Gly Ser Asp Pro Phe Gly Ala Gly Asn Met
    50                  55                  60

Ile Arg Pro Trp Asn Lys Tyr Ser Gly Met Asp Leu Ala Lys Ala Arg
65                  70                  75                  80

Val Glu Ala Ala Phe Glu Phe Glu Lys Leu Asn Ile Pro Phe Phe
                85                  90                  95

Cys Phe His Asp Val Asp Ile Ala Pro Glu Gly Glu Thr Leu Lys Glu
            100                 105                 110

Thr Tyr Lys Asn Leu Asp Ile Ile Val Asp Met Ile Glu Glu Tyr Met
        115                 120                 125

Lys Thr Ser Lys Thr Lys Leu Leu Trp Asn Thr Ala Asn Leu Phe Thr
    130                 135                 140

His Pro Arg Phe Val His Gly Ala Ala Thr Ser Cys Asn Ala Asp Val
145                 150                 155                 160

Phe Ala Tyr Ala Ala Ala Lys Val Lys Lys Gly Leu Glu Ile Ala Lys
                165                 170                 175

Arg Leu Gly Ala Glu Asn Tyr Val Phe Trp Gly Gly Arg Glu Gly Tyr
            180                 185                 190

Glu Thr Leu Leu Asn Thr Asp Met Lys Leu Glu Leu Asp Asn Leu Ala
        195                 200                 205

Arg Phe Leu His Met Ala Val Asp Tyr Ala Lys Glu Ile Gly Phe Asp
    210                 215                 220

Gly Gln Phe Leu Ile Glu Pro Lys Pro Lys Glu Pro Thr Lys His Gln
```

```
                    225                 230                 235                 240

Tyr Asp Phe Asp Val Ala Thr Ala Leu Ala Phe Leu Gln Thr Tyr Gly
                245                 250                 255

Leu Lys Asp Tyr Phe Lys Phe Asn Ile Glu Ala Asn His Ala Thr Leu
                260                 265                 270

Ala Gly His Thr Phe Glu His Glu Leu Arg Val Ala Arg Ile His Gly
                275                 280                 285

Met Leu Gly Ser Val Asp Ala Asn Gln Gly Asp Met Leu Leu Gly Trp
                290                 295                 300

Asp Thr Asp Glu Phe Pro Thr Asp Leu Tyr Ser Thr Thr Leu Ala Met
305                 310                 315                 320

Tyr Glu Ile Leu Lys Asn Gly Leu Gly Arg Gly Leu Asn Phe
                325                 330                 335

Asp Ala Lys Val Arg Arg Gly Ser Phe Glu Pro Glu Asp Leu Phe Tyr
                340                 345                 350

Ala His Ile Ala Gly Met Asp Ser Phe Ala Val Gly Leu Lys Val Ala
                355                 360                 365

His Arg Leu Ile Glu Asp Arg Val Phe Asp Glu Phe Ile Glu Glu Arg
                370                 375                 380

Tyr Lys Ser Tyr Thr Glu Gly Ile Gly Arg Glu Ile Val Glu Gly Thr
385                 390                 395                 400

Val Asp Phe His Lys Leu Glu Ala His Ala Leu Gln Leu Gly Glu Ile
                405                 410                 415

Gln Asn Gln Ser Gly Arg Gln Glu Arg Leu Lys Thr Leu Leu Asn Gln
                420                 425                 430

Tyr Leu Leu Glu Val Cys Ala Ala Arg
                435                 440

<210> SEQ ID NO 10
<211> LENGTH: 388
<212> TYPE: PRT
<213> ORGANISM: Streptomyces olivochromogenes

<400> SEQUENCE: 10

Met Ser Tyr Gln Pro Thr Pro Glu Asp Arg Phe Thr Phe Gly Leu Trp
1                 5                  10                  15

Thr Val Gly Trp Gln Gly Arg Asp Pro Phe Gly Asp Ala Thr Arg Pro
                20                  25                  30

Ala Leu Asp Pro Val Glu Thr Val Gln Arg Leu Ala Glu Leu Gly Ala
                35                  40                  45

His Gly Val Thr Phe His Asp Asp Leu Ile Pro Phe Gly Ser Ser
            50                  55                  60

Asp Thr Glu Arg Glu Ser His Ile Lys Arg Phe Arg Gln Ala Leu Asp
65                  70                  75                  80

Ala Thr Gly Met Thr Val Pro Met Ala Thr Thr Asn Leu Phe Thr His
                85                  90                  95

Pro Val Phe Lys Asp Gly Gly Phe Thr Ala Asn Asp Arg Asp Val Arg
                100                 105                 110

Arg Tyr Ala Leu Arg Lys Thr Ile Arg Asn Ile Asp Leu Ala Val Glu
                115                 120                 125

Leu Gly Ala Lys Thr Tyr Val Ala Trp Gly Gly Arg Glu Gly Ala Glu
                130                 135                 140

Ser Gly Ala Ala Lys Asp Val Arg Val Ala Leu Asp Arg Met Lys Glu
145                 150                 155                 160
```

```
Ala Phe Asp Leu Leu Gly Glu Tyr Val Thr Ser Gln Gly Tyr Asp Thr
            165                 170                 175
Arg Phe Ala Ile Glu Pro Lys Pro Asn Glu Pro Arg Gly Asp Ile Leu
        180                 185                 190
Leu Pro Thr Val Gly His Ala Leu Ala Phe Ile Glu Arg Leu Glu Arg
    195                 200                 205
Pro Glu Leu Tyr Gly Val Asn Pro Glu Val Gly His Glu Gln Met Ala
210                 215                 220
Gly Leu Asn Phe Pro His Gly Ile Ala Gln Leu Trp Ala Gly Lys
225                 230                 235                 240
Leu Phe His Ile Asp Leu Asn Gly Gln Ser Gly Ile Lys Tyr Asp Gln
                245                 250                 255
Asp Leu Arg Phe Gly Ala Gly Asp Leu Arg Ala Ala Phe Trp Leu Val
            260                 265                 270
Asp Leu Glu Ser Ala Gly Tyr Glu Gly Pro Arg His Phe Asp Phe
        275                 280                 285
Lys Pro Pro Arg Thr Glu Asp Ile Asp Gly Val Trp Ala Ser Ala Ala
    290                 295                 300
Gly Cys Met Arg Asn Tyr Leu Ile Leu Lys Glu Arg Ala Ala Ala Phe
305                 310                 315                 320
Arg Ala Asp Pro Glu Val Gln Glu Ala Leu Arg Ala Ser Arg Leu Asp
                325                 330                 335
Glu Leu Ala Gln Pro Thr Ala Ala Asp Gly Val Gln Glu Leu Leu Ala
            340                 345                 350
Asp Arg Thr Ala Phe Glu Asp Phe Asp Val Asp Ala Ala Ala Ala Arg
        355                 360                 365
Gly Met Ala Phe Glu Arg Leu Asp Gln Leu Ala Met Asp His Leu Leu
    370                 375                 380
Gly Ala Arg Gly
385

<210> SEQ ID NO 11
<211> LENGTH: 1398
<212> TYPE: DNA
<213> ORGANISM: Thermoanaerobacter mathranii

<400> SEQUENCE: 11
atgcaaacca agaaaaagcc gcaaatagga tttttaggca ttatgcaaga gttgtacgat      60
gatatgttac caggcattac tgaaagacaa gaaaatatg caagagaagt tatagaacaa     120
cttcaagatg ttgccgattt tcattttcct aaagcagcaa agaatagaca ggacattgaa     180
catattgtga agaatttaa tgaaaagac cttgatggta ttatgatagt aatgcttacg      240
tatggacctg ctacaaatat tgttaatgca ctaaggaata taaactacc tattatgctt      300 gcgaacattc aacctgttcc gacagtaaca gaggattggg atatgggaga tttgacatac     360
aatcaaggtg ttcacggtgc ccaagataca gcaaatgcca ttttaaggat gggaattaag     420
tgtcctatta ttacagaaga atggcattca gaagaattta aaaaatttgt tggagattgg     480
gctaaagctg tgcagacaat taagcattg cgaaacatga aaatagcgca gtttggaaga     540
atgcatggaa tgtatgatat tttgggagat gatgcagcct ttacaagaaa aataggtccg     600
caaattaatc aagaatacat tggcgaagtt tatagatata tggaaactgc gacagaagag     660
gagattaatg cggttattga agagaataga aagaatttt atatcgatcc aaatcttagc     720
gaagaaagcc atagatatgc tgcaagatta caaattggat ttaaaaaatt tcttattaat     780
```

```
aaaggatatg acggatttac tgcgcatttc gatgtgttta aaggagatgg aagattcaag    840
caaattccaa tgatggctgc gtcaaattta atggctgaag atatggata tgcagcagag     900 ggtgatgctg taactgcaag tttggttgcg gcaggtcatg tattgatagg agatgcacat    960
tttactgaga tgtacgctat ggattttaag agaaattcaa ttttaatgag ccatatgggc   1020
gaaggtaact ggaaaatagc aagaaaggat agaccgatta aacttattga tagagaactg   1080
ggcattggaa acttgataa tccgccgaca attgtgttta tggcacaacc tgggccagca    1140
actcttgttt ctttagtatc cttagaagga gaaagatata ggttagttgt gtcaaaagga   1200
gaaattctgg atacgaaga agcaaagtat attgaaatgc catatttcca ctttagacct    1260
tcaacaggtg tgaaggcatg tcttgatgga tggcttacaa atggaggaac acatcatgaa   1320
tgtttaaatc taggtgataa cacacggaga tggaaaatat tatgtaacct cttggacatt   1380
gaatatgtag aagtatag                                                  1398
```

<210> SEQ ID NO 12
<211> LENGTH: 465
<212> TYPE: PRT
<213> ORGANISM: Thermoanaerobacter mathranii

<400> SEQUENCE: 12

```
Met Gln Thr Lys Lys Pro Gln Ile Gly Phe Leu Gly Ile Met Gln
1               5                   10                  15

Glu Leu Tyr Asp Asp Met Leu Pro Gly Ile Thr Glu Arg Gln Glu Lys
            20                  25                  30

Tyr Ala Arg Glu Val Ile Glu Gln Leu Gln Asp Val Ala Asp Phe His
        35                  40                  45

Phe Pro Lys Ala Ala Lys Asn Arg Gln Asp Ile Glu His Ile Val Lys
    50                  55                  60

Glu Phe Asn Glu Lys Asp Leu Asp Gly Ile Met Ile Val Met Leu Thr
65                  70                  75                  80

Tyr Gly Pro Ala Thr Asn Ile Val Asn Ala Leu Arg Asn Asn Lys Leu
                85                  90                  95

Pro Ile Met Leu Ala Asn Ile Gln Pro Val Pro Thr Val Thr Glu Asp
            100                 105                 110

Trp Asp Met Gly Asp Leu Thr Tyr Asn Gln Gly Val His Gly Ala Gln
        115                 120                 125

Asp Thr Ala Asn Ala Ile Leu Arg Met Gly Ile Lys Cys Pro Ile Ile
    130                 135                 140

Thr Glu Glu Trp His Ser Glu Glu Phe Lys Lys Phe Val Gly Asp Trp
145                 150                 155                 160

Ala Lys Ala Val Gln Thr Ile Lys Ala Leu Arg Asn Met Lys Ile Ala
                165                 170                 175

Gln Phe Gly Arg Met His Gly Met Tyr Asp Ile Leu Gly Asp Asp Ala
            180                 185                 190

Ala Phe Thr Arg Lys Ile Gly Pro Gln Ile Asn Gln Glu Tyr Ile Gly
        195                 200                 205

Glu Val Tyr Arg Tyr Met Glu Thr Ala Thr Glu Glu Ile Asn Ala
    210                 215                 220

Val Ile Glu Glu Asn Arg Lys Asn Phe Tyr Ile Asp Pro Asn Leu Ser
225                 230                 235                 240

Glu Glu Ser His Arg Tyr Ala Ala Arg Leu Gln Ile Gly Phe Lys Lys
                245                 250                 255

Phe Leu Ile Asn Lys Gly Tyr Asp Gly Phe Thr Ala His Phe Asp Val
```

```
                    260                 265                 270
Phe Lys Gly Asp Gly Arg Phe Lys Gln Ile Pro Met Met Ala Ala Ser
                275                 280                 285
Asn Leu Met Ala Glu Gly Tyr Gly Tyr Ala Ala Glu Gly Asp Ala Val
                290                 295                 300
Thr Ala Ser Leu Val Ala Ala Gly His Val Leu Ile Gly Asp Ala His
305                 310                 315                 320
Phe Thr Glu Met Tyr Ala Met Asp Phe Lys Arg Asn Ser Ile Leu Met
                325                 330                 335
Ser His Met Gly Glu Gly Asn Trp Lys Ile Ala Arg Lys Asp Arg Pro
                340                 345                 350
Ile Lys Leu Ile Asp Arg Glu Leu Gly Ile Gly Lys Leu Asp Asn Pro
                355                 360                 365
Pro Thr Ile Val Phe Met Ala Gln Pro Gly Pro Ala Thr Leu Val Ser
                370                 375                 380
Leu Val Ser Leu Glu Gly Glu Arg Tyr Arg Leu Val Val Ser Lys Gly
385                 390                 395                 400
Glu Ile Leu Asp Thr Glu Ala Lys Tyr Ile Glu Met Pro Tyr Phe
                405                 410                 415
His Phe Arg Pro Ser Thr Gly Val Lys Ala Cys Leu Asp Gly Trp Leu
                420                 425                 430
Thr Asn Gly Gly Thr His His Glu Cys Leu Asn Leu Gly Asp Asn Thr
                435                 440                 445
Arg Arg Trp Lys Ile Leu Cys Asn Leu Leu Asp Ile Glu Tyr Val Glu
                450                 455                 460
Val
465

<210> SEQ ID NO 13
<211> LENGTH: 1329
<212> TYPE: DNA
<213> ORGANISM: Artificial Sequence
<220> FEATURE:
<223> OTHER INFORMATION: Nucleotide coding sequence with optimized codon
      frequency

<400> SEQUENCE: 13
atgccatact tcgacaacat cagcacgatc gcttatgaag gcccggcttc taaaaacccg        60
cttgcattca aattctacaa ccctgaagaa aaagtgggag acaaaacaat ggaagaacac       120
cttcgtttct ctgttgctta ctggcacacg ttcactggtg acggttctga tccattcggt       180
gctggaaaca tgatccgtcc ttggaacaaa tacagcggca tggatttggc aaaagcacgc       240
gttgaagctg cttttgaatt cttttgaaaaa ctgaacatcc cattcttctg cttccacgat       300
gtggatatcg ctcctgaagg agaaacgctg aaagaaactt acaaaaacct tgatatcatc       360
gttgatatga tcgaagaata catgaaaaca agcaaaacaa aactttttgtg gaacactgca       420 aacctgttca ctcacccacg tttcgttcac ggtgctgcaa cttcttgtaa cgctgatgtg       480
tttgcttacg cagctgcaaa agtaaaaaaa ggtcttgaaa tcgcaaaacg tcttggtgct       540
gaaaactacg tattctgggg cggacgtgaa ggctatgaaa cattgctgaa cactgatatg       600
aaacttgaac ttgataaccct tgctcgtttc cttcacatgg ctgttgatta cgcaaaagaa       660
atcggcttcg acggacaatt cctgatcgaa ccaaaaccaa agaaccgac aaaacaccaa       720 tacgatttcg acgttgcaac tgctcttgca ttccttcaaa cgtacggatt gaagactac       780 ttcaaattca acatcgaagc aaaccacgca actcttgctg acacacgtt tgaacatgag       840
```

```
cttcgtgtgg ctcgtattca cggcatgctt ggttctgttg atgcaaacca aggtgacatg    900
ctgcttggct gggacactga tgaattccca actgatcttt attcaactac tcttgcaatg    960
tacgaaattt taaaaaacgg cggacttgga cgcggcggat taaacttcga tgcaaaagtg   1020
cgccgcggaa gctttgaacc tgaagatttg ttctacgctc acatcgctgg tatggacagc   1080
ttcgctgtag gtttgaaagt ggctcaccgc ctgatcgaag accgtgtatt cgatgaattc   1140
atcgaagaac gttacaaatc atacactgaa ggcatcggcc gtgaaatcgt tgaaggcact   1200
gttgatttcc acaaacttga agctcacgct cttcaattag gtgaaatcca aaaccaaagc   1260
ggacgtcaag aacgcctgaa aacgctttta accaatacc ttcttgaagt atgtgctgcg   1320
cgctaataa                                                          1329

<210> SEQ ID NO 14
<211> LENGTH: 1170
<212> TYPE: DNA
<213> ORGANISM: Artificial Sequence
<220> FEATURE:
<223> OTHER INFORMATION: synthetic coding sequence with optimized codon
      frequency

<400> SEQUENCE: 14
atgagctacc aaccaactcc agaagaccgt ttcacattcg gtttgtggac ggtaggctgg     60
caaggccgtg atccattcgg agatgcaact cgtcctgctc ttgatcctgt tgaaactgtt    120
caacgtcttg ctgaacttgg tgctcacggc gtaacgttcc acgatgatga tctgatccca    180
ttcggaagct ctgacactga acgtgaaagc cacatcaaac gtttccgtca agctcttgat    240
gcaactggta tgactgttcc aatggcaaca acaaacctgt tcactcaccc tgtattcaaa    300 gacgcggat tcactgcaaa cgaccgtgac gttcgtcgtt acgctcttcg caaaacgatc    360
cgcaacatcg atcttgctgt tgaacttggt gcaaaaacgt acgtggcttg ggcggacgt    420 gaaggcgctg aaagcggagc tgcaaaagat gtgcgtgtgg ctcttgaccg catgaaagaa    480
gcattcgatt tgcttggtga atacgtgact tctcaaggct acgatactcg tttcgcaatc    540
gaaccaaaac caaacgaacc acgcggagat attttgctgc caactgtagg acacgctctt    600
gcattcatcg aacgtcttga acgtcctgaa ctttacggtg taaaccctga agtgggacac    660
gaacaaatgg caggcctgaa ctcccacac ggtatcgctc aagctttgtg ggcaggaaaa    720
ctgttccaca ttgatttaaa cggacaaagc ggaatcaaat acgatcaaga tcttcgtttc    780
ggtgctggtg accttcgtgc tgctttctgg cttgttgatt tgcttgaatc tgctggttat    840
gaaggcccgc gtcacttcga cttcaaaccg ccgcgtactg aagatattga cggtgtttgg    900
gcttctgctg caggctgtat gagaaactat ttgatttaa aagaacgtgc tgctgctttc    960
cgtgctgatc ctgaagtgca agaagcactt cgtgcaagcc gtcttgatga actggctcaa   1020
ccaactgctg ctgacggcgt tcaagaactg cttgctgacc gtactgcttt tgaagatttc   1080
gacgttgatg ctgctgctgc acgcggtatg gcttttgaac gtcttgatca gcttgcaatg   1140
gaccaccttc ttggcgctcg tggataataa                                    1170

<210> SEQ ID NO 15
<211> LENGTH: 1401
<212> TYPE: DNA
<213> ORGANISM: Artificial Sequence
<220> FEATURE:
<223> OTHER INFORMATION: synthetic coding sequence with optimized codon
      frequency
```

```
<400> SEQUENCE: 15
atgcaaacga aaaaaaaacc gcaaatcggc ttccttggca tcatgcaaga actttacgat      60
gatatgcttc ctggaattac agaacgtcaa gaaaaatacg ctcgtgaagt gatcgaacaa     120
ttgcaagatg tggctgattt ccacttccca aaagcagcaa aaaccgtca  agatattgaa     180
catatcgtaa agaattcaa  cgaaaagat  cttgacggca tcatgatcgt gatgctgact     240
tacggaccgg caacaaacat cgtaaacgct ttcgcaaca  acaaacttcc aatcatgctt     300
gcaaacatcc aaccagtgcc gactgttact gaagactggg atatgggaga tttgacttac     360
aaccaaggtg ttcacggcgc tcaagacact gcaaacgcaa tccttcgcat gggtatcaaa     420
tgtccgatca tcactgaaga tggcacagc  gaagaattca aaaaattcgt tggtgactgg     480
gcaaaagctg ttcaaacgat caaagcactt cgcaacatga aaatcgctca attcggacgc     540
atgcacggta tgtacgatat ccttggagat gacgctgctt tcactcgtaa aatcggtcct     600
caaatcaacc aagaatacat cggtgaagtg taccgttaca tggaaacggc aactgaagaa     660
gaaatcaacg ctgttatcga agaaaaccgt aaaaacttct acatcgatcc aaaccttcct     720
gaagaaagcc accgttacgc tgctcgtctt caaatcggct tcaaaaaatt cctgatcaac     780
aaaggctatg acggcttcac tgctcacttc gatgtattca aggtgacgg  ccgtttcaaa     840
caaatcccaa tgatggctgc ttctaacctg atggctgaag ctacggata  cgctgctgaa     900
ggagatgctg taactgcttc tcttgttgct gctggacacg tgctgatcgg agatgctcac     960
ttcactgaaa tgtacgcaat ggatttcaaa cgcaacagca tttaatgtc  tcacatgggt    1020
gaaggaaact ggaaatcgc  tcgtaaagac cgtccaatca aactgattga ccgtgaactt    1080
ggcatcggaa aacttgataa cccgccgaca atcgtattca tggctcaacc aggtcctgct    1140
acgcttgttt ctcttgttc  tcttgaaggt gaacgttacc gtcttgttgt ttctaaaggt    1200
gaaatccttg atacagaaga agcaaaatac atcgaaatgc cttacttcca cttccgtcca    1260
agcactggtg tgaaagcatg ccttgacggc tggctgacga acggcggaac tcaccacgaa    1320
tgcctgaacc ttggagacaa cactcgccgc tggaaaatcc tttgcaacct tcttgatatt    1380
gaatacgttg aagtctaata a                                              1401

<210> SEQ ID NO 16
<211> LENGTH: 1329
<212> TYPE: DNA
<213> ORGANISM: Artificial Sequence
<220> FEATURE:
<223> OTHER INFORMATION: synthetic coding sequence with optimized codon
      frequency

<400> SEQUENCE: 16
atgccgtatt ttgataacat ttcaacaatc gcatacgaag gccctgcttc taaaaatcca      60
ttagcattca aattttataa cccggaagaa aaagttggag ataaaactat ggaagaacat     120
cttcgtttca gcgtggctta ctggcacacg tttacaggtg atggctcaga tcctttcgga     180
gcaggtaata tgattcgccc gtggaacaaa tattctggca tggatttggc taaagcaaga     240
gtagaagctg catttgaatt cttttgaaaaa ctgaatatcc cattcttttg tttccatgat     300
gttgatattg ctcctgaagg agaaacttta aagaaacgt  ataaaaacct tgatattatc     360
gtggatatga ttgaagaata catgaaaaca agcaaaacta aattgctgtg gaatacagca     420
aacttattta cgcatccgcg tttcgtacac ggtgctgcaa catcatgcaa tgctgatgtt     480
tttgcttatg ctgcagctaa agttaaaaaa ggccttgaaa tcgcaaaacg cttaggagct     540
```

```
gaaaactacg tgttctgggg tggcagagaa ggatatgaaa ctcttttgaa cacagatatg      600
aaactggaat tagataatct tgcacgtttt ttgcacatgg ctgtagatta tgcaaaagaa      660
attggtttcg atggccaatt tctgattgaa cctaaaccga agaaccaac taaacatcaa       720 tacgatttcg atgttgctac ggcattagct tttcttcaaa catacggatt aaaagattac      780
ttcaaattta acatcgaagc aaatcatgct actcttgcag gtcacacatt cgaacatgaa      840
ttgcgcgtgg ctagaattca tggcatgctg ggatctgttg atgcaaacca aggtgatatg      900
ttacttggct gggatacgga tgaatttcct acagatttat atagcactac acttgctatg      960
tatgaaatct tgaaaaatgg aggtctgggc cgtggaggtt aaacttcga tgcaaaagta     1020 cgccgtggct catttgaacc ggaagatctt ttctacgctc atattgcagg aatggattct     1080
tttgctgttg gtttgaaagt ggcacacaga ctgattgaag atcgcgtttt cgatgaattt     1140
atcgaagaac gttataaaag ctacacggaa ggcattggaa gagaaatcgt agaaggtact     1200
gtggatttcc ataaattaga agctcatgca cttcaattag gcgaaattca aaatcaatca     1260
ggacgccaag aacgtcttaa aacattgctg aaccaatatt tacttgaagt ttgtgctgca     1320
cgctaataa                                                            1329

<210> SEQ ID NO 17
<211> LENGTH: 1170
<212> TYPE: DNA
<213> ORGANISM: Artificial Sequence
<220> FEATURE:
<223> OTHER INFORMATION: synthetic coding sequence with optimized codon
      frequency

<400> SEQUENCE: 17
atgtcatatc aaccgactcc ggaagataga tttacttttg gcttatggac agttggctgg       60
caaggtagag atccgtttgg agatgctaca cgtccggcac tggacccggt agaaacagta      120
caacgtctgg cagaactggg agcacatggc gttactttc atgacgatga cttaattcca      180
tttggtagca gcgacactga agagaatca catattaaaa gatttagaca agcattagac      240
gctacaggta tgacagtgcc tatggctaca acaaatttgt ttacgcatcc tgttttaaa      300 gatggaggat ttacagctaa cgatagagat gttcgtagat atgcattaag aaaaacgatc      360
cgtaacatcg acttggcagt ggaactgggc gctaaaactt atgtagcatg gggaggcaga      420
gaaggcgctg aatctggtgc tgctaaagac gtgagagttg ctttagatag aatgaaagaa      480
gctttcgatc tgctgggaga atacgttact tctcaaggtt atgatacacg cttcgcaatt      540
gaacctaaac ctaatgaacc tcgcggtgat atcttattac ctacggtagg tcatgcatta      600
gctttcattg aacgtttgga aagaccagaa ttgtatggtg ttaatcctga agtgggacat      660
gaacaaatgg caggccttaa cttcctcat ggaatcgctc aagctctttg ggctggaaaa      720 cttttcata tcgatcttaa tggccaaagc ggcattaaat atgaccaaga tttgagattt      780
ggcgctggtg acttacgtgc tgcattttgg ttggttgact tgttgaaatc tgcaggctac      840
gaaggcccgc gtcactttga ctttaaacct ccgagaacgg aagatattga tggagtgtgg      900
gctagcgctg ctggatgtat gcgcaattat cttattctta aagaacgcgc agcagcattt      960
agagcagatc ctgaagttca agaagcttta cgcgcttcac gtttggatga attggctcaa     1020
cctacagctg cagacggagt gcaagaattg ttggctgatc gcacggcttt cgaagatttc     1080
gatgttgatg cagcagctgc tagaggtatg gctttcgaaa gattggacca attggctatg     1140
gatcatctgc tgggagctcg tggttaataa                                      1170
```

-continued

```
<210> SEQ ID NO 18
<211> LENGTH: 1170
<212> TYPE: DNA
<213> ORGANISM: Artificial Sequence
<220> FEATURE:
<223> OTHER INFORMATION: synthetic coding sequence with optimized codon
      frequency

<400> SEQUENCE: 18
atgtcttatc aacctactcc ggaagataga ttcacttttg gtctgtggac agtgggttgg      60
caaggtagag atcccttcgg cgatgcaacg cgcccggcat tagatcccgt agaaacagtg     120
caaagattag cagaattggg cgcacatgga gttacattcc acgacgacga ccttatcccg     180
tttggtagct cagatacaga acgcgaatca catattaaaa gattcagaca agcattggac     240
gcaacgggaa tgacagtacc tatggcaacg actaaccttt ttacgcaccc cgttttaaa     300 gatggtggat ttacagctaa tgatagagat gttcgtagat atgctcttag gaaaactatt     360
agaaatatcg atctggcagt ggaattggga gctaaaacat acgtagcatg gggtggtcgc     420
gaaggagcag aatctggagc agctaaagat gttagagtag cactggatag aatgaaagaa     480
gctttcgatt tattgggcga atatgttact agtcaaggtt acgacacaag atttgctatc     540
gaacccaaac ctaatgaacc tcgtggcgat attctgttgc caacggtggg tcatgcatta     600
gctttcatag aaagattaga aagacctgaa ttatatggag ttaatcctga agttggtcat     660
gaacaaatgg ctggcttgaa ctttccacat ggaatagctc aagcactgtg ggctggcaaa     720 cttttttcaca tagaccttaa tggccaatca ggaattaaat acgaccaaga cttacgcttt     780
ggagctggcg acttgagagc tgcattttgg ttggtggact tattggaaag cgctggctac     840
gaaggcccta gacattttga ttttaaacca ccgcgtaccg aagatattga tggagtttgg     900
gctagcgcag ctggttgcat gaggaactac ttaatactta aagaaagagc tgcagcattc     960
agagccgacc cggaagtaca agaagcccctt agagcatcac gattggacga attagctcaa    1020
ccgaccgcag cagatggagt gcaagaatta ttagctgatc gcacagcatt tgaagatttc    1080
gatgttgacg cagcagcagc tagaggcatg gccttcgaac gtctggatca actggcaatg    1140
gatcatctgt tgggcgcacg gggataataa                                      1170
```

METHOD FOR ACHIEVING IMPROVED POLYPEPTIDE EXPRESSION

This application is the U.S. national phase under 35 U.S.C. 371 of International Application No. PCT/EP2007/055943, filed 15 Jun. 2007, which designated the U.S. and claims priority to Europe Application No. 06076328.1, filed 29 Jun. 2006; the entire contents of each of which are hereby incorporated by reference.

FIELD OF THE INVENTION

The present invention relates to a method for producing a polypeptide in a host cell, wherein the nucleotide sequences encoding the polypeptide have been modified with respect to their codon-usage, in particular the codon-pairs that are used, to obtain improved expression of the nucleotide sequence encoding the polypeptide and/or improved production of the polypeptide.

BACKGROUND OF THE ART

The present invention relates to improved methods for producing polypeptides. Numerous approaches have been applied in generating strains for protein over-expression and/or production. This includes, but is not limited to, making strains with multi-copies of the gene encoding the protein of interest (POI) and applying strong promoter sequences.

Each specific amino acid is encoded by a minimum of one codon and a maximum of six codons. Prior research has shown that codon usage in genes encoding the cell's polypeptides is biased among species (Kanaya, S, Y. Yamada, Y. Kudo and T. Ikemura (1999) Studies of codon usage and tRNA genes at 18 unicellular organisms and quantification of *Bacillus subtilis* tRNAs: gene expression level and species-specific diversity of codon usage based on multivariate analysis. *Gene* 238:143-155). Prior publications disclose optimization of codon use in a given host cell to improve polypeptide production (as example see WO 97/11086). More specifically, WO 03/70957 describes optimized codon use in filamentous fungi for producing plant polypeptides. In all these cases of 'classic' codon optimization, a native codon has been substituted by the most frequent codon from a reference set of genes, whereas the rate of codon translation for each amino acid is designed to be high (optimized).

More recently, in WO 03/85114 a harmonization of codon use was described which takes into effect the distribution of all codons in genes of the host organism, assuming that these effect protein folding.

The availability of fully sequenced genomes of many organisms in recent years, e.g. *Bacillus subtilis* (Kunst et al. 1997), *Bacillus amiloliquefaciens, Aspergillus niger* (Pel et al., 2007, Nat Biotech. 25: 221-231), *Kluyveromyces lactis, Saccharomyces cerevisiae*, various plant genomes, mouse, rat and human, has offered the possibility of analyzing different aspects of the gene sequences themselves in relation to their natural expression level (mRNA or protein level). A good example is codon usage (bias) analysis, and subsequent single-codon optimization. Note that single-codon optimization is herein understood to refer to codon optimization or codon harmonization techniques that focus on the optimization of codons as single independent entities, in contrast to codon-pair optimization, which is the topic of the current invention.

Whereas single-codon usage (bias) has been studied extensively before (for an overview, see Gustafsson et al., 2004, Trends Biotechnol. 22:346-353), there are only a few reports on codon pair usage and for optimization of codon-pairs.

The effect of a few specific codon-pairs on ribosomal frameshifts in *E. coli* has e.g. been investigated for the AGG-AGG codon-pair (Spanjaard and van Duin, 1988, Proc. Natl. Acad. Sci. USA 85:7967-7971; Gurvich et al., 2005, J. Bacteriol. 187:4023-432), and for UUU-YNN sites (Schwarz and Curran, 1997, Nucleic Acids Res. 25:2005-2011).

Gutman and Hatfield (1989, Proc. Natl. Acad. Sci. USA 86:3699-3703) analyzed a larger set of sequences for all possible codon pairs for *E. coli* and found that codon pairs are directionally biased. In addition, they observed that highly underrepresented pairs are used almost used twice as frequently as overrepresented ones in highly expressed genes, whereas in poorly expressed genes overrepresented pairs are used more frequently. U.S. Pat. No. 5,082,767 (Hatfield and Gutman, 1992) discloses a method for determining relative native codon pairing preferences in an organism and altering codon pairing of a gene of interest in accordance with said codon pairing preferences to change the translational kinetics of said gene in a predetermined manner, with examples for *E. coli* and *S. cerevisiae*. However, in their method, Hatfield and Gutman only optimize individual pairs of adjacent codons. Moreover, in their patent (U.S. Pat. No. 5,082,767), it is claimed to increase translational kinetics of at least a portion of a gene by a modified sequence in which codon pairing is altered to increase the number of codon pairs that, in comparison to random codon pair usage, are the more abundant and yet more under-represented codon pairs in a organism. The present invention discloses a method to increase translation by a modified sequence in which codon pairing is altered to increase the number of codon pairs that, in comparison to random codon pair usage, are the more over-represented codon pairs in an organism.

Moura et al. (2005, Genome Biology, 6:R28) analyzed the entire *S. cerevisae* ORFeome but did not find a statistically significant bias for about 47% of the codon pairs. The respective values differed from one species to another, resulting in "codon context maps" that can be regarded as "species-specific fingerprints" of the codon pair usage.

Boycheva et al. (2003, Bioinformatics 19(8):987-998) identified two sets of codon pairs in *E. coli* referred to as hypothetically attenuating and hypothetically non-attenuating by looking for over- and under-represented codon pairs among genes with high and poor expression. However, they do not propose a method to apply this finding, nor gave any experimental prove for their hypothesis. Note that these groups are defined completely opposite to the ones defined by Gutman and Hatfield (1989, 1992, supra), who proposed a non-attenuating effect for highly underrepresented pairs in highly expressed genes.

Buchan, Aucott and Stanfield (2006, *Nucleic Acids Research* 34(3):1015-1027) analyzed tRNA properties with respect to codon pair bias.

As for the implications of biases in codon pair utilization, Irwin et al. (1995, J. Biol. Chem. 270:22801-22806) demonstrated in *E. coli* that the rate of synthesis actually decreased substantially when replacing a highly underrepresented codon pair by a highly overrepresented one and increased when exchanging a slightly underrepresented codon pair for a more highly underrepresented. This is quite remarkable as it is rather the opposite of what one would expect given the influence of single codon bias on protein levels.

However, none of the above-cited art discloses how to optimize the codon-pair usage of a full-length codon sequence taking account of the fact that by definition codon pairs overlap and that therefore optimization of each individual codon pair affects the bias of the overlapping up- and downstream codon pairs. Moreover, none of the cited art discloses a method that combines optimization of both single codons as well as codon pairs. Codon pair optimization taking into account said codon pair overlapping and optional combination of said codon-pair optimization with single-codon optimization would greatly improve expression of the nucleotide sequence encoding the polypeptide of interest and/or improve production of said polypeptide.

There is thus still a need in the art for novel methods for optimization of coding sequences for improving the production a polypeptide in a host cell.

SUMMARY OF THE INVENTION

An object of the present invention is to provide a method for optimizing the coding sequence for efficient gene transcription and protein translation. To that effect, the invention provides a method of optimization of a nucleotide sequence encoding a predetermined amino acid sequence, whereby the coding sequence is optimized for expression in a predetermined host cell, the method comprising: (a) generating at least one original coding sequence that codes for the predetermined amino acid sequence; (b) generating at least one newly generated coding sequence from this at least one original coding sequence by replacing in this at least one original coding sequence one or more codons by a synonymous codon; (c) determining a fitness value of said at least one original coding sequence and a fitness value of said at least one newly generated coding sequence while using a fitness function that determines at least one of single codon fitness and codon pair fitness for the predetermined host cell; (d) choosing one or more selected coding sequence amongst said at least one original coding sequence and said at least one newly generated coding sequence in accordance with a predetermined selection criterion such that the higher is said fitness value, the higher is a chance of being chosen; and (e) repeating actions b) through d) while treating said one or more selected coding sequence as one or more original coding sequence in actions b) through d) until a predetermined iteration stop criterion is fulfilled.

In embodiments, the invention addresses aspects like single codon usage, codon harmonization, dinucleotide usage, and related to that codon-pair bias. The method can be performed by a computer program running on a computer that uses a mathematical algorithm for sequence analysis and sequence optimization that may be implemented in MAT-LAB.

In addition to positive codon optimization (e.g. for modulation of gene expression and protein production in a positive way), the invention also provides a method for adapting codons towards "bad" codon pairs (i.e. negative codon-pair optimization). The latter method is useful for control purposes as well as for modulating gene expression in a negative way.

BRIEF DESCRIPTION OF THE DRAWINGS

It is observed that the present invention will be illustrated with reference to several figures which are only intended to illustrate the invention and not to limit its scope which is defined by the annexed claims and its equivalents.

FIG. 5 shows a codon bias map for *A. niger*. The bias values range from −0.67 to 0.54, where in other organisms they might even get slightly above +−0.9 (see also FIG. 3). The highest intensities of black in these diagrams represent values of 0.9 (FIGS. 5A and 5C for the positive values, green in the original) and −0.9 (FIGS. 5B and 5D for the negative values, red in the original).

FIG. 6 shows a codon bias map for *B. subtilus*. The bias values range from −0.97 to 0.87, where in other organisms they might even get slightly above +−0.9 (see also FIG. 3). The highest intensities of black in these diagrams represent values of 0.9 (FIG. 6A for the positive values, green in the original) and −0.9 (FIG. 6B for the negative values, red in the original).

FIG. 12 shows two diagrams that show the sequence quality of the first 20 (out of 499) codons of the aforementioned FUA (see also Example 2). The black dots indicate the desired codon ratios, whereas the x-marks show the actual ones (in the whole gene), connected via a dashed line. Single codon fitness can then be interpreted as the average of the lengths of these dashed lines (note that for codons where desired and actual ratio are equal, as for example TGG (which has no synonymous codons) on position 4 and 5, this "length" is zero; note also that "length" can never be negative). The black bars, in turn, show the weights of the pair formed by the two adjacent codons. The black dots (in the middle, below the bars) indicate the minimum weight of any codon pair that encodes the same dipeptide. The codon pair fitness is then the average height of these bars (note that height as used here can well be negative).

FIG. 21 also provides a representative map for plasmid pGBFINFUA-2 and pGBFINFUA-3. All clones originate from the pGBFIN-12 (described in WO99/32617) expression vector. Indicated are the glaA flanking regions relative to the variant sequences of the amyB promoter and the A. niger amyB cDNA sequence encoding alpha-amylase. The E. coli DNA can be removed by digestion with restriction enzyme NotI, prior to transformation of the A. niger strains.

DETAILED DESCRIPTION OF THE INVENTION

Figure 1:
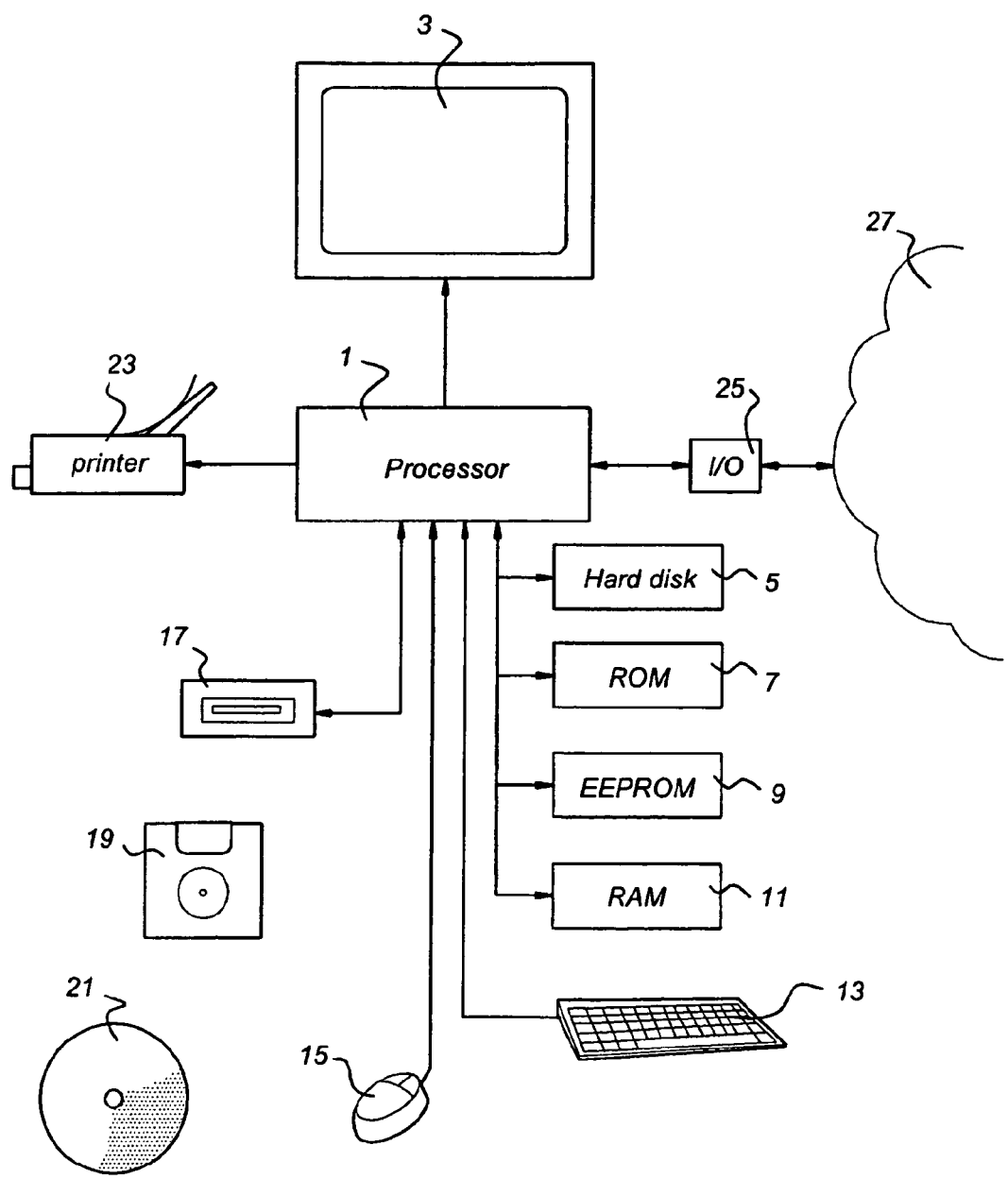
FIG. 1 shows a computer arrangement on which the method of the invention can be performed.

In addition to single codon bias, other structures in the nucleotide sequence are likely to influence protein expression as well, e.g. dinucleotides or repeats of certain short nucleotide sequences (codon usage after all can be interpreted as a pattern in tri-nucleotide sequences in line with the reading frame). This work presents a method for identifying a preference for certain codon pairs, i.e. whether codons appear in the gene as if they were selected according to the identified codon usage ratios, but then distributed randomly in the gene (with respect to the amino acid sequence), or whether some codons appear more often next to certain codons and less often next to others.

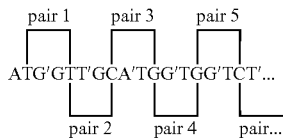

An analysis of codon pairs also covers other aspects, namely dinucleotide usage around the reading frame borders and a possible preference for certain single nucleotides next to a codon. The present invention discloses methods for generating a codon-pair bias table for a given host organism whereby either all identified ORFs of sequenced full genomes are used as input or selected groups of genes, e.g. highly expressed genes. The present invention discloses a method wherein a codon-pair bias table thus identified is subsequently applied for optimization of codon-pair distribution in a gene of interest (GOI) for improving the expression of the corresponding protein of interest (POI).

Single codon optimization offers a good starting point for improving expression levels of proteins of interest. Whereas others tried to overcome drawbacks resulting from the presence of rejected codons in the gene of interest by adaptation of the host organism, inserting additional copies of tRNA genes for tRNAs with low abundance (e.g. Stratagene BL-21 CodonPlus™ competent cells, Novagen Rosetta™ host strains, both *E. coli*), the present inventors have focused on the adaptation of the genes of interest themselves. Unwanted codons in a genetic sequence have been replaced by synonymous ones so that the single codon distribution of the resulting sequence was as close as possible to previously identified desired codon ratios.

This codon harmonization, however, still has a very large number of possible genes that are equally "optimal" since the overall codon distribution in an optimized gene is the selection criterion, so further desired properties of the codon sequence can easily be taken into account, for example the absence of certain enzyme's restriction sites or codon pairs known to cause frameshifts. One step further, one could optimize codon pair usage to a limited extent. But when optimizing codon pairs of a gene, e.g. towards the usage of the most abundant ones, the single codon usage of the resulting sequence might not be close to the optimum, since there might be preferred codon pairs consisting of underrepresented single codons, so a balance between single codon and codon pair optimization must be found. The present invention discloses methods that allow balancing both single codon and codon pair optimization. Codon pair optimization taking into account codon pair overlapping and optional combination of said codon-pair optimization with single-codon optimization greatly improve expression of the nucleotide sequence encoding the polypeptide of interest and/or improve production of said polypeptide.

In the context of this invention, a nucleotide coding sequence or coding sequence is defined as a nucleotide sequence encoding a polypeptide. The boundaries of the coding sequence are generally determined by the start codon (usually ATG in eukaryotes, while it can be one of ATG, CTG, GTG, TTG in prokaryotes) located at the beginning of the open reading frame at the 5' end of the mRNA and a stop codon (generally one of TAA, TGA, TAG, although exceptions to this 'universal' coding exists) located just downstream of the open reading frame at the 3' end of the mRNA. A coding sequence can include, but is not limited to, DNA, cDNA, RNA, and recombinant nucleic acid (DNA, cDNA, RNA) sequences (note that it is well known in the art that Uracil, U, replaces the deoxynucleotide Thymine, T, in RNA). If the coding sequence is intended for expression in a eukaryotic cell, a polyadenylation signal and transcription termination sequence will usually be located 3' to the coding sequence. A coding sequence comprises a translational initiator coding sequence, and optionally a signal sequence, and optionally one or more intron sequences. Even though the terms "coding sequence" and "gene" strictly do not refer to the same entity, both term are frequently used interchangeably herein and the skilled person will understand from the context whether the term refers to a full gene or only its coding sequence.

Method and Computer Arrangement for Single Codon and/or Codon Pair Adaptation

As for the single codon usage properties of highly expressed genes, a "manual" comparison of single codon ratios in all genes and a group of highly expressed ones has lead to some "desired codon ratios" for the improvement of genes with respect to their expression level.

Single codon adaptation of a gene can then be performed by: (1) calculating the actual ratios in the gene, repeatedly picking a codon (e.g. randomly) whose desired ratio is lower than the actual one and replacing it by a synonymous one with a too low ratio; or (2) calculating the desired number of each codon using the "desired codon ratios", making groups of synonymous codons, and repeatedly picking a codon (e.g. randomly) from a synonymous group coding for the pre-specified amino acid, for each position in the gene; making multiple variants using method (1) and/or (2) and based on additional selection criteria picking the most relevant gene (e.g. wanted and unwanted restriction sites and/or folding energy).

Yet this approach is not suitable for codon pair adaptation, firstly because visual inspection of bias data for all codon pairs is out of the question in view of the complexity and secondly because altering of one codon pair, which means replacing at least one of the two participating codons, will also affect at least one of the adjacent codon pairs, so "desired codon pair ratios" would be unachievable. Because of the constraints implied by this, a deterministic approach was considered too complex and not promising enough and a "genetic algorithm" approach was then chosen.

It is observed that the term "genetic algorithm" may be confusing in the sense that it seems to relate to genetic engineering. However, a "genetic algorithm" is an approach from computer science that is used to approximate solutions to multidimensional optimization problems (Michalewicz, Z., Genetic Algorithms+Data Structure=Evolution Programs, Springer Verlag 1994; David E. Goldberg. Genetic Algorithms in Search, Optimization and Machine Learning. Addison-Wesley, Reading Mass., 1989. In the present invention, this approach is used in solving the optimization problem of selecting the "best" possible gene, i.e. coding sequence for a particular protein of interest. In this approach, each position in the gene, i.e. each codon can be considered one dimension, with the set of values being discrete and determined by the available synonymous codons.

Generally, in a genetic algorithm, at first a set of possible "solutions" to the problem is often generated randomly, or by variations on initial provided solutions (although many other methods approaches exist). This set is called "population"; its elements are "individuals" or "chromosomes", mostly represented by vectors (in the mathematical sense) containing coordinates for each dimension. Since genetic algorithms were modeled after processes involved in natural selection, much of the terminology is borrowed from genetics. However, since they are (unlike in this case) mostly applied in the field of computer science and to, but also some example to application of genetic algorithms in biological science problems have been presented, e.g. for protein secondary structure prediction (Armano et al. 2005 BMC Bioinformatics 1(6) Suppl. 4:S3); in silico metabolic network optimization (Patil et al. 2005 *BMC Bioinformatics.* 23(6):308); clustering gene expression data (Di Gesu et al. 2005 BMC Bioinformatics. 7(6):289).

In the present case, a vector contains codons. From that population, new individuals are created by altering certain positions of an existing individual ("mutation") or by combining a part (i.e. certain coordinates) of an individual with another part (i.e. the coordinates for the other dimensions) from another individual ("crossover"). It is then examined how good these individuals are (since the new ones are also possible solutions to the initial optimization problem) and the better ("fittest") of the individuals are taken again as initial population for generating new individuals ("next generation"; e.g., the best 10, 20, 30, 40, 50, 60% are kept, but many other possibilities exist to selecting a subset for offspring for obtaining a convergence toward fitter individuals, e.g. roulette wheel selecting, see Michalewicz, Z, 1994). When allowing the best individual from the initial population to be taken over to the next generation, it is ensured that with every population the quality of the possible solutions gets better or at least stays the same. It is then assumed that with a run of this algorithm for many generations (=iterations; some hundred to several thousand, depending on the complexity of the problem) one will get a solution close to the optimum. Genetic algorithms have been investigated closely in computer science, including properties such as optimal proportion of population size and number of generations, how to prevent the algorithm from getting stuck in local optima etc., but this should not matter much here now. For information on how to set these parameters for the actual optimization procedure, see the description implemented genetic algorithm in MATLAB in Example 2.

Figure 2:
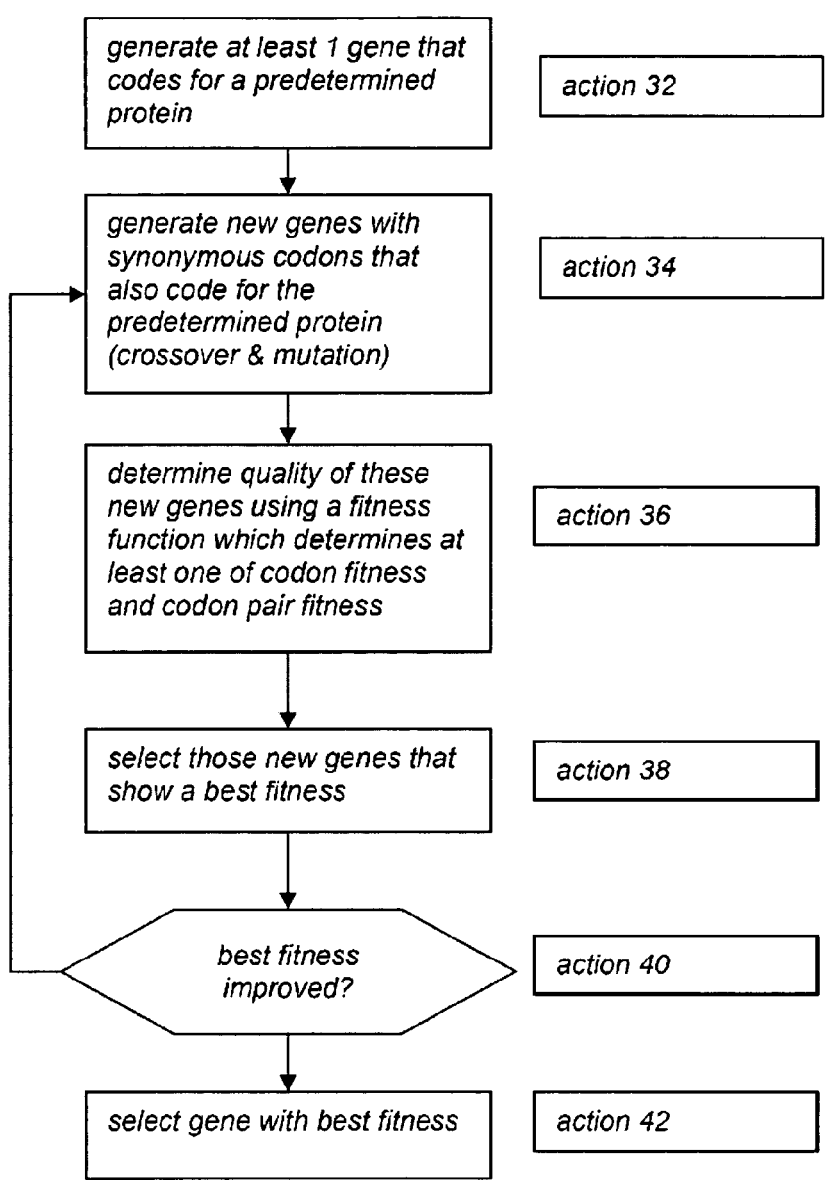
FIG. 2 shows a flow chart of an embodiment of the invention.

This will be explained in detail with reference to FIG. 2. FIG. 2 shows a flow chart of a genetic algorithm for gene optimization. Such a genetic algorithm can be performed on a suitably programmed computer, an example of which will be shown in and explained first with reference to FIG. 1. FIG. 1 shows an overview of a computer arrangement that can be used to carry out the method according to the invention. The arrangement comprises a processor 1 for carrying out arithmetic operations.

Note that genetic algorithms are generally non-deterministic as they involve randomized steps (e.g. randomized selection criteria and/or randomized operator choice and/or randomized generation of potential solutions), however, exceptions exist that perform in a deterministic way. "Genetic algorithms" is a generic tool for those algorithms that deal with a group (called population) of potential solutions, which is by screening and/or selection and/or removal, and/or (re) introduction of (newly) generated solutions driven toward and optimal solution by using one or multiple objectives. Considering this definition, also methods described as evolutionary programming, evolutionary algorithms, classic genetic algorithms, real-coded genetic algorithms, simulated annealing, ant algorithms, and also Monte-Carlo and chemotaxis methods, belong to a similar class of algorithms, opposite to methods that are based on the convergence of a single potential solutions toward an optimal solution using a deterministic algorithm, like linear programming and gradient algorithms. Furthermore, a skilled person will understand from the context whether another original term refers to the same class of algorithms. Moreover, although a genetic algorithm is the preferred method, we do not exclude any other method than genetic algorithms for solving the single-codon and/or codon-pair optimization problem as described within this invention.

The processor 1 is connected to a plurality of memory components, including a hard disk 5, Read Only Memory (ROM) 7, Electrically Erasable Programmable Read Only Memory (EEPROM) 9, and Random Access Memory (RAM) 11. Not all of these memory types need necessarily be provided. Moreover, these memory components need not be located physically close to the processor 1 but may be located remote from the processor 1.

The processor 1 is also connected to means for inputting instructions, data etc. by a user, like a keyboard 13, and a mouse 15. Other input means, such as a touch screen, a track ball and/or a voice converter, known to persons skilled in the art may be provided too.

A reading unit 17 connected to the processor 1 is provided. The reading unit 17 is arranged to read data from and possibly write data on a data carrier like a floppy disk 19 or a CDROM 21. Other data carriers may be tapes, DVD, memory sticks etc. as is known to persons skilled in the art.

The processor 1 is also connected to a printer 23 for printing output data on paper, as well as to a display 3, for instance, a monitor or LCD (Liquid Crystal Display) screen, or any other type of display known to persons skilled in the art.

The processor 1 may be connected to a communication network 27, for instance, the Public Switched Telephone Network (PSTN), a Local Area Network (LAN), a Wide Area Network (WAN), etc. by means of I/O means 25. The processor 1 may be arranged to communicate with other communication arrangements through the network 27.

The data carrier 19, 21 may comprise a computer program product in the form of data and instructions arranged to provide the processor with the capacity to perform a method in accordance with the invention. However, such computer program product may, alternatively, be downloaded via the telecommunication network 27.

The processor 1 may be implemented as stand alone system, or as a plurality of parallel operating processors each arranged to carry out subtasks of a larger computer program, or as one or more main processors with several sub-processors. Parts of the functionality of the invention may even be carried out by remote processors communicating with processor 1 through the network 27.

Now the genetic algorithm of FIG. 2 will be explained, as may be performed on processor 1 when it runs a computer program stored in its memory.

In action 32 the computer generates one or more genes that code for a predetermined protein. This can be done by taking data to that effect from a table stored in the memory of the computer. Such genes may e.g. be:

```
ATG'GTT'GCA'TGG'TGG'TCT' . . .

ATG'GTA'GCA'TGG'TGG'TCA' . . .

. . .
```

For the purpose of the algorithm, these generated genes are termed "original genes".

After action 32, the computer program performs one or more iteration loops by performing actions 34-40 one or more times.

In action 34, the computer program generates new genes by replacing one or more of the codons in the original gene(s) by synonymous codons such that the newly generated gene(s) still code for the predetermined protein (crossover & mutation process). To be able to do so, the memory of the computer stores a codon usage table which shows which codons code for which amino acids. (Note that deviations from the "universal code" exist and are taken into account if this is the case for the specified host organisms, see for example Laplaza et al., 2006, Enzyme and Microbial Technology, 38:741-747). Knowing the sequence of amino acids in the protein, the computer program can select alternative codons from the table as are well known in the art.

Using the example of action 32, the newly generated genes may be (indicated in bold):

```
ATG'GTT'GCA'TGG'TGG'TCT' . . .

ATG'GTA'GCA'TGG'TGG'TCA' . . .

ATG'GTT'GCA'TGG'TGG'TCA' . . .

ATG'GTA'GCA'TGG'TGG'TCA' . . .

ATG'GTA'GCC'TGG'TGG'TCA' . . .
```

In action 36, a quality value of all genes including the original and the newly generated genes is determined by the computer program using a fitness function which determines at least one of codon fitness and codon pair fitness. Examples of such fitness functions will be explained in detail below in the section "Performing codon pair optimization".

In action 38, a number of genes showing a best fitness based on the fitness function are selected for taking part in the "breeding process" (crossover and mutation), and a number of genes showing worst fitness based on the fitness function are selected for removal from the population. These numbers may be predetermined numbers or depend on a predetermined amount of improvement of fitness. The selection of those genes might be deterministic, but generally a stochastic process is followed where the "fittest genes" having a higher change for being selected for breeding, and the opposite for deletion from the population. This method is called roulette-wheel selection.

The resulting selected genes for breeding may e.g. be (non-selected genes are shown with a deletion line):

```
ATG'GTT'GCA'TGG'TGG'TCT'...

ATG'GTT'GCA'TGG'TGG'TCA'...
```

In action 40, the computer program tests whether one or multiple termination criteria are fulfilled. Often one of the termination criteria is a predetermined maximum number of iterations. Alternative criteria are checking if the fitness obtained by the selected genes is improved with at least a minimum threshold value relative to the fitness of the original genes, or checking if the fitness obtained by the selected genes is improved with at least a minimum threshold value relative to the fitness of the gene with had best fitness n iterations ago (preferably n is a value in <10,100> is chosen). If the overall termination coterie is not fulfilled the computer program jumps back to action 34 while treating the selected genes as "original genes".

If, in action 40, the computer program establishes that the improvement is below the minimum threshold value further iteration of the actions 34-38 does not make much sense and the computer program continues with action 42.

It is to be understood that any other suitable iteration stop criterion, like the number of iterations performed, can be used in action 40 to leave the iteration actions 34-40 and continue with action 42.

In action 42, the gene with the best fitness amongst all selected genes is selected and presented to the user, e.g. via the monitor or via a printout by means of printer.

In the case of gene adaptation using a genetic algorithm, it has to be assured that the crossover is always performed at a reading frame position, because otherwise the resulting amino acid sequence might be changed when combining one nucleotide of one and two nucleotides of another codon. For better convergence, a modified mutation operator is proposed that for this mutation operator only those synonymous codon replacements have been allowed that result in at least one of better single codon or better codon pair usage.

So an important question for codon pair optimization now is how to measure the quality of the individuals. This so-called fitness function can be regarded the central part of the genetic algorithm, since it is the actual function to be optimized. In the present invention, a preferred approach is to assign a real number (called weight) to each codon pair and take the average of the weights in a gene as its "fitness", thus resulting in a function to be minimized.

It the current description, the inventors describe the process of gene optimization as a minimization problem. This is a rather arbitrarily approach. Note that, if a function $f$ were to be maximized, one could as well look for the minimum of $-f$, so this is no restriction to generality.

Hence, a method for determining codon pair weights has to be identified, where codon pairs considered good for expression level have a low weight and pairs considered bad a high one.

Identification of Codon Pair Weights for Gene Adaptation

For identification of codon pair weights that relate to a higher transcription/expression level, and which may serve as input for adaptation of codon pair usage, the following methods may be applied, which are herein exemplified by *A. niger*, for which a transcription levels for most of the expressed genes are known, and for *B. subtilis*, for which data on transcription levels was available and also a set of 300 highly expressed genes.

In *A. niger*, where a complete ranking extracted from GeneChip data was available for the aforementioned set of 4,584 actually expressed genes (see Example 1), the mean codon pair weights of each gene (i.e. the equivalent of the $fit_{cp}(g)$ values) were calculated. Then the genes were sorted according to fitness values (ascending order) and expression level (descending order). Since highly expressed genes are supposed to have low codon pair fitness values, these two rankings would be equal when using ideal codon pair weights, so a comparison of these two rankings can give information about the quality of the weights used in the fitness function (where slightly more attention was given to the "correct" ranking of the highly expressed genes than to the ranking of the mediocre ones). Additionally, the correlation coefficient (covariance divided by the standard deviation of each variable) between ranking and average codon pair weights of the 4,584 genes was calculated.

Several possible sets of weights may be used in the methods of the invention, including on or more selected from the group consisting of: (i) bias values from the whole genome; (ii) bias values from a group of highly expressed genes; (iii) bias with all the values that do not have a certain minimum z-score set to zero (whereby the z-score is determined as described in Example 1.1.4); (iv) bias values raised to the power of 2 or 3, 4, 5 or higher (to give highly preferred or rejected codons a lower/higher influence); (v) z-scores themselves; (vi) difference of bias values/z-scores from the highly expressed group and the full genome; and, (vii) combinations of one or more of (i)-(vi).

For the genetic algorithm, their negations have been used, since preferred codon pairs had been arbitrarily identified with positive values, whereas the genetic algorithm performs minimization. This applies to all the above-mentioned weights.

A more preferred weight matrix may be obtained—as described above—by calculating the codon pair "bias" in a highly expressed group using expected values calculated based on the codon ratios of the whole genome. Let $r_{sc}^{all}(c_k)$ still denote the single codon ratio of $c_k$ in the whole genome data set and $n_{obs}^{high}((c_i,c_j))$ the occurrences of a pair $(c_i,c_j)$ in the highly expressed group, then the calculation of the "combined expected values" $n_{exp}^{combi}((c_i,c_j))$ corresponds to $$n_{exp}^{combi}((c_i, c_j)) = r_{sc}^{all}(c_i) \cdot r_{sc}^{all}(c_j) \cdot \sum_{\substack{c_k \in syn(c_i) \\ c_l \in syn(c_j)}} n_{obs}^{high}((c_k, c_l))$$

and thus $$w((c_i, c_j)) = \frac{n_{exp}^{combi}((c_i, c_j)) - n_{obs}^{high}((c_i, c_j))}{\max(n_{obs}^{high}((c_i, c_j)), n_{exp}^{combi}((c_i, c_j)))}.$$

Where $w((c_i,c_j))$ is defined as a weight of a codon pair $(c_i,c_j)$ in a sequence g of codons. Note that since the optimization function will look for a minimum average weight, the two terms of the numerator have been reversed compared to the equation for the bias values, but this does not affect the correlation with the expression levels other than that it changes the sign.

Unlike all other weight sets tested, codon pairs involving codons that are more underrepresented in the highly expressed group get a slight disadvantage here. Thus, these weights are the only ones that also reflect the different single codon bias of the highly expressed group and all genes. Using these weights carries the risk of rejecting some codon pairs that actually have a positive bias in the highly expressed group, but consist of (in the highly expressed group) rarely used codons. However, since our desired single codon ratios are usually not identical to those in the group of genes with high expression, but more "extreme" than these, single codon optimization would replace these underrepresented anyway, so we can consider the weights described above very convenient for codon pair optimization. Thus, although the codon pair weights also reflect single codon bias to a limited extend, for the optimization, single codon usage is regarded as a separate, additional issue.

Optimization of Single Codons and Codon Pairs Using a Genetic Algorithm

In the method of the invention preferably a computer arrangement programmed to perform a genetic algorithm as described herein above is used to perform codon pair adaptation or combined single codon and codon pair adaptation have been performed. Applying a genetic algorithm for single codon adaptation is also possible and not excluded from the invention, but here undesired codons can be replaced by synonymous codons without constraints with respect to neighboring codons and therefore using a genetic algorithm is not really necessary.

As for codon pairs, changing a single codon will usually alter the weight of two codon pairs, and therefore codon pair optimization is heavily constrained because a single codon change replacing an unwanted codon pair will always change another codon pair, and this is not necessarily a change for the better, and correcting a change for the worse in an adjacent codon pair will then again alter another pair, and so on.

For the mutation operator, only those alterations of the codon sequence have been allowed that did not change the encoded peptide sequence and that improved at least one of single codon fitness and codon pair fitness, i.e. before changing a codon the mutation operator looks for synonymous codons that are either underrepresented (according to the desired single codon ratios) or one where the two codon pairs it is involved in have better weights. It is selected randomly which one of the two types of mutation is performed. Performing the former "mutation" operator on every single codon is sufficient for creating a single-codon-optimized gene without any use of the genetic algorithm.

The quality of a gene is determined considering two aspects, namely single codon "fitness" and codon pair "fitness". The latter is simply the average of the weights $w((c(k), c(k+1))$ of all codon pairs in a sequence g of codons (or gene). I.e., when g again symbolizes the sequence of codons, |g| its length (in codons) and c(k) its k-th codon:

$$fit_{cp}(g) = \frac{1}{|g|-1} \cdot \sum_{k=1}^{|g|-1} w((c(k), c(k+1))).$$

Single codon fitness is defined to be the difference of the actual codon ratios in the gene and the target codon ratios, normalized for the number of occurrences of every codon. Single codon ratios are defined and may be determined as described in Example 1.1.2 herein. Let $r_{sc}^{target}(c(k))$ be the desired ratio (or frequency) of codon $c_k$ and $r_{sc}^{g}(c(k))$ as before the actual ratio in the gene g, then the single codon fitness is defined as $$fit_{sc}(g) = \frac{1}{|g|} \cdot \sum_{k=1}^{|g|} |r_{sc}^{target}(c(k)) - r_{sc}^{g}(c(k))|.$$

Thus, $fit_{sc}$ can reach values in [0,1] with the optimal sequence being close to 0, whereas $fit_{cp}$ is limited by the weights, which here are also in [−1,1].

To optimize for both aspects, in an embodiment, a combined fitness function has been introduced:

$$fit_{combi}(g) = \frac{fit_{cp}(g)}{cpi + fit_{sc}(g)}.$$

Here, cpi, which stands for "codon pair importance", is a real value greater than zero and determines which of the two fitness functions has more influence on the combined fitness. With cpi close to zero, the denominator approaches zero when $fit_{sc}(g)$ gets better (i.e. also close to zero) and thus small changes in $fit_{sc}(g)$ influence $fit_{combi}(g)$ more than small changes in $fit_{cp}(g)$, whereas with a high cpi slight improvements in $fit_{cp}(g)$ may have a larger effect on $fit_{combi}(g)$ than medium improvements in $fit_{sc}(g)$. Note that $fit_{combi}$ values that are obtained using different values of cpi are not comparable (cpi close to 0 might result in $fit_{combi}$ values close to −100, whereas is $fit_{combi}$ usually between 0 and −1 for cpi>0.2).

In an embodiment, a "penalty" is added if g contains certain unwanted sequences, e.g. restriction sites or sequences resulting in undesired secondary structures in mRNA. This may be useful when constructing synthetic genes, but in itself is unrelated to optimization of single codon and codon pair usage. A modified fitness function becomes:

$$fit_{combi}^{*}(g) = \frac{fit_{cp}(g)}{cpi + fit_{sc}(g)} + P(g)$$

where P(g) denotes a penalty function that creates a positive weight in case an unwanted sequence structure is part of gene g.

It is to be understood that in the embodiments of the invention herein the nucleotide and amino acid sequences may be theoretical sequences that exist only on e.g. paper or another preferably computer readable data carrier, or they may exist as a tangibly, physically created embodiment.

In a first aspect the invention therefore relates to a method of optimization of a nucleotide coding sequence that codes for a predetermined amino acid sequence, whereby the coding sequence is optimized for expression in a predetermined host cell. The method preferably comprises the steps of: (a) generating at least one original coding sequence that codes for the predetermined amino acid sequence; (b) generating at least one newly generated coding sequence from this at least one original coding sequence by replacing in this at least one original coding sequence one or more codons by a synonymous codon; (c) determining a fitness value of said at least one original coding sequence and a fitness value of said at least one newly generated coding sequence while using a fitness function that determines at least one of single codon fitness and codon pair fitness for the predetermined host cell; (d) choosing one or more selected coding sequence amongst said at least one original gene and said at least one newly generated coding sequence in accordance with a predetermined selection criterion such that the higher is said fitness value, the higher is a chance of being chosen; and, (e) repeating actions b) through d) while treating said one or more selected coding sequence as one or more original coding sequence in actions b) through d) until a predetermined iteration stop criterion is fulfilled.

According to an embodiment of the invention, the method preferably comprises the steps of: (a) generating at least one original coding sequence that codes for the predetermined amino acid sequence; (b) generating at least one newly generated coding sequence from this at least one original coding sequence by replacing in this at least one original coding sequence one or more codons by a synonymous codon; (c) determining a fitness value of said at least one original coding sequence and a fitness value of said at least one newly generated coding sequence while using a fitness function that determines codon pair fitness for the predetermined host cell; (d) choosing one or more selected coding sequence amongst said at least one original gene and said at least one newly generated coding sequence in accordance with a predetermined selection criterion such that the higher is said fitness value, the higher is a chance of being chosen; and, (e) repeating actions b) through d) while treating said one or more selected coding sequence as one or more original coding sequence in actions b) through d) until a predetermined iteration stop criterion is fulfilled.

According to another embodiment of the invention, the method preferably comprises the steps of: (a) generating at least one original coding sequence that codes for the predetermined amino acid sequence; (b) generating at least one newly generated coding sequence from this at least one original coding sequence by replacing in this at least one original coding sequence one or more codons by a synonymous codon; (c) determining a fitness value of said at least one original coding sequence and a fitness value of said at least one newly generated coding sequence while using a fitness function that comprises determining single codon fitness and codon pair fitness for the predetermined host cell; (d) choosing one or more selected coding sequence amongst said at least one original gene and said at least one newly generated coding sequence in accordance with a predetermined selection criterion such that the higher is said fitness value, the higher is a chance of being chosen; and, (e) repeating actions b) through d) while treating said one or more selected coding sequence as one or more original coding sequence in actions b) through d) until a predetermined iteration stop criterion is fulfilled.

In the methods preferably the predetermined selection criterion is such that said one or more selected coding sequence have a best fitness value according to a predetermined criterion. The methods according to the invention, may further comprises, after action e): selecting a best individual coding sequence amongst said one or more selected coding sequences where said best individual coding sequence has a better fitness value than other selected coding sequences.

In the methods of the invention, the said predetermined iteration stop criterion preferably is at least one of: (a) testing whether at least one of said selected coding sequences have a best fitness value above a predetermined threshold value; (b) testing whether none of said selected coding sequences has a best fitness value below said predetermined threshold value; (c) testing whether at least one of said selected coding sequences has at least 30% of the codon pairs with associated positive codon pair weights for the predetermined host cell in said original coding sequence being transformed into codon pairs with associated negative weights; and, (d) testing whether at least one of said selected coding sequences has at least 10, 20, 30, 40, 50, 60, 70, 80 or 90% of the codon pairs with associated positive weights above 0 for the predetermined host cell in said original coding sequence being transformed into codon pairs with associated weights below 0.

In the methods of the invention the fitness function preferably defines single codon fitness by means of:

$$fit_c(g) = 100 - \frac{1}{|g|} \cdot \sum_{k=1}^{|g|} |r_c^{target}(c(k)) - r_c^g(c(k))| \cdot 100$$

where g symbolizes a coding sequence, |g| its length, g(k) its k-th codon, $r_c^{target}(c(k))$ is a desired ratio of codon c(k) (APPENDIX 2; CR vectors) and $r_c^g(c(k))$ an actual ratio in the nucleotide coding sequence g.

In the methods of the invention the fitness function preferably defines codon pair fitness by means of:

$$fit_{cp}(g) = \frac{1}{|g|-1} \cdot \sum_{k=1}^{|g|-1} w((c(k), c(k+1))$$

where w((c(k), c(k+1)) is a weight of a codon pair in a coding sequence g, |g| is length of said nucleotide coding sequence and c(k) is k-th codon in said coding sequence.

More preferably, in the methods of the invention the fitness function is defined by means of:

$$fit_{combi}(g) = \frac{fit_{cp}(g)}{cpi + fit_{sc}(g)}$$

where $$fit_{cp}(g) = \frac{1}{|g|-1} \cdot \sum_{k=1}^{|g|-1} w((c(k), c(k+1))$$

$$fit_{sc}(g) = \frac{1}{|g|} \cdot \sum_{k=1}^{|g|} |r_{sc}^{target}(c(k)) - r_{sc}^g(c(k))|$$

cpi is a real value greater or equal zero, $fit_{cp}(g)$ is codon pair fitness function, $fit_{sc}(g)$ is a single codon fitness function, w((c(k), c(k+1)) is a weight of a codon pair in a coding sequence g (APPENDIX 3; CPW matrix), |g| is length of said coding sequence, c(k) is k-th codon in said sequence of codons, $r_{sc}^{target}(c(k))$ is a desired ratio of codon c(k) and $r_{sc}^g(c(k))$ an actual ratio in the coding sequence g. Preferably cpi is between 0 and 10, more preferably between 0 and 0.5 and most preferably about 0.2.

In the methods of the invention, the codon pair weights w (APPENDIX 3) may be taken from a 64×64 codon pair matrix including stop codons. Note that the weights for stop:sense pairs and stop:stop pairs are always zero. The codon pair weights w are preferably calculated on the basis of a computer-based method, using as input at least one of: (a) a genome sequence of the predetermined host cell for which at least 5, 10, 20 or 80% of the protein encoding nucleotide sequences are sequenced; (b) a genome sequence of a related species to the predetermined host cell for which at least 5, 10, 20 or 80% of the protein encoding nucleotide sequences are sequenced; (c) a group of nucleotide sequences consisting of at least 200 coding sequences of the predetermined host cell; and, (d) a group of nucleotide sequences consisting of at least 200 coding sequences of a species related to the predetermined host cell. A related species is herein understood to refer to a species of which the nucleotide sequence of the small subunit ribosomal RNA has at least 60, 70, 80, or 90% identity with the nucleotide sequence of the small subunit ribosomal RNA of the predetermined host cell (Wuyts et al., 2004, Nucleic Acids Res. 32: D101-D103).

The codon pair weights w need not be determined for all of the possible 61×64 codon pairs including the termination signal as stop codon but may be determined for only a fraction thereof, e.g. for at least 5%, 10%, 20%, 50%, and preferably 100% of the possible 61×64 codon pairs including the termination signal as stop codon.

Selection Highly Expressed Genes

For calculation of the codon pair weight matrices and the single codon target ratio vectors one can apply a set of nucleotide sequences from the specified host cell itself, a set of nucleotide sequences from a related species, or a combination of both. The set A of nucleotide sequences is called the 'reference set all'. Most preferably this set contains the full set of open reading frames (ORFs) for an organism that is completely sequenced (>95%).

In a preferred embodiment of the invention, a subset B is selected that contains a subset that is overrepresented with highly expressed genes or genes coding for highly expressed proteins. This set can be determined using measurements, and subsequent ranking, like a mRNA hybridization using array technology, e.g. arrays from Affymetrix, Nimblegen, Agilent or any other source for the reference set A. Other measurements can be RT-PCR, protein gels, MS-MS analysis, or any other measurement technique known by the person skilled in the art. Besides making a ranking on the basis of measurements, one can also apply bioinformatics tools to either predict directly a group of highly expressed genes, for example by selecting the most biased genes (Carbone et al, 2003), or by selecting genes known to be highly expressed in a wide range of organisms. Among these are, ribosomal proteins, glycolytic and TCA cycle genes involved in primary metabolism, genes involved in transcription and translation.

Preferably, the codon pair weights w are calculated on the basis of a computer-based method, using as input the group of highly expressed genes in the predetermined host cell. Highly expressed genes are herein understood to mean genes whose mRNA's can be detected at a level of at least 10, preferably 20, more preferably 50, more preferably 100, more preferably 500 and most preferably at least 1,000 copies per cell. For example, Gygi et al. measured 15,000 mRNA molecules per yeast cell. The abundance of specific mRNAs was determined to be in the range of 0.1-470 per cell (Gygi, S. P., Y. Rochon, B. R. Franza and R. Aebersold (1999). Correlation between protein and mRNA abundance in yeast. *Mol. Cel. Biol.* 19(3): 1720-30) or a factor 10 lower: 0.01-50 per cell (by Akashi, H. (2003). Translational selection and yeast proteome evolution. *Genetics* 164(4): 1291-1303.).

Alternatively, the group of highly expressed genes in the predetermined host cell may be the group comprising the 1000, 500, 400, 300, or 200 or 100 most abundant mRNA's or proteins. The skilled person will recognize that for calculation of single-codon ratio's the group-size of highly expressed genes might be small, since at maximum only 64 target values are being specified. Here a reference set with high-expressed genes might be as low as 1 gene, but generally one considers 1% of the genome size a representative set of the highly expressed genes, see for example Carbone, A. et al. (2003) (Codon adaptation index as a measure of dominating codon bias. *Bioinformatics*. 19(16):2005-15). For the calculation of a codon-pair weight matrix, usually a set of 200-500 reference genes fulfils, which corresponds with 2-7% of a bacterial genome (3000-15000 genes).

Another possibility is to derive a subset of presumably highly expressed genes from literature. For example, for *Bacillus subtilis*, being a model organism, quite some literature on single-codon bias exists. A good overview on the state-of-the-art for *B. subtilis* is given by the work of Kanaya et al. (1999). In our approach, see example 4, we group the data in a subset of highly-expressed groups on the basis of mRNA levels measured by Affymetrix technology, and compare these sequences with the whole set of genome ORFs. Other options that have been used in literature are protein expression data, and functional categorical groups of (expected) genes like ribosomal proteins, proteins involved in translation and transcription, sporulation, energy metabolism, and the flagellar system (Kanaya et al., 1999; Karlin and Mrazek, 2000).

Indeed one often finds, for example, high codon bias in the ribosomal proteins, as well as in the other named groups. However, generally not all genes in the latter groups show such behavior. Also, we do not know how ribosomal proteins react in low-growth production conditions. Therefore, a straightforward measurement technique to deriving a subset of highly expressed genes seems to be logic. Then we can choose transcriptomics (TX) and/or proteomics (PX) data. For both there are pros and cons. TX gives a rather complete picture for mRNA levels of genes in the full genome, while PX data might be biased by overrepresentation of water-soluble proteins. TX data is a direct measure for the available mRNA that is subject to translation, while protein is part of an accumulation process in which turnover also plays an important role. Anyway, TX and PX data are shown to correlate for the highly-expressed genes (Gygi et al, 1999). Another interesting work is the prediction of highly-expressed (PHX) genes by deviation from the average codon usage and similarity to ribosomal proteins, and those involved in translation and transcription processing factors, and to chaperone degradation proteins (Karlin and Mrazek, 2000). In particular for fast growing organisms, like *Bacillus*, *E. coli*, etc., major glycolytic genes and tricarboxylic acid cycle genes are found to belong to the above group. The method prediction compares well with known highly-expressed genes at mRNA data and protein expression.

The skilled person will appreciate that both the single codon weights and codon-pair weights w may be determined for modified host cells that have been modified with respect to the content and nature of their tRNA encoding genes, i.e. host cells comprising additional copies of existing tRNA genes, new (exogenous) tRNA genes, including non-natural tRNA genes, including genes encoding tuna's that have been modified to include non-natural amino-acids or other chemical compounds, as well as host cells in which one or more tRNA genes have been inactivated or deleted.

In the method of the invention, the original coding nucleotide sequence that codes for predetermined amino acid sequence may be selected from: (a) a wild-type nucleotide sequence that codes for the predetermined amino acid sequence; (b) a reverse translation of the predetermined amino acid sequence whereby a codon for an amino acid position in the predetermined amino acid sequence is randomly chosen from the synonymous codons coding for the amino acid; and, (c) a reverse translation of the predetermined amino acid sequence whereby a codon for an amino acid position in the predetermined amino acid sequence is chosen in accordance with a single-codon bias for the predetermined host cell or a species related to the host cell.

Host Cells

In the methods of the invention the predetermined host may be any host cell or organism that is suitable for the production of a polypeptide of interest by means of expression of an optimized nucleotide coding sequence. The host cell may thus be a prokaryotic or a eukaryotic host cell. The host cell may be a host cell that is suitable for culture in liquid or on solid media. Alternatively, the host cell may be a cell that is part of a multicellular tissue or and multicellular organism such as a (transgenic) plant, animal or human.

The host cells may be microbial or non-microbial. Suitable non-microbial host cells include e.g. mammalian host cells such as Hamster cells: CHO (Chinese hamster ovary), BHK (Baby Hamster Kidney) cells, mouse cells (e.g. NS0), monkey cells such as COS or Vero; human cells such as PER.C6™ or HEK-293 cells; or insect cells such as *Drosophila* S2 and *Spodoptera* Sf9 or Sf21 cells; or plant cells such as tobacco, tomato, potato, oilseed rape, cabbage, pea, wheat, corn, rice, *Taxus* species such as *Taxus brevifolia*, *Arabidopsis* species such as *Arabidopsis thaliana*, and *Nicotiana* species such as *Nicotiana tabacum*. Such non-microbial cells are particularly suitable for the production of mammalian or human proteins for use in mammalian or human therapy.

The host cell may also be microbial host cells such as bacterial or fungal cells. Suitable bacterial host cells include both Gram-positive and Gram-negative bacteria. Examples of suitable bacterial host cells include bacteria from the genera *Bacillus*, *Actinomycetis*, *Escherichia*, *Streptomyces* as well as lactic acid bacteria such as *Lactobacillus*, *Streptococcus*, *Lactococcus*, *Oenococcus*, *Leuconostoc*, *Pediococcus*, *Carnobacterium*, *Propionibacterium*, *Enterococcus* and *Bifidobacterium*. Particularly preferred are *Bacillus subtilis*, *Bacillus amyloliquefaciens*, *Bacillus licheniformis*, *Escherichia coli*, *Streptomyces coelicolor*, *Streptomyces clavuligerus*, and *Lactobacillus plantarum*, *Lactococcus lactis*.

Alternatively, the host cell may be a eukaryotic microorganism such as a yeast or a filamentous fungus. Preferred yeasts as host cells belong to the genera *Saccharomyces*, *Kluyveromyces*, *Candida*, *Pichia*, *Schizosaccharomyces*, *Hansenula*, *Kloeckera*, *Schwanniomyces*, and *Yarrowia*. Particularly preferred *Debaromyces* host cells include *Saccharomyces cerevisiae*, and *Kluyveromyces lactis*.

According to a more preferred embodiment, the host cell of the present invention is a cell of a filamentous fungus. "Filamentous fungi" include all filamentous forms of the subdivision Eumycota and Oomycota (as defined by Hawksworth et al., 1995, supra). The filamentous fungi are characterized by a mycelia wall composed of chitin, cellulose, glucan, chitosan, mannan, and other complex polysaccharides. Vegetative growth is by hyphal elongation and carbon catabolism is obligatory aerobic. Filamentous fungal genera of which strains may be used as host cells in the present invention include, but are not limited to, strains of the genera *Acremonium*, *Aspergillus*, *Aureobasidium*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Piromyces*, *Schizophyllum*, *Chrysosporium*, *Talaromyces*, *Thermoascus*, *Thielavia*, *Tolypocladium*, and *Trichoderma*. Preferably a filamentous fungus belonging to a species selected from the group consisting of *Aspergillus niger*, *Aspergillus oryzae*, *Aspergillus sojae*, *Trichoderma reesei* or *Penicillium chrysogenum*. Example of suitable host strains include: *Aspergillus niger* CBS 513.88 (Pel et al., 2007, Nat. Biotech. 25: 221-231), *Aspergillus oryzae* ATCC 20423, IFO 4177, ATCC 1011, ATCC 9576, ATCC14488-

14491, ATCC 11601, ATCC12892, *P. chrysogenum* CBS 455.95, *Penicillium citrinum* ATCC 38065, *Penicillium chrysogenum* P2, *Acremonium chrysogenum* ATCC 36225 or ATCC 48272, *Trichoderma reesei* ATCC 26921 or ATCC 56765 or ATCC 26921, *Aspergillus sojae* ATCC11906, *Chrysosporium lucknowense* ATCC44006 and derivatives thereof.

The host cell may be a wild type filamentous fungus host cell or a variant, a mutant or a genetically modified filamentous fungus host cell. Such modified filamentous fungal host cells include e.g. host cells with reduced protease levels, such as the protease deficient strains as *Aspergillus oryzae* JaL 125 (described in WO 97/35956 or EP 429 490); the tripeptidyl-aminopeptidases-deficient *A. niger* strain as disclosed in WO 96/14404, or host cells with reduced production of the protease transcriptional activator (prtT; as described in WO 01/68864, US2004/0191864A1 and WO 2006/040312); host strains like the *Aspergillus oryzae* BECh2, wherein three TAKA amylase genes, two protease genes, as well as the ability to form the metabolites cyclopiazonic acid and kojic acid have been inactivated (BECh2 is described in WO 00/39322); filamentous fungal host cells comprising an elevated unfolded protein response (UPR) compared to the wild type cell to enhance production abilities of a polypeptide of interest (described in US2004/0186070A1, US2001/0034045A1, WO01/72783A2 and WO2005/123763); host cells with an oxalate deficient phenotype (described in WO2004/070022A2 and WO2000/50576); host cells with a reduced expression of an abundant endogenous polypeptide such as a glucoamylase, neutral alpha-amylase A, neutral alpha-amylase B, alpha-1,6-transglucosidase, proteases, cellobiohydrolase and/or oxalic acid hydrolase (as may be obtained by genetic modification according to the techniques described in US2004/0191864A1); host cells with an increased efficiency of homologous recombination (having deficient hdfA or hdfB gene as described in WO2005/095624); and host cells having any possible combination of these modifications.

In a method of the invention, the predetermined amino acid sequence may be an amino acid sequence (of a polypeptide of interest) that is heterologous to said predetermined host cell, or it may be an amino acid sequence (of a polypeptide of interest) that is homologous to said predetermined host cell.

The term "heterologous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which it is introduced, but has been obtained from another cell or synthetically or recombinantly produced. Generally, though not necessarily, such nucleic acids encode proteins that are not normally produced by the cell in which the nucleic acid is expressed. Any nucleic acid or protein that one of skill in the art would recognize as heterologous or foreign to the cell in which it is expressed is herein encompassed by the term heterologous nucleic acid or protein. The term heterologous also applies to non-natural combinations of nucleic acid or amino acid sequences, i.e. combinations where at least two of the combined sequences are foreign with respect to each other.

The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain.

The predetermined amino acid sequence may be the sequence of any polypeptide of interest having a commercial or industrial applicability or utility. Thus, the polypeptide of interest may be an antibody or a portion thereof, an antigen, a clotting factor, an enzyme, a hormone or a hormone variant, a receptor or portions thereof, a regulatory protein, a structural protein, a reporter, or a transport protein, intracellular protein, protein involved in secretion process, protein involved in folding process, chaperone, peptide amino acid transporter, glycosylation factor, transcription factor. Preferably, the polypeptide of interest is secreted into the extracellular environment of the host cell by the classical secretion pathway, by a non-classical secretion pathway or by an alternative secretion pathway (described in WO 2006/040340). In case the polypeptide of interest is an enzyme it may e.g. be an oxidoreductase, transferase, hydrolase, lyase, isomerase, ligase, catalase, cellulase, chitinase, cutinase, deoxyribonuclease, dextranase, esterase. More preferred enzymes include e.g. carbohydrases, e.g. cellulases such as endoglucanases, β-glucanases, cellobiohydrolases or β-glucosidases, hemicellulases or pectinolytic enzymes such as xylanases, xylosidases, mannanases, galactanases, galactosidases, pectin methyl esterases, pectin lyases, pectate lyases, endopolygalacturonases, exopolygalacturonases rhamnogalacturonases, arabanases, arabinofuranosidases, arabinoxylan hydrolases, galacturonases, lyases, or amylolytic enzymes; hydrolase, isomerase, or ligase, phosphatases such as phytases, esterases such as lipases, proteolytic enzymes, oxidoreductases such as oxidases, transferases, or isomerases, phytases, aminopeptidases, carboxypeptidases, endo-proteases, metallo-proteases, serine-proteases, catalases, chitinases, cutinases, cyclodextrin glycosyltransferases, deoxyribonucleases, alpha-galactosidases, beta-galactosidases, glucoamylases, alpha-glucosidases, beta-glucosidases, haloperoxidases, invertases, laccases, mannosidase, mutanases, peroxidases, phospholipases, polyphenoloxidases, ribonucleases, transglutaminases, glucose oxidases, hexose oxidases, and monooxygenases. Several therapeutic proteins of interest include e.g. antibodies and fragment thereof, human insulin and analogs thereof, human lactoferrin and analogs thereof, human growth hormone, erythropoietin, tissue plasminogen activator (tPA) or insulinotropin. The polypeptide may be involved in the synthesis of a metabolite, preferably citric acid. Such polypeptides e.g. include: aconitate hydratase, aconitase hydroxylase, 6-phosphofructokinase, citrate synthase, carboxyphosphonoenolpyruvate phosphonomutase, glycolate reductase, glucose oxidase precursor goxC, nucleoside-diphosphate-sugar epimerase, glucose oxidase, Manganese-superoxide-dismutase, citrate lyase, ubiquinone reductase, carrier proteins, citrate transporter proteins, mitochondrial respiratory proteins and metal transporter proteins.

Computer, Program and Data Carrier

In a further aspect the invention relates to a computer comprising a processor and memory, the processor being arranged to read from said memory and write into said memory, the memory comprising data and instructions arranged to provide said processor with the capacity to perform the method of the invention.

In another aspect the invention relates to a computer program product comprising data and instructions and arranged to be loaded in a memory of a computer that also comprises a processor, the processor being arranged to read from said memory and write into said memory, the data and instructions being arranged to provide said processor with the capacity to perform the method of the invention.

In yet another aspect the invention relates to a data carrier provided with a computer program product as defined above.
Nucleic Acid Molecules In a further aspect the invention relates to a nucleic acid molecule comprising a coding sequence coding for a predetermined amino acid sequence. The coding sequence preferably is a nucleotide sequence that does not resemble a naturally occurring coding sequence. Rather the coding sequence in the nucleic acid molecule is a nucleotide sequence that is not found in nature but is an artificial, i.e. an engineered, man-made nucleotide sequence that was generated on the basis of the method for optimization of single codon and/or codon pair bias for a predetermined host cell in accordance with the methods defined herein and that was subsequently synthesized as a tangible nucleic acid molecule. Preferably, the coding sequence has a $\text{fit}_{sc}(g)$ of at least below 0.2, or more preferably below 0.1 and most preferably below 0.02 for a predetermined host cell. More preferably, the coding sequence has a $\text{fit}_{cp}(g)$ of at least below 0 for a predetermined host cell. Most preferably, the coding sequence has a $\text{fit}_{cp}(g)$ of at least below −0.1 for a predetermined host cell, or more preferably at least below −0.2. Preferably the number of codon-pair in an optimized gene g contains at least 60, 70, 75, 80, 85% codon pairs and most preferably at least 90% codon pairs with associated negative codon-pairs for the specified host organisms The predetermined amino acid sequence encoded by the coding sequence may be any polypeptide of interest as herein defined above and also the predetermined host cell may be any host cell as defined above herein.

In the nucleic acid molecule, the coding sequence preferably is operably linked to an expression control sequence that are capable of directing expression of the coding sequence in the predetermined host cell. In the context of the invention, a control sequence is defined as a nucleotide sequence operatively associated to a coding sequence when present together and which include all components necessary or advantageous for expression of the nucleotide sequence encoding the polypeptide to be produced. Each control sequence may be native or foreign to the nucleotide sequence encoding the polypeptide to be produced. Such control sequences may include, but are not limited to, a leader sequence, a polyadenylation sequence, a propeptide sequence, a promoter, a translational initiator sequence, a translational initiator coding sequence, a translational transcription terminator and a transcription terminator sequence. The control sequences may be provided with linkers, e.g., for the purpose of introducing specific restriction sites facilitating ligation of the control sequences with the coding region of the nucleotide sequence encoding a polypeptide.

Expression control sequences will usually minimally comprise a promoter. As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active under most environmental and developmental conditions. An "inducible" promoter is a promoter that is active under environmental or developmental regulation.

A DNA segment such as an expression control sequence is "operably linked" when it is placed into a functional relationship with another DNA segment. For example, a promoter or enhancer is operably linked to a coding sequence if it stimulates the transcription of the sequence. DNA for a signal sequence is operably linked to DNA encoding a polypeptide if it is expressed as a pre-protein that participates in the secretion of the polypeptide. Generally, DNA sequences that are operably linked are contiguous, and, in the case of a signal sequence, both contiguous and in reading phase. However, enhancers need not be contiguous with the coding sequences whose transcription they control. Linking is accomplished by ligation at convenient restriction sites or at adapters, linkers, or PCR fragments by means know in the art.

The selection of an appropriate promoter sequence generally depends upon the host cell selected for the expression of the DNA segment. Examples of suitable promoter sequences include prokaryotic, and eukaryotic promoters well known in the art (see, e.g. Sambrook and Russell, 2001, "Molecular Cloning: A Laboratory Manual ($3^{rd}$ edition), Cold Spring Harbor Laboratory, Cold Spring Harbor Laboratory Press, New York). The transcriptional regulatory sequences typically include a heterologous enhancer or promoter that is recognized by the host. The selection of an appropriate promoter depends upon the host, but promoters such as the trp, lac and phage promoters, tRNA promoters and glycolytic enzyme promoters are known and available (see, e.g. Sambrook and Russell, 2001, supra). Examples of preferred inducible promoters that can be used are a starch-, copper-, oleic acid-inducible promoters. Preferred promoters for filamentous fungal host cells e.g. include the glucoamylase promoter of *A. niger* or the TAKA amylase promoter of *A. oryzae* and the promoters described in WO2005/100573.

The nucleotide sequence of the invention may further comprise a signal sequence, or rather a signal peptide-coding region. A signal sequence codes for an amino acid sequence linked to the amino terminus of the polypeptide, which can direct the expressed polypeptide into the cell's secretory pathway. Signal sequences usually contain a hydrophobic core of about 4-15 amino acids, which is often immediately preceded by a basic amino acid. At the carboxyl-terminal end of the signal peptide there are a pair of small, uncharged amino acids separated by a single intervening amino acid that defines the signal peptide cleavage site. von Heijne, G. (1990) J. Membrane Biol. 115: 195-201. Despite their overall structural and functional similarities, native signal peptides do not have a consensus sequence. Suitable signal peptide-coding regions may be obtained from a glucoamylase or an amylase gene from an *Aspergillus* species, a lipase or proteinase gene from a *Rhizomucor* species, the gene for the alpha-factor from *Saccharomyces cerevisiae*, an amylase or a protease gene from a *Bacillus* species, or the calf pre-pro-chymosin gene. However, any signal peptide-coding region capable of directing the expressed protein into the secretory pathway of a host cell of choice may be used in the present invention. Preferred signal peptide coding regions for filamentous fungus host cells are the signal peptide coding region obtained from *Aspergillus oryzae* TAKA amylase gene (EP 238 023), *Aspergillus niger* neutral amylase gene, *Aspergillus niger* glucoamylase, the *Rhizomucor miehei* aspartic proteinase gene, the *Humicola lanuginosa* cellulase gene, *Humicola insolens* cellulase, *Humicola insolens* cutinase the *Candida antarctica* lipase B gene or the *Rhizomucor miehei* lipase gene and mutant, truncated, and hybrid signal sequence thereof. In a preferred embodiment of the invention the nucleotide sequence encoding the signal sequence is an integral part of the coding sequence that is optimized with respect to single codon and/or codon pair bias for the predetermined host.

In the nucleic acid molecule of the invention, the coding sequence is further preferably operably linked to a translational initiator sequence. In eukaryotes, the nucleotide consensus sequence (6-12 nucleotides) before the initiator ATG-codon is often called Kozak consensus sequence due to the initial work on this topic (Kozak, M. (1987): an analysis of 5'-noncoding sequences from 699 vertebrate messenger RNAs. Nucl. Acid Res. 15(20): 8125-47). The original Kozak consensus sequence CCCGCCGCCrCC(ATG)G, including a +4 nucleotide derived by Kozak is associated with the initiation of translation in higher eukaryotes. For prokaryote host cells the corresponding Shine-Delgarno sequence (AG-GAGG) is preferably present in the 5'-untranslated region of prokaryotic mRNAs to serve as a translational start site for ribosomes.

In the context of this invention, the term "translational initiator sequence" is defined as the ten nucleotides immediately upstream of the initiator or start codon of the open reading frame of a DNA sequence coding for a polypeptide. The initiator or start codon encodes for the amino acid methionine. The initiator codon is typically ATG, but may also be any functional start codon such as GTG, TTG or CTG.

In a particularly preferred embodiment of the invention, the nucleic acid molecule comprises a coding sequence coding for a predetermined amino acid sequence that is to be expressed in a fungal host cell, i.e. the predetermined host cell is preferably a fungus of which filamentous fungi are most preferred. Nucleic acid molecules comprising coding sequences that are optimized for expression in fungi in accordance with the invention may further comprise the one or more of the following elements: 1) a fungal consensus translational initiator sequence; 2) a fungal translational initiator coding sequence; and 3) a fungal translational termination sequence.

A consensus fungal translational initiator sequence preferably is defined by the following sequences: 5'-mwChky-CAmv-3', using ambiguity codes for nucleotides: m (A/C); r (A/G); w (A/T); s (C/G); y (C/T); k (G/T); v (A/C/G); h (A/C/T); d (A/G/T); b (C/G/T); n (A/C/G/T). According to a more preferred embodiment, the sequences are: 5'-mwChky-CAAA-3'; 5'-mwChkyCACA-3' or 5'-mwChkyCAAG-3'. Most preferably the translational initiation consensus sequence is 5'-CACCGTCAAA-3' or 5'-CGCAGTCAAG-3'.

In the context of this invention, the term "consensus translational initiator coding sequence" is defined herein as the nine nucleotides immediately downstream of the initiator codon of the open reading frame of a coding sequence (the initiator codon is typically ATG, but may also be any functional start codon such as GTG). A preferred fungal consensus translational initiator coding sequence has the following nucleotide sequence: 5'-GCTnCCyyC-3', using ambiguity codes for nucleotides y (C/T) and n (A/C/G/T). This leads to 16 variants for the translational initiator coding sequence of which 5'-GCT TCC TTC-3' is most preferred. Using a consensus translational initiator coding sequence, the following amino acids are allowed at the amino acid positions mentioned: alanine at +2, alanine, serine, proline, or threonine at +3, and phenylalanine, serine, leucine or proline at +4 position in the polypeptide that is encoded. Preferably in the present invention, the consensus translational initiator coding sequence is foreign to the nucleic acid sequence encoding the polypeptide to be produced, but the consensus translational initiator may be native to the fungal host cell.

In the context of this invention, the term "translational termination sequence" is defined as the four nucleotides starting from the translational stop codon at the 3' end of the open reading frame or coding sequence. Preferred fungal translational termination sequence include: 5'-TAAG-3',5'-TAGA-3' and 5'-TAAA-3', of which 5'-TAAA-3' is most preferred.

A coding sequence coding for a predetermined amino acid sequence that is to be expressed in a fungal host cell is further preferably optimized with respect to single codon frequency such that at least one, two, three, four or five original codons, more preferably at least 1%, 2%, 3%, 4%, 5%, 10%, 15%, 20%, 25%, 50%, 75%, 80%, 85%, 90%, or 95% of the original codons have been exchanged with a synonymous codon, the synonymous codon encoding the same amino acid as the native codon and having a higher frequency in the codon usage as defined in the Table A than the original codon.

TABLE A

Optimal filamentous fungal codon frequency for synonymous codons in %.

| | .T. | .C. | .A. | .G. | |
|---|---|---|---|---|---|
| T.. | Phe | Ser | Tyr | Cys | ..T |
| | 0 | 21 | 0 | 0 | |
| T.. | Phe | Ser | Tyr | Cys | ..C |
| | 100 | 44 | 100 | 100 | |
| T.. | Leu | Ser | Stop | Stop | ..A |
| | 0 | 0 | 100 | 0 | |
| T.. | Leu | Ser | Stop | Trp | ..G |
| | 13 | 14 | 0 | 100 | |
| C.. | Leu | Pro | His | Arg | ..T |
| | 17 | 36 | 0 | 49 | |
| C.. | Leu | Pro | His | Arg | ..C |
| | 38 | 64 | 100 | 51 | |
| C.. | Leu | Pro | Gln | Arg | ..A |
| | 0 | 0 | 0 | 0 | |
| C.. | Leu | Pro | Gln | Arg | ..G |
| | 32 | 0 | 100 | 0 | |
| A.. | Ile | Thr | Asn | Ser | ..T |
| | 27 | 30 | 0 | 0 | |
| A.. | Ile | Thr | Asn | Ser | ..C |
| | 73 | 70 | 100 | 21 | |
| A.. | Ile | Thr | Lys | Arg | ..A |
| | 0 | 0 | 0 | 0 | |
| A.. | Met | Thr | Lys | Arg | ..G |
| | 100 | 0 | 100 | 0 | |
| G.. | Val | Ala | Asp | Gly | ..T |
| | 27 | 38 | 36 | 49 | |
| G.. | Val | Ala | Asp | Gly | ..C |
| | 54 | 51 | 64 | 35 | |
| G.. | Val | Ala | Glu | Gly | ..A |
| | 0 | 0 | 26 | 16 | |
| G.. | Val | Ala | Glu | Gly | ..G |
| | 19 | 11 | 74 | 0 | |

A even more preferred coding sequence coding for a predetermined amino acid sequence that is to be expressed in a fungal host cell is further preferably optimized with respect to single codon frequency such that at least one, two, three, four or five original codons, more preferably at least 1%, 2%, 3%, 4%, 5%, 10%, 15%, 20%, 25%, 50%, 75%, 80%, 85%, 90%, or 95% of the original codons have been exchanged with a synonymous codon, the synonymous codon changing the codon frequency such that the value of the absolute difference between the percentage for said codon in said frequency and listed optimal percentage becomes smaller after modification, applying the following list of optimal percentages: cysteine encoded by TGC (100%); phenylalanine by TTC (100%); histidine by CAC (100%); lysine by AAG (100%); asparagine by AAC (100%); glutamine by CAG (100%); tyrosine by TAC (100%); alanine by GCT (38.0%), GCC (50.7%), or GCG (11.3%); aspartate by GAC (63.2%);

glutamate by GAG (74.2%); glycine by GGT (49.0%), GGC (35.9%), GGA (15.1%); isoleucine by ATT (26.7%), ATC (73.3%); leucine by TTG (12.7%), CTT (17.4%), CTC (38.7%), CTG (31.2%); proline by CCT (35.6%), CCC (64.4%); arginine by CGT (49.1%), CGC (50.9%); serine by TCT (20.8%), TCC (44.0%), TCG (14.4%), AGC (20.8%); threonine by ACT (29.7%), ACC (70.3%) and/or valine by GTT (27.4%), GTC (54.5%), GTG (18.1%); all other possible amino acid encoding codons (0%).

The above defined nucleic acid molecules comprising the coding sequences of the invention (for expression in a predetermined host cell) may further comprise the elements that are usually found in expression vectors such as a selectable marker, an origin of replication and/or sequences that facilitate integration, preferably through homologous recombination at a predetermined site in the genome. Such further elements are well known in the art and need no further specification herein.

In a further aspect the invention pertains to a host cell comprising a nucleic acid molecule as defined herein above. The host cell preferably is a host cell as herein defined above.

In yet a further aspect the invention relates to a method for producing a polypeptide having the predetermined amino acid sequence. The method preferably comprises culturing a host cell comprising a nucleic acid molecule as defined herein above, under conditions conducive to the expression of the polypeptide and, optionally, recovery of the polypeptide.

In again a further aspect the invention relates to method for producing at least one of an intracellular and an extracellular metabolite. The method comprising culturing a host cell as defined in herein above under conditions conducive to the production of the metabolite. Preferably, in the host the polypeptide having the predetermined amino acid sequence (that is encoded by the nucleic acid molecule as defined above) is involved in the production of the metabolite. The metabolite (be it a primary or secondary metabolite, or both; be it intra-, extracellular or both) may be any fermentation product that may be produced in a fermentation process. Such fermentation products e.g. include amino acids such as lysine, glutamic acid, leucin, threonin, tryptophan; antibiotics, including e.g. ampicilline, bacitracin, cephalosporins, erythromycin, monensin, penicillins, streptomycin, tetracyclines, tylosin, macrolides, and quinolones; preferred antibiotics are cephalosporins and beta-lactams; lipids and fatty acids including e.g. poly unsaturated fatty acids (PUFAs); alkanol such as ethanol, propanol and butanol; polyols such as 1,3-propane-diol, butandiol, glycerol and xylitol; ketons such as aceton; amines, diamines, ethylene; isoprenoids such as carotenoids, carotene, astaxanthin, lycopene, lutein; acrylic acid, sterols such as cholesterol and ergosterol; vitamins including e.g. the vitamins A, B2 B12, C, D, E and K, and organic acids including e.g. glucaric acid, gluconic acid, glutaric acid, adipic acid, succinic acid, tartaric acid, oxalic acid, acetic acid, lactic acid, formic acid, malic acid, maleic acid, malonic acid, citric acid, fumaric acid, itaconic acid, levulinic acid, xylonic acid, aconitic acid, ascorbic acid, kojic acid, and comeric acid; a preferred organic acid is citric acid.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

EXAMPLES

1. Example 1

Analysis of Codon Pair Bias 1.1 Material and Methods 1.1.1 Data and Software

Codon pair analysis may be performed on coding sequences (CDS) in whole genome sequence data as well as partial groups derived of those (or a partial genome sequence, like for example cDNA/EST libraries, or even partial genome data from multiple genomes from related organisms). The tools used in the present invention read these data using FASTA files as input. The vast majority of all calculations have been performed in MATLAB 7.01 (The MathWorks, Inc., but for some detailed analyses of the obtained results Spotfire DecisionSite 8.0 (Spotfire, Inc.) was used.

For *A. niger*, a FASTA file with predicted cDNA sequences for the full genome of CBS513.88 (Pel et al., 2007, Nat. Biotech. 25: 221-231) and a group of 479 highly expressed genes were used. Furthermore, since usually less than half of the >14,000 genes in *A. niger* are expressed at the same time under pilot-scale fermentation conditions, data from 24 GeneChips obtained using such conditions was used to extract a second set of genes that includes only genes that are actually expressed within various experiments (taking only genes with at least 18 'present' calls into account, using Affymetrix MAS5.0 array analysis software; this set comprised 4,584 genes) and to rank them according to observed mRNA level (since no other data was available at that time), so a set of (presumably) highly expressed genes of any size can be identified easily. This second set was created to be able to rank the data according to their expression level.

For this analysis we have used transcription levels of the genes. Alternatively one can also apply quantitative protein expression data, e.g. by two-dimensional gel electrophoresis of the proteins and subsequent identification via mass spectrometry. However, generating protein expression on large sets of proteins is still quite time consuming in comparison with determination of mRNA levels (e.g. using genechips). Therefore, what is done here is to study the effect of codon bias on translation before translation has actually happened. Gygi et al. (Yeast. Mol. Cel. Biol. 19(3):1720-30) actually found a "correlation of protein and mRNA expression levels with codon bias" in *E. coli*, even although the correlation of mRNA and protein expression levels was rather rudimentary only. Hence, the term "expression level" will be used in this text when actually only the effect on the transcription level has been determined.

For *Bacillus subtilis*, an organism containing around 4,000 genes, a group of 300 highly expressed genes was available and has been analyzed. See Table 1.1 for an overview of the basic properties of the genomes of all organisms that have been taken into account in this study (however, not all of them will be described in detail).

In every analysis, (putative) genes that included one or more stop codons at another position than the end and sequences with a length not divisible by three (i.e. where a frameshift might have occurred during sequencing) have been ignored. Also the first five and the last five codons of every gene have not been taken into account because these sites might be involved in protein binding and releasing efficiency and therefore be subject to different selection pressures than the other parts of the sequence, so codon and codon pair bias there might not be representative. ORFs (ORF=open reading frame) shorter than 20 codons have also been omitted from the analysis. In Table 1.1 this is already taken into account.

TABLE 1.1

Nucleotide content of several organisms, including number of ORF's and genome size in Megabasepair (Mbp).

| name of organism | # of ORFs | Mbp | nucleotide content | | | |
|---|---|---|---|---|---|---|
| | | | A | C | G | T |
| A. nidulans | 7,782 | 10.61 | 24% | 28% | 26% | 22% |
| A. niger | 13,962 | 18.41 | 24% | 27% | 26% | 22% |
| A. oryzae | 12,074 | 16.29 | 25% | 26% | 26% | 23% |
| B. amyloliquefaciens | 4,449 | 3.54 | 26% | 24% | 27% | 23% |
| B. subtilis | 4,104 | 3.66 | 30% | 20% | 24% | 26% |
| E. coli K12 | 4,289 | 4.09 | 24% | 25% | 27% | 24% |
| K. lactis | 5,336 | 7.52 | 32% | 19% | 21% | 28% |
| P. chrysogenum | 13,164 | 17.54 | 24% | 27% | 25% | 23% |
| S. cerevisiae | 6,499 | 9.01 | 33% | 19% | 20% | 28% |
| S. coelicolor | 7,894 | 7.62 | 14% | 37% | 35% | 13% |
| T. reesei | 8,331 | 11.45 | 23% | 30% | 28% | 20% |

1.1.2 Expected Occurrences of Codon Pairs

In order to analyze codon pair usage, first the occurrences of every single codon and every codon pair have been counted, below denoted by $n_{obs}((c_i,c_j))$, where obs stands for observed. The double parenthesis are necessary to indicate that "observed number", i.e. $n_{obs}$, is a function with just one argument, which itself is a pair (in that case: a pair of codons, i.e. $(c_i,c_j)$). The same applies to all functions on codon pairs defined below. The indices i, j and also k can be 1 to 64, indicating the number of the codon in the internal representation (according to their alphabetical order). $(c_i,c_j)$ denoting a codon pair with $c_i$ being the left codon (i.e. the 5' triplet of the 6-nucleotide sequence) and right $c_j$ one (i.e. closer to the 3'-end), as well as the number of occurrences $n_{sc}^{all}(c_k)$ for every codon $c_k$ (where the subscript sc stands for single codon and the superscript all indicates that the number refers to the full genome, as opposed to $n_{sc}^g(c_k)$, which will be used to denote codon ratios in a single gene g; functions of codon pairs like $n_{obs}((c_i,c_j))$ always refer to the number in the full genome or a larger group of genes). Single codon ratios (Note that in some papers these ratios are also called frequencies. However, codon frequencies may also refer to the number of occurrences of a codon divided by the total number of all codons) were then calculated $$r_{sc}^{all}(c_k) = n_{sc}^{all}(c_k) / \sum_{c_l \in syn(c_k)} n_{sc}^{all}(c_l)$$

where $syn(c_k)$ denotes the set of codons that encode for the same amino acid as $c_k$ and are thus synonymous to $c_k$. Thus, the value of the sum below the fraction bar equals the number of occurrences of the amino acid encoded by $c_i$ in the whole proteome. See Appendix 1 for a concise list of the most important symbols and formulas used here.

To reveal whether certain alleged codon pair preferences are only the result of preferences of the individual codons, it is necessary to calculate expected values for every codon pair based on individual codon frequencies. These have been calculated using the formula $$n_{exp}^{own}((c_i, c_j)) = r_{sc}^{all}(c_i) \cdot r_{sc}^{all}(c_j) \cdot \sum_{\substack{c_m \in syn(c_i) \\ c_n \in syn(c_j)}} n_{obs}((c_m, c_n))$$

The superscript own is used to distinguish the values from those obtained using other methods mentioned later. In the last factor of this equation, the actual numbers of occurrences of all synonymous codon pairs are summed up. Thus, the expected amount of each codon pair is the product of the individual codon usage ratios and the number of occurrences of the respective amino acid pair.

Gutman and Hatfield (1989, Proc. Natl. Acad. Sci. USA 86:3699-3703) proposed another method of calculating expected values. Their initial approach was to calculate the codon frequencies (i.e. the amount of codons in a gene g divided by the total number of codons in g, denoted |g|) for every gene individually, and then multiply these values pair wise and with the number of codon pairs in that sequence (which is |g|−1).

$$n_{exp}^{gh1}((c_i, c_j)) = \sum_{g \in ORFs} \frac{n_{sc}^g(c_i)}{|g|} \cdot \frac{n_{sc}^g(c_j)}{|g|} \cdot (|g| - 1).$$

In this equation "gh1" denotes Gutman and Hatfield method 1 (1989, supra). This results in expected codon pair values for each gene (the part after the sum operator in the equation above), which are then added up, resulting in final expected values that are by definition adjusted for possible deviations in single codon usage among different genes of the same genome, but do not take a possible bias in amino acid pair usage into account. This means that if certain amino acids tend to be next to each other more often than others, or, in other words, if the numbers of occurrences of the amino acid pairs are not similar to what they would be in randomized sequences with the same amino acid composition, the expected values would also be significantly different in that codon pairs encoding rather rarely used amino acid pairs would have too high expected values and those of more often used amino acid pairs too low ones.

Gutman and Hatfield (1989, supra) also proposed a method of normalizing their expected values for amino acid pair bias. Therefore, they simply compared the expected number of amino acid pairs according to their methods with the observed ones and scaled the expected values of all affected codon pairs accordingly to make the former match the latter:

$$n_{exp}^{gh2}((c_i, c_j)) = n_{exp}^{gh1}((c_i, c_j)) \cdot \frac{\sum_{\substack{c_m \in syn(c_i) \\ c_n \in syn(c_j)}} n_{obs}((c_m, c_n))}{\sum_{\substack{c_m \in syn(c_i) \\ c_n \in syn(c_j)}} n_{exp}^{gh1}((c_m, c_n))}$$

In this equation "gh2" denotes Gutman and Hatfield method 2 (1989, supra).

1.1.3 Calculating Codon Pair Bias

The actual codon pair bias $bias((c_i,c_j))$ should then result from the difference between the expected and actual (observed) numbers of the codon pairs (where any of these methods for the expected values can be used). The initial approach was to calculate it simply by $$bias_1((c_i, c_j)) = \frac{n_{obs}((c_i, c_j)) - n_{exp}((c_i, c_j))}{n_{exp}((c_i, c_j))}.$$

This way, the bias value would indicate how many percent more or less often than expected the codon pair is actually used (if multiplied by 100%, that is). For amino acid pairs not occurring in an analyzed set of genes, the bias value according to the formula would be 0/0 for all corresponding codon pairs. In that case, it is defined to be 0. The lower limit of the bias values would thus be −1, whereas there is no clear upper limit. This was considered somewhat impractical, so instead $$bias((c_i, c_j)) = \frac{n_{obs}((c_i, c_j)) - n_{exp}((c_i, c_j))}{\max(n_{obs}((c_i, c_j)), n_{exp}((c_i, c_j)))}$$

was used, where max(a,b) denotes the greater of the two values a and b, which always results in a bias value in (−1,1). This means that the bias value can be −1, but not +1. The former happens when a certain codon pair is not used at all to encode for an amino acid pair that really occurs; the value +1 can not be reached because $n_{exp}((c_i, c_j))$ would have to be 0 then, but this is only possible when $n_{obs}((c_i, c_j))$ is 0, too.

The interpretation given above is still valid for bias values <0 (which means that $n_{obs}((c_i,c_j))<n_{exp}((c_i,c_j))$, so both formulas have the same result). If $n_{obs}((c_i, c_j))>n_{exp}((c_i,c_j))$, the bias values (which are >0 then) indicate how many percent lower than the observed value the expected value is (i.e. in that case the baseline is changed).

1.1.4 Statistical Significance of the Bias

Gutman and Hatfield (1989, supra) used a $\chi^2$-test to determine the statistical significance of their results. This test is used to check how likely it is that certain observed results occurred by chance under a specific hypothesis. When examining codon pairs, this hypothesis would be that the codon pair usage is the result of a random selection of every codon independently. To test this hypothesis, a $\chi^2$-value is calculated $$\chi^2 = \sum_{(c_m,c_n) \in CP} \frac{(n_{obs}((c_m, c_n)) - n_{exp}((c_m, c_n)))^2}{n_{exp}((c_m, c_n))}$$

(with CP denoting the set of all codon pairs not including a stop codon). The number of degrees of freedom is then 3720 (61*61−1). If codon pair selection were random, one would expect the $\chi^2$-value to be around 3720 (equal to the number of degrees of freedom) with a standard deviation equal to the square root of 2*degrees of freedom.

This way, the overall statistical significance of the observed bias can be tested. However, one can also deduce the statistical significance of the bias of individual codon pairs. As for the method of calculating expected values proposed earlier, the number of occurrences of a codon pair is considered to be the result of a sequence of independent yes/no experiments (yes: these two codons are selected for encoding the respective amino acid pair; no: another codon pair is selected), so it follows a binomial distribution, which can be approximated by a normal distribution if the set of analyzed genes is sufficiently large. This is considered a good approximation if n*p>4, where n stands for the number of experiments and p for the probability of "yes", which is also the expected value. Therefore, for every codon pair a standard deviation can be calculated according to the formula $$\sigma((c_i, c_j)) = \sqrt{n_{exp}((c_i, c_j)) \cdot (1 - r_{sc}^{all}(c_i) \cdot r_{sc}^{all}(c_j))}.$$

Then, the standard scores, also referred to as z-scores, can be calculated $$z((c_i, c_j)) = \frac{(n_{obs}((c_i, c_j)) - n_{exp}((c_i, c_j)))}{\sigma((c_i, c_j))}.$$

The absolute value of the z-score tells how many standard deviations away from the expected value the actual (observed) value is. Assuming a normal distribution, approximately 95% of all observations should be within two standard deviations from the expected value and >99% within three.

1.2 Results 1.2.1 Existence of Codon Pair Bias

Using the above methods we have found that significant codon pair biases exist. For all investigated organisms, the $\chi^2$-test delivered $\chi^2$-values several times as high as the number of degrees of freedom and thus also many standard deviations above the expected value. As for the bias of individual codon pairs, the finding of Moura et al. that in yeast "about 47% of codon-pair contexts fall within the interval −3 to +3" standard deviations away from the expected values (although they calculated the expected values in a different way), which corresponds to the z-scores in our analysis, could be confirmed. Overall, there are significantly more codon pairs with rather high z-scores than there should be if codon pair usage were random. See Table 1.2: with a random selection, which would result approximately in a normal distribution, for example only about 5% of all codon pairs should have a z-score greater than 2 or less than −2, but in the whole genome of the selected four organisms, this actually applies to more than two thirds.

TABLE 1.2

Z-scores in different organisms

| |z-score| | >1 | >2 | >3 |
|---|---|---|---|
| normal distribution | 68.3% | 5.0% | 0.3% |
| A. nidulans | 86.1% | 73.7% | 60.4% |
| A. niger | 89.2% | 79.1% | 69.7% |
| A. oryzae | 88.4% | 76.7% | 65.1% |
| B. amyloliquefaciens | 88.1% | 76.4% | 64.0% |
| B. subtilis | 86.1% | 72.0% | 59.3% |
| E. coli K12 | 86.1% | 74.8% | 64.0% |
| K. lactis | 82.6% | 67.0% | 53.4% |
| P. chrysogenum | 89.3% | 79.1% | 69.0% |
| S. cerevisiae | 82.7% | 67.6% | 52.1% |
| S. coelicolor | 82.0% | 66.5% | 53.5% |
| T. reesei | 89.0% | 79.8% | 71.0% |

Note that these values are somewhat correlated with genome size (see Table 1.1 for a comparison), i.e. organism with larger genomes tend to have codon pairs with more extreme z-scores. Especially when analyzing smaller groups of genes (e.g. 479 highly expressed ones in A. niger), the values are lower (for this example: 65.1%, 37.2% and 19.7%, respectively), as smaller numbers of occurrences lead to higher standard deviations (compared to the expected values) and thus to less statistical significance of the results. This leads to the conclusion that codon pair usage is not the result of a random selection of the codons according to the single codon ratios.

Figure 3:
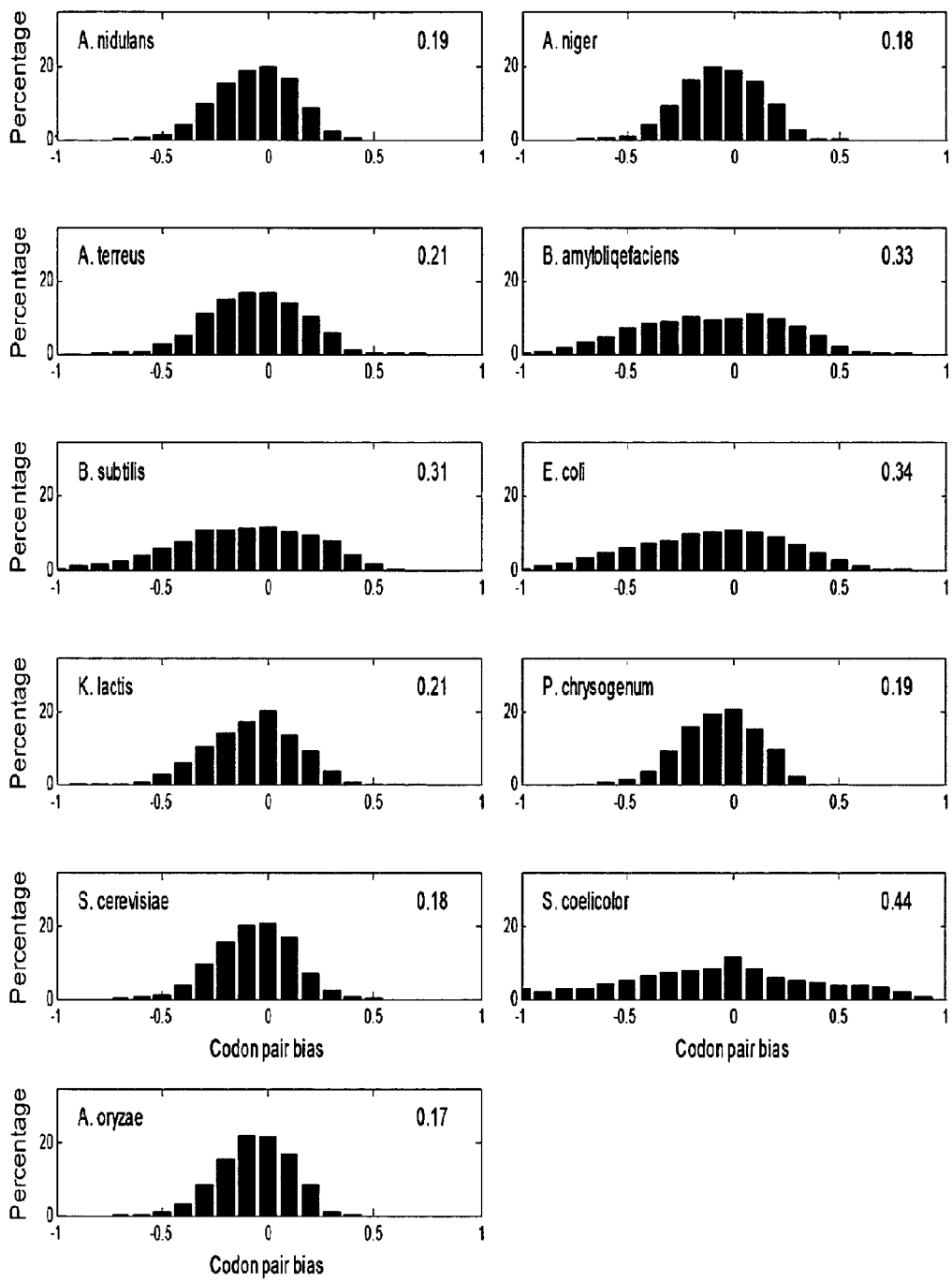
FIG. 3 shows a distribution of codon pair bias values for 3,721 sense:sense codon pairs in different organisms. The numbers in the top right corner of each histogram are the standard deviations for the observed distribution; the mean values (not shown) are between −0.06 and −0.01 for all organisms.

The distribution of the bias values themselves differs from one organism to another. This can be explained with reference to FIG. 3 which shows the distribution of codon pair bias values for the 3,721 sense:sense codon pairs in different organisms. The numbers in the top right corner of each histogram in FIG. 3 are the standard deviations for the observed distribution; the mean values (not shown) are between −0.06 and −0.01 for all organisms. In the histograms shown in FIG. 3, one can see that out of the ten tested organisms, the bacteria *E. coli, B. subtilus, B. amiloliquefaciens* and *S. coelicolor* have the most extreme codon pair bias, whereas bias in the fungi *A. niger, A. oryzae, A. terreus, A. nidulans, P. chrysogenum* and yeasts *S. cerevisiae* and *K. lactis*, is less extreme.

Figure 4:
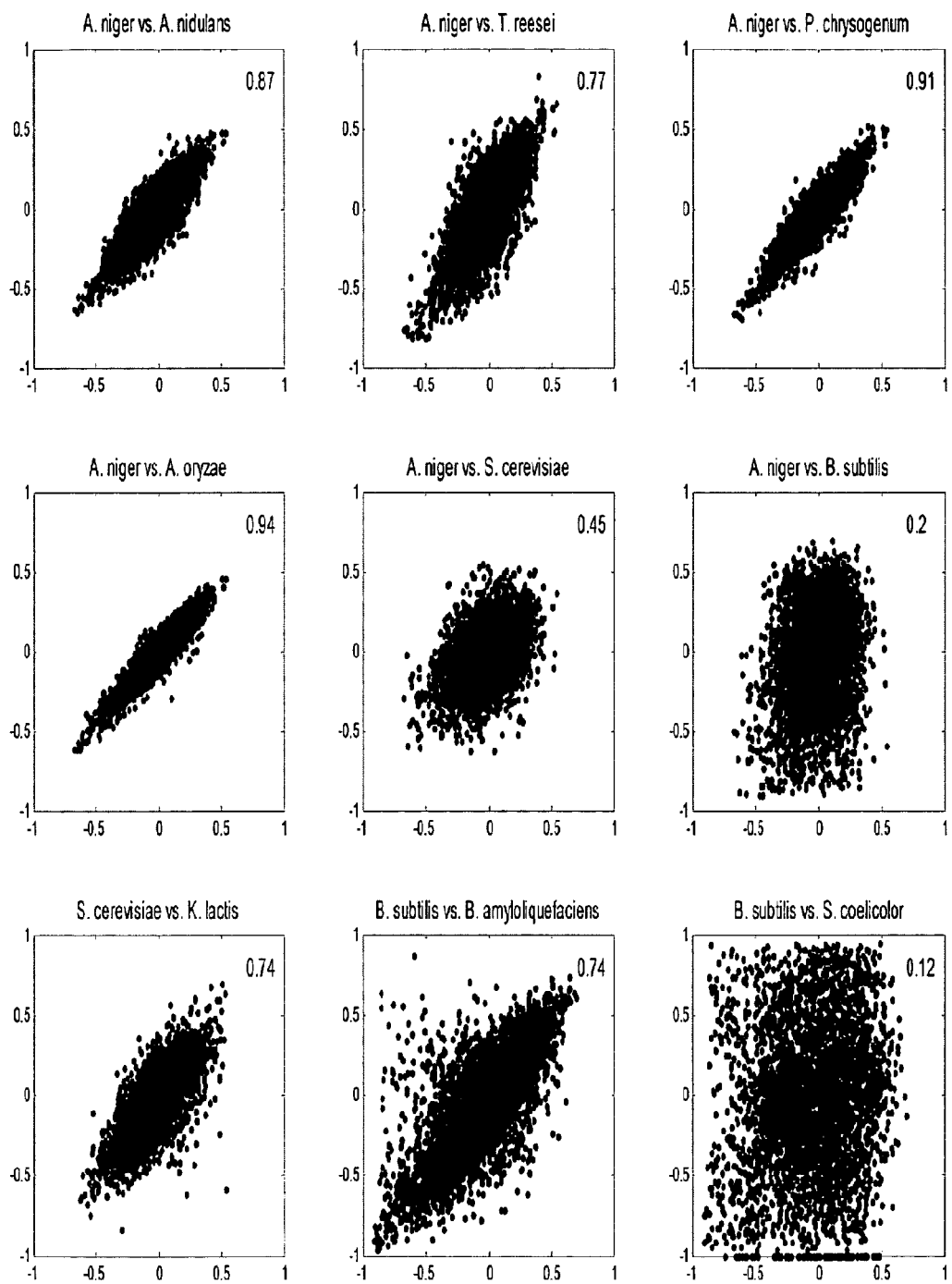
FIG. 4 shows the correlation in codon pair bias of various organisms. The correlation coefficient is shown in the top right corner of each subplot.

Another interesting observation can be made when comparing codon pair bias of different organisms. Bias values from related organisms show a higher correlation than those from unrelated organisms. This is explained with reference to FIG. 4. FIG. 4 shows correlation in codon pair bias of various organisms. A correlation coefficient is shown in the top right corner of each subplot. In this analysis, the highest correlations could be observed between *A. niger* vs. *P. chrysogenum*, and *A. niger* vs. *A. oryzae*, the lowest, i.e. effectively no correlation could be observed between *B. subtilis* and *S. coelicolor*. Interestingly, no negative correlations have been observed. This means that although organisms with a high GC-content (like *S. coelicolor*) mostly prefer those codons that are the less used ones in AT-rich organisms (like *S. cerevisiae* or, although not extremely AT-rich, *B. subtilis*), there are no two organism where the preferred pairs of one organism were likely to be rejected in the other and vice versa. This could mean that although bias of almost every single codon is organism-dependent, there are several codon pairs that are preferred and/or rejected in almost every organism (e.g. because of their likeliness to cause frameshifts or tRNAs with not matching structure).

1.2.2 Patterns in Codon Pair Bias

In order to visualize the observed codon pair bias, so-called maps can be drawn as has been done by Moura et al. (2005) (they refer to these maps as "codon context maps"). This can be most easily explained with reference to colored images that consist of colored rectangles for every codon pair, with the rows representing the first and the columns representing the second codon of the pair. Red colors indicate a negative and green ones a positive bias. White represents codon pairs that really have a bias equal 0 (which is the case for ATG-ATG, for example, since that is the only way to encode the amino acid pair Met-Met) and pairs incorporating a stop codon.

Figure 5A:
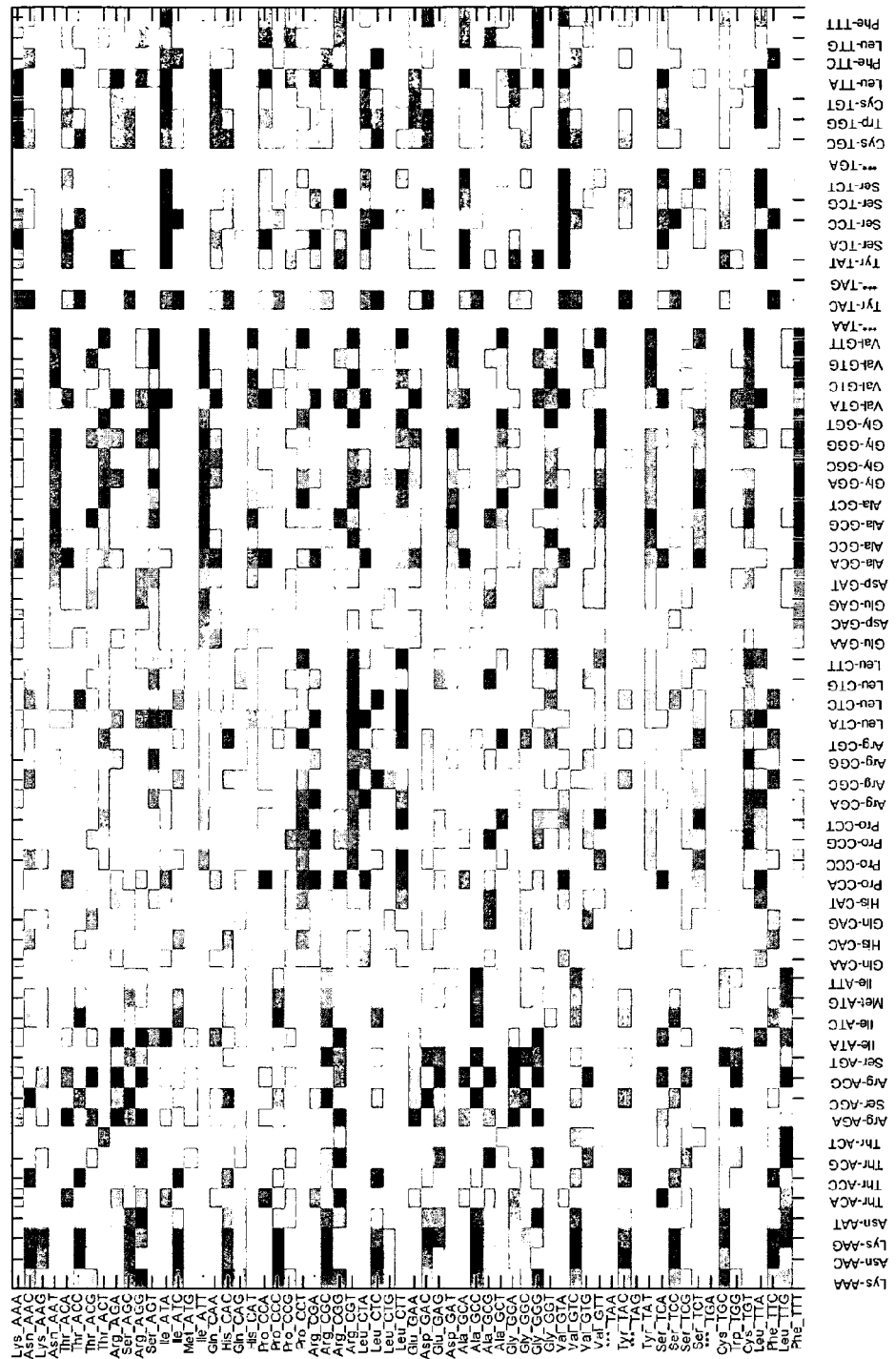
In FIGS. 5A and B the rows and columns are sorted according to the codons their alphabetical order.

However, colored images cannot be part of the disclosure of a patent application. For black & white visualization, the image will be split in two images in this example. FIG. 5A displays the positive codon pairs for *A. niger*, while FIG. 5B displays the negative codon pairs for *A. niger* (see also Appendix 3, Table C1). The more biased the codon-pair, the more black the corresponding rectangle. The bias values here range from −0.67 to 0.54, where in other organisms they might even get slightly above +/−0.9 (see also FIG. 3). The highest intensities of black (original green (top) and black (original red (bottom)) in these diagrams represent values of 0.9 and −0.9, respectively (not reached here; mostly, the absolute values of the maximum bias are slightly lower than those of the minimum bias.

Figure 5C:
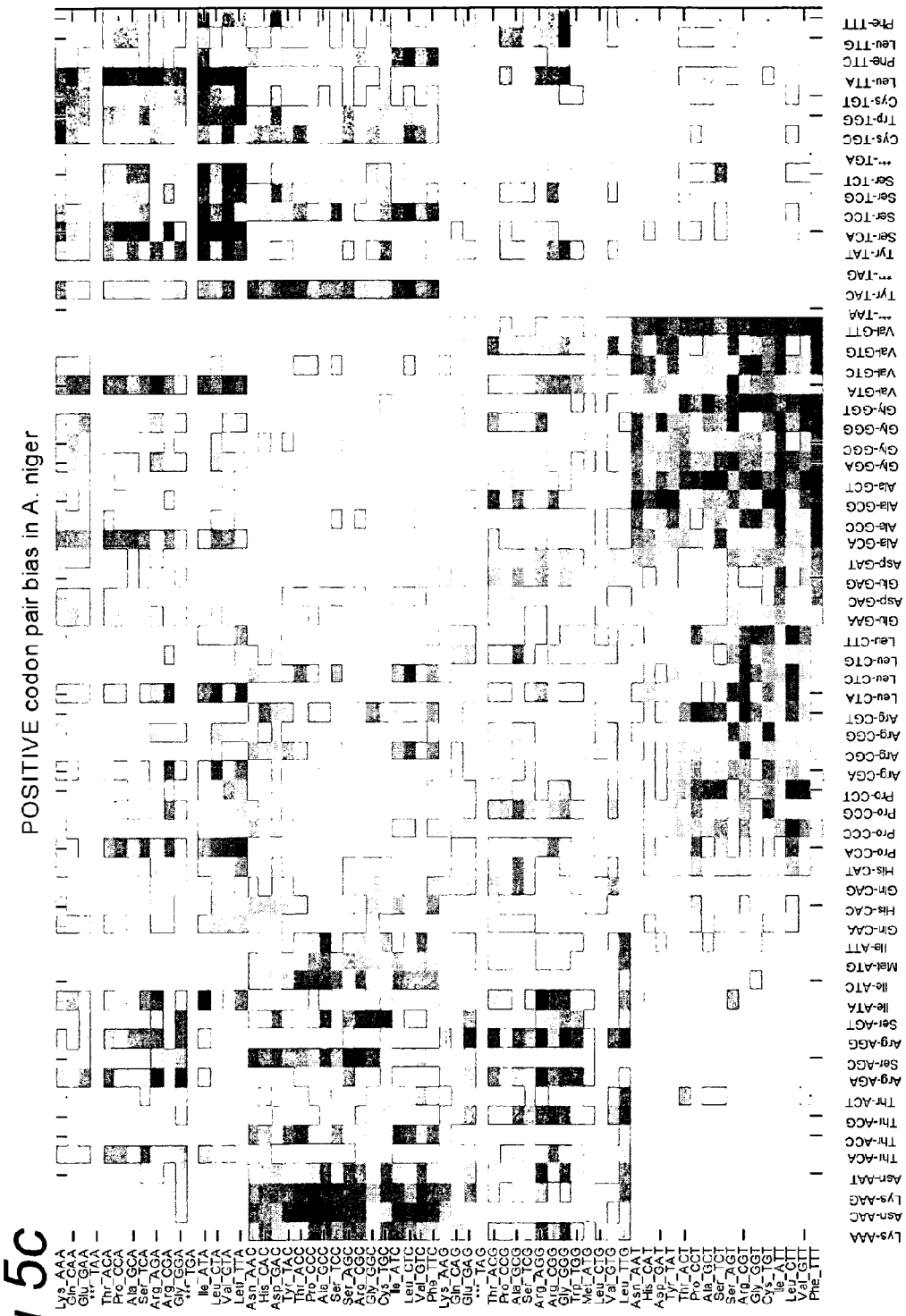
In FIGS. 5C and 5D the rows are sorted according to the alphabetical order of the third position nucleotide as first sorting criterion and the middle position nucleotide as second sorting criterion, and first position nucleotide as third sorting criterion.
Figure 5D:
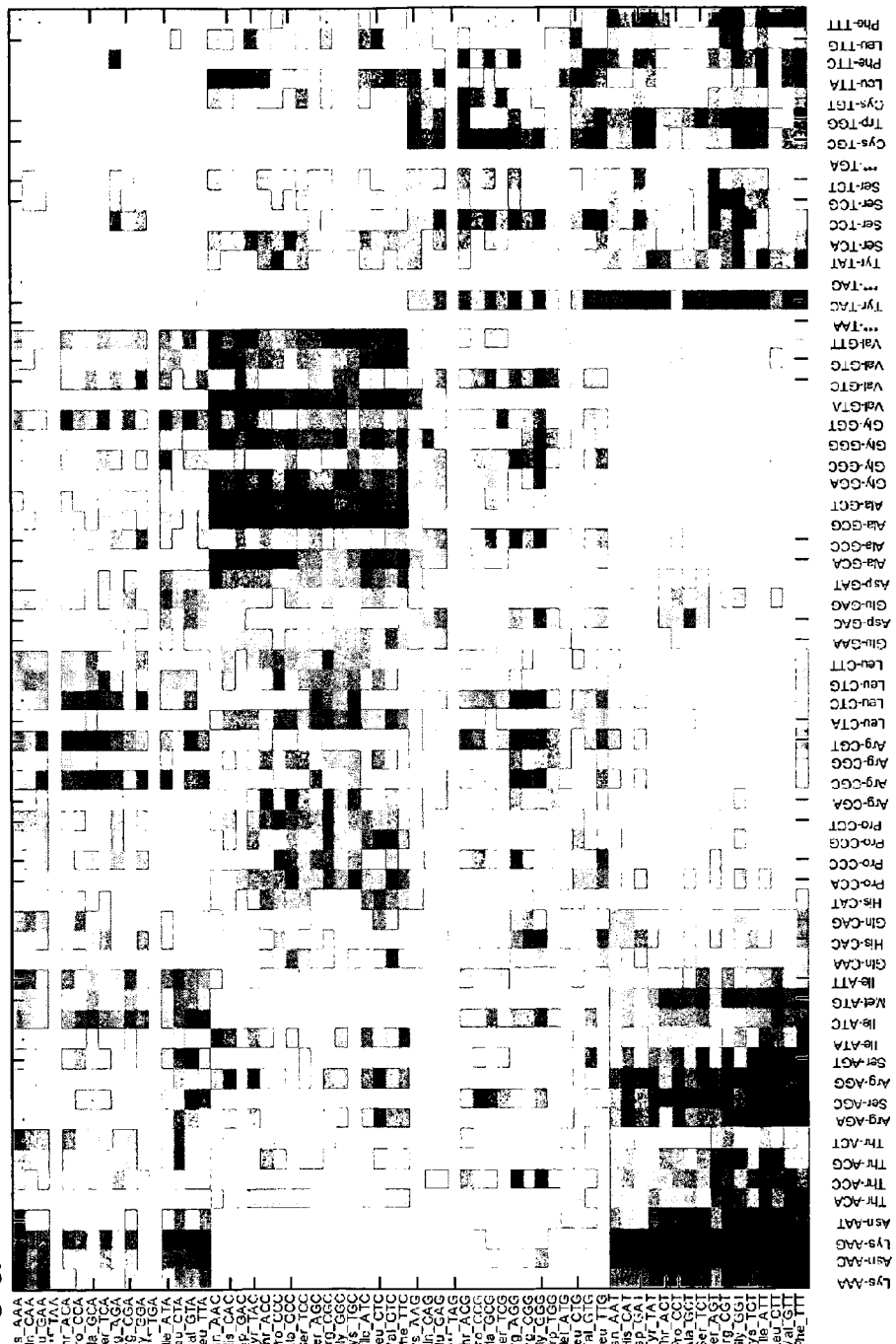

In addition, we refer to CPW matrix-tables in Appendix 3, which contain the numerical values of the bias of the codon pairs and we refer to FIG. 5 as a black and white example of the colored image, whereby the skilled person may reconstruct a colored version using the numerical values from the tables in Appendix 3.

The first approach to these codon pair maps was to have the rows and columns sorted according to their alphabetical order (as this is the order of their internal representation). What could be seen in that map was that the diagonals seemed to contain slightly more green than red spots, which indicates that many codons have a preference for the same codon as its neighbor. Furthermore, most neighboring columns were somewhat similar where neighboring rows were mostly not (data not shown) see FIGS. 5A and 5B and Appendix 3, Table C1. However most rows were similar to a row separated by three others, i.e. there was some similarity of every fourth row.

Figure 7B:
FIG. 7 shows a codon bias map for *E. coli*. The bias values range from −0.97 to 0.85, where in other organisms they might even get slightly above +−0.9 (see also FIG. 3). The highest intensities of black in these diagrams represent values of 0.9 (FIG. 7A for the positive values, green in the original) and −0.9 (FIG. 7B for the negative values, red in the original).

Since the common property of every fourth row is the last nucleotide of the first codon of the pairs, it is more preferred to sort rows sorted according to the alphabetical order of the third position as first sorting criterion and the middle position as second. What can then be seen in the map for *A. niger* (FIGS. 5C and D, and Appendix 3, Table C1) is that bias seems to correlate indeed mainly with the last nucleotide of the first (5') and the first nucleotide of the second (3') codon, as most values of the respective blocks of 16*16 codon pairs have the same color. For example, a general rule that can be identified in *Aspergillus* is that codon pairs like xxT-Axx (x denoting any nucleotide, indicating that the one at the respective position is not important for the specified rule) are rejected (red block in the lower left corner), whereas the pattern xxA-Txx characterizes preferred codons (green block in the top right corner), again indicating that codon pair bias is directional. However, not all bias can be explained just with patterns in the two neighboring nucleotides in the "middle" of the codon pair. xxC-Axx codon pairs, for example (see second block from top on the very left), are not generally preferred or rejected, but there is a clear preference for pairs of the pattern xxC-AAx (note the four green columns on the left of the block just mentioned). Bias can also depend on not neighboring nucleotides (e.g. the strong rejection of CxA-Gxx pairs in *B. subtilis*; see FIGS. 6A and 6B and Appendix 3, Table C4). Unfortunately, codon pair bias cannot always be attributed to such "simple" patterns (see for example the rather chaotic map for *E. coli* in FIGS. 7A and B and Appendix 3, Table C5) even when performing a cluster analysis using Spotfire DecisionSite 8.0 no general properties could be found (data not shown), i.e. the identified clusters consisted mostly of unrelated codons (i.e. no common nucleotides at the same position).

1.2.3 Relation of Bias and Expression Level

Figure 8A:
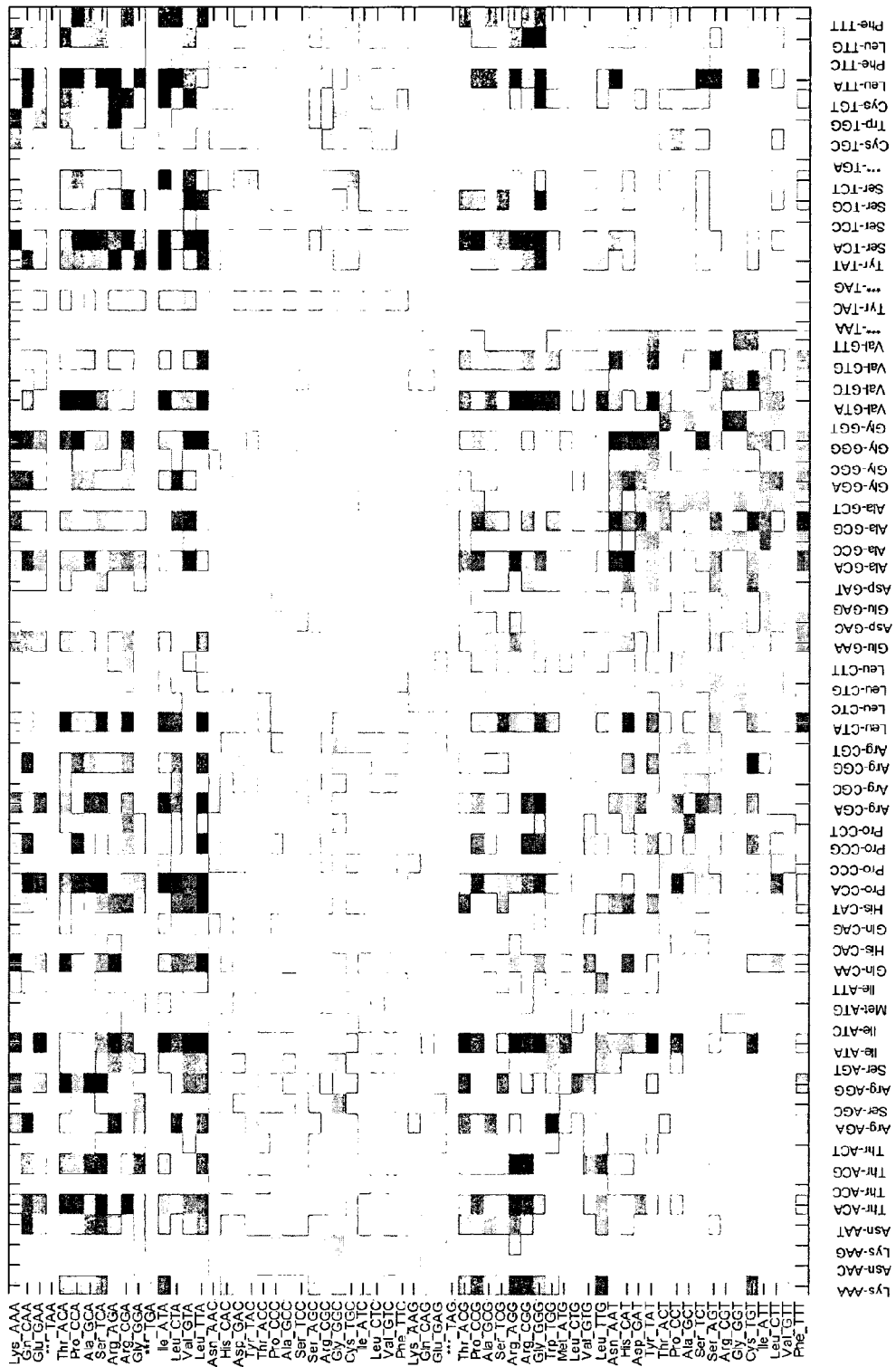
FIG. 8 shows a codon bias map for 479 highly transcribed genes of *A. niger*, analogous to the previous FIGS. 5-7. The highest intensities of black in these diagrams represent values of 0.9 (FIG. 8A for the positive values, green in the original) and −0.9 (FIG. 8B for the negative values, red in the original). The maximum bias value in this group is 0.91 the minimum is −1, i.e. some possible codon pairs do not occur at all, although their individual codons and the encoded amino acid pair do. This might be a result of the smaller size of 188,067 codon pairs, compared to 5,885,942 in the full genome. However, the main reason will be the real under representation of such pairs due to selection in highly expressed genes.

Looking at the bias map for the genes with high expression level (or better: presumably high expression level, since they were identified by looking at transcription levels only) of *A. niger* (see FIG. 8), the existence of larger groups, i.e. blocks in the diagram, is not as obvious (or, in other words, simple rules as described above might not exist at all). Yet since two thirds of all codon pairs occur 36 or less times in this group, and because of the on average much lower z-scores as mentioned above, one can attribute this to a large extent to random fluctuations.

Figure 9:
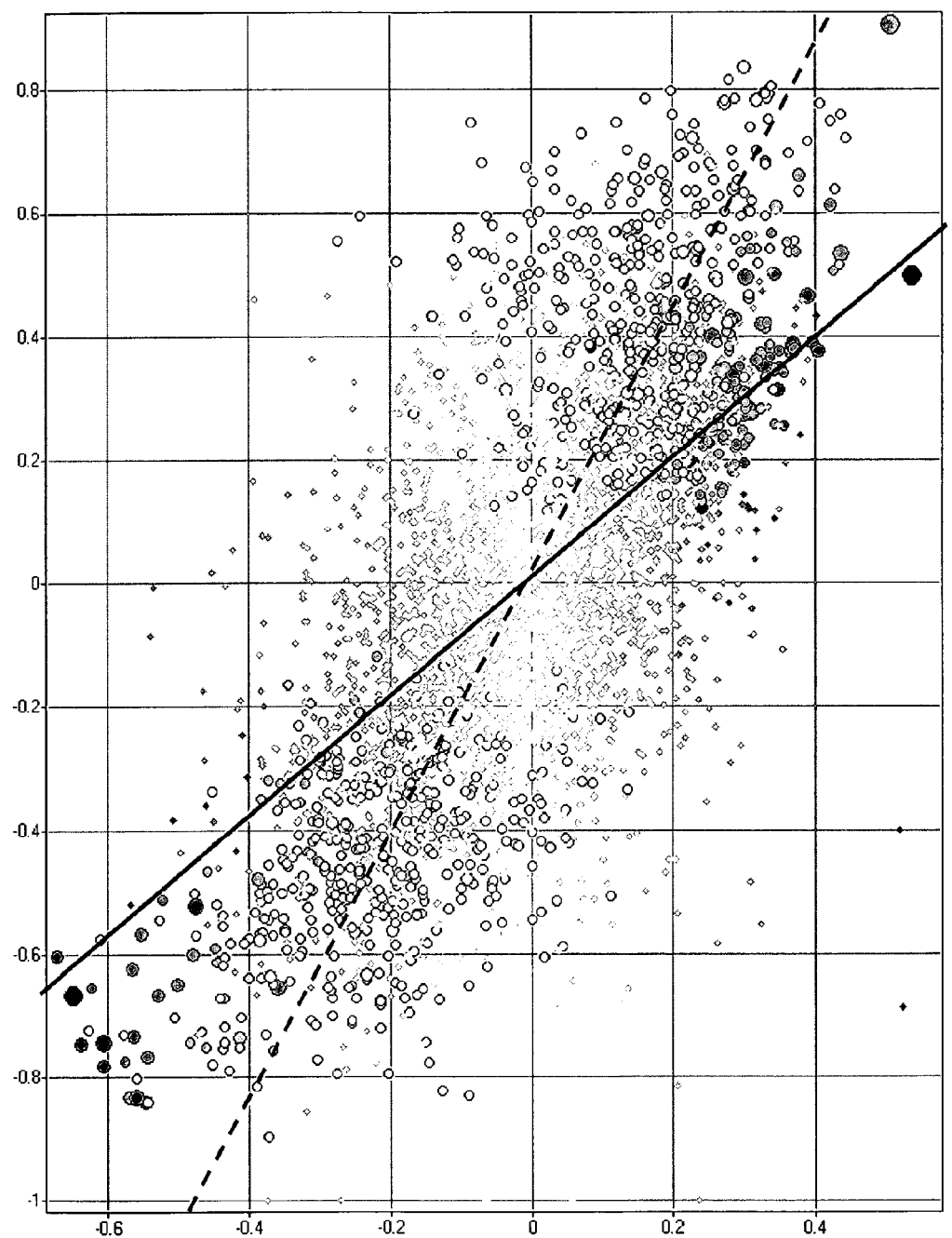
FIG. 9 shows a Scatter plot of bias in a group of 479 highly expressed genes (vertical axis) versus the bias in all genes (horizontal) of *A. niger*. All 3,721 codon pairs not involving stop codons are shown. Colours from light grey to black were assigned according to the absolute values of the z-scores in the overall genome, i.e. light dots in the plot do not have a significant bias in all genes), as were sizes according to the absolute z-scores in the highly expressed group, i.e. very small dots do not have a significant bias there (here |z-score|<1.9). The solid black line indicates where both bias values are equal; the dashed line shows the best linear approximation of the actual correlation (identified by principal component analysis); its slope is around 2.1.

FIG. 9 shows a scatter plot of bias in a group of 479 highly expressed genes (vertical axis) versus the bias in all genes (horizontal) of *A. niger*. All 3,721 codon pairs not involving stop codons are shown.

Shading from light gray to black were assigned according to the absolute values of the z-scores in the overall genome, i.e. light dots in the plot do not have a significant bias in all genes), as were sizes according to the absolute z-scores in the highly expressed group, i.e. very small dots do not have a significant bias there (here |z-score|<1.9). The solid black line indicates where both bias values are equal; the dashed black line shows the best linear approximation of the actual correlation (identified by principal component analysis); its slope is around 2.1.

When comparing the two bias values of each codon pair in the highly expressed group and in the full genome (see the scatter plot in FIG. 9), one can see that for most pairs the bias in the highly transcribed group is more extreme, i.e. lower if it is below 0 and higher if it is positive, but there are some pairs where the bias values are quite different and even have a different sign. However, these are mostly codon pairs with a small number of occurrences in the top group, and most pairs where the bias is highly significant (blue, large circles) have similar biases in both groups (i.e. they are close to the blue line that indicates where both bias values are equal).

No specific patterns regarding similar bias differences of codons that share two of the three nucleotides could be found (neither for *A. niger* nor for *B. subtilis*), i.e. in plots of the bias difference analogous to the one above there were no larger groups with similar bias difference.

1.3. Details of the Identification of Codon Pair Weights for Gene Adaptation Codon pair weight for adaptation can be determined now according the described methods (Appendix 1: Codon pair weights—method one sequence group (or genome)):
1. based on the full set of genes; based on a subset of 1.
2. being identified as the fraction of highly expressed genes.

In addition, we started a search to identify codon pair weights that clearly relate to a higher transcription level, which is required for a improved method for adaptation of codon pair usage, the following methods have been applied: In *A. niger*, where a complete ranking extracted from GeneChip data was available for the aforementioned set of 4,584 actually expressed genes (see "Data" in "Materials and Methods"), the mean codon pair weights of each gene (i.e. the equivalent of the fitcp(g) values) were calculated. Then the genes were sorted according to fitness values (ascending order) and expression level (descending order). Since highly expressed genes are supposed to have low codon pair fitness values, these two rankings would be equal when using ideal codon pair weights, so a comparison of these two rankings can give information about the quality of the weights used in the fitness function (where slightly more attention was given to the "correct" ranking of the highly expressed genes than to the ranking of the mediocre ones). Additionally, the correlation coefficient (covariance divided by the standard deviation of each variable) between ranking and average codon pair weights of the 4,584 genes was calculated.

Several possible sets of weights have been examined, including
  i. bias values from the whole genome,
  ii. bias values of the highly expressed group,
  iii. bias with all the values that do not have a certain minimum z-score set to zero
  iv. bias values raised to the power of 2 (and some other values) to give highly preferred or rejected codons a lower/higher influence
  v. combinations thereof
  vi. z-scores themselves
  vii. difference of bias values/z-scores from the highly expressed group and the full genome.

For the genetic algorithm (GA), their negations have been used, since preferred codon pairs had been identified with positive values (rather arbitrarily), but the GA performs minimization. This applies to all weights mentioned.

Figure 10:
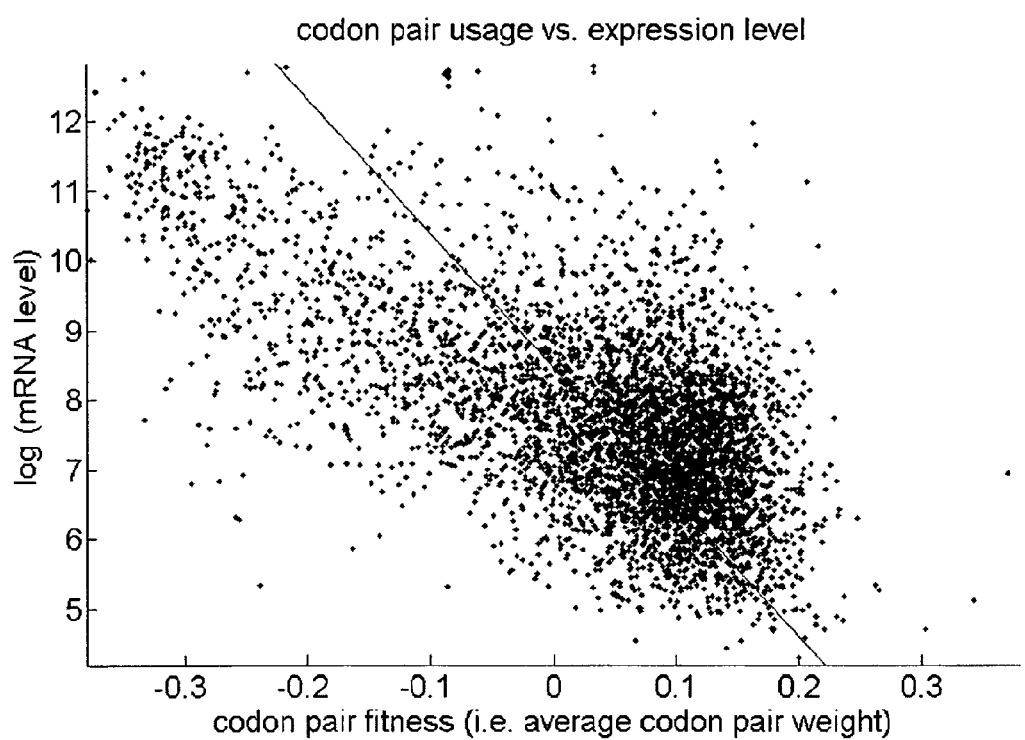
FIG. 10 Fitness values of the 4,584 *A. niger* genes compared to the logarithm of their transcription levels. The correlation coefficient is −0.62.

Out of these, the "best" weight matrix turned out to be a combination of item ii to iv, however, an even better one could be obtained—as described above—by calculating the codon pair "bias" in the highly expressed group using expected values calculated based on the codon ratios of the whole genome. FIG. 10 shows the correlation that is observed.

Unlike all other weight sets tested, codon pairs involving codons that are more underrepresented in the highly expressed group get a slight disadvantage here. Thus, these weights are the only ones that also reflect the different single codon bias of the highly expressed group and all genes. Using these weights carries the risk of rejecting some codon pairs that actually have a positive bias in the highly expressed group, but consist of (in the highly expressed group) rarely used codons. However, since our desired single codon ratios are usually not identical to those in the group of genes with high expression, but more "extreme" than these, single codon optimization would replace these underrepresented anyway, so we can consider the weights described above very convenient for codon pair optimization.

Concluding, a potentially improved codon pair weight matrix for gene adaptation has been identified as described above. The equation is given in Appendix 1: Codon pair weights—method highly expressed group with reference group (or genome).

1.4. Single Codon and Codon Pair Optimization in Silico

1.4.1 Material and Methods

The developed MATLAB toolbox for analyzing and optimizing genes consists of several functions that have been organized in different directories according to their capacities. In order to use them, it is therefore necessary to make all of them known to the MATLAB environment. To do this, select "Set Path" from the File menu and then click "Add with subfolders" and select the path where the toolbox is installed (usually called "Matlab-bio"). Also add the location of FASTA and other files that should be analyzed. All individual MATLAB functions are briefly described in "contents.m" (type "help Matlab-bio" to display this file in the MATLAB environment and use "help" followed by a function's name to get detailed information about it). For gene optimization focusing on codon pair usage, the two important functions are "fullanalysis" and "geneopt".

If the full genome of an organism you want to adapt a gene to is located in the file, say, "Aniger_ORF.fasta" and the identifiers of its highly expressed genes are in "an-high.txt" type "fullanalysis ('Aniger_ORF.fasta', 'an-high.txt', 'an');" and you will get (i) a codon pair bias map for the full genome, (ii) a codon pair bias map for the group of genes in the second file and (iii) several variables (i.e. sets of temporarily stored data) in the MATLAB workspace for further use. The third parameter of "fullanalysis" determines only how these variables are named and can be omitted if only one genome is to be analyzed at the same time. Among the mentioned variables are: (i) codon pair usage and bias data for the full genome (named "cpan" in this example), (ii) the same for the special group of genes specified by the second parameter (named "cpans") and (iii) structure with target single codon ratios and codon pair weights that can be used for the genetic algorithm.

"fullanalysis ('Xyz_ORF.fasta');" will only show the codon pair bias map and store the bias data for the respective genome.

Although the second parameter may be any file that includes gene identifiers (e.g. a set of genes with low expression or genes with a certain common function), it is always treated like a set of highly expressed genes regarding this (potential) parameter (named "optparamforan" in the example, which stands for the optimization parameterfor the specified organism). Note that the single codon ratios here are simply calculated $r_{sc}^{target}(c_k)=2 \cdot r_{sc}^{high}(c_k)-r_{sc}^{all}(c_k)$, which is an acceptable approximation. Target ratios might be as well identified by other methods that include the details of the single codon distribution (see main text) in order to further improve specification of desired ratios. In addition, target ratios may be left empty when no specific bias is found, in order to give the codon-pair algorithm more freedom in finding solutions with a higher codon-pair fitness. Several of such pre-determined single-codon target vectors are given in Appendix 1, for various host organisms.

To use pre-specified single-codon target ratio's for the genetic algorithm, change the field "cr" of the parameter by typing "optparamforan.cr=[", then paste the single codon ratios (e.g. copied from an Excel sheet; note that they should be in alphabetical order of the codons), type "];" if the ratios are available as a 64-element row or "]';" if they are copied from a column and press enter (note the additional single quotation mark or apostrophe following the closing bracket in the latter case). Unimportant codon ratios, i.e. codons where no specific target ratio is desired, may be assigned the "value" NaN (not a number) and they will be ignored when single codon fitness is calculated.

To exclude certain short sequences from the optimized gene, set the parameter "rs" in the same way, where each sequence must be enclosed by single quotation marks and all sequences together must be enclosed in braces, e.g. (without the line break) "optparamforan.rs={'CTGCAG' 'GCG-GCGCC' };". Finally, the field cpi of the parameter might be changed to give single codon optimization or codon pair optimization a higher importance in the combined fitness function (see the subsection "performing codon pair optimization" in "results and discussion"). The default value is 0.2. Set it to a lower value if the results of the experiments with codon pair optimized genes reveal little improvement of codon pair optimized genes compared to single codon optimized ones; in the opposite case, a higher cpi might be better.

The actual optimization of the gene using the genetic algorithm can then be performed using the function geneopt. The only parameters needed are the sequence to be optimized and the structure containing codon pair weights, target ratios and restriction sites as described above, so geneopt("MUVAR-NEQST*", optparamforan); could for example be used to optimize the given (rather short) protein sequence for high expression in A. niger; the '*' is used to denote that the resulting genetic sequence should have a stop codon at the end (however, as the optimal stop signal in A. niger is believed to be the tetramer TAAA, this is not necessary). Note that the sequence to be optimized must again be enclosed in single quotation marks; if the sequence contains only the letters A, C, G, T or U and its length is a factor of 3, it is automatically regarded a nucleotide sequence. The genetic algorithm then runs for 1000 generations with a population size of 200, of which 80 each are kept for the generation (the 79 best and one randomly picked) and used to generate new individuals, where 40% of the new individuals are generated using crossover and 60% using the mutation operator. These default values turned out to be very convenient for the optimization, i.e. changes in these parameters will only, if at all, lead to very slightly "better" genes, but they can be changed as well, for example if significantly more or less calculation time should be spent on the optimization (an average run of geneopt with a gene of about 500 codons takes about 15 minutes on a 1.4 GHz Pentium M Processor). geneopt (seq, optparamforan, [50 750 5 0 0.6]) will, for example, let the genetic algorithm calculate 750 generations of a population where 50 individuals are kept for each new generation and 250 are newly generated (5*50; i.e. 300 individuals are examined in each generation), only the best (and no randomly picked) individuals are kept and 60% of the recombinations are performed using the crossover operator. For more details on how to specify these parameters, type help geneopt and help geneticalgorithm.

Note that although the procedure of generating codon pair weights from analyzing the corresponding FASTA files is shown and described here for A. niger and B. subtilis, just for these two organisms this is not necessary because these calculations have already been performed for previous gene optimizations. For easier use, the respective parameters for the genetic algorithms have been stored (type "load gadata_for_an" or "load gadata_for_bs", respectively; note that the parameters there are now just simply called an_param and bs_param.

1.4.2 Results

Figure 11:
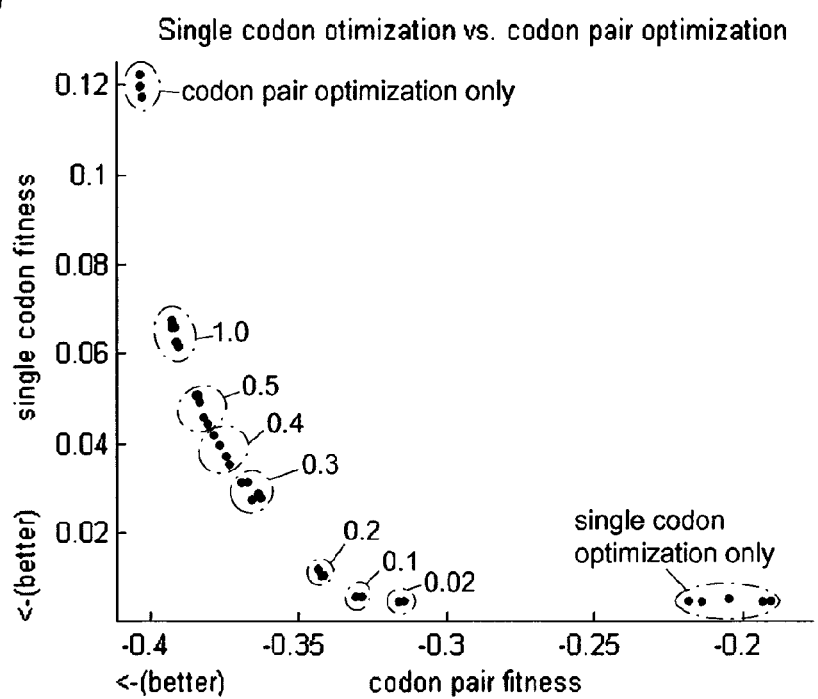
FIG. 11 shows single codon vs. codon pair optimization. The wild type ($\text{fit}_{sc}(g_{FUA})=0.165$, $\text{fit}_{cp}(g_{FUA})=0.033$) does not fit on this plot (it would be far to the right and above). It is clear that the cpi parameter determines a trade-off between single codon and codon pair fitness. The optimal gene is always the one with the lowest values for $\text{fit}_{sc}$ and $\text{fit}_{cp}$. Given the position of the dots, it is therefore not clear for which value of cpi the best gene could be obtained, since we do not know yet whether single codon usage or codon pair usage is more important. Although, the examples provides strong evidence that codon pair fitness is very important in addition to single-codon fitness, which means that cpi should be chosen at least >0.

FIG. 11 shows fitness values of five optimized versions each for different values of cpi (see legend of the diagram in FIG. 11). The protein is a fungal α-amylase (FUA; also referred to as AmyB) that was optimized for the host A. niger (see Example 2). Additionally, the results of "pure" single codon optimization (black dots on the right) and codon pair optimization are shown (group top left). The optimized versions were obtained by running the genetic algorithm for around 1000 generations with a population size of 400, which took about 17 minutes for each run on a 1.4 GHz Pentium M. Note that pure single codon optimization and pure codon pair optimization took only about 60% of that time.

In FIG. 11 the wild type ($fit_{sc}(g_{fua})$=0.165, $fit_{cp}(g_{fua})$=0.033) does not fit on this plot (it would be far to the right and above). The optimal gene is always the one with the lowest values for $fit_{sc}$ and $fit_{cp}$. Given the position of the dots, it is therefore not clear for which value of cpi the most improved gene could be obtained, since we do not know yet whether single codon usage or codon pair usage is more important. However, a fare trade-off seems to appear in case of cpi=0.2.

The improvement in single codon and codon pair usage can be visualized in so-called sequence quality plots proposed in this work. FIG. 12 illustrates two diagrams which show the sequence quality of the first 20 (out of 499) codons of the aforementioned FUA (see also Example 2).

Note that these sequence quality diagrams not only depend on the sequence itself, but also on the set of weights and the desired single codon ratios and thus on the organism. Note also that it is possible to define target single codon ratios as "don't care" for those codons with low or no codon bias, i.e. the usage of a certain codon is not considered positive or negative for expression compared to its synonymous codons. In that case, only the blue x-mark is shown for the actual ratio of the respective codon in the gene and that particular position is ignored when calculating single codon fitness (see 1.4. Single codon and codon pair optimization in silico).

1.5 Conclusions

A significant correlation of codon pair usage and transcription levels has been established in a wide range of organisms. It was demonstrated that this bias cannot only be explained by dinucleotide bias around the reading frame site. Since possible explanations for preference or rejection of certain codon pairs all focus on the translation, it should be assumed that both are caused by natural selection acting at the same time on characteristics that affect translation and other characteristics that affect transcription in order to minimize the cell's efforts to produce enzymes or at least the more important of them.

Optimizing codon pair usage in polypeptide coding sequences can thus be considered for achieving improved overexpression, in addition to classic single-codon optimization or single codon harmonization, where only single codons frequencies are considered for optimization. Codon pair adaptation and single codon adaptation of the same gene interfere only slightly for the investigated fungal host class and the bacilli in this example, i.e. both can be performed at the same time and the result will have "better" single codon usage and "better" codon pair usage than the wild-type gene, and any of the two aspects can only be improved slightly when ignoring the other one.

To read the FASTA files and perform the analysis and optimization, user-friendly MATLAB functions have been designed. New methods of visualizing codon pair bias and codon pair usage of single genes have been introduced as well, see Example 2 and Example 4. The genetic algorithm designed for the optimization allows effective dealing with the constraints imposed by interdependence of adjacent codon pairs while the specially designed mutation operators that always improve one of the two aspects of sequence quality (single codon an codon pair fitness) help to circumvent the inefficiency usually accompanying genetic algorithms because of their trait of generating many bad possible solutions in the recombination step after the first few generations.

The proper codon pair usage influences enzyme production, which will be shown experimentally in the following examples. Codon pair optimized variants of three genes to be expressed in *B. subtilis* have been prepared, of which one each will be compared to a synthetic gene that has adapted single codon usage only and another one to a synthetic gene that has gone through the optimization process using the negation of the presumably positive weights, but still been optimized for single codon usage the same way as before, see Example 4 and Example 5. This way, the notion of Irwin et al. (1995) that underrepresented codons stimulate translation, which was rejected here, will also put to the test. For *A. niger*, a codon pair optimized version of the aforementioned amyB will be tested and compared to the wild-type and synthetic gene with single codon harmonization, see Examples 2 and 3.

2. Example 2

Use of a Method of the Invention for Construction of Improved DNA Sequences for Improving Production of the *Aspergillus Niger* Fungal Amylase Enzyme in *A. Niger*

Below, the method of the invention is applied to design novel nucleotide sequences for the AmyB (FUA) gene of *A. niger*, which are optimized in single codon and/or codon pair usage for improved expression in *A. niger*. This method can be applied the same way for the improvement of codon use of any nucleotide sequence.

2.1 Introduction

A concept of single-codon optimization by means of codon-harmonization was previously developed by the applicants of this invention and reported in the main text (see also example 3). In this example we show how one applied the method of the invention to design a gene that were optimized for both single codon and codon pair usage. In this specific case weight matrices are applied that have been created by applying two subsets of 2% and 4% of highly expressed genes of the full *A. niger* genome that contains 14,000 genes. For the single-codon usage the algorithm has driven the solution to a gene with synonymous codon-frequencies as defined by Table B.1 (=column 3 of Table 2.1), while for the codon-pair usage, it will optimized toward an optimal set of codon-pairs with a high frequency of them having associated negative weights (in Table C.2), being the codon-pairs that are over-represented with respect to its expected values in the set of 4% highly expressed genes. Note that in case one does not have a defined list of highly expressed genes for a specified host, one can also (i) apply the weight matrices of a similar host organism, for example the P. *chrysogenum* matrices can be applied for *A niger*; or (ii) apply the full genome sequence data or a subset of it to derive good, but less optimal weight matrices.

2.2 Materials and Methods

2.2.1 Wild-Type AmyB Coding Sequence Encoding *A. Niger* Alpha-Amylase AmyB The DNA sequence of the amyB gene encoding the alpha-amylase protein was disclosed in J. Biochem. Mol. Biol. 37(4):429-438 (2004) (Matsubara T., Ammar Y. B., Anindyawati T., Yamamoto S., Ito K., Iizuka M., Minamiura N. "Molecular cloning and determination of the nucleotide sequence of raw starch digesting alpha-amylase from *Aspergillus awamori* KT-11.") and also can be retrieved from EMBL Nucleotide Sequence Database under accession number AB083159. The genomic sequence of the native *A. niger* amyB gene is shown as SEQ ID NO. 1. The corresponding coding or cDNA sequence of amyB is shown as SEQ ID NO. 2. The translated sequence of SEQ ID NO. 2 is assigned as the SEQ ID NO. 3, representing the *A. niger* alpha-amylase protein AmyB. This sequence has also a 100% similarity with the *A. oryzae* alpha-amylase protein Wirsel S., Lachmund A., Wildhardt G., Ruttkowski E., "Three alpha-amylase genes of *Aspergillus oryzae* exhibit identical intron-exon organization."; Mol. Microbiol. 3:3-14(1989, UniProt accession nr. P10529, P11763 or Q00250). Optimization according a method of the invention has been performed on the amyB cDNA sequence.

2.3 Design Procedure

The optimized coding nucleotide sequence SEQ ID NO 6 is the result of a run with the described software method. The applied parameters were: population size=200; number of iterations=1000; cpi=0.20, CPW matrix="Table C.2. CPW: *Aspergillus niger*—highly expressed sequences" and the CR matrix="Table B.1 column 4: CR table ANS: *Aspergillus niger*—highly expressed sequences". Moreover, a penalty value of +1 is added to $\text{fit}_{combi}$ for each occurrence of a PstI (CTGCAG) and NotI (GCGGCCGC) site.

Figure 13:
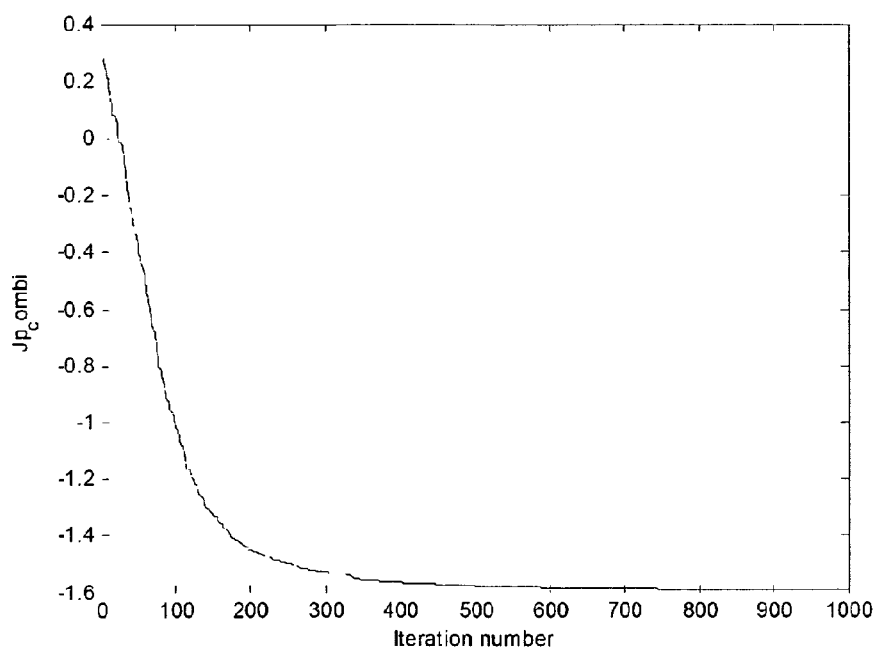
FIG. 13 depicts the convergence of $\text{fit}_{combi}$ using the described genetic algorithm approach of the invention for optimization of the amyB gene that results in SEQ ID NO. 6.
Figure 14:
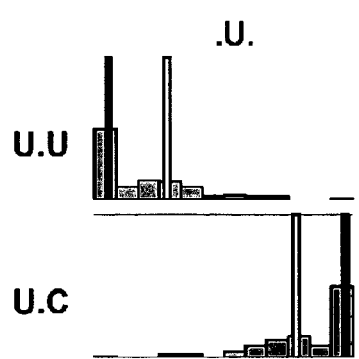
FIG. 14 depicts, for reasons of explanation, a part of a single-codon distribution diagram, like one is shown for example in FIG. 15. The two graphs indicate the single-codon usage for the two synonymous codons that code for phenylalanine: UUU (top) and UUC (bottom). The X-axis and Y-axis of both graphs goes from 0% to 100%. The grey histogram is a codon-usage histogram, normalized for each amino acid (group of synonymous codons), for a group of 250 highly expressed A. niger genes, where the genes are binned in groups having 0%, >0-<10%, 10-<20%, ... , 90-<100%, 100%. For example, 50% of the highly-expressed genes fall in the group with 0% usage of the UUU codon, and consequently 100% usage of the UUC codon for coding phenylalanine. The white bar gives the codon-usage of gene A (WT amyB in this case) in similar bins as for the histogram; thus 100% in bin 20-30% (20% with 3/15 codons being UUU) for gene A, and consequently 100% in bin 80-<90% (80% with 12/15 being UUC). The black bar gives the statistics for gene B (the single-codon optimized variant for amyB in this case). In a similar way, one can create a matrix of 16 times 4 graphs, showing statistics for all 64 codons, see for example FIG. 15.
Figure 15:
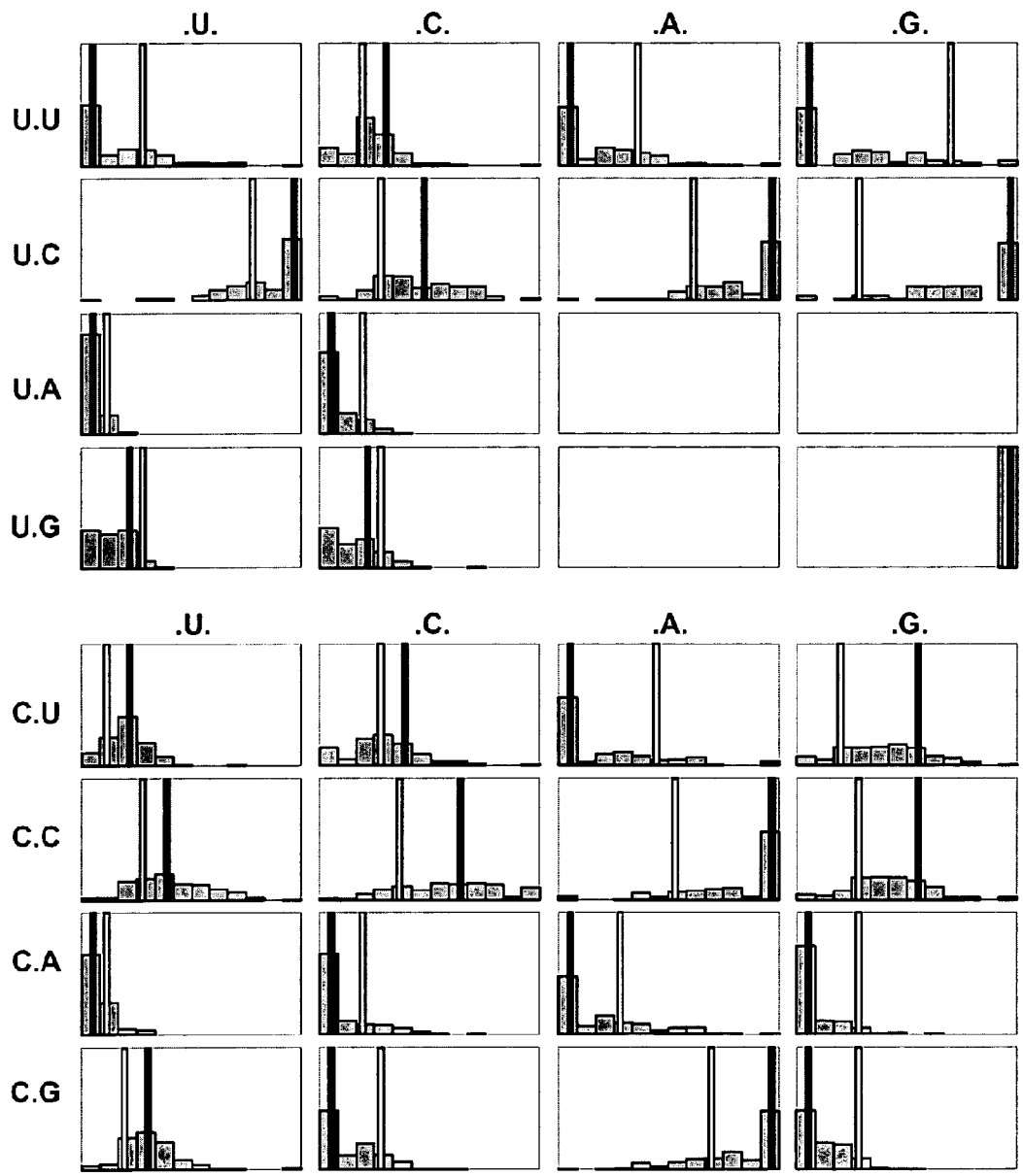
FIG. 15 (parts 1 and 2) depicts the single-codon frequency for the single-codon optimized amyB gene (black) versus the wild-type amyB gene (white). The grey histogram depicts the statistics for 250 highly-expressed genes in A. niger. It is clear that certain codons, like the one for cysteine (UGU/UGC), histidine (CAU/CAC), tyrosine (UAU/UAC) and others were subject to real improvements.
Figure 15:
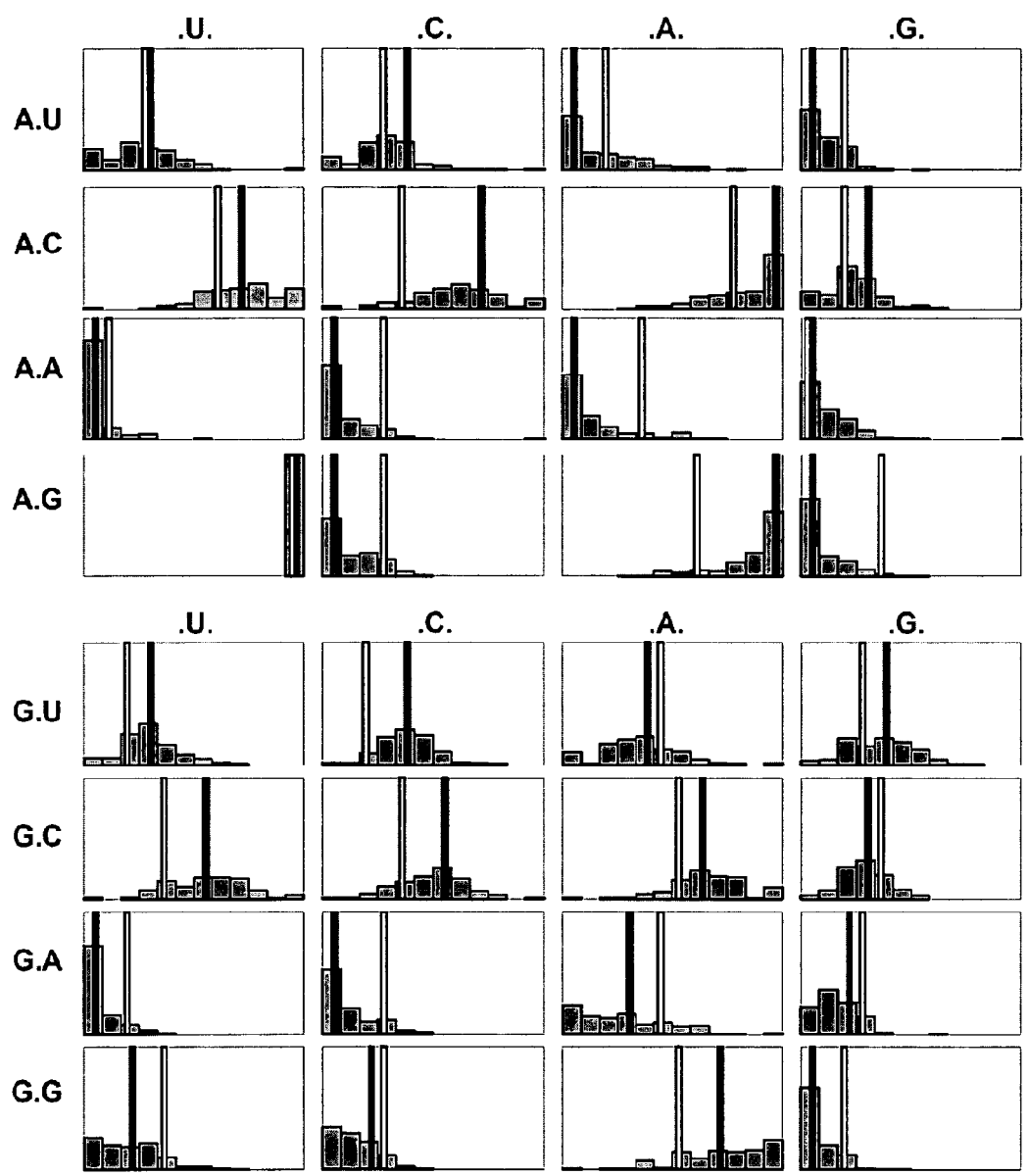
Figure 16:
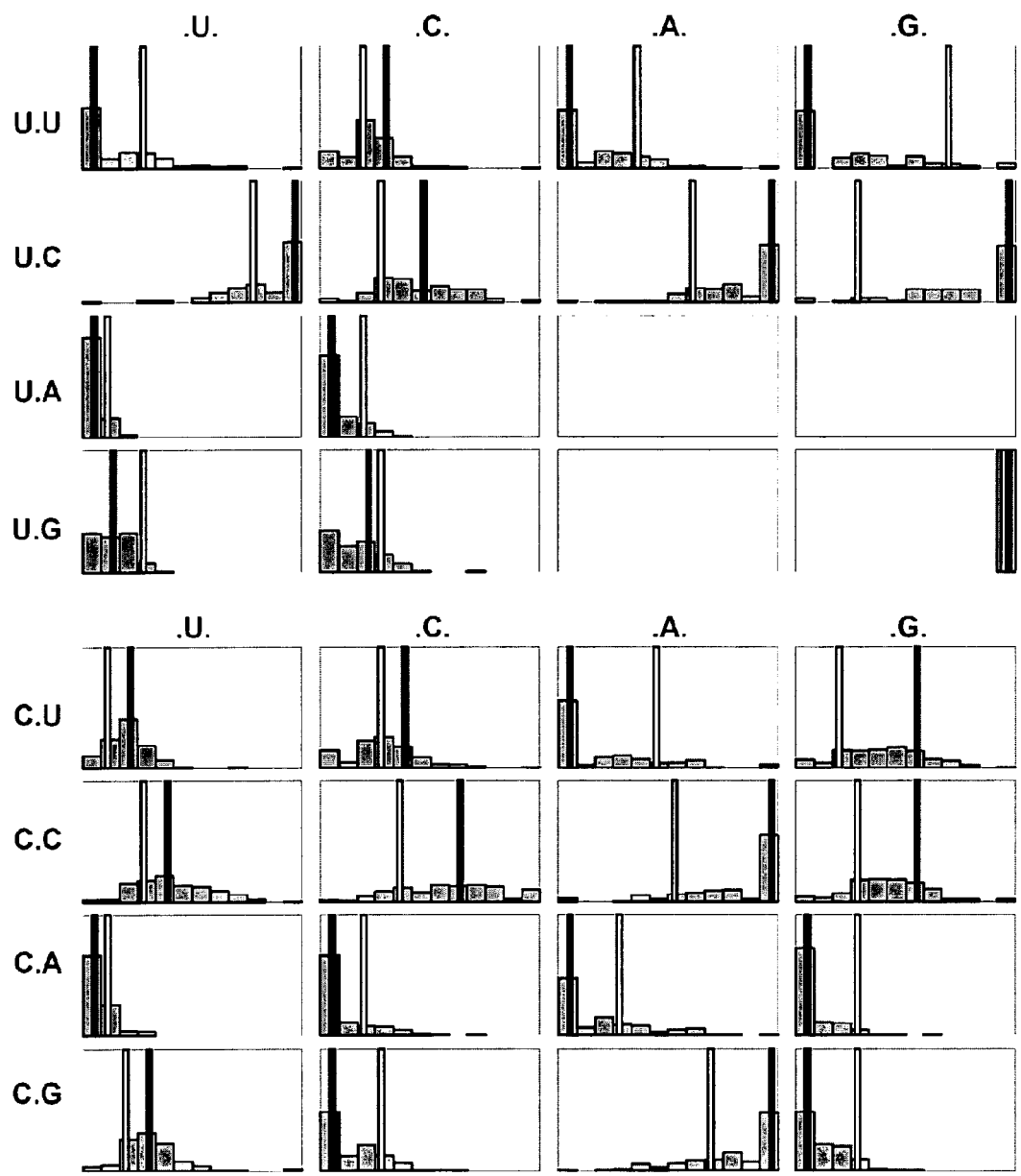
FIG. 16 (parts 1 and 2) depicts the single-codon frequency for an amyB gene that has been optimized with respect to both single-codon and codon-pairs (black) versus the wild-type amyB gene (white). The grey histogram depicts the statistics for 250 highly-expressed genes in A. niger. It is clear that these graphs highly resemble the situation for the single-codon optimized gene depicted in FIG. 15.
Figure 16:
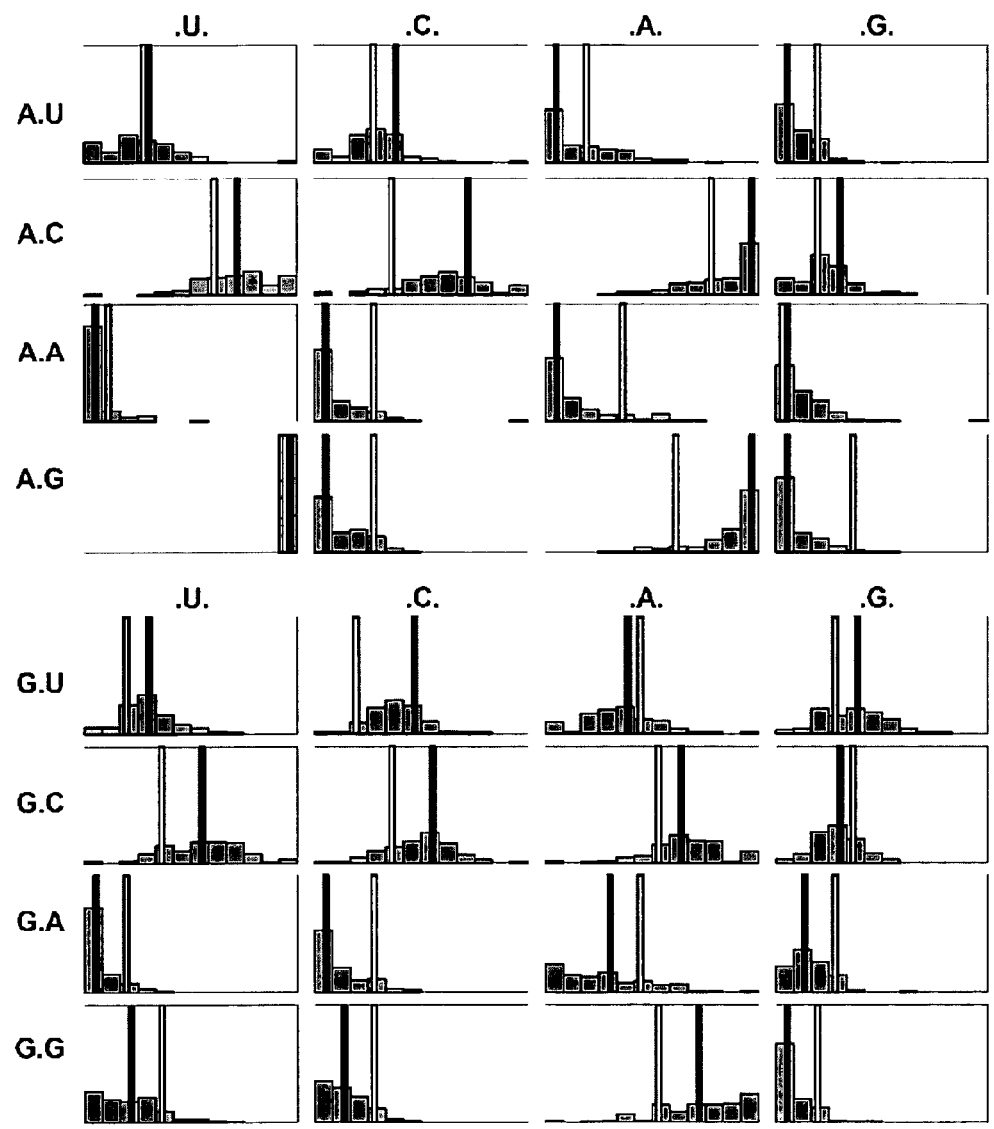
Figure 17:
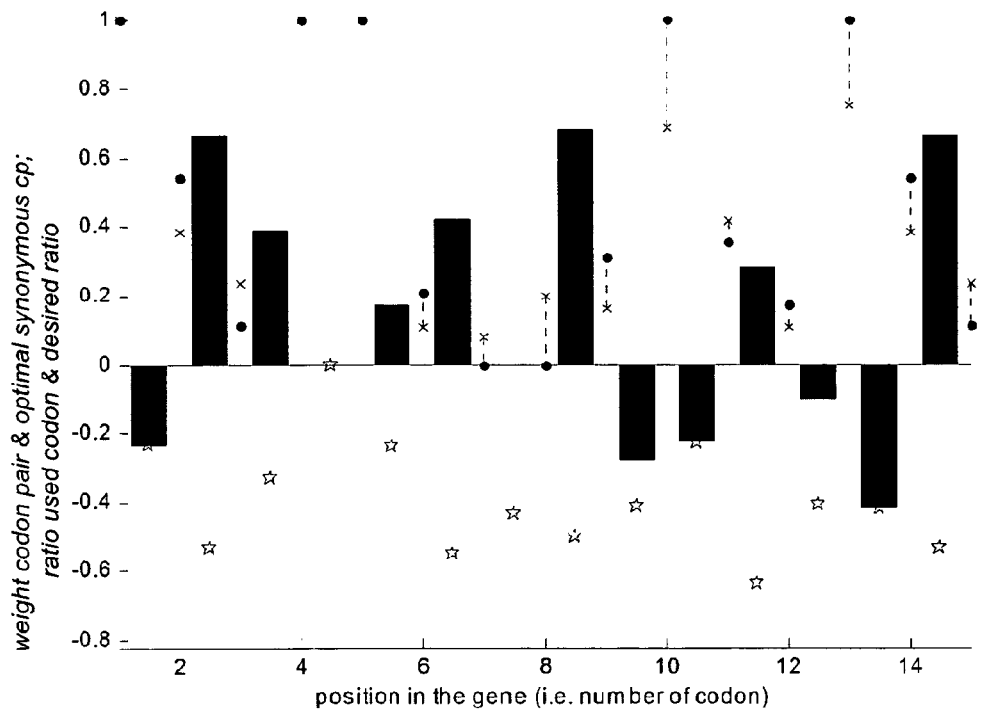
FIG. 17 depicts a part of the full diagram (FIG. 18) with single-codon and codon pair statistics for the WT amyB gene of A. niger. On the X-axis, one finds the subsequent codons in a gene starting at position 1 with the start-codon ATG. The black dot '.' indicates the target single-codon ratio for the codon at this position with respect to its synonymous codons. For ATG this is 1.0 (100%). The cross 'x' is the actual codon ratio it the shown gene; a dotted line shows the difference between the target ratio and the actual ratio. The codon-pair weight is a value between −1 and 1. The bar indicates the actual codon-pair weight of the adjacent codons, while the pentagram indicates the weight of the optimal achievable synonymous codon-pair (not taking into account the neighboring pairs). For example the first bar is −0.23 which is the weight for 'ATG-GTC', second is 0.66 being the weight for 'GTC-GCG'.
Figure 18:
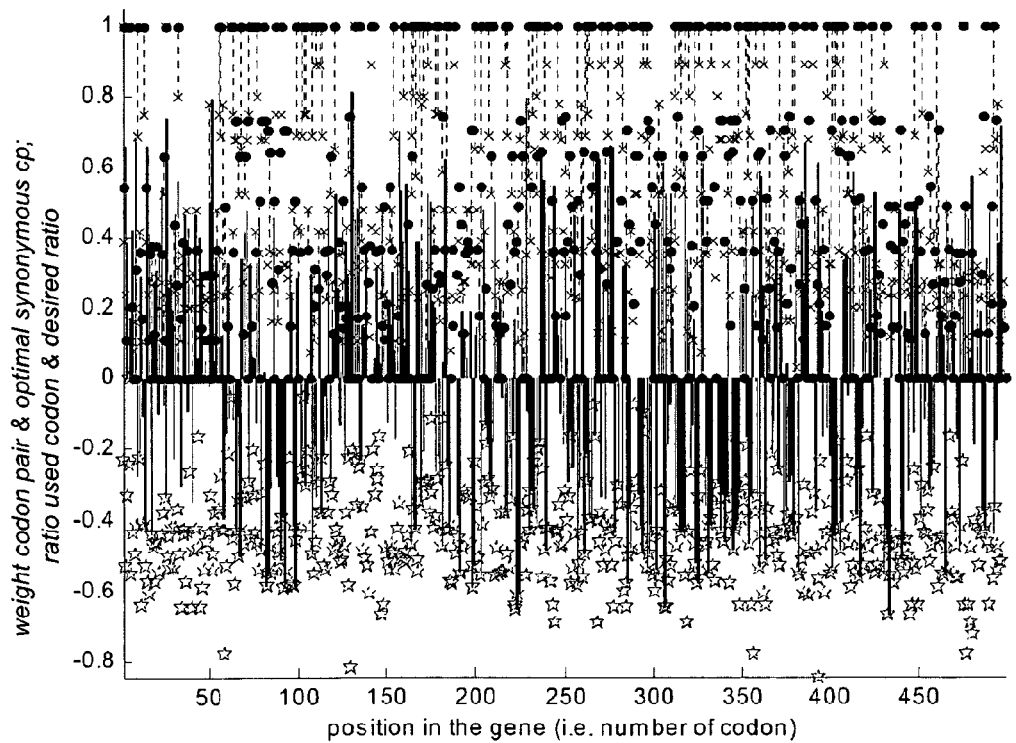
FIG. 18 depicts the single codon and codon pair statistics for SEQ ID NO. 2 (WT AmyB).
Figure 19:
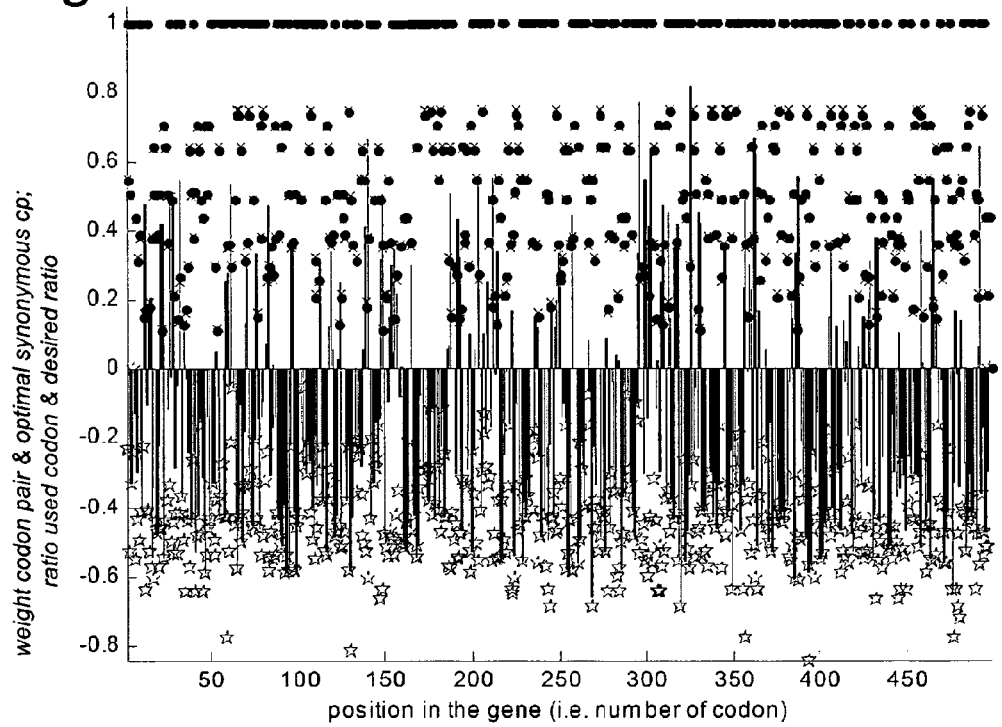
FIG. 19 depict the single codon and codon pair statistics for SEQ ID NO. 5 (single codon-optimized AmyB).
Figure 20:
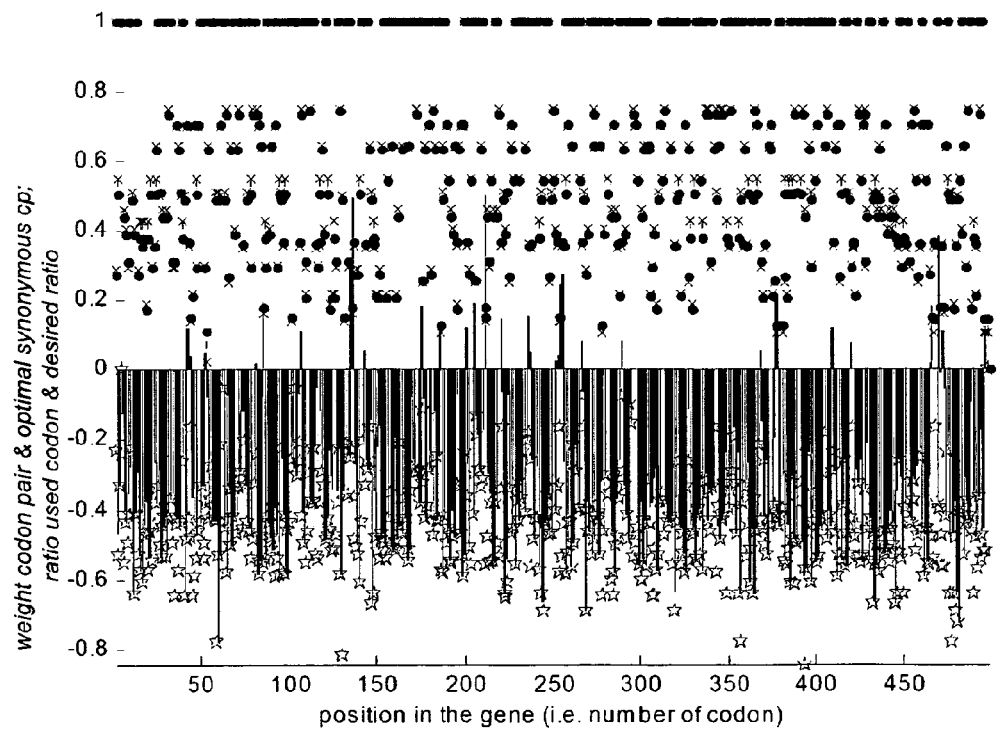
FIG. 20 depict the single codon and codon pair statistics for SEQ ID NO. 6 (single codon and codon pair optimized WT AmyB).

Convergence of the solution toward a minimal value for $\text{fit}_{combi}$ is shown in FIG. 13. The obtained objective values for SEQ ID NO. 6 are given in Table 2.2, together with those for SEQ ID NO. 2 and SEQ ID NO. 5. FIG. 14 explains the single codon statistics for these genes as is shown in FIGS. 15 and 16, and Table 2.2 gives the actual values for the codons in the three sequences. FIG. 18-20 show both single-codon and codon pair statistics for the three gene variants. This type of graph is explained in detail in FIG. 17 and its description. From these graphs it is clear that single-codon statistics are highly similar for SEQ ID NO. 5 and SEQ ID NO. 6. However, the method of the invention leads to a gene with an improved number of codon pairs with associated negative weights ($w_{cp}(g) \leq 0$), 93% vs. 74%, and also a further reduction in $fit_{cp}$ from −0.18 to −0.34 indicating a more optimal usage of codon pairs having more negative weights associated with them.

TABLE 2.1

Codon optimization for amyB.

| AA | Codon | Optimal codon distribution [%] | amyB w.t. [# codons] | amyB w.t. [% codons/AA] | amyB sc optimized [# codons] | amyB sc & cp optimized [# codons] |
|---|---|---|---|---|---|---|
| A | Ala_GCT | 38 | 5 | 11.9 | 16 | 18 |
|   | Ala_GCC | 51 | 15 | 35.7 | 21 | 23 |
|   | Ala_GCA | 0 | 12 | 28.6 | 0 | 0 |
|   | Ala_GCG | 11 | 10 | 23.8 | 5 | 1 |
| C | Cys_TGT | 0 | 7 | 77.8 | 0 | 0 |
|   | Cys_TGC | 100 | 2 | 22.2 | 9 | 9 |
| D | Asp_GAT | 36 | 20 | 47.6 | 15 | 15 |
|   | Asp_GAC | 64 | 22 | 52.4 | 27 | 27 |
| E | Glu_GAA | 26 | 5 | 41.7 | 3 | 3 |
|   | Glu_GAG | 74 | 7 | 58.3 | 9 | 9 |
| F | Phe_TTT | 0 | 3 | 20.0 | 0 | 0 |
|   | Phe_TTC | 100 | 12 | 80.0 | 15 | 15 |
| G | Gly_GGT | 49 | 10 | 23.3 | 21 | 22 |
|   | Gly_GGC | 35 | 18 | 41.9 | 15 | 15 |
|   | Gly_GGA | 16 | 10 | 23.3 | 7 | 6 |
|   | Gly_GGG | 0 | 5 | 11.6 | 0 | 0 |
| H | His_CAT | 0 | 3 | 42.9 | 0 | 0 |
|   | His_CAC | 100 | 4 | 57.1 | 7 | 7 |
| I | Ile_ATT | 27 | 7 | 25.0 | 7 | 7 |
|   | Ile_ATC | 73 | 19 | 67.9 | 21 | 21 |
|   | Ile_ATA | 0 | 2 | 7.1 | 0 | 0 |
| K | Lys_AAA | 0 | 7 | 35.0 | 0 | 0 |
|   | Lys_AAG | 100 | 13 | 65.0 | 20 | 20 |
| L | Leu_TTA | 0 | 1 | 2.7 | 0 | 0 |
|   | Leu_TTG | 13 | 10 | 27.0 | 5 | 4 |
|   | Leu_CTT | 17 | 4 | 10.8 | 6 | 7 |
|   | Leu_CTC | 38 | 13 | 35.1 | 14 | 15 |
|   | Leu_CTA | 0 | 3 | 8.1 | 0 | 0 |
|   | Leu_CTG | 32 | 6 | 16.2 | 12 | 11 |
| M | Met_ATG | 100 | 10 | 100.0 | 10 | 10 |
| N | Asn_AAT | 0 | 3 | 11.5 | 0 | 0 |
|   | Asn_AAC | 100 | 23 | 88.5 | 26 | 26 |
| P | Pro_CCT | 36 | 6 | 27.3 | 8 | 8 |
|   | Pro_CCC | 64 | 8 | 36.4 | 14 | 14 |
|   | Pro_CCA | 0 | 3 | 13.6 | 0 | 0 |
|   | Pro_CCG | 0 | 5 | 22.7 | 0 | 0 |
| Q | Gln_CAA | 0 | 5 | 25.0 | 0 | 0 |
|   | Gln_CAG | 100 | 15 | 75.0 | 20 | 20 |
| R | Arg_CGT | 49 | 1 | 10.0 | 5 | 5 |
|   | Arg_CGC | 51 | 2 | 20.0 | 5 | 5 |
|   | Arg_CGA | 0 | 2 | 20.0 | 0 | 0 |
|   | Arg_CGG | 0 | 2 | 20.0 | 0 | 0 |
|   | Arg_AGA | 0 | 0 | 0.0 | 0 | 0 |
|   | Arg_AGG | 0 | 3 | 8.1 | 0 | 0 |
| S | Ser_TCT | 21 | 4 | 10.8 | 8 | 8 |
|   | Ser_TCC | 44 | 9 | 24.3 | 16 | 17 |
|   | Ser_TCA | 0 | 4 | 10.8 | 0 | 0 |
|   | Ser_TCG | 14 | 10 | 27.0 | 5 | 4 |
|   | Ser_AGT | 0 | 4 | 10.8 | 0 | 0 |
|   | Ser_AGC | 21 | 6 | 16.2 | 8 | 8 |
| T | Thr_ACT | 30 | 9 | 22.5 | 12 | 12 |
|   | Thr_ACC | 70 | 13 | 32.5 | 28 | 28 |
|   | Thr_ACA | 0 | 10 | 25.0 | 0 | 0 |
|   | Thr_ACG | 0 | 8 | 20.0 | 0 | 0 |
| V | Val_GTT | 27 | 5 | 16.1 | 8 | 9 |
|   | Val_GTC | 54 | 12 | 38.7 | 17 | 17 |
|   | Val_GTA | 0 | 4 | 12.9 | 0 | 0 |
|   | Val_GTG | 19 | 10 | 32.3 | 6 | 5 |
| W | Trp_TGG | 100 | 12 | 100.0 | 12 | 12 |
| Y | Tyr_TAT | 0 | 11 | 31.4 | 0 | 0 |
|   | Tyr_TAC | 100 | 24 | 68.6 | 35 | 35 |

TABLE 2.2

Codon optimization for amyB.

| Sequence | Type | $fit_{sc}$ | $fit_{cp}$ | $w_{cp}(g) \leq 0$ | $fit_{combi}$ (cpi = 0.2) |
|---|---|---|---|---|---|
| SEQ ID NO. 2 | WT | 0.1652 | 0.0329 | 37.3% | 0.090 |
| SEQ ID NO. 5 | sc optimized | 0.0046 | −0.1765 | 73.9% | −0.862 |
| SEQ ID NO. 6 | sc + cp optimized | 0.0109 | −0.3420 | 92.6% | −1.621 |

All three sequences listed in table 2.2 are coding sequences of which the translated sequence is assigned as SEQ ID NO. 3.

3. Example 3

Testing of the Method of the Invention for Construction of Improved DNA Sequences for Providing Improved Production of the *Aspergillus niger* Fungal Amylase Enzyme in *A. niger*

The method of the invention is below applied to the improvement of single codon and codon pair use of the AmyB gene of *A. niger*. This method can be applied the same way for the improvement of codon use and improved expression of any nucleotide sequence.

3.1 Material and Methods 3.1.1 Strains

WT 1: This *A. niger* strain is used as a wild-type strain. This strain is deposited at the CBS Institute under the deposit number CBS 513.88.

WT 2: This *A. niger* strain is a WT 1 strain comprising a deletion of the gene encoding glucoamylase (glaA). WT 2 was constructed by using the "MARKER-GENE FREE" approach as described in EP 0 635 574 B1. In this patent it is extensively described how to delete glaA specific DNA sequences in the genome of CBS 513.88. The procedure resulted in a MARKER-GENE FREE ΔglaA recombinant *A. niger* CBS 513.88 strain, possessing finally no foreign DNA sequences at all.

WT 3: This *A. niger* strain is a WT 2 strain comprising a mutation which results in an oxalate deficient *A. niger* strain. WT 3 was constructed by using the method as described in EP1590444. In this patent application, it is extensively described how to screen for an oxalate deficient *A. niger* strain. Strain WT3 was constructed according to the methods of Examples 1 and 2 of EP1590444, strain WT 3 is mutant strain 22 of EP1590444 (designated FINAL in EP1590444).

WT 4: This *A. niger* strain is a WT 3 strain comprising the deletion of three genes encoding alpha-amylases (amyB, amyBI and amyBII) in three subsequent steps. The construction of deletion vectors and genomic deletion of these three genes has been described in detail in WO2005095624. The vectors pDEL-AMYA, pDEL-AMYBI and pDEL-AMYBII, described in WO2005095624, have been used according the "MARKER-GENE FREE" approach as described in EP 0 635 574 B1. The procedure described above resulted in an oxalate deficient, MARKER-GENE FREE ΔglaA, ΔamyA, ΔamyBI and ΔamyBII amylase-negative recombinant *A. niger* CBS 513.88 strain, possessing finally no foreign DNA sequences at all. As such, WT 4 is more optimized for alpha-amylase expression compared to WT1.

3.1.2 *A. niger* Shake Flask Fermentations

*A. niger* strains were pre-cultured in 20 ml pre-culture medium as described in the Examples: "*A. niger* shake flask fermentations" section of WO99/32617. After overnight growth, 10 ml of this culture was transferred to fermentation medium 1 (FM1) for alpha-amylase fermentations. Fermentation is performed in 500 ml flasks with baffle with 100 ml fermentation broth at 34° C. and 170 rpm for the number of days indicated, generally as described in WO99/32617.

This FM1 medium contains per liter: 52.570 g glucose, 8.5 g maltose, 25 g Caseinhydrolysate, 12.5 g Yeast extract, 1 g $KH_2PO_4$, 2 g $K_2SO_4$, 0.5 g $MgSO_4.7H_2O$, 0.03 g $ZnCl_2$, 80.02 g $CaCl_2$, 0.01 g $MnSO_4.4H_2O$, 0.3 g $FeSO_4.7H_2O$, 10 ml Pen-Strep (Invitrogen, cat. nr. 10378-016), 48 g MES, adjusted to pH 5.6 with 4 N $H_2SO_4$.

3.1.3 Fungal Alpha-Amylase Activity

To determine the alpha-amylase activity in *A. niger* culture broth, the Megazyme cereal alpha-amylase kit is used (Megazyme, CERALPHA alpha amylase assay kit, catalogue. ref. K-CERA, year 2000-2001), according protocol of the supplier. The measured activity is based on hydrolysis of non-reducing-end blocked ρ-nitrophenyl maltoheptaoside in the presence of excess glucoamylase and α-glucosidase. The amount of formed ρ-nitrophenol is a measure for alpha-amylase activity present in a sample.

3.2 Construction of an *Aspergillus* Expression Construct for the Wild-Type AmyB Coding Sequence Encoding *A. Niger* Alpha-Amylase AmyB The DNA sequence of the wild-type amyB gene have been described under 2.2.1. For expression analysis in *Aspergillus* species of *A. niger* amyB constructs, the strong amyB promoter is applied for over-expression of the alpha amylase enzyme in *A. niger* using pGBFIN-based expression constructs (as described in WO99/32617). The translational initiation sequence of the amyB promoter including ATG start codon of amyB is 5'-GGCATTTATG ATG-3' or 5'-GAAG-GCATTT ATG-3', dependent on which ATG is selected as start codon. This translational initiation sequence of PamyB has been modified into 5'-CACCGTCAAA ATG-3' in all subsequent amyB expression constructs generated below.

Appropriate restriction sites were introduced at both ends to allow cloning in an expression vector. The native amyB gene contains a 'TGA' stop codon. In all amyB constructs made below, the 5'-TGA-3' translational termination sequence was replaced by 5'-TAAA-3' followed by the 5'-TTAATTAA-3' of the PacI restriction site. At the 5'-end an XhoI site was introduced and at the 3'-end a PacI site. Therefore, a fragment comprising a modified genomic amyB promoter and amyB cDNA sequence was completely synthesized, cloned and the sequence was confirmed by sequence analysis.

Figure 21:
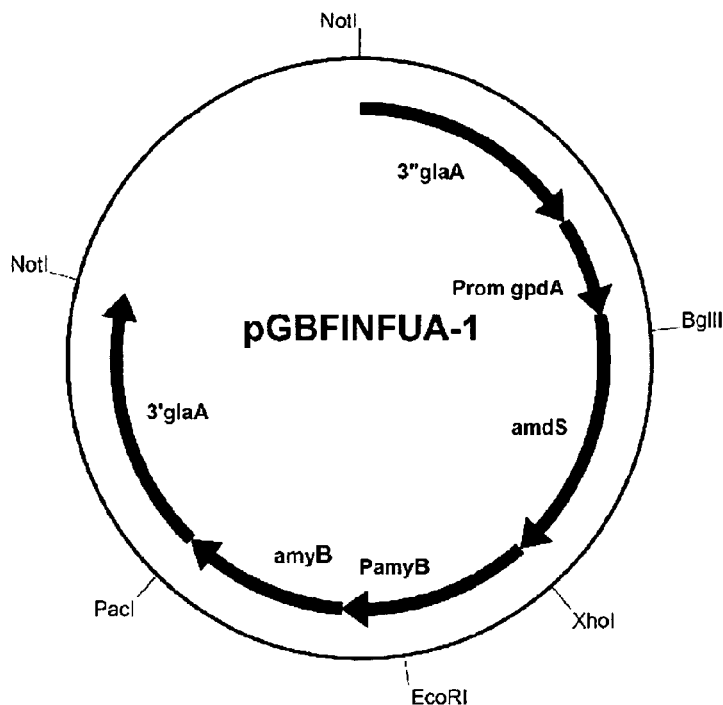
FIG. 21 depicts a plasmid map of expression vector pGBFINFUA-1.

This fragment comprising the alpha-amylase promoter with modified translational initiation sequence and amyB cDNA sequence with modified translational termination sequence was digested with XhoI and PacI and introduced in an XhoI and PacI digested pGBFIN-12 vector (construction and layout as described in WO99/32617), generating pGBFINFUA-1 (FIG. 21). The sequence of the introduced PCR fragment was confirmed by sequence analysis and its sequence is presented in SEQ ID NO. 4.

3.3 Improvement of the Single-Codon Usage for the Alpha-Amylase Coding Sequence AmyB for Expression in *A. Niger*

A method of single-codon optimization is applied below for the improvement of codon use of the amyB gene of *A. niger*. The nucleotide coding sequence of the native amyB is shown as SEQ ID NO. 2.

The codon use of the native amyB gene of *A. niger* and the synthetic optimized variant are given in Table 2.1 below. For the native and single-codon optimized synthetic amyB gene, the exact numbers for each codon are given as well as the distribution per amino acid. Additionally, the third column provides the proposed optimal distribution, which is the target for optimization.

For the group 1 amino acids, there is only one possibility. Group 1 consists of methionine that is always encoded by ATG and tryptophane that is always encoded by TGG.

The group 2 amino acids are subject to optimization according to the extreme frequency of 0% or 100%, the strategy is clear. All codons for a group 2 AA are specifically changed into the optimal variant of the two possible codons. More specifically for cysteine, a codon, TGT is replaced by TGC; for phenylalanine, TTT by TTC; for histidine, CAT by CAC; for lysine, AAA by AAG, for asparagine, AAT by AAC; for glutamine, CAA by CAG; for tyrosine, TAT by TAC.

The group 3 amino acids can be encoded by several codons as indicated in Table 3.1; each codon being present in a preferred codon frequency: for alanine GCT, GCC, GCA, GCG; for aspartate, GAT, GAC; for glutamate, GAA, GAG; for glycine, GGT, GGC, GGA, GGG; for isoleucine, ATT, ATC, ATA; for leucine, TTA, TTG, CTT, CTC, CTA, CTG; for proline, CCT, CCC, CCA, CCG; for arginine, CGT, CGC, CGA, CGG, AGA, AGG; for serine, TCT, TCC, TCA, TCG, AGT, AGC; for threonine, ACT, ACC, ACA, ACG; for valine, GTT, GTC, GTA, GTG, are optimized according the following methodology:

For the group 3 amino acids (AA) and their encoding codons, the calculation of the optimal occurrence of each possible codon within a given coding sequence is performed according to the following methodology:

i. sum for each of the respective group 3 AA, the total number of residues encoded in the given sequence, see column A1 (Table 3.1), ii. for each AA and codon encoding that AA, multiply the total number for that AA by the optimal codon distribution in Table 2.1, resulting in a raw codon distribution, which generally may contain decimal numbers, see column A2 (Table 3.2), iii. round off the values of the raw codon distribution (ii), by removing the digits, resulting in a rounded off codon distribution, see column A3 (Table 3.2), iv. sum for each of the AA, the total number of AA represented in the rounded off codon distribution (iii), see column A4 (Table 3.1), v. calculate the total missing number of residues for each of the respective AA in the rounded off codon distribution, by subtracting the total number of residues encoded in the given sequence (i) with the total number of AA represented in the rounded off codon distribution (iv), see column A5 (Table 3.1), vi. calculate for each codon, the decimal difference between the raw codon distribution (ii) and the rounded off codon distribution (iii) by subtraction, see column A6 (Table 3.2), vii. multiply for each codon, the decimal difference (vi) and the optimal codon distribution in table 1, giving a weight value for each codon, see column A7 (Table 3.2), viii. for each of the respective AA, select for the amount of missing residues (v), the respective amount of codons that have the highest weight value (vii), see column A8 (Table 3.2), ix. the calculation of the final optimal codon distribution within a given sequence encoding a polypeptide is calculated by summing the rounded off codon distribution (iii) and the selected amount of missing residues (viii) for each codon, see column A9 (Table 3.2).

TABLE 3.1

| AA(i) | I | A1 | A4 | A5 |
|---|---|---|---|---|
| Ala | 1 | 42 | 40 | 2 |
| Asp | 2 | 42 | 41 | 1 |
| Glu | 3 | 12 | 11 | 1 |
| Gly | 4 | 43 | 42 | 1 |
| Ile | 5 | 28 | 27 | 1 |
| Leu | 6 | 37 | 35 | 2 |
| Pro | 7 | 22 | 21 | 1 |
| Arg | 8 | 10 | 9 | 1 |
| Ser | 9 | 37 | 35 | 2 |
| Thr | 10 | 40 | 40 | 0 |
| Val | 11 | 31 | 29 | 2 |

TABLE 3.2

| Codon | A2 | A3 | A6 | A7 | A8 | A9 |
|---|---|---|---|---|---|---|
| Ala_GCT | 15.96 | 15 | 0.96 | 0.365 | 1 | 16 |
| Ala_GCC | 21.42 | 21 | 0.42 | 0.014 | 1 | 21 |
| Ala_GCA | 0 | 0 | 0 | 0.000 | 0 | 0 |
| Ala_GCG | 4.62 | 4 | 0.62 | 0.068 | 0 | 5 |
| Asp_GAT | 15.12 | 15 | 0.12 | 0.043 | 0 | 15 |
| Asp_GAC | 26.88 | 26 | 0.88 | 0.563 | 1 | 27 |
| Glu_GAA | 3.12 | 3 | 0.12 | 0.031 | 0 | 3 |
| Glu_GAG | 8.88 | 8 | 0.88 | 0.651 | 1 | 9 |
| Gly_GGT | 21.07 | 21 | 0.07 | 0.034 | 0 | 21 |
| Gly_GGC | 15.05 | 15 | 0.05 | 0.018 | 0 | 15 |
| Gly_GGA | 6.88 | 6 | 0.88 | 0.141 | 1 | 7 |
| Gly_GGG | 0 | 0 | 0 | 0.000 | 0 | 0 |
| Ile_ATT | 7.56 | 7 | 0.56 | 0.151 | 0 | 7 |
| Ile_ATC | 20.44 | 20 | 0.44 | 0.321 | 1 | 21 |
| Ile_ATA | 0 | 0 | 0 | 0.000 | 0 | 0 |
| Leu_TTA | 0 | 0 | 0 | 0.000 | 0 | 0 |
| Leu_TTG | 4.81 | 4 | 0.81 | 0.105 | 1 | 5 |
| Leu_CTT | 6.29 | 6 | 0.29 | 0.049 | 0 | 6 |
| Leu_CTC | 14.06 | 14 | 0.06 | 0.023 | 0 | 14 |
| Leu_CTA | 0 | 0 | 0 | 0.000 | 0 | 0 |
| Leu_CTG | 11.84 | 11 | 0.84 | 0.269 | 1 | 12 |
| Pro_CCT | 7.92 | 7 | 0.92 | 0.331 | 1 | 8 |
| Pro_CCC | 14.08 | 14 | 0.08 | 0.051 | 0 | 14 |
| Pro_CCA | 0 | 0 | 0 | 0.000 | 0 | 0 |
| Pro_CCG | 0 | 0 | 0 | 0.000 | 0 | 0 |
| Arg_CGT | 4.9 | 4 | 0.9 | 0.441 | 1 | 5 |
| Arg_CGC | 5.1 | 5 | 0.1 | 0.051 | 0 | 5 |
| Arg_CGA | 0 | 0 | 0 | 0.000 | 0 | 0 |
| Arg_CGG | 0 | 0 | 0 | 0.000 | 0 | 0 |
| Arg_AGA | 0 | 0 | 0 | 0.000 | 0 | 0 |
| Arg_AGG | 0 | 0 | 0 | 0.000 | 0 | 0 |
| Ser_TCT | 7.77 | 7 | 0.77 | 0.162 | 1 | 8 |
| Ser_TCC | 16.28 | 16 | 0.28 | 0.123 | 0 | 16 |
| Ser_TCA | 0 | 0 | 0 | 0.000 | 0 | 0 |
| Ser_TCG | 5.18 | 5 | 0.18 | 0.025 | 0 | 5 |
| Ser_AGT | 0 | 0 | 0 | 0.000 | 0 | 0 |
| Ser_AGC | 7.77 | 7 | 0.77 | 0.162 | 1 | 8 |
| Thr_ACT | 12 | 12 | 0 | 0.000 | 0 | 12 |
| Thr_ACC | 28 | 28 | 0 | 0.000 | 0 | 28 |
| Thr_ACA | 0 | 0 | 0 | 0.000 | 0 | 0 |
| Thr_ACG | 0 | 0 | 0 | 0.000 | 0 | 0 |
| Val_GTT | 8.37 | 8 | 0.37 | 0.100 | 0 | 8 |
| Val_GTC | 16.74 | 16 | 0.74 | 0.400 | 1 | 17 |
| Val_GTA | 0 | 0 | 0 | 0.000 | 0 | 0 |
| Val_GTG | 5.89 | 5 | 0.89 | 0.169 | 1 | 6 |

Subsequently, a completely new nucleotide coding sequence was created by random distribution of the proposed number of synonymous codons (Table 2.1) for each amino acid in the original amyB peptide. The synthetic amyB sequence, resulting from the process described above, is indicated in SEQ ID NO. 5. Secondary structures in the modified coding sequence were checked using the Clone Manager 7 program (Sci. Ed. Central: Scientific & Educational software, version 7.02) for possible occurrence of harmful secondary structures.

3.4 Optimization of the Coding Sequence According a the Combined Single-Codon and Codon-Pair Method of the Invention for the Alpha-Amylase Coding Sequence amyB for Expression in *A. niger*

A method of the invention is applied for the improvement of the coding sequence of the amyB gene of *A. niger*. The optimized amyB sequence, resulting from the process described in Example 2, is indicated in SEQ ID NO. 6. Secondary structures in the modified coding sequence were checked using the Clone Manager 7 program (Sci. Ed. Central: Scientific & Educational software, version 7.02) for possible occurrence of harmful secondary structures.

3.5 Construction of Modified amyB Expression Vectors for Expressing *A. niger* Alpha-Amylase AmyB Encoded by Coding Sequences Described in Examples 3.2 and 3.3

The DNA sequence of the XhoI-PacI fragment of pGBFINFUA-1 (FIG. 21) is shown as SEQ ID NO. 4 and comprises the amyB promoter and wild-type amyB cDNA sequence with a modified translational initiation sequence and modified translation stop sequence. The DNA sequence comprising a variant of the translational initiation sequence of the alpha-amylase promoter combined with a codon optimized coding sequence for the alpha-amylase encoding amyB gene, as described in Example 1.2, is shown as SEQ ID NO. 7. The DNA sequence comprising a variant of the translational initiation sequence of the alpha-amylase promoter combined with an optimized coding sequence according the combined single-codon and codon-pair method of the invention for the alpha-amylase encoding amyB gene, as described in Example 3.3, is shown as SEQ ID NO. 8.

For cloning these modified sequence variants in an expression vector, the two synthetic gene fragments were digested with XhoI and PacI and introduced in the large fragment of an XhoI and PacI digested pGBFINFUA-1 vector (FIG. 21), generating variant expression vectors. After checking the integration of the correct fragment, the variant expression constructs were named pGBFINFUA-2 and pGBFINFUA-3, as described below in Table 3.3.

TABLE 3.3

Modified expression constructs for alpha-amylase expression in A. niger

| Plasmid name | SEQ ID NO | Translation initiation sequence | Coding sequence | Translation stop sequence |
|---|---|---|---|---|
| pGBFINFUA-1 | 4 | Modified (CACCGTCAAA ATG) | w.t. | Modified (TAA ATA) |
| pGBFINFUA-2 | 7 | Modified (CACCGTCAAA ATG) | Single-codon optimized | Modified (TAA ATA) |
| pGBFINFUA-3 | 8 | Modified (CACCGTCAAA ATG) | Modified according invention | Modified (TAA ATA) |

The translated sequences of the amyB coding sequences of plasmid pGBFINFUA-1 to pGBFINFUA-3 are according to the amino acid sequence as depicted in SEQ ID NO 3, representing the wild-type *A. niger* alpha-amylase enzyme.

Figure 22:
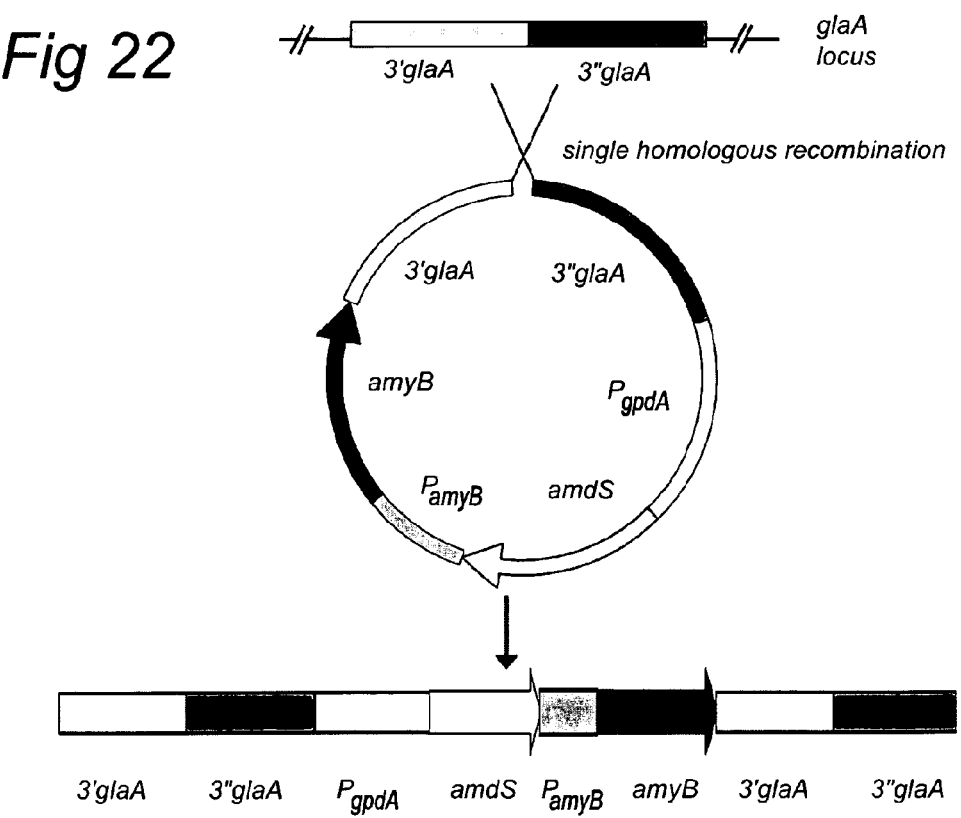
FIG. 22 depicts a schematic representation of integration through single homologous recombination. The expression vector comprises the selectable amdS marker, and the glaA promoter connected to the amyB gene. These features are flanked by homologous regions of the glaA locus (3' glaA and 3" glaA, respectively) to direct integration at the genomic glaA locus.

3.6 Expression in *A. Niger* of Modified pGBFINFUA-Expression Constructs of *A. Niger* Alpha-Amylase The pGBFINFUA-1, -2 and -3 expression constructs, prepared as described above, were introduced in *A. niger* by transformation as described below and according to the strategy depicted in FIG. 22.

In order to introduce the three pGBFINFUA-1, -2 and -3 vectors (Table 3.3) in WT 4, a transformation and subsequent selection of transformants was carried out as described in WO98/46772 and WO99/32617. In brief, linear DNA of the pGBFINFUA-constructs was isolated and used to transform *A. niger*. Transformants were selected on acetamide media and colony purified according standard procedures. Colonies were diagnosed for integration at the glaA locus and for copy number using PCR. Ten independent transformants of each of the pGBFINFUA-1, -2 and -3 constructs with similar estimated copy numbers (low copy: 1-3) were selected and numbered using the name of the transforming plasmid, as for example FUA-1-1 (for the first pGBFINFUA-1 transformant) and FUA-3-1 (for the first pGBFINFUA-3 transformant), respectively.

The selected FUA-strains and *A. niger* WT 4 were used to perform shake flask experiments in 100 ml of the medium and under conditions as described above. After 3 and 4 days of fermentation, samples were taken.

The production of alpha-amylase enzyme was measured in all three different *A. niger* FUA-transformants. As can be learned from FIG. 23, optimization of the coding sequence according the method of the invention shows a higher improvement on expression of AmyB compared to the other method tested called single-codon optimization. These figures have been summarized in Table 3.4 below.

TABLE 3.4

Figure 23:
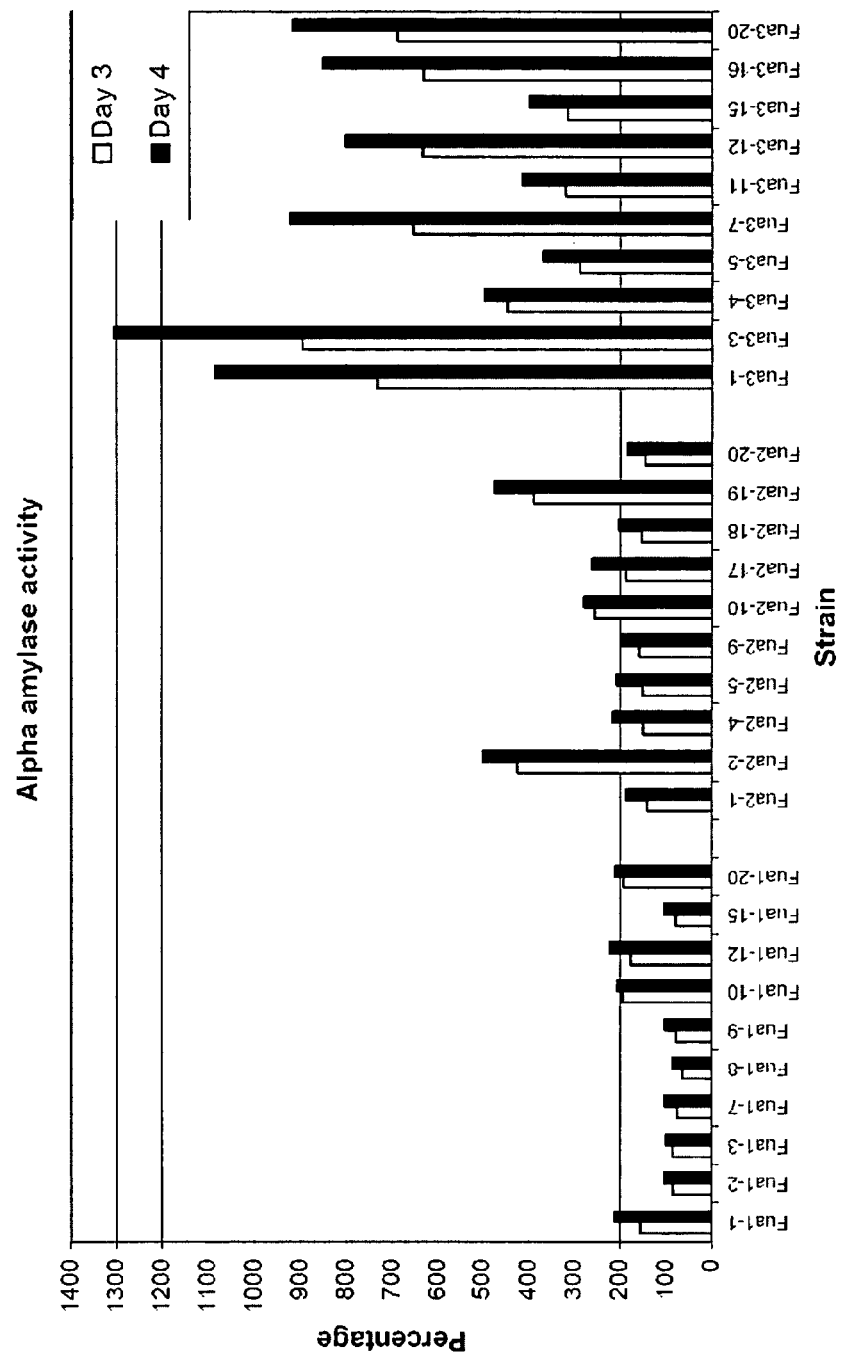
FIG. 23 depicts alpha-amylase activity in culture broth for A. niger strains expressing three different constructs. Depicted is the alpha-amylase activity in culture broth of A. niger strains expressing a native amyB construct, wherein (1) the translation initiation sequence and the translation termination sequence were modified (pGBFINFUA-1), and (2) the translation initiation sequence, the translation termination sequence and the single-codon usage were modified (pGBFINFUA-2), and (3) the translation initiation sequence, the translation termination sequence and the single-codon usage and codon-pair usage were modified (pGBFINFUA-3) according a method of the invention. Alpha-amylase activities are depicted in relative units [AU], with the average of the 6 one-copy strains of the FUA1 group of 10 strains at day 4 set at 100%. The ten transformants per group indicated are independently isolated and cultivated transformants.

Relative average alpha-amylase activities of transformants with wild-type construct compared to those with modified amyB coding sequences (as concluded from FIG. 23).

| Strain type | SEQ ID NO | Coding sequence | Alpha-amylase activity |
|---|---|---|---|
| FUA-1 | 4 | w.t. | 100% |
| FUA-2 | 7 | Single-codon optimized | 200% |
| FUA-3 | 8 | Modified according invention | 400% |

These results indicate clearly that the method of the invention can be applied to improve protein expression in a host, although the expression construct and host has already several other optimizations, such as for example a strong promoter, an improved translation initiation sequence, an improved translation stop sequence, an optimal single-codon usage and/or an improved host for protein expression.

4. Example 4

Design of Improved DNA Sequences for Expression of Three Heterologous Enzymes in *Bacillus* Species: *Bacillus subtilis* and *Bacillus amiloliquefaciens*

4.1. Introduction

Example 4 describes the experiment design and application of a method of the invention described in this patent for (improved) expression of heterologous proteins in both *Bacillus* species, more specifically in this example *Bacillus subtilis* and *Bacillus* amiloliquefaciens. A preferred expression host is *Bacillus* amiloliquefaciens.

The *Bacillus subtilis* genome was published in 1997 and other *Bacillus* species followed (Kunst, F. et al. 1997. The complete genome sequence of the Gram-positive bacterium *Bacillus subtilis*. Nature 390:249-56; Rey, M. W. et al. (2004). Complete genome sequence of the industrial bacterium *Bacillus licheniformis* and comparisons with closely related *Bacillus* species. Genome Biology 5:R77; Rasko D. A. et al. (2005). Genomics of the *Bacillus cereus* group of organisms. FEMS Microbiology Reviews 29:303-329).

In this example, the full sequence of *B. subtilis* was chosen as the basis for calculating single-codon frequencies and codon-pair weights. Comparison of GC-content and tRNAs provided a similar picture for the *Bacillus* species mentioned (vide supra). This is an indication that the same statistics are applicable for other related *Bacillus* species. Moreover, from example 1 (see also FIG. 4), it was already clear that related species show similar codon-pair frequencies.

In FIG. 4 (see also example 1), a codon-pair comparison plot, based on full genome statistics for *B. subtilis* vs. *B. amyloliquefaciens* can be found. A good correlation between both data sets is observed. Moreover, it seems that *B. amyloliquefaciens* is more versatile, since there is a subgroup of codon-pair combinations that is well accepted in *B. amiloliquefaciens*, while it has highly negative values for *B. subtilis*; the opposite is not observed.

4.2. Experiment Design

Three proteins sequences were selected for expression in both *Bacillus subtilis* and *Bacillus amiloliquefaciens*:
Protein 1: Xylose (glucose) isomerase xylA (EC.5.3.1.5) from *Bacillus stearothermophilus*;
Protein 2: Xylose (glucose) isomerase xylA (EC.5.3.1.5) from *Streptomyces olivochromogenes*;
Protein 3: L-arabinose isomerase (EC 5.3.1.4) from *Thermoanaerobacter mathranii*.

TABLE 4.1

Overview gene constructs; Protein 2 was chosen to further explore the codon-pair concept in broader sense.

| Gene | Protein | Single codon-optimization | Single codon & positive codon-pair optimization | Single codon & negative codon-pair optimization |
|---|---|---|---|---|
| Protein 1 | | SEQ ID NO. 9 | SEQ ID NO. 16 | SEQ ID NO. 13 |
| Protein 2 | | SEQ ID NO. 10 | SEQ ID NO. 17 | SEQ ID NO. 14 | SEQ ID NO. 18 |
| Protein 3 | SEQ ID NO. 11 | SEQ ID NO. 12 | | SEQ ID NO. 15 |

Table 4.1 provides an overview of the methods applied to the 3 genes described above. For Protein 1, Protein 2 and Protein 3, the codon-pair optimization of the method of the invention is applied in addition to the single codon optimization developed before.

As a control, the effect of single codon optimization and negative codon pair optimization was tested experimentally by including 2 additional constructs for protein 2. One variant (SEQ. ID. 18) is designed where it is 'optimized' toward bad codon pairs (i.e. negative codon-pair optimization), and a second one with only single-codon optimization (SEQ. ID. 17). Protein 2 was chosen, since *Streptomyces* species show highly different codon-pair bias, see example 1 and FIG. 4.

All designed *B. amyloliquefaciens* genes avoided the occurrence of NdeI (CATATG) and BamHI (GGATTC) restriction sites. Additionally, they contained a single restriction site for removing the *E. coli* part of the cloning vector pBHA12.

4.3. Single Codon Optimization

Single-codon optimized variants for Protein 1 and Protein 2 were designed using the method described in Example 3.3 for single-codon optimization, resulting in SEQ ID NO. 16 and SEQ ID NO. 17, respectively. The applied single-codon distribution table (Table 4.2) was determined using the 50 most-highly expressed genes as determined by 24 Affymetrix GeneChips for *B. subtilus* 168 using 6 independent fermentation time-series. All GeneChips were normalized with respect to their arithmetic mean. The expression list excludes those genes that were deliberately over expressed in strain engineering, and hence their measured expression level cannot be correlated with their codon usage.

Determination of single codon distribution table 4.2 is done by visual inspection of codon frequency histograms of 50, 100, 200, 400 highest expressed sequences and of all *B. subtilis* sequences. In case of a clear trend toward either 0% or 100% for the most highly expressed genes, an assignment of 0% and 100% was made, respectively. For the other codons that were not assigned, the average usage was calculated and normalized to the set of synonymous codons, by leaving out the assigned codons. The resulting target single-codon frequencies are given in Table 4.2, column 3.

TABLE 4.2

Figure 24:
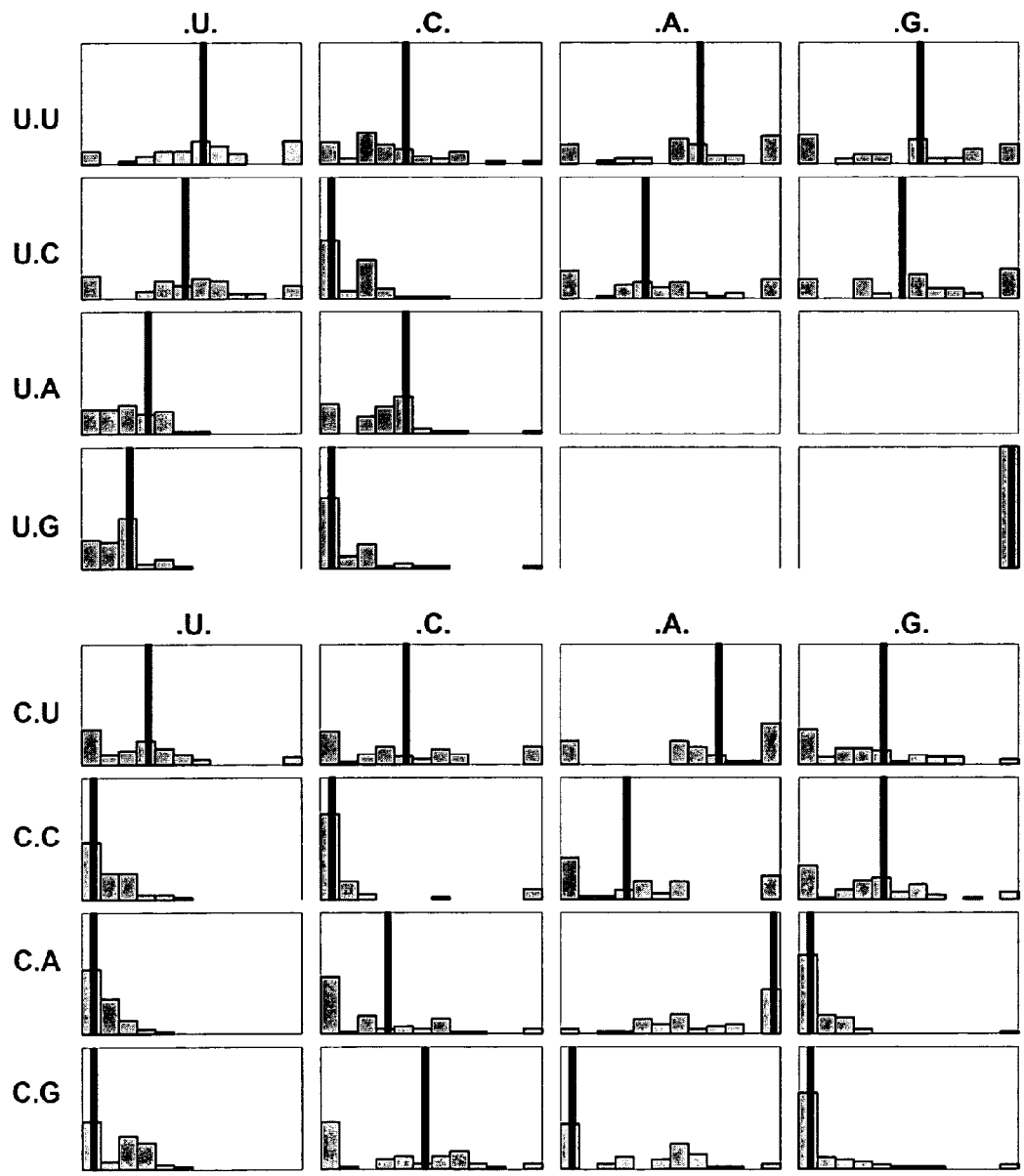
FIG. 24 (A and B) depicts the single-codon frequency for the single-codon optimization for Bacillus species. An explanation of the sub-graphs is given by FIG. 14. The grey histogram presents the codon distribution for the 50 highest expressed genes in B. subtilis, see text. The black bars indicate the target single-codon frequency.
Figure 24:
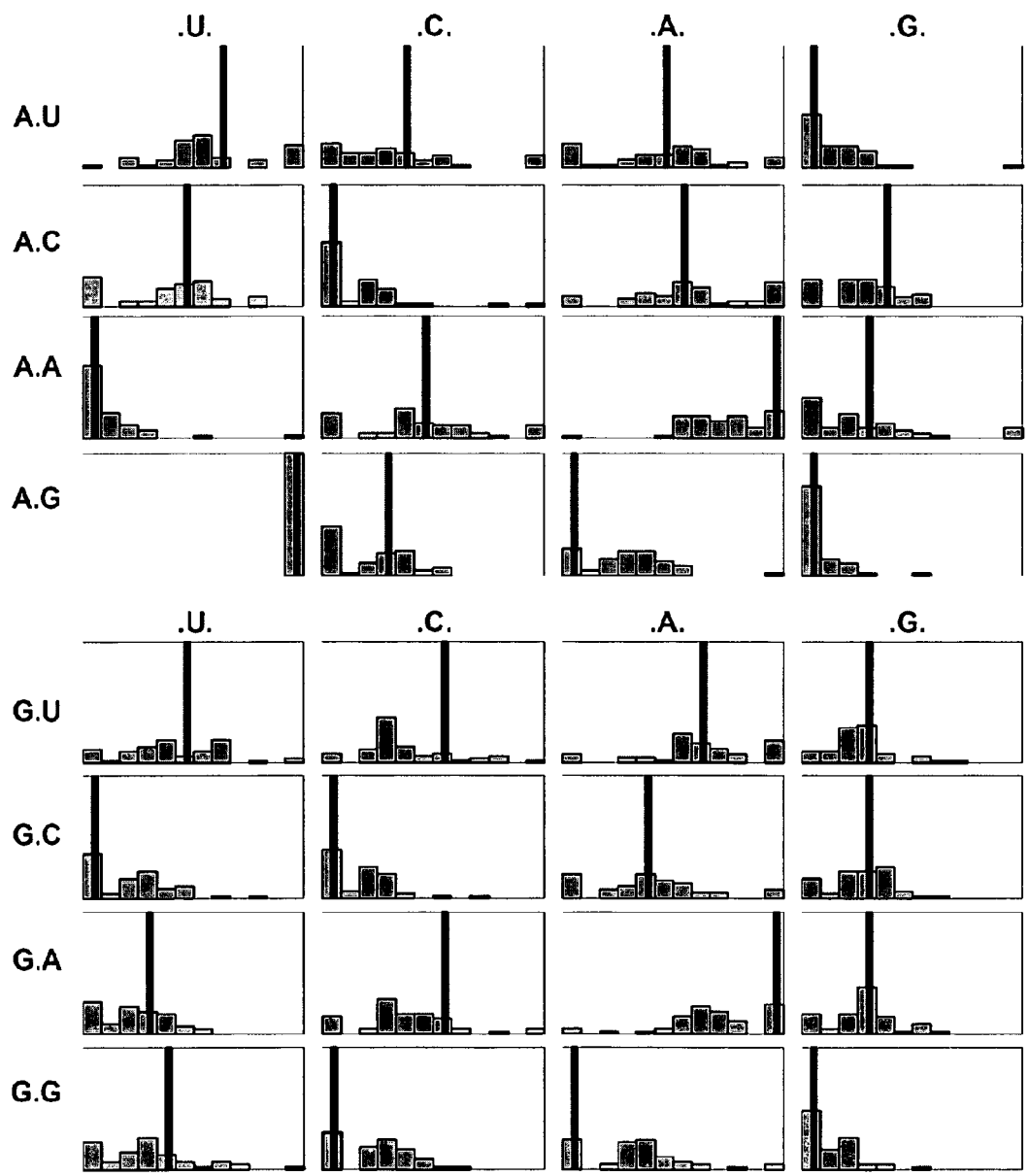
Figure 25A:
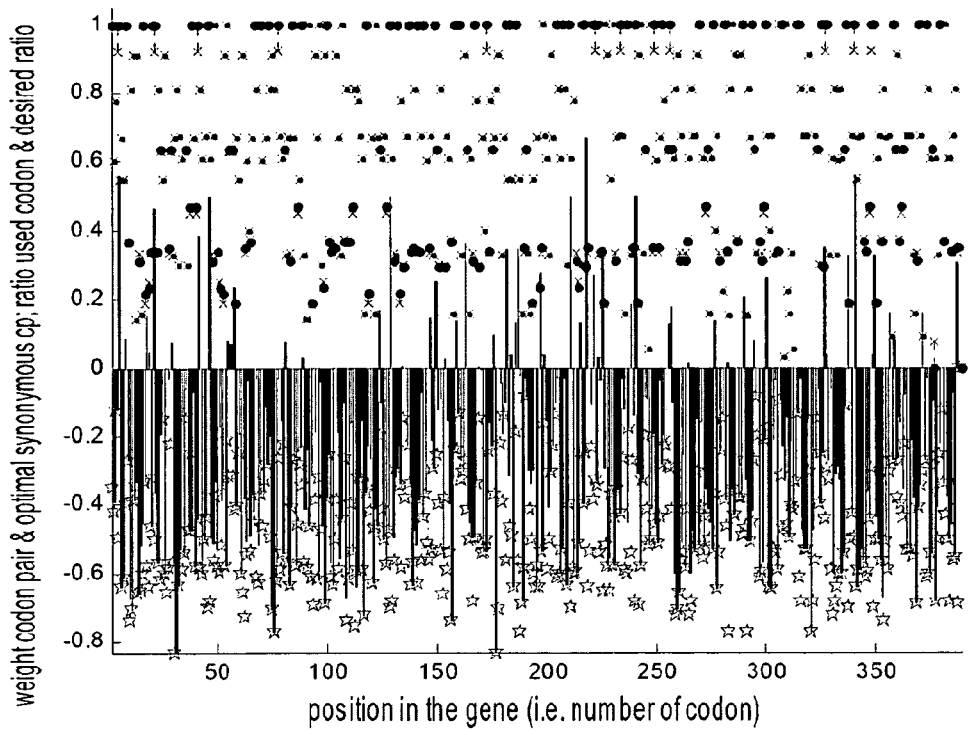
FIG. 25 depicts the single codon and codon pair statistics for SEQ ID NO. 14 (1/3), SEQ ID NO. 17 (2/3) and SEQ ID NO. 14 (3/3), the sequenced optimized using codon pair+ single codon (1/3), single-codon (2/3), and negative codon-pair+single codon optimization (3/3), respectively. See FIG. 17 for an explanation of the graph.
Figure 25B:
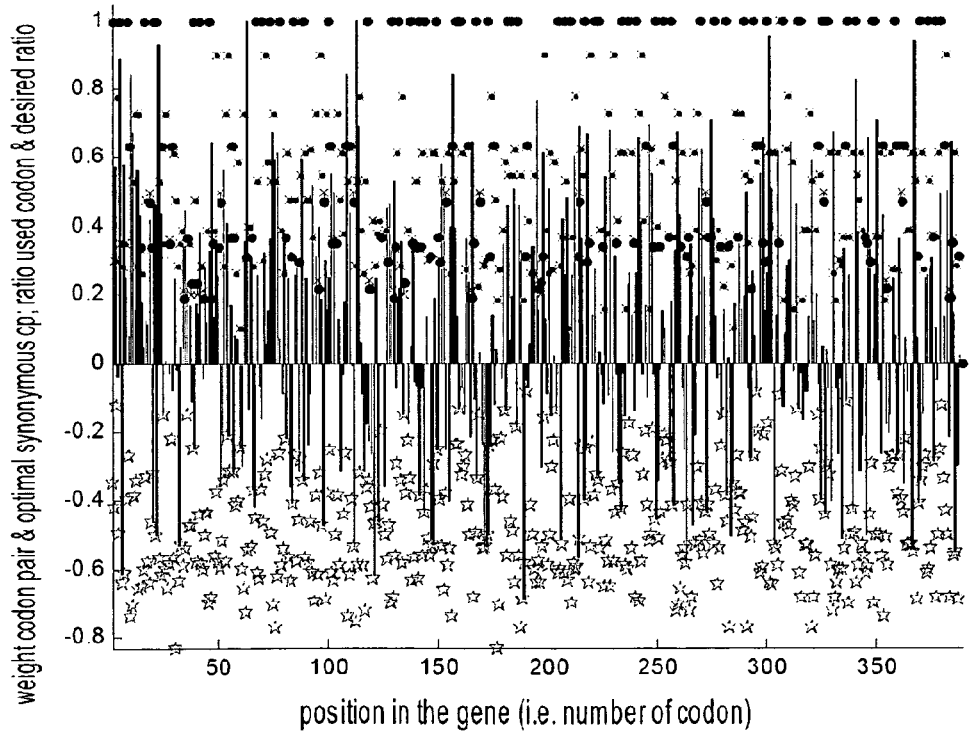
Figure 25C:
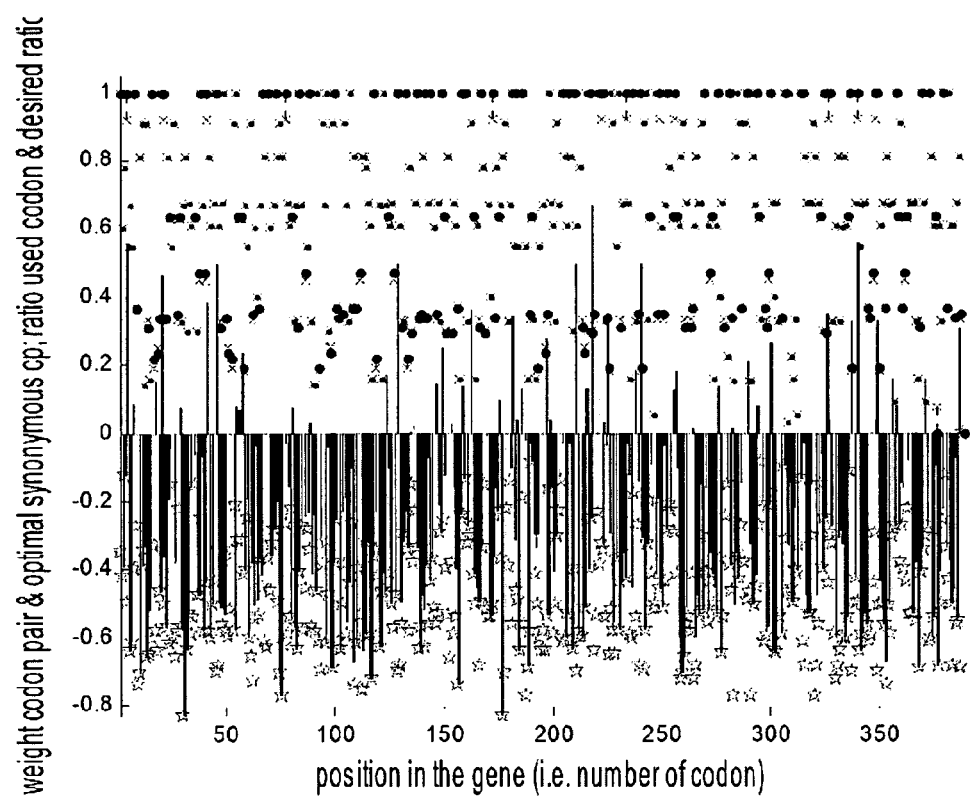

Codon-usage distribution for synthetic gene design on the basis of the 50 most highly-expressed genes and visual inspection of single codon usage histograms, e.g. FIG. 24; Don't care terms can be applied during codon-pair optimization to let the choice for those codons free, thus not taking into account single-codon optimization for these codons.

| | | Single codon distribution % | Don't care = 0 care = 1 |
|---|---|---|---|
| A | Ala_GCT | 50 | 0 |
| | Ala_GCC | 0 | 1 |

TABLE 4.2-continued

Codon-usage distribution for synthetic gene design on the basis of the 50 most highly-expressed genes and visual inspection of single codon usage histograms, e.g. FIG. 24; Don't care terms can be applied during codon-pair optimization to let the choice for those codons free, thus not taking into account single-codon optimization for these codons.

| | | Single codon distribution % | Don't care = 0 care = 1 |
|---|---|---|---|
| | Ala_GCA | 50 | 0 |
| | Ala_GCG | 0 | 1 |
| C | Cys_TGT | 51 | 0 |
| | Cys_TGC | 49 | 0 |
| D | Asp_GAT | 63 | 1 |
| | Asp_GAC | 37 | 1 |
| E | Glu_GAA | 100 | 1 |
| | Glu_GAG | 0 | 1 |
| F | Phe_TTT | 55 | 0 |
| | Phe_TTC | 45 | 0 |
| G | Gly_GGT | 31 | 1 |
| | Gly_GGC | 34 | 1 |
| | Gly_GGA | 35 | 1 |
| | Gly_GGG | 0 | 1 |
| H | His_CAT | 71 | 0 |
| | His_CAC | 29 | 0 |
| I | Ile_ATT | 60 | 0 |
| | Ile_ATC | 40 | 0 |
| | Ile_ATA | 0 | 1 |
| K | Lys_AAA | 100 | 1 |
| | Lys_AAG | 0 | 1 |
| L | Leu_TTA | 39 | 0 |
| | Leu_TTG | 24 | 0 |
| | Leu_CTT | 37 | 0 |
| | Leu_CTC | 0 | 1 |

TABLE 4.2-continued

Codon-usage distribution for synthetic gene design on the basis of the 50 most highly-expressed genes and visual inspection of single codon usage histograms, e.g. FIG. 24; Don't care terms can be applied during codon-pair optimization to let the choice for those codons free, thus not taking into account single-codon optimization for these codons.

|   |   | Single codon distribution % | Don't care = 0 care = 1 |
|---|---|---|---|
|   | Leu_CTA | 0 | 1 |
|   | Leu_CTG | 0 | 1 |
| M | Met_ATG | 100 | 1 |
| N | Asn_AAT | 45 | 0 |
|   | Asn_AAC | 55 | 0 |
| P | Pro_CCT | 35 | 0 |
|   | Pro_CCC | 0 | 1 |
|   | Pro_CCA | 22 | 0 |
|   | Pro_CCG | 43 | 0 |
| Q | Gln_CAA | 100 | 1 |
|   | Gln_CAG | 0 | 1 |
| R | Arg_CGT | 38 | 0 |
|   | Arg_CGC | 34 | 0 |
|   | Arg_CGA | 0 | 1 |
|   | Arg_CGG | 0 | 1 |
|   | Arg_AGA | 28 | 0 |
|   | Arg_AGG | 0 | 1 |
| S | Ser_TCT | 34 | 0 |
|   | Ser_TCC | 0 | 1 |
|   | Ser_TCA | 34 | 0 |
|   | Ser_TCG | 0 | 1 |
|   | Ser_AGT | 0 | 1 |
|   | Ser_AGC | 32 | 0 |
| T | Thr_ACT | 33 | 0 |
|   | Thr_ACC | 0 | 1 |
|   | Thr_ACA | 46 | 0 |
|   | Thr_ACG | 22 | 1 |
| V | Val_GTT | 47 | 1 |
|   | Val_GTC | 0 | 1 |
|   | Val_GTA | 23 | 1 |
|   | Val_GTG | 30 | 1 |
| W | Trp_TGG | 100 | 1 |
| Y | Tyr_TAT | 62 | 0 |
|   | Tyr_TAC | 38 | 0 |
|   | Stop_TGA | 0 | 1 |
|   | Stop_TAG | 0 | 1 |
|   | Stop_TAA | 100 | 1 |

4.4. Codon Pair Optimization

Codon pair optimization was performed according the method of the invention. The optimized coding nucleotide sequences SEQ ID NO. 13-15 are the result of a run with the described software method. The applied parameters were: population size=200; number of iterations=1000; cpi=0.20, CPW matrix="Table C.4. CPW: *Bacillus subtilis*—highly expressed sequences" and the CR matrix="Table B.1 column 5: CR table BAS: *Bacillus subtilis*—highly expressed sequences" (also in Table 4.2) and 'don't care elements as in Table 4.2. Moreover, a penalty value of +1 is added to $fit_{combi}$ for each occurrence of a NdeI (CATATG) and BamHI (GGATTC) restriction site.

The optimized coding nucleotide sequences SEQ ID NO. 18 is the result of a run with the described software method. The applied parameters were: population size=200; number of iterations=1000; cpi=0.20, CPW matrix=–1 times "Table C.4. CPW: *Bacillus subtilis*—highly expressed sequences" (for obtaining codon-pair optimization toward bad codon pairs) and the CR matrix="Table B.1 column 5: CR table BAS: *Bacillus subtilis*—highly expressed sequences" (also in Table 4.2) and 'don't care elements as in Table 4.2. Moreover, a penalty value of +1 is added to $fit_{combi}$ for each occurrence of a NdeI (CATATG) and BamHI (GGATTC) restriction site.

'Don't care' elements in Table 4.2 are chosen for those codons that do not show codon bias. This was done by visual inspection of the single-codon bias graph, see 4.3. The usage of such elements provides additional freedom to the codon-pair part of the optimization.

All optimizations converged toward a minimal value for $fit_{combi}$. The obtained objective values for SEQ ID NO. 13-15 and SEQ ID NO. 18 are given in Table 4.2, together with those for SEQ ID NO. 11, SEQ ID NO. 16 and SEQ ID NO. 17. From that data it is clear that single codon statistics are highly similar for SEQ ID NO. 16 and SEQ ID NO. 17 in comparison with SEQ ID NO. 14 and SEQ ID NO. 15. However, the method of the invention leads to a gene with an improved number of codon pairs with associated negative weights, indicating a more optimal usage of codon pairs having more negative weights associated with them, see Table 4.3.

'Optimizing' using maximization of $fit_{cp}$ leads to a gene with an increased number of codon pairs with associated positive weights, indicating an increased usage of codon pairs having more positive weights associated with them, thus bad influence on translation characteristics is expected. For SEQ ID NO. 18 ($w_{cp}(g) \leq 0$) is 24% vs. 85% for SEQ ID NO. 14, and also $fit_{cp}$ increased from 1.20 to −1.43.

TABLE 4.3

Codon optimization; objective fitness values for genes for expression in *B. subtilis* and *B. amyloliquefaciens*.

| Sequence | Type | $fit_{sc}$ | $fit_{cp}$ | $W_{cp}$ (g) ≤ 0 | $fit_{combi}$ (cpi = 0.2) |
|---|---|---|---|---|---|
| SEQ ID NO. 11 | WT | 0.078 | 0.097 | 41.1% | 0.350 |
| SEQ ID NO. 13 | sc + cp optimized | 0.004 | −0.293 | 89.1% | −1.439 |
| SEQ ID NO. 14 | sc + cp optimized | 0.004 | −0.292 | 84.8% | −1.431 |
| SEQ ID NO. 15 | sc + cp optimized | 0.003 | −0.303 | 89.2% | −1.493 |
| SEQ ID NO. 16 | sc optimized | 0.002 | −0.023 | 56.9% | −0.114 |
| SEQ ID NO. 17 | sc optimized | 0.003 | 0.087 | 44.3% | 0.428 |
| SEQ ID NO. 18 | sc + negative cp optimized | 0.015 | 0.257 | 23.5% | 1.196 |

5. Example 5

Testing the Method of the Invention for Expression of Three Heterologous Enzymes in *Bacillus subtilis* and *Bacillus Amyloliquefaciens*

5.1 Introduction

Example 5 describes the experiment and results of the expression of 3 heterologous genes with sequence variants of these in both *Bacillus subtilis* and *Bacillus amiloliquefaciens* hosts cells. Variants are made according the method of the invention, as described in Example 4.

5.2 Materials and Methods 5.2.1 *Bacillus* Growth Media
2*TY (per L): tryptone peptone 16 g, yeast extract Difco 10 g, NaCl 5 g.
5.2.2 Transformation of *B. subtilis*
Media
2× Spizizen Medium:
28 g $K_2HPO_4$; 12 g $KH_2PO_4$; 4 g $(NH_4)_2SO_4$; 2.3 g $Na_3$-citrate.$2H_2O$; 0.4 g $MgSO_4 \cdot 7H_2O$; $H_2O$ to 900 ml and adjust to pH 7.0-7.4 with 4N NaOH. Add $H_2O$ to 1 liter. Autoclave 20 minutes at 120° C.

1× Spizizen-Plus Medium:
    add to 50 ml 2× Spizizen medium 50 ml milliQ; 1 ml 50% glucose and 100 μl casamino acids (20 μg/ml final concentration).

A single Bacillus colony (or an aliquot from a deep freeze vessel) from a non-selective 2×TY agar plate was inoculated in 10 ml 2×TY broth in a 100 ml shake flask. Cells were grown overnight in an incubator shaker at 37° C. and ±250 rpm. The OD was measured at 600 nm and the culture was diluted with 1× Spizizen-plus medium till $OD_{600} \approx 0.1$. Cells were grown at 37° C. and 250-300 rpm till the culture $OD_{600}$ is 0.4-0.6. The culture was diluted 1:1 with 1× Spizizen medium supplemented with 0.5% glucose (starvation medium) and it was incubated for 90 min at 37° C. and 250-300 rpm. The culture was centrifuged at 4500 rpm in a tabletop centrifuge for 10 minutes. 90% of the supernatant was removed and pellet was suspended in rest volume. DNA (1-5 μg in a maximum of 20 μl) was mixed with 0.5 ml competent cells in a universal and incubated for 1 hour at 37° C. in a rotary shaking water bath under firm shaking (≈5/6). Cells were plated (20 to 200 μl) on selective 2×TY agar plates containing 25-μg/ml kanamycin and incubated over night at 37° C.

5.2.3 Preparation of Cell-Free Extract

The pellet obtained from 1 ml culture was resuspended in buffer A containing 10 mM Thris-HCl (pH 7.5), 10 mM EDTA, F50 mM NaCl, 1 mg/ml lysozyme and protease inhibitors (Complete EDTA-free protease inhibitor cocktail, Roche). The resuspended pellets were incubated for 30 min at 37° C., for protoplastation and subsequently sonicated as follows: 30 sec, 10 amplitude microns (3 cycles), with 15 sec. cooling between cycles. After sonification cell debris was spun down by centrifugation (10 min, 13000 rpm at 4° C.), and the clear lysates were used for further analysis.

5.2.4 Selection of Glucose Isomerase and L-Arabinose Isomerase Encoding Genes and Design of Synthetic Genes for Expression in Bacillus amyloliquefaciens and Bacillus subtilis Three enzymes selected are:
1. Bacillus stearothermophilus xylose isomerase (P54272 Swissprot); protein sequence SEQ ID NO. 9,
2. Streptomyces olivochromogenes xylose isomerase (P15587 Swissprot); protein SEQ ID NO. 10,
3. Thermoanaerobacter mathranii L-arabinose isomerase (AJ 582623.1 EMBL, and also US2003/012971A1), protein SEQ ID NO. 11, nucleotide SEQ ID NO. 12.

As seen above the selected enzymes have different microbial origin. With the aim to overproduce these enzymes in Bacillus subtilis or Bacillus amyloliquefaciens we have optimized the nucleotide sequence for each protein in such a way that it is suitable for expression in Bacillus species, see Example 4.

We have optimized the nucleotide sequences that encode the above mentioned enzymes. The sequences are listed in the sequence list under the SEQ ID NO. 13. (Bacillus stearothermophilus glucose (xylose) isomerase), SEQ ID NO. 14. (Streptomyces olivochromogenes glucose (xylose) isomerase), SEQ ID NO. 15. (Thermoanaerobacter mathranii L-arabinose isomerase). As a control, one variant with a single-codon optimization without codon-pair optimization, SEQ ID NO. 16-17, and one with single-codon optimization with "negative codon-pair optimization" SEQ ID NO. 18, were generated, see example 4 and Table 4.1.

Figure 26:
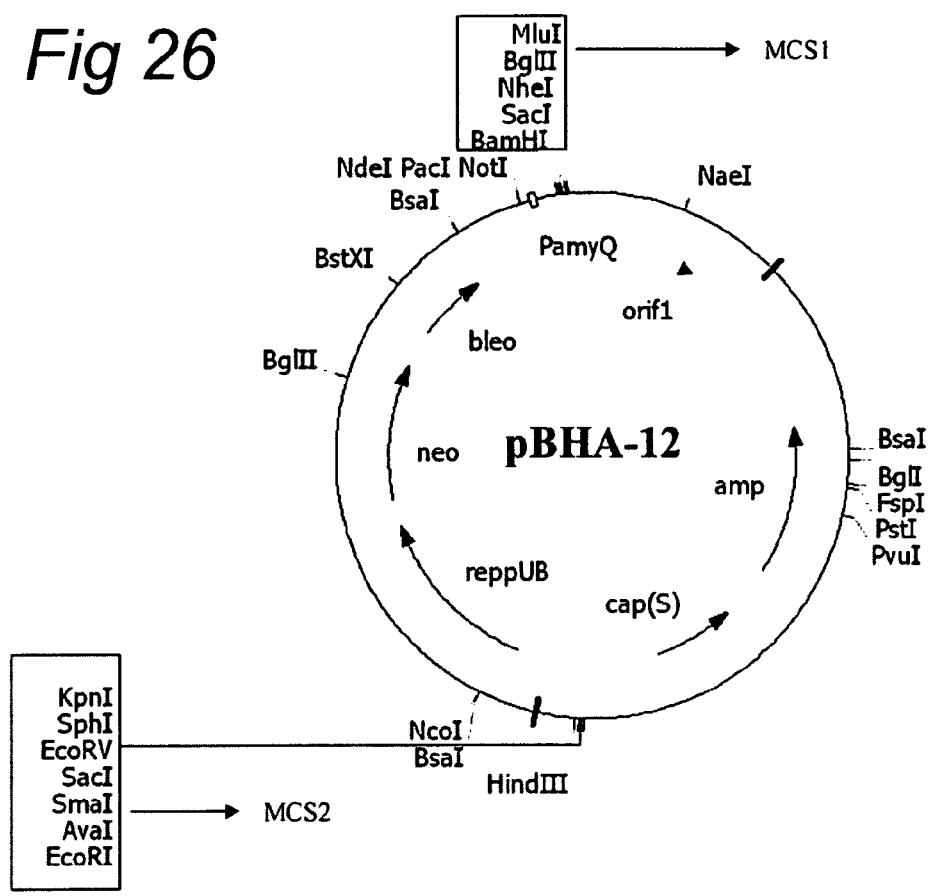
FIG. 26. E. coli/Bacillus shuttle vector pBHA-12. The multiple cloning sites (MCS) 1 and 2 are depicted.

5.3 Cloning of the Glucose Isomerase and L-Arabinose Isomerase Encoding Genes in the E. coli/Bacillus Shuttle Vector and Transformation to Bacilli For the expression of the selected genes in Bacilli we have used the pBHA12 E. coli/Bacillus shuffle vector (FIG. 26). This vector is essentially derived from the expression vector pBHA-1 (EP 340878) in which a promoter derived from the amyQ gene of Bacillus amyloliquefaciens replaced the HpaII promoter. The pBHA12 plasmid contains two multiple cloning sites (FIG. 26). All selected and optimized genes were made synthetically (DNA 2.0, Menlo Park, Calif., U.S.A.) as two fragments (A and B). The A fragment corresponding to the 5' end of the gene was clone behind the amyQ promoter. Both fragments have been extended with specific restriction endonuclease sites in order to allow direct cloning in the multiple cloning sites 1 and 2 (see FIG. 27). The 3' end of the fragment A and 5' end of the fragment B overlap by a unique restriction endonuclease site that allows excision of the E. coli part of the vector and back ligation prior to the transformation of Bacillus subtilis (CBS 363.94). During the procedure of cloning and transformation of B. subtilis, E. coli was used as an intermediate host. The two-step cloning approach in pBHA12 was chosen in order to avoid possible problems during cloning and propagation of the expression vectors in E. coli. In Table 5.1 the restriction enzyme recognition sites added to fragments A and B are listed as well as the unique restriction site that allows back ligation and as such reconstruction of an entire and functional gene. All the 5' ends of the A fragments contain NdeI site (recognition sequence CATATG) that allows cloning of genes as a fragment starting exactly at their respective start codon (ATG).

TABLE 5.1

The summary of the restriction endonuclease (RE) cloning sites that have been added to the gene fragments to facilitate the cloning in pBHA12.

| Gene/RE | Fragment A | | Fragment B | | Unique RE site (position in the gene) |
|---|---|---|---|---|---|
| | 5' end | 3' end | 5' end | 3' end | |
| B. stearothermophilus GI | NdeI | BamHI | SmaI | KpnI | PvuII (496 bp) |
| S. olivochromogenes GI | NdeI | MluI | EcoRV | KpnI | ClaI (372 bp) |
| T. mathranii ARAA | NdeI | MluI | SacI | KpnI | ClaI (708 bp) |

Figure 27:
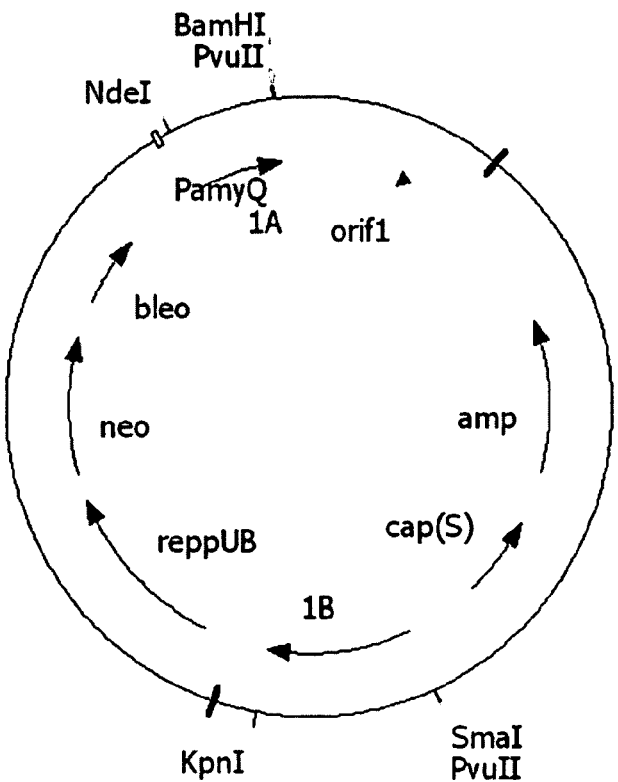
FIG. 27. An example of cloning of a gene in the E. coli/Bacillus shuttle vector pBHA-12. The Figure shows the cloned part A and B (grey arrows) of the SEQ ID NO. 9. The cloning sites of the part 1A are depicted: NdeI and BamHI, for the part 1B SmaI and KpnI. The *E. coli* part was excised using PvuII.

The A and B fragments of 5 genes have been cloned in two steps in the MCS1 and 2, respectively, as shown for the SEQ ID NO. 13 in FIG. 27, using the standard molecular biology methods (Sambrook & Russell, Molecular Cloning: A Laboratory Manual, 3rd Ed., CSHL Press, Cold Spring Harbor, N.Y., 2001; and Ausubel et al., Current Protocols in Molecular Biology, Wiley InterScience, N.Y., 1995). The transformation was performed in the E. coli TOP10 (Invitrogen) or INVI 10 (Invitrogen) in the case of using methylation sensitive restriction endonucleases in a further step. Several E. coli ampicilline resistant transformants for each expression construct were isolated using the mini or midi plasmid isolation kits (Macherey-Nagel and Sigma, respectively). The correct ligation of the corresponding A and B fragments in the pBHA12 vector was confirmed by restriction analysis. In the next step the pBHA12 plasmids that contained the A and B fragments of the genes were digested with the unique restriction endonuclease (see Table 5.1) to excise the E. coli part of the vector. The Bacillus part of the vector that contained the interrupted gene was isolated from the agarose gel using gel extraction kit (Macherey-Nagel) and back ligated. The ligation mixture was transformed to B. subtilis CBS 363.94 strain by competent cell transformation. Several B. subtilis kanamycin resistant transformants for each expression construct were isolated using the mini or midi plasmid isolation kits (Macherey-Nagel and Sigma, respectively). The expression constructs were checked by restriction analysis for the correct pattern after the excision of the E. coli part and the back ligation of the Bacillus part of the pBHA12 vector. For each construct three B. subtilis transformants were selected for analysis of the cell free extract.

5.4 Detection of Overproduced Enzymes in Bacilli

Three B. subtilis transformants and three B. amyloliquefaciens transformants for each construct were used to analyze the cell free extract for the presence of the corresponding protein-glucose or L-arabinose isomerase. The 2×TY fermentation media were used to grow the strains. Samples (1 ml) were taken at 24 hours of fermentation (in shake flask) and the cell free extract was prepared including protease inhibitors in the extraction buffer. 13 µl of the cell free extract were analyzed on SDS-PAGE (Invitrogen). For several transformants a clear band corresponding to the expected Mw of the overexpressed protein was detected. A visual comparison of the bands is given in Table 5.2. It is clear that the method of the invention improved protein production for Bacillus stearothermophilus xylose isomerase, Streptomyces olivochromogenes xylose isomerase and Thermoanaerobacter mathranii L-arabinose isomerase, by using the codon-pair method, i.e. this results in improved protein production in comparison with either the WT reference gene or the single-codon optimized variants. Moreover, if negative codon-pair optimization was applied together with single-codon optimization, no product was detected.

TABLE 5.2

Overexpression of three heterologous genes in Bacilli.

| | B. subtilis | | | | B. amyloliquefaciens | | |
|---|---|---|---|---|---|---|---|
| | WT | sc | sc & cp | sc & cp⁻ | WT | sc | sc & cp | sc & cp⁻ |
| Bacillus stearothermophilus xylose isomerase (SEQ ID NO. 16, 13) | + | | +++ | | | + | +++ | |
| Streptomyces olivochromogenes xylose isomerase (SEQ ID NO. 17, 14, 18) | | + | ++ | 0 | | + | ++ | 0 |
| Thermoanaerobacter mathranii L-arabinose isomerase (SEQ ID 12, 15) | 0/+ | | ++ | | 0 | | ++ | |

WT: Wild type;
Sc: single codon optimization;
cp: codon pair optimization;
cp: negative codon pair optimization.

REFERENCES

Boycheva, S., Chkodrov, G. & Ivanov, I. (2003). Codon pairs in the genome of Escherichia coli. Bioinformatics 19(8): 987-998

Gurvich, O. L., Baranov, P. V., Gesteland, R. F., Atkins, J. F. (2005). Expression levels influence ribosomal frameshifting at the tandem rare arginine codons AGG_AGG and AGA_AGA. J. Bacteriol. 187:4023-4032.

Gustafsson, C., Govindarajan, S. & Minshull, J. (2004). Codon bias and heterologous protein expression. Trends Biotechnol. 22(7):346-353

Gutman, G. A. & Hatfield, G. W. (1989). Nonrandom utilization of codon pairs in Escherichia coli. PNAS 86:3699-3703

Gygi, S. P., Rochon, Y., Franza, B. R., & Aebersold, R. (1999). Correlation between protein and mRNA abundance in Yeast. Mol. Cel. Biol. 19(3):1720-30

Hatfield, G. W. & Gutman, G. A. (1992). Codon pair utilization. U.S. Pat. No. 5,082,767

Irwin, B., Heck, D. & Hatfield, G. W. (1995). Codon pair utilization biases influence translational elongation step times. J Biol Chem 270:22801-22806

Karlin et al. (2001). Characterization of highly expressed genes of four fast-growing bacteria. J. of Bacteriology 183(17):5025-39.

Kunst, F. et al. (1997). The complete genome sequence of the Gram-positive bacterium Bacillus subtilis. Nature 390:249-256

Lithwick, G. & Margalit, H. (2003). Hierarchy of sequence-dependent features associated with prokaryotic translation. Genome Res. 13(12): 2665-73.

Makrides, S. C. (1996). Strategies for achieving high-level expression of genes in Escherichia coli. Microbiol. Rev. 60:512-538

Moura, G. et al. (2005). Comparative context analysis of codon pairs on an ORFeome scale. Genome Biology 2005, 6:R28

Nevalainen, K. M. H., Te'o, V. S. J. & Bergquist, P. L. (2005). Heterologous protein expression in filamentous fungi. Trends Biotechnol. 2005 23(9):468-474

Pel, H. J., et al. (2007). Genome sequencing and analysis of the versatile cell factory Aspergillus niger CBS513.88. Nat. Biotech. 2007 25(2): 221-231

Punt, P. J., van Biezen, N., Conesa, A., Albers, A., Mangnus, J. & van den Hondel, C. (2005). Filamentous fungi as cell factories for heterologous protein production. Trends Biotechnol. 20(5):200-206

Rocha, E. P. C., A. Danchin and A. Viari (1999). Translation in Bacillus subtilis: roles and trends of initiation and termination, insights from a genome analysis. NAR, 27(17): 3567-76. Boycheva, S., Chkodrov, G. & Ivanov, I. (2003). Codon pairs in the genome of Escherichia coli. Bioinformatics 19(8):987-998

Schwartz, S. & Curran, J. F. (1997). Analyses of frameshifting at UUU-pyrimidine sites. NAR 25(10):2005-2011

Spanjaard, R. A. & van Duin, J. (1988). Translation of the sequence AGG-AGG yields 50% ribosomal frameshift. PNAS 85:7967-7971

APPENDIX 1

List of Symbols and Equations

Single codon:
$c_i$
Codons encoding the same amino acid:
$syn(c_i)$
Number of occurrences of the codon $c_i$:
$n_{sc}(c_i)$
Ratio of the codon $c_k$ (compared to its synonyms):

$$r_{sc}(c_k) = n_{sc}(c_k) \bigg/ \sum_{c_l \in syn(c_k)} n_{sc}(c_l)$$

Codon pair:
$(c_i, c_j)$
Occurrences (observed number) of codon pair:
$n_{obs}((c_i, c_j))$
Expected number of this codon pair:

$$n_{exp}^{own}((c_i, c_j)) = r_{sc}^{all}(c_i) \cdot r_{sc}^{all}(c_j) \cdot \sum_{\substack{c_m \in syn(c_i) \\ c_n \in syn(c_j)}} n_{obs}((c_m, c_n))$$

Corresponding standard deviation:

$$\sigma((c_i, c_j)) = \sqrt{n_{exp}((c_i, c_j)) \cdot (1 - r_{sc}^{all}(c_i) \cdot r_{sc}^{all}(c_j))}$$

Corresponding standard score (z-score):

$$z((c_i, c_j)) = \frac{(n_{obs}((c_i, c_j)) - n_{exp}((c_i, c_j)))}{\sigma((c_i, c_j))}$$

Bias coefficient for a codon pair:

$$bias((c_i, c_j)) = \frac{n_{obs}((c_i, c_j)) - n_{exp}((c_i, c_j))}{\max(n_{obs}((c_i, c_j)), n_{exp}((c_i, c_j)))}$$

Combined "expected" values (for weights):

$$n_{exp}^{combi}((c_i, c_j)) = r_{sc}^{all}(c_i) \cdot r_{sc}^{all}(c_j) \cdot \sum_{\substack{c_k \in syn(c_i) \\ c_l \in syn(c_j)}} n_{obs}^{high}((c_k, c_l))$$

Codon pair weights—method one sequence group (or genome):

$$w((c_i, c_j)) = \frac{n_{exp}^{all}((c_i, c_j)) - n_{obs}^{all}((c_i, c_j))}{\max(n_{obs}^{all}((c_i, c_j)), n_{exp}^{all}((c_i, c_j)))}$$

Codon pair weights—method highly expressed group with reference group (or genome):

$$w((c_i, c_j)) = \frac{n_{exp}^{combi}((c_i, c_j)) - n_{obs}^{high}((c_i, c_j))}{\max(n_{obs}^{high}((c_i, c_j)), n_{exp}^{combi}((c_i, c_j)))}$$

APPENDIX 2

CR Vectors

TABLE B.1

CR matrix values for the following organisms in columns: (1) AN: *A. niger* full genome - method: statistical distribution; (2) ANS: *A. niger* 250 highly-expressed genes - method: visual inspection, (3) AN_d: *A. niger* care-don't care (0-1) vector; (4) BS: *B. subtilis* full genome - method: statistical distribution; (5) BSS: *B. subtilis* 50 highly-expressed genes - method: visual inspection, (6) BS_d: *B. subtilis* care-don't care (0-1) vector; (7) EC: *E. coli* full genome 4298 seq; - method: statistical distribution; (8) ECS *E. coli* highly expressed group 100 seq from Carbone et al. (2003) - method: visual inspection; (9) EC_d: *E. coli* care-don't care (0-1) vector; (10) BA: *B. amyloliquefaciens* full genome - method: statistical distribution; (11) BAS: *B. amyolliquefaciens* 50 highly-expressed genes - method: visual inspection, (12) BS_d: *B. amyolliquefaciens* care-don't care (0-1) vector; (13) SC: *S. cerevisiae* full genome - method: statistical distribution; (14) SCS: *S. cerevisiae* 200 highly-expressed genes - method: visual inspection, (15) SC_d: *S. cerevisiae* care-don't care (0-1) vector; (16) SCO: *S. coelicolor* A3(2) full genome - method: statistical distribution

| | | 1 AN | 2 ANS | 3 AN_d | 4 BS | 5 BSS | 6 BS_d | 7 EC | 8 ECS | 9 EC_d | 10 BA | 11 BAS | 12 BA_d |
|---|---|---|---|---|---|---|---|---|---|---|---|---|---|
| 1 | AAA | 33 | 0 | 1 | 71 | 100 | 1 | 75 | 81 | 0 | 69 | 100 | 1 |
| 2 | AAC | 58 | 100 | 1 | 43 | 55 | 0 | 73 | 100 | 0 | 66 | 50 | 0 |
| 3 | AAG | 67 | 100 | 1 | 29 | 0 | 1 | 25 | 19 | 0 | 31 | 0 | 1 |
| 4 | AAT | 42 | 0 | 1 | 57 | 45 | 0 | 66 | 0 | 0 | 76 | 50 | 0 |
| 5 | ACA | 21 | 0 | 1 | 41 | 46 | 0 | 14 | 0 | 0 | 29 | 30 | 0 |
| 6 | ACC | 35 | 70 | 1 | 16 | 0 | 1 | 42 | 57 | 1 | 21 | 0 | 1 |
| 7 | ACG | 22 | 0 | 1 | 26 | 22 | 1 | 26 | 0 | 0 | 38 | 40 | 0 |
| 8 | ACT | 23 | 30 | 1 | 17 | 33 | 0 | 18 | 43 | 1 | 13 | 30 | 0 |
| 9 | AGA | 13 | 0 | 1 | 27 | 28 | 0 | 5 | 0 | 0 | 14 | 20 | 0 |
| 10 | AGC | 18 | 21 | 1 | 22 | 32 | 0 | 27 | 28 | 1 | 22 | 30 | 0 |
| 11 | AGG | 12 | 0 | 1 | 10 | 0 | 1 | 3 | 0 | 0 | 7 | 0 | 1 |
| 12 | AGT | 13 | 0 | 1 | 11 | 0 | 1 | 16 | 0 | 0 | 9 | 0 | 1 |
| 13 | ATA | 14 | 0 | 1 | 14 | 0 | 1 | 9 | 0 | 0 | 15 | 0 | 1 |
| 14 | ATC | 52 | 73 | 1 | 35 | 40 | 0 | 41 | 72 | 1 | 42 | 40 | 0 |
| 15 | ATG | 100 | 100 | 1 | 100 | 100 | 1 | 100 | 100 | 0 | 100 | 100 | 1 |
| 16 | ATT | 34 | 27 | 1 | 51 | 60 | 0 | 51 | 28 | 1 | 44 | 60 | 0 |
| 17 | CAA | 40 | 0 | 1 | 53 | 100 | 1 | 36 | 17 | 0 | 42 | 60 | 0 |
| 18 | CAC | 51 | 100 | 1 | 32 | 29 | 0 | 42 | 81 | 0 | 41 | 40 | 0 |
| 19 | CAG | 60 | 100 | 1 | 47 | 0 | 1 | 64 | 83 | 0 | 58 | 40 | 0 |
| 20 | CAT | 49 | 0 | 1 | 68 | 71 | 0 | 58 | 19 | 0 | 59 | 60 | 0 |
| 21 | CCA | 22 | 0 | 1 | 20 | 22 | 0 | 20 | 14 | 0 | 11 | 0 | 1 |
| 22 | CCC | 29 | 64 | 1 | 10 | 0 | 1 | 13 | 0 | 0 | 17 | 0 | 1 |

TABLE B.1-continued

CR matrix values for the following organisms in columns: (1) AN: *A. niger* full genome - method: statistical distribution; (2) ANS: *A. niger* 250 highly-expressed genes - method: visual inspection, (3) AN_d: *A. niger* care-don't care (0-1) vector; (4) BS: *B. subtilis* full genome - method: statistical distribution; (5) BSS: *B. subtilis* 50 highly-expressed genes - method: visual inspection, (6) BS_d: *B. subtilis* care-don't care (0-1) vector; (7) EC: *E. coli* full genome 4298 seq; - method: statistical distribution; (8) ECS *E. coli* highly expressed group 100 seq from Carbone et al. (2003) - method: visual inspection; (9) EC_d: *E. coli* care-don't care (0-1) vector; (10) BA: *B. amyloliquefaciens* full genome - method: statistical distribution; (11) BAS: *B. amyolliquefaciens* 50 highly-expressed genes - method: visual inspection, (12) BS_d: *B. amyolliquefaciens* care-don't care (0-1) vector; (13) SC: *S. cerevisiae* full genome - method: statistical distribution; (14) SCS: *S. cerevisiae* 200 highly-expressed genes - method: visual inspection, (15) SC_d: *S. cerevisiae* care-don't care (0-1) vector; (16) SCO:*S. coelicolor* A3(2) full genome - method: statistical distribution

| # | Codon | AN | ANS | AN_d | BA | BAS | BA_d | EC | ECS | EC_d | BS | BSS | BS_d |
|---|---|---|---|---|---|---|---|---|---|---|---|---|---|
| 23 | CCG | 24 | 0 | 1 | 41 | 43 | 0 | 49 | 86 | 0 | 52 | 60 | 0 |
| 24 | CCT | 25 | 36 | 1 | 29 | 35 | 0 | 17 | 0 | 0 | 20 | 40 | 0 |
| 25 | CGA | 15 | 0 | 1 | 10 | 0 | 1 | 7 | 0 | 0 | 12 | 0 | 1 |
| 26 | CGC | 25 | 51 | 1 | 19 | 34 | 0 | 38 | 34 | 0 | 32 | 40 | 0 |
| 27 | CGG | 18 | 0 | 1 | 15 | 0 | 1 | 10 | 0 | 0 | 20 | 0 | 1 |
| 28 | CGT | 16 | 49 | 1 | 18 | 38 | 0 | 36 | 66 | 0 | 15 | 40 | 0 |
| 29 | CTA | 10 | 0 | 1 | 5 | 0 | 1 | 4 | 0 | 0 | 4 | 0 | 1 |
| 30 | CTC | 24 | 38 | 1 | 11 | 0 | 1 | 10 | 0 | 0 | 17 | 0 | 1 |
| 31 | CTG | 25 | 32 | 1 | 23 | 0 | 1 | 47 | 100 | 0 | 28 | 20 | 0 |
| 32 | CTT | 17 | 17 | 1 | 23 | 37 | 0 | 11 | 0 | 0 | 21 | 30 | 0 |
| 33 | GAA | 42 | 26 | 1 | 69 | 100 | 1 | 69 | 80 | 0 | 66 | 40 | 0 |
| 34 | GAC | 49 | 64 | 1 | 36 | 37 | 1 | 37 | 64 | 1 | 44 | 40 | 0 |
| 35 | GAG | 58 | 74 | 1 | 31 | 0 | 1 | 31 | 20 | 0 | 34 | 60 | 0 |
| 36 | GAT | 51 | 36 | 1 | 64 | 63 | 1 | 63 | 36 | 1 | 56 | 60 | 0 |
| 37 | GCA | 21 | 0 | 1 | 29 | 50 | 0 | 22 | 30 | 0 | 18 | 30 | 0 |
| 38 | GCC | 32 | 51 | 1 | 20 | 0 | 1 | 27 | 0 | 0 | 26 | 0 | 1 |
| 39 | GCG | 21 | 11 | 1 | 25 | 0 | 1 | 34 | 23 | 0 | 38 | 30 | 0 |
| 40 | GCT | 26 | 38 | 1 | 26 | 50 | 0 | 17 | 47 | 0 | 18 | 40 | 0 |
| 41 | GGA | 24 | 16 | 1 | 32 | 35 | 1 | 12 | 0 | 0 | 26 | 30 | 0 |
| 42 | GGC | 32 | 35 | 1 | 33 | 34 | 1 | 39 | 42 | 1 | 41 | 40 | 0 |
| 43 | GGG | 19 | 0 | 1 | 16 | 0 | 1 | 15 | 0 | 0 | 17 | 0 | 1 |
| 44 | GGT | 25 | 49 | 1 | 19 | 31 | 1 | 34 | 58 | 1 | 16 | 30 | 0 |
| 45 | GTA | 11 | 0 | 1 | 21 | 23 | 1 | 16 | 29 | 0 | 16 | 25 | 0 |
| 46 | GTC | 35 | 54 | 1 | 24 | 0 | 1 | 21 | 0 | 0 | 32 | 25 | 0 |
| 47 | GTG | 30 | 19 | 1 | 26 | 30 | 1 | 36 | 19 | 0 | 28 | 25 | 0 |
| 48 | GTT | 24 | 27 | 1 | 29 | 47 | 1 | 26 | 53 | 0 | 23 | 25 | 0 |
| 49 | TAA | 27 | 100 | 1 | 62 | 100 | 1 | 59 | 100 | 0 | 41 | 100 | 1 |
| 50 | TAC | 58 | 100 | 1 | 34 | 38 | 0 | 42 | 76 | 1 | 59 | 50 | 0 |
| 51 | TAG | 31 | 0 | 1 | 22 | 0 | 1 | 32 | 0 | 0 | 21 | 0 | 1 |
| 52 | TAT | 42 | 0 | 1 | 66 | 62 | 0 | 58 | 24 | 1 | 16 | 50 | 0 |
| 53 | TCA | 13 | 0 | 1 | 24 | 34 | 0 | 13 | 0 | 0 | 16 | 30 | 0 |
| 54 | TCC | 23 | 44 | 1 | 12 | 0 | 1 | 14 | 31 | 1 | 16 | 0 | 1 |
| 55 | TCG | 17 | 14 | 1 | 10 | 0 | 1 | 14 | 0 | 0 | 61 | 40 | 0 |
| 56 | TCT | 17 | 21 | 1 | 21 | 34 | 0 | 15 | 41 | 1 | 100 | 30 | 0 |
| 57 | TGA | 42 | 0 | 1 | 16 | 0 | 1 | 9 | 0 | 0 | 39 | 20 | 0 |
| 58 | TGC | 59 | 100 | 1 | 54 | 49 | 0 | 55 | 100 | 0 | 17 | 30 | 0 |
| 59 | TGG | 100 | 100 | 1 | 100 | 100 | 1 | 100 | 100 | 0 | 41 | 0 | 1 |
| 60 | TGT | 41 | 0 | 1 | 46 | 51 | 0 | 45 | 0 | 0 | 14 | 0 | 1 |
| 61 | TTA | 6 | 0 | 1 | 21 | 39 | 0 | 14 | 0 | 0 | 59 | 0 | 1 |
| 62 | TTC | 65 | 100 | 1 | 30 | 45 | 0 | 41 | 77 | 1 | 69 | 40 | 0 |
| 63 | TTG | 18 | 13 | 1 | 16 | 24 | 0 | 13 | 0 | 0 | 66 | 100 | 1 |
| 64 | TTT | 35 | 0 | 1 | 70 | 55 | 0 | 59 | 23 | 1 | 31 | 60 | 0 |

|   | AN | ANS | AN_d | BA | BAS | BA_d | EC | ECS | EC_d | BS | BSS | BS_d |
|---|---|---|---|---|---|---|---|---|---|---|---|---|
|   | 1 | 2 | 3 | 4 | 5 | 6 | 7 | 8 | 9 | 10 | 11 | 12 |

|   | 13 | 14 | 15 | 16 | 17 | 18 | 19 | 20 | 21 | 22 | 23 | 24 |
|---|---|---|---|---|---|---|---|---|---|---|---|---|
|   | SC | SCS | SC_d | SCO |   |   |   |   |   |   |   |   |

| # | Codon | SC | SCS | SC_d | SCO |
|---|---|---|---|---|---|
| 1 | AAA | 59 | 21 | 1 | 5 |
| 2 | AAC | 40 | 75 | 1 | 96 |
| 3 | AAG | 41 | 79 | 1 | 95 |
| 4 | AAT | 60 | 25 | 1 | 4 |
| 5 | ACA | 31 | 6 | 1 | 2 |
| 6 | ACC | 21 | 40 | 1 | 65 |
| 7 | ACG | 14 | 2 | 1 | 31 |
| 8 | ACT | 34 | 52 | 1 | 2 |
| 9 | AGA | 47 | 76 | 1 | 1 |
| 10 | AGC | 11 | 3 | 1 | 25 |
| 11 | AGG | 21 | 3 | 1 | 4 |
| 12 | AGT | 16 | 4 | 1 | 3 |
| 13 | ATA | 28 | 0 | 1 | 2 |
| 14 | ATC | 26 | 48 | 1 | 96 |
| 15 | ATG | 100 | 100 | 1 | 100 |
| 16 | ATT | 46 | 58 | 1 | 2 |
| 17 | CAA | 69 | 90 | 1 | 5 |

TABLE B.1-continued

CR matrix values for the following organisms in columns: (1) AN: *A. niger* full genome - method: statistical distribution; (2) ANS: *A. niger* 250 highly-expressed genes - method: visual inspection, (3) AN_d: *A. niger* care-don't care (0-1) vector; (4) BS: *B. subtilis* full genome - method: statistical distribution; (5) BSS: *B. subtilis* 50 highly-expressed genes - method: visual inspection, (6) BS_d: *B. subtilis* care-don't care (0-1) vector; (7) EC: *E. coli* full genome 4298 seq; - method: statistical distribution; (8) ECS *E. coli* highly expressed group 100 seq from Carbone et al. (2003) - method: visual inspection; (9) EC_d: *E. coli* care-don't care (0-1) vector; (10) BA: *B. amyloliquefaciens* full genome - method: statistical distribution; (11) BAS: *B. amyolliquefaciens* 50 highly-expressed genes - method: visual inspection, (12) BS_d: *B. amyolliquefaciens* care-don't care (0-1) vector; (13) SC: *S. cerevisiae* full genome - method: statistical distribution; (14) SCS: *S. cerevisiae* 200 highly-expressed genes - method: visual inspection, (15) SC_d: *S. cerevisiae* care-don't care (0-1) vector; (16) SCO: *S. coelicolor* A3(2) full genome - method: statistical distribution

| # | Codon | | | | |
|---|---|---|---|---|---|
| 18 | CAC | 36 | 59 | 1 | 93 |
| 19 | CAG | 31 | 10 | 1 | 95 |
| 20 | CAT | 64 | 41 | 1 | 7 |
| 21 | CCA | 41 | 74 | 1 | 2 |
| 22 | CCC | 16 | 5 | 1 | 41 |
| 23 | CCG | 13 | 0 | 1 | 54 |
| 24 | CCT | 31 | 23 | 1 | 2 |
| 25 | CGA | 7 | 0 | 1 | 3 |
| 26 | CGC | 6 | 1 | 1 | 47 |
| 27 | CGG | 4 | 0 | 1 | 39 |
| 28 | CGT | 14 | 25 | 1 | 6 |
| 29 | CTA | 14 | 9 | 1 | 0 |
| 30 | CTC | 6 | 0 | 1 | 36 |
| 31 | CTG | 11 | 5 | 1 | 60 |
| 32 | CTT | 13 | 3 | 1 | 2 |
| 33 | GAA | 70 | 85 | 1 | 15 |
| 34 | GAC | 35 | 51 | 1 | 95 |
| 35 | GAG | 30 | 15 | 1 | 85 |
| 36 | GAT | 65 | 49 | 1 | 5 |
| 37 | GCA | 30 | 2 | 1 | 4 |
| 38 | GCC | 22 | 33 | 1 | 58 |
| 39 | GCG | 11 | 0 | 1 | 36 |
| 40 | GCT | 37 | 64 | 1 | 2 |
| 41 | GGA | 23 | 0 | 1 | 7 |
| 42 | GGC | 20 | 8 | 1 | 64 |
| 43 | GGG | 12 | 1 | 1 | 19 |
| 44 | GGT | 45 | 95 | 1 | 10 |
| 45 | GTA | 22 | 0 | 1 | 3 |
| 46 | GTC | 20 | 39 | 1 | 55 |
| 47 | GTG | 19 | 8 | 1 | 40 |
| 48 | GTT | 39 | 54 | 1 | 2 |
| 49 | TAA | — | 100 | 1 | — |
| 50 | TAC | 43 | 74 | 1 | 95 |
| 51 | TAG | — | 0 | 1 | — |
| 52 | TAT | 57 | 26 | 1 | 5 |
| 53 | TCA | 21 | 8 | 1 | 2 |
| 54 | TCC | 16 | 32 | 1 | 41 |
| 55 | TCG | 10 | 5 | 1 | 28 |
| 56 | TCT | 26 | 48 | 1 | 1 |
| 57 | TGA | — | 0 | 1 | — |
| 58 | TGC | 38 | 13 | 1 | 91 |
| 59 | TGG | 100 | 100 | 1 | 100 |
| 60 | TGT | 62 | 87 | 1 | 9 |
| 61 | TTA | 28 | 21 | 1 | 0 |
| 62 | TTC | 41 | 71 | 1 | 98 |
| 63 | TTG | 28 | 62 | 1 | 2 |
| 64 | TTT | 59 | 29 | 1 | 2 |
| | | SC | SCS | 1 | SCO | | | | | | | |
| | | 13 | 14 | 15 | 16 | 17 | 18 | 19 | 20 | 21 | 22 | 23 | 24 |

Note:

For fungal microorganisms, and more specific *P. chrysogenum, A. Oryzae, A. terreus, A. nidulans, A. fumigatus, T. reesei, N. fischerii*, the CR vector derived using the *A. niger* sequences applies. For yeast in general, and more specific *K. lactis* and *S. pombe*, the CR vector derived using the *S. cerevisiae* sequences applies. For *Streptomyces* species the CR vector derived using *S. coelicolor* A3(2) applies.

APPENDIX 3

CPW Matrices

TABLE C.1

CPW matrix *Aspergillus niger* full genome (left codon indicated in column 2, right codon indicated in row 2). Host cell: *A. niger*; Sequence data: full *A. niger* genome.

| | | 1<br>AAA | 2<br>AAC | 3<br>AAG | 4<br>AAT | 5<br>ACA | 6<br>ACC | 7<br>ACG | 8<br>ACT | 9<br>AGA | 10<br>AGC | 11<br>AGG | 12<br>AGT |
|---|---|---|---|---|---|---|---|---|---|---|---|---|---|
| 1 | AAA | 0.62 | 0.37 | 0.38 | 0.34 | −0.16 | 0.07 | 0.18 | 0.29 | −0.19 | −0.03 | −0.14 | 0.11 |
| 2 | AAC | −0.17 | −0.28 | −0.23 | −0.05 | 0.08 | −0.25 | −0.01 | 0.03 | 0.02 | −0.30 | 0.17 | −0.04 |
| 3 | AAG | −0.02 | −0.20 | −0.24 | −0.05 | −0.02 | −0.04 | −0.12 | 0.03 | −0.14 | −0.05 | −0.18 | −0.03 |
| 4 | AAT | 0.24 | 0.45 | 0.44 | 0.22 | 0.16 | 0.16 | 0.15 | 0.06 | 0.19 | 0.17 | 0.23 | 0.08 |
| 5 | ACA | 0.00 | 0.09 | 0.25 | 0.04 | −0.25 | 0.04 | 0.14 | 0.20 | −0.25 | −0.01 | −0.22 | 0.10 |
| 6 | ACC | −0.17 | −0.35 | −0.28 | −0.07 | 0.11 | −0.30 | 0.17 | 0.01 | −0.08 | −0.22 | 0.07 | −0.02 |
| 7 | ACG | −0.18 | 0.01 | −0.06 | −0.05 | 0.00 | 0.21 | −0.14 | 0.10 | −0.25 | 0.15 | −0.36 | 0.00 |
| 8 | ACT | 0.36 | 0.57 | 0.53 | 0.40 | 0.13 | 0.17 | 0.17 | −0.22 | 0.03 | 0.27 | 0.15 | 0.20 |
| 9 | AGA | −0.01 | 0.05 | 0.06 | −0.08 | −0.18 | 0.19 | 0.10 | 0.11 | −0.37 | −0.17 | −0.30 | −0.15 |
| 10 | AGC | −0.28 | −0.26 | −0.26 | −0.25 | 0.00 | −0.06 | 0.04 | 0.03 | −0.20 | −0.31 | −0.04 | −0.21 |
| 11 | AGG | −0.31 | 0.08 | −0.22 | −0.32 | −0.17 | 0.31 | −0.25 | 0.01 | −0.39 | 0.10 | −0.52 | −0.18 |
| 12 | AGT | 0.21 | 0.35 | 0.47 | 0.17 | 0.24 | 0.37 | 0.28 | 0.13 | 0.21 | 0.28 | 0.27 | 0.05 |
| 13 | ATA | 0.06 | 0.25 | 0.38 | 0.16 | −0.21 | 0.03 | 0.08 | 0.04 | −0.10 | 0.07 | −0.07 | 0.17 |
| 14 | ATC | −0.27 | −0.35 | −0.31 | −0.15 | 0.03 | −0.30 | −0.03 | −0.04 | 0.14 | −0.10 | 0.20 | 0.02 |
| 15 | ATG | 0.02 | −0.06 | −0.01 | 0.09 | 0.05 | 0.01 | −0.10 | 0.04 | −0.13 | −0.14 | −0.08 | 0.00 |
| 16 | ATT | 0.50 | 0.55 | 0.56 | 0.45 | 0.34 | 0.26 | 0.26 | 0.16 | 0.41 | 0.44 | 0.46 | 0.38 |
| 17 | CAA | 0.27 | 0.21 | 0.25 | 0.10 | −0.15 | −0.01 | 0.14 | 0.20 | −0.07 | −0.09 | 0.05 | 0.03 |
| 18 | CAC | −0.29 | −0.25 | −0.26 | −0.18 | −0.05 | −0.22 | 0.01 | −0.03 | 0.11 | −0.25 | 0.32 | −0.09 |
| 19 | CAG | −0.17 | −0.08 | −0.13 | −0.11 | −0.08 | 0.09 | −0.09 | −0.06 | −0.08 | −0.01 | 0.02 | −0.01 |
| 20 | CAT | 0.23 | 0.44 | 0.46 | 0.09 | 0.08 | 0.18 | 0.15 | 0.04 | 0.42 | 0.29 | 0.50 | 0.22 |
| 21 | CCA | 0.10 | 0.16 | 0.24 | 0.01 | −0.24 | 0.01 | 0.12 | 0.02 | −0.12 | 0.13 | −0.11 | 0.17 |
| 22 | CCC | −0.28 | −0.36 | −0.37 | −0.15 | 0.09 | −0.15 | 0.03 | −0.04 | −0.12 | −0.17 | 0.05 | −0.06 |
| 23 | CCG | −0.14 | 0.07 | 0.06 | −0.09 | −0.12 | 0.08 | −0.14 | 0.00 | −0.04 | 0.32 | −0.06 | 0.14 |
| 24 | CCT | 0.38 | 0.46 | 0.48 | 0.26 | 0.09 | 0.18 | 0.16 | −0.02 | 0.31 | 0.38 | 0.33 | 0.23 |
| 25 | CGA | 0.17 | 0.19 | 0.28 | 0.12 | −0.19 | 0.06 | 0.16 | 0.17 | −0.03 | −0.14 | 0.01 | 0.03 |
| 26 | CGC | −0.24 | −0.25 | −0.26 | −0.22 | −0.07 | −0.16 | −0.16 | 0.03 | 0.01 | −0.32 | 0.18 | −0.27 |
| 27 | CGG | −0.22 | 0.13 | 0.01 | −0.15 | −0.26 | 0.15 | −0.31 | −0.11 | −0.24 | 0.07 | −0.19 | −0.18 |
| 28 | CGT | 0.51 | 0.45 | 0.67 | 0.48 | 0.29 | 0.24 | 0.32 | 0.17 | 0.63 | 0.44 | 0.58 | 0.40 |
| 29 | CTA | 0.24 | 0.26 | 0.43 | 0.25 | −0.03 | 0.03 | 0.33 | 0.27 | 0.24 | 0.12 | 0.18 | 0.25 |
| 30 | CTC | −0.23 | −0.30 | −0.20 | −0.11 | 0.03 | −0.24 | 0.09 | −0.02 | 0.29 | −0.17 | 0.33 | −0.06 |
| 31 | CTG | −0.16 | −0.12 | −0.13 | 0.04 | 0.12 | 0.07 | 0.02 | 0.09 | 0.12 | 0.01 | 0.04 | 0.09 |
| 32 | CTT | 0.54 | 0.52 | 0.64 | 0.48 | 0.19 | 0.23 | 0.26 | 0.11 | 0.56 | 0.44 | 0.55 | 0.38 |
| 33 | GAA | 0.46 | 0.27 | 0.24 | 0.09 | −0.09 | 0.06 | 0.09 | 0.17 | −0.23 | −0.16 | −0.14 | −0.12 |
| 34 | GAC | −0.18 | −0.21 | −0.28 | −0.19 | 0.01 | −0.13 | −0.03 | 0.00 | 0.01 | −0.31 | 0.05 | −0.23 |
| 35 | GAG | −0.07 | −0.07 | −0.23 | −0.19 | −0.05 | 0.10 | −0.22 | −0.03 | −0.19 | −0.09 | −0.31 | −0.20 |
| 36 | GAT | 0.24 | 0.34 | 0.36 | 0.09 | 0.06 | 0.12 | 0.02 | −0.01 | 0.20 | 0.19 | 0.27 | 0.01 |
| 37 | GCA | 0.08 | 0.09 | 0.15 | 0.00 | −0.16 | 0.07 | 0.05 | 0.04 | −0.19 | 0.07 | −0.23 | 0.06 |
| 38 | GCC | −0.28 | −0.36 | −0.28 | −0.23 | 0.10 | −0.11 | −0.04 | −0.05 | −0.05 | −0.25 | −0.01 | −0.26 |
| 39 | GCG | −0.07 | 0.11 | −0.06 | −0.08 | −0.16 | 0.15 | −0.26 | 0.00 | −0.18 | 0.28 | −0.31 | 0.05 |
| 40 | GCT | 0.38 | 0.60 | 0.48 | 0.38 | 0.16 | 0.21 | 0.10 | −0.12 | 0.18 | 0.31 | 0.22 | 0.13 |
| 41 | GGA | 0.03 | −0.09 | −0.11 | −0.19 | −0.21 | 0.07 | −0.09 | −0.05 | −0.37 | −0.20 | −0.30 | −0.28 |
| 42 | GGC | −0.12 | −0.13 | −0.19 | −0.04 | −0.10 | −0.12 | −0.11 | −0.04 | 0.10 | −0.25 | 0.15 | −0.27 |
| 43 | GGG | −0.33 | 0.21 | −0.17 | −0.29 | −0.15 | 0.34 | −0.26 | −0.02 | −0.31 | 0.20 | −0.52 | −0.25 |
| 44 | GGT | 0.34 | 0.31 | 0.65 | 0.32 | 0.24 | 0.17 | 0.38 | 0.03 | 0.31 | 0.21 | 0.45 | −0.02 |
| 45 | GTA | 0.22 | 0.30 | 0.38 | 0.09 | −0.13 | 0.09 | 0.08 | 0.12 | 0.18 | 0.38 | 0.07 | 0.39 |
| 46 | GTC | −0.20 | −0.34 | −0.33 | −0.24 | 0.14 | −0.18 | 0.00 | −0.18 | 0.18 | −0.19 | 0.15 | −0.11 |
| 47 | GTG | −0.01 | 0.03 | −0.06 | 0.06 | −0.01 | 0.09 | −0.22 | −0.12 | 0.03 | 0.16 | −0.27 | 0.24 |
| 48 | GTT | 0.53 | 0.55 | 0.50 | 0.38 | 0.35 | 0.31 | 0.13 | −0.03 | 0.43 | 0.37 | 0.24 | 0.28 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | −0.18 | −0.29 | −0.24 | −0.06 | 0.13 | −0.23 | 0.00 | 0.01 | 0.15 | −0.20 | 0.34 | −0.06 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.33 | 0.44 | 0.41 | 0.24 | 0.18 | 0.14 | 0.05 | 0.05 | 0.32 | 0.33 | 0.31 | 0.21 |
| 53 | TCA | 0.01 | 0.22 | 0.29 | −0.03 | −0.33 | 0.02 | 0.05 | −0.09 | −0.18 | 0.11 | −0.27 | 0.14 |
| 54 | TCC | −0.21 | −0.30 | −0.30 | −0.07 | 0.07 | −0.21 | 0.10 | 0.00 | −0.01 | −0.19 | 0.08 | 0.13 |
| 55 | TCG | −0.14 | 0.06 | −0.02 | −0.11 | −0.09 | 0.00 | −0.20 | −0.09 | −0.07 | 0.21 | −0.21 | 0.10 |
| 56 | TCT | 0.44 | 0.55 | 0.56 | 0.37 | 0.03 | 0.15 | 0.17 | −0.13 | 0.22 | 0.35 | 0.30 | 0.37 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | −0.26 | −0.19 | −0.25 | −0.23 | −0.10 | −0.10 | −0.15 | −0.07 | −0.09 | −0.10 | −0.04 | −0.26 |
| 59 | TGG | −0.09 | 0.02 | 0.05 | −0.03 | −0.03 | 0.15 | −0.15 | −0.04 | −0.28 | −0.01 | −0.29 | −0.22 |
| 60 | TGT | 0.27 | 0.43 | 0.61 | 0.31 | 0.16 | 0.25 | 0.14 | 0.08 | 0.39 | 0.47 | 0.37 | 0.32 |

TABLE C.1-continued

CPW matrix *Aspergillus niger* full genome (left codon indicated in column 2, right codon indicated in row 2). Host cell: *A. niger*; Sequence data: full *A. niger* genome.

| | | | | | | | | | | | | |
|---|---|---|---|---|---|---|---|---|---|---|---|---|
| 61 | TTA | 0.31 | 0.39 | 0.41 | 0.20 | −0.05 | 0.13 | 0.11 | 0.09 | 0.04 | 0.24 | −0.01 | 0.13 |
| 62 | TTC | −0.18 | −0.30 | −0.27 | −0.08 | 0.14 | −0.24 | 0.05 | −0.06 | 0.19 | −0.09 | 0.20 | 0.02 |
| 63 | TTG | −0.17 | −0.12 | −0.26 | −0.24 | −0.17 | −0.08 | −0.34 | −0.29 | −0.08 | 0.08 | −0.35 | −0.12 |
| 64 | TTT | 0.54 | 0.58 | 0.61 | 0.46 | 0.25 | 0.19 | 0.09 | 0.08 | 0.40 | 0.41 | 0.29 | 0.29 |

| | | AAA 1 | AAC 2 | AAG 3 | AAT 4 | ACA 5 | ACC 6 | ACG 7 | ACT 8 | AGA 9 | AGC 10 | AGG 11 | AGT 12 |
|---|---|---|---|---|---|---|---|---|---|---|---|---|---|
| | | 13 ATA | 14 ATC | 15 ATG | 16 ATT | 17 CAA | 18 CAC | 19 CAG | 20 CAT | 21 CCA | 22 CCC | 23 CCG | 24 CCT |
| 1 | AAA | −0.14 | 0.21 | 0.19 | 0.31 | −0.14 | −0.07 | 0.16 | −0.08 | −0.11 | −0.04 | 0.05 | 0.19 |
| 2 | AAC | 0.24 | −0.17 | −0.09 | 0.08 | −0.02 | −0.18 | −0.11 | 0.10 | 0.05 | −0.19 | −0.05 | 0.08 |
| 3 | AAG | −0.04 | −0.13 | −0.08 | −0.01 | 0.06 | 0.00 | −0.06 | 0.08 | 0.03 | −0.09 | 0.00 | 0.05 |
| 4 | AAT | 0.06 | 0.08 | 0.14 | 0.04 | 0.06 | 0.16 | 0.15 | 0.02 | 0.07 | 0.05 | 0.10 | 0.05 |
| 5 | ACA | −0.11 | 0.20 | 0.04 | 0.20 | −0.07 | 0.01 | 0.05 | 0.00 | −0.22 | −0.02 | 0.00 | 0.05 |
| 6 | ACC | 0.11 | −0.29 | −0.14 | −0.07 | 0.09 | −0.12 | 0.08 | 0.20 | 0.19 | 0.02 | 0.11 | 0.21 |
| 7 | ACG | −0.16 | 0.12 | −0.05 | 0.09 | −0.06 | −0.02 | −0.19 | −0.07 | −0.03 | 0.10 | −0.15 | 0.04 |
| 8 | ACT | 0.12 | 0.18 | 0.26 | 0.09 | −0.01 | −0.01 | 0.04 | −0.02 | −0.02 | −0.16 | −0.07 | −0.19 |
| 9 | AGA | −0.31 | 0.19 | 0.06 | 0.09 | −0.14 | −0.05 | −0.05 | −0.15 | −0.10 | 0.15 | 0.10 | 0.14 |
| 10 | AGC | −0.08 | −0.09 | −0.20 | −0.09 | 0.00 | −0.05 | −0.09 | −0.12 | 0.13 | 0.22 | 0.13 | 0.16 |
| 11 | AGG | −0.44 | 0.19 | −0.09 | −0.11 | 0.05 | 0.20 | 0.10 | 0.02 | −0.15 | 0.27 | −0.05 | 0.01 |
| 12 | AGT | −0.20 | 0.03 | 0.11 | −0.02 | −0.04 | 0.11 | 0.07 | −0.12 | 0.04 | 0.07 | −0.05 | 0.02 |
| 13 | ATA | −0.34 | 0.17 | 0.10 | 0.21 | −0.14 | 0.11 | 0.07 | −0.07 | −0.20 | −0.08 | −0.02 | −0.09 |
| 14 | ATC | 0.21 | −0.25 | −0.19 | 0.00 | 0.04 | −0.18 | −0.02 | 0.17 | 0.16 | −0.09 | 0.21 | 0.19 |
| 15 | ATG | −0.09 | 0.01 | 0.00 | 0.03 | 0.04 | −0.04 | −0.03 | 0.04 | −0.01 | 0.01 | −0.02 | 0.02 |
| 16 | ATT | 0.24 | 0.19 | 0.32 | 0.16 | −0.03 | 0.07 | 0.03 | −0.01 | 0.03 | −0.19 | −0.03 | −0.16 |
| 17 | CAA | −0.21 | 0.14 | 0.15 | 0.25 | −0.16 | 0.02 | 0.22 | −0.03 | −0.15 | 0.02 | 0.10 | 0.14 |
| 18 | CAC | 0.21 | −0.16 | −0.13 | −0.02 | −0.14 | −0.18 | 0.00 | 0.14 | 0.07 | −0.01 | 0.06 | 0.15 |
| 19 | CAG | −0.09 | −0.07 | −0.09 | −0.07 | 0.01 | 0.04 | −0.06 | −0.04 | −0.11 | 0.04 | 0.00 | −0.01 |
| 20 | CAT | −0.04 | 0.16 | 0.15 | 0.01 | −0.06 | 0.14 | 0.15 | −0.05 | −0.07 | −0.04 | −0.03 | −0.11 |
| 21 | CCA | −0.02 | 0.24 | 0.09 | 0.08 | −0.05 | 0.11 | 0.21 | 0.08 | −0.30 | 0.08 | −0.03 | 0.10 |
| 22 | CCC | −0.06 | −0.29 | −0.20 | −0.12 | 0.06 | 0.16 | 0.02 | 0.15 | 0.19 | 0.56 | 0.06 | 0.29 |
| 23 | CCG | −0.14 | 0.09 | −0.04 | 0.05 | −0.08 | 0.02 | −0.07 | −0.10 | −0.08 | 0.18 | −0.19 | 0.01 |
| 24 | CCT | 0.07 | 0.20 | 0.26 | 0.08 | −0.12 | −0.17 | 0.01 | −0.19 | −0.23 | −0.17 | −0.20 | −0.25 |
| 25 | CGA | 0.07 | 0.28 | 0.18 | 0.25 | −0.15 | −0.11 | −0.08 | −0.04 | −0.27 | 0.05 | −0.23 | −0.03 |
| 26 | CGC | −0.01 | −0.23 | −0.20 | −0.14 | 0.07 | 0.07 | −0.04 | −0.07 | 0.23 | 0.20 | 0.23 | 0.31 |
| 27 | CGG | −0.33 | 0.18 | −0.06 | −0.03 | 0.07 | 0.30 | 0.17 | 0.05 | −0.23 | 0.12 | −0.14 | −0.08 |
| 28 | CGT | 0.11 | 0.01 | 0.31 | 0.19 | −0.08 | −0.10 | 0.02 | −0.09 | −0.13 | −0.22 | −0.20 | −0.20 |
| 29 | CTA | 0.03 | 0.25 | 0.24 | 0.32 | −0.19 | −0.15 | −0.04 | −0.10 | −0.26 | −0.08 | −0.05 | −0.06 |
| 30 | CTC | 0.06 | −0.22 | −0.08 | −0.03 | 0.06 | −0.03 | 0.17 | 0.23 | 0.14 | −0.12 | 0.31 | 0.13 |
| 31 | CTG | 0.05 | 0.00 | −0.02 | 0.06 | 0.02 | −0.06 | −0.12 | 0.05 | 0.15 | 0.09 | 0.15 | 0.09 |
| 32 | CTT | 0.21 | 0.25 | 0.39 | 0.20 | −0.12 | −0.13 | 0.04 | −0.18 | −0.23 | −0.34 | −0.04 | −0.33 |
| 33 | GAA | −0.07 | 0.11 | 0.13 | 0.14 | −0.05 | 0.07 | 0.17 | 0.00 | 0.00 | 0.09 | 0.10 | 0.16 |
| 34 | GAC | 0.10 | 0.00 | −0.10 | −0.03 | −0.04 | −0.15 | −0.12 | −0.03 | 0.16 | −0.12 | −0.02 | −0.01 |
| 35 | GAG | −0.05 | −0.01 | −0.09 | −0.14 | 0.01 | 0.03 | −0.09 | −0.07 | −0.09 | 0.02 | −0.09 | −0.09 |
| 36 | GAT | −0.01 | 0.06 | 0.11 | −0.08 | 0.10 | 0.22 | 0.09 | −0.02 | 0.10 | −0.02 | −0.04 | 0.02 |
| 37 | GCA | 0.09 | 0.30 | 0.18 | 0.17 | 0.04 | 0.10 | 0.07 | −0.02 | −0.18 | 0.10 | −0.10 | −0.02 |
| 38 | GCC | 0.13 | −0.27 | −0.24 | −0.28 | 0.21 | 0.00 | 0.04 | 0.14 | 0.28 | 0.20 | 0.15 | 0.20 |
| 39 | GCG | 0.01 | 0.23 | 0.02 | 0.08 | −0.10 | 0.02 | −0.24 | −0.23 | −0.09 | 0.06 | −0.28 | −0.07 |
| 40 | GCT | 0.12 | 0.18 | 0.24 | −0.07 | 0.04 | 0.04 | −0.02 | −0.06 | 0.04 | −0.13 | −0.01 | −0.26 |
| 41 | GGA | −0.11 | 0.21 | 0.02 | 0.07 | 0.00 | 0.17 | −0.01 | −0.01 | −0.08 | 0.16 | −0.05 | 0.04 |
| 42 | GGC | 0.12 | −0.04 | −0.14 | −0.10 | −0.05 | −0.15 | −0.14 | −0.12 | 0.16 | 0.07 | 0.09 | 0.00 |
| 43 | GGG | −0.30 | 0.26 | −0.08 | −0.15 | 0.16 | 0.33 | 0.06 | −0.04 | −0.15 | 0.01 | −0.20 | −0.18 |
| 44 | GGT | 0.15 | −0.13 | 0.26 | −0.03 | 0.04 | 0.06 | 0.11 | −0.02 | 0.11 | −0.02 | 0.06 | −0.15 |
| 45 | GTA | −0.04 | 0.30 | 0.22 | 0.20 | −0.17 | −0.02 | −0.04 | −0.16 | −0.29 | −0.04 | −0.11 | −0.21 |
| 46 | GTC | 0.13 | −0.22 | −0.18 | −0.23 | 0.23 | −0.02 | 0.10 | 0.19 | 0.33 | 0.11 | 0.27 | 0.15 |
| 47 | GTG | 0.02 | 0.19 | −0.01 | −0.06 | 0.01 | 0.03 | −0.21 | −0.08 | 0.14 | 0.10 | −0.15 | −0.07 |
| 48 | GTT | 0.14 | 0.22 | 0.25 | 0.00 | 0.01 | 0.00 | 0.04 | −0.08 | −0.05 | −0.21 | −0.02 | −0.32 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.18 | −0.17 | −0.11 | 0.04 | 0.02 | −0.15 | −0.05 | 0.13 | 0.17 | −0.02 | 0.17 | 0.15 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.08 | 0.13 | 0.18 | 0.05 | −0.01 | 0.11 | 0.06 | −0.04 | −0.06 | −0.15 | −0.15 | −0.15 |
| 53 | TCA | −0.24 | 0.20 | 0.04 | 0.07 | 0.00 | 0.18 | 0.14 | 0.12 | −0.28 | 0.00 | 0.00 | −0.02 |
| 54 | TCC | −0.01 | −0.25 | −0.11 | 0.03 | 0.13 | −0.02 | 0.08 | 0.16 | 0.12 | 0.12 | 0.09 | 0.18 |
| 55 | TCG | −0.14 | 0.12 | 0.00 | 0.15 | −0.12 | 0.05 | −0.11 | −0.12 | −0.04 | 0.04 | −0.14 | −0.09 |
| 56 | TCT | 0.08 | 0.21 | 0.33 | 0.21 | −0.08 | −0.01 | 0.02 | −0.09 | −0.15 | −0.21 | −0.13 | −0.27 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | −0.05 | −0.01 | −0.14 | −0.17 | 0.04 | −0.04 | −0.06 | −0.05 | 0.26 | 0.17 | 0.06 | 0.15 |
| 59 | TGG | −0.09 | 0.09 | 0.00 | −0.09 | 0.05 | 0.00 | −0.03 | 0.00 | −0.02 | 0.06 | −0.07 | 0.02 |
| 60 | TGT | −0.02 | 0.16 | 0.23 | 0.12 | −0.06 | 0.15 | 0.09 | −0.01 | −0.13 | −0.11 | −0.27 | −0.21 |
| 61 | TTA | −0.25 | 0.27 | 0.09 | 0.18 | −0.18 | −0.01 | 0.00 | −0.20 | −0.32 | −0.01 | −0.12 | −0.15 |

TABLE C.1-continued

CPW matrix *Aspergillus niger* full genome (left codon indicated in column 2, right codon indicated in row 2). Host cell: *A. niger*; Sequence data: full *A. niger* genome.

| | | | | | | | | | | | | |
|---|---|---|---|---|---|---|---|---|---|---|---|---|
| 62 | TTC | 0.30 | −0.21 | −0.13 | −0.02 | 0.04 | −0.20 | −0.14 | 0.12 | 0.20 | −0.11 | 0.11 | −0.02 |
| 63 | TTG | −0.23 | −0.12 | −0.28 | −0.26 | 0.15 | 0.27 | −0.02 | 0.05 | 0.21 | 0.27 | 0.09 | 0.08 |
| 64 | TTT | 0.28 | 0.21 | 0.29 | 0.13 | 0.10 | 0.17 | 0.19 | 0.07 | 0.00 | −0.09 | −0.01 | −0.07 |

| | ATA 13 | ATC 14 | ATG 15 | ATT 16 | CAA 17 | CAC 18 | CAG 19 | CAT 20 | CCA 21 | CCC 22 | CCG 23 | CCT 24 |
|---|---|---|---|---|---|---|---|---|---|---|---|---|

| | | 25 CGA | 26 CGC | 27 CGG | 28 CGT | 29 CTA | 30 CTC | 31 CTG | 32 CTT | 33 GAA | 34 GAC | 35 GAG | 36 GAT |
|---|---|---|---|---|---|---|---|---|---|---|---|---|---|
| 1 | AAA | −0.14 | 0.13 | 0.00 | 0.25 | −0.12 | 0.05 | 0.15 | 0.18 | −0.15 | −0.18 | 0.07 | −0.04 |
| 2 | AAC | 0.02 | −0.18 | −0.06 | −0.11 | 0.11 | −0.20 | −0.08 | 0.05 | 0.11 | 0.02 | 0.09 | 0.29 |
| 3 | AAG | 0.13 | 0.01 | 0.08 | 0.07 | 0.04 | −0.06 | −0.10 | −0.04 | 0.10 | 0.09 | −0.04 | 0.04 |
| 4 | AAT | −0.02 | 0.09 | −0.06 | 0.17 | −0.10 | 0.03 | −0.01 | 0.06 | −0.12 | −0.17 | −0.13 | −0.20 |
| 5 | ACA | −0.01 | 0.23 | 0.14 | 0.44 | −0.12 | 0.27 | 0.14 | 0.16 | −0.10 | −0.09 | 0.05 | 0.03 |
| 6 | ACC | 0.25 | −0.06 | 0.20 | 0.08 | 0.13 | −0.23 | 0.08 | 0.18 | 0.09 | −0.11 | 0.11 | 0.17 |
| 7 | ACG | −0.01 | 0.05 | −0.04 | 0.28 | −0.07 | 0.15 | −0.11 | 0.07 | −0.06 | −0.05 | −0.19 | −0.13 |
| 8 | ACT | −0.15 | −0.16 | −0.07 | −0.22 | −0.07 | −0.10 | −0.07 | −0.11 | 0.00 | 0.15 | 0.04 | 0.04 |
| 9 | AGA | 0.00 | 0.26 | −0.16 | 0.24 | −0.18 | 0.25 | 0.11 | 0.06 | −0.14 | 0.01 | 0.04 | −0.04 |
| 10 | AGC | 0.06 | 0.20 | 0.02 | 0.02 | 0.23 | 0.30 | 0.19 | 0.09 | −0.02 | −0.05 | 0.03 | 0.14 |
| 11 | AGG | 0.19 | 0.37 | 0.21 | 0.37 | −0.22 | 0.36 | 0.05 | −0.09 | −0.14 | 0.18 | −0.22 | −0.21 |
| 12 | AGT | −0.21 | −0.08 | −0.26 | −0.05 | −0.27 | −0.08 | −0.20 | −0.16 | −0.16 | −0.14 | −0.11 | −0.22 |
| 13 | ATA | −0.12 | 0.32 | 0.08 | 0.17 | −0.24 | 0.13 | 0.15 | −0.06 | 0.03 | 0.17 | 0.25 | 0.22 |
| 14 | ATC | 0.07 | −0.18 | −0.01 | −0.09 | 0.12 | −0.18 | 0.08 | 0.17 | 0.14 | −0.04 | 0.13 | 0.25 |
| 15 | ATG | 0.07 | −0.01 | 0.06 | 0.06 | 0.00 | 0.00 | −0.09 | −0.07 | 0.03 | 0.00 | −0.02 | 0.00 |
| 16 | ATT | −0.16 | −0.11 | −0.13 | −0.11 | −0.09 | −0.15 | −0.09 | −0.12 | −0.19 | −0.21 | −0.24 | −0.19 |
| 17 | CAA | −0.03 | 0.13 | 0.03 | 0.15 | −0.07 | 0.08 | 0.20 | 0.16 | −0.18 | −0.06 | 0.12 | −0.08 |
| 18 | CAC | 0.02 | −0.14 | 0.06 | −0.23 | 0.19 | −0.07 | 0.12 | 0.11 | 0.03 | 0.05 | 0.09 | 0.17 |
| 19 | CAG | −0.04 | −0.06 | 0.00 | −0.02 | −0.04 | 0.00 | −0.15 | −0.10 | 0.01 | 0.12 | 0.02 | −0.02 |
| 20 | CAT | −0.12 | −0.09 | −0.10 | −0.14 | −0.19 | −0.08 | −0.07 | −0.13 | −0.14 | −0.02 | 0.00 | −0.17 |
| 21 | CCA | −0.09 | 0.26 | 0.06 | 0.33 | −0.08 | 0.28 | 0.13 | 0.14 | −0.11 | −0.04 | 0.06 | 0.00 |
| 22 | CCC | 0.00 | 0.08 | 0.07 | −0.12 | 0.22 | −0.05 | 0.33 | 0.21 | −0.04 | −0.09 | −0.02 | 0.07 |
| 23 | CCG | 0.02 | 0.01 | 0.00 | 0.21 | −0.09 | 0.19 | −0.11 | 0.04 | −0.03 | −0.01 | −0.11 | −0.09 |
| 24 | CCT | −0.20 | −0.15 | −0.07 | −0.34 | −0.11 | −0.12 | −0.01 | −0.24 | 0.06 | 0.15 | 0.18 | 0.02 |
| 25 | CGA | −0.29 | 0.09 | −0.15 | 0.18 | −0.31 | 0.04 | −0.17 | 0.03 | 0.04 | 0.10 | 0.17 | 0.13 |
| 26 | CGC | 0.24 | 0.04 | 0.13 | −0.02 | 0.25 | 0.18 | 0.18 | 0.27 | 0.02 | −0.04 | 0.09 | 0.10 |
| 27 | CGG | 0.08 | 0.24 | 0.05 | 0.26 | −0.01 | 0.33 | −0.05 | 0.09 | 0.02 | 0.14 | 0.00 | −0.08 |
| 28 | CGT | −0.18 | −0.31 | −0.17 | −0.36 | −0.29 | −0.33 | −0.26 | −0.24 | −0.06 | −0.12 | 0.04 | −0.12 |
| 29 | CTA | −0.32 | −0.03 | −0.18 | 0.05 | −0.32 | 0.06 | 0.16 | −0.07 | −0.03 | 0.01 | 0.15 | 0.11 |
| 30 | CTC | 0.03 | −0.25 | 0.17 | −0.10 | 0.09 | −0.31 | 0.19 | 0.09 | 0.06 | −0.09 | 0.14 | 0.20 |
| 31 | CTG | 0.02 | −0.15 | −0.05 | −0.04 | 0.16 | 0.10 | −0.04 | 0.09 | −0.10 | −0.10 | −0.11 | −0.02 |
| 32 | CTT | −0.19 | −0.12 | −0.03 | −0.25 | −0.28 | −0.30 | −0.11 | −0.32 | 0.00 | −0.05 | 0.09 | −0.02 |
| 33 | GAA | 0.07 | 0.27 | 0.06 | 0.26 | −0.04 | 0.16 | 0.18 | 0.12 | −0.14 | −0.14 | 0.01 | −0.10 |
| 34 | GAC | −0.03 | −0.11 | −0.09 | −0.17 | 0.17 | −0.04 | −0.01 | −0.02 | 0.13 | 0.06 | 0.08 | 0.19 |
| 35 | GAG | 0.06 | 0.07 | 0.01 | 0.02 | −0.03 | 0.08 | −0.17 | −0.12 | 0.12 | 0.22 | −0.02 | −0.02 |
| 36 | GAT | 0.01 | 0.08 | −0.08 | 0.07 | −0.03 | 0.05 | −0.06 | −0.03 | −0.05 | −0.04 | −0.12 | −0.17 |
| 37 | GCA | −0.04 | 0.31 | 0.04 | 0.34 | 0.11 | 0.39 | 0.17 | 0.21 | −0.07 | −0.12 | −0.08 | −0.12 |
| 38 | GCC | 0.26 | 0.02 | 0.17 | −0.06 | 0.23 | 0.00 | 0.08 | 0.15 | 0.10 | −0.06 | 0.12 | 0.09 |
| 39 | GCG | 0.01 | −0.05 | −0.15 | 0.08 | 0.07 | 0.20 | −0.26 | 0.01 | 0.00 | 0.02 | −0.21 | −0.12 |
| 40 | GCT | −0.04 | −0.03 | −0.02 | −0.30 | 0.01 | −0.04 | −0.08 | −0.14 | 0.05 | 0.30 | 0.04 | −0.01 |
| 41 | GGA | −0.08 | 0.30 | −0.08 | 0.16 | 0.02 | 0.39 | 0.07 | 0.18 | −0.04 | 0.11 | −0.05 | 0.01 |
| 42 | GGC | 0.12 | 0.01 | 0.10 | −0.20 | 0.19 | 0.14 | 0.14 | 0.14 | 0.12 | 0.04 | 0.00 | 0.11 |
| 43 | GGG | 0.09 | 0.35 | 0.15 | 0.26 | −0.12 | 0.32 | −0.10 | −0.12 | 0.02 | 0.28 | −0.19 | −0.17 |
| 44 | GGT | 0.07 | −0.10 | −0.04 | −0.22 | −0.08 | −0.20 | −0.16 | −0.27 | −0.05 | −0.10 | 0.15 | −0.19 |
| 45 | GTA | −0.14 | 0.21 | −0.12 | 0.26 | −0.13 | 0.21 | 0.16 | −0.05 | 0.08 | 0.20 | 0.20 | 0.14 |
| 46 | GTC | 0.13 | −0.12 | 0.07 | −0.05 | 0.23 | −0.08 | 0.11 | 0.06 | 0.22 | −0.05 | 0.08 | 0.17 |
| 47 | GTG | −0.02 | −0.13 | −0.14 | 0.16 | 0.09 | 0.16 | −0.15 | −0.03 | −0.05 | 0.07 | −0.13 | −0.17 |
| 48 | GTT | −0.06 | −0.06 | −0.02 | −0.14 | −0.08 | −0.10 | −0.10 | −0.20 | −0.07 | −0.01 | −0.15 | −0.13 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.05 | −0.17 | 0.03 | −0.16 | 0.18 | −0.15 | 0.02 | 0.12 | 0.10 | −0.03 | 0.06 | 0.18 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | −0.10 | −0.11 | −0.07 | −0.02 | −0.12 | −0.16 | −0.10 | −0.13 | −0.06 | −0.05 | −0.12 | −0.14 |
| 53 | TCA | −0.07 | 0.32 | −0.01 | 0.36 | −0.11 | 0.28 | 0.26 | 0.10 | −0.06 | −0.03 | 0.13 | 0.12 |
| 54 | TCC | 0.14 | −0.02 | 0.17 | 0.07 | 0.14 | −0.19 | 0.16 | 0.13 | 0.03 | −0.13 | 0.09 | 0.17 |
| 55 | TCG | −0.07 | 0.00 | −0.09 | 0.15 | −0.07 | 0.15 | −0.11 | −0.03 | −0.06 | 0.01 | −0.12 | −0.08 |
| 56 | TCT | −0.14 | −0.12 | −0.05 | −0.25 | −0.16 | −0.12 | 0.02 | −0.15 | 0.02 | 0.15 | 0.14 | 0.05 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.20 | 0.13 | 0.12 | −0.05 | 0.29 | 0.27 | 0.17 | 0.17 | 0.09 | 0.04 | 0.03 | 0.12 |
| 59 | TGG | 0.15 | 0.08 | 0.17 | 0.17 | −0.14 | 0.09 | −0.05 | −0.07 | 0.01 | 0.12 | −0.01 | −0.10 |
| 60 | TGT | −0.23 | −0.16 | −0.29 | −0.09 | −0.21 | −0.16 | −0.19 | −0.23 | −0.11 | 0.01 | −0.04 | −0.19 |
| 61 | TTA | −0.23 | 0.25 | −0.14 | 0.19 | −0.33 | −0.01 | −0.06 | −0.20 | 0.04 | 0.13 | 0.16 | 0.11 |

TABLE C.1-continued

CPW matrix *Aspergillus niger* full genome (left codon indicated in column 2, right codon indicated in row 2). Host cell: *A. niger*; Sequence data: full *A. niger* genome.

| | | | | | | | | | | | | |
|---|---|---|---|---|---|---|---|---|---|---|---|---|
| 62 | TTC | 0.01 | −0.22 | −0.08 | −0.20 | 0.18 | −0.21 | −0.01 | 0.01 | 0.14 | 0.04 | 0.11 | 0.24 |
| 63 | TTG | 0.12 | 0.20 | 0.09 | 0.27 | 0.16 | 0.25 | 0.06 | 0.04 | −0.03 | 0.14 | −0.14 | −0.14 |
| 64 | TTT | −0.07 | 0.11 | 0.09 | 0.18 | 0.01 | 0.00 | 0.11 | 0.01 | −0.13 | −0.20 | −0.22 | −0.21 |

| | | CGA 25 | CGC 26 | CGG 27 | CGT 28 | CTA 29 | CTC 30 | CTG 31 | CTT 32 | GAA 33 | GAC 34 | GAG 35 | GAT 36 |
|---|---|---|---|---|---|---|---|---|---|---|---|---|---|

| | | 37 GCA | 38 GCC | 39 GCG | 40 GCT | 41 GGA | 42 GGC | 43 GGG | 44 GGT | 45 GTA | 46 GTC | 47 GTG | 48 GTT |
|---|---|---|---|---|---|---|---|---|---|---|---|---|---|
| 1 | AAA | −0.27 | −0.15 | −0.04 | 0.06 | −0.15 | −0.15 | −0.13 | 0.21 | −0.26 | −0.12 | 0.04 | 0.18 |
| 2 | AAC | 0.31 | 0.04 | 0.41 | 0.39 | 0.26 | 0.01 | 0.31 | 0.27 | 0.42 | 0.09 | 0.30 | 0.32 |
| 3 | AAG | 0.16 | 0.05 | 0.00 | 0.04 | 0.09 | 0.01 | 0.10 | −0.03 | 0.22 | −0.03 | 0.02 | −0.02 |
| 4 | AAT | −0.23 | −0.26 | −0.35 | −0.23 | −0.23 | −0.26 | −0.29 | −0.02 | −0.13 | −0.30 | −0.23 | −0.25 |
| 5 | ACA | −0.29 | −0.07 | 0.01 | 0.06 | −0.02 | 0.06 | −0.01 | 0.34 | −0.24 | 0.10 | 0.06 | 0.18 |
| 6 | ACC | 0.28 | 0.16 | 0.35 | 0.38 | 0.25 | 0.00 | 0.31 | 0.11 | 0.35 | −0.07 | 0.21 | 0.18 |
| 7 | ACG | −0.08 | 0.01 | −0.30 | −0.01 | 0.02 | 0.01 | −0.21 | 0.07 | −0.09 | 0.06 | −0.25 | 0.03 |
| 8 | ACT | −0.19 | −0.17 | −0.15 | −0.27 | −0.23 | −0.20 | −0.19 | −0.28 | −0.12 | −0.14 | −0.02 | −0.27 |
| 9 | AGA | −0.16 | 0.15 | 0.01 | 0.04 | −0.22 | 0.09 | −0.19 | 0.08 | −0.35 | 0.19 | 0.08 | 0.14 |
| 10 | AGC | 0.18 | 0.15 | 0.31 | 0.27 | 0.16 | 0.08 | 0.21 | 0.16 | 0.27 | 0.13 | 0.17 | 0.20 |
| 11 | AGG | 0.00 | 0.32 | −0.08 | −0.03 | −0.02 | 0.28 | −0.25 | 0.08 | −0.21 | 0.25 | −0.13 | −0.13 |
| 12 | AGT | −0.09 | −0.05 | −0.23 | −0.17 | −0.29 | −0.17 | −0.32 | −0.30 | −0.31 | −0.16 | −0.31 | −0.30 |
| 13 | ATA | −0.16 | 0.14 | 0.14 | 0.13 | 0.16 | 0.28 | 0.12 | 0.37 | −0.28 | 0.22 | 0.19 | 0.22 |
| 14 | ATC | 0.28 | 0.04 | 0.33 | 0.35 | 0.17 | 0.06 | 0.25 | 0.15 | 0.43 | 0.04 | 0.24 | 0.35 |
| 15 | ATG | 0.02 | 0.02 | −0.04 | −0.01 | 0.01 | −0.05 | 0.05 | 0.02 | −0.04 | 0.01 | 0.00 | 0.00 |
| 16 | ATT | −0.23 | −0.30 | −0.30 | −0.28 | −0.28 | −0.23 | −0.28 | −0.20 | −0.16 | −0.32 | −0.26 | −0.30 |
| 17 | CAA | −0.23 | −0.10 | 0.04 | −0.02 | −0.18 | −0.20 | −0.16 | 0.11 | −0.28 | −0.11 | 0.06 | 0.08 |
| 18 | CAC | 0.30 | 0.03 | 0.33 | 0.27 | 0.21 | −0.03 | 0.32 | 0.15 | 0.44 | 0.02 | 0.48 | 0.21 |
| 19 | CAG | 0.07 | 0.14 | 0.00 | 0.02 | 0.08 | 0.08 | 0.25 | 0.00 | 0.06 | 0.03 | 0.03 | 0.03 |
| 20 | CAT | −0.22 | −0.11 | −0.25 | −0.16 | −0.12 | −0.16 | −0.16 | −0.04 | −0.20 | −0.23 | −0.10 | −0.28 |
| 21 | CCA | −0.25 | 0.01 | 0.11 | −0.07 | −0.11 | 0.02 | −0.03 | 0.20 | −0.27 | 0.05 | 0.04 | 0.12 |
| 22 | CCC | 0.25 | 0.03 | 0.28 | 0.20 | 0.16 | 0.04 | 0.20 | −0.02 | 0.25 | −0.09 | 0.18 | 0.16 |
| 23 | CCG | 0.03 | 0.13 | −0.13 | −0.03 | 0.00 | 0.16 | −0.12 | 0.10 | −0.07 | 0.17 | −0.13 | −0.05 |
| 24 | CCT | −0.16 | 0.01 | −0.08 | −0.28 | −0.17 | −0.07 | −0.11 | −0.22 | −0.09 | −0.06 | 0.02 | −0.25 |
| 25 | CGA | −0.23 | 0.08 | −0.07 | 0.08 | −0.12 | −0.05 | −0.01 | 0.23 | −0.25 | 0.03 | 0.01 | 0.16 |
| 26 | CGC | 0.14 | −0.06 | 0.24 | 0.31 | 0.16 | −0.01 | 0.21 | 0.13 | 0.23 | 0.11 | 0.11 | 0.31 |
| 27 | CGG | 0.02 | 0.17 | −0.24 | −0.06 | 0.06 | 0.25 | 0.18 | 0.14 | −0.23 | 0.19 | −0.15 | −0.02 |
| 28 | CGT | −0.05 | −0.23 | −0.15 | −0.26 | −0.22 | −0.19 | −0.01 | −0.44 | −0.15 | −0.28 | −0.13 | −0.27 |
| 29 | CTA | −0.26 | −0.08 | 0.11 | 0.00 | −0.19 | −0.13 | 0.06 | 0.19 | −0.26 | −0.05 | 0.18 | 0.14 |
| 30 | CTC | 0.31 | −0.02 | 0.40 | 0.29 | 0.24 | 0.10 | 0.35 | 0.16 | 0.33 | −0.08 | 0.32 | 0.24 |
| 31 | CTG | −0.06 | −0.06 | −0.13 | −0.09 | −0.15 | −0.05 | −0.02 | −0.12 | −0.04 | −0.03 | −0.09 | −0.01 |
| 32 | CTT | −0.14 | −0.10 | −0.13 | −0.22 | −0.23 | 0.01 | −0.18 | −0.23 | −0.01 | −0.18 | 0.03 | −0.27 |
| 33 | GAA | −0.21 | −0.14 | −0.08 | −0.06 | −0.17 | −0.13 | −0.22 | 0.06 | −0.26 | −0.09 | −0.01 | 0.01 |
| 34 | GAC | 0.32 | 0.17 | 0.38 | 0.39 | 0.29 | 0.13 | 0.21 | 0.26 | 0.36 | 0.28 | 0.25 | 0.30 |
| 35 | GAG | 0.14 | 0.19 | −0.04 | 0.06 | 0.16 | 0.17 | −0.02 | 0.04 | 0.04 | 0.18 | −0.03 | −0.02 |
| 36 | GAT | −0.16 | −0.17 | −0.34 | −0.23 | −0.18 | −0.15 | −0.31 | −0.07 | −0.19 | −0.13 | −0.25 | −0.29 |
| 37 | GCA | −0.30 | 0.05 | −0.02 | −0.02 | −0.11 | 0.01 | 0.00 | 0.17 | −0.21 | 0.19 | 0.02 | 0.13 |
| 38 | GCC | 0.30 | 0.10 | 0.34 | 0.28 | 0.27 | 0.17 | 0.27 | 0.00 | 0.23 | 0.01 | 0.08 | 0.17 |
| 39 | GCG | 0.13 | 0.23 | −0.23 | 0.14 | 0.15 | 0.14 | −0.08 | 0.07 | −0.04 | 0.26 | −0.14 | 0.09 |
| 40 | GCT | −0.12 | −0.13 | −0.18 | −0.40 | −0.18 | −0.11 | −0.22 | −0.37 | −0.11 | −0.15 | −0.15 | −0.30 |
| 41 | GGA | −0.06 | 0.23 | 0.10 | 0.08 | −0.12 | 0.11 | −0.09 | 0.09 | −0.11 | 0.26 | 0.07 | 0.17 |
| 42 | GGC | 0.12 | 0.09 | 0.24 | 0.18 | 0.25 | 0.05 | 0.27 | 0.14 | 0.25 | 0.20 | 0.15 | 0.26 |
| 43 | GGG | 0.02 | 0.33 | −0.12 | 0.01 | 0.28 | 0.42 | 0.28 | 0.21 | −0.23 | 0.37 | −0.20 | −0.03 |
| 44 | GGT | −0.14 | −0.27 | −0.09 | −0.40 | −0.22 | −0.18 | −0.07 | −0.54 | −0.20 | −0.32 | −0.18 | −0.39 |
| 45 | GTA | −0.25 | −0.04 | −0.01 | 0.00 | −0.09 | 0.16 | −0.08 | 0.37 | −0.31 | 0.13 | 0.14 | 0.23 |
| 46 | GTC | 0.25 | 0.10 | 0.31 | 0.22 | 0.17 | 0.00 | 0.18 | 0.04 | 0.39 | 0.09 | 0.25 | 0.27 |
| 47 | GTG | 0.03 | 0.12 | −0.08 | −0.09 | 0.04 | 0.15 | 0.03 | 0.16 | −0.19 | −0.28 | 0.19 | −0.09 |
| 48 | GTT | −0.15 | −0.10 | −0.25 | −0.32 | −0.22 | −0.15 | −0.31 | −0.30 | −0.01 | −0.17 | −0.14 | −0.34 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.35 | 0.03 | 0.34 | 0.33 | 0.17 | −0.07 | 0.28 | 0.20 | 0.42 | 0.13 | 0.19 | 0.30 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | −0.17 | −0.24 | −0.38 | −0.19 | −0.17 | −0.17 | −0.18 | −0.03 | −0.11 | −0.23 | −0.26 | −0.25 |
| 53 | TCA | −0.24 | 0.02 | 0.14 | 0.03 | 0.00 | 0.17 | −0.07 | 0.31 | −0.27 | 0.09 | 0.12 | 0.18 |
| 54 | TCC | 0.17 | −0.08 | 0.32 | 0.23 | 0.21 | 0.00 | 0.22 | 0.10 | 0.28 | −0.07 | 0.19 | 0.21 |
| 55 | TCG | 0.07 | 0.09 | −0.08 | 0.03 | 0.07 | 0.12 | −0.06 | 0.23 | −0.12 | 0.09 | −0.11 | 0.06 |
| 56 | TCT | −0.26 | −0.18 | −0.19 | −0.35 | −0.24 | −0.14 | −0.18 | −0.20 | −0.10 | −0.08 | −0.05 | −0.20 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.18 | 0.04 | 0.24 | 0.20 | 0.25 | 0.18 | 0.14 | −0.03 | 0.19 | 0.21 | 0.17 | 0.29 |
| 59 | TGG | 0.02 | 0.11 | −0.12 | −0.04 | −0.07 | 0.07 | 0.18 | −0.14 | −0.20 | 0.24 | −0.12 | −0.05 |
| 60 | TGT | −0.06 | −0.15 | −0.29 | −0.22 | −0.17 | −0.03 | −0.21 | −0.26 | −0.22 | −0.21 | −0.21 | −0.31 |
| 61 | TTA | −0.11 | 0.15 | 0.13 | 0.03 | 0.00 | 0.17 | −0.15 | 0.19 | −0.28 | 0.20 | 0.11 | 0.07 |

TABLE C.1-continued

CPW matrix *Aspergillus niger* full genome (left codon indicated in column 2, right codon indicated in row 2). Host cell: *A. niger*; Sequence data: full *A. niger* genome.

| | | | | | | | | | | | | |
|---|---|---|---|---|---|---|---|---|---|---|---|---|
| 62 | TTC | 0.40 | 0.12 | 0.38 | 0.35 | 0.30 | 0.21 | 0.32 | 0.16 | 0.45 | 0.06 | 0.30 | 0.29 |
| 63 | TTG | 0.09 | 0.17 | −0.15 | −0.05 | −0.01 | 0.21 | −0.16 | 0.08 | −0.01 | 0.13 | −0.14 | −0.12 |
| 64 | TTT | −0.29 | −0.33 | −0.42 | −0.36 | −0.29 | −0.28 | −0.40 | −0.27 | −0.15 | −0.30 | −0.33 | −0.31 |

| | | GCA | GCC | GCG | GCT | GGA | GGC | GGG | GGT | GTA | GTC | GTG | GTT |
|---|---|---|---|---|---|---|---|---|---|---|---|---|---|
| | | 37 | 38 | 39 | 40 | 41 | 42 | 43 | 44 | 45 | 46 | 47 | 48 |

| | | 49 TAA | 50 TAC | 51 TAG | 52 TAT | 53 TCA | 54 TCC | 55 TCG | 56 TCT | 57 TGA | 58 TGC | 59 TGG | 60 TGT |
|---|---|---|---|---|---|---|---|---|---|---|---|---|---|
| 1 | AAA | 0.00 | −0.25 | 0.00 | −0.18 | −0.32 | −0.22 | −0.04 | −0.04 | 0.00 | −0.37 | −0.34 | −0.29 |
| 2 | AAC | 0.00 | −0.25 | 0.00 | 0.06 | 0.15 | −0.09 | −0.11 | 0.12 | 0.00 | −0.19 | −0.12 | 0.16 |
| 3 | AAG | 0.00 | 0.14 | 0.00 | 0.14 | 0.11 | 0.13 | 0.04 | 0.13 | 0.00 | 0.27 | 0.24 | 0.22 |
| 4 | AAT | 0.00 | 0.30 | 0.00 | 0.14 | 0.04 | 0.16 | 0.14 | 0.10 | 0.00 | 0.09 | 0.19 | 0.11 |
| 5 | ACA | 0.00 | −0.14 | 0.00 | −0.21 | −0.25 | −0.12 | −0.06 | −0.18 | 0.00 | −0.14 | −0.22 | −0.14 |
| 6 | ACC | 0.00 | −0.27 | 0.00 | 0.17 | 0.17 | −0.22 | −0.01 | 0.12 | 0.00 | −0.23 | −0.11 | 0.12 |
| 7 | ACG | 0.00 | 0.23 | 0.00 | 0.06 | 0.19 | 0.36 | 0.09 | 0.19 | 0.00 | 0.33 | 0.31 | 0.34 |
| 8 | ACT | 0.00 | 0.31 | 0.00 | 0.21 | −0.07 | 0.02 | −0.04 | −0.07 | 0.00 | 0.03 | 0.17 | −0.01 |
| 9 | AGA | 0.00 | −0.05 | 0.00 | −0.25 | −0.05 | 0.25 | 0.15 | 0.09 | 0.00 | −0.18 | −0.18 | −0.17 |
| 10 | AGC | 0.00 | −0.23 | 0.00 | −0.13 | 0.10 | 0.08 | 0.10 | 0.09 | 0.00 | −0.21 | −0.21 | −0.14 |
| 11 | AGG | 0.00 | 0.44 | 0.00 | −0.02 | −0.05 | 0.43 | 0.12 | 0.19 | 0.00 | 0.39 | 0.21 | 0.05 |
| 12 | AGT | 0.00 | 0.30 | 0.00 | 0.02 | 0.21 | 0.44 | 0.38 | 0.34 | 0.00 | 0.15 | 0.21 | 0.16 |
| 13 | ATA | 0.00 | −0.20 | 0.00 | −0.31 | −0.51 | −0.32 | −0.27 | −0.37 | 0.00 | −0.21 | −0.26 | −0.29 |
| 14 | ATC | 0.00 | −0.27 | 0.00 | 0.12 | 0.17 | −0.23 | 0.03 | 0.10 | 0.00 | −0.10 | −0.10 | 0.10 |
| 15 | ATG | 0.00 | −0.01 | 0.00 | 0.02 | 0.08 | 0.07 | 0.02 | 0.00 | 0.00 | −0.01 | 0.00 | 0.02 |
| 16 | ATT | 0.00 | 0.41 | 0.00 | 0.38 | 0.13 | 0.07 | 0.20 | 0.13 | 0.00 | 0.20 | 0.31 | 0.13 |
| 17 | CAA | 0.00 | −0.07 | 0.00 | −0.13 | −0.19 | −0.10 | 0.07 | 0.06 | 0.00 | −0.22 | −0.20 | −0.24 |
| 18 | CAC | 0.00 | −0.21 | 0.00 | −0.02 | 0.11 | −0.15 | −0.06 | 0.05 | 0.00 | −0.21 | −0.15 | 0.08 |
| 19 | CAG | 0.00 | 0.13 | 0.00 | 0.00 | −0.08 | 0.14 | 0.02 | 0.06 | 0.00 | 0.22 | 0.16 | 0.16 |
| 20 | CAT | 0.00 | 0.29 | 0.00 | 0.00 | −0.07 | 0.09 | 0.02 | 0.04 | 0.00 | 0.17 | 0.19 | 0.06 |
| 21 | CCA | 0.00 | −0.07 | 0.00 | −0.09 | −0.38 | −0.15 | −0.13 | −0.17 | 0.00 | −0.11 | −0.18 | −0.17 |
| 22 | CCC | 0.00 | −0.17 | 0.00 | 0.23 | 0.15 | −0.16 | 0.13 | 0.04 | 0.00 | −0.08 | −0.02 | 0.10 |
| 23 | CCG | 0.00 | 0.13 | 0.00 | −0.16 | −0.06 | 0.19 | −0.08 | 0.01 | 0.00 | 0.26 | 0.06 | 0.21 |
| 24 | CCT | 0.00 | 0.11 | 0.00 | 0.09 | −0.11 | 0.02 | 0.05 | −0.12 | 0.00 | −0.06 | 0.16 | −0.09 |
| 25 | CGA | 0.00 | −0.06 | 0.00 | −0.16 | −0.33 | 0.07 | −0.17 | 0.03 | 0.00 | −0.16 | −0.16 | −0.11 |
| 26 | CGC | 0.00 | −0.16 | 0.00 | 0.00 | 0.04 | −0.11 | 0.05 | 0.06 | 0.00 | −0.14 | −0.09 | 0.07 |
| 27 | CGG | 0.00 | 0.12 | 0.00 | −0.20 | −0.15 | 0.18 | −0.24 | −0.01 | 0.00 | 0.20 | 0.09 | 0.08 |
| 28 | CGT | 0.00 | 0.32 | 0.00 | 0.19 | 0.19 | 0.16 | 0.25 | 0.09 | 0.00 | 0.09 | 0.26 | 0.04 |
| 29 | CTA | 0.00 | −0.18 | 0.00 | −0.15 | −0.34 | −0.21 | −0.08 | −0.17 | 0.00 | −0.14 | −0.23 | −0.20 |
| 30 | CTC | 0.00 | −0.32 | 0.00 | 0.08 | 0.09 | −0.34 | 0.13 | −0.01 | 0.00 | −0.23 | −0.18 | −0.09 |
| 31 | CTG | 0.00 | 0.13 | 0.00 | 0.03 | 0.07 | 0.14 | 0.05 | 0.12 | 0.00 | 0.21 | 0.15 | 0.19 |
| 32 | CTT | 0.00 | 0.19 | 0.00 | 0.16 | −0.03 | −0.06 | 0.06 | −0.14 | 0.00 | −0.10 | 0.07 | −0.06 |
| 33 | GAA | 0.00 | −0.12 | 0.00 | −0.12 | −0.12 | −0.03 | 0.09 | 0.01 | 0.00 | −0.17 | −0.22 | −0.22 |
| 34 | GAC | 0.00 | −0.25 | 0.00 | −0.11 | 0.13 | −0.07 | −0.23 | −0.03 | 0.00 | −0.22 | −0.23 | −0.15 |
| 35 | GAG | 0.00 | 0.20 | 0.00 | −0.03 | 0.15 | 0.25 | −0.01 | 0.12 | 0.00 | 0.23 | 0.21 | 0.08 |
| 36 | GAT | 0.00 | 0.32 | 0.00 | 0.12 | 0.14 | 0.28 | 0.12 | 0.20 | 0.00 | 0.29 | 0.30 | 0.16 |
| 37 | GCA | 0.00 | −0.15 | 0.00 | −0.24 | −0.30 | −0.07 | −0.18 | −0.24 | 0.00 | −0.10 | −0.09 | −0.06 |
| 38 | GCC | 0.00 | −0.22 | 0.00 | 0.11 | 0.24 | −0.08 | −0.03 | 0.07 | 0.00 | −0.06 | −0.11 | −0.09 |
| 39 | GCG | 0.00 | 0.26 | 0.00 | −0.14 | 0.12 | 0.31 | −0.03 | 0.14 | 0.00 | 0.32 | 0.07 | 0.16 |
| 40 | GCT | 0.00 | 0.38 | 0.00 | 0.13 | 0.03 | 0.09 | 0.06 | −0.07 | 0.00 | 0.06 | 0.18 | −0.14 |
| 41 | GGA | 0.00 | −0.14 | 0.00 | −0.23 | −0.12 | 0.17 | 0.02 | −0.02 | 0.00 | −0.02 | −0.17 | −0.22 |
| 42 | GGC | 0.00 | −0.11 | 0.00 | −0.04 | 0.01 | −0.08 | 0.00 | −0.14 | 0.00 | −0.17 | −0.16 | −0.12 |
| 43 | GGG | 0.00 | 0.26 | 0.00 | −0.27 | 0.01 | 0.38 | 0.00 | 0.00 | 0.00 | 0.32 | 0.09 | −0.14 |
| 44 | GGT | 0.00 | 0.36 | 0.00 | 0.27 | 0.28 | 0.27 | 0.29 | 0.15 | 0.00 | 0.32 | 0.37 | 0.17 |
| 45 | GTA | 0.00 | −0.24 | 0.00 | −0.33 | −0.43 | −0.30 | −0.30 | −0.43 | 0.00 | −0.29 | −0.26 | −0.18 |
| 46 | GTC | 0.00 | −0.21 | 0.00 | −0.02 | 0.14 | −0.17 | 0.01 | −0.01 | 0.00 | −0.20 | −0.12 | 0.02 |
| 47 | GTG | 0.00 | 0.28 | 0.00 | −0.05 | 0.11 | 0.29 | −0.09 | −0.02 | 0.00 | 0.26 | 0.18 | 0.12 |
| 48 | GTT | 0.00 | 0.33 | 0.00 | 0.15 | 0.03 | 0.07 | 0.04 | −0.10 | 0.00 | 0.17 | 0.14 | 0.00 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.00 | −0.27 | 0.00 | −0.03 | 0.22 | −0.14 | −0.17 | −0.01 | 0.00 | −0.17 | −0.16 | 0.01 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.00 | 0.37 | 0.00 | 0.23 | 0.09 | 0.14 | 0.02 | 0.03 | 0.00 | 0.24 | 0.27 | 0.05 |
| 53 | TCA | 0.00 | −0.13 | 0.00 | −0.11 | −0.43 | −0.21 | −0.15 | −0.24 | 0.00 | −0.15 | −0.23 | −0.18 |
| 54 | TCC | 0.00 | −0.21 | 0.00 | 0.16 | 0.16 | −0.23 | 0.10 | 0.00 | 0.00 | −0.12 | −0.01 | 0.18 |
| 55 | TCG | 0.00 | 0.20 | 0.00 | −0.01 | 0.03 | 0.14 | −0.15 | 0.00 | 0.00 | 0.30 | 0.11 | 0.23 |
| 56 | TCT | 0.00 | 0.28 | 0.00 | 0.18 | −0.12 | −0.13 | −0.02 | −0.25 | 0.00 | 0.05 | 0.26 | −0.02 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.00 | −0.15 | 0.00 | −0.21 | 0.07 | −0.19 | −0.16 | −0.09 | 0.00 | −0.13 | −0.16 | −0.16 |
| 59 | TGG | 0.00 | 0.08 | 0.00 | −0.10 | 0.02 | 0.12 | 0.04 | 0.00 | 0.00 | 0.08 | 0.00 | −0.10 |

TABLE C.1-continued

CPW matrix *Aspergillus niger* full genome (left codon indicated in column 2, right codon indicated in row 2). Host cell: *A. niger*; Sequence data: full *A. niger* genome.

| | | TAA 49 | TAC 50 | TAG 51 | TAT 52 | TCA 53 | TCC 54 | TCG 55 | TCT 56 | TGA 57 | TGC 58 | TGG 59 | TGT 60 |
|---|---|---|---|---|---|---|---|---|---|---|---|---|---|
| 60 | TGT | 0.00 | 0.44 | 0.00 | 0.12 | 0.04 | 0.20 | 0.15 | 0.12 | 0.00 | 0.32 | 0.27 | 0.10 |
| 61 | TTA | 0.00 | 0.02 | 0.00 | −0.23 | −0.44 | −0.13 | −0.26 | −0.29 | 0.00 | −0.05 | −0.26 | −0.30 |
| 62 | TTC | 0.00 | −0.24 | 0.00 | 0.04 | 0.12 | −0.23 | −0.04 | 0.00 | 0.00 | −0.10 | −0.12 | −0.05 |
| 63 | TTG | 0.00 | 0.29 | 0.00 | 0.04 | 0.19 | 0.28 | 0.03 | 0.08 | 0.00 | 0.38 | 0.28 | 0.13 |
| 64 | TTT | 0.00 | 0.35 | 0.00 | 0.25 | 0.15 | 0.08 | −0.03 | −0.03 | 0.00 | 0.17 | 0.24 | 0.16 |

| | | 61 TTA | 62 TTC | 63 TTG | 64 TTT |
|---|---|---|---|---|---|
| 1 | AAA | −0.29 | −0.15 | −0.09 | −0.02 |
| 2 | AAC | 0.33 | −0.19 | 0.14 | −0.10 |
| 3 | AAG | 0.24 | 0.02 | 0.12 | 0.14 |
| 4 | AAT | −0.04 | 0.21 | 0.14 | 0.34 |
| 5 | ACA | −0.41 | −0.04 | −0.13 | −0.11 |
| 6 | ACC | 0.23 | −0.17 | 0.08 | −0.04 |
| 7 | ACG | 0.12 | 0.26 | 0.06 | 0.00 |
| 8 | ACT | −0.14 | 0.09 | −0.10 | 0.21 |
| 9 | AGA | −0.35 | 0.27 | 0.01 | 0.01 |
| 10 | AGC | −0.16 | −0.07 | −0.14 | −0.16 |
| 11 | AGG | −0.25 | 0.28 | −0.19 | −0.06 |
| 12 | AGT | −0.11 | 0.20 | −0.07 | 0.24 |
| 13 | ATA | −0.42 | −0.23 | −0.18 | −0.33 |
| 14 | ATC | 0.17 | −0.21 | 0.18 | 0.14 |
| 15 | ATG | 0.22 | 0.02 | 0.15 | −0.03 |
| 16 | ATT | 0.23 | 0.27 | 0.19 | 0.46 |
| 17 | CAA | −0.36 | −0.11 | −0.03 | −0.07 |
| 18 | CAC | 0.26 | −0.11 | 0.11 | −0.10 |
| 19 | CAG | 0.12 | 0.06 | 0.14 | 0.09 |
| 20 | CAT | −0.04 | 0.09 | 0.04 | 0.18 |
| 21 | CCA | −0.32 | 0.01 | −0.20 | −0.17 |
| 22 | CCC | 0.04 | −0.12 | −0.04 | 0.09 |
| 23 | CCG | −0.17 | 0.12 | −0.22 | −0.09 |
| 24 | CCT | −0.17 | 0.06 | −0.11 | 0.13 |
| 25 | CGA | −0.24 | −0.06 | −0.02 | −0.07 |
| 26 | CGC | 0.03 | −0.19 | 0.16 | 0.03 |
| 27 | CGG | −0.27 | −0.13 | −0.19 | −0.20 |
| 28 | CGT | −0.05 | 0.14 | 0.24 | 0.40 |
| 29 | CTA | −0.28 | −0.04 | 0.13 | −0.14 |
| 30 | CTC | 0.20 | −0.29 | 0.29 | −0.01 |
| 31 | CTG | 0.34 | 0.15 | 0.23 | 0.17 |
| 32 | CTT | 0.00 | −0.01 | 0.07 | 0.23 |
| 33 | GAA | −0.19 | 0.00 | −0.08 | −0.08 |
| 34 | GAC | 0.29 | −0.10 | −0.08 | −0.33 |
| 35 | GAG | 0.23 | 0.08 | −0.03 | −0.09 |
| 36 | GAT | 0.10 | 0.24 | 0.03 | 0.25 |
| 37 | GCA | −0.26 | 0.02 | −0.21 | −0.20 |
| 38 | GCC | 0.13 | −0.04 | −0.08 | −0.16 |
| 39 | GCG | 0.12 | 0.24 | −0.23 | −0.11 |
| 40 | GCT | −0.17 | 0.08 | −0.15 | 0.10 |
| 41 | GGA | −0.26 | 0.03 | −0.13 | −0.15 |
| 42 | GGC | 0.00 | −0.10 | −0.09 | −0.04 |
| 43 | GGG | −0.33 | 0.00 | −0.37 | −0.36 |
| 44 | GGT | 0.12 | 0.23 | 0.28 | 0.43 |
| 45 | GTA | −0.38 | −0.13 | −0.13 | −0.25 |
| 46 | GTC | 0.23 | −0.19 | 0.04 | −0.11 |
| 47 | GTG | 0.26 | 0.28 | −0.10 | −0.17 |
| 48 | GTT | 0.22 | 0.20 | 0.06 | 0.34 |
| 49 | TAA | 0.00 | 0.00 | 0.00 | 0.00 |
| 50 | TAC | 0.25 | −0.15 | 0.21 | −0.11 |
| 51 | TAG | 0.00 | 0.00 | 0.00 | 0.00 |
| 52 | TAT | 0.18 | 0.21 | 0.15 | 0.25 |
| 53 | TCA | −0.39 | −0.08 | −0.13 | −0.14 |
| 54 | TCC | 0.05 | −0.12 | 0.08 | 0.06 |
| 55 | TCG | −0.01 | 0.14 | −0.02 | 0.03 |
| 56 | TCT | −0.13 | 0.02 | −0.05 | 0.10 |
| 57 | TGA | 0.00 | 0.00 | 0.00 | 0.00 |
| 58 | TGC | −0.10 | −0.07 | −0.13 | −0.17 |
| 59 | TGG | 0.04 | 0.04 | 0.10 | −0.06 |

TABLE C.1-continued

CPW matrix *Aspergillus niger* full genome (left codon indicated in column 2, right codon indicated in row 2). Host cell: *A. niger*; Sequence data: full *A. niger* genome.

| | | | | | |
|---|---|---|---|---|---|
| 60 | TGT | −0.09 | 0.19 | 0.01 | 0.15 |
| 61 | TTA | −0.39 | −0.03 | −0.14 | −0.21 |
| 62 | TTC | 0.19 | −0.24 | 0.00 | −0.01 |
| 63 | TTG | 0.17 | 0.23 | −0.05 | 0.03 |
| 64 | TTT | 0.28 | 0.29 | 0.15 | 0.56 |
| | | TTA | TTC | TTG | TTT |
| | | 61 | 62 | 63 | 64 |

TABLE C.2

CPW matrix *A. niger* highly expressed sequences (left codon indicated in column 2, right codon indicated in row 2). Host cell: *A. niger*; Sequence data: full *A. niger* genome; Highly expressed group: 400 seqs.

| | | 1 AAA | 2 AAC | 3 AAG | 4 AAT | 5 ACA | 6 ACC | 7 ACG | 8 ACT | 9 AGA | 10 AGC | 11 AGG | 12 AGT |
|---|---|---|---|---|---|---|---|---|---|---|---|---|---|
| 1 | AAA | 0.93 | 0.64 | 0.65 | 0.92 | 0.61 | 0.65 | 0.67 | 0.57 | 0.07 | 0.61 | −0.09 | 0.75 |
| 2 | AAC | 0.44 | −0.48 | −0.42 | 0.49 | 0.57 | −0.50 | 0.16 | −0.33 | 0.33 | −0.25 | 0.60 | 0.13 |
| 3 | AAG | 0.51 | −0.42 | −0.36 | 0.48 | 0.27 | −0.46 | 0.43 | −0.18 | −0.23 | −0.14 | 0.13 | 0.23 |
| 4 | AAT | 0.60 | 0.68 | 0.75 | 0.65 | 0.35 | 0.63 | 0.44 | 0.80 | 0.75 | 0.36 | 0.80 | 0.31 |
| 5 | ACA | 0.29 | 0.45 | 0.56 | 0.71 | 0.22 | 0.43 | 0.15 | 0.66 | 0.33 | 0.58 | −0.14 | 0.28 |
| 6 | ACC | 0.34 | −0.58 | −0.53 | 0.45 | 0.33 | −0.59 | 0.43 | −0.46 | 0.31 | −0.41 | −0.20 | 0.15 |
| 7 | ACG | 0.25 | −0.02 | 0.39 | 0.16 | 0.56 | 0.08 | 0.52 | 0.47 | 0.01 | 0.59 | −0.30 | 0.57 |
| 8 | ACT | 0.50 | 0.81 | 0.48 | 0.48 | 0.66 | 0.10 | 0.60 | 0.20 | −0.36 | 0.26 | 0.64 | 0.62 |
| 9 | AGA | 0.64 | −0.07 | 0.01 | 0.27 | 0.56 | 0.27 | 0.63 | 0.29 | −0.32 | 0.34 | 0.09 | 0.27 |
| 10 | AGC | 0.34 | −0.39 | −0.44 | 0.08 | 0.40 | −0.34 | 0.33 | −0.38 | 0.42 | −0.39 | −0.30 | 0.20 |
| 11 | AGG | −0.20 | 0.24 | −0.29 | 0.17 | −0.44 | −0.33 | −0.44 | 0.17 | −0.04 | 0.58 | 0.72 | 0.33 |
| 12 | AGT | 0.78 | 0.56 | 0.79 | 0.51 | 0.28 | 0.58 | 0.54 | 0.45 | 0.49 | 0.71 | 0.89 | 0.75 |
| 13 | ATA | 0.02 | 0.86 | 0.62 | 0.58 | 0.44 | 0.61 | 0.53 | 0.74 | 0.41 | 0.68 | 0.69 | 0.50 |
| 14 | ATC | 0.12 | −0.53 | −0.44 | 0.29 | 0.52 | −0.58 | 0.12 | −0.03 | 0.38 | −0.14 | 0.04 | 0.21 |
| 15 | ATG | 0.41 | −0.21 | −0.13 | 0.44 | 0.56 | −0.25 | 0.28 | −0.16 | −0.08 | −0.36 | 0.31 | 0.26 |
| 16 | ATT | 0.63 | 0.77 | 0.82 | 0.82 | 0.66 | 0.38 | 0.61 | 0.47 | 0.76 | 0.61 | 0.75 | 0.58 |
| 17 | CAA | 0.70 | 0.52 | 0.58 | 0.01 | −0.25 | 0.44 | 0.03 | 0.57 | −0.45 | 0.19 | −0.06 | 0.53 |
| 18 | CAC | −0.13 | −0.47 | −0.47 | −0.04 | 0.41 | −0.55 | −0.29 | −0.05 | 0.02 | −0.28 | −0.31 | 0.16 |
| 19 | CAG | 0.29 | −0.29 | −0.37 | 0.18 | 0.45 | −0.39 | 0.49 | −0.27 | 0.15 | −0.24 | 0.22 | 0.13 |
| 20 | CAT | 0.74 | 0.74 | 0.84 | 0.55 | 0.49 | 0.48 | 0.61 | 0.70 | 0.77 | 0.77 | 0.84 | 0.57 |
| 21 | CCA | 0.61 | 0.76 | 0.31 | 0.48 | −0.33 | 0.31 | 0.04 | 0.41 | 0.32 | 0.29 | 0.28 | 0.66 |
| 22 | CCC | 0.57 | −0.56 | −0.62 | 0.12 | 0.38 | −0.44 | 0.25 | −0.31 | −0.06 | −0.51 | −0.40 | 0.28 |
| 23 | CCG | 0.13 | 0.08 | 0.59 | 0.27 | 0.33 | 0.36 | 0.46 | 0.19 | 0.19 | 0.59 | 0.84 | 0.61 |
| 24 | CCT | 0.53 | 0.24 | 0.55 | 0.43 | −0.13 | −0.22 | 0.51 | −0.16 | 0.80 | −0.24 | 0.57 | −0.18 |
| 25 | CGA | 0.73 | 0.37 | 0.77 | 0.77 | −0.07 | 0.38 | 0.61 | 0.62 | 0.72 | 0.35 | 0.80 | 0.52 |
| 26 | CGC | 0.34 | −0.49 | −0.56 | −0.03 | 0.51 | −0.40 | 0.26 | −0.29 | −0.36 | −0.47 | −0.10 | −0.08 |
| 27 | CGG | 0.20 | 0.32 | 0.58 | 0.48 | 0.14 | 0.48 | 0.11 | 0.34 | 0.58 | 0.51 | 0.25 | 0.40 |
| 28 | CGT | 0.77 | −0.21 | 0.21 | 0.59 | 0.11 | −0.48 | 0.09 | 0.08 | 0.66 | 0.48 | 0.78 | 0.53 |
| 29 | CTA | 0.80 | 0.47 | 0.71 | 0.91 | −0.07 | 0.19 | 0.83 | 0.51 | −0.26 | 0.12 | 0.45 | 0.38 |
| 30 | CTC | 0.20 | −0.46 | −0.49 | 0.14 | 0.40 | −0.44 | 0.39 | −0.07 | 0.28 | −0.32 | 0.49 | −0.25 |
| 31 | CTG | 0.42 | −0.34 | −0.22 | 0.38 | 0.61 | −0.42 | 0.38 | 0.08 | 0.30 | −0.24 | −0.42 | 0.24 |
| 32 | CTT | 0.32 | 0.40 | 0.74 | 0.81 | 0.42 | −0.04 | 0.43 | −0.02 | 0.70 | 0.48 | 0.84 | 0.51 |
| 33 | GAA | 0.79 | 0.31 | 0.58 | 0.58 | 0.10 | 0.33 | 0.47 | 0.64 | 0.48 | 0.34 | 0.01 | 0.49 |
| 34 | GAC | 0.37 | −0.42 | −0.50 | 0.13 | 0.34 | −0.47 | 0.46 | −0.18 | 0.23 | −0.39 | 0.50 | −0.26 |
| 35 | GAG | 0.52 | −0.37 | −0.43 | 0.28 | 0.54 | −0.43 | 0.33 | −0.40 | 0.06 | −0.38 | 0.22 | 0.09 |
| 36 | GAT | 0.66 | 0.42 | 0.66 | 0.42 | −0.16 | 0.19 | 0.57 | 0.31 | 0.59 | 0.52 | 0.23 | 0.44 |
| 37 | GCA | 0.24 | 0.21 | 0.48 | 0.42 | 0.46 | 0.32 | −0.10 | 0.43 | 0.20 | 0.17 | −0.35 | 0.58 |
| 38 | GCC | 0.38 | −0.61 | −0.54 | 0.25 | 0.19 | −0.47 | 0.11 | −0.37 | −0.08 | −0.44 | 0.52 | −0.14 |
| 39 | GCG | 0.66 | 0.26 | 0.42 | 0.30 | 0.50 | 0.42 | 0.54 | 0.24 | 0.06 | 0.53 | 0.63 | 0.73 |
| 40 | GCT | 0.38 | 0.66 | 0.32 | 0.78 | 0.49 | −0.20 | 0.50 | −0.27 | −0.21 | 0.19 | 0.54 | 0.48 |
| 41 | GGA | 0.67 | −0.01 | −0.01 | 0.40 | 0.33 | 0.05 | −0.03 | −0.02 | 0.11 | −0.36 | 0.53 | 0.02 |
| 42 | GGC | 0.11 | −0.38 | −0.51 | 0.33 | 0.52 | −0.30 | 0.26 | −0.05 | −0.13 | −0.48 | −0.23 | −0.13 |
| 43 | GGG | 0.72 | 0.53 | 0.61 | 0.64 | 0.64 | 0.44 | 0.70 | 0.57 | 0.83 | 0.66 | 0.91 | 0.57 |
| 44 | GGT | 0.48 | −0.29 | 0.42 | 0.48 | 0.62 | −0.53 | 0.57 | −0.35 | 0.58 | 0.01 | 0.78 | 0.15 |
| 45 | GTA | 0.79 | 0.65 | 0.64 | 0.58 | 0.56 | 0.50 | 0.75 | 0.35 | 0.70 | 0.59 | 0.68 | 0.34 |
| 46 | GTC | 0.25 | −0.60 | −0.56 | 0.39 | 0.66 | −0.55 | 0.32 | −0.22 | 0.33 | −0.33 | −0.26 | −0.02 |
| 47 | GTG | 0.63 | 0.21 | 0.37 | 0.71 | 0.32 | −0.22 | 0.19 | 0.20 | 0.22 | 0.22 | −0.23 | 0.67 |
| 48 | GTT | 0.60 | 0.51 | 0.54 | 0.64 | 0.72 | 0.01 | 0.56 | 0.05 | 0.83 | 0.41 | 0.69 | 0.75 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.34 | −0.49 | −0.45 | 0.39 | 0.49 | −0.52 | 0.59 | −0.31 | −0.42 | −0.25 | 0.68 | 0.08 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.84 | 0.72 | 0.81 | 0.74 | 0.52 | 0.48 | 0.73 | 0.22 | 1.00 | 0.62 | −0.17 | 0.80 |
| 53 | TCA | 0.40 | 0.60 | 0.66 | −0.06 | −0.64 | 0.33 | −0.43 | 0.57 | 0.36 | 0.33 | −0.63 | 0.36 |
| 54 | TCC | 0.42 | −0.55 | −0.57 | 0.35 | 0.69 | −0.47 | 0.48 | −0.28 | 0.05 | −0.30 | −0.28 | 0.13 |
| 55 | TCG | 0.18 | −0.02 | 0.13 | −0.09 | 0.13 | 0.02 | 0.29 | 0.24 | 0.39 | 0.30 | 0.07 | 0.43 |
| 56 | TCT | 0.70 | 0.75 | 0.64 | 0.74 | 0.50 | 0.02 | 0.21 | −0.05 | 0.22 | 0.29 | 0.70 | 0.82 |

TABLE C.2-continued

CPW matrix *A. niger* highly expressed sequences (left codon indicated in column 2,
right codon indicated in row 2). Host cell: *A. niger*; Sequence data: full *A. niger* genome;
Highly expressed group: 400 seqs.

| | | | | | | | | | | | | |
|---|---|---|---|---|---|---|---|---|---|---|---|---|
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.57 | −0.33 | −0.33 | −0.17 | 0.20 | −0.46 | 0.11 | −0.31 | −0.05 | 0.39 | −0.52 | 0.41 |
| 59 | TGG | 0.19 | −0.20 | −0.06 | 0.43 | 0.63 | −0.28 | 0.65 | −0.34 | −0.50 | 0.03 | 0.09 | −0.12 |
| 60 | TGT | 0.20 | 0.74 | 0.42 | 0.50 | 0.67 | 0.41 | 0.81 | 0.64 | 0.42 | 0.77 | 1.00 | 0.38 |
| 61 | TTA | 0.85 | 0.85 | 0.45 | 0.51 | 0.49 | 0.69 | 0.36 | 0.69 | 0.41 | 0.53 | 0.16 | 0.56 |
| 62 | TTC | 0.18 | −0.45 | −0.35 | 0.42 | 0.33 | −0.46 | 0.36 | −0.18 | 0.46 | −0.14 | 0.17 | 0.09 |
| 63 | TTG | −0.26 | −0.02 | 0.10 | −0.05 | 0.25 | −0.21 | −0.06 | −0.22 | 0.42 | 0.30 | 0.59 | 0.17 |
| 64 | TTT | 0.70 | 0.82 | 0.82 | 0.77 | 0.53 | 0.49 | 0.54 | 0.62 | −0.23 | 0.52 | −0.27 | 0.76 |

| | | AAA 1 | AAC 2 | AAG 3 | AAT 4 | ACA 5 | ACC 6 | ACG 7 | ACT 8 | AGA 9 | AGC 10 | AGG 11 | AGT 12 |
|---|---|---|---|---|---|---|---|---|---|---|---|---|---|
| | | 13 ATA | 14 ATC | 15 ATG | 16 ATT | 17 CAA | 18 CAC | 19 CAG | 20 CAT | 21 CCA | 22 CCC | 23 CCG | 24 CCT |
| 1 | AAA | 0.11 | 0.75 | 0.53 | 0.32 | −0.36 | −0.09 | 0.55 | 0.56 | 0.61 | 0.29 | 0.53 | 0.80 |
| 2 | AAC | 0.76 | −0.39 | −0.10 | −0.08 | 0.35 | −0.44 | −0.46 | 0.40 | 0.62 | −0.56 | 0.04 | −0.15 |
| 3 | AAG | 0.63 | −0.36 | −0.16 | 0.17 | 0.47 | −0.37 | −0.26 | 0.55 | 0.53 | −0.51 | 0.23 | −0.08 |
| 4 | AAT | 0.18 | 0.60 | 0.19 | 0.53 | 0.79 | 0.61 | 0.63 | 0.15 | 0.79 | 0.55 | 0.77 | 0.16 |
| 5 | ACA | 0.70 | 0.59 | 0.37 | 0.47 | −0.15 | 0.35 | −0.17 | 0.49 | 0.03 | 0.05 | 0.73 | 0.16 |
| 6 | ACC | 0.31 | −0.53 | −0.41 | −0.28 | 0.37 | −0.53 | −0.28 | 0.68 | 0.62 | −0.54 | −0.01 | 0.03 |
| 7 | ACG | −0.24 | 0.58 | 0.52 | 0.47 | 0.53 | 0.27 | 0.34 | 0.27 | 0.61 | 0.53 | 0.53 | 0.39 |
| 8 | ACT | 0.70 | 0.14 | 0.37 | 0.55 | 0.38 | −0.25 | −0.22 | 0.17 | 0.31 | −0.51 | 0.57 | −0.31 |
| 9 | AGA | 0.12 | −0.39 | 0.10 | 0.62 | −0.14 | −0.26 | 0.06 | 0.25 | 0.50 | 0.30 | 0.31 | 0.02 |
| 10 | AGC | 0.64 | −0.23 | −0.26 | −0.01 | 0.43 | −0.05 | −0.28 | 0.38 | 0.58 | −0.16 | 0.15 | −0.11 |
| 11 | AGG | −0.60 | 0.55 | 0.05 | 0.75 | 0.20 | −0.39 | 0.47 | 0.65 | 0.15 | 0.63 | 0.76 | −0.21 |
| 12 | AGT | 0.55 | 0.22 | 0.39 | 0.45 | 0.49 | 0.21 | 0.23 | 0.54 | 0.27 | 0.29 | 0.53 | 0.15 |
| 13 | ATA | −0.15 | 0.74 | 0.56 | 0.62 | 0.06 | 0.74 | −0.04 | 0.84 | −0.38 | −0.07 | 0.88 | 0.46 |
| 14 | ATC | 0.58 | −0.43 | −0.31 | −0.07 | 0.33 | −0.52 | −0.29 | 0.52 | 0.04 | −0.39 | 0.25 | 0.09 |
| 15 | ATG | −0.07 | −0.16 | 0.00 | 0.33 | 0.10 | −0.26 | −0.06 | 0.41 | 0.22 | −0.41 | 0.28 | 0.43 |
| 16 | ATT | 0.84 | 0.48 | 0.57 | 0.28 | 0.07 | 0.24 | 0.34 | 0.42 | 0.63 | −0.10 | 0.18 | 0.01 |
| 17 | CAA | 0.77 | 0.30 | 0.25 | 0.56 | 0.21 | −0.19 | 0.44 | 0.28 | −0.32 | −0.05 | −0.13 | 0.22 |
| 18 | CAC | 0.93 | −0.49 | −0.20 | −0.10 | −0.37 | −0.52 | −0.18 | 0.57 | 0.38 | −0.55 | 0.39 | −0.26 |
| 19 | CAG | −0.08 | −0.32 | −0.12 | 0.08 | 0.20 | −0.17 | −0.30 | 0.24 | 0.49 | −0.29 | 0.43 | −0.07 |
| 20 | CAT | 0.44 | 0.53 | 0.30 | 0.62 | 0.09 | 0.49 | 0.61 | 0.25 | 0.26 | 0.62 | 0.62 | −0.08 |
| 21 | CCA | 0.62 | 0.22 | 0.65 | 0.57 | 0.39 | 0.66 | 0.68 | 0.66 | 0.17 | 0.26 | −0.33 | −0.08 |
| 22 | CCC | 0.17 | −0.48 | −0.42 | −0.34 | 0.40 | −0.57 | −0.51 | 0.54 | 0.37 | 0.26 | −0.08 | −0.05 |
| 23 | CCG | 0.20 | 0.42 | 0.11 | 0.23 | 0.34 | 0.49 | 0.35 | 0.57 | 0.10 | 0.52 | 0.26 | 0.69 |
| 24 | CCT | −0.28 | 0.34 | 0.32 | 0.29 | 0.25 | −0.46 | −0.22 | 0.17 | −0.45 | −0.41 | 0.14 | −0.39 |
| 25 | CGA | 0.66 | 0.44 | 0.48 | 0.57 | 0.73 | 0.57 | 0.49 | 0.49 | 0.69 | 0.64 | 0.41 | −0.25 |
| 26 | CGC | 0.73 | −0.09 | −0.34 | −0.07 | 0.26 | −0.40 | −0.45 | 0.57 | 0.52 | −0.57 | 0.23 | −0.20 |
| 27 | CGG | 0.24 | 0.40 | 0.36 | 0.48 | 0.46 | 0.51 | 0.71 | 0.71 | −0.14 | 0.50 | 0.42 | 0.76 |
| 28 | CGT | −0.19 | −0.61 | 0.00 | −0.01 | 0.02 | −0.55 | −0.48 | −0.18 | 0.44 | −0.62 | 0.18 | −0.29 |
| 29 | CTA | 0.33 | 0.80 | 0.47 | 0.57 | −0.16 | −0.38 | 0.48 | 0.37 | −0.30 | −0.21 | 0.48 | 0.05 |
| 30 | CTC | 0.65 | −0.35 | −0.18 | −0.08 | 0.50 | −0.38 | −0.41 | 0.62 | 0.58 | −0.48 | 0.35 | −0.01 |
| 31 | CTG | 0.71 | −0.40 | −0.25 | −0.05 | 0.34 | −0.35 | −0.20 | 0.32 | 0.62 | −0.30 | 0.31 | 0.20 |
| 32 | CTT | 0.61 | 0.44 | 0.56 | 0.56 | −0.24 | −0.16 | −0.10 | 0.39 | −0.41 | −0.46 | 0.50 | −0.37 |
| 33 | GAA | −0.20 | 0.25 | 0.42 | 0.39 | −0.16 | −0.22 | 0.45 | 0.55 | −0.17 | 0.49 | 0.73 | 0.27 |
| 34 | GAC | 0.59 | −0.26 | −0.31 | −0.11 | 0.34 | −0.43 | −0.43 | 0.19 | 0.53 | −0.54 | 0.27 | −0.31 |
| 35 | GAG | 0.59 | −0.33 | −0.21 | 0.17 | 0.32 | −0.38 | −0.29 | 0.57 | 0.35 | −0.46 | 0.29 | −0.27 |
| 36 | GAT | 0.01 | 0.11 | 0.47 | 0.36 | 0.62 | 0.29 | 0.20 | 0.39 | 0.44 | 0.23 | 0.46 | 0.27 |
| 37 | GCA | 0.75 | 0.46 | 0.56 | 0.50 | 0.43 | 0.26 | 0.49 | 0.69 | −0.08 | 0.53 | 0.38 | 0.41 |
| 38 | GCC | 0.52 | −0.49 | −0.39 | −0.37 | 0.53 | −0.39 | −0.33 | 0.47 | 0.81 | −0.34 | 0.54 | 0.01 |
| 39 | GCG | 0.91 | 0.69 | 0.47 | 0.55 | 0.54 | 0.05 | 0.01 | 0.68 | 0.25 | 0.55 | 0.38 | 0.30 |
| 40 | GCT | 0.33 | −0.10 | 0.08 | 0.15 | 0.41 | −0.51 | −0.42 | 0.35 | 0.57 | −0.60 | 0.40 | −0.61 |
| 41 | GGA | 0.71 | 0.45 | 0.06 | 0.36 | 0.53 | −0.03 | 0.15 | 0.44 | −0.23 | 0.13 | 0.40 | −0.13 |
| 42 | GGC | 0.63 | −0.01 | −0.11 | 0.04 | 0.24 | −0.41 | −0.40 | 0.37 | 0.05 | −0.22 | 0.50 | −0.15 |
| 43 | GGG | −0.41 | 0.59 | 0.72 | 0.76 | 0.53 | 0.34 | 0.46 | 0.65 | 0.40 | 0.55 | 0.49 | 0.37 |
| 44 | GGT | 0.78 | −0.58 | −0.20 | 0.00 | 0.41 | −0.37 | −0.26 | 0.42 | 0.61 | −0.51 | 0.61 | −0.42 |
| 45 | GTA | 0.18 | 0.82 | 0.78 | 0.69 | 0.41 | 0.34 | 0.56 | 0.39 | 0.44 | 0.39 | 0.57 | 0.61 |
| 46 | GTC | 0.80 | −0.52 | −0.40 | −0.28 | 0.68 | −0.49 | −0.32 | 0.49 | 0.74 | −0.41 | 0.62 | 0.13 |
| 47 | GTG | 0.69 | 0.39 | 0.30 | 0.55 | 0.18 | 0.05 | −0.10 | 0.66 | 0.72 | −0.05 | 0.37 | −0.01 |
| 48 | GTT | 0.58 | 0.11 | 0.37 | 0.16 | −0.19 | −0.27 | −0.04 | 0.27 | 0.39 | −0.56 | −0.01 | −0.47 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.71 | −0.34 | −0.30 | 0.03 | −0.15 | −0.46 | −0.21 | 0.28 | 0.35 | −0.53 | 0.30 | −0.05 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | −0.29 | 0.48 | 0.69 | 0.32 | 0.24 | 0.55 | 0.47 | 0.53 | 0.66 | 0.27 | 0.41 | 0.32 |
| 53 | TCA | 0.52 | 0.09 | 0.50 | 0.54 | 0.42 | 0.59 | 0.19 | 0.33 | −0.48 | 0.66 | 0.61 | 0.01 |
| 54 | TCC | 0.44 | −0.54 | −0.37 | −0.23 | 0.30 | −0.45 | −0.45 | 0.09 | 0.55 | −0.46 | −0.16 | −0.01 |
| 55 | TCG | 0.40 | 0.16 | 0.30 | 0.27 | 0.29 | 0.25 | 0.25 | 0.27 | 0.27 | 0.10 | 0.41 | 0.24 |
| 56 | TCT | 0.61 | 0.22 | 0.29 | 0.75 | 0.32 | −0.45 | −0.16 | 0.03 | −0.02 | −0.42 | 0.16 | −0.35 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.44 | 0.12 | −0.25 | −0.36 | 0.02 | −0.46 | −0.27 | 0.43 | 0.37 | −0.56 | 0.73 | 0.07 |
| 59 | TGG | −0.24 | 0.02 | 0.00 | 0.08 | 0.10 | −0.26 | −0.05 | 0.42 | −0.12 | −0.18 | 0.23 | 0.15 |
| 60 | TGT | 0.07 | −0.10 | 0.56 | 0.52 | −0.25 | 0.27 | 0.79 | 0.62 | 0.53 | 0.45 | −0.07 | 0.10 |
| 61 | TTA | 0.23 | 0.90 | 0.78 | 0.51 | −0.39 | 0.80 | 0.74 | −0.08 | 0.48 | 0.47 | −0.16 | 0.37 |

TABLE C.2-continued

CPW matrix *A. niger* highly expressed sequences (left codon indicated in column 2, right codon indicated in row 2). Host cell: *A. niger*; Sequence data: full *A. niger* genome; Highly expressed group: 400 seqs.

| | | | | | | | | | | | | |
|---|---|---|---|---|---|---|---|---|---|---|---|---|
| 62 | TTC | 0.63 | −0.30 | −0.24 | −0.21 | 0.41 | −0.42 | −0.39 | 0.35 | 0.17 | −0.48 | 0.31 | −0.14 |
| 63 | TTG | 0.50 | −0.05 | −0.12 | −0.31 | 0.58 | 0.01 | 0.34 | 0.38 | 0.59 | 0.38 | 0.38 | 0.12 |
| 64 | TTT | 0.75 | 0.49 | 0.72 | 0.68 | 0.40 | 0.71 | 0.69 | 0.32 | 0.60 | 0.39 | 0.73 | 0.41 |

| | | ATA 13 | ATC 14 | ATG 15 | ATT 16 | CAA 17 | CAC 18 | CAG 19 | CAT 20 | CCA 21 | CCC 22 | CCG 23 | CCT 24 |
|---|---|---|---|---|---|---|---|---|---|---|---|---|---|
| | | 25 CGA | 26 CGC | 27 CGG | 28 CGT | 29 CTA | 30 CTC | 31 CTG | 32 CTT | 33 GAA | 34 GAC | 35 GAG | 36 GAT |
| 1 | AAA | 0.29 | 0.27 | 0.75 | 0.72 | 0.56 | 0.49 | 0.73 | 0.55 | 0.35 | 0.35 | 0.37 | 0.19 |
| 2 | AAC | −0.07 | −0.52 | 0.42 | −0.45 | −0.12 | −0.36 | −0.36 | −0.10 | 0.19 | −0.34 | −0.29 | 0.30 |
| 3 | AAG | 0.60 | −0.26 | 0.35 | −0.47 | 0.09 | −0.42 | −0.18 | −0.09 | 0.27 | −0.24 | −0.28 | 0.12 |
| 4 | AAT | 0.57 | 0.30 | 0.75 | 0.22 | 0.72 | 0.41 | 0.48 | 0.66 | 0.42 | 0.17 | 0.22 | 0.22 |
| 5 | ACA | 0.55 | −0.33 | 0.52 | 0.81 | −0.25 | 0.52 | 0.53 | 0.27 | 0.25 | 0.37 | 0.43 | 0.38 |
| 6 | ACC | 0.69 | −0.38 | 0.27 | −0.53 | −0.45 | −0.52 | −0.30 | −0.02 | 0.22 | −0.42 | −0.30 | 0.12 |
| 7 | ACG | 0.57 | 0.63 | 0.68 | 0.61 | 0.61 | 0.50 | 0.35 | 0.27 | 0.36 | 0.25 | 0.13 | 0.47 |
| 8 | ACT | 0.48 | −0.37 | 0.41 | −0.51 | 0.53 | −0.31 | −0.21 | −0.01 | 0.39 | −0.24 | −0.38 | 0.08 |
| 9 | AGA | 0.63 | 0.22 | 0.29 | 0.45 | 0.29 | −0.11 | 0.38 | −0.30 | 0.31 | 0.42 | 0.46 | 0.62 |
| 10 | AGC | 0.32 | −0.08 | 0.41 | −0.34 | 0.71 | 0.18 | 0.30 | −0.05 | −0.19 | 0.02 | 0.04 | 0.41 |
| 11 | AGG | 0.70 | −0.35 | 0.55 | 0.71 | 0.25 | 0.47 | 0.50 | −0.17 | 0.09 | −0.40 | 0.23 | 0.56 |
| 12 | AGT | 0.38 | 0.36 | 0.47 | 0.32 | 0.24 | −0.07 | −0.23 | 0.20 | 0.15 | 0.09 | 0.00 | 0.04 |
| 13 | ATA | 0.44 | 0.78 | 0.66 | −0.20 | −0.33 | 0.38 | 0.12 | 0.52 | 0.26 | 0.78 | 0.77 | 0.81 |
| 14 | ATC | 0.44 | −0.37 | 0.44 | −0.61 | 0.67 | −0.33 | −0.34 | 0.02 | 0.30 | −0.10 | −0.06 | 0.14 |
| 15 | ATG | 0.40 | −0.26 | 0.37 | −0.19 | 0.57 | −0.18 | −0.01 | −0.30 | 0.13 | −0.08 | −0.08 | 0.09 |
| 16 | ATT | 0.67 | 0.02 | 0.31 | 0.01 | 0.36 | −0.03 | 0.14 | 0.03 | 0.18 | −0.34 | −0.39 | −0.02 |
| 17 | CAA | 0.59 | 0.60 | 0.42 | 0.06 | 0.46 | 0.40 | 0.37 | 0.28 | 0.23 | 0.31 | 0.45 | 0.27 |
| 18 | CAC | 0.60 | −0.36 | −0.01 | −0.66 | −0.26 | −0.46 | −0.41 | −0.10 | −0.12 | −0.43 | −0.22 | 0.35 |
| 19 | CAG | 0.50 | −0.33 | 0.45 | −0.51 | 0.66 | −0.44 | −0.28 | −0.15 | 0.28 | −0.21 | −0.35 | −0.06 |
| 20 | CAT | 0.65 | 0.66 | 0.47 | 0.23 | −0.30 | 0.60 | 0.52 | 0.76 | 0.24 | 0.32 | 0.29 | 0.19 |
| 21 | CCA | 0.78 | 0.39 | 0.33 | 0.57 | 0.35 | 0.65 | 0.10 | 0.49 | 0.19 | 0.45 | 0.33 | 0.50 |
| 22 | CCC | 0.49 | −0.31 | 0.55 | −0.69 | −0.29 | −0.34 | 0.04 | 0.09 | 0.07 | −0.32 | −0.46 | −0.17 |
| 23 | CCG | 0.66 | 0.42 | 0.53 | 0.71 | 0.50 | 0.49 | 0.24 | −0.05 | 0.51 | −0.09 | 0.45 | 0.45 |
| 24 | CCT | −0.22 | −0.34 | 0.61 | −0.64 | 0.43 | −0.35 | −0.41 | −0.33 | 0.14 | −0.31 | −0.13 | 0.29 |
| 25 | CGA | 0.64 | 0.62 | 0.46 | 0.69 | 0.10 | 0.73 | 0.45 | 0.35 | 0.34 | 0.30 | 0.69 | 0.71 |
| 26 | CGC | −0.13 | −0.45 | 0.37 | −0.62 | 0.17 | −0.30 | −0.11 | 0.35 | 0.17 | 0.01 | −0.22 | 0.20 |
| 27 | CGG | 0.19 | 0.63 | 0.76 | 0.60 | 0.53 | 0.78 | 0.62 | 0.58 | 0.56 | 0.36 | 0.46 | 0.20 |
| 28 | CGT | 0.48 | −0.45 | 0.21 | −0.69 | −0.16 | −0.63 | −0.59 | −0.47 | 0.09 | −0.62 | −0.64 | −0.33 |
| 29 | CTA | 0.45 | −0.51 | −0.01 | −0.25 | −0.36 | −0.30 | 0.52 | 0.55 | 0.73 | 0.29 | 0.39 | 0.17 |
| 30 | CTC | 0.69 | −0.54 | 0.07 | −0.65 | 0.70 | −0.44 | −0.18 | −0.28 | 0.14 | −0.29 | −0.33 | 0.02 |
| 31 | CTG | 0.54 | −0.22 | 0.52 | −0.35 | 0.69 | −0.18 | −0.01 | 0.04 | 0.13 | −0.10 | −0.18 | 0.13 |
| 32 | CTT | 0.58 | 0.02 | 0.60 | −0.33 | 0.33 | −0.31 | −0.24 | −0.05 | 0.26 | −0.34 | −0.30 | 0.10 |
| 33 | GAA | 0.14 | 0.49 | 0.63 | 0.22 | 0.79 | 0.25 | 0.49 | 0.42 | 0.24 | −0.08 | 0.30 | 0.22 |
| 34 | GAC | 0.52 | −0.44 | −0.15 | −0.58 | −0.09 | −0.33 | −0.10 | −0.26 | 0.32 | −0.05 | −0.21 | 0.34 |
| 35 | GAG | 0.40 | −0.32 | 0.39 | −0.58 | 0.57 | −0.42 | −0.29 | −0.34 | 0.34 | −0.11 | −0.34 | 0.05 |
| 36 | GAT | −0.09 | 0.44 | 0.66 | 0.30 | 0.61 | 0.06 | 0.02 | −0.07 | 0.50 | −0.29 | −0.21 | 0.13 |
| 37 | GCA | 0.39 | 0.64 | 0.60 | 0.67 | 0.48 | 0.73 | 0.52 | 0.39 | 0.41 | 0.35 | 0.17 | 0.47 |
| 38 | GCC | 0.72 | −0.34 | 0.49 | −0.56 | 0.72 | −0.36 | −0.19 | −0.23 | 0.42 | −0.38 | −0.25 | −0.12 |
| 39 | GCG | 0.74 | 0.65 | 0.52 | 0.31 | 0.23 | 0.26 | 0.35 | 0.44 | 0.37 | −0.08 | 0.36 | 0.34 |
| 40 | GCT | 0.59 | −0.53 | 0.48 | −0.65 | 0.62 | −0.47 | −0.36 | −0.37 | 0.20 | 0.13 | −0.44 | 0.09 |
| 41 | GGA | 0.71 | 0.14 | 0.62 | −0.10 | 0.64 | 0.56 | 0.58 | 0.48 | 0.48 | 0.51 | 0.30 | 0.25 |
| 42 | GGC | 0.33 | −0.35 | 0.60 | −0.60 | 0.08 | 0.17 | 0.08 | 0.29 | 0.33 | 0.17 | −0.18 | 0.37 |
| 43 | GGG | −0.13 | 0.81 | 0.81 | 0.15 | 0.45 | 0.35 | 0.72 | 0.62 | 0.59 | 0.41 | 0.64 | 0.65 |
| 44 | GGT | 0.65 | −0.27 | 0.59 | −0.64 | −0.11 | −0.64 | −0.54 | −0.47 | −0.12 | −0.58 | −0.47 | −0.26 |
| 45 | GTA | 0.77 | 0.16 | 0.91 | 0.66 | 0.78 | 0.56 | 0.62 | 0.46 | 0.75 | 0.71 | 0.70 | 0.48 |
| 46 | GTC | 0.57 | −0.52 | 0.25 | −0.62 | 0.28 | −0.40 | −0.23 | −0.31 | 0.43 | −0.28 | −0.23 | 0.15 |
| 47 | GTG | 0.66 | −0.03 | 0.52 | 0.45 | 0.78 | 0.06 | 0.15 | 0.07 | 0.36 | 0.19 | 0.15 | 0.50 |
| 48 | GTT | 0.78 | −0.20 | 0.53 | −0.25 | −0.07 | −0.37 | −0.14 | −0.10 | 0.01 | −0.48 | −0.47 | 0.07 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.57 | −0.42 | 0.23 | −0.54 | 0.38 | −0.36 | −0.24 | −0.21 | 0.18 | −0.28 | −0.33 | 0.25 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.57 | 0.63 | 0.39 | 0.56 | −0.11 | 0.22 | −0.07 | 0.48 | 0.50 | 0.16 | 0.26 | 0.09 |
| 53 | TCA | −0.18 | 0.68 | 0.63 | 0.34 | −0.55 | 0.24 | 0.46 | 0.46 | 0.54 | 0.27 | 0.11 | −0.03 |
| 54 | TCC | 0.77 | −0.48 | 0.14 | −0.52 | −0.21 | −0.40 | −0.30 | −0.01 | 0.34 | −0.54 | −0.38 | 0.09 |
| 55 | TCG | 0.49 | 0.20 | 0.53 | 0.55 | −0.54 | 0.34 | 0.10 | 0.32 | 0.42 | 0.20 | 0.18 | 0.19 |
| 56 | TCT | −0.02 | −0.47 | 0.43 | −0.55 | 0.42 | −0.15 | −0.30 | −0.32 | 0.14 | 0.16 | −0.20 | 0.26 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.82 | 0.05 | 0.73 | −0.59 | −0.22 | −0.02 | −0.04 | 0.34 | 0.09 | 0.02 | −0.20 | 0.13 |
| 59 | TGG | 0.74 | −0.28 | 0.61 | −0.02 | −0.43 | −0.12 | 0.05 | 0.17 | 0.21 | 0.11 | −0.12 | −0.10 |
| 60 | TGT | 0.41 | 0.71 | −0.19 | −0.46 | 0.09 | −0.05 | −0.11 | −0.09 | 0.24 | 0.32 | 0.16 | −0.37 |

TABLE C.2-continued

CPW matrix *A. niger* highly expressed sequences (left codon indicated in column 2, right codon indicated in row 2). Host cell: *A. niger*; Sequence data: full *A. niger* genome; Highly expressed group: 400 seqs.

|    |     | TTA | TTC | TTG | TTT | | | | | | | | |
|----|-----|-----|-----|-----|-----|---|---|---|---|---|---|---|---|
| 61 | TTA | 0.10 | 0.93 | 0.43 | 0.78 | −0.05 | 0.48 | 0.40 | 1.00 | 0.43 | 0.23 | 0.85 | 0.81 |
| 62 | TTC | 0.67 | −0.37 | 0.43 | −0.61 | 0.04 | −0.26 | −0.35 | −0.15 | 0.31 | −0.17 | −0.21 | 0.25 |
| 63 | TTG | 0.56 | 0.63 | 0.59 | 0.30 | −0.13 | −0.01 | 0.29 | 0.01 | 0.37 | 0.24 | 0.08 | 0.22 |
| 64 | TTT | 0.82 | 0.64 | 0.77 | 0.68 | −0.50 | 0.64 | 0.68 | 0.45 | 0.03 | −0.35 | 0.10 | 0.45 |

|    |     | CGA | CGC | CGG | CGT | CTA | CTC | CTG | CTT | GAA | GAC | GAG | GAT |
|----|-----|-----|-----|-----|-----|-----|-----|-----|-----|-----|-----|-----|-----|
|    |     | 25 | 26 | 27 | 28 | 29 | 30 | 31 | 32 | 33 | 34 | 35 | 36 |
|    |     | 37 | 38 | 39 | 40 | 41 | 42 | 43 | 44 | 45 | 46 | 47 | 48 |
|    |     | GCA | GCC | GCG | GCT | GGA | GGC | GGG | GGT | GTA | GTC | GTG | GTT |
| 1  | AAA | 0.41 | 0.43 | 0.35 | 0.59 | −0.15 | 0.24 | 0.21 | 0.76 | 0.90 | 0.31 | 0.57 | 0.60 |
| 2  | AAC | 0.66 | −0.30 | 0.33 | −0.04 | 0.12 | −0.32 | 0.53 | −0.22 | 0.92 | −0.40 | 0.38 | −0.03 |
| 3  | AAG | 0.49 | −0.43 | 0.52 | −0.27 | 0.38 | −0.14 | 0.85 | −0.47 | 0.73 | −0.42 | 0.29 | −0.20 |
| 4  | AAT | −0.06 | −0.11 | 0.24 | −0.13 | 0.34 | 0.11 | 0.36 | 0.27 | 0.57 | −0.07 | 0.14 | 0.15 |
| 5  | ACA | 0.53 | 0.45 | 0.57 | 0.54 | 0.64 | 0.46 | 0.45 | 0.53 | 0.06 | 0.55 | 0.37 | 0.69 |
| 6  | ACC | 0.30 | −0.14 | 0.53 | −0.14 | 0.19 | −0.17 | 0.69 | −0.46 | 0.77 | −0.45 | 0.29 | −0.31 |
| 7  | ACG | 0.24 | −0.12 | 0.50 | 0.18 | 0.41 | 0.41 | 0.70 | 0.29 | 0.04 | 0.57 | 0.18 | 0.12 |
| 8  | ACT | −0.18 | −0.47 | 0.05 | −0.54 | −0.03 | −0.30 | 0.55 | −0.61 | 0.24 | −0.38 | 0.25 | −0.30 |
| 9  | AGA | 0.16 | 0.27 | 0.50 | 0.47 | 0.18 | 0.63 | 0.82 | 0.21 | 0.42 | 0.54 | 0.35 | 0.45 |
| 10 | AGC | 0.59 | 0.14 | 0.58 | −0.08 | 0.53 | −0.05 | 0.71 | −0.35 | 0.73 | 0.05 | 0.17 | −0.12 |
| 11 | AGG | −0.34 | 0.09 | 0.82 | 0.44 | 0.57 | 0.49 | 0.81 | 0.39 | −0.18 | 0.21 | 0.51 | 0.47 |
| 12 | AGT | 0.46 | −0.26 | 0.24 | 0.05 | 0.35 | 0.16 | 0.53 | −0.32 | 0.36 | −0.16 | −0.17 | −0.09 |
| 13 | ATA | 0.60 | 0.70 | 0.79 | 0.77 | 0.16 | 0.86 | 0.83 | 0.83 | −0.54 | 0.73 | 0.52 | 0.69 |
| 14 | ATC | 0.61 | −0.06 | 0.62 | −0.04 | 0.40 | 0.20 | 0.79 | −0.44 | 0.72 | −0.26 | 0.53 | 0.15 |
| 15 | ATG | 0.30 | −0.24 | 0.38 | −0.08 | 0.33 | 0.06 | 0.36 | −0.33 | 0.58 | −0.23 | 0.30 | −0.11 |
| 16 | ATT | 0.29 | −0.55 | 0.02 | −0.44 | −0.03 | −0.21 | 0.39 | −0.47 | 0.00 | −0.45 | 0.07 | −0.23 |
| 17 | CAA | −0.02 | 0.24 | 0.48 | 0.37 | 0.08 | 0.17 | 0.68 | 0.03 | 0.50 | 0.34 | 0.54 | 0.55 |
| 18 | CAC | 0.20 | −0.34 | 0.32 | −0.27 | −0.04 | −0.15 | 0.80 | −0.44 | 0.45 | −0.43 | 0.71 | −0.35 |
| 19 | CAG | 0.33 | −0.29 | 0.27 | −0.33 | 0.32 | −0.12 | 0.75 | −0.45 | 0.57 | −0.42 | 0.16 | −0.29 |
| 20 | CAT | −0.42 | 0.39 | 0.43 | 0.45 | 0.01 | 0.16 | 0.52 | 0.27 | 0.92 | −0.15 | 0.48 | 0.20 |
| 21 | CCA | 0.45 | 0.57 | 0.35 | 0.09 | 0.35 | −0.07 | −0.29 | 0.38 | −0.25 | 0.57 | 0.54 | 0.55 |
| 22 | CCC | 0.57 | −0.43 | 0.57 | −0.29 | 0.09 | −0.20 | 0.64 | −0.57 | 0.12 | −0.48 | −0.08 | −0.31 |
| 23 | CCG | 0.14 | 0.22 | 0.09 | −0.17 | 0.56 | 0.49 | 0.64 | 0.53 | 0.68 | 0.43 | 0.42 | 0.12 |
| 24 | CCT | 0.53 | −0.26 | 0.55 | −0.44 | 0.12 | 0.05 | 0.60 | −0.48 | 0.59 | −0.28 | 0.11 | −0.17 |
| 25 | CGA | 0.68 | 0.66 | 0.75 | 0.60 | 0.47 | −0.17 | 0.53 | 0.70 | 0.78 | 0.13 | 0.47 | 0.58 |
| 26 | CGC | 0.22 | −0.15 | 0.65 | −0.15 | 0.44 | 0.10 | 0.60 | −0.06 | 0.09 | 0.14 | 0.20 | 0.12 |
| 27 | CGG | 0.52 | 0.43 | 0.39 | 0.30 | 0.63 | 0.58 | 0.74 | 0.42 | 0.25 | 0.55 | 0.11 | 0.27 |
| 28 | CGT | 0.09 | −0.69 | −0.02 | −0.66 | −0.35 | −0.43 | 0.45 | −0.82 | 0.51 | −0.73 | −0.26 | −0.46 |
| 29 | CTA | 0.53 | −0.13 | −0.23 | −0.32 | −0.39 | −0.22 | 0.66 | 0.73 | 0.44 | 0.56 | 0.75 | −0.22 |
| 30 | CTC | 0.48 | −0.22 | 0.52 | −0.07 | 0.13 | 0.05 | 0.78 | −0.35 | 0.67 | −0.38 | 0.38 | −0.01 |
| 31 | CTG | 0.24 | −0.28 | 0.20 | −0.26 | 0.07 | −0.07 | 0.65 | −0.32 | 0.35 | −0.35 | 0.11 | −0.09 |
| 32 | CTT | 0.34 | −0.45 | 0.45 | −0.46 | −0.32 | −0.26 | 0.58 | −0.58 | −0.07 | −0.33 | 0.18 | −0.28 |
| 33 | GAA | 0.16 | 0.03 | 0.21 | 0.38 | 0.30 | 0.05 | 0.49 | 0.31 | 0.70 | −0.16 | 0.34 | 0.34 |
| 34 | GAC | 0.60 | −0.12 | 0.49 | 0.26 | 0.40 | −0.16 | 0.69 | −0.14 | 0.59 | 0.06 | 0.49 | 0.02 |
| 35 | GAG | 0.51 | −0.29 | 0.44 | −0.37 | 0.34 | −0.15 | 0.77 | −0.49 | 0.69 | −0.31 | 0.37 | −0.32 |
| 36 | GAT | 0.53 | −0.42 | 0.09 | −0.29 | 0.04 | −0.17 | 0.06 | −0.07 | 0.36 | −0.36 | 0.15 | −0.27 |
| 37 | GCA | 0.29 | 0.66 | 0.42 | 0.51 | 0.23 | 0.30 | 0.39 | 0.50 | −0.22 | 0.51 | 0.37 | 0.53 |
| 38 | GCC | 0.61 | −0.28 | 0.42 | −0.06 | 0.54 | 0.23 | 0.75 | −0.49 | 0.59 | −0.41 | 0.34 | −0.28 |
| 39 | GCG | 0.46 | 0.28 | 0.44 | 0.48 | 0.51 | 0.51 | 0.74 | 0.32 | 0.16 | 0.45 | 0.45 | 0.51 |
| 40 | GCT | 0.31 | −0.53 | 0.12 | −0.58 | −0.05 | −0.35 | 0.57 | −0.64 | 0.07 | −0.40 | 0.19 | −0.36 |
| 41 | GGA | 0.14 | 0.38 | 0.50 | 0.42 | 0.45 | 0.46 | 0.80 | 0.31 | 0.78 | 0.50 | 0.63 | 0.23 |
| 42 | GGC | 0.51 | 0.36 | 0.75 | 0.11 | 0.49 | 0.28 | 0.75 | 0.08 | 0.64 | 0.47 | 0.54 | 0.28 |
| 43 | GGG | 0.61 | 0.78 | 0.84 | 0.46 | 0.60 | 0.83 | 0.89 | 0.78 | 0.73 | 0.73 | 0.74 | 0.77 |
| 44 | GGT | 0.39 | −0.66 | 0.32 | −0.67 | −0.15 | −0.33 | 0.63 | −0.78 | 0.63 | −0.66 | −0.22 | −0.69 |
| 45 | GTA | −0.11 | −0.05 | 0.34 | 0.73 | 0.51 | 0.51 | −0.21 | 0.89 | 0.66 | 0.39 | 0.46 | 0.70 |
| 46 | GTC | 0.43 | −0.16 | 0.66 | −0.20 | 0.22 | −0.14 | 0.47 | −0.53 | 0.67 | −0.36 | 0.41 | −0.04 |
| 47 | GTG | 0.59 | 0.14 | 0.58 | 0.21 | 0.50 | 0.37 | 0.71 | 0.55 | 0.75 | 0.22 | 0.39 | 0.38 |
| 48 | GTT | −0.13 | −0.47 | 0.22 | −0.53 | 0.02 | −0.17 | 0.41 | −0.56 | 0.57 | −0.51 | 0.06 | −0.50 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.66 | −0.32 | 0.52 | −0.24 | 0.41 | −0.22 | 0.06 | −0.22 | 0.77 | −0.16 | −0.10 | 0.15 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.45 | −0.26 | 0.59 | −0.13 | 0.38 | −0.14 | 0.52 | 0.11 | 0.36 | −0.04 | 0.20 | −0.25 |
| 53 | TCA | 0.55 | 0.54 | 0.16 | 0.31 | 0.43 | 0.82 | 0.62 | 0.78 | 0.44 | 0.22 | 0.49 | 0.57 |
| 54 | TCC | 0.10 | −0.39 | 0.53 | −0.32 | 0.00 | −0.37 | 0.52 | −0.50 | 0.47 | −0.54 | 0.10 | −0.36 |
| 55 | TCG | 0.21 | 0.20 | 0.40 | 0.13 | 0.41 | 0.39 | 0.66 | 0.35 | 0.57 | 0.37 | 0.27 | 0.35 |
| 56 | TCT | 0.20 | −0.44 | 0.26 | −0.51 | 0.08 | −0.42 | 0.06 | −0.37 | 0.33 | −0.09 | 0.33 | −0.16 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.63 | 0.14 | 0.31 | −0.43 | 0.41 | 0.26 | 0.16 | −0.43 | −0.17 | 0.35 | 0.58 | 0.23 |
| 59 | TGG | 0.35 | 0.00 | 0.00 | −0.19 | 0.42 | 0.12 | 0.68 | −0.45 | −0.15 | 0.49 | −0.17 | −0.31 |

TABLE C.2-continued

CPW matrix *A. niger* highly expressed sequences (left codon indicated in column 2, right codon indicated in row 2). Host cell: *A. niger*; Sequence data: full *A. niger* genome; Highly expressed group: 400 seqs.

| | | | | | | | | | | | | |
|---|---|---|---|---|---|---|---|---|---|---|---|---|
| 60 | TGT | 0.50 | −0.23 | 0.25 | −0.23 | 0.21 | 0.31 | 0.44 | −0.40 | 0.66 | −0.58 | 0.35 | −0.46 |
| 61 | TTA | 0.68 | 0.70 | 0.70 | 0.45 | 0.92 | 0.95 | −0.02 | 0.81 | 0.36 | 0.79 | −0.14 | 1.00 |
| 62 | TTC | 0.77 | −0.26 | 0.66 | −0.24 | 0.46 | 0.06 | 0.80 | −0.43 | 0.09 | −0.35 | 0.45 | 0.01 |
| 63 | TTG | 0.55 | 0.29 | 0.45 | 0.27 | 0.47 | 0.47 | 0.78 | 0.00 | 0.23 | 0.34 | 0.33 | 0.01 |
| 64 | TTT | 0.19 | −0.27 | 0.01 | −0.17 | 0.06 | −0.02 | 0.55 | −0.29 | 0.74 | −0.14 | 0.23 | 0.26 |

| | | GCA 37 | GCC 38 | GCG 39 | GCT 40 | GGA 41 | GGC 42 | GGG 43 | GGT 44 | GTA 45 | GTC 46 | GTG 47 | GTT 48 |
|---|---|---|---|---|---|---|---|---|---|---|---|---|---|

| | | 49 TAA | 50 TAC | 51 TAG | 52 TAT | 53 TCA | 54 TCC | 55 TCG | 56 TCT | 57 TGA | 58 TGC | 59 TGG | 60 TGT |
|---|---|---|---|---|---|---|---|---|---|---|---|---|---|
| 1 | AAA | 0.00 | 0.05 | 0.00 | 0.44 | −0.60 | 0.47 | 0.21 | 0.51 | 0.00 | 0.06 | −0.07 | 0.16 |
| 2 | AAC | 0.00 | −0.38 | 0.00 | 0.11 | 0.51 | −0.47 | −0.17 | −0.17 | 0.00 | −0.39 | −0.30 | 0.08 |
| 3 | AAG | 0.00 | −0.27 | 0.00 | 0.43 | 0.32 | −0.38 | 0.04 | 0.04 | 0.00 | −0.17 | 0.03 | 0.25 |
| 4 | AAT | 0.00 | 0.47 | 0.00 | 0.74 | 0.47 | 0.66 | 0.45 | 0.43 | 0.00 | 0.58 | 0.72 | 0.65 |
| 5 | ACA | 0.00 | 0.10 | 0.00 | 0.36 | 0.29 | 0.26 | 0.35 | 0.18 | 0.00 | 0.31 | −0.11 | 0.26 |
| 6 | ACC | 0.00 | −0.54 | 0.00 | 0.41 | 0.29 | −0.58 | −0.30 | −0.01 | 0.00 | −0.44 | −0.22 | 0.29 |
| 7 | ACG | 0.00 | 0.11 | 0.00 | 0.59 | 0.18 | 0.40 | 0.22 | 0.46 | 0.00 | 0.52 | 0.03 | 0.65 |
| 8 | ACT | 0.00 | 0.47 | 0.00 | 0.54 | 0.38 | −0.12 | 0.33 | −0.22 | 0.00 | −0.19 | 0.53 | −0.02 |
| 9 | AGA | 0.00 | −0.27 | 0.00 | −0.51 | 0.12 | −0.31 | 0.72 | −0.19 | 0.00 | 0.27 | −0.66 | −0.17 |
| 10 | AGC | 0.00 | −0.45 | 0.00 | 0.29 | −0.12 | −0.28 | 0.22 | −0.22 | 0.00 | −0.11 | −0.40 | −0.06 |
| 11 | AGG | 0.00 | 0.71 | 0.00 | 0.46 | 0.18 | −0.43 | 0.56 | 0.30 | 0.00 | 0.87 | 0.49 | 0.36 |
| 12 | AGT | 0.00 | 0.28 | 0.00 | 0.33 | 0.31 | 0.55 | 0.70 | 0.47 | 0.00 | 0.30 | 0.65 | 0.61 |
| 13 | ATA | 0.00 | 0.30 | 0.00 | −0.42 | −0.84 | 0.70 | 0.67 | −0.57 | 0.00 | 0.40 | 0.58 | −0.54 |
| 14 | ATC | 0.00 | −0.41 | 0.00 | 0.35 | 0.64 | −0.59 | 0.23 | −0.05 | 0.00 | −0.17 | −0.32 | −0.17 |
| 15 | ATG | 0.00 | −0.22 | 0.00 | 0.45 | 0.34 | −0.17 | 0.39 | 0.09 | 0.00 | −0.11 | 0.00 | 0.21 |
| 16 | ATT | 0.00 | 0.55 | 0.00 | 0.47 | 0.69 | 0.41 | 0.48 | 0.48 | 0.00 | 0.51 | 0.62 | 0.25 |
| 17 | CAA | 0.00 | 0.06 | 0.00 | −0.09 | 0.59 | 0.19 | 0.29 | 0.40 | 0.00 | 0.16 | −0.04 | −0.42 |
| 18 | CAC | 0.00 | −0.47 | 0.00 | 0.35 | 0.17 | −0.54 | −0.01 | −0.33 | 0.00 | −0.50 | −0.35 | −0.04 |
| 19 | CAG | 0.00 | −0.16 | 0.00 | 0.32 | 0.43 | −0.42 | −0.05 | −0.08 | 0.00 | −0.10 | 0.03 | 0.45 |
| 20 | CAT | 0.00 | 0.51 | 0.00 | 0.45 | 0.54 | 0.42 | 0.38 | 0.23 | 0.00 | 0.66 | 0.64 | 0.89 |
| 21 | CCA | 0.00 | 0.09 | 0.00 | 0.52 | 0.29 | 0.25 | 0.37 | −0.05 | 0.00 | 0.26 | 0.45 | 0.38 |
| 22 | CCC | 0.00 | −0.50 | 0.00 | 0.51 | 0.76 | −0.59 | 0.33 | −0.17 | 0.00 | −0.42 | −0.33 | 0.37 |
| 23 | CCG | 0.00 | −0.02 | 0.00 | 0.23 | −0.33 | 0.39 | 0.37 | 0.19 | 0.00 | 0.64 | 0.38 | 1.00 |
| 24 | CCT | 0.00 | 0.10 | 0.00 | 0.52 | 0.67 | −0.12 | 0.17 | −0.06 | 0.00 | −0.45 | −0.07 | −0.07 |
| 25 | CGA | 0.00 | −0.22 | 0.00 | 0.71 | −0.43 | 0.17 | 0.26 | 0.67 | 0.00 | 0.45 | 0.55 | 0.08 |
| 26 | CGC | 0.00 | −0.35 | 0.00 | 0.43 | 0.26 | −0.53 | −0.27 | −0.36 | 0.00 | −0.61 | 0.00 | 0.40 |
| 27 | CGG | 0.00 | 0.34 | 0.00 | 0.56 | 0.36 | 0.32 | 0.56 | 0.50 | 0.00 | 0.51 | 0.44 | 0.53 |
| 28 | CGT | 0.00 | −0.39 | 0.00 | 0.50 | 0.26 | −0.28 | 0.22 | 0.14 | 0.00 | −0.08 | −0.02 | 0.43 |
| 29 | CTA | 0.00 | −0.15 | 0.00 | 0.61 | 0.59 | −0.25 | 0.54 | 0.57 | 0.00 | 0.47 | −0.11 | 1.00 |
| 30 | CTC | 0.00 | −0.41 | 0.00 | 0.24 | 0.11 | −0.46 | 0.27 | −0.13 | 0.00 | −0.42 | −0.44 | −0.11 |
| 31 | CTG | 0.00 | −0.28 | 0.00 | 0.31 | −0.10 | −0.21 | 0.11 | −0.15 | 0.00 | −0.01 | 0.11 | 0.23 |
| 32 | CTT | 0.00 | 0.20 | 0.00 | 0.59 | 0.25 | −0.18 | 0.03 | −0.30 | 0.00 | −0.51 | 0.32 | 0.36 |
| 33 | GAA | 0.00 | −0.21 | 0.00 | 0.33 | 0.46 | 0.07 | 0.18 | 0.35 | 0.00 | 0.45 | −0.13 | 0.26 |
| 34 | GAC | 0.00 | −0.47 | 0.00 | 0.42 | 0.61 | −0.44 | −0.12 | −0.32 | 0.00 | −0.43 | −0.33 | 0.00 |
| 35 | GAG | 0.00 | −0.20 | 0.00 | 0.48 | 0.56 | −0.40 | 0.20 | −0.09 | 0.00 | −0.38 | 0.10 | 0.36 |
| 36 | GAT | 0.00 | 0.30 | 0.00 | 0.56 | 0.68 | 0.20 | 0.44 | 0.29 | 0.00 | 0.62 | 0.52 | 0.25 |
| 37 | GCA | 0.00 | 0.13 | 0.00 | 0.38 | −0.11 | 0.03 | 0.23 | 0.21 | 0.00 | 0.17 | 0.10 | 0.45 |
| 38 | GCC | 0.00 | −0.59 | 0.00 | 0.38 | 0.57 | −0.56 | 0.17 | −0.13 | 0.00 | −0.25 | −0.33 | −0.23 |
| 39 | GCG | 0.00 | 0.54 | 0.00 | 0.55 | 0.18 | 0.52 | 0.52 | 0.27 | 0.00 | 0.69 | 0.39 | 0.68 |
| 40 | GCT | 0.00 | 0.44 | 0.00 | 0.27 | 0.49 | −0.32 | 0.26 | −0.13 | 0.00 | −0.26 | 0.27 | −0.15 |
| 41 | GGA | 0.00 | −0.25 | 0.00 | 0.03 | 0.23 | −0.15 | 0.19 | 0.39 | 0.00 | 0.02 | 0.03 | −0.26 |
| 42 | GGC | 0.00 | −0.26 | 0.00 | 0.31 | 0.46 | −0.37 | 0.38 | −0.28 | 0.00 | −0.22 | −0.40 | −0.07 |
| 43 | GGG | 0.00 | 0.56 | 0.00 | 0.12 | 0.33 | 0.61 | 0.40 | 0.37 | 0.00 | 0.68 | 0.70 | 0.29 |
| 44 | GGT | 0.00 | −0.16 | 0.00 | 0.49 | 0.75 | −0.32 | 0.51 | 0.06 | 0.00 | −0.10 | 0.42 | 0.38 |
| 45 | GTA | 0.00 | −0.30 | 0.00 | 0.58 | 0.11 | 0.08 | −0.05 | −0.52 | 0.00 | 0.43 | 0.45 | 0.22 |
| 46 | GTC | 0.00 | −0.44 | 0.00 | 0.25 | 0.51 | −0.55 | 0.22 | −0.30 | 0.00 | −0.50 | −0.30 | 0.26 |
| 47 | GTG | 0.00 | 0.19 | 0.00 | 0.48 | 0.11 | 0.39 | 0.46 | 0.08 | 0.00 | 0.03 | 0.06 | 0.70 |
| 48 | GTT | 0.00 | 0.08 | 0.00 | 0.57 | 0.02 | −0.27 | 0.43 | 0.16 | 0.00 | 0.24 | 0.42 | 0.52 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.00 | −0.43 | 0.00 | 0.18 | 0.23 | −0.40 | 0.04 | −0.50 | 0.00 | −0.43 | −0.28 | 0.13 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.00 | 0.61 | 0.00 | 0.71 | 0.84 | 0.43 | 0.60 | 0.27 | 0.00 | 0.78 | 0.65 | 0.57 |
| 53 | TCA | 0.00 | 0.39 | 0.00 | 0.41 | −0.19 | −0.07 | 0.58 | −0.10 | 0.00 | 0.34 | 0.21 | 0.32 |
| 54 | TCC | 0.00 | −0.47 | 0.00 | 0.31 | 0.27 | −0.52 | 0.47 | −0.22 | 0.00 | −0.48 | −0.25 | 0.36 |
| 55 | TCG | 0.00 | 0.34 | 0.00 | 0.52 | 0.11 | 0.22 | 0.11 | 0.14 | 0.00 | 0.38 | 0.48 | 0.74 |
| 56 | TCT | 0.00 | 0.17 | 0.00 | 0.14 | 0.22 | −0.48 | 0.02 | −0.34 | 0.00 | −0.40 | 0.12 | 0.28 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.00 | −0.32 | 0.00 | 0.35 | 0.30 | −0.47 | −0.45 | −0.47 | 0.00 | −0.30 | −0.25 | −0.08 |
| 59 | TGG | 0.00 | −0.19 | 0.00 | 0.38 | −0.24 | −0.13 | 0.28 | 0.17 | 0.00 | 0.11 | 0.00 | −0.16 |
| 60 | TGT | 0.00 | 0.34 | 0.00 | 0.14 | 0.61 | 0.51 | 0.75 | 0.49 | 0.00 | 0.50 | 0.56 | 0.50 |

TABLE C.2-continued

CPW matrix *A. niger* highly expressed sequences (left codon indicated in column 2, right codon indicated in row 2). Host cell: *A. niger*; Sequence data: full *A. niger* genome; Highly expressed group: 400 seqs.

| | | | | | | | | | | | | | |
|---|---|---|---|---|---|---|---|---|---|---|---|---|---|
| 61 | TTA | 0.00 | 0.54 | 0.00 | 0.36 | −0.20 | 0.56 | 0.41 | 0.49 | 0.00 | 0.83 | 0.55 | 0.72 |
| 62 | TTC | 0.00 | −0.42 | 0.00 | 0.33 | 0.51 | −0.49 | 0.38 | −0.19 | 0.00 | −0.08 | −0.21 | −0.35 |
| 63 | TTG | 0.00 | 0.20 | 0.00 | 0.09 | 0.43 | 0.31 | 0.43 | 0.25 | 0.00 | 0.79 | 0.54 | 0.25 |
| 64 | TTT | 0.00 | 0.68 | 0.00 | 0.77 | 0.65 | 0.27 | 0.43 | −0.09 | 0.00 | 0.74 | 0.59 | 0.30 |

| | TAA 49 | TAC 50 | TAG 51 | TAT 52 | TCA 53 | TCC 54 | TCG 55 | TCT 56 | TGA 57 | TGC 58 | TGG 59 | TGT 60 |
|---|---|---|---|---|---|---|---|---|---|---|---|---|

| | | 61 TTA | 62 TTC | 63 TTG | 64 TTT |
|---|---|---|---|---|---|
| 1 | AAA | 0.72 | 0.34 | 0.10 | 0.50 |
| 2 | AAC | 0.79 | −0.39 | 0.00 | 0.31 |
| 3 | AAG | 0.15 | −0.27 | 0.34 | 0.39 |
| 4 | AAT | 0.46 | 0.65 | 0.37 | 0.45 |
| 5 | ACA | 0.00 | 0.14 | 0.08 | 0.37 |
| 6 | ACC | 0.89 | −0.37 | 0.19 | 0.54 |
| 7 | ACG | 0.81 | 0.46 | 0.68 | −0.10 |
| 8 | ACT | 0.82 | −0.09 | 0.21 | 0.15 |
| 9 | AGA | 0.10 | 0.21 | 0.18 | 0.66 |
| 10 | AGC | 0.55 | −0.12 | −0.01 | 0.21 |
| 11 | AGG | 0.05 | 0.52 | −0.18 | 0.71 |
| 12 | AGT | 0.42 | 0.37 | 0.20 | 0.66 |
| 13 | ATA | 0.29 | 0.42 | 0.71 | 0.42 |
| 14 | ATC | 0.50 | −0.41 | 0.24 | 0.29 |
| 15 | ATG | 0.52 | −0.16 | 0.35 | 0.45 |
| 16 | ATT | 0.85 | 0.54 | 0.20 | 0.53 |
| 17 | CAA | 0.05 | 0.11 | −0.12 | 0.34 |
| 18 | CAC | 0.73 | −0.37 | 0.05 | 0.07 |
| 19 | CAG | 0.70 | −0.26 | 0.51 | 0.46 |
| 20 | CAT | 0.79 | 0.34 | 0.33 | 0.71 |
| 21 | CCA | −0.07 | 0.31 | 0.36 | 0.22 |
| 22 | CCC | 0.55 | −0.51 | −0.32 | 0.32 |
| 23 | CCG | 0.41 | 0.39 | 0.25 | 0.40 |
| 24 | CCT | 0.57 | 0.01 | 0.37 | 0.66 |
| 25 | CGA | 1.00 | 0.42 | 0.54 | 0.43 |
| 26 | CGC | −0.29 | −0.44 | 0.11 | −0.20 |
| 27 | CGG | 0.61 | 0.30 | 0.03 | 0.57 |
| 28 | CGT | 1.00 | −0.37 | 0.02 | 0.46 |
| 29 | CTA | −0.64 | −0.19 | 0.53 | 0.00 |
| 30 | CTC | 0.65 | −0.44 | 0.10 | 0.18 |
| 31 | CTG | 0.68 | −0.06 | 0.25 | 0.25 |
| 32 | CTT | 0.49 | 0.00 | 0.07 | 0.49 |
| 33 | GAA | 0.55 | 0.13 | 0.20 | 0.39 |
| 34 | GAC | 0.71 | −0.41 | 0.19 | −0.13 |
| 35 | GAG | 0.78 | −0.28 | 0.22 | 0.43 |
| 36 | GAT | 0.87 | 0.44 | 0.37 | 0.78 |
| 37 | GCA | 0.50 | 0.46 | 0.13 | 0.26 |
| 38 | GCC | 0.82 | −0.17 | 0.03 | 0.17 |
| 39 | GCG | 0.46 | 0.20 | 0.44 | −0.07 |
| 40 | GCT | 0.49 | −0.36 | 0.11 | 0.46 |
| 41 | GGA | 0.31 | −0.14 | 0.18 | 0.36 |
| 42 | GGC | 0.76 | −0.12 | 0.12 | 0.43 |
| 43 | GGG | 0.53 | 0.63 | −0.05 | 0.35 |
| 44 | GGT | 0.94 | −0.44 | 0.52 | 0.75 |
| 45 | GTA | 0.57 | 0.27 | 0.48 | 0.63 |
| 46 | GTC | 0.58 | −0.43 | 0.26 | 0.29 |
| 47 | GTG | 0.93 | 0.10 | 0.30 | 0.35 |
| 48 | GTT | 0.59 | 0.22 | 0.39 | 0.51 |
| 49 | TAA | 0.00 | 0.00 | 0.00 | 0.00 |
| 50 | TAC | 0.87 | −0.37 | 0.27 | 0.14 |
| 51 | TAG | 0.00 | 0.00 | 0.00 | 0.00 |
| 52 | TAT | 0.79 | 0.56 | 0.58 | 0.65 |
| 53 | TCA | 0.09 | 0.29 | 0.12 | 0.49 |
| 54 | TCC | 0.65 | −0.32 | 0.19 | 0.39 |
| 55 | TCG | 0.62 | −0.11 | 0.44 | 0.33 |
| 56 | TCT | −0.41 | −0.32 | 0.27 | 0.27 |
| 57 | TGA | 0.00 | 0.00 | 0.00 | 0.00 |
| 58 | TGC | 0.30 | −0.28 | −0.18 | 0.20 |
| 59 | TGG | 0.77 | −0.14 | 0.11 | 0.37 |

TABLE C.2-continued

CPW matrix *A. niger* highly expressed sequences (left codon indicated in column 2, right codon indicated in row 2). Host cell: *A. niger*; Sequence data: full *A. niger* genome; Highly expressed group: 400 seqs.

| | | | | | |
|---|---|---|---|---|---|
| 60 | TGT | −0.14 | 0.33 | 0.44 | 0.38 |
| 61 | TTA | 0.66 | 0.79 | 0.67 | 0.40 |
| 62 | TTC | 0.75 | −0.37 | 0.13 | 0.34 |
| 63 | TTG | 0.59 | 0.40 | 0.33 | 0.39 |
| 64 | TTT | 0.77 | 0.63 | 0.50 | 0.80 |
| | | TTA | TTC | TTG | TTT |
| | | 61 | 62 | 63 | 64 |

TABLE C.3

CPW matrix *Bacillus subtilis* full genome (left codon indicated in column 2, right codon indicated in row 2). Host cell: *B. subtilis*; Sequence data: full *B. subtilis* genome.

| | | 1 AAA | 2 AAC | 3 AAG | 4 AAT | 5 ACA | 6 ACC | 7 ACG | 8 ACT | 9 AGA | 10 AGC | 11 AGG | 12 AGT |
|---|---|---|---|---|---|---|---|---|---|---|---|---|---|
| 1 | AAA | 0.02 | −0.28 | −0.11 | 0.04 | −0.28 | −0.13 | −0.23 | 0.44 | 0.16 | −0.39 | −0.02 | 0.04 |
| 2 | AAC | −0.04 | −0.22 | 0.01 | −0.16 | 0.09 | 0.10 | 0.06 | 0.10 | −0.17 | −0.63 | −0.38 | −0.54 |
| 3 | AAG | 0.00 | 0.33 | 0.18 | 0.36 | 0.43 | 0.59 | 0.38 | 0.50 | 0.48 | 0.22 | 0.28 | 0.05 |
| 4 | AAT | −0.03 | 0.11 | 0.13 | 0.24 | −0.08 | −0.05 | −0.20 | 0.29 | 0.61 | 0.57 | 0.56 | 0.32 |
| 5 | ACA | −0.22 | −0.31 | −0.27 | −0.16 | −0.13 | −0.24 | −0.13 | −0.33 | −0.45 | −0.30 | −0.51 | −0.25 |
| 6 | ACC | 0.40 | 0.19 | 0.43 | −0.13 | 0.42 | 0.10 | 0.61 | −0.12 | 0.05 | 0.37 | 0.16 | 0.02 |
| 7 | ACG | −0.06 | 0.22 | −0.20 | 0.04 | −0.18 | 0.17 | 0.01 | −0.31 | −0.37 | 0.26 | −0.22 | −0.02 |
| 8 | ACT | 0.57 | 0.69 | 0.54 | 0.49 | 0.45 | 0.53 | 0.68 | 0.18 | 0.36 | 0.75 | 0.32 | 0.46 |
| 9 | AGA | −0.31 | −0.31 | −0.32 | −0.18 | −0.09 | −0.30 | −0.37 | 0.22 | −0.44 | −0.34 | −0.59 | −0.20 |
| 10 | AGC | −0.09 | 0.05 | −0.15 | −0.14 | −0.07 | −0.15 | −0.10 | −0.20 | −0.31 | −0.32 | −0.59 | −0.38 |
| 11 | AGG | 0.30 | 0.52 | 0.23 | 0.29 | 0.35 | 0.51 | 0.45 | 0.43 | −0.07 | 0.44 | −0.02 | 0.26 |
| 12 | AGT | 0.10 | 0.54 | 0.28 | 0.28 | 0.03 | 0.52 | 0.03 | 0.15 | 0.71 | 0.87 | 0.82 | 0.80 |
| 13 | ATA | −0.40 | −0.15 | −0.37 | −0.08 | 0.24 | −0.23 | 0.12 | −0.14 | −0.11 | 0.28 | −0.43 | 0.06 |
| 14 | ATC | −0.15 | −0.17 | 0.07 | −0.29 | −0.05 | −0.13 | 0.15 | −0.21 | −0.44 | −0.47 | −0.48 | |
| 15 | ATG | 0.11 | 0.08 | −0.21 | −0.06 | 0.02 | 0.14 | −0.10 | −0.01 | −0.31 | −0.09 | −0.32 | −0.19 |
| 16 | ATT | 0.20 | 0.21 | 0.31 | 0.31 | −0.02 | 0.03 | −0.03 | 0.18 | 0.69 | 0.85 | 0.66 | 0.60 |
| 17 | CAA | −0.27 | −0.43 | −0.38 | −0.26 | −0.10 | −0.46 | −0.26 | −0.02 | −0.18 | −0.40 | −0.18 | −0.17 |
| 18 | CAC | 0.14 | −0.04 | −0.04 | −0.22 | 0.26 | −0.08 | 0.10 | 0.10 | −0.32 | −0.52 | −0.40 | −0.44 |
| 19 | CAG | 0.47 | 0.58 | 0.40 | 0.52 | 0.31 | 0.41 | 0.16 | 0.33 | 0.50 | 0.65 | 0.29 | 0.63 |
| 20 | CAT | −0.06 | 0.01 | 0.02 | 0.15 | −0.12 | 0.01 | −0.09 | 0.11 | 0.61 | 0.66 | 0.62 | 0.47 |
| 21 | CCA | −0.34 | −0.49 | −0.45 | −0.34 | 0.09 | −0.33 | 0.11 | −0.37 | −0.51 | −0.48 | −0.51 | −0.50 |
| 22 | CCC | 0.50 | 0.35 | 0.59 | −0.09 | 0.55 | 0.25 | 0.69 | −0.11 | 0.14 | 0.30 | 0.83 | 0.11 |
| 23 | CCG | −0.02 | 0.18 | −0.13 | −0.12 | −0.31 | −0.09 | −0.03 | −0.51 | −0.22 | 0.37 | 0.39 | 0.07 |
| 24 | CCT | 0.31 | 0.49 | 0.33 | 0.39 | 0.49 | 0.45 | 0.67 | 0.28 | 0.55 | 0.80 | 0.54 | 0.58 |
| 25 | CGA | −0.47 | −0.52 | −0.32 | −0.45 | −0.08 | −0.21 | −0.16 | 0.01 | −0.32 | −0.55 | 0.17 | −0.22 |
| 26 | CGC | 0.31 | 0.13 | 0.10 | −0.10 | 0.15 | −0.06 | 0.14 | 0.27 | −0.13 | −0.33 | −0.15 | −0.31 |
| 27 | CGG | 0.21 | 0.48 | 0.21 | 0.04 | −0.25 | 0.24 | −0.43 | −0.04 | 0.38 | 0.45 | 0.31 | 0.46 |
| 28 | CGT | 0.42 | 0.61 | 0.51 | 0.50 | 0.24 | 0.59 | 0.17 | 0.36 | 0.89 | 0.90 | 0.90 | 0.85 |
| 29 | CTA | −0.36 | −0.20 | −0.43 | −0.27 | 0.29 | −0.36 | 0.28 | −0.06 | −0.37 | −0.31 | −0.47 | −0.23 |
| 30 | CTC | 0.37 | 0.34 | 0.27 | −0.02 | 0.34 | −0.09 | 0.50 | −0.11 | −0.39 | −0.38 | −0.04 | −0.33 |
| 31 | CTG | −0.10 | 0.03 | −0.20 | −0.13 | −0.26 | −0.18 | −0.23 | −0.41 | 0.09 | 0.45 | 0.10 | 0.39 |
| 32 | CTT | 0.67 | 0.61 | 0.68 | 0.55 | 0.56 | 0.44 | 0.61 | 0.31 | 0.54 | 0.74 | 0.60 | 0.68 |
| 33 | GAA | −0.09 | −0.25 | −0.06 | −0.03 | −0.20 | −0.16 | −0.21 | 0.28 | 0.08 | −0.37 | 0.15 | −0.15 |
| 34 | GAC | −0.05 | −0.16 | −0.05 | −0.21 | 0.13 | 0.01 | 0.18 | −0.07 | −0.35 | −0.65 | −0.52 | −0.58 |
| 35 | GAG | 0.20 | 0.40 | 0.17 | 0.32 | 0.36 | 0.57 | 0.16 | 0.35 | 0.34 | 0.23 | 0.50 | 0.14 |
| 36 | GAT | −0.01 | 0.07 | 0.14 | 0.18 | −0.09 | 0.09 | −0.15 | 0.13 | 0.72 | 0.77 | 0.72 | 0.56 |
| 37 | GCA | −0.29 | −0.29 | −0.24 | −0.19 | −0.21 | −0.32 | −0.07 | −0.38 | −0.46 | −0.27 | −0.39 | −0.35 |
| 38 | GCC | 0.13 | −0.10 | 0.05 | −0.35 | 0.16 | 0.12 | 0.44 | −0.31 | −0.47 | −0.23 | 0.06 | −0.25 |
| 39 | GCG | −0.07 | 0.30 | −0.15 | 0.04 | −0.25 | 0.21 | 0.05 | −0.26 | −0.25 | 0.44 | 0.31 | 0.26 |
| 40 | GCT | 0.43 | 0.44 | 0.47 | 0.50 | 0.33 | 0.53 | 0.56 | 0.13 | 0.65 | 0.87 | 0.76 | 0.61 |
| 41 | GGA | −0.33 | −0.38 | −0.11 | −0.24 | −0.21 | −0.23 | −0.36 | −0.14 | −0.29 | −0.45 | −0.20 | −0.26 |
| 42 | GGC | 0.30 | 0.27 | 0.21 | 0.11 | 0.10 | 0.07 | 0.14 | −0.01 | −0.27 | −0.30 | −0.36 | −0.27 |
| 43 | GGG | −0.24 | −0.01 | −0.13 | −0.16 | 0.10 | 0.34 | 0.10 | 0.22 | 0.07 | 0.10 | 0.21 | −0.02 |
| 44 | GGT | 0.32 | 0.52 | 0.51 | 0.51 | 0.23 | 0.62 | 0.23 | 0.08 | 0.81 | 0.88 | 0.85 | 0.84 |
| 45 | GTA | −0.34 | −0.34 | −0.37 | −0.22 | −0.09 | −0.23 | −0.21 | 0.05 | −0.28 | −0.09 | −0.40 | 0.00 |
| 46 | GTC | 0.00 | 0.01 | 0.43 | −0.26 | 0.01 | −0.26 | 0.03 | −0.19 | −0.55 | −0.56 | −0.38 | −0.47 |
| 47 | GTG | −0.21 | 0.05 | −0.29 | −0.16 | −0.25 | −0.05 | −0.17 | 0.02 | 0.22 | 0.55 | 0.19 | 0.42 |
| 48 | GTT | 0.56 | 0.49 | 0.49 | 0.53 | 0.41 | 0.36 | 0.41 | 0.13 | 0.68 | 0.87 | 0.76 | 0.66 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.01 | −0.32 | 0.10 | −0.20 | −0.04 | −0.03 | −0.03 | 0.02 | −0.36 | −0.60 | −0.49 | −0.58 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | −0.06 | 0.11 | 0.09 | 0.24 | −0.05 | 0.20 | −0.12 | 0.24 | 0.65 | 0.75 | 0.68 | 0.54 |
| 53 | TCA | −0.19 | −0.22 | −0.19 | −0.22 | −0.16 | −0.27 | −0.04 | −0.44 | −0.32 | −0.23 | −0.36 | −0.16 |
| 54 | TCC | 0.25 | 0.06 | 0.37 | −0.26 | 0.28 | 0.06 | 0.45 | −0.15 | −0.42 | −0.22 | 0.29 | −0.30 |
| 55 | TCG | −0.02 | 0.32 | −0.14 | −0.06 | −0.05 | 0.08 | 0.24 | −0.28 | −0.03 | 0.58 | 0.22 | 0.20 |
| 56 | TCT | 0.15 | 0.27 | 0.24 | 0.24 | 0.23 | 0.31 | 0.51 | −0.13 | 0.70 | 0.86 | 0.56 | 0.58 |

TABLE C.3-continued

CPW matrix *Bacillus subtilis* full genome (left codon indicated in column 2, right codon indicated in row 2). Host cell: *B. subtilis*; Sequence data: full *B. subtilis* genome.

| | | | | | | | | | | | | |
|---|---|---|---|---|---|---|---|---|---|---|---|---|
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.06 | −0.09 | −0.14 | −0.15 | 0.21 | −0.20 | 0.05 | 0.31 | 0.08 | −0.39 | −0.34 | −0.12 |
| 59 | TGG | 0.13 | 0.06 | −0.23 | −0.04 | −0.02 | 0.29 | −0.19 | 0.15 | −0.28 | −0.20 | 0.04 | −0.13 |
| 60 | TGT | 0.01 | 0.33 | 0.02 | 0.05 | 0.01 | −0.26 | −0.30 | 0.20 | 0.82 | 0.91 | 0.83 | 0.70 |
| 61 | TTA | −0.35 | −0.36 | −0.37 | −0.35 | −0.17 | −0.33 | −0.32 | −0.33 | −0.26 | −0.16 | −0.19 | −0.21 |
| 62 | TTC | −0.09 | 0.02 | 0.02 | −0.04 | 0.12 | −0.18 | 0.29 | −0.29 | −0.54 | −0.49 | −0.58 | −0.46 |
| 63 | TTG | −0.08 | 0.10 | −0.22 | −0.19 | 0.15 | 0.04 | 0.10 | −0.18 | 0.00 | 0.43 | 0.11 | 0.16 |
| 64 | TTT | −0.02 | 0.03 | 0.14 | −0.01 | 0.02 | −0.16 | 0.00 | 0.05 | 0.49 | 0.80 | 0.50 | 0.57 |

| | | AAA 1 | AAC 2 | AAG 3 | AAT 4 | ACA 5 | ACC 6 | ACG 7 | ACT 8 | AGA 9 | AGC 10 | AGG 11 | AGT 12 |
|---|---|---|---|---|---|---|---|---|---|---|---|---|---|
| | | 13 ATA | 14 ATC | 15 ATG | 16 ATT | 17 CAA | 18 CAC | 19 CAG | 20 CAT | 21 CCA | 22 CCC | 23 CCG | 24 CCT |
| 1 | AAA | −0.36 | −0.29 | −0.14 | 0.22 | 0.07 | 0.14 | 0.15 | 0.35 | 0.07 | 0.35 | 0.19 | 0.45 |
| 2 | AAC | 0.17 | 0.01 | 0.04 | 0.06 | 0.09 | 0.02 | 0.32 | 0.17 | 0.20 | 0.17 | 0.19 | 0.12 |
| 3 | AAG | 0.01 | 0.32 | 0.38 | 0.29 | −0.12 | −0.37 | −0.28 | −0.41 | −0.20 | −0.31 | −0.41 | −0.42 |
| 4 | AAT | −0.25 | −0.06 | −0.03 | 0.05 | −0.23 | 0.04 | −0.02 | −0.14 | −0.26 | −0.27 | −0.11 | 0.06 |
| 5 | ACA | 0.16 | 0.23 | 0.04 | 0.36 | 0.02 | 0.09 | −0.05 | 0.22 | 0.08 | 0.27 | −0.03 | 0.05 |
| 6 | ACC | −0.05 | −0.23 | 0.19 | −0.52 | 0.00 | −0.05 | 0.11 | −0.29 | 0.29 | 0.40 | 0.47 | 0.36 |
| 7 | ACG | −0.35 | −0.19 | −0.35 | −0.37 | 0.05 | 0.18 | 0.30 | 0.24 | −0.32 | 0.05 | −0.24 | −0.33 |
| 8 | ACT | 0.51 | 0.78 | 0.64 | 0.66 | −0.34 | −0.39 | −0.08 | −0.33 | 0.05 | 0.14 | 0.29 | −0.09 |
| 9 | AGA | −0.14 | −0.09 | −0.11 | 0.11 | 0.21 | 0.23 | −0.19 | 0.28 | 0.44 | 0.23 | 0.26 | 0.36 |
| 10 | AGC | −0.09 | 0.06 | −0.21 | −0.02 | −0.20 | −0.07 | −0.20 | −0.13 | 0.35 | 0.36 | 0.10 | 0.34 |
| 11 | AGG | −0.14 | 0.31 | 0.21 | 0.25 | −0.13 | −0.26 | −0.40 | −0.27 | −0.29 | −0.02 | −0.33 | −0.31 |
| 12 | AGT | −0.22 | 0.24 | −0.06 | −0.08 | 0.08 | 0.43 | 0.18 | 0.01 | −0.21 | −0.31 | 0.00 | −0.07 |
| 13 | ATA | 0.02 | 0.68 | 0.56 | 0.72 | −0.19 | 0.04 | −0.09 | 0.01 | −0.05 | −0.13 | −0.17 | 0.05 |
| 14 | ATC | −0.11 | −0.24 | −0.19 | −0.26 | 0.31 | 0.38 | 0.38 | 0.24 | 0.20 | 0.11 | 0.28 | 0.32 |
| 15 | ATG | 0.09 | 0.02 | 0.00 | −0.04 | 0.27 | −0.04 | −0.22 | 0.02 | 0.26 | 0.10 | −0.11 | −0.02 |
| 16 | ATT | 0.22 | 0.03 | 0.03 | 0.07 | −0.23 | −0.25 | −0.10 | −0.13 | −0.21 | −0.29 | −0.12 | −0.08 |
| 17 | CAA | −0.21 | −0.33 | −0.30 | −0.14 | 0.64 | 0.76 | 0.70 | 0.74 | 0.69 | 0.73 | 0.87 | 0.81 |
| 18 | CAC | 0.26 | 0.05 | 0.05 | 0.05 | 0.15 | 0.00 | 0.17 | 0.00 | −0.01 | 0.07 | 0.17 | 0.13 |
| 19 | CAG | 0.45 | 0.42 | 0.45 | 0.19 | −0.31 | −0.44 | −0.48 | −0.43 | −0.40 | −0.44 | −0.46 | −0.47 |
| 20 | CAT | 0.04 | −0.03 | −0.02 | −0.06 | −0.05 | −0.03 | −0.09 | 0.01 | −0.10 | −0.26 | 0.00 | −0.02 |
| 21 | CCA | −0.02 | −0.22 | −0.32 | 0.07 | 0.58 | 0.54 | 0.65 | 0.64 | 0.40 | 0.71 | 0.87 | 0.65 |
| 22 | CCC | 0.42 | 0.15 | 0.36 | 0.06 | −0.03 | −0.35 | 0.34 | −0.11 | 0.13 | 0.69 | 0.44 | −0.02 |
| 23 | CCG | 0.12 | −0.12 | −0.18 | −0.36 | −0.24 | −0.09 | −0.14 | −0.15 | −0.40 | −0.24 | −0.22 | −0.35 |
| 24 | CCT | 0.43 | 0.57 | 0.52 | 0.46 | −0.08 | −0.02 | −0.09 | −0.12 | −0.05 | 0.08 | 0.23 | 0.03 |
| 25 | CGA | −0.15 | −0.37 | −0.38 | −0.23 | 0.68 | 0.60 | 0.59 | 0.57 | 0.64 | 0.79 | 0.71 | 0.85 |
| 26 | CGC | 0.27 | −0.05 | 0.18 | 0.08 | −0.06 | −0.29 | −0.32 | −0.31 | 0.28 | −0.07 | −0.12 | 0.01 |
| 27 | CGG | −0.05 | −0.03 | −0.15 | −0.30 | 0.00 | −0.14 | −0.12 | −0.25 | 0.17 | −0.22 | −0.23 | −0.20 |
| 28 | CGT | 0.33 | 0.22 | 0.34 | 0.21 | 0.14 | 0.24 | 0.32 | 0.23 | −0.24 | −0.43 | −0.32 | −0.28 |
| 29 | CTA | −0.17 | 0.20 | 0.12 | 0.38 | 0.54 | 0.65 | 0.60 | 0.48 | 0.75 | 0.76 | 0.80 | 0.79 |
| 30 | CTC | −0.04 | −0.10 | −0.11 | −0.24 | 0.21 | 0.37 | 0.44 | 0.17 | 0.22 | −0.09 | 0.15 | 0.10 |
| 31 | CTG | 0.29 | −0.25 | −0.22 | −0.21 | −0.23 | −0.14 | −0.04 | 0.01 | −0.25 | −0.12 | −0.32 | −0.26 |
| 32 | CTT | 0.47 | 0.53 | 0.58 | 0.48 | −0.25 | −0.42 | −0.23 | −0.30 | −0.20 | −0.29 | −0.18 | −0.32 |
| 33 | GAA | −0.17 | −0.20 | −0.10 | 0.13 | 0.12 | 0.28 | 0.10 | 0.37 | 0.25 | 0.40 | 0.22 | 0.51 |
| 34 | GAC | 0.16 | 0.07 | −0.02 | −0.06 | 0.11 | 0.16 | 0.16 | −0.06 | 0.32 | 0.21 | 0.10 | −0.06 |
| 35 | GAG | 0.16 | 0.22 | 0.24 | 0.02 | −0.06 | −0.33 | −0.29 | −0.46 | −0.37 | −0.30 | −0.42 | −0.44 |
| 36 | GAT | −0.09 | 0.02 | 0.01 | 0.00 | −0.06 | 0.11 | −0.09 | −0.06 | −0.16 | −0.18 | −0.01 | 0.01 |
| 37 | GCA | 0.14 | 0.17 | −0.05 | 0.32 | 0.05 | 0.22 | −0.08 | 0.33 | 0.09 | 0.11 | 0.21 | 0.14 |
| 38 | GCC | −0.10 | −0.22 | −0.06 | −0.41 | −0.05 | −0.08 | 0.12 | −0.28 | 0.43 | 0.39 | 0.52 | 0.37 |
| 39 | GCG | −0.09 | −0.12 | −0.28 | −0.34 | −0.08 | 0.09 | 0.10 | 0.08 | −0.34 | −0.17 | −0.33 | −0.34 |
| 40 | GCT | 0.38 | 0.57 | 0.53 | 0.41 | −0.16 | −0.20 | 0.16 | −0.12 | 0.04 | −0.29 | 0.10 | −0.16 |
| 41 | GGA | 0.10 | 0.01 | −0.07 | 0.16 | −0.14 | 0.03 | −0.19 | 0.04 | 0.29 | 0.46 | 0.10 | 0.22 |
| 42 | GGC | 0.02 | −0.07 | −0.07 | −0.15 | 0.19 | 0.10 | 0.07 | 0.01 | 0.41 | 0.36 | 0.06 | 0.11 |
| 43 | GGG | −0.26 | 0.17 | −0.03 | −0.22 | −0.18 | −0.27 | −0.31 | −0.39 | −0.37 | −0.26 | −0.44 | −0.38 |
| 44 | GGT | 0.13 | 0.21 | 0.30 | 0.13 | 0.38 | 0.29 | 0.38 | 0.39 | 0.09 | −0.31 | −0.10 | −0.08 |
| 45 | GTA | 0.40 | 0.51 | 0.36 | 0.66 | 0.22 | 0.20 | −0.17 | 0.29 | 0.43 | 0.28 | 0.34 | 0.38 |
| 46 | GTC | −0.14 | −0.39 | −0.37 | −0.43 | 0.42 | 0.34 | 0.53 | 0.16 | 0.57 | 0.51 | 0.48 | 0.44 |
| 47 | GTG | 0.08 | −0.04 | −0.14 | −0.18 | 0.17 | 0.04 | −0.16 | 0.20 | −0.03 | −0.09 | −0.41 | −0.28 |
| 48 | GTT | 0.35 | 0.27 | 0.43 | 0.32 | −0.32 | −0.36 | −0.29 | −0.33 | −0.23 | −0.39 | −0.12 | −0.31 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | −0.39 | 0.10 | 0.07 | 0.17 | 0.32 | 0.29 | 0.39 | 0.21 | 0.39 | 0.41 | 0.19 | 0.31 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | −0.18 | −0.10 | −0.04 | 0.09 | −0.23 | −0.20 | −0.07 | −0.06 | −0.23 | −0.12 | −0.16 | 0.00 |
| 53 | TCA | 0.05 | 0.17 | 0.08 | 0.22 | 0.05 | 0.17 | 0.17 | 0.26 | −0.13 | 0.22 | 0.28 | −0.07 |
| 54 | TCC | −0.09 | −0.21 | −0.10 | −0.36 | 0.22 | −0.12 | 0.36 | 0.02 | 0.17 | 0.21 | 0.54 | 0.32 |
| 55 | TCG | −0.24 | −0.08 | 0.02 | −0.38 | 0.07 | 0.17 | 0.30 | −0.02 | −0.37 | −0.30 | −0.18 | −0.48 |
| 56 | TCT | 0.19 | 0.33 | 0.29 | 0.18 | −0.28 | −0.21 | 0.04 | −0.14 | −0.39 | −0.40 | 0.03 | −0.32 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.09 | −0.01 | −0.02 | 0.36 | −0.20 | −0.37 | −0.22 | −0.05 | 0.25 | 0.43 | −0.08 | 0.31 |

TABLE C.3-continued

CPW matrix *Bacillus subtilis* full genome (left codon indicated in column 2, right codon indicated in row 2). Host cell: *B. subtilis*; Sequence data: full *B. subtilis* genome.

| | | | | | | | | | | | | |
|---|---|---|---|---|---|---|---|---|---|---|---|---|
| 59 | TGG | −0.17 | 0.09 | 0.00 | −0.01 | 0.39 | −0.06 | −0.29 | 0.03 | 0.42 | 0.41 | −0.23 | 0.04 |
| 60 | TGT | −0.38 | −0.24 | 0.02 | −0.07 | 0.51 | 0.20 | 0.13 | 0.31 | −0.04 | −0.31 | −0.17 | −0.10 |
| 61 | TTA | −0.24 | −0.16 | −0.22 | 0.02 | 0.40 | 0.51 | 0.31 | 0.24 | 0.69 | 0.61 | 0.81 | 0.64 |
| 62 | TTC | 0.26 | 0.13 | 0.25 | 0.18 | −0.08 | −0.07 | 0.28 | −0.01 | −0.08 | −0.08 | −0.16 | −0.33 |
| 63 | TTG | −0.01 | −0.05 | −0.05 | −0.28 | 0.07 | 0.10 | −0.23 | 0.14 | −0.04 | 0.19 | −0.24 | −0.14 |
| 64 | TTT | −0.01 | −0.17 | −0.10 | −0.01 | −0.10 | 0.13 | 0.02 | −0.04 | −0.02 | −0.02 | 0.16 | 0.18 |

| | | ATA 13 | ATC 14 | ATG 15 | ATT 16 | CAA 17 | CAC 18 | CAG 19 | CAT 20 | CCA 21 | CCC 22 | CCG 23 | CCT 24 |
|---|---|---|---|---|---|---|---|---|---|---|---|---|---|
| | | 25 CGA | 26 CGC | 27 CGG | 28 CGT | 29 CTA | 30 CTC | 31 CTG | 32 CTT | 33 GAA | 34 GAC | 35 GAG | 36 GAT |
| 1 | AAA | −0.37 | 0.05 | −0.23 | 0.30 | 0.00 | 0.43 | 0.29 | 0.57 | −0.09 | −0.17 | 0.04 | 0.22 |
| 2 | AAC | −0.36 | −0.39 | −0.23 | −0.43 | −0.29 | 0.17 | −0.15 | −0.09 | 0.33 | 0.28 | 0.42 | 0.26 |
| 3 | AAG | −0.17 | 0.07 | −0.44 | −0.06 | −0.53 | −0.53 | −0.69 | −0.60 | 0.03 | −0.02 | 0.29 | −0.19 |
| 4 | AAT | 0.01 | 0.40 | 0.23 | 0.25 | −0.33 | −0.06 | 0.08 | 0.13 | −0.29 | −0.20 | 0.00 | −0.16 |
| 5 | ACA | 0.15 | 0.29 | 0.43 | 0.25 | 0.27 | 0.08 | 0.27 | 0.21 | −0.02 | −0.08 | −0.16 | 0.05 |
| 6 | ACC | −0.05 | −0.31 | −0.15 | −0.32 | 0.20 | 0.21 | 0.33 | 0.06 | 0.41 | 0.39 | 0.29 | 0.04 |
| 7 | ACG | 0.45 | 0.49 | 0.47 | 0.55 | −0.27 | −0.33 | −0.41 | −0.47 | 0.27 | 0.43 | 0.33 | 0.12 |
| 8 | ACT | 0.57 | 0.28 | 0.47 | −0.26 | −0.22 | 0.44 | 0.62 | 0.01 | −0.42 | −0.37 | −0.36 | −0.35 |
| 9 | AGA | −0.30 | 0.06 | −0.20 | 0.22 | 0.58 | 0.45 | 0.33 | 0.58 | −0.13 | −0.21 | −0.23 | 0.16 |
| 10 | AGC | −0.36 | −0.37 | −0.41 | −0.41 | 0.11 | 0.11 | −0.08 | 0.14 | 0.43 | 0.35 | 0.25 | 0.37 |
| 11 | AGG | −0.27 | −0.12 | −0.39 | 0.04 | −0.27 | −0.55 | −0.68 | −0.51 | 0.04 | 0.15 | −0.14 | −0.05 |
| 12 | AGT | 0.40 | 0.84 | 0.70 | 0.78 | −0.27 | 0.04 | 0.17 | 0.04 | −0.52 | −0.44 | −0.47 | −0.44 |
| 13 | ATA | −0.17 | 0.15 | 0.06 | 0.21 | −0.24 | 0.07 | 0.26 | 0.31 | −0.24 | −0.22 | −0.18 | −0.13 |
| 14 | ATC | 0.10 | −0.42 | 0.14 | −0.26 | 0.15 | 0.29 | 0.37 | 0.25 | 0.28 | 0.31 | 0.39 | 0.39 |
| 15 | ATG | 0.45 | 0.26 | 0.15 | 0.21 | 0.14 | −0.22 | −0.43 | −0.18 | 0.10 | −0.05 | −0.18 | 0.03 |
| 16 | ATT | 0.14 | 0.08 | 0.38 | 0.14 | −0.06 | −0.12 | 0.34 | 0.15 | −0.19 | −0.10 | 0.00 | −0.21 |
| 17 | CAA | 0.49 | 0.73 | 0.68 | 0.78 | 0.43 | 0.81 | 0.82 | 0.85 | 0.14 | 0.02 | −0.11 | 0.19 |
| 18 | CAC | −0.19 | −0.53 | −0.27 | −0.46 | 0.10 | 0.21 | 0.31 | 0.11 | 0.27 | 0.36 | 0.14 | 0.12 |
| 19 | CAG | −0.39 | −0.43 | −0.52 | −0.45 | −0.36 | −0.50 | −0.58 | −0.58 | −0.03 | 0.04 | −0.10 | −0.19 |
| 20 | CAT | 0.10 | 0.25 | 0.13 | 0.13 | 0.03 | 0.10 | 0.26 | 0.26 | −0.06 | −0.14 | −0.17 | −0.06 |
| 21 | CCA | 0.60 | 0.67 | 0.73 | 0.60 | 0.53 | 0.69 | 0.77 | 0.72 | 0.25 | 0.07 | −0.02 | 0.25 |
| 22 | CCC | −0.48 | −0.62 | −0.11 | −0.57 | 0.21 | 0.19 | 0.61 | 0.40 | 0.25 | 0.08 | −0.17 | −0.17 |
| 23 | CCG | −0.12 | −0.22 | −0.15 | −0.22 | −0.26 | −0.55 | −0.33 | −0.52 | 0.21 | 0.36 | 0.28 | 0.31 |
| 24 | CCT | 0.45 | 0.38 | 0.63 | 0.04 | 0.15 | 0.29 | 0.65 | 0.24 | −0.33 | −0.32 | −0.34 | −0.40 |
| 25 | CGA | 0.53 | 0.65 | 0.68 | 0.70 | 0.51 | 0.64 | 0.59 | 0.66 | 0.36 | 0.28 | 0.05 | 0.30 |
| 26 | CGC | 0.09 | −0.51 | −0.23 | −0.51 | 0.10 | 0.09 | −0.06 | 0.14 | 0.58 | 0.29 | 0.24 | 0.35 |
| 27 | CGG | −0.01 | 0.36 | 0.16 | 0.21 | 0.12 | −0.37 | −0.51 | −0.41 | −0.04 | −0.04 | −0.14 | −0.06 |
| 28 | CGT | 0.85 | 0.76 | 0.85 | 0.48 | −0.03 | −0.30 | −0.05 | −0.11 | −0.27 | −0.34 | −0.17 | −0.33 |
| 29 | CTA | 0.85 | 0.82 | 0.76 | 0.72 | 0.15 | 0.72 | 0.78 | 0.70 | 0.19 | 0.24 | −0.11 | 0.16 |
| 30 | CTC | 0.08 | −0.32 | 0.07 | −0.30 | 0.42 | 0.28 | 0.49 | 0.38 | 0.35 | 0.10 | 0.49 | −0.06 |
| 31 | CTG | 0.10 | −0.12 | −0.18 | −0.13 | 0.09 | −0.32 | −0.44 | −0.31 | 0.30 | 0.39 | 0.05 | 0.27 |
| 32 | CTT | 0.10 | −0.31 | 0.02 | −0.21 | 0.06 | −0.14 | 0.34 | 0.11 | −0.35 | −0.09 | −0.38 | −0.44 |
| 33 | GAA | −0.23 | 0.20 | −0.11 | 0.33 | 0.29 | 0.48 | 0.27 | 0.58 | −0.02 | −0.07 | −0.13 | 0.16 |
| 34 | GAC | −0.38 | −0.54 | −0.45 | −0.51 | 0.27 | 0.28 | 0.32 | 0.25 | 0.36 | 0.39 | 0.25 | 0.25 |
| 35 | GAG | −0.13 | −0.21 | −0.49 | −0.34 | −0.39 | −0.35 | −0.60 | −0.63 | 0.10 | 0.08 | 0.17 | −0.23 |
| 36 | GAT | 0.16 | 0.49 | 0.33 | 0.39 | 0.04 | 0.06 | 0.17 | 0.10 | −0.18 | −0.18 | −0.09 | −0.13 |
| 37 | GCA | 0.17 | 0.19 | 0.36 | 0.26 | 0.16 | 0.15 | 0.24 | 0.24 | 0.00 | −0.05 | −0.02 | 0.14 |
| 38 | GCC | −0.01 | −0.46 | −0.18 | −0.38 | 0.40 | 0.31 | 0.47 | 0.27 | 0.43 | 0.37 | 0.18 | 0.20 |
| 39 | GCG | 0.10 | 0.21 | 0.10 | −0.01 | −0.11 | −0.39 | −0.37 | −0.48 | 0.13 | 0.24 | 0.14 | 0.21 |
| 40 | GCT | 0.68 | 0.64 | 0.73 | 0.22 | 0.03 | 0.15 | 0.53 | 0.03 | −0.31 | −0.36 | −0.29 | −0.35 |
| 41 | GGA | −0.11 | −0.05 | 0.06 | 0.03 | 0.25 | 0.30 | 0.27 | 0.27 | −0.14 | −0.28 | −0.04 | 0.06 |
| 42 | GGC | 0.00 | −0.08 | −0.16 | −0.31 | 0.33 | 0.46 | 0.32 | 0.14 | 0.41 | 0.30 | 0.18 | 0.27 |
| 43 | GGG | −0.09 | −0.13 | −0.16 | 0.02 | −0.17 | −0.36 | −0.53 | −0.56 | 0.05 | 0.21 | 0.27 | 0.12 |
| 44 | GGT | 0.71 | 0.79 | 0.79 | 0.67 | 0.14 | 0.02 | 0.34 | −0.20 | −0.37 | −0.38 | −0.28 | −0.28 |
| 45 | GTA | 0.32 | 0.32 | 0.30 | 0.37 | 0.14 | 0.22 | 0.30 | 0.51 | −0.06 | −0.12 | −0.18 | 0.12 |
| 46 | GTC | 0.20 | −0.32 | 0.18 | −0.18 | 0.47 | 0.45 | 0.50 | 0.50 | 0.49 | 0.46 | 0.37 | 0.18 |
| 47 | GTG | 0.18 | 0.12 | −0.07 | 0.00 | −0.10 | −0.37 | −0.55 | −0.42 | 0.18 | 0.27 | 0.14 | 0.25 |
| 48 | GTT | 0.21 | 0.01 | 0.16 | −0.02 | −0.05 | −0.21 | 0.18 | 0.04 | −0.35 | −0.31 | −0.27 | −0.35 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | −0.33 | −0.42 | −0.39 | −0.40 | 0.05 | 0.34 | 0.42 | 0.36 | 0.29 | 0.29 | 0.19 | 0.16 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | −0.11 | 0.32 | 0.08 | 0.29 | −0.12 | 0.11 | 0.39 | 0.36 | −0.18 | −0.16 | 0.04 | −0.06 |
| 53 | TCA | 0.24 | 0.28 | 0.26 | 0.39 | −0.14 | 0.08 | 0.34 | 0.16 | 0.03 | −0.07 | −0.14 | 0.07 |
| 54 | TCC | −0.07 | −0.45 | −0.11 | −0.41 | 0.12 | 0.27 | 0.51 | 0.17 | 0.55 | 0.46 | 0.34 | 0.30 |
| 55 | TCG | 0.39 | 0.37 | 0.23 | 0.10 | −0.36 | −0.38 | −0.31 | −0.47 | 0.26 | 0.33 | 0.21 | 0.18 |
| 56 | TCT | 0.40 | 0.60 | 0.65 | 0.35 | −0.19 | −0.16 | 0.41 | −0.12 | −0.25 | −0.20 | −0.15 | −0.30 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | −0.49 | −0.53 | −0.45 | −0.47 | 0.13 | 0.27 | −0.02 | 0.35 | 0.50 | 0.43 | 0.14 | 0.39 |
| 59 | TGG | 0.22 | 0.10 | −0.08 | 0.36 | −0.04 | −0.28 | −0.41 | −0.17 | 0.08 | 0.16 | −0.14 | −0.08 |
| 60 | TGT | 0.84 | 0.83 | 0.64 | 0.77 | −0.31 | −0.21 | 0.00 | 0.03 | −0.29 | −0.36 | −0.37 | −0.31 |

TABLE C.3-continued

CPW matrix *Bacillus subtilis* full genome (left codon indicated in column 2, right codon indicated in row 2). Host cell: *B. subtilis*; Sequence data: full *B. subtilis* genome.

| | | | | | | | | | | | | |
|---|---|---|---|---|---|---|---|---|---|---|---|---|
| 61 | TTA | 0.49 | 0.64 | 0.43 | 0.65 | 0.15 | 0.55 | 0.58 | 0.66 | 0.03 | 0.10 | −0.10 | 0.07 |
| 62 | TTC | −0.33 | −0.50 | −0.26 | −0.53 | −0.01 | 0.24 | 0.32 | 0.28 | 0.44 | 0.48 | 0.53 | 0.44 |
| 63 | TTG | −0.23 | −0.25 | −0.26 | −0.25 | −0.22 | −0.32 | −0.47 | −0.35 | 0.27 | 0.23 | 0.11 | 0.15 |
| 64 | TTT | 0.43 | 0.42 | 0.38 | 0.43 | −0.08 | −0.06 | 0.37 | 0.39 | −0.22 | −0.18 | −0.07 | −0.17 |

| | CGA | CGC | CGG | CGT | CTA | CTC | CTG | CTT | GAA | GAC | GAG | GAT |
|---|---|---|---|---|---|---|---|---|---|---|---|---|
| | 25 | 26 | 27 | 28 | 29 | 30 | 31 | 32 | 33 | 34 | 35 | 36 |

| | | 37 | 38 | 39 | 40 | 41 | 42 | 43 | 44 | 45 | 46 | 47 | 48 |
|---|---|---|---|---|---|---|---|---|---|---|---|---|---|
| | | GCA | GCC | GCG | GCT | GGA | GGC | GGG | GGT | GTA | GTC | GTG | GTT |
| 1 | AAA | −0.18 | 0.02 | −0.30 | 0.25 | −0.07 | −0.17 | −0.30 | 0.17 | −0.19 | 0.17 | −0.21 | 0.47 |
| 2 | AAC | 0.15 | 0.03 | 0.20 | 0.26 | −0.30 | −0.31 | −0.21 | −0.24 | 0.09 | 0.19 | 0.30 | 0.33 |
| 3 | AAG | 0.26 | 0.49 | 0.08 | 0.24 | 0.21 | 0.37 | 0.25 | 0.42 | −0.13 | 0.09 | −0.27 | −0.12 |
| 4 | AAT | −0.06 | −0.26 | −0.17 | 0.07 | 0.22 | 0.37 | 0.30 | 0.32 | −0.25 | −0.21 | −0.23 | 0.09 |
| 5 | ACA | 0.06 | 0.06 | 0.07 | −0.10 | 0.02 | −0.11 | −0.16 | −0.11 | 0.22 | 0.23 | 0.26 | 0.28 |
| 6 | ACC | 0.12 | 0.20 | 0.37 | −0.20 | −0.31 | −0.30 | −0.27 | −0.33 | −0.12 | −0.03 | 0.19 | −0.34 |
| 7 | ACG | −0.03 | 0.40 | 0.25 | −0.12 | 0.17 | 0.55 | 0.39 | 0.30 | 0.14 | 0.17 | 0.23 | −0.20 |
| 8 | ACT | −0.28 | −0.23 | 0.01 | −0.40 | 0.04 | 0.16 | 0.28 | −0.19 | −0.40 | −0.36 | −0.15 | −0.51 |
| 9 | AGA | −0.07 | −0.01 | −0.33 | 0.28 | −0.26 | −0.15 | −0.38 | 0.19 | 0.21 | 0.19 | −0.15 | 0.49 |
| 10 | AGC | 0.36 | 0.20 | 0.35 | 0.43 | −0.38 | −0.29 | −0.33 | −0.28 | 0.30 | 0.43 | 0.30 | 0.49 |
| 11 | AGG | −0.03 | 0.24 | −0.22 | 0.20 | −0.34 | 0.06 | 0.36 | 0.54 | 0.05 | 0.34 | −0.29 | 0.07 |
| 12 | AGT | −0.10 | −0.09 | −0.21 | −0.06 | 0.59 | 0.82 | 0.80 | 0.56 | −0.37 | −0.28 | −0.44 | −0.28 |
| 13 | ATA | 0.24 | 0.20 | 0.13 | 0.22 | 0.28 | 0.23 | 0.10 | 0.13 | 0.53 | 0.65 | 0.68 | 0.70 |
| 14 | ATC | 0.06 | −0.22 | 0.24 | 0.05 | −0.30 | −0.48 | −0.39 | −0.47 | −0.09 | −0.11 | 0.16 | −0.09 |
| 15 | ATG | 0.08 | 0.28 | −0.18 | −0.08 | 0.07 | 0.14 | −0.32 | 0.05 | 0.13 | 0.12 | −0.18 | 0.01 |
| 16 | ATT | 0.00 | −0.30 | 0.01 | 0.05 | 0.51 | 0.45 | 0.51 | 0.41 | −0.10 | −0.22 | −0.11 | −0.01 |
| 17 | CAA | 0.11 | 0.01 | 0.02 | 0.16 | −0.15 | −0.19 | −0.34 | −0.17 | −0.11 | −0.04 | −0.24 | 0.28 |
| 18 | CAC | 0.18 | −0.29 | 0.15 | −0.13 | −0.32 | −0.49 | −0.37 | −0.38 | 0.13 | 0.08 | 0.23 | 0.06 |
| 19 | CAG | −0.13 | 0.24 | −0.17 | −0.12 | 0.11 | 0.42 | 0.00 | 0.47 | 0.25 | 0.17 | −0.18 | −0.02 |
| 20 | CAT | 0.06 | −0.13 | −0.04 | 0.15 | 0.37 | 0.31 | 0.32 | 0.33 | −0.11 | −0.11 | −0.20 | 0.21 |
| 21 | CCA | 0.36 | 0.20 | 0.47 | −0.04 | 0.31 | 0.12 | −0.01 | −0.25 | 0.35 | 0.16 | 0.39 | 0.17 |
| 22 | CCC | −0.23 | −0.27 | 0.10 | −0.58 | −0.56 | −0.63 | −0.31 | −0.57 | −0.01 | −0.22 | 0.16 | −0.31 |
| 23 | CCG | −0.06 | 0.36 | 0.26 | −0.14 | −0.07 | 0.21 | 0.24 | 0.04 | 0.35 | 0.37 | 0.36 | −0.11 |
| 24 | CCT | −0.08 | −0.11 | −0.02 | −0.28 | 0.25 | 0.33 | 0.43 | −0.20 | −0.25 | −0.37 | 0.04 | −0.47 |
| 25 | CGA | 0.47 | 0.57 | 0.20 | 0.22 | 0.22 | 0.12 | 0.05 | 0.31 | 0.47 | 0.12 | −0.22 | 0.42 |
| 26 | CGC | 0.26 | 0.04 | 0.10 | 0.17 | −0.41 | −0.45 | −0.22 | −0.37 | 0.31 | −0.03 | 0.20 | 0.29 |
| 27 | CGG | −0.22 | 0.18 | −0.27 | 0.05 | 0.03 | 0.38 | 0.32 | 0.60 | −0.05 | 0.19 | −0.29 | 0.13 |
| 28 | CGT | −0.02 | −0.24 | −0.21 | 0.00 | 0.69 | 0.77 | 0.71 | 0.68 | −0.39 | −0.41 | −0.39 | −0.21 |
| 29 | CTA | 0.42 | 0.14 | 0.36 | 0.13 | 0.30 | −0.09 | −0.08 | −0.17 | 0.11 | −0.09 | 0.20 | 0.15 |
| 30 | CTC | 0.09 | −0.22 | 0.24 | −0.13 | −0.42 | −0.64 | −0.48 | −0.65 | −0.10 | −0.49 | −0.13 | −0.47 |
| 31 | CTG | 0.06 | 0.20 | 0.03 | 0.01 | 0.52 | 0.47 | 0.34 | 0.54 | 0.63 | 0.47 | 0.45 | 0.46 |
| 32 | CTT | −0.14 | −0.40 | −0.08 | −0.29 | −0.03 | −0.25 | 0.05 | −0.19 | −0.26 | −0.49 | −0.34 | −0.35 |
| 33 | GAA | −0.10 | −0.01 | −0.32 | 0.15 | −0.09 | −0.21 | −0.22 | 0.14 | −0.08 | 0.08 | −0.29 | 0.32 |
| 34 | GAC | 0.18 | 0.05 | 0.17 | 0.13 | −0.43 | −0.48 | −0.40 | −0.42 | 0.27 | 0.34 | 0.32 | 0.26 |
| 35 | GAG | 0.19 | 0.52 | 0.14 | 0.26 | 0.28 | 0.31 | 0.18 | 0.44 | 0.09 | 0.26 | −0.05 | −0.16 |
| 36 | GAT | −0.04 | −0.19 | −0.08 | 0.03 | 0.39 | 0.50 | 0.50 | 0.42 | −0.23 | −0.07 | −0.23 | −0.05 |
| 37 | GCA | 0.00 | −0.09 | 0.19 | 0.01 | 0.06 | −0.04 | −0.06 | −0.16 | 0.26 | 0.20 | 0.26 | 0.23 |
| 38 | GCC | 0.07 | 0.17 | 0.32 | −0.19 | −0.41 | −0.33 | −0.24 | −0.49 | 0.16 | 0.09 | 0.37 | −0.10 |
| 39 | GCG | −0.19 | 0.32 | 0.11 | −0.11 | −0.01 | 0.30 | 0.06 | 0.13 | 0.17 | 0.27 | 0.21 | −0.12 |
| 40 | GCT | −0.07 | −0.17 | 0.10 | −0.23 | 0.37 | 0.53 | 0.52 | 0.24 | −0.36 | −0.34 | −0.03 | −0.46 |
| 41 | GGA | 0.05 | 0.13 | −0.21 | 0.19 | 0.17 | 0.25 | 0.24 | 0.56 | 0.38 | 0.49 | 0.41 | 0.50 |
| 42 | GGC | 0.10 | 0.03 | 0.19 | −0.02 | −0.54 | −0.40 | −0.38 | −0.46 | −0.04 | 0.03 | 0.08 | −0.13 |
| 43 | GGG | −0.11 | 0.47 | −0.03 | 0.09 | 0.17 | 0.52 | 0.59 | 0.79 | 0.23 | 0.44 | 0.38 | 0.06 |
| 44 | GGT | −0.22 | −0.10 | −0.25 | −0.19 | 0.62 | 0.80 | 0.70 | 0.60 | −0.51 | −0.48 | −0.45 | −0.51 |
| 45 | GTA | 0.07 | −0.08 | 0.02 | 0.07 | 0.21 | 0.25 | −0.12 | −0.02 | 0.43 | 0.48 | 0.49 | 0.58 |
| 46 | GTC | 0.17 | 0.07 | 0.46 | 0.04 | −0.42 | −0.58 | −0.45 | −0.61 | −0.01 | −0.16 | −0.05 | −0.20 |
| 47 | GTG | −0.12 | 0.28 | −0.10 | 0.06 | 0.63 | 0.68 | 0.49 | 0.72 | 0.56 | 0.48 | 0.31 | 0.42 |
| 48 | GTT | 0.01 | −0.34 | −0.11 | −0.20 | 0.30 | 0.47 | 0.40 | 0.12 | −0.31 | −0.50 | −0.32 | −0.35 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.10 | 0.11 | 0.02 | 0.00 | −0.45 | −0.45 | −0.43 | −0.34 | 0.25 | 0.39 | 0.23 | 0.44 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | −0.03 | −0.13 | −0.11 | 0.18 | 0.33 | 0.39 | 0.47 | 0.45 | −0.30 | −0.17 | −0.24 | 0.13 |
| 53 | TCA | −0.10 | −0.14 | −0.03 | −0.20 | −0.07 | −0.13 | 0.00 | −0.21 | 0.22 | 0.21 | 0.34 | 0.14 |
| 54 | TCC | 0.06 | −0.14 | 0.44 | −0.31 | −0.14 | −0.35 | −0.12 | −0.44 | 0.26 | −0.02 | 0.54 | −0.25 |
| 55 | TCG | −0.18 | 0.25 | 0.16 | −0.13 | 0.11 | 0.38 | 0.17 | 0.09 | 0.19 | 0.21 | 0.21 | −0.20 |
| 56 | TCT | −0.11 | −0.16 | 0.13 | −0.31 | 0.44 | 0.58 | 0.56 | 0.23 | −0.31 | −0.40 | 0.09 | −0.49 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.23 | −0.01 | 0.00 | 0.36 | −0.49 | −0.38 | −0.35 | −0.17 | 0.33 | 0.39 | 0.37 | 0.58 |
| 59 | TGG | −0.06 | 0.29 | −0.19 | 0.08 | −0.23 | 0.09 | 0.00 | 0.32 | 0.06 | 0.33 | −0.30 | 0.05 |
| 60 | TGT | −0.29 | −0.05 | −0.23 | 0.08 | 0.69 | 0.89 | 0.80 | 0.63 | −0.46 | −0.44 | −0.36 | −0.02 |

TABLE C.3-continued

CPW matrix *Bacillus subtilis* full genome (left codon indicated in column 2, right codon indicated in row 2). Host cell: *B. subtilis*; Sequence data: full *B. subtilis* genome.

|    |     |       |       |       |       |       |       |       |       |       |       |       |       |
|----|-----|-------|-------|-------|-------|-------|-------|-------|-------|-------|-------|-------|-------|
| 61 | TTA |  0.25 |  0.21 |  0.26 |  0.27 |  0.10 |  0.12 | -0.17 | -0.07 |  0.29 |  0.34 |  0.25 |  0.32 |
| 62 | TTC |  0.20 | -0.05 |  0.45 |  0.16 | -0.33 | -0.44 | -0.33 | -0.40 |  0.33 |  0.25 |  0.56 |  0.08 |
| 63 | TTG | -0.15 |  0.31 | -0.03 | -0.13 |  0.39 |  0.48 |  0.34 |  0.57 |  0.48 |  0.33 |  0.05 | -0.06 |
| 64 | TTT |  0.01 | -0.28 | -0.09 |  0.04 |  0.35 |  0.19 |  0.37 |  0.33 |  0.07 | -0.31 | -0.06 | -0.07 |

|      | GCA | GCC | GCG | GCT | GGA | GGC | GGG | GGT | GTA | GTC | GTG | GTT |
|------|-----|-----|-----|-----|-----|-----|-----|-----|-----|-----|-----|-----|
|      | 37  | 38  | 39  | 40  | 41  | 42  | 43  | 44  | 45  | 46  | 47  | 48  |

|    |     | 49    | 50    | 51    | 52    | 53    | 54    | 55    | 56    | 57    | 58    | 59    | 60    |
|----|-----|-------|-------|-------|-------|-------|-------|-------|-------|-------|-------|-------|-------|
|    |     | TAA   | TAC   | TAG   | TAT   | TCA   | TCC   | TCG   | TCT   | TGA   | TGC   | TGG   | TGT   |
|  1 | AAA | 0.00  | -0.18 | 0.00  |  0.06 | -0.19 |  0.23 | -0.21 |  0.40 | 0.00  | -0.09 | -0.03 |  0.08 |
|  2 | AAC | 0.00  | -0.08 | 0.00  | -0.09 |  0.23 |  0.09 |  0.31 |  0.27 | 0.00  | -0.29 | -0.25 | -0.25 |
|  3 | AAG | 0.00  |  0.11 | 0.00  |  0.08 |  0.34 |  0.39 |  0.18 |  0.27 | 0.00  |  0.17 |  0.07 | -0.10 |
|  4 | AAT | 0.00  |  0.01 | 0.00  |  0.11 |  0.06 |  0.27 |  0.09 |  0.28 | 0.00  |  0.30 |  0.26 |  0.30 |
|  5 | ACA | 0.00  |  0.00 | 0.00  |  0.12 | -0.12 | -0.03 | -0.01 |  0.06 | 0.00  |  0.05 |  0.00 |  0.00 |
|  6 | ACC | 0.00  |  0.11 | 0.00  | -0.17 |  0.30 | -0.09 | -0.20 | -0.13 | 0.00  | -0.14 |  0.42 | -0.01 |
|  7 | ACG | 0.00  | -0.03 | 0.00  | -0.07 |  0.21 |  0.24 |  0.39 |  0.18 | 0.00  |  0.05 |  0.10 |  0.53 |
|  8 | ACT | 0.00  | -0.12 | 0.00  |  0.07 | -0.32 | -0.15 |  0.02 | -0.38 | 0.00  | -0.04 | -0.37 | -0.48 |
|  9 | AGA | 0.00  |  0.18 | 0.00  |  0.38 |  0.36 |  0.45 |  0.03 |  0.50 | 0.00  |  0.14 | -0.16 |  0.44 |
| 10 | AGC | 0.00  | -0.13 | 0.00  | -0.18 |  0.23 |  0.24 | -0.02 |  0.18 | 0.00  | -0.31 | -0.39 | -0.29 |
| 11 | AGG | 0.00  |  0.23 | 0.00  |  0.26 |  0.25 |  0.35 | -0.17 |  0.42 | 0.00  |  0.19 |  0.10 |  0.30 |
| 12 | AGT | 0.00  |  0.44 | 0.00  |  0.16 | -0.22 |  0.21 | -0.05 |  0.14 | 0.00  |  0.82 |  0.48 |  0.41 |
| 13 | ATA | 0.00  | -0.24 | 0.00  | -0.03 | -0.12 | -0.23 | -0.38 | -0.06 | 0.00  | -0.30 | -0.45 | -0.21 |
| 14 | ATC | 0.00  |  0.38 | 0.00  |  0.25 |  0.35 |  0.33 |  0.45 |  0.40 | 0.00  |  0.22 |  0.28 |  0.20 |
| 15 | ATG | 0.00  | -0.19 | 0.00  |  0.12 |  0.14 |  0.08 | -0.07 |  0.05 | 0.00  | -0.09 |  0.00 |  0.12 |
| 16 | ATT | 0.00  | -0.15 | 0.00  | -0.16 | -0.16 | -0.25 |  0.00 | -0.32 | 0.00  | -0.03 | -0.01 | -0.09 |
| 17 | CAA | 0.00  | -0.27 | 0.00  | -0.21 | -0.18 | -0.28 | -0.39 | -0.04 | 0.00  | -0.35 | -0.19 | -0.21 |
| 18 | CAC | 0.00  |  0.28 | 0.00  |  0.09 |  0.24 | -0.07 |  0.13 |  0.10 | 0.00  | -0.21 | -0.07 |  0.07 |
| 19 | CAG | 0.00  |  0.40 | 0.00  |  0.27 |  0.25 |  0.13 |  0.21 |  0.24 | 0.00  |  0.39 |  0.24 |  0.47 |
| 20 | CAT | 0.00  | -0.08 | 0.00  | -0.07 | -0.08 | -0.27 | -0.02 | -0.06 | 0.00  |  0.17 |  0.04 | -0.08 |
| 21 | CCA | 0.00  | -0.30 | 0.00  | -0.18 | -0.28 | -0.17 | -0.06 | -0.39 | 0.00  | -0.36 | -0.38 | -0.16 |
| 22 | CCC | 0.00  |  0.42 | 0.00  |  0.00 |  0.13 | -0.16 |  0.28 |  0.23 | 0.00  | -0.13 |  0.71 |  0.22 |
| 23 | CCG | 0.00  |  0.32 | 0.00  |  0.33 |  0.21 |  0.30 |  0.44 |  0.07 | 0.00  |  0.37 |  0.29 |  0.43 |
| 24 | CCT | 0.00  | -0.15 | 0.00  | -0.30 | -0.21 | -0.40 | -0.24 | -0.35 | 0.00  | -0.19 | -0.20 | -0.33 |
| 25 | CGA | 0.00  | -0.16 | 0.00  | -0.20 |  0.25 |  0.03 | -0.01 |  0.25 | 0.00  | -0.05 |  0.15 | -0.01 |
| 26 | CGC | 0.00  | -0.25 | 0.00  | -0.27 | -0.06 | -0.28 |  0.04 |  0.00 | 0.00  | -0.54 | -0.47 | -0.56 |
| 27 | CGG | 0.00  |  0.34 | 0.00  |  0.24 |  0.24 |  0.51 | -0.06 |  0.43 | 0.00  |  0.56 |  0.59 |  0.42 |
| 28 | CGT | 0.00  | -0.14 | 0.00  | -0.25 | -0.42 | -0.42 | -0.50 | -0.45 | 0.00  |  0.59 |  0.63 |  0.35 |
| 29 | CTA | 0.00  | -0.37 | 0.00  | -0.37 | -0.28 | -0.37 | -0.47 | -0.20 | 0.00  | -0.50 | -0.53 | -0.51 |
| 30 | CTC | 0.00  |  0.26 | 0.00  |  0.17 |  0.22 |  0.28 |  0.34 |  0.21 | 0.00  |  0.28 |  0.28 | -0.16 |
| 31 | CTG | 0.00  |  0.11 | 0.00  |  0.11 |  0.06 | -0.05 | -0.01 | -0.02 | 0.00  |  0.29 |  0.18 |  0.60 |
| 32 | CTT | 0.00  | -0.06 | 0.00  | -0.13 | -0.09 | -0.29 | -0.07 | -0.44 | 0.00  | -0.15 |  0.11 | -0.11 |
| 33 | GAA | 0.00  | -0.16 | 0.00  |  0.05 | -0.07 |  0.08 | -0.22 |  0.28 | 0.00  | -0.15 |  0.00 | -0.03 |
| 34 | GAC | 0.00  |  0.28 | 0.00  |  0.18 |  0.50 |  0.34 |  0.36 |  0.38 | 0.00  | -0.24 | -0.21 | -0.11 |
| 35 | GAG | 0.00  |  0.13 | 0.00  |  0.05 |  0.28 |  0.50 |  0.15 |  0.29 | 0.00  |  0.18 |  0.00 |  0.29 |
| 36 | GAT | 0.00  | -0.08 | 0.00  | -0.12 | -0.12 | -0.15 | -0.11 |  0.01 | 0.00  |  0.20 |  0.15 |  0.05 |
| 37 | GCA | 0.00  | -0.04 | 0.00  |  0.15 |  0.00 | -0.23 | -0.08 | -0.01 | 0.00  |  0.01 | -0.11 |  0.00 |
| 38 | GCC | 0.00  |  0.08 | 0.00  | -0.08 |  0.31 |  0.16 |  0.33 |  0.07 | 0.00  | -0.39 |  0.11 | -0.29 |
| 39 | GCG | 0.00  |  0.29 | 0.00  |  0.26 |  0.39 |  0.41 |  0.53 |  0.29 | 0.00  |  0.40 |  0.35 |  0.34 |
| 40 | GCT | 0.00  | -0.25 | 0.00  | -0.27 | -0.41 | -0.45 | -0.25 | -0.48 | 0.00  |  0.18 | -0.24 | -0.10 |
| 41 | GGA | 0.00  |  0.10 | 0.00  |  0.10 | -0.05 |  0.79 |  0.07 |  0.42 | 0.00  |  0.13 |  0.27 |  0.31 |
| 42 | GGC | 0.00  | -0.20 | 0.00  | -0.17 |  0.22 |  0.11 |  0.18 |  0.17 | 0.00  | -0.39 | -0.46 | -0.47 |
| 43 | GGG | 0.00  |  0.29 | 0.00  |  0.24 |  0.42 |  0.60 |  0.39 |  0.41 | 0.00  |  0.28 |  0.46 |  0.47 |
| 44 | GGT | 0.00  |  0.25 | 0.00  | -0.10 | -0.51 | -0.11 | -0.39 | -0.41 | 0.00  |  0.76 |  0.70 |  0.63 |
| 45 | GTA | 0.00  | -0.35 | 0.00  | -0.08 | -0.29 | -0.32 | -0.39 | -0.27 | 0.00  |  0.01 | -0.36 | -0.33 |
| 46 | GTC | 0.00  |  0.48 | 0.00  |  0.21 |  0.41 |  0.36 |  0.44 |  0.44 | 0.00  | -0.04 |  0.29 |  0.04 |
| 47 | GTG | 0.00  | -0.10 | 0.00  | -0.02 |  0.23 |  0.26 |  0.23 |  0.21 | 0.00  |  0.36 |  0.11 |  0.42 |
| 48 | GTT | 0.00  |  0.07 | 0.00  | -0.12 | -0.14 | -0.40 | -0.01 | -0.37 | 0.00  | -0.12 |  0.03 | -0.21 |
| 49 | TAA | 0.00  |  0.00 | 0.00  |  0.00 |  0.00 |  0.00 |  0.00 |  0.00 | 0.00  |  0.00 |  0.00 |  0.00 |
| 50 | TAC | 0.00  |  0.00 | 0.00  |  0.05 |  0.29 |  0.08 |  0.05 |  0.18 | 0.00  | -0.10 | -0.05 | -0.20 |
| 51 | TAG | 0.00  |  0.00 | 0.00  |  0.00 |  0.00 |  0.00 |  0.00 |  0.00 | 0.00  |  0.00 |  0.00 |  0.00 |
| 52 | TAT | 0.00  | -0.02 | 0.00  | -0.02 | -0.09 | -0.14 | -0.01 |  0.09 | 0.00  |  0.07 |  0.03 |  0.11 |
| 53 | TCA | 0.00  |  0.18 | 0.00  |  0.30 |  0.08 | -0.09 |  0.13 | -0.10 | 0.00  |  0.26 |  0.10 |  0.32 |
| 54 | TCC | 0.00  | -0.10 | 0.00  | -0.29 | -0.01 | -0.13 |  0.14 | -0.17 | 0.00  | -0.40 |  0.20 | -0.32 |
| 55 | TCG | 0.00  |  0.24 | 0.00  |  0.16 |  0.29 |  0.30 |  0.51 |  0.14 | 0.00  |  0.38 |  0.25 |  0.55 |
| 56 | TCT | 0.00  | -0.08 | 0.00  | -0.11 | -0.30 | -0.27 | -0.12 | -0.40 | 0.00  |  0.12 |  0.10 | -0.17 |
| 57 | TGA | 0.00  |  0.00 | 0.00  |  0.00 |  0.00 |  0.00 |  0.00 |  0.00 | 0.00  |  0.00 |  0.00 |  0.00 |
| 58 | TGC | 0.00  | -0.08 | 0.00  | -0.05 |  0.09 |  0.19 | -0.28 |  0.25 | 0.00  | -0.31 | -0.32 | -0.41 |
| 59 | TGG | 0.00  | -0.10 | 0.00  |  0.06 |  0.15 |  0.32 | -0.03 | -0.01 | 0.00  |  0.06 |  0.00 | -0.07 |
| 60 | TGT | 0.00  |  0.27 | 0.00  | -0.03 | -0.30 | -0.17 | -0.30 |  0.07 | 0.00  |  0.86 |  0.56 |  0.45 |

TABLE C.3-continued

CPW matrix *Bacillus subtilis* full genome (left codon indicated in column 2, right codon indicated in row 2). Host cell: *B. subtilis*; Sequence data: full *B. subtilis* genome.

| | | TAA | TAC | TAG | TAT | TCA | TCC | TCG | TCT | TGA | TGC | TGG | TGT |
|---|---|---|---|---|---|---|---|---|---|---|---|---|---|
| | | 49 | 50 | 51 | 52 | 53 | 54 | 55 | 56 | 57 | 58 | 59 | 60 |
| 61 | TTA | 0.00 | 0.03 | 0.00 | −0.15 | −0.20 | −0.20 | −0.21 | −0.05 | 0.00 | −0.34 | −0.29 | −0.10 |
| 62 | TTC | 0.00 | 0.13 | 0.00 | 0.21 | 0.01 | −0.05 | 0.04 | −0.07 | 0.00 | −0.09 | −0.09 | −0.19 |
| 63 | TTG | 0.00 | 0.22 | 0.00 | 0.17 | 0.17 | 0.12 | 0.27 | −0.01 | 0.00 | 0.07 | 0.22 | 0.49 |
| 64 | TTT | 0.00 | −0.06 | 0.00 | −0.09 | −0.11 | −0.10 | −0.05 | −0.17 | 0.00 | 0.14 | 0.05 | −0.01 |

| | | 61 TTA | 62 TTC | 63 TTG | 64 TTT |
|---|---|---|---|---|---|
| 1 | AAA | 0.34 | −0.27 | 0.31 | 0.26 |
| 2 | AAC | 0.22 | −0.27 | 0.24 | −0.06 |
| 3 | AAG | 0.63 | −0.10 | 0.72 | −0.12 |
| 4 | AAT | −0.09 | −0.13 | −0.07 | 0.25 |
| 5 | ACA | 0.06 | 0.00 | −0.22 | 0.16 |
| 6 | ACC | 0.12 | −0.15 | −0.08 | −0.30 |
| 7 | ACG | 0.15 | 0.07 | 0.58 | −0.10 |
| 8 | ACT | −0.11 | 0.13 | −0.03 | 0.19 |
| 9 | AGA | 0.48 | 0.44 | 0.29 | 0.48 |
| 10 | AGC | 0.26 | 0.21 | 0.10 | −0.01 |
| 11 | AGG | 0.46 | 0.29 | 0.68 | 0.29 |
| 12 | AGT | −0.27 | 0.38 | −0.26 | 0.10 |
| 13 | ATA | −0.45 | −0.39 | −0.48 | −0.10 |
| 14 | ATC | 0.35 | 0.21 | 0.49 | 0.28 |
| 15 | ATG | 0.74 | −0.02 | 0.76 | 0.01 |
| 16 | ATT | −0.47 | −0.32 | −0.45 | 0.04 |
| 17 | CAA | 0.11 | −0.12 | 0.14 | −0.17 |
| 18 | CAC | 0.09 | 0.05 | −0.11 | 0.17 |
| 19 | CAG | 0.66 | 0.27 | 0.68 | 0.16 |
| 20 | CAT | −0.31 | 0.02 | −0.43 | −0.09 |
| 21 | CCA | −0.22 | −0.22 | −0.18 | −0.28 |
| 22 | CCC | 0.38 | 0.42 | 0.10 | 0.22 |
| 23 | CCG | 0.40 | 0.23 | 0.67 | −0.04 |
| 24 | CCT | −0.27 | 0.15 | 0.01 | 0.05 |
| 25 | CGA | −0.24 | −0.34 | −0.22 | −0.24 |
| 26 | CGC | 0.33 | 0.04 | 0.18 | 0.05 |
| 27 | CGG | 0.41 | 0.41 | 0.72 | 0.00 |
| 28 | CGT | −0.36 | −0.40 | −0.37 | −0.45 |
| 29 | CTA | −0.49 | −0.30 | −0.57 | −0.28 |
| 30 | CTC | 0.35 | 0.32 | 0.04 | 0.23 |
| 31 | CTG | 0.19 | 0.10 | 0.49 | −0.19 |
| 32 | CTT | −0.05 | 0.25 | −0.33 | 0.41 |
| 33 | GAA | 0.20 | −0.04 | 0.02 | 0.03 |
| 34 | GAC | 0.12 | 0.20 | 0.07 | 0.18 |
| 35 | GAG | 0.52 | 0.22 | 0.58 | −0.11 |
| 36 | GAT | −0.33 | −0.10 | −0.40 | −0.10 |
| 37 | GCA | −0.05 | 0.18 | −0.20 | −0.02 |
| 38 | GCC | 0.35 | 0.26 | 0.14 | 0.05 |
| 39 | GCG | 0.21 | 0.34 | 0.56 | −0.09 |
| 40 | GCT | −0.36 | −0.08 | −0.32 | −0.19 |
| 41 | GGA | −0.01 | 0.10 | −0.14 | 0.03 |
| 42 | GGC | 0.27 | 0.08 | 0.11 | 0.13 |
| 43 | GGG | 0.19 | 0.43 | 0.40 | −0.02 |
| 44 | GGT | −0.40 | −0.13 | −0.46 | −0.34 |
| 45 | GTA | −0.24 | −0.36 | −0.36 | −0.25 |
| 46 | GTC | 0.53 | 0.32 | 0.42 | 0.29 |
| 47 | GTG | 0.14 | 0.17 | 0.45 | −0.15 |
| 48 | GTT | −0.25 | 0.00 | −0.24 | 0.09 |
| 49 | TAA | 0.00 | 0.00 | 0.00 | 0.00 |
| 50 | TAC | −0.07 | 0.08 | −0.05 | 0.13 |
| 51 | TAG | 0.00 | 0.00 | 0.00 | 0.00 |
| 52 | TAT | −0.43 | −0.21 | −0.50 | 0.03 |
| 53 | TCA | −0.13 | 0.02 | −0.20 | 0.01 |
| 54 | TCC | 0.09 | −0.11 | 0.02 | −0.24 |
| 55 | TCG | −0.17 | 0.10 | 0.56 | −0.28 |
| 56 | TCT | −0.33 | 0.09 | −0.09 | 0.09 |
| 57 | TGA | 0.00 | 0.00 | 0.00 | 0.00 |
| 58 | TGC | 0.23 | 0.13 | 0.09 | 0.10 |
| 59 | TGG | 0.70 | 0.01 | 0.83 | −0.01 |
| 60 | TGT | −0.31 | 0.17 | −0.33 | −0.22 |

TABLE C.3-continued

CPW matrix *Bacillus subtilis* full genome (left codon indicated in column 2, right codon indicated in row 2). Host cell: *B. subtilis*; Sequence data: full *B. subtilis* genome.

| | | | | | |
|---|---|---|---|---|---|
| 61 | TTA | −0.17 | −0.09 | −0.20 | −0.15 |
| 62 | TTC | −0.22 | −0.26 | 0.15 | −0.14 |
| 63 | TTG | 0.24 | −0.05 | 0.58 | −0.24 |
| 64 | TTT | −0.44 | −0.25 | −0.36 | 0.30 |
| | | TTA | TTC | TTG | TTT |
| | | 61 | 62 | 63 | 64 |

TABLE C.4

CPW matrix *Bacillus subtilis* highly expressed sequences (left codon indicated in column 2, right codon indicated in row 2). Host cell: *B. subtilis*; Sequence data: full *B. subtilis* genome; Highly expressed group: 415 seqs.

| | | 1 AAA | 2 AAC | 3 AAG | 4 AAT | 5 ACA | 6 ACC | 7 ACG | 8 ACT | 9 AGA | 10 AGC | 11 AGG | 12 AGT |
|---|---|---|---|---|---|---|---|---|---|---|---|---|---|
| 1 | AAA | −0.03 | −0.38 | −0.04 | 0.19 | −0.34 | 0.00 | −0.23 | 0.22 | 0.36 | −0.17 | 0.48 | 0.25 |
| 2 | AAC | −0.30 | −0.53 | −0.05 | −0.02 | −0.18 | 0.39 | 0.03 | −0.11 | 0.03 | −0.69 | 0.26 | 0.06 |
| 3 | AAG | 0.03 | 0.24 | 0.17 | 0.48 | 0.59 | 0.79 | 0.50 | 0.58 | 0.82 | 0.26 | 0.88 | −0.11 |
| 4 | AAT | 0.15 | 0.27 | 0.48 | 0.49 | −0.10 | 0.19 | −0.16 | 0.60 | 0.87 | 0.83 | 0.89 | 0.27 |
| 5 | ACA | −0.32 | −0.46 | −0.18 | −0.09 | −0.24 | 0.00 | 0.24 | −0.59 | −0.24 | −0.49 | −0.13 | 0.11 |
| 6 | ACC | 0.51 | 0.51 | 0.75 | 0.30 | 0.43 | 0.64 | 0.78 | −0.31 | 0.23 | 0.79 | 1.00 | 0.09 |
| 7 | ACG | 0.14 | −0.14 | −0.14 | 0.32 | −0.12 | 0.03 | −0.08 | −0.16 | −0.21 | 0.32 | 0.25 | 0.33 |
| 8 | ACT | 0.44 | 0.35 | 0.10 | 0.68 | 0.50 | 1.00 | 0.89 | −0.39 | 0.08 | 0.48 | −0.52 | 1.00 |
| 9 | AGA | −0.18 | −0.33 | −0.19 | 0.35 | −0.12 | 0.22 | −0.28 | 0.11 | 0.10 | −0.01 | −0.25 | −0.50 |
| 10 | AGC | −0.17 | −0.10 | 0.12 | 0.14 | −0.05 | 0.39 | −0.23 | −0.18 | −0.39 | −0.13 | −0.36 | −0.47 |
| 11 | AGG | 0.88 | 0.84 | 0.86 | 0.49 | 0.76 | 1.00 | 1.00 | 1.00 | 0.33 | 1.00 | 0.39 | 0.45 |
| 12 | AGT | −0.01 | 0.72 | 0.68 | 0.67 | −0.20 | 0.47 | 0.05 | −0.06 | 0.79 | 0.84 | 1.00 | 0.66 |
| 13 | ATA | 0.01 | 0.26 | 0.53 | 0.43 | 0.73 | 0.65 | 0.17 | 0.83 | 0.48 | 0.67 | 1.00 | 0.76 |
| 14 | ATC | −0.28 | −0.44 | 0.07 | −0.20 | −0.08 | 0.29 | 0.20 | −0.48 | −0.09 | −0.52 | −0.30 | −0.56 |
| 15 | ATG | 0.13 | −0.27 | −0.24 | 0.29 | 0.25 | −0.06 | −0.11 | −0.27 | −0.23 | 0.17 | 0.43 | −0.25 |
| 16 | ATT | 0.15 | 0.09 | 0.12 | 0.42 | −0.30 | 0.31 | 0.15 | 0.01 | 0.90 | 0.84 | 0.91 | 0.76 |
| 17 | CAA | −0.32 | −0.54 | −0.43 | −0.08 | −0.29 | −0.25 | −0.42 | 0.20 | 0.12 | −0.46 | 0.49 | 0.33 |
| 18 | CAC | −0.14 | −0.44 | 0.26 | 0.35 | 0.11 | 0.24 | −0.19 | −0.34 | −0.37 | −0.65 | −0.31 | −0.58 |
| 19 | CAG | 0.57 | 0.60 | 0.61 | 0.56 | 0.62 | 0.45 | −0.02 | 0.45 | 0.61 | 0.84 | 0.29 | 0.88 |
| 20 | CAT | −0.04 | −0.19 | 0.15 | 0.31 | −0.09 | 0.35 | −0.05 | 0.16 | 0.74 | 0.73 | 1.00 | 0.56 |
| 21 | CCA | −0.31 | −0.64 | −0.46 | −0.17 | −0.09 | 0.00 | 0.17 | −0.64 | −0.60 | −0.66 | −0.41 | −0.31 |
| 22 | CCC | 0.69 | 0.39 | 1.00 | 0.84 | 1.00 | 0.58 | 1.00 | 0.58 | 0.56 | 1.00 | 1.00 | 0.38 |
| 23 | CCG | 0.07 | 0.09 | −0.17 | −0.09 | −0.43 | 0.65 | 0.13 | −0.61 | −0.07 | 0.65 | 0.75 | −0.21 |
| 24 | CCT | 0.06 | 0.30 | 0.39 | 0.51 | 0.38 | 0.47 | 0.77 | 0.74 | 0.73 | 0.47 | 1.00 | 0.81 |
| 25 | CGA | 0.16 | −0.47 | 0.74 | −0.42 | 0.20 | 0.41 | 0.48 | 0.71 | −0.42 | −0.31 | 1.00 | −0.05 |
| 26 | CGC | −0.36 | −0.41 | −0.22 | 0.09 | −0.02 | 0.04 | −0.18 | −0.08 | −0.53 | −0.41 | 0.45 | −0.63 |
| 27 | CGG | 0.48 | 0.61 | 0.20 | 0.40 | −0.05 | 0.46 | −0.28 | 1.00 | 0.74 | 0.26 | 1.00 | 0.35 |
| 28 | CGT | −0.23 | 0.24 | 0.30 | −0.20 | −0.42 | 0.69 | −0.40 | −0.51 | 1.00 | 1.00 | 1.00 | 1.00 |
| 29 | CTA | −0.24 | −0.30 | −0.25 | 0.01 | 0.59 | 0.74 | 1.00 | −0.04 | −0.36 | −0.52 | 0.29 | 0.58 |
| 30 | CTC | 0.47 | 0.09 | 0.29 | 0.35 | 0.46 | 0.30 | 0.31 | −0.28 | 0.08 | −0.38 | 0.37 | −0.10 |
| 31 | CTG | −0.13 | −0.29 | 0.03 | −0.05 | −0.30 | −0.12 | −0.31 | −0.57 | 0.25 | 0.64 | −0.03 | 0.65 |
| 32 | CTT | 0.47 | 0.54 | 0.72 | 0.69 | 0.49 | 0.62 | 0.81 | −0.08 | 0.62 | 0.72 | 0.56 | 0.65 |
| 33 | GAA | −0.08 | −0.35 | 0.05 | 0.13 | −0.25 | −0.09 | −0.11 | −0.07 | 0.26 | −0.37 | 0.75 | −0.08 |
| 34 | GAC | −0.23 | −0.33 | −0.02 | −0.14 | −0.10 | 0.29 | 0.32 | −0.37 | −0.08 | −0.71 | −0.04 | −0.61 |
| 35 | GAG | 0.09 | 0.23 | 0.14 | 0.42 | 0.21 | 0.84 | 0.53 | 0.32 | 0.64 | 0.25 | 0.55 | 0.23 |
| 36 | GAT | 0.00 | −0.03 | 0.41 | 0.34 | −0.12 | 0.30 | −0.01 | 0.10 | 0.85 | 0.78 | 0.83 | 0.76 |
| 37 | GCA | −0.29 | −0.44 | 0.02 | 0.51 | −0.41 | −0.06 | 0.42 | −0.57 | −0.43 | −0.29 | 0.47 | −0.62 |
| 38 | GCC | 0.39 | −0.31 | 0.43 | 0.04 | 0.58 | 0.64 | 0.72 | 0.04 | −0.24 | 0.11 | 0.28 | −0.08 |
| 39 | GCG | −0.23 | −0.06 | −0.22 | −0.01 | −0.29 | 0.15 | 0.10 | −0.52 | −0.31 | 0.39 | 0.58 | 0.14 |
| 40 | GCT | 0.19 | −0.04 | 0.54 | 0.47 | 0.25 | 0.80 | 0.40 | −0.17 | 0.94 | 0.95 | 0.85 | 0.39 |
| 41 | GGA | −0.14 | −0.45 | 0.24 | −0.16 | −0.38 | 0.36 | −0.38 | −0.24 | −0.10 | −0.51 | 0.67 | −0.28 |
| 42 | GGC | 0.12 | −0.02 | 0.09 | 0.31 | 0.10 | 0.61 | 0.25 | 0.17 | −0.05 | −0.28 | 0.40 | 0.20 |
| 43 | GGG | −0.13 | 0.40 | 0.38 | 0.12 | 0.52 | 0.49 | 0.76 | 0.59 | 0.54 | 0.62 | 0.79 | 0.67 |
| 44 | GGT | −0.27 | −0.19 | 0.37 | 0.68 | −0.31 | 0.37 | 0.09 | −0.52 | 0.93 | 1.00 | 1.00 | 0.70 |
| 45 | GTA | −0.45 | −0.51 | −0.19 | −0.17 | −0.32 | −0.14 | −0.39 | −0.52 | −0.30 | −0.11 | 0.78 | 0.07 |
| 46 | GTC | 0.11 | 0.12 | 0.57 | −0.11 | −0.08 | 0.37 | 0.52 | −0.24 | −0.40 | −0.51 | 0.84 | −0.51 |
| 47 | GTG | −0.20 | −0.26 | −0.35 | 0.15 | −0.19 | 0.18 | −0.05 | −0.01 | 0.58 | 0.35 | 0.51 | 0.12 |
| 48 | GTT | 0.52 | 0.20 | 0.52 | 0.69 | 0.46 | 0.71 | 0.39 | −0.24 | 0.62 | 0.82 | 0.55 | 0.76 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | −0.21 | −0.66 | −0.04 | 0.14 | −0.43 | 0.42 | 0.23 | −0.46 | −0.31 | −0.51 | 0.50 | −0.68 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.03 | 0.37 | 0.28 | 0.46 | 0.36 | 0.54 | −0.30 | 0.31 | 0.76 | 1.00 | 1.00 | 0.76 |
| 53 | TCA | −0.24 | −0.49 | 0.29 | 0.22 | 0.12 | −0.23 | −0.11 | −0.66 | −0.36 | −0.32 | 0.24 | −0.53 |
| 54 | TCC | 0.59 | −0.03 | 0.31 | −0.34 | 0.41 | 0.36 | 0.49 | −0.42 | −0.54 | −0.34 | 1.00 | −0.28 |
| 55 | TCG | 0.20 | 0.56 | −0.30 | 0.21 | 0.36 | 0.73 | 0.84 | 0.46 | −0.07 | 1.00 | −0.15 | −0.05 |
| 56 | TCT | −0.15 | −0.23 | −0.07 | 0.16 | −0.21 | 0.46 | 0.52 | −0.25 | 0.79 | 1.00 | 1.00 | 0.31 |
| 57 | TGA | 0.00 | 0.00 | 0.00 | 0.00 | 0.00 | 0.00 | 0.00 | 0.00 | 0.00 | 0.00 | 0.00 | 0.00 |

TABLE C.4-continued

CPW matrix *Bacillus subtilis* highly expressed sequences (left codon indicated in column 2, right codon indicated in row 2). Host cell: *B. subtilus*; Sequence data: full *B. subtilus* genome; Highly expressed group: 415 seqs.

| | | | | | | | | | | | | |
|---|---|---|---|---|---|---|---|---|---|---|---|---|
| 58 | TGC | −0.17 | −0.18 | 0.30 | 0.24 | −0.05 | 1.00 | −0.28 | 0.33 | −0.44 | −0.38 | 1.00 | 0.00 |
| 59 | TGG | 0.18 | −0.22 | −0.30 | 0.22 | 0.13 | 0.55 | −0.33 | −0.04 | −0.35 | −0.47 | 0.04 | −0.31 |
| 60 | TGT | −0.09 | −0.16 | 0.43 | 0.07 | −0.21 | −0.18 | 0.28 | −0.18 | 1.00 | 1.00 | 1.00 | 1.00 |
| 61 | TTA | −0.33 | −0.52 | −0.32 | −0.14 | −0.19 | 0.40 | −0.32 | −0.48 | −0.31 | −0.11 | 0.46 | 0.04 |
| 62 | TTC | −0.38 | −0.39 | −0.06 | 0.49 | −0.38 | 0.33 | 0.07 | −0.19 | −0.55 | −0.62 | −0.46 | −0.54 |
| 63 | TTG | −0.23 | −0.12 | −0.18 | 0.00 | 0.27 | 0.23 | 0.09 | −0.44 | 0.33 | 0.75 | 0.31 | 0.46 |
| 64 | TTT | 0.16 | −0.12 | 0.34 | 0.11 | 0.13 | −0.27 | 0.31 | 0.16 | 0.59 | 0.88 | 0.75 | 0.73 |

| | AAA 1 | AAC 2 | AAG 3 | AAT 4 | ACA 5 | ACC 6 | ACG 7 | ACT 8 | AGA 9 | AGC 10 | AGG 11 | AGT 12 |
|---|---|---|---|---|---|---|---|---|---|---|---|---|
| | 13 ATA | 14 ATC | 15 ATG | 16 ATT | 17 CAA | 18 CAC | 19 CAG | 20 CAT | 21 CCA | 22 CCC | 23 CCG | 24 CCT |
| 1 AAA | 0.42 | −0.44 | −0.15 | 0.14 | −0.04 | −0.12 | 0.37 | 0.57 | 0.04 | 0.46 | 0.21 | 0.20 |
| 2 AAC | 0.66 | −0.46 | −0.33 | 0.09 | −0.30 | −0.15 | 0.04 | −0.14 | −0.24 | 0.53 | −0.15 | 0.13 |
| 3 AAG | 0.92 | 0.46 | 0.39 | 0.21 | −0.19 | −0.51 | −0.33 | −0.39 | −0.04 | 0.84 | −0.36 | −0.49 |
| 4 AAT | 0.54 | −0.11 | 0.38 | 0.24 | −0.01 | −0.18 | 0.33 | 0.30 | −0.08 | −0.08 | −0.08 | 0.36 |
| 5 ACA | 0.70 | −0.18 | −0.12 | 0.23 | −0.14 | −0.28 | 0.06 | 0.24 | −0.34 | 0.33 | −0.11 | 0.04 |
| 6 ACC | 0.08 | 0.08 | 0.38 | −0.32 | 0.47 | −0.33 | 0.45 | 0.63 | 0.51 | 0.66 | 0.93 | 0.68 |
| 7 ACG | −0.42 | −0.27 | −0.26 | −0.39 | 0.31 | 0.22 | 0.16 | 0.40 | −0.51 | 0.59 | 0.00 | −0.34 |
| 8 ACT | 0.54 | 0.95 | 0.58 | 0.74 | −0.47 | −0.62 | −0.34 | −0.36 | −0.61 | 0.66 | 0.58 | 0.04 |
| 9 AGA | 0.41 | −0.10 | 0.39 | 0.24 | 0.61 | −0.29 | 0.20 | 0.15 | 0.48 | 1.00 | −0.16 | 0.43 |
| 10 AGC | 0.37 | −0.19 | 0.01 | −0.22 | −0.16 | −0.36 | −0.18 | 0.36 | 0.14 | 0.70 | 0.07 | 0.24 |
| 11 AGG | 0.35 | 0.57 | 0.61 | 0.60 | 0.70 | 0.57 | 0.38 | 0.16 | 0.53 | 1.00 | 0.18 | 0.38 |
| 12 AGT | 0.17 | 0.54 | 0.23 | 0.12 | 0.73 | 0.43 | 0.44 | 0.30 | 0.37 | 0.34 | 0.32 | −0.03 |
| 13 ATA | 0.81 | 0.80 | 0.93 | 0.71 | 0.15 | 0.33 | 0.05 | 0.13 | 0.16 | 0.64 | −0.08 | 0.11 |
| 14 ATC | 0.15 | −0.51 | −0.36 | −0.20 | 0.05 | 0.26 | 0.34 | 0.12 | −0.20 | 0.64 | 0.07 | 0.44 |
| 15 ATG | 0.55 | −0.13 | 0.00 | −0.03 | 0.19 | −0.21 | −0.17 | 0.13 | −0.11 | 0.44 | 0.11 | −0.18 |
| 16 ATT | 0.66 | −0.03 | 0.18 | 0.21 | −0.22 | −0.48 | −0.04 | 0.19 | −0.25 | 0.47 | −0.19 | −0.06 |
| 17 CAA | 0.21 | −0.49 | −0.32 | −0.14 | 0.59 | 0.90 | 0.82 | 0.61 | 0.56 | 0.81 | 0.89 | 0.83 |
| 18 CAC | 1.00 | −0.11 | −0.14 | −0.33 | 0.04 | −0.57 | 0.09 | −0.05 | −0.21 | 1.00 | 0.04 | −0.04 |
| 19 CAG | 0.70 | 0.50 | 0.49 | 0.31 | −0.26 | −0.42 | −0.53 | −0.42 | −0.50 | 0.04 | −0.46 | −0.49 |
| 20 CAT | 0.56 | −0.03 | 0.08 | 0.05 | 0.13 | 0.32 | −0.16 | 0.18 | −0.32 | 0.51 | −0.07 | 0.18 |
| 21 CCA | 0.75 | −0.50 | −0.23 | 0.08 | −0.02 | −0.37 | 0.79 | 0.90 | 0.12 | 1.00 | 1.00 | 0.13 |
| 22 CCC | 1.00 | 1.00 | 0.63 | 1.00 | 0.35 | −0.21 | 1.00 | 0.17 | 0.07 | 1.00 | 1.00 | 0.39 |
| 23 CCG | 0.57 | −0.38 | −0.28 | −0.43 | −0.39 | 0.05 | 0.50 | −0.12 | −0.42 | −0.17 | −0.32 | −0.47 |
| 24 CCT | 1.00 | 0.56 | 0.60 | 0.64 | −0.33 | 0.21 | −0.15 | −0.26 | 0.42 | 1.00 | 0.50 | −0.13 |
| 25 CGA | −0.20 | −0.20 | −0.24 | −0.07 | 0.41 | 1.00 | 0.70 | 0.80 | 0.54 | 1.00 | 0.80 | 1.00 |
| 26 CGC | 0.85 | 0.12 | −0.24 | −0.20 | −0.23 | −0.26 | −0.43 | −0.12 | −0.33 | 0.55 | −0.10 | −0.11 |
| 27 CGG | 0.04 | 0.10 | −0.09 | −0.27 | 0.37 | 0.49 | 0.26 | 0.00 | 0.16 | 1.00 | 0.64 | 0.26 |
| 28 CGT | 0.67 | −0.36 | −0.20 | −0.24 | −0.62 | −0.36 | 0.03 | −0.29 | −0.55 | −0.03 | −0.53 | −0.63 |
| 29 CTA | 1.00 | 0.18 | −0.01 | −0.01 | 0.42 | 1.00 | 1.00 | 0.56 | 0.67 | 1.00 | 0.86 | 1.00 |
| 30 CTC | 0.46 | −0.03 | −0.13 | −0.20 | 0.55 | 0.61 | 0.60 | 0.32 | 0.28 | 0.69 | 0.25 | 0.24 |
| 31 CTG | 0.24 | −0.40 | −0.27 | −0.22 | −0.11 | 0.54 | 0.19 | 0.19 | −0.30 | 0.86 | −0.24 | 0.02 |
| 32 CTT | 0.75 | 0.37 | 0.61 | 0.65 | −0.47 | −0.58 | −0.22 | −0.46 | −0.36 | 0.42 | −0.27 | −0.60 |
| 33 GAA | 0.35 | −0.34 | −0.14 | 0.10 | 0.27 | 0.63 | 0.13 | 0.37 | 0.35 | 0.91 | 0.38 | 0.46 |
| 34 GAC | 0.53 | −0.08 | 0.08 | 0.07 | −0.29 | −0.34 | 0.38 | −0.16 | −0.15 | 0.46 | 0.23 | 0.00 |
| 35 GAG | 0.56 | 0.22 | 0.36 | 0.10 | −0.19 | −0.58 | −0.38 | −0.43 | −0.28 | −0.09 | −0.53 | −0.56 |
| 36 GAT | 0.30 | −0.07 | −0.04 | −0.08 | 0.13 | 0.23 | −0.10 | 0.14 | −0.05 | 0.49 | −0.15 | −0.06 |
| 37 GCA | 0.59 | −0.19 | −0.22 | 0.34 | −0.15 | 0.15 | −0.25 | 0.35 | −0.17 | 0.82 | −0.07 | −0.07 |
| 38 GCC | 0.45 | −0.08 | 0.23 | −0.19 | 0.23 | 0.11 | 0.43 | 0.07 | 0.53 | 0.75 | 0.50 | 0.69 |
| 39 GCG | 0.13 | −0.35 | −0.25 | −0.39 | 0.02 | −0.37 | 0.51 | −0.03 | −0.27 | 0.42 | −0.28 | −0.25 |
| 40 GCT | 0.45 | 0.42 | 0.49 | 0.46 | −0.42 | −0.33 | 0.22 | 0.00 | −0.15 | 0.79 | 0.15 | −0.47 |
| 41 GGA | 0.82 | −0.03 | 0.24 | 0.15 | −0.20 | −0.54 | −0.05 | 0.17 | 0.08 | 0.41 | −0.16 | 0.09 |
| 42 GGC | 0.35 | −0.19 | 0.03 | −0.02 | −0.04 | −0.06 | 0.22 | 0.13 | 0.24 | 0.64 | 0.01 | 0.39 |
| 43 GGG | 0.54 | 0.39 | 0.25 | −0.13 | 0.10 | −0.33 | 0.01 | 0.05 | −0.06 | 0.25 | −0.41 | −0.47 |
| 44 GGT | 0.19 | −0.43 | −0.41 | −0.07 | 0.11 | 0.08 | −0.02 | 0.61 | 0.06 | 0.67 | 0.12 | −0.12 |
| 45 GTA | 0.62 | 0.15 | 0.35 | 0.74 | 0.14 | −0.19 | −0.14 | 0.29 | −0.01 | 0.52 | 0.08 | −0.04 |
| 46 GTC | 0.57 | −0.37 | −0.34 | −0.37 | 0.52 | 0.61 | 0.65 | 0.62 | 0.83 | 0.46 | 0.74 | 0.44 |
| 47 GTG | 0.57 | −0.11 | −0.06 | 0.14 | 0.35 | 0.22 | 0.02 | 0.16 | −0.02 | 0.46 | −0.46 | −0.32 |
| 48 GTT | 0.35 | −0.36 | 0.28 | 0.25 | −0.44 | −0.51 | −0.37 | −0.40 | −0.24 | 0.18 | 0.03 | −0.39 |
| 49 TAA | 0.00 | 0.00 | 0.00 | 0.00 | 0.00 | 0.00 | 0.00 | 0.00 | 0.00 | 0.00 | 0.00 | 0.00 |
| 50 TAC | −0.12 | −0.43 | −0.26 | 0.32 | −0.12 | −0.06 | 0.24 | 0.04 | −0.25 | 0.37 | 0.29 | 0.02 |
| 51 TAG | 0.00 | 0.00 | 0.00 | 0.00 | 0.00 | 0.00 | 0.00 | 0.00 | 0.00 | 0.00 | 0.00 | 0.00 |
| 52 TAT | 0.30 | −0.05 | 0.19 | 0.10 | −0.04 | 0.05 | −0.01 | −0.03 | −0.26 | 0.49 | −0.17 | 0.21 |
| 53 TCA | 0.76 | 0.06 | −0.21 | 0.25 | −0.21 | −0.01 | 0.13 | 0.32 | −0.20 | 0.12 | 0.16 | −0.27 |
| 54 TCC | 0.56 | −0.26 | −0.20 | −0.35 | 0.78 | −0.38 | 0.43 | 0.55 | 0.24 | 0.46 | 0.56 | 0.83 |
| 55 TCG | 1.00 | −0.19 | 0.37 | −0.38 | 0.02 | −0.31 | 0.28 | 0.28 | 0.04 | 0.32 | −0.40 | −0.48 |
| 56 TCT | 0.17 | −0.14 | 0.14 | 0.31 | −0.53 | −0.46 | 0.29 | −0.32 | −0.61 | 1.00 | 0.11 | −0.40 |
| 57 TGA | 0.00 | 0.00 | 0.00 | 0.00 | 0.00 | 0.00 | 0.00 | 0.00 | 0.00 | 0.00 | 0.00 | 0.00 |
| 58 TGC | 0.49 | −0.16 | 0.09 | 0.63 | −0.22 | −0.50 | −0.37 | −0.19 | −0.23 | 0.32 | 0.16 | −0.06 |
| 59 TGG | −0.23 | 0.05 | 0.00 | 0.04 | 0.46 | −0.29 | −0.32 | 0.20 | 0.34 | 1.00 | 0.00 | −0.35 |
| 60 TGT | −0.18 | −0.59 | −0.10 | 0.40 | 0.69 | 0.39 | 0.36 | 0.70 | 0.61 | 0.17 | −0.01 | −0.35 |
| 61 TTA | 0.90 | −0.38 | −0.20 | 0.07 | 0.37 | 0.55 | 0.12 | 0.22 | 0.50 | 0.64 | 0.78 | 0.34 |
| 62 TTC | 0.59 | −0.23 | −0.16 | 0.02 | −0.51 | −0.58 | −0.37 | −0.41 | −0.55 | 0.27 | −0.36 | −0.65 |

TABLE C.4-continued

CPW matrix *Bacillus subtilis* highly expressed sequences (left codon indicated in column 2, right codon indicated in row 2). Host cell: *B. subtilus*; Sequence data: full *B. subtilus* genome; Highly expressed group: 415 seqs.

| | | | | | | | | | | | | |
|---|---|---|---|---|---|---|---|---|---|---|---|---|
| 63 | TTG | 0.60 | −0.28 | 0.06 | −0.22 | 0.00 | −0.13 | −0.15 | 0.36 | 0.25 | 0.10 | −0.20 | 0.23 |
| 64 | TTT | 0.23 | 0.02 | 0.09 | −0.05 | 0.31 | 0.49 | 0.47 | 0.41 | 0.27 | 0.66 | 0.37 | 0.68 |

| | | ATA 13 | ATC 14 | ATG 15 | ATT 16 | CAA 17 | CAC 18 | CAG 19 | CAT 20 | CCA 21 | CCC 22 | CCG 23 | CCT 24 |
|---|---|---|---|---|---|---|---|---|---|---|---|---|---|
| | | 25 CGA | 26 CGC | 27 CGG | 28 CGT | 29 CTA | 30 CTC | 31 CTG | 32 CTT | 33 GAA | 34 GAC | 35 GAG | 36 GAT |
| 1 | AAA | −0.20 | −0.38 | −0.04 | −0.20 | −0.17 | 0.49 | 0.50 | 0.26 | −0.13 | −0.26 | −0.06 | 0.25 |
| 2 | AAC | −0.22 | −0.55 | 0.04 | −0.70 | −0.61 | 0.17 | −0.31 | −0.46 | 0.13 | −0.10 | 0.39 | 0.18 |
| 3 | AAG | 0.30 | −0.03 | 0.07 | −0.50 | −0.39 | −0.31 | −0.66 | −0.68 | 0.25 | −0.12 | 0.38 | −0.05 |
| 4 | AAT | 0.33 | 0.53 | 0.73 | −0.20 | 0.33 | 0.29 | 0.25 | 0.03 | −0.19 | −0.27 | −0.02 | 0.12 |
| 5 | ACA | 1.00 | 0.04 | 0.42 | −0.02 | 0.36 | 0.37 | 0.17 | −0.08 | −0.20 | 0.05 | 0.05 | 0.20 |
| 6 | ACC | 0.19 | 0.43 | 0.75 | 0.13 | 0.34 | 0.56 | 0.45 | −0.14 | 0.57 | 0.37 | 0.33 | 0.21 |
| 7 | ACG | 0.52 | 0.44 | 0.56 | 0.23 | −0.36 | −0.17 | −0.23 | −0.49 | 0.27 | 0.55 | 0.68 | 0.25 |
| 8 | ACT | 0.19 | −0.47 | 1.00 | −0.83 | 0.02 | 0.57 | 0.73 | −0.02 | −0.42 | −0.67 | −0.45 | −0.43 |
| 9 | AGA | −0.34 | −0.09 | 0.60 | 0.19 | 0.78 | 0.70 | 0.35 | 0.72 | −0.07 | −0.27 | 0.03 | 0.44 |
| 10 | AGC | 0.49 | −0.60 | −0.08 | −0.33 | 0.09 | 0.30 | −0.04 | −0.24 | 0.34 | 0.31 | 0.40 | 0.50 |
| 11 | AGG | 1.00 | 0.73 | −0.31 | 0.69 | 0.39 | −0.08 | −0.44 | 0.24 | 0.53 | 0.32 | 0.34 | −0.26 |
| 12 | AGT | 0.45 | 0.49 | 0.32 | 0.71 | 0.01 | 0.78 | 0.07 | −0.12 | −0.51 | −0.54 | −0.51 | −0.44 |
| 13 | ATA | −0.03 | 0.36 | 1.00 | 0.63 | 0.61 | −0.04 | 0.59 | 0.67 | 0.43 | 0.56 | 0.46 | 0.15 |
| 14 | ATC | 0.07 | −0.63 | 0.36 | −0.62 | 0.07 | 0.36 | 0.48 | −0.41 | −0.10 | −0.01 | 0.31 | 0.17 |
| 15 | ATG | 0.86 | −0.13 | 0.41 | −0.32 | 0.67 | 0.18 | −0.40 | −0.43 | 0.02 | −0.12 | −0.04 | 0.08 |
| 16 | ATT | 0.15 | 0.01 | 0.74 | −0.39 | 0.22 | −0.14 | 0.52 | −0.02 | −0.14 | −0.20 | −0.04 | −0.08 |
| 17 | CAA | 0.34 | 0.54 | 0.90 | 0.38 | 0.59 | 0.94 | 0.91 | 0.86 | 0.04 | 0.21 | −0.30 | 0.18 |
| 18 | CAC | 0.07 | −0.54 | −0.56 | −0.71 | 0.18 | 0.82 | 0.15 | −0.38 | −0.11 | 0.23 | 0.26 | 0.08 |
| 19 | CAG | 0.32 | −0.52 | −0.58 | −0.54 | −0.46 | −0.49 | −0.44 | −0.68 | 0.05 | 0.18 | 0.25 | −0.29 |
| 20 | CAT | 0.77 | 0.36 | 0.44 | 0.15 | 0.40 | 0.65 | 0.50 | 0.46 | 0.14 | −0.21 | −0.23 | 0.05 |
| 21 | CCA | 0.45 | −0.02 | 0.66 | −0.32 | 1.00 | 0.64 | 0.58 | 0.66 | 0.08 | 0.05 | −0.26 | 0.13 |
| 22 | CCC | 1.00 | −0.77 | 1.00 | 0.38 | 1.00 | 0.23 | 0.82 | 0.64 | 0.46 | 0.53 | 0.32 | 0.82 |
| 23 | CCG | −0.30 | 0.34 | 0.27 | −0.51 | −0.43 | −0.39 | −0.20 | −0.62 | 0.25 | 0.33 | 0.51 | 0.28 |
| 24 | CCT | 1.00 | 0.33 | 0.33 | −0.35 | 0.19 | 0.29 | 0.61 | 0.05 | −0.40 | −0.39 | −0.33 | −0.45 |
| 25 | CGA | 1.00 | 0.73 | 1.00 | 0.70 | 0.41 | 0.74 | 0.39 | 0.63 | 0.54 | 0.18 | 0.79 | 0.44 |
| 26 | CGC | 0.20 | −0.66 | −0.12 | −0.76 | −0.27 | −0.32 | −0.38 | −0.08 | 0.43 | −0.13 | 0.10 | 0.22 |
| 27 | CGG | 1.00 | 0.51 | 0.36 | 0.81 | 0.27 | 0.36 | −0.33 | −0.22 | 0.50 | 0.30 | 0.34 | 0.37 |
| 28 | CGT | 1.00 | 0.29 | 0.44 | −0.64 | −0.55 | −0.40 | −0.05 | −0.60 | −0.52 | −0.62 | −0.63 | −0.19 |
| 29 | CTA | 1.00 | 1.00 | 1.00 | 1.00 | −0.26 | 0.10 | 0.86 | 0.86 | 0.03 | 0.33 | −0.16 | 0.02 |
| 30 | CTC | 0.70 | −0.11 | 0.26 | −0.23 | 0.70 | 0.74 | 0.57 | 0.50 | 0.53 | 0.11 | 0.67 | −0.12 |
| 31 | CTG | 0.72 | −0.11 | 0.48 | −0.27 | 0.44 | −0.27 | −0.22 | −0.43 | 0.49 | 0.45 | 0.22 | 0.48 |
| 32 | CTT | −0.22 | −0.72 | 0.13 | −0.60 | −0.11 | −0.30 | 0.01 | −0.50 | −0.53 | −0.40 | −0.43 | −0.54 |
| 33 | GAA | −0.02 | −0.03 | 0.22 | −0.03 | 0.24 | 0.33 | 0.33 | 0.50 | −0.11 | −0.27 | −0.20 | 0.08 |
| 34 | GAC | −0.42 | −0.74 | −0.37 | −0.67 | 0.23 | 0.26 | 0.31 | 0.02 | 0.05 | 0.29 | 0.24 | 0.17 |
| 35 | GAG | 0.22 | −0.53 | −0.21 | −0.61 | −0.48 | −0.46 | −0.50 | −0.70 | 0.30 | 0.22 | 0.43 | 0.15 |
| 36 | GAT | 0.59 | 0.43 | 0.65 | 0.57 | 0.20 | 0.10 | 0.23 | −0.10 | −0.11 | −0.31 | 0.06 | 0.07 |
| 37 | GCA | 0.87 | −0.38 | 0.61 | −0.19 | 0.26 | 0.19 | 0.36 | −0.06 | 0.12 | −0.07 | 0.20 | 0.20 |
| 38 | GCC | 0.83 | 0.11 | 0.47 | −0.55 | 0.67 | 0.63 | 0.45 | 0.59 | 0.39 | 0.63 | 0.43 | 0.31 |
| 39 | GCG | 0.32 | −0.17 | 0.67 | −0.40 | −0.04 | −0.25 | −0.37 | −0.59 | 0.14 | 0.12 | 0.19 | 0.26 |
| 40 | GCT | 0.41 | 0.32 | 0.82 | −0.54 | −0.35 | 0.38 | 0.54 | −0.16 | −0.43 | −0.56 | −0.31 | −0.27 |
| 41 | GGA | 0.26 | −0.51 | 0.42 | −0.48 | 0.61 | 0.43 | 0.41 | −0.04 | −0.11 | −0.27 | 0.15 | −0.03 |
| 42 | GGC | 0.33 | −0.30 | 0.05 | −0.57 | −0.16 | 0.42 | 0.34 | −0.12 | 0.34 | 0.12 | 0.20 | 0.35 |
| 43 | GGG | 0.39 | 0.15 | 0.26 | 0.24 | 0.50 | 0.23 | −0.16 | −0.45 | 0.40 | 0.33 | 0.66 | 0.36 |
| 44 | GGT | 0.82 | 0.58 | 0.89 | −0.25 | −0.35 | −0.32 | 0.63 | −0.65 | −0.49 | −0.59 | −0.44 | −0.05 |
| 45 | GTA | 0.58 | −0.32 | 0.36 | −0.19 | −0.43 | 0.14 | 0.23 | −0.17 | −0.11 | −0.15 | −0.34 | 0.06 |
| 46 | GTC | 0.68 | −0.46 | 0.81 | −0.46 | 0.56 | 0.35 | 0.66 | 0.54 | 0.56 | 0.51 | 0.60 | 0.31 |
| 47 | GTG | 0.37 | 0.04 | 0.61 | −0.09 | 0.41 | −0.43 | −0.51 | −0.47 | 0.47 | 0.28 | 0.38 | 0.35 |
| 48 | GTT | 0.28 | −0.40 | 0.47 | −0.54 | 0.06 | −0.20 | 0.58 | −0.27 | −0.47 | −0.43 | −0.30 | −0.35 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | −0.17 | −0.63 | −0.25 | −0.70 | −0.33 | 0.20 | 0.19 | −0.23 | 0.16 | 0.42 | 0.29 | −0.23 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.35 | 0.22 | 0.68 | 0.10 | 0.20 | 0.07 | 0.50 | 0.30 | −0.15 | −0.17 | 0.04 | 0.14 |
| 53 | TCA | 1.00 | 0.20 | 0.85 | −0.04 | 0.34 | −0.14 | 0.18 | 0.00 | 0.12 | 0.14 | −0.02 | 0.21 |
| 54 | TCC | 1.00 | −0.60 | 0.18 | −0.40 | −0.17 | 0.65 | 0.58 | 0.09 | 0.69 | 0.56 | 0.34 | 0.26 |
| 55 | TCG | 0.43 | 0.74 | 0.65 | −0.17 | −0.35 | −0.11 | −0.37 | −0.50 | 0.60 | 0.89 | 0.49 | 0.19 |
| 56 | TCT | 0.72 | −0.15 | 1.00 | −0.39 | −0.43 | 0.45 | 0.43 | −0.29 | −0.40 | −0.49 | −0.31 | −0.34 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | −0.15 | −0.63 | −0.30 | −0.60 | 0.21 | 0.30 | −0.32 | −0.13 | 0.61 | 0.30 | −0.19 | 0.52 |
| 59 | TGG | 0.69 | −0.01 | 0.24 | 0.17 | 0.62 | −0.41 | −0.30 | −0.16 | 0.05 | −0.14 | −0.09 | 0.09 |
| 60 | TGT | 1.00 | 1.00 | 1.00 | 1.00 | 0.04 | 0.15 | 0.60 | −0.28 | −0.20 | −0.16 | −0.43 | −0.42 |

TABLE C.4-continued

CPW matrix Bacillus subtilis highly expressed sequences (left codon indicated in column 2, right codon indicated in row 2). Host cell: *B. subtilis*; Sequence data: full *B. subtilis* genome; Highly expressed group: 415 seqs.

| | | | | | | | | | | | | |
|---|---|---|---|---|---|---|---|---|---|---|---|---|
| 61 | TTA | 0.65 | 0.67 | 0.68 | 0.34 | 0.65 | 0.47 | 0.64 | 0.50 | 0.07 | 0.35 | 0.20 | 0.40 |
| 62 | TTC | −0.22 | −0.60 | −0.29 | −0.77 | −0.30 | 0.11 | −0.27 | −0.44 | 0.24 | −0.15 | 0.64 | 0.36 |
| 63 | TTG | 1.00 | −0.04 | 0.04 | −0.24 | −0.24 | −0.31 | −0.33 | −0.45 | 0.42 | 0.30 | 0.37 | 0.34 |
| 64 | TTT | 0.64 | 0.66 | 0.85 | 0.61 | 0.46 | 0.40 | 0.58 | 0.41 | −0.27 | −0.27 | 0.23 | 0.09 |

| | CGA 25 | CGC 26 | CGG 27 | CGT 28 | CTA 29 | CTC 30 | CTG 31 | CTT 32 | GAA 33 | GAC 34 | GAG 35 | GAT 36 |
|---|---|---|---|---|---|---|---|---|---|---|---|---|

| | | 37 GCA | 38 GCC | 39 GCG | 40 GCT | 41 GGA | 42 GGC | 43 GGG | 44 GGT | 45 GTA | 46 GTC | 47 GTG | 48 GTT |
|---|---|---|---|---|---|---|---|---|---|---|---|---|---|
| 1 | AAA | −0.24 | −0.06 | −0.31 | 0.08 | 0.09 | −0.31 | −0.15 | −0.16 | −0.44 | 0.20 | −0.08 | 0.24 |
| 2 | AAC | −0.05 | 0.57 | −0.13 | −0.25 | −0.42 | −0.39 | −0.10 | −0.50 | −0.35 | 0.11 | 0.04 | −0.11 |
| 3 | AAG | 0.38 | 0.77 | 0.32 | 0.46 | 0.51 | 0.34 | 0.60 | 0.36 | 0.11 | 0.45 | 0.06 | −0.08 |
| 4 | AAT | −0.08 | 0.20 | −0.22 | 0.30 | 0.47 | 0.55 | 0.51 | 0.47 | −0.02 | 0.15 | −0.11 | 0.27 |
| 5 | ACA | 0.25 | 0.34 | 0.18 | −0.32 | 0.00 | 0.00 | 0.02 | −0.36 | 0.18 | 0.10 | 0.28 | 0.11 |
| 6 | ACC | 0.49 | 0.62 | 0.34 | −0.09 | −0.09 | 0.04 | 0.04 | −0.41 | 0.24 | 0.11 | 0.55 | −0.18 |
| 7 | ACG | −0.15 | 0.77 | 0.39 | −0.21 | 0.38 | 0.57 | 0.89 | 0.29 | 0.15 | 0.06 | 0.55 | −0.23 |
| 8 | ACT | −0.56 | −0.31 | 0.10 | −0.59 | −0.26 | −0.24 | 0.42 | −0.63 | −0.56 | −0.21 | −0.13 | −0.58 |
| 9 | AGA | 0.13 | 0.58 | −0.43 | 0.47 | 0.11 | 0.14 | 0.15 | 0.08 | 0.54 | 0.71 | 0.30 | 0.52 |
| 10 | AGC | 0.39 | 0.47 | 0.49 | 0.51 | −0.52 | −0.35 | 0.16 | 0.01 | −0.13 | 0.61 | 0.47 | 0.47 |
| 11 | AGG | 0.58 | 0.43 | 0.55 | 0.68 | −0.17 | 0.63 | 0.48 | 0.54 | 0.16 | 0.52 | 0.36 | 0.85 |
| 12 | AGT | −0.29 | −0.13 | −0.34 | −0.34 | 0.68 | 0.78 | 0.85 | 0.60 | −0.45 | −0.05 | −0.33 | −0.42 |
| 13 | ATA | 0.73 | 0.46 | 0.50 | 0.92 | 0.81 | 0.72 | 0.29 | 0.79 | 1.00 | 0.86 | 0.78 | 0.74 |
| 14 | ATC | −0.18 | −0.03 | 0.21 | −0.35 | −0.42 | −0.51 | −0.39 | −0.67 | −0.44 | −0.19 | 0.12 | −0.27 |
| 15 | ATG | 0.03 | 0.65 | −0.05 | −0.34 | 0.23 | −0.03 | 0.10 | −0.30 | 0.09 | 0.08 | 0.05 | −0.15 |
| 16 | ATT | −0.15 | −0.12 | 0.16 | −0.07 | 0.70 | 0.58 | 0.77 | 0.33 | 0.24 | −0.07 | 0.12 | −0.16 |
| 17 | CAA | 0.07 | 0.23 | 0.01 | −0.03 | 0.13 | −0.37 | −0.18 | −0.50 | −0.42 | −0.06 | −0.14 | 0.16 |
| 18 | CAC | 0.07 | −0.03 | 0.19 | 0.04 | −0.19 | −0.53 | 0.05 | −0.58 | −0.29 | −0.06 | −0.07 | −0.42 |
| 19 | CAG | −0.16 | 0.43 | −0.04 | −0.27 | 0.44 | 0.52 | 0.04 | 0.37 | 0.25 | 0.44 | −0.06 | 0.04 |
| 20 | CAT | 0.13 | −0.11 | −0.16 | 0.01 | 0.31 | 0.26 | 0.61 | 0.31 | −0.02 | 0.15 | −0.09 | 0.52 |
| 21 | CCA | 0.09 | 0.38 | 0.43 | −0.23 | 0.07 | 0.21 | 0.23 | −0.56 | 0.18 | 0.38 | 0.31 | −0.17 |
| 22 | CCC | 0.03 | 0.78 | −0.03 | −0.22 | 0.15 | −0.35 | 0.73 | −0.17 | 1.00 | 0.41 | 0.56 | 0.47 |
| 23 | CCG | 0.05 | 0.29 | 0.34 | −0.24 | 0.05 | 0.21 | 0.50 | −0.15 | 0.17 | 0.40 | 0.49 | −0.19 |
| 24 | CCT | 0.00 | −0.13 | 0.20 | −0.53 | −0.15 | 0.28 | 0.16 | −0.50 | −0.47 | −0.41 | 0.09 | −0.48 |
| 25 | CGA | 0.86 | 0.63 | 0.86 | 0.69 | 0.48 | −0.07 | 0.75 | 0.78 | 0.59 | 0.85 | 0.38 | 0.44 |
| 26 | CGC | −0.17 | 0.40 | −0.12 | −0.07 | −0.68 | −0.44 | 0.18 | −0.69 | −0.38 | −0.01 | −0.18 | −0.31 |
| 27 | CGG | 0.33 | 0.55 | 0.20 | −0.12 | 0.92 | 0.56 | 0.69 | 0.86 | 0.62 | 0.62 | −0.12 | 0.40 |
| 28 | CGT | −0.31 | −0.21 | −0.68 | −0.47 | 0.30 | 0.62 | 0.46 | −0.30 | −0.66 | −0.51 | −0.55 | −0.49 |
| 29 | CTA | 0.48 | 0.65 | −0.19 | 0.12 | 0.48 | −0.36 | −0.21 | −0.65 | −0.25 | 0.16 | 0.15 | −0.46 |
| 30 | CTC | 0.14 | 0.23 | 0.39 | 0.02 | −0.38 | −0.67 | 0.22 | −0.68 | −0.37 | −0.33 | 0.55 | −0.55 |
| 31 | CTG | 0.28 | 0.64 | 0.26 | 0.08 | 0.65 | 0.53 | 0.74 | 0.54 | 0.72 | 0.76 | 0.68 | 0.65 |
| 32 | CTT | −0.41 | −0.45 | −0.22 | −0.50 | −0.21 | −0.46 | 0.27 | −0.50 | −0.42 | −0.52 | −0.34 | −0.52 |
| 33 | GAA | −0.27 | 0.18 | −0.33 | −0.07 | 0.07 | −0.39 | 0.18 | −0.25 | −0.24 | 0.16 | −0.25 | 0.05 |
| 34 | GAC | 0.26 | 0.34 | 0.16 | −0.22 | −0.50 | −0.57 | 0.00 | −0.61 | 0.28 | 0.45 | 0.30 | −0.16 |
| 35 | GAG | 0.45 | 0.78 | 0.36 | 0.27 | 0.42 | 0.41 | 0.71 | 0.49 | 0.04 | 0.37 | 0.46 | −0.08 |
| 36 | GAT | 0.07 | −0.02 | −0.19 | −0.08 | 0.55 | 0.64 | 0.79 | 0.39 | −0.40 | 0.22 | −0.12 | −0.01 |
| 37 | GCA | −0.09 | 0.21 | 0.15 | −0.18 | 0.18 | −0.04 | −0.05 | −0.15 | 0.25 | 0.20 | 0.45 | 0.16 |
| 38 | GCC | 0.31 | 0.40 | 0.55 | 0.13 | −0.41 | −0.27 | 0.35 | −0.54 | 0.45 | 0.55 | 0.58 | 0.13 |
| 39 | GCG | −0.04 | 0.58 | 0.23 | −0.19 | 0.09 | 0.47 | 0.27 | −0.17 | 0.14 | 0.40 | 0.19 | −0.19 |
| 40 | GCT | −0.21 | 0.10 | −0.24 | −0.53 | 0.14 | 0.34 | 0.68 | −0.25 | −0.54 | −0.38 | 0.00 | −0.58 |
| 41 | GGA | 0.13 | 0.49 | −0.21 | 0.15 | 0.50 | 0.35 | 0.30 | 0.64 | 0.16 | 0.73 | 0.66 | 0.62 |
| 42 | GGC | 0.10 | 0.07 | 0.18 | −0.07 | −0.63 | −0.46 | 0.15 | −0.57 | −0.17 | 0.22 | 0.19 | −0.36 |
| 43 | GGG | 0.37 | 0.70 | 0.38 | 0.38 | 0.37 | 0.66 | 0.86 | 0.68 | 0.19 | 0.58 | 0.62 | −0.02 |
| 44 | GGT | −0.32 | 0.14 | −0.56 | −0.51 | 0.61 | 0.82 | 0.75 | 0.39 | −0.59 | −0.53 | −0.37 | −0.57 |
| 45 | GTA | 0.14 | 0.11 | −0.38 | −0.19 | 0.28 | 0.05 | 0.07 | −0.30 | 0.38 | 0.11 | 0.66 | 0.46 |
| 46 | GTC | 0.26 | 0.44 | 0.50 | 0.03 | −0.46 | −0.57 | −0.05 | −0.64 | −0.22 | 0.55 | 0.16 | −0.34 |
| 47 | GTG | 0.35 | 0.60 | −0.03 | 0.03 | 0.67 | 0.61 | 0.71 | 0.64 | 0.79 | 0.65 | 0.55 | 0.62 |
| 48 | GTT | −0.21 | −0.34 | −0.28 | −0.26 | 0.37 | 0.42 | 0.73 | −0.18 | −0.51 | −0.40 | −0.36 | −0.53 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | −0.19 | 0.05 | 0.13 | −0.32 | −0.34 | −0.55 | −0.25 | −0.60 | 0.12 | 0.20 | 0.00 | 0.03 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.06 | 0.19 | −0.03 | 0.10 | 0.47 | 0.44 | 0.59 | 0.51 | −0.15 | −0.06 | −0.15 | 0.19 |
| 53 | TCA | 0.25 | −0.12 | 0.11 | −0.34 | 0.48 | −0.22 | 0.26 | −0.38 | −0.05 | 0.16 | 0.39 | 0.15 |
| 54 | TCC | 0.01 | 0.38 | 0.68 | −0.42 | −0.02 | −0.45 | 0.51 | −0.42 | 0.66 | 0.57 | 0.91 | −0.14 |
| 55 | TCG | 0.42 | 0.74 | 0.49 | 0.23 | 0.11 | 0.70 | 0.53 | 0.03 | 0.14 | 0.78 | 0.46 | −0.08 |
| 56 | TCT | −0.05 | 0.03 | −0.18 | −0.65 | 0.40 | 0.45 | 0.54 | −0.45 | −0.56 | −0.48 | 0.14 | −0.56 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.47 | 0.28 | −0.35 | 0.24 | −0.50 | −0.45 | −0.03 | −0.15 | −0.28 | 0.47 | 0.47 | 0.52 |
| 59 | TGG | −0.18 | 0.13 | −0.10 | 0.26 | 0.05 | −0.34 | 0.50 | 0.41 | −0.18 | 0.54 | −0.27 | 0.00 |

TABLE C.4-continued

CPW matrix *Bacillus subtilis* highly expressed sequences (left codon indicated in column 2, right codon indicated in row 2). Host cell: *B. subtilis*; Sequence data: full *B. subtilus* genome; Highly expressed group: 415 seqs.

|    |     |       |       |       |       |       |       |       |       |       |       |       |       |
|----|-----|-------|-------|-------|-------|-------|-------|-------|-------|-------|-------|-------|-------|
| 60 | TGT | 0.04  | −0.23 | −0.16 | −0.09 | 1.00  | 0.74  | 0.64  | 0.52  | −0.29 | −0.48 | −0.33 | 0.22  |
| 61 | TTA | 0.01  | 0.55  | 0.19  | 0.51  | 0.30  | 0.26  | 0.29  | −0.07 | −0.08 | 0.18  | 0.61  | 0.10  |
| 62 | TTC | −0.05 | 0.01  | 0.16  | 0.04  | −0.38 | −0.49 | −0.39 | −0.65 | −0.17 | 0.04  | 0.57  | −0.36 |
| 63 | TTG | −0.36 | 0.49  | 0.29  | −0.05 | 0.62  | 0.53  | 0.75  | 0.71  | 0.27  | 0.62  | 0.45  | 0.25  |
| 64 | TTT | 0.11  | 0.13  | −0.22 | −0.01 | 0.44  | 0.43  | 0.65  | 0.35  | 0.00  | −0.12 | 0.19  | 0.01  |

|    |     | GCA | GCC | GCG | GCT | GGA | GGC | GGG | GGT | GTA | GTC | GTG | GTT |
|----|-----|-----|-----|-----|-----|-----|-----|-----|-----|-----|-----|-----|-----|
|    |     | 37  | 38  | 39  | 40  | 41  | 42  | 43  | 44  | 45  | 46  | 47  | 48  |

|    |     | 49    | 50    | 51   | 52    | 53    | 54    | 55    | 56    | 57   | 58    | 59    | 60    |
|----|-----|-------|-------|------|-------|-------|-------|-------|-------|------|-------|-------|-------|
|    |     | TAA   | TAC   | TAG  | TAT   | TCA   | TCC   | TCG   | TCT   | TGA  | TGC   | TGG   | TGT   |
| 1  | AAA | 0.00  | −0.21 | 0.00 | 0.10  | −0.35 | 0.10  | −0.04 | 0.11  | 0.00 | −0.23 | −0.06 | −0.19 |
| 2  | AAC | 0.00  | −0.46 | 0.00 | −0.15 | −0.28 | −0.12 | 0.68  | −0.45 | 0.00 | −0.52 | −0.39 | −0.41 |
| 3  | AAG | 0.00  | −0.12 | 0.00 | 0.17  | 0.23  | 0.50  | 0.62  | 0.18  | 0.00 | 0.66  | 0.15  | 0.59  |
| 4  | AAT | 0.00  | 0.38  | 0.00 | 0.28  | 0.41  | 0.51  | 0.50  | 0.57  | 0.00 | 0.73  | 0.50  | 0.67  |
| 5  | ACA | 0.00  | −0.04 | 0.00 | 0.19  | −0.32 | −0.18 | 0.18  | 0.01  | 0.00 | −0.37 | 0.05  | 0.05  |
| 6  | ACC | 0.00  | 0.28  | 0.00 | 0.29  | 0.39  | 0.63  | 0.77  | 0.54  | 0.00 | −0.25 | 0.40  | 1.00  |
| 7  | ACG | 0.00  | −0.33 | 0.00 | 0.00  | 0.34  | 0.02  | 0.31  | 0.39  | 0.00 | 0.01  | 0.28  | 1.00  |
| 8  | ACT | 0.00  | −0.58 | 0.00 | 0.35  | −0.38 | −0.32 | 0.07  | −0.54 | 0.00 | 0.00  | −0.50 | −0.38 |
| 9  | AGA | 0.00  | 0.54  | 0.00 | 0.69  | 0.82  | 0.84  | −0.19 | 0.70  | 0.00 | 0.43  | −0.10 | −0.03 |
| 10 | AGC | 0.00  | −0.39 | 0.00 | −0.17 | −0.05 | 0.49  | 0.52  | −0.03 | 0.00 | 0.27  | −0.32 | −0.32 |
| 11 | AGG | 0.00  | 0.37  | 0.00 | 1.00  | 1.00  | 1.00  | −0.11 | 0.72  | 0.00 | 1.00  | 0.62  | 1.00  |
| 12 | AGT | 0.00  | 0.84  | 0.00 | 0.39  | −0.18 | 1.00  | −0.53 | −0.28 | 0.00 | 1.00  | 0.71  | 0.35  |
| 13 | ATA | 0.00  | 0.80  | 0.00 | −0.05 | 0.57  | 0.03  | 0.26  | 0.27  | 0.00 | 0.39  | 0.55  | 1.00  |
| 14 | ATC | 0.00  | −0.05 | 0.00 | 0.33  | 0.28  | 0.22  | 0.25  | 0.02  | 0.00 | 0.59  | 0.40  | −0.11 |
| 15 | ATG | 0.00  | −0.21 | 0.00 | 0.15  | 0.03  | −0.35 | 0.32  | 0.13  | 0.00 | −0.18 | 0.00  | 0.26  |
| 16 | ATT | 0.00  | −0.47 | 0.00 | 0.17  | −0.10 | −0.23 | 0.27  | −0.44 | 0.00 | −0.34 | −0.30 | −0.16 |
| 17 | CAA | 0.00  | −0.36 | 0.00 | −0.24 | −0.09 | 0.00  | −0.46 | −0.41 | 0.00 | −0.26 | −0.29 | −0.39 |
| 18 | CAC | 0.00  | −0.01 | 0.00 | −0.20 | 0.07  | 0.04  | 1.00  | 0.10  | 0.00 | 0.45  | −0.12 | −0.01 |
| 19 | CAG | 0.00  | 0.29  | 0.00 | 0.48  | 0.49  | 0.53  | 0.29  | −0.26 | 0.00 | 0.54  | 0.42  | 0.44  |
| 20 | CAT | 0.00  | 0.00  | 0.00 | 0.12  | −0.27 | 0.17  | 0.70  | −0.10 | 0.00 | −0.18 | 0.07  | 0.01  |
| 21 | CCA | 0.00  | −0.56 | 0.00 | −0.04 | −0.14 | 0.53  | 0.70  | −0.48 | 0.00 | −0.52 | −0.18 | −0.40 |
| 22 | CCC | 0.00  | 0.66  | 0.00 | 1.00  | 0.18  | 0.50  | −0.21 | 0.69  | 0.00 | 1.00  | 0.57  | 1.00  |
| 23 | CCG | 0.00  | 0.09  | 0.00 | 0.48  | −0.01 | 0.59  | 0.35  | −0.48 | 0.00 | 1.00  | 0.29  | 0.64  |
| 24 | CCT | 0.00  | −0.53 | 0.00 | −0.12 | 0.06  | 0.53  | 0.41  | −0.43 | 0.00 | −0.45 | −0.32 | −0.55 |
| 25 | CGA | 0.00  | 0.39  | 0.00 | 0.01  | 0.77  | 0.15  | 1.00  | 0.73  | 0.00 | −0.33 | 0.27  | −0.63 |
| 26 | CGC | 0.00  | −0.42 | 0.00 | −0.27 | −0.30 | 1.00  | 0.00  | −0.46 | 0.00 | −0.68 | −0.61 | −0.53 |
| 27 | CGG | 0.00  | 0.44  | 0.00 | 0.50  | 0.57  | 0.48  | 0.67  | 0.84  | 0.00 | 1.00  | 0.78  | 0.44  |
| 28 | CGT | 0.00  | −0.59 | 0.00 | −0.53 | −0.67 | 0.09  | −0.51 | −0.80 | 0.00 | 1.00  | 0.80  | 1.00  |
| 29 | CTA | 0.00  | −0.48 | 0.00 | −0.18 | 0.26  | 0.66  | −0.41 | −0.32 | 0.00 | −0.41 | −0.60 | −0.51 |
| 30 | CTC | 0.00  | 0.14  | 0.00 | 0.31  | 0.02  | 1.00  | 0.81  | 0.44  | 0.00 | 0.25  | 0.18  | 1.00  |
| 31 | CTG | 0.00  | 0.33  | 0.00 | −0.10 | −0.18 | 0.37  | 0.65  | −0.12 | 0.00 | 0.30  | 0.48  | 0.79  |
| 32 | CTT | 0.00  | −0.59 | 0.00 | −0.16 | −0.21 | −0.50 | −0.19 | −0.66 | 0.00 | −0.52 | 0.23  | 0.36  |
| 33 | GAA | 0.00  | −0.34 | 0.00 | 0.32  | −0.16 | 0.21  | −0.14 | 0.14  | 0.00 | 0.40  | 0.13  | −0.25 |
| 34 | GAC | 0.00  | −0.20 | 0.00 | 0.18  | 0.31  | 0.31  | 0.27  | 0.14  | 0.00 | −0.51 | −0.38 | 0.17  |
| 35 | GAG | 0.00  | 0.00  | 0.00 | −0.09 | 0.22  | 0.47  | 0.33  | 0.45  | 0.00 | −0.41 | −0.22 | 0.49  |
| 36 | GAT | 0.00  | −0.28 | 0.00 | 0.19  | −0.06 | −0.19 | 0.59  | 0.23  | 0.00 | 0.38  | 0.35  | 0.16  |
| 37 | GCA | 0.00  | −0.09 | 0.00 | 0.14  | 0.04  | −0.27 | 0.08  | 0.09  | 0.00 | −0.41 | −0.18 | 0.21  |
| 38 | GCC | 0.00  | 0.53  | 0.00 | 0.28  | 0.57  | 0.71  | 0.25  | 0.69  | 0.00 | −0.05 | 0.28  | 0.36  |
| 39 | GCG | 0.00  | −0.01 | 0.00 | 0.34  | 0.28  | 0.54  | 0.61  | 0.18  | 0.00 | 0.31  | 0.28  | 0.50  |
| 40 | GCT | 0.00  | −0.50 | 0.00 | −0.29 | −0.26 | −0.53 | −0.36 | −0.64 | 0.00 | 0.41  | −0.23 | −0.49 |
| 41 | GGA | 0.00  | −0.10 | 0.00 | 0.12  | 0.04  | 0.72  | 0.38  | 0.21  | 0.00 | 0.48  | 0.34  | 0.62  |
| 42 | GGC | 0.00  | −0.16 | 0.00 | −0.10 | 0.47  | 0.17  | 0.59  | 0.08  | 0.00 | −0.42 | −0.47 | −0.59 |
| 43 | GGG | 0.00  | 0.26  | 0.00 | 0.35  | 0.63  | 0.87  | 0.83  | 0.49  | 0.00 | 0.40  | 0.58  | 0.27  |
| 44 | GGT | 0.00  | 0.34  | 0.00 | −0.24 | −0.65 | 0.17  | −0.17 | −0.73 | 0.00 | 1.00  | 0.53  | 0.36  |
| 45 | GTA | 0.00  | −0.64 | 0.00 | −0.17 | −0.38 | −0.18 | −0.07 | −0.55 | 0.00 | −0.32 | −0.11 | −0.37 |
| 46 | GTC | 0.00  | 0.59  | 0.00 | 0.53  | 0.61  | 0.79  | 0.28  | 0.60  | 0.00 | −0.19 | 0.23  | 0.10  |
| 47 | GTG | 0.00  | −0.08 | 0.00 | 0.41  | 0.18  | 0.50  | 0.46  | 0.29  | 0.00 | 0.51  | 0.15  | 0.70  |
| 48 | GTT | 0.00  | −0.33 | 0.00 | −0.03 | −0.12 | −0.23 | 0.26  | −0.53 | 0.00 | 0.21  | −0.21 | −0.33 |
| 49 | TAA | 0.00  | 0.00  | 0.00 | 0.00  | 0.00  | 0.00  | 0.00  | 0.00  | 0.00 | 0.00  | 0.00  | 0.00  |
| 50 | TAC | 0.00  | −0.13 | 0.00 | 0.21  | 0.41  | −0.07 | 0.09  | −0.44 | 0.00 | −0.17 | −0.09 | −0.49 |
| 51 | TAG | 0.00  | 0.00  | 0.00 | 0.00  | 0.00  | 0.00  | 0.00  | 0.00  | 0.00 | 0.00  | 0.00  | 0.00  |
| 52 | TAT | 0.00  | 0.04  | 0.00 | −0.08 | −0.06 | −0.13 | −0.18 | 0.16  | 0.00 | 0.57  | 0.05  | −0.04 |
| 53 | TCA | 0.00  | −0.31 | 0.00 | 0.57  | 0.32  | 0.26  | 0.38  | −0.19 | 0.00 | −0.29 | −0.03 | 0.43  |
| 54 | TCC | 0.00  | −0.37 | 0.00 | 0.29  | 0.26  | 0.33  | −0.12 | 0.02  | 0.00 | 0.14  | 1.00  | 0.48  |
| 55 | TCG | 0.00  | 0.50  | 0.00 | 0.64  | 0.69  | 0.72  | 0.64  | 0.29  | 0.00 | 0.45  | 0.40  | 1.00  |
| 56 | TCT | 0.00  | −0.42 | 0.00 | −0.19 | −0.38 | −0.35 | 0.47  | −0.54 | 0.00 | −0.38 | −0.38 | −0.49 |
| 57 | TGA | 0.00  | 0.00  | 0.00 | 0.00  | 0.00  | 0.00  | 0.00  | 0.00  | 0.00 | 0.00  | 0.00  | 0.00  |
| 58 | TGC | 0.00  | 0.13  | 0.00 | −0.20 | 0.11  | −0.18 | −0.03 | −0.01 | 0.00 | −0.55 | 1.00  | −0.26 |
| 59 | TGG | 0.00  | 0.20  | 0.00 | −0.09 | 0.89  | 0.81  | 0.26  | −0.31 | 0.00 | −0.34 | 0.00  | 0.63  |

TABLE C.4-continued

CPW matrix *Bacillus subtilis* highly expressed sequences (left codon indicated in column 2, right codon indicated in row 2). Host cell: *B. subtilus*; Sequence data: full *B. subtilus* genome; Highly expressed group: 415 seqs.

| | | | | | | | | | | | | | |
|---|---|---|---|---|---|---|---|---|---|---|---|---|---|
| 60 | TGT | 0.00 | 0.65 | 0.00 | −0.12 | −0.38 | 0.02 | −0.20 | 0.08 | 0.00 | 1.00 | −0.55 | 1.00 |
| 61 | TTA | 0.00 | 0.34 | 0.00 | 0.33 | −0.29 | −0.27 | 0.23 | −0.31 | 0.00 | −0.54 | 0.05 | 1.00 |
| 62 | TTC | 0.00 | −0.57 | 0.00 | −0.13 | −0.46 | 0.07 | −0.24 | −0.57 | 0.00 | −0.18 | −0.52 | −0.33 |
| 63 | TTG | 0.00 | 0.16 | 0.00 | 0.60 | 0.34 | 0.78 | 0.58 | 0.11 | 0.00 | −0.27 | −0.45 | 0.33 |
| 64 | TTT | 0.00 | 0.25 | 0.00 | 0.27 | 0.25 | 0.35 | 0.59 | 0.11 | 0.00 | 0.23 | 0.51 | 0.07 |

| | | TAA 49 | TAC 50 | TAG 51 | TAT 52 | TCA 53 | TCC 54 | TCG 55 | TCT 56 | TGA 57 | TGC 58 | TGG 59 | TGT 60 |
|---|---|---|---|---|---|---|---|---|---|---|---|---|---|

| | | 61 TTA | 62 TTC | 63 TTG | 64 TTT |
|---|---|---|---|---|---|
| 1 | AAA | 0.32 | −0.44 | 0.42 | 0.38 |
| 2 | AAC | 0.12 | −0.58 | 0.11 | −0.10 |
| 3 | AAG | 0.70 | −0.02 | 0.66 | −0.03 |
| 4 | AAT | 0.32 | −0.14 | 0.52 | 0.66 |
| 5 | ACA | 0.01 | −0.33 | −0.32 | 0.04 |
| 6 | ACC | 0.07 | −0.04 | 0.36 | 0.34 |
| 7 | ACG | 0.30 | −0.34 | 0.43 | −0.06 |
| 8 | ACT | −0.34 | 0.30 | 0.04 | 0.56 |
| 9 | AGA | 0.43 | 0.31 | 0.27 | 0.68 |
| 10 | AGC | 0.42 | −0.29 | 0.33 | −0.13 |
| 11 | AGG | 0.53 | 0.53 | 1.00 | 0.67 |
| 12 | AGT | −0.12 | 0.36 | 0.19 | 0.39 |
| 13 | ATA | −0.10 | −0.41 | −0.35 | 0.42 |
| 14 | ATC | 0.05 | −0.36 | 0.27 | 0.36 |
| 15 | ATG | 0.80 | −0.41 | 0.86 | 0.33 |
| 16 | ATT | −0.41 | −0.49 | −0.30 | 0.35 |
| 17 | CAA | 0.16 | −0.33 | 0.10 | −0.05 |
| 18 | CAC | −0.40 | −0.43 | −0.25 | 0.18 |
| 19 | CAG | 0.67 | 0.06 | 0.63 | 0.27 |
| 20 | CAT | −0.37 | −0.18 | −0.43 | 0.19 |
| 21 | CCA | −0.04 | −0.60 | −0.42 | −0.30 |
| 22 | CCC | 0.78 | 1.00 | 0.44 | 0.61 |
| 23 | CCG | 0.32 | −0.08 | 0.71 | 0.01 |
| 24 | CCT | −0.09 | 0.22 | 0.04 | 0.35 |
| 25 | CGA | 0.55 | −0.37 | 1.00 | −0.15 |
| 26 | CGC | −0.05 | −0.48 | −0.30 | −0.09 |
| 27 | CGG | 0.63 | 0.86 | 0.88 | 0.15 |
| 28 | CGT | −0.48 | −0.71 | −0.51 | −0.12 |
| 29 | CTA | −0.47 | −0.69 | −0.49 | −0.15 |
| 30 | CTC | 0.54 | −0.18 | −0.14 | 0.53 |
| 31 | CTG | 0.39 | −0.31 | 0.50 | −0.04 |
| 32 | CTT | −0.22 | 0.02 | −0.19 | 0.66 |
| 33 | GAA | 0.37 | −0.33 | 0.26 | 0.16 |
| 34 | GAC | 0.08 | −0.38 | 0.00 | 0.34 |
| 35 | GAG | 0.46 | 0.14 | 0.67 | 0.09 |
| 36 | GAT | −0.09 | −0.26 | −0.41 | 0.14 |
| 37 | GCA | −0.09 | −0.30 | 0.04 | 0.13 |
| 38 | GCC | 0.53 | 0.15 | −0.07 | 0.20 |
| 39 | GCG | 0.10 | −0.05 | 0.70 | −0.16 |
| 40 | GCT | −0.40 | −0.15 | −0.12 | 0.16 |
| 41 | GGA | 0.17 | −0.23 | −0.01 | 0.35 |
| 42 | GGC | 0.18 | −0.46 | 0.11 | 0.25 |
| 43 | GGG | 0.87 | 0.53 | 0.59 | 0.52 |
| 44 | GGT | −0.37 | −0.50 | −0.52 | −0.23 |
| 45 | GTA | −0.37 | −0.69 | −0.34 | −0.14 |
| 46 | GTC | 0.74 | 0.24 | 0.43 | 0.29 |
| 47 | GTG | 0.36 | 0.30 | 0.62 | 0.01 |
| 48 | GTT | −0.14 | 0.05 | −0.15 | 0.30 |
| 49 | TAA | 0.00 | 0.00 | 0.00 | 0.00 |
| 50 | TAC | 0.08 | −0.28 | 0.03 | −0.11 |
| 51 | TAG | 0.00 | 0.00 | 0.00 | 0.00 |
| 52 | TAT | −0.22 | −0.25 | −0.50 | 0.32 |
| 53 | TCA | −0.43 | 0.07 | 0.21 | −0.12 |
| 54 | TCC | 0.39 | 0.09 | −0.30 | 0.51 |
| 55 | TCG | 0.35 | 0.17 | 0.50 | −0.20 |
| 56 | TCT | −0.29 | −0.49 | 0.02 | 0.39 |
| 57 | TGA | 0.00 | 0.00 | 0.00 | 0.00 |
| 58 | TGC | −0.17 | −0.47 | 0.49 | 0.11 |
| 59 | TGG | 0.51 | −0.18 | 0.63 | 0.11 |
| 60 | TGT | 0.51 | 0.23 | −0.36 | 0.28 |

TABLE C.4-continued

CPW matrix *Bacillus subtilis* highly expressed sequences (left codon indicated in column 2, right codon indicated in row 2). Host cell: *B. subtilus*; Sequence data: full *B. subtilus* genome; Highly expressed group: 415 seqs.

| | | | | | |
|---|---|---|---|---|---|
| 61 | TTA | 0.34 | −0.22 | 0.49 | 0.16 |
| 62 | TTC | −0.41 | −0.67 | −0.23 | −0.18 |
| 63 | TTG | 0.33 | −0.49 | 0.71 | −0.13 |
| 64 | TTT | −0.29 | −0.05 | −0.05 | 0.58 |
| | | TTA | TTC | TTG | TTT |
| | | 61 | 62 | 63 | 64 |

TABLE C.5

CPW matrix *Escherichia coli* K12 full genome (left codon indicated in column 2, right codon indicated in row 2). Host cell: *E. coli*; Sequence data: full *E. coli* genome.

| | | 1 AAA | 2 AAC | 3 AAG | 4 AAT | 5 ACA | 6 ACC | 7 ACG | 8 ACT | 9 AGA | 10 AGC | 11 AGG | 12 AGT |
|---|---|---|---|---|---|---|---|---|---|---|---|---|---|
| 1 | AAA | 0.19 | 0.01 | −0.04 | −0.10 | −0.31 | −0.06 | −0.24 | 0.18 | −0.03 | 0.08 | 0.20 | 0.07 |
| 2 | AAC | 0.13 | 0.09 | 0.01 | 0.25 | 0.38 | −0.08 | 0.34 | 0.18 | −0.32 | −0.41 | −0.33 | −0.36 |
| 3 | AAG | −0.35 | 0.14 | −0.17 | 0.17 | 0.15 | 0.53 | 0.47 | 0.58 | −0.17 | 0.14 | −0.12 | −0.13 |
| 4 | AAT | −0.13 | −0.10 | −0.05 | −0.24 | 0.04 | −0.23 | −0.04 | −0.14 | 0.27 | 0.16 | 0.47 | 0.15 |
| 5 | ACA | −0.19 | 0.32 | −0.21 | −0.05 | −0.52 | 0.20 | −0.27 | −0.07 | −0.37 | 0.66 | −0.54 | 0.43 |
| 6 | ACC | −0.21 | −0.29 | 0.08 | −0.19 | 0.01 | −0.25 | −0.17 | −0.26 | −0.10 | −0.47 | −0.06 | −0.39 |
| 7 | ACG | 0.41 | 0.74 | 0.28 | 0.55 | 0.10 | 0.52 | 0.23 | 0.40 | 0.68 | 0.91 | 0.50 | 0.88 |
| 8 | ACT | 0.01 | −0.36 | 0.20 | 0.00 | 0.37 | 0.11 | 0.24 | 0.28 | 0.83 | 0.87 | 0.93 | 0.85 |
| 9 | AGA | −0.41 | 0.01 | −0.53 | −0.59 | −0.74 | −0.22 | −0.50 | 0.02 | −0.85 | 0.41 | −0.72 | −0.59 |
| 10 | AGC | −0.21 | −0.05 | −0.22 | −0.21 | 0.24 | 0.23 | 0.28 | 0.33 | 0.07 | −0.10 | −0.29 | −0.27 |
| 11 | AGG | 0.11 | 0.43 | −0.46 | −0.05 | −0.49 | 0.70 | 0.29 | 0.11 | −0.67 | 0.51 | −0.04 | −0.31 |
| 12 | AGT | −0.28 | −0.19 | −0.42 | −0.41 | 0.06 | 0.16 | 0.03 | 0.20 | 0.41 | 0.05 | 0.71 | 0.02 |
| 13 | ATA | −0.39 | 0.15 | −0.34 | −0.35 | −0.45 | −0.16 | −0.23 | −0.24 | −0.74 | −0.13 | −0.70 | 0.02 |
| 14 | ATC | −0.03 | −0.25 | −0.12 | 0.06 | 0.50 | −0.34 | 0.44 | −0.32 | 0.07 | −0.36 | −0.46 | −0.34 |
| 15 | ATG | 0.11 | 0.01 | −0.27 | −0.01 | 0.22 | −0.04 | −0.12 | 0.18 | 0.62 | −0.03 | 0.28 | −0.06 |
| 16 | ATT | 0.16 | 0.15 | 0.02 | 0.16 | 0.49 | −0.02 | 0.38 | −0.05 | 0.47 | 0.43 | 0.86 | 0.58 |
| 17 | CAA | −0.34 | −0.34 | −0.31 | −0.35 | −0.39 | −0.27 | −0.37 | −0.25 | 0.08 | −0.38 | 0.04 | −0.45 |
| 18 | CAC | 0.17 | −0.10 | 0.13 | 0.12 | 0.36 | −0.19 | 0.38 | −0.02 | 0.44 | −0.36 | 0.10 | −0.41 |
| 19 | CAG | 0.28 | 0.22 | 0.22 | 0.34 | 0.04 | 0.35 | 0.13 | 0.25 | 0.60 | 0.30 | 0.52 | 0.34 |
| 20 | CAT | −0.12 | −0.13 | −0.05 | 0.19 | 0.20 | −0.13 | 0.10 | −0.10 | 0.16 | 0.28 | 0.90 | 0.47 |
| 21 | CCA | −0.19 | −0.16 | 0.11 | −0.18 | −0.56 | −0.28 | −0.44 | −0.12 | −0.35 | 0.25 | 0.31 | 0.39 |
| 22 | CCC | 0.13 | −0.21 | 0.47 | −0.38 | −0.23 | −0.04 | 0.11 | −0.01 | −0.59 | −0.51 | −0.52 | −0.28 |
| 23 | CCG | −0.11 | 0.10 | −0.06 | 0.22 | −0.16 | 0.31 | −0.08 | 0.10 | 0.72 | 0.56 | 0.75 | 0.59 |
| 24 | CCT | 0.39 | −0.04 | 0.40 | 0.18 | 0.19 | 0.40 | 0.41 | 0.29 | 0.93 | 0.87 | 0.88 | 0.91 |
| 25 | CGA | −0.08 | 0.50 | 0.12 | −0.19 | −0.42 | −0.10 | 0.03 | −0.17 | −0.33 | 0.25 | −0.42 | 0.35 |
| 26 | CGC | 0.18 | 0.21 | −0.07 | −0.04 | −0.08 | −0.01 | 0.14 | 0.05 | −0.10 | −0.33 | −0.28 | −0.42 |
| 27 | CGG | 0.55 | 0.79 | 0.18 | 0.71 | −0.41 | 0.60 | 0.20 | 0.25 | 0.05 | 0.79 | 0.02 | 0.43 |
| 28 | CGT | −0.07 | −0.20 | −0.30 | −0.24 | 0.25 | −0.11 | 0.34 | −0.33 | 0.67 | 0.06 | 0.63 | 0.20 |
| 29 | CTA | −0.41 | −0.01 | −0.21 | −0.18 | −0.38 | −0.10 | −0.11 | 0.05 | −0.51 | −0.27 | −0.54 | −0.38 |
| 30 | CTC | 0.19 | −0.50 | −0.11 | −0.55 | 0.25 | −0.33 | 0.32 | −0.35 | −0.24 | −0.06 | −0.55 | −0.24 |
| 31 | CTG | −0.09 | 0.29 | 0.06 | 0.14 | 0.00 | 0.09 | −0.10 | 0.09 | 0.75 | 0.60 | 0.59 | 0.56 |
| 32 | CTT | 0.34 | −0.26 | −0.16 | −0.43 | 0.43 | 0.22 | 0.55 | 0.09 | 0.39 | −0.16 | 0.65 | 0.43 |
| 33 | GAA | 0.00 | −0.14 | 0.18 | −0.03 | −0.21 | −0.21 | −0.24 | 0.11 | 0.09 | −0.13 | −0.15 | −0.17 |
| 34 | GAC | 0.01 | −0.03 | 0.01 | 0.25 | 0.21 | −0.19 | 0.12 | 0.00 | −0.68 | −0.58 | −0.71 | −0.52 |
| 35 | GAG | −0.04 | 0.25 | −0.21 | 0.20 | 0.05 | 0.87 | 0.03 | 0.56 | 0.06 | 0.07 | 0.01 | −0.05 |
| 36 | GAT | −0.02 | −0.20 | 0.05 | 0.18 | 0.25 | −0.13 | 0.16 | 0.10 | 0.53 | 0.23 | 0.77 | 0.51 |
| 37 | GCA | −0.21 | 0.18 | 0.10 | 0.14 | −0.44 | −0.02 | −0.44 | 0.01 | −0.36 | 0.34 | −0.52 | 0.27 |
| 38 | GCC | 0.12 | −0.23 | 0.62 | −0.26 | −0.01 | −0.11 | −0.11 | −0.12 | −0.74 | −0.65 | −0.60 | −0.65 |
| 39 | GCG | −0.09 | 0.44 | −0.27 | 0.24 | −0.19 | 0.34 | −0.07 | 0.29 | 0.40 | 0.67 | 0.38 | 0.65 |
| 40 | GCT | 0.14 | −0.41 | 0.37 | −0.08 | 0.27 | 0.30 | 0.32 | 0.22 | 0.85 | 0.85 | 0.70 | 0.91 |
| 41 | GGA | −0.15 | 0.36 | 0.10 | −0.31 | −0.62 | 0.05 | −0.54 | −0.24 | −0.72 | −0.01 | −0.52 | −0.40 |
| 42 | GGC | 0.10 | −0.01 | 0.02 | −0.08 | −0.01 | −0.04 | 0.04 | −0.01 | −0.36 | −0.31 | −0.50 | −0.34 |
| 43 | GGG | 0.24 | 0.72 | 0.33 | 0.15 | −0.24 | 0.72 | −0.05 | 0.05 | 0.07 | 0.63 | 0.46 | 0.16 |
| 44 | GGT | −0.16 | −0.15 | −0.11 | −0.10 | 0.19 | 0.58 | −0.27 | −0.25 | 0.50 | 0.05 | 0.76 | 0.32 |
| 45 | GTA | −0.27 | 0.15 | 0.21 | −0.05 | −0.22 | 0.22 | −0.33 | −0.05 | −0.54 | 0.22 | −0.29 | 0.09 |
| 46 | GTC | 0.29 | 0.03 | 0.67 | −0.25 | −0.03 | −0.37 | −0.10 | −0.47 | −0.59 | −0.59 | −0.68 | −0.58 |
| 47 | GTG | −0.16 | 0.41 | −0.30 | 0.05 | 0.10 | 0.26 | −0.16 | 0.04 | 0.29 | 0.43 | 0.33 | 0.20 |
| 48 | GTT | 0.25 | −0.31 | −0.02 | −0.08 | 0.44 | 0.23 | 0.44 | 0.11 | 0.58 | 0.46 | 0.84 | 0.58 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | −0.11 | −0.40 | 0.02 | 0.39 | 0.29 | −0.43 | 0.41 | −0.02 | 0.02 | −0.48 | 0.11 | −0.24 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.05 | −0.16 | 0.12 | 0.55 | 0.52 | −0.20 | 0.38 | 0.49 | 0.65 | 0.31 | 0.72 | 0.67 |
| 53 | TCA | −0.08 | 0.36 | 0.11 | 0.21 | −0.56 | −0.08 | −0.43 | −0.04 | −0.23 | 0.62 | −0.47 | 0.44 |
| 54 | TCC | 0.50 | −0.12 | 0.56 | 0.25 | −0.17 | −0.38 | −0.16 | −0.39 | −0.33 | −0.58 | −0.47 | −0.53 |
| 55 | TCG | 0.05 | 0.53 | 0.06 | 0.38 | −0.16 | 0.28 | −0.14 | 0.39 | 0.67 | 0.75 | 0.65 | 0.70 |
| 56 | TCT | 0.45 | −0.24 | 0.46 | 0.31 | 0.18 | −0.07 | 0.28 | −0.07 | 0.83 | 0.97 | 0.70 | 0.92 |
| 57 | TGA | 0.00 | 0.00 | 0.00 | 0.00 | 0.00 | 0.00 | 0.00 | 0.00 | 0.00 | 0.00 | 0.00 | 0.00 |

TABLE C.5-continued

CPW matrix *Escherichia coli* K12 full genome (left codon indicated in column 2, right codon indicated in row 2). Host cell: *E. coli*; Sequence data: full *E. coli* genome.

| | | | | | | | | | | | | |
|---|---|---|---|---|---|---|---|---|---|---|---|---|
| 58 | TGC | 0.05 | 0.36 | 0.49 | 0.08 | 0.11 | 0.02 | 0.46 | 0.27 | −0.15 | 0.22 | −0.26 | 0.32 |
| 59 | TGG | 0.06 | 0.02 | −0.16 | −0.03 | −0.21 | 0.27 | −0.28 | 0.13 | 0.57 | 0.15 | 0.97 | −0.09 |
| 60 | TGT | −0.14 | −0.11 | −0.22 | −0.33 | −0.16 | −0.13 | −0.24 | −0.29 | 0.51 | 0.30 | 0.64 | 0.23 |
| 61 | TTA | −0.07 | 0.42 | 0.10 | −0.15 | −0.11 | −0.33 | −0.40 | −0.15 | −0.51 | −0.47 | −0.46 | −0.59 |
| 62 | TTC | 0.01 | 0.03 | 0.12 | 0.22 | 0.49 | −0.15 | 0.44 | −0.23 | −0.24 | −0.25 | −0.63 | −0.11 |
| 63 | TTG | 0.20 | 0.55 | 0.14 | 0.08 | 0.30 | 0.38 | 0.12 | 0.31 | 0.34 | 0.23 | 0.23 | −0.20 |
| 64 | TTT | −0.04 | −0.10 | 0.04 | −0.05 | 0.49 | −0.25 | 0.35 | −0.22 | 0.44 | 0.31 | 0.83 | 0.38 |

| | | AAA 1 | AAC 2 | AAG 3 | AAT 4 | ACA 5 | ACC 6 | ACG 7 | ACT 8 | AGA 9 | AGC 10 | AGG 11 | AGT 12 |
|---|---|---|---|---|---|---|---|---|---|---|---|---|---|

| | | 13 ATA | 14 ATC | 15 ATG | 16 ATT | 17 CAA | 18 CAC | 19 CAG | 20 CAT | 21 CCA | 22 CCC | 23 CCG | 24 CCT |
|---|---|---|---|---|---|---|---|---|---|---|---|---|---|
| 1 | AAA | −0.42 | −0.08 | 0.05 | 0.20 | 0.14 | 0.12 | 0.20 | 0.12 | 0.16 | 0.04 | 0.07 | 0.10 |
| 2 | AAC | 0.54 | 0.11 | 0.22 | 0.31 | 0.48 | −0.11 | −0.02 | 0.09 | 0.10 | 0.30 | −0.18 | 0.29 |
| 3 | AAG | −0.33 | −0.03 | −0.14 | −0.02 | −0.42 | −0.26 | −0.34 | −0.30 | −0.41 | −0.29 | −0.16 | −0.11 |
| 4 | AAT | 0.04 | −0.26 | −0.21 | −0.22 | −0.08 | −0.03 | −0.19 | 0.03 | 0.01 | −0.08 | 0.05 | −0.03 |
| 5 | ACA | −0.45 | 0.39 | −0.09 | 0.31 | −0.39 | 0.21 | 0.12 | 0.06 | −0.49 | −0.25 | −0.20 | −0.38 |
| 6 | ACC | 0.38 | −0.29 | −0.09 | −0.19 | 0.46 | −0.04 | 0.21 | 0.24 | 0.52 | 0.61 | 0.68 | 0.58 |
| 7 | ACG | −0.01 | 0.61 | −0.04 | 0.33 | −0.45 | −0.03 | 0.04 | −0.07 | −0.67 | −0.29 | −0.47 | −0.39 |
| 8 | ACT | 0.34 | −0.25 | 0.39 | −0.13 | 0.03 | −0.42 | −0.29 | −0.03 | 0.52 | 0.08 | 0.35 | 0.34 |
| 9 | AGA | −0.74 | 0.38 | −0.11 | −0.01 | −0.12 | 0.56 | 0.42 | 0.02 | 0.03 | −0.33 | 0.21 | −0.14 |
| 10 | AGC | 0.41 | 0.25 | 0.31 | 0.12 | 0.47 | −0.20 | −0.40 | −0.21 | 0.35 | 0.51 | 0.07 | 0.53 |
| 11 | AGG | −0.72 | 0.24 | −0.14 | 0.28 | −0.47 | 0.40 | −0.13 | −0.03 | −0.51 | −0.42 | −0.30 | −0.19 |
| 12 | AGT | 0.13 | 0.04 | −0.01 | −0.13 | 0.49 | 0.19 | −0.20 | 0.04 | 0.48 | 0.45 | 0.36 | 0.42 |
| 13 | ATA | −0.64 | 0.32 | −0.13 | 0.30 | −0.23 | 0.18 | 0.14 | 0.23 | 0.07 | −0.44 | 0.23 | −0.17 |
| 14 | ATC | 0.68 | −0.20 | −0.04 | 0.19 | 0.66 | −0.08 | 0.12 | 0.25 | 0.30 | −0.24 | 0.01 | −0.06 |
| 15 | ATG | 0.06 | −0.08 | 0.00 | 0.07 | 0.09 | −0.12 | −0.04 | 0.10 | −0.14 | 0.06 | 0.05 | −0.02 |
| 16 | ATT | 0.45 | −0.14 | 0.05 | −0.02 | 0.30 | −0.10 | −0.35 | −0.11 | 0.14 | −0.28 | 0.12 | −0.26 |
| 17 | CAA | −0.48 | −0.29 | −0.06 | −0.21 | −0.31 | 0.07 | 0.23 | −0.12 | 0.02 | −0.23 | −0.05 | −0.26 |
| 18 | CAC | 0.55 | 0.15 | 0.40 | 0.16 | 0.68 | 0.00 | 0.11 | 0.09 | 0.39 | 0.44 | 0.22 | 0.23 |
| 19 | CAG | −0.08 | 0.24 | 0.03 | 0.20 | −0.28 | 0.15 | 0.21 | −0.07 | −0.19 | 0.35 | 0.10 | 0.04 |
| 20 | CAT | 0.26 | −0.11 | −0.23 | −0.17 | −0.04 | −0.02 | −0.25 | −0.05 | −0.07 | −0.21 | −0.16 | −0.30 |
| 21 | CCA | −0.35 | 0.03 | −0.22 | 0.13 | −0.45 | −0.05 | 0.04 | 0.06 | −0.37 | 0.18 | −0.15 | −0.11 |
| 22 | CCC | −0.51 | −0.35 | 0.51 | −0.28 | 0.75 | 0.44 | 0.59 | 0.21 | 0.65 | 0.16 | 0.74 | 0.11 |
| 23 | CCG | −0.17 | 0.28 | −0.17 | −0.08 | −0.35 | −0.09 | −0.10 | −0.14 | −0.47 | 0.12 | −0.02 | 0.09 |
| 24 | CCT | −0.01 | 0.03 | 0.63 | 0.25 | 0.67 | 0.41 | 0.66 | 0.05 | 0.18 | −0.20 | 0.53 | 0.04 |
| 25 | CGA | −0.57 | 0.13 | −0.47 | −0.25 | −0.33 | 0.35 | 0.29 | −0.12 | −0.37 | −0.24 | −0.06 | −0.51 |
| 26 | CGC | 0.40 | 0.14 | 0.31 | −0.03 | 0.68 | 0.01 | −0.21 | −0.10 | 0.24 | 0.11 | −0.10 | 0.18 |
| 27 | CGG | −0.62 | 0.23 | −0.61 | −0.10 | −0.40 | 0.39 | −0.10 | −0.01 | 0.24 | 0.40 | 0.83 | 0.06 |
| 28 | CGT | 0.46 | 0.07 | 0.25 | −0.14 | 0.65 | −0.02 | −0.24 | −0.03 | 0.13 | 0.36 | −0.23 | 0.02 |
| 29 | CTA | −0.25 | 0.24 | 0.05 | 0.07 | −0.71 | −0.36 | −0.29 | −0.39 | −0.40 | −0.60 | −0.41 | −0.52 |
| 30 | CTC | 0.48 | 0.17 | 0.72 | 0.30 | 0.81 | 0.40 | 0.46 | 0.42 | 0.86 | −0.10 | 0.72 | 0.42 |
| 31 | CTG | 0.13 | 0.21 | −0.09 | −0.01 | −0.40 | 0.08 | 0.71 | −0.09 | 0.06 | 0.17 | 0.10 | 0.17 |
| 32 | CTT | 0.27 | −0.21 | 0.75 | 0.15 | 0.70 | 0.39 | 0.30 | 0.08 | 0.53 | −0.30 | 0.49 | −0.20 |
| 33 | GAA | −0.25 | −0.04 | 0.20 | 0.18 | 0.07 | 0.25 | 0.33 | 0.16 | 0.36 | −0.03 | 0.09 | 0.02 |
| 34 | GAC | 0.63 | 0.19 | 0.29 | 0.37 | 0.45 | −0.07 | −0.08 | 0.04 | 0.38 | 0.35 | −0.09 | 0.42 |
| 35 | GAG | −0.32 | −0.22 | −0.31 | 0.06 | −0.43 | −0.33 | −0.29 | −0.29 | −0.42 | 0.65 | −0.24 | −0.18 |
| 36 | GAT | 0.33 | −0.26 | −0.15 | −0.10 | −0.03 | −0.19 | −0.07 | 0.19 | 0.10 | −0.23 | −0.07 | −0.11 |
| 37 | GCA | −0.33 | 0.24 | −0.13 | 0.18 | −0.32 | 0.22 | 0.14 | 0.14 | −0.40 | 0.07 | −0.35 | −0.29 |
| 38 | GCC | 0.29 | −0.02 | 0.36 | −0.19 | 0.66 | 0.17 | 0.27 | 0.18 | 0.54 | 0.04 | 0.60 | 0.33 |
| 39 | GCG | −0.27 | 0.36 | −0.31 | −0.13 | −0.42 | −0.13 | −0.17 | −0.18 | −0.43 | 0.31 | −0.13 | 0.03 |
| 40 | GCT | 0.24 | −0.27 | 0.59 | 0.00 | 0.57 | −0.22 | 0.09 | 0.02 | 0.38 | −0.05 | 0.19 | 0.28 |
| 41 | GGA | −0.61 | 0.61 | −0.37 | 0.02 | −0.35 | −0.01 | 0.13 | −0.29 | −0.33 | 0.13 | −0.20 | 0.10 |
| 42 | GGC | 0.34 | 0.27 | 0.19 | 0.01 | 0.82 | 0.54 | 0.53 | 0.53 | 0.29 | 0.24 | 0.01 | 0.44 |
| 43 | GGG | −0.47 | −0.28 | −0.43 | −0.28 | −0.73 | 0.10 | −0.45 | −0.50 | −0.67 | 0.72 | −0.52 | −0.02 |
| 44 | GGT | 0.43 | −0.01 | 0.30 | −0.09 | 0.40 | −0.32 | −0.24 | −0.19 | 0.39 | 0.64 | 0.10 | 0.33 |
| 45 | GTA | −0.04 | 0.52 | −0.11 | 0.41 | −0.34 | 0.07 | −0.33 | −0.10 | −0.15 | −0.09 | −0.36 | −0.12 |
| 46 | GTC | 0.26 | 0.02 | 0.30 | −0.13 | 0.86 | 0.42 | 0.45 | 0.16 | 0.76 | 0.18 | 0.62 | 0.31 |
| 47 | GTG | −0.05 | −0.01 | −0.35 | −0.20 | −0.13 | 0.36 | −0.20 | −0.18 | −0.19 | 0.28 | −0.21 | −0.01 |
| 48 | GTT | 0.47 | −0.22 | 0.59 | 0.13 | 0.59 | −0.31 | −0.13 | −0.07 | 0.42 | −0.27 | 0.03 | −0.30 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.44 | −0.20 | 0.13 | 0.17 | 0.65 | 0.02 | 0.17 | 0.24 | 0.35 | 0.10 | 0.15 | 0.30 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.03 | −0.19 | −0.09 | 0.17 | −0.03 | −0.37 | −0.27 | 0.25 | 0.18 | −0.35 | −0.19 | −0.03 |
| 53 | TCA | −0.54 | 0.28 | −0.33 | 0.17 | −0.39 | 0.13 | 0.26 | 0.19 | −0.45 | −0.38 | −0.33 | −0.28 |
| 54 | TCC | 0.08 | −0.28 | 0.22 | −0.10 | 0.73 | 0.22 | 0.39 | 0.41 | 0.35 | −0.16 | 0.42 | −0.06 |
| 55 | TCG | −0.38 | 0.29 | −0.43 | −0.17 | −0.49 | 0.11 | 0.01 | −0.01 | −0.62 | −0.34 | −0.31 | −0.23 |
| 56 | TCT | −0.08 | −0.21 | 0.41 | −0.12 | 0.47 | −0.32 | 0.33 | 0.12 | 0.14 | −0.14 | 0.07 | −0.14 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.13 | 0.27 | 0.19 | 0.10 | 0.48 | −0.19 | −0.28 | −0.13 | −0.02 | 0.43 | −0.35 | 0.09 |
| 59 | TGG | −0.49 | 0.01 | 0.00 | 0.12 | −0.09 | 0.08 | 0.05 | −0.06 | 0.10 | 0.26 | −0.06 | −0.09 |
| 60 | TGT | −0.22 | −0.10 | −0.19 | −0.24 | 0.71 | 0.32 | −0.16 | 0.17 | 0.52 | 0.62 | 0.09 | 0.38 |

TABLE C.5-continued

CPW matrix *Escherichia coli* K12 full genome (left codon indicated in column 2, right codon indicated in row 2). Host cell: *E. coli*; Sequence data: full *E. coli* genome.

| | | TTA | TTC | TTG | TTT | | | | | | | | |
|---|---|---|---|---|---|---|---|---|---|---|---|---|---|
| 61 | TTA | −0.27 | −0.06 | −0.25 | −0.20 | −0.31 | 0.11 | −0.24 | 0.03 | 0.09 | −0.57 | −0.21 | −0.36 |
| 62 | TTC | 0.68 | 0.30 | 0.57 | 0.53 | 0.84 | −0.35 | −0.50 | −0.08 | 0.26 | −0.27 | −0.45 | −0.26 |
| 63 | TTG | −0.39 | −0.05 | −0.33 | −0.40 | −0.45 | −0.17 | −0.54 | −0.27 | −0.37 | −0.45 | −0.27 | −0.40 |
| 64 | TTT | 0.18 | −0.29 | −0.30 | −0.25 | 0.52 | 0.32 | 0.15 | 0.13 | 0.54 | 0.02 | 0.45 | 0.12 |

| | | ATA | ATC | ATG | ATT | CAA | CAC | CAG | CAT | CCA | CCC | CCG | CCT |
|---|---|---|---|---|---|---|---|---|---|---|---|---|---|
| | | 13 | 14 | 15 | 16 | 17 | 18 | 19 | 20 | 21 | 22 | 23 | 24 |
| | | 25 | 26 | 27 | 28 | 29 | 30 | 31 | 32 | 33 | 34 | 35 | 36 |
| | | CGA | CGC | CGG | CGT | CTA | CTC | CTG | CTT | GAA | GAC | GAG | GAT |
| 1 | AAA | 0.27 | 0.06 | 0.16 | 0.21 | 0.20 | −0.06 | 0.05 | 0.20 | 0.14 | −0.10 | −0.46 | −0.14 |
| 2 | AAC | 0.10 | −0.17 | 0.02 | −0.16 | 0.66 | −0.15 | −0.09 | 0.00 | 0.03 | −0.14 | 0.18 | 0.02 |
| 3 | AAG | −0.56 | −0.25 | −0.50 | −0.27 | −0.51 | −0.23 | −0.38 | −0.06 | 0.61 | 0.56 | 0.41 | 0.42 |
| 4 | AAT | 0.10 | 0.12 | 0.12 | 0.34 | 0.04 | −0.40 | 0.07 | −0.30 | −0.13 | −0.13 | 0.02 | 0.19 |
| 5 | ACA | −0.18 | 0.21 | 0.02 | 0.38 | −0.47 | −0.15 | 0.25 | −0.23 | −0.19 | 0.26 | −0.10 | 0.20 |
| 6 | ACC | −0.10 | −0.12 | 0.19 | 0.08 | 0.53 | 0.38 | 0.54 | 0.46 | 0.01 | −0.24 | 0.16 | −0.15 |
| 7 | ACG | −0.46 | −0.03 | −0.30 | −0.21 | −0.72 | −0.42 | −0.53 | −0.47 | 0.16 | 0.54 | 0.49 | 0.45 |
| 8 | ACT | 0.49 | −0.06 | 0.81 | 0.17 | 0.35 | 0.14 | 0.42 | 0.31 | −0.40 | −0.49 | 0.07 | 0.01 |
| 9 | AGA | −0.54 | 0.30 | −0.31 | 0.31 | −0.13 | 0.30 | 0.43 | −0.28 | 0.05 | 0.41 | 0.07 | 0.28 |
| 10 | AGC | 0.14 | −0.09 | −0.09 | −0.12 | 0.66 | 0.16 | 0.06 | 0.32 | −0.25 | −0.16 | −0.12 | −0.26 |
| 11 | AGG | −0.63 | 0.20 | −0.30 | 0.21 | −0.70 | −0.28 | −0.18 | −0.62 | 0.01 | 0.44 | −0.19 | −0.12 |
| 12 | AGT | 0.28 | 0.24 | −0.15 | 0.32 | 0.62 | 0.30 | 0.19 | 0.18 | −0.39 | 0.01 | −0.20 | −0.06 |
| 13 | ATA | −0.23 | 0.31 | 0.10 | 0.20 | −0.31 | −0.21 | 0.41 | −0.33 | 0.06 | 0.47 | 0.11 | 0.33 |
| 14 | ATC | 0.69 | −0.21 | 0.55 | 0.06 | 0.84 | −0.59 | 0.31 | −0.05 | 0.08 | −0.42 | 0.30 | 0.15 |
| 15 | ATG | 0.21 | −0.08 | 0.31 | −0.09 | 0.05 | −0.17 | −0.02 | 0.19 | −0.03 | 0.02 | 0.07 | −0.01 |
| 16 | ATT | 0.50 | −0.19 | 0.54 | −0.08 | 0.62 | −0.44 | 0.07 | −0.30 | −0.12 | 0.25 | −0.11 | −0.01 |
| 17 | CAA | −0.38 | 0.10 | −0.31 | −0.09 | −0.16 | −0.30 | −0.21 | −0.39 | 0.44 | 0.59 | 0.11 | 0.56 |
| 18 | CAC | 0.10 | 0.00 | 0.02 | −0.04 | 0.80 | 0.29 | 0.19 | 0.14 | 0.13 | −0.28 | 0.14 | −0.16 |
| 19 | CAG | −0.43 | 0.29 | −0.20 | −0.09 | −0.31 | 0.16 | 0.47 | −0.32 | −0.15 | −0.17 | −0.15 | −0.26 |
| 20 | CAT | 0.24 | −0.15 | −0.19 | 0.13 | −0.06 | −0.26 | −0.10 | −0.42 | −0.12 | −0.08 | −0.02 | 0.37 |
| 21 | CCA | −0.52 | −0.20 | −0.38 | 0.20 | −0.36 | 0.21 | 0.18 | 0.18 | −0.14 | −0.06 | −0.10 | 0.28 |
| 22 | CCC | −0.22 | 0.25 | −0.16 | 0.31 | 0.57 | 0.61 | 0.74 | 0.42 | 0.50 | −0.05 | 0.54 | −0.31 |
| 23 | CCG | −0.11 | −0.17 | 0.55 | −0.20 | −0.52 | −0.06 | −0.30 | 0.10 | −0.13 | 0.16 | 0.21 | 0.11 |
| 24 | CCT | 0.50 | 0.39 | 0.56 | 0.35 | 0.36 | 0.54 | 0.61 | 0.30 | −0.15 | −0.39 | 0.10 | −0.18 |
| 25 | CGA | −0.34 | −0.05 | −0.38 | −0.04 | −0.53 | −0.27 | −0.39 | −0.30 | 0.26 | 0.61 | 0.27 | 0.45 |
| 26 | CGC | 0.37 | 0.02 | 0.27 | 0.01 | 0.81 | 0.51 | 0.12 | 0.45 | 0.13 | −0.21 | 0.01 | −0.22 |
| 27 | CGG | −0.56 | 0.21 | −0.64 | −0.06 | −0.56 | 0.34 | −0.25 | −0.25 | −0.26 | 0.64 | 0.08 | 0.26 |
| 28 | CGT | 0.30 | −0.02 | −0.10 | 0.01 | 0.56 | 0.25 | −0.20 | 0.01 | −0.13 | −0.10 | 0.04 | 0.17 |
| 29 | CTA | −0.54 | −0.52 | −0.54 | −0.37 | −0.46 | −0.41 | −0.16 | −0.41 | 0.79 | 0.92 | 0.77 | 0.84 |
| 30 | CTC | 0.68 | 0.77 | 0.33 | 0.79 | 0.93 | 0.66 | 0.81 | 0.62 | 0.00 | −0.68 | 0.47 | −0.50 |
| 31 | CTG | 0.20 | −0.06 | 0.28 | −0.17 | 0.04 | 0.15 | 0.02 | 0.10 | −0.30 | 0.24 | −0.20 | −0.12 |
| 32 | CTT | 0.69 | 0.52 | 0.58 | 0.56 | 0.50 | 0.22 | 0.69 | 0.25 | −0.17 | −0.01 | −0.53 | −0.49 |
| 33 | GAA | 0.30 | 0.24 | 0.11 | 0.19 | 0.29 | 0.30 | −0.01 | 0.29 | 0.07 | −0.04 | −0.49 | −0.27 |
| 34 | GAC | −0.01 | −0.13 | −0.09 | −0.18 | 0.66 | 0.05 | 0.14 | 0.17 | 0.08 | −0.04 | 0.15 | −0.08 |
| 35 | GAG | −0.45 | −0.19 | −0.51 | −0.34 | −0.49 | 0.67 | −0.31 | −0.21 | 0.59 | 0.61 | 0.47 | 0.53 |
| 36 | GAT | 0.54 | −0.05 | 0.23 | 0.25 | 0.28 | −0.49 | 0.15 | −0.15 | −0.05 | −0.14 | −0.07 | 0.16 |
| 37 | GCA | −0.33 | 0.27 | −0.08 | 0.27 | −0.33 | 0.31 | 0.01 | 0.17 | −0.26 | 0.26 | −0.22 | 0.19 |
| 38 | GCC | 0.06 | −0.02 | 0.02 | 0.04 | 0.73 | 0.52 | 0.52 | 0.52 | 0.17 | −0.24 | 0.14 | −0.30 |
| 39 | GCG | −0.44 | 0.15 | −0.37 | −0.20 | −0.58 | 0.08 | −0.42 | −0.11 | 0.21 | 0.57 | 0.40 | 0.33 |
| 40 | GCT | 0.55 | 0.18 | 0.66 | 0.21 | 0.45 | 0.51 | 0.47 | 0.45 | −0.39 | −0.47 | 0.05 | −0.27 |
| 41 | GGA | −0.63 | −0.34 | −0.54 | −0.35 | −0.29 | 0.42 | 0.04 | −0.26 | 0.19 | 0.51 | 0.09 | 0.45 |
| 42 | GGC | 0.61 | 0.56 | 0.61 | 0.55 | 0.73 | 0.54 | 0.25 | 0.42 | −0.07 | −0.20 | −0.13 | −0.35 |
| 43 | GGG | −0.71 | −0.36 | −0.59 | −0.46 | −0.69 | 0.78 | −0.51 | −0.52 | 0.36 | 0.76 | 0.31 | 0.52 |
| 44 | GGT | 0.45 | 0.01 | 0.25 | −0.17 | 0.64 | 0.84 | −0.04 | 0.31 | −0.13 | 0.10 | 0.05 | 0.10 |
| 45 | GTA | −0.08 | −0.20 | −0.04 | −0.34 | −0.04 | 0.00 | −0.32 | −0.25 | −0.03 | 0.40 | 0.00 | 0.30 |
| 46 | GTC | 0.67 | 0.45 | 0.43 | 0.42 | 0.89 | 0.55 | 0.70 | 0.58 | 0.13 | 0.23 | −0.01 | −0.45 |
| 47 | GTG | 0.06 | −0.12 | −0.27 | −0.25 | −0.20 | −0.03 | −0.40 | −0.04 | 0.25 | 0.55 | 0.23 | 0.23 |
| 48 | GTT | 0.42 | 0.13 | 0.58 | 0.12 | 0.56 | 0.17 | 0.40 | 0.28 | −0.25 | −0.11 | −0.37 | −0.33 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.31 | −0.02 | −0.06 | 0.10 | 0.76 | 0.07 | 0.22 | 0.31 | 0.06 | −0.33 | 0.18 | 0.02 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.10 | −0.26 | 0.01 | 0.15 | 0.15 | −0.53 | −0.13 | −0.33 | −0.10 | −0.31 | 0.00 | 0.47 |
| 53 | TCA | −0.15 | −0.08 | −0.29 | 0.30 | −0.57 | −0.25 | −0.11 | −0.28 | 0.01 | 0.41 | 0.28 | 0.40 |
| 54 | TCC | −0.15 | −0.23 | 0.04 | 0.01 | 0.66 | 0.38 | 0.51 | 0.41 | 0.48 | −0.12 | 0.38 | 0.00 |
| 55 | TCG | −0.28 | −0.19 | −0.42 | −0.07 | −0.69 | −0.33 | −0.53 | −0.44 | 0.42 | 0.67 | 0.68 | 0.62 |
| 56 | TCT | 0.68 | 0.10 | 0.75 | 0.24 | 0.26 | 0.22 | 0.20 | −0.09 | −0.17 | −0.50 | 0.42 | 0.00 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.02 | −0.13 | −0.24 | −0.14 | 0.73 | −0.07 | −0.24 | 0.04 | 0.06 | −0.21 | 0.24 | 0.00 |
| 59 | TGG | −0.50 | 0.22 | −0.40 | 0.00 | −0.47 | 0.57 | −0.11 | 0.22 | −0.08 | 0.26 | 0.19 | −0.13 |
| 60 | TGT | −0.10 | 0.42 | −0.54 | 0.35 | 0.49 | 0.38 | −0.07 | 0.05 | −0.18 | 0.00 | 0.02 | 0.20 |

TABLE C.5-continued

CPW matrix *Escherichia coli* K12 full genome (left codon indicated in column 2, right codon indicated in row 2). Host cell: *E. coli*; Sequence data: full *E. coli* genome.

| | | CGA 25 | CGC 26 | CGG 27 | CGT 28 | CTA 29 | CTC 30 | CTG 31 | CTT 32 | GAA 33 | GAC 34 | GAG 35 | GAT 36 |
|---|---|---|---|---|---|---|---|---|---|---|---|---|---|
| 61 | TTA | 0.12 | −0.29 | −0.12 | −0.20 | 0.00 | −0.28 | −0.04 | −0.21 | 0.66 | 0.74 | 0.62 | 0.56 |
| 62 | TTC | 0.64 | −0.42 | 0.23 | −0.33 | 0.83 | −0.66 | −0.12 | −0.29 | 0.26 | −0.07 | 0.30 | 0.15 |
| 63 | TTG | −0.28 | −0.21 | −0.28 | −0.28 | −0.54 | −0.44 | −0.49 | −0.43 | 0.84 | 0.90 | 0.83 | 0.69 |
| 64 | TTT | 0.64 | 0.22 | 0.54 | 0.34 | 0.63 | −0.29 | 0.51 | −0.14 | −0.19 | −0.06 | −0.12 | −0.04 |

| | | 37 GCA | 38 GCC | 39 GCG | 40 GCT | 41 GGA | 42 GGC | 43 GGG | 44 GGT | 45 GTA | 46 GTC | 47 GTG | 48 GTT |
|---|---|---|---|---|---|---|---|---|---|---|---|---|---|
| 1 | AAA | 0.00 | −0.15 | −0.21 | 0.31 | 0.11 | −0.16 | −0.28 | −0.01 | 0.29 | −0.08 | −0.22 | 0.18 |
| 2 | AAC | 0.41 | −0.36 | 0.27 | 0.14 | 0.19 | −0.21 | 0.36 | −0.20 | 0.12 | −0.36 | 0.07 | −0.10 |
| 3 | AAG | 0.28 | 0.52 | 0.18 | 0.25 | −0.05 | 0.41 | 0.17 | 0.68 | −0.04 | 0.19 | 0.10 | 0.11 |
| 4 | AAT | 0.20 | −0.34 | 0.13 | −0.05 | 0.35 | −0.04 | 0.56 | 0.10 | 0.35 | −0.22 | 0.29 | 0.13 |
| 5 | ACA | −0.24 | 0.28 | 0.15 | 0.06 | −0.43 | 0.26 | −0.13 | 0.10 | −0.15 | 0.37 | 0.25 | 0.33 |
| 6 | ACC | 0.02 | −0.19 | 0.30 | −0.11 | −0.40 | −0.04 | −0.32 | −0.20 | −0.03 | −0.01 | 0.19 | −0.22 |
| 7 | ACG | −0.32 | 0.70 | −0.19 | 0.22 | 0.20 | 0.48 | 0.24 | 0.43 | −0.45 | 0.17 | −0.27 | 0.06 |
| 8 | ACT | −0.06 | −0.25 | −0.08 | −0.26 | 0.03 | −0.30 | 0.67 | 0.11 | 0.04 | −0.03 | 0.47 | 0.04 |
| 9 | AGA | −0.30 | 0.45 | −0.02 | 0.09 | −0.54 | 0.27 | −0.14 | 0.33 | −0.21 | −0.02 | 0.14 | 0.07 |
| 10 | AGC | 0.17 | −0.39 | 0.34 | 0.55 | −0.15 | −0.14 | 0.10 | −0.16 | −0.12 | −0.16 | −0.01 | 0.01 |
| 11 | AGG | −0.49 | 0.51 | 0.04 | −0.23 | −0.26 | 0.51 | 0.41 | 0.60 | 0.17 | 0.55 | −0.10 | −0.06 |
| 12 | AGT | 0.12 | −0.14 | 0.03 | 0.01 | 0.04 | 0.20 | 0.29 | 0.09 | 0.45 | 0.40 | 0.37 | 0.37 |
| 13 | ATA | 0.21 | 0.00 | 0.40 | 0.33 | 0.26 | 0.39 | 0.05 | 0.31 | 0.40 | 0.03 | 0.43 | 0.19 |
| 14 | ATC | 0.45 | −0.43 | 0.45 | −0.19 | 0.64 | −0.13 | 0.44 | −0.13 | 0.53 | −0.38 | 0.34 | −0.13 |
| 15 | ATG | −0.05 | 0.52 | −0.29 | 0.12 | −0.14 | −0.10 | −0.36 | 0.43 | 0.29 | 0.08 | −0.21 | 0.14 |
| 16 | ATT | 0.46 | −0.41 | 0.30 | −0.26 | 0.68 | −0.22 | 0.59 | −0.24 | 0.59 | −0.39 | 0.14 | −0.21 |
| 17 | CAA | 0.61 | 0.43 | 0.54 | 0.54 | −0.04 | 0.34 | −0.27 | 0.27 | 0.60 | 0.61 | 0.58 | 0.55 |
| 18 | CAC | 0.21 | −0.34 | 0.14 | −0.21 | 0.16 | −0.35 | 0.05 | −0.41 | −0.24 | −0.33 | 0.87 | −0.36 |
| 19 | CAG | −0.32 | 0.21 | −0.36 | −0.19 | −0.31 | −0.08 | −0.45 | 0.36 | −0.31 | −0.01 | −0.27 | −0.28 |
| 20 | CAT | 0.35 | −0.11 | 0.10 | −0.04 | 0.32 | 0.29 | 0.52 | 0.28 | 0.25 | −0.15 | 0.04 | −0.10 |
| 21 | CCA | 0.01 | 0.24 | 0.33 | 0.19 | −0.41 | −0.03 | −0.09 | 0.15 | −0.07 | 0.55 | 0.26 | 0.44 |
| 22 | CCC | −0.37 | −0.46 | 0.06 | −0.40 | −0.47 | −0.41 | 0.34 | −0.35 | 0.05 | −0.20 | 0.30 | −0.29 |
| 23 | CCG | −0.25 | 0.76 | 0.09 | 0.34 | −0.04 | 0.33 | 0.01 | 0.35 | −0.42 | 0.31 | −0.14 | −0.06 |
| 24 | CCT | −0.29 | −0.45 | −0.38 | −0.46 | −0.22 | −0.44 | 0.05 | −0.08 | −0.06 | −0.08 | 0.40 | −0.22 |
| 25 | CGA | 0.09 | 0.36 | 0.11 | 0.11 | −0.11 | 0.57 | 0.17 | 0.54 | −0.19 | 0.24 | −0.07 | 0.40 |
| 26 | CGC | −0.04 | −0.28 | 0.22 | −0.07 | −0.06 | −0.21 | 0.01 | −0.14 | −0.27 | −0.12 | −0.15 | −0.13 |
| 27 | CGG | −0.52 | 0.23 | −0.49 | −0.21 | −0.45 | 0.52 | 0.16 | 0.55 | −0.66 | −0.19 | −0.55 | −0.21 |
| 28 | CGT | 0.25 | 0.24 | 0.14 | 0.00 | −0.03 | −0.01 | 0.17 | −0.07 | 0.36 | 0.43 | 0.48 | 0.31 |
| 29 | CTA | 0.76 | 0.73 | 0.75 | 0.78 | 0.73 | 0.71 | 0.59 | 0.74 | 0.83 | 0.72 | 0.81 | 0.72 |
| 30 | CTC | 0.43 | −0.34 | 0.42 | 0.11 | −0.20 | −0.59 | −0.34 | −0.54 | 0.71 | 0.39 | 0.75 | 0.47 |
| 31 | CTG | −0.43 | 0.48 | −0.46 | −0.12 | 0.01 | 0.23 | −0.27 | 0.29 | −0.29 | −0.12 | −0.49 | −0.15 |
| 32 | CTT | 0.29 | −0.33 | 0.33 | −0.21 | 0.17 | −0.39 | −0.23 | −0.08 | 0.64 | 0.31 | 0.73 | 0.37 |
| 33 | GAA | 0.02 | −0.13 | −0.25 | 0.09 | −0.07 | −0.13 | −0.42 | −0.16 | 0.21 | −0.07 | −0.33 | 0.02 |
| 34 | GAC | 0.29 | −0.16 | 0.24 | −0.02 | 0.15 | −0.23 | 0.02 | −0.28 | 0.16 | −0.06 | 0.18 | −0.16 |
| 35 | GAG | 0.32 | 0.51 | 0.12 | 0.42 | 0.45 | 0.59 | 0.21 | 0.67 | 0.44 | 0.44 | 0.25 | 0.40 |
| 36 | GAT | 0.26 | −0.25 | 0.01 | −0.13 | 0.34 | −0.04 | 0.59 | 0.10 | 0.29 | −0.19 | −0.01 | −0.02 |
| 37 | GCA | −0.13 | 0.41 | 0.18 | 0.10 | −0.25 | −0.03 | −0.21 | −0.12 | −0.16 | 0.42 | 0.25 | 0.38 |
| 38 | GCC | −0.17 | −0.15 | 0.28 | −0.18 | −0.68 | 0.87 | −0.56 | −0.09 | 0.00 | 0.05 | 0.31 | −0.12 |
| 39 | GCG | −0.33 | 0.70 | −0.19 | 0.33 | −0.06 | 0.26 | 0.05 | 0.19 | −0.50 | 0.28 | −0.32 | 0.01 |
| 40 | GCT | −0.20 | −0.31 | −0.13 | −0.30 | 0.01 | −0.15 | 0.21 | −0.02 | −0.23 | 0.08 | 0.43 | −0.11 |
| 41 | GGA | 0.11 | 0.38 | 0.26 | 0.44 | −0.01 | 0.65 | 0.54 | 0.71 | 0.41 | 0.63 | 0.63 | 0.62 |
| 42 | GGC | −0.46 | 0.96 | −0.28 | −0.11 | −0.21 | −0.38 | −0.15 | −0.37 | −0.42 | −0.14 | −0.33 | −0.27 |
| 43 | GGG | −0.12 | 0.44 | −0.24 | 0.23 | 0.30 | 0.73 | 0.67 | 0.84 | −0.03 | 0.60 | 0.31 | 0.32 |
| 44 | GGT | −0.05 | 0.04 | −0.02 | 0.01 | 0.21 | 0.17 | 0.21 | −0.07 | 0.13 | 0.24 | 0.20 | 0.12 |
| 45 | GTA | 0.24 | 0.46 | 0.14 | 0.41 | 0.26 | 0.42 | −0.07 | 0.20 | 0.28 | 0.39 | 0.07 | 0.46 |
| 46 | GTC | 0.27 | −0.35 | 0.13 | −0.26 | −0.04 | −0.31 | −0.43 | −0.44 | 0.46 | 0.12 | 0.30 | 0.04 |
| 47 | GTG | −0.03 | 0.66 | −0.34 | 0.20 | 0.32 | 0.46 | −0.01 | 0.36 | −0.13 | −0.06 | −0.48 | −0.16 |
| 48 | GTT | 0.21 | −0.37 | 0.23 | −0.37 | 0.44 | −0.26 | 0.06 | −0.17 | 0.45 | 0.08 | 0.49 | −0.04 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.24 | −0.33 | 0.25 | −0.08 | 0.34 | −0.31 | 0.24 | −0.29 | 0.31 | −0.12 | 0.34 | −0.11 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.24 | −0.33 | 0.18 | 0.16 | 0.37 | 0.02 | 0.60 | 0.15 | 0.29 | −0.35 | 0.11 | −0.17 |
| 53 | TCA | −0.17 | 0.15 | 0.19 | 0.35 | −0.28 | 0.41 | 0.21 | 0.30 | −0.21 | 0.20 | 0.27 | 0.35 |
| 54 | TCC | −0.16 | −0.07 | 0.38 | −0.20 | −0.09 | −0.39 | −0.36 | −0.06 | −0.47 | −0.10 | 0.38 | −0.11 |
| 55 | TCG | −0.27 | 0.64 | −0.14 | 0.22 | 0.45 | 0.74 | 0.47 | 0.61 | −0.52 | 0.02 | −0.42 | 0.03 |
| 56 | TCT | −0.12 | −0.39 | −0.16 | −0.33 | 0.41 | −0.24 | 0.76 | −0.31 | −0.20 | −0.07 | 0.44 | −0.31 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.05 | −0.17 | 0.23 | 0.09 | 0.01 | −0.04 | 0.08 | −0.13 | −0.18 | 0.02 | −0.11 | 0.18 |
| 59 | TGG | −0.09 | 0.46 | −0.25 | 0.10 | −0.58 | 0.01 | −0.08 | 0.46 | −0.32 | 0.33 | −0.08 | 0.12 |
| 60 | TGT | −0.08 | −0.06 | −0.04 | −0.08 | 0.16 | 0.07 | 0.28 | −0.06 | 0.12 | −0.13 | 0.05 | 0.11 |
| 61 | TTA | 0.55 | 0.40 | 0.45 | 0.56 | 0.20 | 0.19 | −0.17 | −0.04 | 0.62 | 0.20 | 0.39 | 0.45 |

TABLE C.5-continued

CPW matrix *Escherichia coli* K12 full genome (left codon indicated in column 2, right codon indicated in row 2). Host cell: *E. coli*; Sequence data: full *E. coli* genome.

| | | | | | | | | | | | | |
|---|---|---|---|---|---|---|---|---|---|---|---|---|
| 62 | TTC | 0.60 | −0.18 | 0.56 | 0.07 | 0.67 | 0.13 | 0.51 | −0.06 | 0.50 | 0.06 | 0.51 | 0.09 |
| 63 | TTG | 0.44 | 0.78 | 0.55 | 0.46 | 0.01 | 0.53 | −0.06 | 0.47 | 0.43 | 0.46 | 0.38 | 0.30 |
| 64 | TTT | 0.44 | −0.53 | 0.31 | −0.41 | 0.65 | −0.23 | 0.62 | −0.34 | 0.32 | −0.49 | 0.11 | −0.29 |

| | | GCA 37 | GCC 38 | GCG 39 | GCT 40 | GGA 41 | GGC 42 | GGG 43 | GGT 44 | GTA 45 | GTC 46 | GTG 47 | GTT 48 |
|---|---|---|---|---|---|---|---|---|---|---|---|---|---|

| | | 49 TAA | 50 TAC | 51 TAG | 52 TAT | 53 TCA | 54 TCC | 55 TCG | 56 TCT | 57 TGA | 58 TGC | 59 TGG | 60 TGT |
|---|---|---|---|---|---|---|---|---|---|---|---|---|---|
| 1 | AAA | 0.00 | −0.03 | 0.00 | −0.03 | −0.11 | 0.01 | −0.21 | 0.13 | 0.00 | −0.01 | 0.05 | 0.05 |
| 2 | AAC | 0.00 | −0.24 | 0.00 | 0.06 | 0.15 | −0.17 | 0.13 | 0.26 | 0.00 | −0.24 | −0.42 | −0.17 |
| 3 | AAG | 0.00 | 0.09 | 0.00 | 0.12 | −0.08 | 0.34 | −0.26 | 0.03 | 0.00 | 0.08 | −0.14 | −0.18 |
| 4 | AAT | 0.00 | 0.03 | 0.00 | 0.20 | 0.15 | 0.44 | 0.50 | 0.37 | 0.00 | 0.29 | 0.90 | 0.37 |
| 5 | ACA | 0.00 | 0.38 | 0.00 | 0.41 | −0.54 | 0.01 | −0.34 | 0.02 | 0.00 | 0.51 | 0.06 | 0.15 |
| 6 | ACC | 0.00 | −0.17 | 0.00 | −0.07 | 0.17 | 0.02 | −0.02 | −0.08 | 0.00 | −0.36 | −0.43 | −0.47 |
| 7 | ACG | 0.00 | 0.75 | 0.00 | 0.45 | −0.04 | 0.54 | 0.05 | 0.35 | 0.00 | 0.88 | 0.66 | 0.84 |
| 8 | ACT | 0.00 | −0.54 | 0.00 | −0.41 | −0.35 | −0.46 | −0.24 | −0.41 | 0.00 | 0.19 | 0.90 | 0.19 |
| 9 | AGA | 0.00 | 0.47 | 0.00 | 0.16 | 0.42 | 0.68 | 0.24 | 0.67 | 0.00 | 0.44 | 0.53 | 0.07 |
| 10 | AGC | 0.00 | −0.28 | 0.00 | −0.19 | 0.58 | 0.31 | 0.43 | 0.55 | 0.00 | 0.13 | −0.30 | 0.30 |
| 11 | AGG | 0.00 | 0.76 | 0.00 | 0.40 | 0.11 | 0.73 | 0.39 | 0.06 | 0.00 | 0.57 | 0.65 | 0.20 |
| 12 | AGT | 0.00 | −0.30 | 0.00 | −0.40 | −0.34 | −0.05 | −0.23 | 0.00 | 0.00 | −0.22 | 0.28 | 0.01 |
| 13 | ATA | 0.00 | 0.38 | 0.00 | −0.09 | −0.36 | 0.06 | −0.09 | −0.24 | 0.00 | 0.21 | 0.05 | −0.30 |
| 14 | ATC | 0.00 | −0.18 | 0.00 | 0.22 | 0.50 | −0.36 | 0.39 | −0.13 | 0.00 | 0.00 | −0.44 | 0.15 |
| 15 | ATG | 0.00 | −0.02 | 0.00 | 0.02 | 0.13 | 0.25 | −0.27 | 0.16 | 0.00 | 0.03 | 0.00 | −0.03 |
| 16 | ATT | 0.00 | 0.08 | 0.00 | −0.12 | 0.13 | −0.16 | 0.20 | −0.12 | 0.00 | −0.05 | 0.65 | −0.04 |
| 17 | CAA | 0.00 | 0.01 | 0.00 | −0.24 | −0.22 | −0.06 | −0.01 | −0.01 | 0.00 | 0.05 | 0.04 | −0.14 |
| 18 | CAC | 0.00 | −0.12 | 0.00 | −0.03 | −0.01 | −0.27 | 0.12 | −0.18 | 0.00 | −0.36 | −0.51 | −0.11 |
| 19 | CAG | 0.00 | 0.01 | 0.00 | 0.15 | −0.06 | 0.38 | −0.20 | 0.23 | 0.00 | −0.01 | −0.02 | 0.07 |
| 20 | CAT | 0.00 | −0.07 | 0.00 | 0.16 | 0.04 | 0.22 | 0.25 | 0.16 | 0.00 | 0.24 | 0.78 | 0.31 |
| 21 | CCA | 0.00 | 0.38 | 0.00 | 0.49 | −0.44 | 0.05 | −0.31 | 0.15 | 0.00 | 0.18 | 0.51 | 0.38 |
| 22 | CCC | 0.00 | −0.17 | 0.00 | −0.21 | −0.22 | −0.38 | 0.04 | −0.27 | 0.00 | −0.56 | −0.42 | −0.51 |
| 23 | CCG | 0.00 | 0.33 | 0.00 | 0.20 | −0.20 | 0.37 | 0.00 | 0.16 | 0.00 | 0.26 | −0.21 | 0.50 |
| 24 | CCT | 0.00 | −0.51 | 0.00 | −0.57 | −0.65 | −0.65 | −0.49 | −0.65 | 0.00 | −0.39 | 0.87 | −0.39 |
| 25 | CGA | 0.00 | 0.48 | 0.00 | 0.25 | 0.42 | 0.20 | 0.14 | 0.36 | 0.00 | 0.55 | 0.38 | 0.43 |
| 26 | CGC | 0.00 | −0.05 | 0.00 | −0.07 | 0.21 | 0.21 | 0.11 | 0.25 | 0.00 | −0.29 | −0.43 | −0.14 |
| 27 | CGG | 0.00 | 0.81 | 0.00 | 0.54 | 0.39 | 0.85 | 0.56 | 0.76 | 0.00 | 0.67 | 0.74 | 0.61 |
| 28 | CGT | 0.00 | −0.05 | 0.00 | −0.25 | −0.22 | −0.18 | −0.08 | −0.32 | 0.00 | 0.01 | 0.46 | 0.03 |
| 29 | CTA | 0.00 | 0.34 | 0.00 | 0.14 | 0.12 | 0.31 | −0.25 | 0.31 | 0.00 | 0.02 | −0.43 | −0.14 |
| 30 | CTC | 0.00 | −0.56 | 0.00 | −0.53 | −0.30 | −0.67 | −0.19 | −0.68 | 0.00 | −0.42 | −0.32 | −0.36 |
| 31 | CTG | 0.00 | 0.33 | 0.00 | 0.25 | 0.43 | 0.82 | 0.21 | 0.53 | 0.00 | 0.30 | 0.17 | 0.37 |
| 32 | CTT | 0.00 | −0.43 | 0.00 | −0.55 | −0.57 | −0.76 | −0.52 | −0.74 | 0.00 | −0.39 | 0.41 | −0.45 |
| 33 | GAA | 0.00 | 0.08 | 0.00 | 0.05 | 0.11 | 0.03 | 0.32 | 0.20 | 0.00 | 0.29 | 0.21 | 0.14 |
| 34 | GAC | 0.00 | −0.09 | 0.00 | 0.25 | 0.16 | −0.21 | 0.34 | 0.14 | 0.00 | −0.36 | −0.60 | −0.09 |
| 35 | GAG | 0.00 | −0.18 | 0.00 | −0.07 | −0.16 | 0.07 | −0.24 | −0.06 | 0.00 | −0.30 | −0.32 | −0.37 |
| 36 | GAT | 0.00 | −0.20 | 0.00 | 0.09 | 0.25 | 0.12 | 0.37 | 0.32 | 0.00 | 0.10 | 0.90 | 0.34 |
| 37 | GCA | 0.00 | 0.53 | 0.00 | 0.48 | −0.05 | 0.31 | −0.21 | 0.23 | 0.00 | 0.72 | −0.02 | 0.41 |
| 38 | GCC | 0.00 | −0.04 | 0.00 | −0.25 | 0.14 | −0.06 | −0.13 | −0.20 | 0.00 | −0.49 | −0.48 | −0.60 |
| 39 | GCG | 0.00 | 0.58 | 0.00 | 0.34 | 0.33 | 0.69 | 0.29 | 0.41 | 0.00 | 0.66 | 0.29 | 0.55 |
| 40 | GCT | 0.00 | −0.56 | 0.00 | −0.56 | −0.36 | −0.42 | −0.27 | −0.48 | 0.00 | 0.08 | 0.94 | −0.22 |
| 41 | GGA | 0.00 | 0.31 | 0.00 | −0.15 | 0.13 | 0.72 | −0.49 | 0.47 | 0.00 | −0.07 | 0.21 | −0.12 |
| 42 | GGC | 0.00 | 0.02 | 0.00 | 0.04 | 0.41 | 0.33 | 0.38 | 0.45 | 0.00 | −0.20 | −0.44 | −0.22 |
| 43 | GGG | 0.00 | 0.70 | 0.00 | 0.31 | 0.52 | 0.84 | 0.42 | 0.68 | 0.00 | 0.79 | 0.78 | 0.46 |
| 44 | GGT | 0.00 | −0.12 | 0.00 | −0.26 | −0.34 | −0.30 | −0.35 | −0.42 | 0.00 | 0.15 | 0.52 | −0.04 |
| 45 | GTA | 0.00 | 0.44 | 0.00 | 0.44 | 0.06 | 0.17 | −0.14 | 0.18 | 0.00 | 0.38 | −0.02 | −0.04 |
| 46 | GTC | 0.00 | −0.08 | 0.00 | −0.22 | 0.31 | −0.13 | 0.23 | −0.16 | 0.00 | −0.35 | −0.61 | −0.29 |
| 47 | GTG | 0.00 | 0.67 | 0.00 | 0.40 | 0.59 | 0.79 | 0.27 | 0.61 | 0.00 | 0.39 | 0.37 | 0.47 |
| 48 | GTT | 0.00 | −0.39 | 0.00 | −0.49 | −0.28 | −0.54 | −0.23 | −0.58 | 0.00 | −0.26 | 0.79 | −0.22 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.00 | −0.30 | 0.00 | 0.32 | 0.29 | −0.27 | 0.23 | 0.04 | 0.00 | −0.33 | −0.51 | 0.17 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.00 | −0.30 | 0.00 | 0.33 | −0.10 | −0.28 | 0.34 | 0.31 | 0.00 | 0.03 | 0.78 | 0.31 |
| 53 | TCA | 0.00 | 0.59 | 0.00 | 0.54 | −0.55 | 0.07 | −0.40 | −0.17 | 0.00 | 0.03 | 0.00 | 0.40 |
| 54 | TCC | 0.00 | 0.11 | 0.00 | 0.46 | 0.04 | −0.15 | 0.27 | −0.10 | 0.00 | −0.53 | −0.45 | −0.50 |
| 55 | TCG | 0.00 | 0.74 | 0.00 | 0.58 | −0.05 | 0.49 | 0.02 | 0.38 | 0.00 | 0.48 | 0.40 | 0.62 |
| 56 | TCT | 0.00 | −0.27 | 0.00 | −0.22 | −0.51 | −0.54 | −0.26 | −0.53 | 0.00 | 0.20 | 0.96 | 0.03 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.00 | −0.14 | 0.00 | 0.09 | −0.03 | 0.13 | 0.19 | −0.04 | 0.00 | −0.15 | −0.33 | −0.18 |
| 59 | TGG | 0.00 | 0.10 | 0.00 | −0.07 | −0.38 | 0.49 | −0.35 | 0.40 | 0.00 | 0.10 | 0.00 | −0.11 |
| 60 | TGT | 0.00 | 0.11 | 0.00 | −0.04 | −0.50 | −0.31 | −0.30 | −0.26 | 0.00 | 0.37 | 0.61 | 0.09 |

TABLE C.5-continued

CPW matrix *Escherichia coli* K12 full genome (left codon indicated in column 2, right codon indicated in row 2). Host cell: *E. coli*; Sequence data: full *E. coli* genome.

| | | | | | | | | | | | | |
|---|---|---|---|---|---|---|---|---|---|---|---|---|
| 61 | TTA | 0.00 | 0.62 | 0.00 | 0.31 | −0.06 | 0.04 | −0.26 | 0.13 | 0.00 | −0.08 | −0.11 | −0.13 |
| 62 | TTC | 0.00 | −0.13 | 0.00 | 0.12 | 0.02 | −0.40 | −0.18 | −0.24 | 0.00 | −0.25 | −0.52 | −0.08 |
| 63 | TTG | 0.00 | 0.38 | 0.00 | 0.01 | −0.17 | 0.55 | −0.35 | 0.34 | 0.00 | 0.03 | −0.21 | −0.17 |
| 64 | TTT | 0.00 | 0.10 | 0.00 | −0.07 | 0.08 | −0.03 | 0.35 | 0.08 | 0.00 | 0.10 | 0.80 | 0.25 |

| TAA | TAC | TAG | TAT | TCA | TCC | TCG | TCT | TGA | TGC | TGG | TGT |
|---|---|---|---|---|---|---|---|---|---|---|---|
| 49 | 50 | 51 | 52 | 53 | 54 | 55 | 56 | 57 | 58 | 59 | 60 |

| | | 61<br>TTA | 62<br>TTC | 63<br>TTG | 64<br>TTT |
|---|---|---|---|---|---|
| 1 | AAA | 0.15 | −0.03 | 0.40 | 0.23 |
| 2 | AAC | 0.46 | −0.30 | 0.58 | 0.19 |
| 3 | AAG | −0.02 | −0.22 | −0.02 | −0.31 |
| 4 | AAT | −0.23 | −0.04 | 0.06 | 0.20 |
| 5 | ACA | −0.50 | 0.16 | −0.40 | −0.13 |
| 6 | ACC | 0.43 | −0.19 | 0.53 | 0.01 |
| 7 | ACG | −0.24 | 0.41 | −0.34 | 0.27 |
| 8 | ACT | 0.24 | −0.34 | 0.32 | −0.09 |
| 9 | AGA | −0.34 | 0.66 | −0.01 | 0.30 |
| 10 | AGC | 0.65 | 0.04 | 0.67 | 0.27 |
| 11 | AGG | −0.24 | 0.61 | −0.44 | 0.37 |
| 12 | AGT | 0.06 | −0.13 | −0.27 | −0.32 |
| 13 | ATA | −0.57 | −0.25 | −0.57 | −0.49 |
| 14 | ATC | 0.66 | −0.16 | 0.69 | 0.37 |
| 15 | ATG | 0.36 | −0.15 | −0.21 | 0.13 |
| 16 | ATT | −0.03 | −0.16 | −0.35 | 0.12 |
| 17 | CAA | −0.11 | 0.39 | 0.05 | 0.05 |
| 18 | CAC | 0.53 | −0.16 | 0.68 | 0.08 |
| 19 | CAG | −0.07 | −0.16 | −0.25 | −0.04 |
| 20 | CAT | −0.24 | 0.03 | −0.21 | 0.03 |
| 21 | CCA | −0.32 | 0.19 | −0.26 | 0.12 |
| 22 | CCC | 0.32 | 0.02 | 0.40 | 0.04 |
| 23 | CCG | −0.03 | −0.09 | −0.12 | 0.00 |
| 24 | CCT | −0.07 | −0.07 | 0.31 | −0.05 |
| 25 | CGA | −0.47 | 0.12 | −0.44 | −0.09 |
| 26 | CGC | 0.38 | 0.10 | 0.48 | −0.08 |
| 27 | CGG | −0.36 | 0.78 | −0.44 | 0.38 |
| 28 | CGT | 0.02 | −0.05 | −0.13 | −0.24 |
| 29 | CTA | −0.46 | 0.18 | −0.47 | −0.33 |
| 30 | CTC | 0.77 | 0.26 | 0.85 | 0.15 |
| 31 | CTG | 0.22 | 0.09 | 0.07 | −0.08 |
| 32 | CTT | 0.12 | 0.15 | 0.30 | 0.03 |
| 33 | GAA | 0.24 | 0.51 | 0.39 | 0.16 |
| 34 | GAC | 0.39 | −0.05 | 0.59 | 0.33 |
| 35 | GAG | −0.25 | −0.38 | −0.35 | −0.42 |
| 36 | GAT | −0.39 | −0.18 | −0.18 | −0.01 |
| 37 | GCA | −0.41 | 0.06 | −0.35 | −0.19 |
| 38 | GCC | 0.47 | 0.16 | 0.57 | −0.03 |
| 39 | GCG | −0.27 | 0.29 | −0.29 | −0.07 |
| 40 | GCT | 0.21 | −0.04 | 0.27 | −0.17 |
| 41 | GGA | −0.66 | −0.18 | −0.45 | −0.37 |
| 42 | GGC | 0.32 | 0.08 | 0.41 | 0.03 |
| 43 | GGG | −0.49 | 0.57 | −0.40 | 0.34 |
| 44 | GGT | −0.19 | 0.12 | −0.18 | −0.23 |
| 45 | GTA | −0.48 | −0.19 | −0.53 | −0.27 |
| 46 | GTC | 0.62 | −0.10 | 0.71 | −0.15 |
| 47 | GTG | 0.12 | 0.16 | −0.28 | 0.14 |
| 48 | GTT | 0.16 | 0.08 | 0.25 | 0.11 |
| 49 | TAA | 0.00 | 0.00 | 0.00 | 0.00 |
| 50 | TAC | 0.66 | −0.28 | 0.72 | 0.28 |
| 51 | TAG | 0.00 | 0.00 | 0.00 | 0.00 |
| 52 | TAT | −0.10 | −0.15 | −0.10 | 0.14 |
| 53 | TCA | −0.53 | 0.09 | −0.33 | −0.18 |
| 54 | TCC | 0.48 | 0.00 | 0.58 | 0.23 |
| 55 | TCG | −0.23 | 0.12 | −0.39 | −0.09 |
| 56 | TCT | 0.14 | −0.09 | 0.01 | 0.02 |
| 57 | TGA | 0.00 | 0.00 | 0.00 | 0.00 |
| 58 | TGC | 0.41 | −0.03 | 0.55 | 0.10 |
| 59 | TGG | 0.09 | 0.22 | 0.01 | −0.14 |
| 60 | TGT | −0.15 | 0.13 | 0.07 | −0.16 |

TABLE C.5-continued

CPW matrix *Escherichia coli* K12 full genome (left codon indicated in column 2, right codon indicated in row 2). Host cell: *E. coli*; Sequence data: full *E. coli* genome.

| | | | | | |
|---|---|---|---|---|---|
| 61 | TTA | −0.42 | 0.19 | −0.43 | 0.00 |
| 62 | TTC | 0.52 | −0.39 | 0.50 | −0.15 |
| 63 | TTG | −0.31 | −0.18 | −0.54 | −0.15 |
| 64 | TTT | −0.34 | 0.14 | −0.23 | 0.39 |
| | | TTA | TTC | TTG | TTT |
| | | 61 | 62 | 63 | 64 |

TABLE C.6

CPW matrix *Escherichi coli* K12 highly expressed sequences (left codon indicated in column 2, right codon indicated in row 2). Host cell: *E. coli*; Sequence data: full *E. coli* genome; Highly expressed group: 100 seqs.

| | | 1<br>AAA | 2<br>AAC | 3<br>AAG | 4<br>AAT | 5<br>ACA | 6<br>ACC | 7<br>ACG | 8<br>ACT | 9<br>AGA | 10<br>AGC | 11<br>AGG | 12<br>AGT |
|---|---|---|---|---|---|---|---|---|---|---|---|---|---|
| 1 | AAA | 0.25 | −0.47 | 0.55 | 0.83 | 0.88 | −0.33 | 0.61 | −0.59 | 1.00 | 0.49 | 1.00 | 0.88 |
| 2 | AAC | −0.40 | −0.58 | −0.48 | 0.29 | 0.78 | −0.61 | 0.68 | −0.35 | 1.00 | −0.55 | 1.00 | 0.80 |
| 3 | AAG | −0.59 | −0.02 | 0.25 | 0.86 | 0.61 | 0.43 | 1.00 | 0.40 | 1.00 | −0.41 | 1.00 | 1.00 |
| 4 | AAT | 0.86 | 0.60 | 1.00 | 1.00 | 1.00 | 0.52 | 1.00 | −0.05 | 1.00 | 1.00 | 1.00 | 1.00 |
| 5 | ACA | 0.79 | 0.75 | 1.00 | 1.00 | 1.00 | 1.00 | 0.70 | 0.52 | 1.00 | 0.64 | 1.00 | 1.00 |
| 6 | ACC | −0.33 | −0.65 | −0.57 | 0.55 | 0.64 | −0.43 | 0.74 | −0.69 | 0.31 | −0.41 | 1.00 | 1.00 |
| 7 | ACG | 0.90 | 0.88 | 0.67 | 1.00 | 1.00 | 0.74 | 0.57 | 0.31 | 1.00 | 1.00 | 1.00 | 1.00 |
| 8 | ACT | −0.22 | −0.36 | −0.06 | 0.52 | 1.00 | −0.56 | 0.31 | −0.62 | 1.00 | 1.00 | 1.00 | 0.48 |
| 9 | AGA | 1.00 | 1.00 | 1.00 | 1.00 | 1.00 | 1.00 | 1.00 | 1.00 | 1.00 | 1.00 | 1.00 | 1.00 |
| 10 | AGC | 0.08 | −0.35 | 0.10 | 0.71 | 1.00 | 0.14 | 0.82 | 1.00 | 1.00 | 0.22 | 1.00 | 1.00 |
| 11 | AGG | 1.00 | 1.00 | 1.00 | 1.00 | 1.00 | 1.00 | 1.00 | 1.00 | 1.00 | 1.00 | 1.00 | 1.00 |
| 12 | AGT | 1.00 | 0.56 | 1.00 | 1.00 | 1.00 | 0.80 | 1.00 | 1.00 | 1.00 | 1.00 | 1.00 | 1.00 |
| 13 | ATA | 1.00 | 1.00 | 1.00 | 1.00 | 1.00 | 1.00 | 1.00 | 1.00 | 1.00 | 1.00 | 1.00 | 1.00 |
| 14 | ATC | −0.53 | −0.72 | −0.38 | 0.55 | 1.00 | −0.58 | 0.85 | −0.77 | 1.00 | −0.20 | 1.00 | 0.67 |
| 15 | ATG | 0.12 | −0.38 | −0.29 | 0.74 | 0.64 | −0.25 | 0.48 | −0.29 | 1.00 | −0.11 | 1.00 | 0.79 |
| 16 | ATT | 0.64 | 0.73 | 0.93 | 0.95 | 0.87 | 0.46 | 0.87 | −0.12 | 1.00 | 0.93 | 1.00 | 1.00 |
| 17 | CAA | 0.71 | 0.47 | 1.00 | 0.68 | 1.00 | 0.65 | 0.81 | 0.07 | 1.00 | 1.00 | 1.00 | 0.54 |
| 18 | CAC | −0.51 | −0.65 | −0.60 | 1.00 | 1.00 | −0.65 | 1.00 | −0.72 | 1.00 | −0.63 | 1.00 | −0.10 |
| 19 | CAG | −0.33 | −0.46 | −0.11 | 0.40 | 0.79 | −0.32 | 1.00 | −0.75 | 1.00 | −0.41 | 1.00 | 1.00 |
| 20 | CAT | 0.92 | 0.00 | 0.73 | 1.00 | 1.00 | 0.57 | 0.77 | 0.24 | 1.00 | 0.55 | 1.00 | 1.00 |
| 21 | CCA | 0.43 | 0.30 | 1.00 | 0.71 | 1.00 | −0.07 | 1.00 | −0.13 | 1.00 | −0.28 | 1.00 | 1.00 |
| 22 | CCC | 1.00 | 1.00 | 1.00 | 1.00 | 1.00 | 1.00 | 1.00 | 1.00 | 1.00 | 1.00 | 1.00 | 1.00 |
| 23 | CCG | −0.43 | −0.64 | −0.08 | 0.79 | 0.47 | −0.52 | 1.00 | −0.71 | 1.00 | 0.01 | 1.00 | 0.54 |
| 24 | CCT | 0.45 | 1.00 | 1.00 | 0.31 | 1.00 | 0.48 | 1.00 | 0.31 | 1.00 | 1.00 | 1.00 | 1.00 |
| 25 | CGA | 1.00 | 1.00 | 1.00 | 1.00 | 1.00 | 1.00 | 1.00 | −0.19 | 1.00 | 1.00 | 1.00 | 1.00 |
| 26 | CGC | 0.43 | −0.39 | 0.17 | 0.91 | 1.00 | 0.42 | 1.00 | −0.14 | 1.00 | 0.52 | 1.00 | 1.00 |
| 27 | CGG | 1.00 | 1.00 | 1.00 | 1.00 | 1.00 | 1.00 | 1.00 | 1.00 | 1.00 | 1.00 | 1.00 | 1.00 |
| 28 | CGT | −0.45 | −0.59 | −0.59 | 0.41 | 0.21 | −0.54 | 0.62 | −0.83 | 1.00 | 0.23 | 1.00 | 0.53 |
| 29 | CTA | 1.00 | 1.00 | 1.00 | 1.00 | 1.00 | 1.00 | 1.00 | 1.00 | 1.00 | 1.00 | 1.00 | 1.00 |
| 30 | CTC | 0.76 | 0.38 | 0.74 | 1.00 | 1.00 | 0.66 | 1.00 | 0.55 | 1.00 | 0.46 | 1.00 | 1.00 |
| 31 | CTG | −0.53 | −0.69 | 0.02 | 0.73 | 0.64 | −0.60 | 0.66 | −0.76 | 1.00 | −0.35 | 1.00 | 0.90 |
| 32 | CTT | 0.84 | 0.79 | 1.00 | 1.00 | 1.00 | 1.00 | 1.00 | 1.00 | 1.00 | 0.73 | 1.00 | 1.00 |
| 33 | GAA | −0.11 | −0.45 | 0.76 | 0.69 | 0.89 | −0.43 | 0.63 | −0.64 | 1.00 | −0.26 | 1.00 | 0.76 |
| 34 | GAC | −0.51 | −0.63 | −0.51 | 0.91 | 0.76 | −0.58 | 0.66 | −0.51 | 1.00 | −0.63 | 1.00 | 1.00 |
| 35 | GAG | −0.15 | −0.21 | −0.14 | 1.00 | 1.00 | 0.79 | 1.00 | 0.24 | 1.00 | 0.86 | 1.00 | 1.00 |
| 36 | GAT | 0.61 | −0.20 | 0.64 | 1.00 | 1.00 | −0.22 | 1.00 | 0.12 | 1.00 | 0.92 | 1.00 | 1.00 |
| 37 | GCA | 0.37 | −0.45 | 0.91 | 1.00 | 0.24 | −0.55 | 0.88 | −0.80 | 1.00 | −0.07 | 1.00 | 0.75 |
| 38 | GCC | 0.71 | 0.49 | 0.93 | 0.94 | 0.80 | 0.65 | 0.91 | 0.39 | 1.00 | 0.17 | 1.00 | 0.81 |
| 39 | GCG | −0.18 | −0.22 | −0.03 | 0.90 | 0.85 | 0.12 | 0.86 | −0.43 | 1.00 | 0.76 | 1.00 | 0.85 |
| 40 | GCT | −0.64 | −0.79 | −0.42 | 0.68 | 1.00 | −0.55 | 0.36 | −0.61 | 1.00 | 0.65 | 1.00 | 1.00 |
| 41 | GGA | 0.94 | 0.68 | 1.00 | 1.00 | 1.00 | 0.84 | 1.00 | 1.00 | 1.00 | 0.76 | 1.00 | 1.00 |
| 42 | GGC | 0.29 | −0.27 | 0.51 | 0.64 | 0.85 | −0.04 | 0.86 | −0.21 | 1.00 | 0.32 | 1.00 | 0.77 |
| 43 | GGG | 0.82 | 1.00 | 1.00 | 1.00 | 1.00 | 1.00 | 1.00 | 0.69 | 1.00 | 1.00 | 1.00 | 1.00 |
| 44 | GGT | −0.57 | −0.64 | −0.24 | 0.44 | 0.64 | −0.29 | 0.32 | −0.86 | 1.00 | −0.04 | 1.00 | 0.86 |
| 45 | GTA | −0.15 | −0.64 | 1.00 | 0.67 | 0.31 | −0.50 | −0.13 | −0.83 | 1.00 | −0.21 | 1.00 | 0.61 |
| 46 | GTC | 0.73 | 0.25 | 0.75 | 1.00 | 1.00 | 0.29 | 1.00 | 0.25 | 1.00 | 0.26 | 1.00 | 1.00 |
| 47 | GTG | 0.04 | 0.23 | 0.63 | 0.93 | 1.00 | 0.04 | 0.86 | −0.50 | 1.00 | 0.83 | 1.00 | 0.68 |
| 48 | GTT | −0.47 | −0.70 | −0.53 | 0.90 | 1.00 | −0.38 | 0.90 | −0.47 | 1.00 | 0.37 | 1.00 | 1.00 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | −0.47 | −0.71 | −0.29 | 0.84 | 1.00 | −0.68 | 1.00 | −0.73 | 1.00 | −0.64 | 1.00 | 1.00 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.52 | 0.50 | 0.82 | 1.00 | 1.00 | 0.47 | 1.00 | 0.80 | 1.00 | 0.72 | 1.00 | 1.00 |
| 53 | TCA | 1.00 | 0.46 | 1.00 | 1.00 | 1.00 | 1.00 | 1.00 | −0.24 | 1.00 | 1.00 | 1.00 | 1.00 |
| 54 | TCC | −0.63 | −0.73 | −0.57 | 0.73 | 0.31 | −0.78 | 1.00 | −0.69 | 1.00 | −0.77 | 1.00 | 1.00 |
| 55 | TCG | 0.51 | 1.00 | 0.68 | 1.00 | 1.00 | 1.00 | 1.00 | 0.49 | 1.00 | 1.00 | 1.00 | 1.00 |
| 56 | TCT | −0.56 | −0.76 | 0.31 | 1.00 | 0.29 | −0.77 | 1.00 | −0.83 | 1.00 | 1.00 | 1.00 | 1.00 |
| 57 | TGA | 0.00 | 0.00 | 0.00 | 0.00 | 0.00 | 0.00 | 0.00 | 0.00 | 0.00 | 0.00 | 0.00 | 0.00 |

TABLE C.6-continued

CPW matrix *Escherichi coli* K12 highly expressed sequences (left codon indicated in column 2, right codon indicated in row 2). Host cell: *E. coli*; Sequence data: full *E. coli* genome; Highly expressed group: 100 seqs.

| | | | | | | | | | | | | |
|---|---|---|---|---|---|---|---|---|---|---|---|---|
| 58 | TGC | −0.22 | −0.28 | 1.00 | 1.00 | 1.00 | −0.48 | 1.00 | 0.27 | 1.00 | −0.23 | 1.00 | 0.20 |
| 59 | TGG | −0.23 | −0.37 | 1.00 | 0.71 | 1.00 | −0.20 | 0.32 | −0.39 | 1.00 | 0.28 | 1.00 | 1.00 |
| 60 | TGT | −0.25 | −0.57 | 1.00 | 1.00 | −0.15 | 0.66 | 1.00 | −0.78 | 1.00 | 1.00 | 1.00 | 1.00 |
| 61 | TTA | 0.94 | 1.00 | 1.00 | 1.00 | 1.00 | 1.00 | 1.00 | 0.64 | 1.00 | 0.78 | 1.00 | 1.00 |
| 62 | TTC | −0.49 | −0.69 | 0.14 | 0.65 | 0.51 | −0.61 | 1.00 | −0.77 | 1.00 | −0.30 | 1.00 | 1.00 |
| 63 | TTG | 0.81 | 0.83 | 1.00 | 1.00 | 0.53 | 1.00 | 1.00 | 0.63 | 1.00 | 0.56 | 1.00 | 1.00 |
| 64 | TTT | 0.54 | 0.47 | 0.49 | 0.94 | 0.82 | 0.73 | 1.00 | 0.00 | 1.00 | 0.76 | 1.00 | 1.00 |

| | | AAA<br>1 | AAC<br>2 | AAG<br>3 | AAT<br>4 | ACA<br>5 | ACC<br>6 | ACG<br>7 | ACT<br>8 | AGA<br>9 | AGC<br>10 | AGG<br>11 | AGT<br>12 |
|---|---|---|---|---|---|---|---|---|---|---|---|---|---|
| | | 13<br>ATA | 14<br>ATC | 15<br>ATG | 16<br>ATT | 17<br>CAA | 18<br>CAC | 19<br>CAG | 20<br>CAT | 21<br>CCA | 22<br>CCC | 23<br>CCG | 24<br>CCT |
| 1 | AAA | 1.00 | −0.36 | −0.04 | 0.44 | 0.20 | −0.51 | 0.16 | 1.00 | −0.17 | 1.00 | 0.05 | 0.38 |
| 2 | AAC | 1.00 | −0.72 | −0.41 | 0.69 | 0.54 | −0.70 | −0.56 | 0.47 | 0.24 | 1.00 | −0.62 | 0.82 |
| 3 | AAG | 1.00 | −0.49 | 0.15 | 0.32 | 0.24 | −0.64 | −0.50 | 0.54 | 0.71 | 1.00 | −0.61 | −0.03 |
| 4 | AAT | 1.00 | 0.62 | 0.87 | 0.94 | 1.00 | 0.71 | 0.70 | 1.00 | 0.81 | 1.00 | 0.46 | 1.00 |
| 5 | ACA | 1.00 | 0.83 | 1.00 | 1.00 | 1.00 | 1.00 | 0.76 | 1.00 | 1.00 | 1.00 | 0.81 | 1.00 |
| 6 | ACC | 1.00 | −0.67 | −0.47 | 0.30 | 0.19 | −0.47 | 0.01 | 0.61 | 0.37 | 1.00 | 0.05 | 0.81 |
| 7 | ACG | 1.00 | 1.00 | 0.73 | 0.80 | 0.56 | 0.44 | 0.88 | 1.00 | 0.49 | 1.00 | 0.36 | 0.69 |
| 8 | ACT | 1.00 | −0.64 | 0.35 | 0.35 | −0.44 | −0.85 | −0.73 | 1.00 | 0.58 | 1.00 | −0.82 | −0.60 |
| 9 | AGA | 1.00 | 1.00 | 1.00 | 1.00 | 1.00 | 1.00 | 1.00 | −0.33 | 1.00 | 1.00 | 1.00 | 1.00 |
| 10 | AGC | 1.00 | −0.37 | 0.38 | 0.63 | 1.00 | −0.51 | −0.17 | 0.78 | 1.00 | 1.00 | −0.29 | 1.00 |
| 11 | AGG | 1.00 | 1.00 | 1.00 | 1.00 | 1.00 | 1.00 | 1.00 | 1.00 | 1.00 | 1.00 | 1.00 | 1.00 |
| 12 | AGT | 1.00 | 0.84 | 1.00 | 0.86 | 0.53 | 1.00 | 1.00 | 1.00 | 1.00 | 1.00 | 0.48 | 1.00 |
| 13 | ATA | 1.00 | 1.00 | 1.00 | 1.00 | 1.00 | 1.00 | 1.00 | 1.00 | 1.00 | 1.00 | 1.00 | 1.00 |
| 14 | ATC | 1.00 | −0.70 | −0.53 | 0.04 | 0.45 | −0.68 | −0.42 | 0.50 | −0.18 | 0.73 | −0.57 | −0.31 |
| 15 | ATG | 1.00 | −0.48 | 0.00 | 0.64 | 0.33 | −0.43 | −0.15 | 0.56 | −0.24 | 1.00 | −0.17 | 0.30 |
| 16 | ATT | 1.00 | 0.23 | 0.82 | 0.88 | 1.00 | −0.09 | −0.24 | 0.72 | 0.86 | 1.00 | 0.02 | 1.00 |
| 17 | CAA | 1.00 | 0.32 | 0.66 | 0.91 | 0.82 | −0.11 | 0.81 | 0.58 | 1.00 | 1.00 | −0.04 | 0.00 |
| 18 | CAC | 1.00 | −0.73 | −0.38 | 0.27 | 1.00 | −0.72 | −0.52 | 0.55 | −0.33 | 1.00 | −0.64 | 1.00 |
| 19 | CAG | 1.00 | −0.58 | −0.26 | 0.31 | 0.52 | −0.58 | −0.48 | 0.78 | 0.78 | 1.00 | −0.49 | 0.48 |
| 20 | CAT | 1.00 | 0.53 | 0.46 | 0.76 | 1.00 | 0.09 | −0.10 | 1.00 | 1.00 | 1.00 | 0.40 | 0.33 |
| 21 | CCA | 1.00 | −0.61 | 0.57 | 0.84 | 0.37 | 0.59 | 0.34 | 0.69 | 1.00 | 1.00 | −0.23 | 1.00 |
| 22 | CCC | 1.00 | 0.70 | 1.00 | 1.00 | 1.00 | 1.00 | 1.00 | 1.00 | 1.00 | 1.00 | 1.00 | 1.00 |
| 23 | CCG | 1.00 | −0.58 | −0.37 | 0.24 | 0.33 | −0.70 | −0.53 | 0.56 | −0.42 | 1.00 | −0.50 | −0.36 |
| 24 | CCT | 1.00 | 0.53 | 0.49 | 1.00 | 1.00 | 1.00 | 0.80 | 0.63 | 1.00 | 1.00 | 1.00 | 1.00 |
| 25 | CGA | 1.00 | 0.58 | 1.00 | 1.00 | 1.00 | 1.00 | 1.00 | 1.00 | 1.00 | 1.00 | 1.00 | 1.00 |
| 26 | CGC | 1.00 | 0.54 | 0.10 | 0.35 | 1.00 | 0.30 | 0.44 | 0.87 | 0.78 | 1.00 | 0.36 | 0.20 |
| 27 | CGG | 1.00 | 1.00 | 1.00 | 1.00 | 1.00 | 1.00 | 1.00 | 1.00 | 1.00 | 1.00 | 1.00 | 1.00 |
| 28 | CGT | 1.00 | −0.74 | −0.40 | 0.14 | 0.55 | −0.73 | −0.69 | 0.02 | 0.29 | 1.00 | −0.66 | −0.61 |
| 29 | CTA | 1.00 | 1.00 | 1.00 | 1.00 | 1.00 | 1.00 | 1.00 | 1.00 | 1.00 | 1.00 | 1.00 | 1.00 |
| 30 | CTC | 1.00 | 0.14 | 0.81 | 0.64 | 0.63 | 0.47 | 0.61 | 1.00 | 1.00 | 1.00 | 0.82 | 1.00 |
| 31 | CTG | 1.00 | −0.71 | −0.43 | 0.25 | −0.28 | −0.75 | −0.54 | 0.67 | −0.48 | 0.84 | −0.60 | −0.02 |
| 32 | CTT | 1.00 | 0.78 | 1.00 | 1.00 | 1.00 | 1.00 | 1.00 | 1.00 | 1.00 | 1.00 | 0.63 | 1.00 |
| 33 | GAA | 1.00 | −0.56 | −0.11 | 0.66 | 0.49 | −0.28 | 0.12 | 0.67 | −0.22 | 1.00 | −0.06 | −0.02 |
| 34 | GAC | 1.00 | −0.66 | −0.35 | 0.38 | 0.87 | −0.66 | −0.57 | 0.34 | 0.51 | 1.00 | −0.40 | 1.00 |
| 35 | GAG | 1.00 | −0.30 | 0.27 | 0.78 | 0.48 | −0.64 | −0.52 | 0.51 | 1.00 | 1.00 | −0.48 | 0.62 |
| 36 | GAT | 1.00 | −0.30 | 0.33 | 0.85 | 0.68 | −0.28 | 0.16 | 0.94 | 0.42 | 1.00 | 0.48 | 0.65 |
| 37 | GCA | 1.00 | −0.56 | −0.41 | 0.47 | 0.76 | −0.47 | −0.36 | 0.69 | 0.41 | 0.55 | −0.62 | −0.06 |
| 38 | GCC | 1.00 | 0.50 | 0.60 | 0.70 | 1.00 | 1.00 | 0.41 | 0.76 | 1.00 | 1.00 | 0.92 | 0.45 |
| 39 | GCG | 1.00 | 0.07 | −0.01 | 0.17 | 0.72 | −0.52 | −0.04 | 0.63 | 0.65 | 0.73 | −0.27 | 1.00 |
| 40 | GCT | 1.00 | −0.78 | −0.07 | 0.49 | 0.37 | −0.76 | −0.70 | 0.18 | 0.22 | 1.00 | −0.70 | 1.00 |
| 41 | GGA | 1.00 | 1.00 | 0.88 | 1.00 | 1.00 | 1.00 | 1.00 | 1.00 | 1.00 | 1.00 | 0.23 | 1.00 |
| 42 | GGC | 1.00 | 0.25 | 0.07 | 0.58 | 0.92 | −0.39 | 0.26 | 0.87 | 0.43 | 0.71 | −0.13 | 0.77 |
| 43 | GGG | 1.00 | 0.71 | 1.00 | 0.84 | 1.00 | 0.07 | 0.88 | 1.00 | 0.49 | 1.00 | 0.27 | 1.00 |
| 44 | GGT | 1.00 | −0.75 | −0.45 | −0.04 | 0.80 | −0.67 | −0.71 | −0.01 | 0.32 | 1.00 | −0.64 | 0.46 |
| 45 | GTA | 1.00 | −0.52 | −0.56 | 0.51 | 0.31 | −0.68 | −0.65 | 0.33 | −0.47 | 1.00 | −0.63 | −0.55 |
| 46 | GTC | 1.00 | 0.44 | 0.77 | 0.83 | 1.00 | 1.00 | 0.49 | 0.76 | 0.21 | 1.00 | 0.53 | 0.37 |
| 47 | GTG | 1.00 | −0.10 | 0.06 | 0.76 | 0.71 | 0.82 | 0.93 | 1.00 | 0.54 | 1.00 | 0.56 | 0.63 |
| 48 | GTT | 1.00 | −0.78 | 0.03 | 0.61 | 0.39 | −0.80 | −0.65 | 0.20 | 0.33 | 1.00 | −0.55 | −0.53 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 1.00 | −0.74 | −0.55 | 0.33 | 1.00 | −0.66 | −0.55 | −0.02 | 0.23 | 1.00 | −0.48 | 1.00 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 1.00 | 0.57 | 0.91 | 0.78 | 1.00 | 0.18 | 0.01 | 1.00 | 0.71 | 1.00 | −0.26 | 0.30 |
| 53 | TCA | 1.00 | 1.00 | 0.72 | 1.00 | 1.00 | 1.00 | 0.69 | 1.00 | 1.00 | 1.00 | 0.68 | 1.00 |
| 54 | TCC | 1.00 | −0.81 | −0.61 | 0.04 | 1.00 | −0.69 | −0.50 | 0.60 | 1.00 | 1.00 | −0.62 | 1.00 |
| 55 | TCG | 1.00 | 0.84 | 0.11 | 0.74 | 1.00 | 1.00 | 1.00 | 1.00 | 0.29 | 1.00 | 0.75 | 1.00 |
| 56 | TCT | 1.00 | −0.78 | −0.47 | 0.72 | 1.00 | −0.86 | −0.82 | 0.58 | 1.00 | 1.00 | −0.83 | 0.09 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 1.00 | −0.24 | −0.07 | 1.00 | 1.00 | −0.58 | −0.45 | 0.55 | 0.05 | 1.00 | −0.58 | 1.00 |
| 59 | TGG | 1.00 | −0.28 | 0.00 | 0.18 | 1.00 | −0.57 | −0.34 | 1.00 | 1.00 | 1.00 | −0.47 | 1.00 |
| 60 | TGT | 1.00 | −0.73 | 0.10 | 1.00 | −0.54 | 0.25 | 1.00 | 0.44 | −0.16 | 1.00 | 0.57 | 1.00 |
| 61 | TTA | 1.00 | 1.00 | 1.00 | 0.85 | 1.00 | 1.00 | 1.00 | 1.00 | 1.00 | 1.00 | 1.00 | 1.00 |
| 62 | TTC | 1.00 | −0.74 | −0.30 | 0.73 | 1.00 | −0.79 | −0.71 | 0.41 | 0.23 | 1.00 | −0.73 | −0.28 |

TABLE C.6-continued

CPW matrix *Escherichi coli* K12 highly expressed sequences (left codon indicated in column 2, right codon indicated in row 2). Host cell: *E. coli*; Sequence data: full *E. coli* genome; Highly expressed group: 100 seqs.

| | | | | | | | | | | | | |
|---|---|---|---|---|---|---|---|---|---|---|---|---|
| 63 | TTG | 1.00 | 0.82 | 0.23 | 1.00 | 1.00 | 1.00 | 0.84 | 0.67 | 0.58 | 1.00 | 0.70 | 1.00 |
| 64 | TTT | 1.00 | 0.19 | 0.32 | 0.86 | 1.00 | 1.00 | 0.90 | 1.00 | 1.00 | 1.00 | 1.00 | 1.00 |

| | | ATA 13 | ATC 14 | ATG 15 | ATT 16 | CAA 17 | CAC 18 | CAG 19 | CAT 20 | CCA 21 | CCC 22 | CCG 23 | CCT 24 |
|---|---|---|---|---|---|---|---|---|---|---|---|---|---|

| | | 25 CGA | 26 CGC | 27 CGG | 28 CGT | 29 CTA | 30 CTC | 31 CTG | 32 CTT | 33 GAA | 34 GAC | 35 GAG | 36 GAT |
|---|---|---|---|---|---|---|---|---|---|---|---|---|---|
| 1 | AAA | 1.00 | 0.43 | 1.00 | −0.36 | 1.00 | 0.76 | −0.46 | 0.84 | −0.17 | −0.53 | −0.32 | 0.26 |
| 2 | AAC | 1.00 | −0.26 | 1.00 | −0.70 | 0.42 | −0.38 | −0.66 | 0.80 | −0.47 | −0.62 | −0.15 | 0.01 |
| 3 | AAG | 0.33 | −0.32 | 1.00 | −0.61 | 1.00 | 0.19 | −0.41 | 0.73 | 0.95 | 0.82 | 1.00 | 0.84 |
| 4 | AAT | 1.00 | 1.00 | 1.00 | 1.00 | 1.00 | 1.00 | 0.74 | 1.00 | 0.82 | 0.59 | 0.79 | 0.85 |
| 5 | ACA | 1.00 | 1.00 | 1.00 | 0.34 | 1.00 | 1.00 | 0.86 | 1.00 | 0.41 | 0.41 | 0.74 | 1.00 |
| 6 | ACC | 1.00 | 0.33 | 1.00 | −0.56 | 1.00 | 0.62 | −0.45 | 0.61 | −0.36 | −0.40 | 0.22 | 0.31 |
| 7 | ACG | 1.00 | 0.90 | 1.00 | 0.79 | 1.00 | 1.00 | −0.31 | 1.00 | 0.89 | 1.00 | 1.00 | 1.00 |
| 8 | ACT | 1.00 | −0.59 | 1.00 | −0.77 | −0.32 | 1.00 | −0.75 | 1.00 | −0.61 | −0.83 | 0.18 | −0.27 |
| 9 | AGA | 1.00 | 1.00 | 1.00 | 1.00 | 1.00 | 1.00 | 1.00 | 1.00 | 1.00 | 1.00 | 1.00 | 1.00 |
| 10 | AGC | 1.00 | 0.07 | 1.00 | −0.69 | 1.00 | 1.00 | −0.43 | 0.45 | −0.20 | −0.19 | 0.75 | 0.33 |
| 11 | AGG | 1.00 | 1.00 | 1.00 | 1.00 | 1.00 | 1.00 | 1.00 | 1.00 | 1.00 | 1.00 | 1.00 | 1.00 |
| 12 | AGT | 1.00 | 1.00 | 1.00 | 1.00 | 1.00 | 1.00 | 0.90 | 1.00 | 0.79 | 0.79 | 1.00 | 0.88 |
| 13 | ATA | 1.00 | 1.00 | 1.00 | 1.00 | 1.00 | 1.00 | 1.00 | 1.00 | 1.00 | 1.00 | 1.00 | 1.00 |
| 14 | ATC | 1.00 | −0.34 | 1.00 | −0.63 | 1.00 | −0.67 | −0.59 | 0.13 | −0.57 | −0.72 | −0.08 | −0.07 |
| 15 | ATG | 1.00 | 0.35 | 1.00 | −0.49 | 1.00 | 0.27 | −0.41 | 0.85 | −0.10 | −0.45 | 0.24 | 0.49 |
| 16 | ATT | 1.00 | 0.55 | 1.00 | −0.12 | 1.00 | 0.64 | −0.13 | 1.00 | 0.53 | 0.57 | 0.86 | 0.80 |
| 17 | CAA | 1.00 | 0.86 | 1.00 | −0.07 | 1.00 | 0.71 | 0.26 | 0.70 | 0.65 | 0.03 | −0.14 | 0.83 |
| 18 | CAC | −0.27 | −0.48 | 1.00 | −0.66 | 1.00 | −0.62 | −0.69 | 0.46 | −0.55 | −0.70 | 0.06 | 0.33 |
| 19 | CAG | 1.00 | 0.01 | 1.00 | −0.57 | 0.56 | −0.07 | −0.53 | 0.22 | −0.36 | −0.40 | 0.60 | −0.04 |
| 20 | CAT | 1.00 | 0.68 | 1.00 | 0.66 | 1.00 | 1.00 | 0.58 | 1.00 | 0.45 | −0.25 | 1.00 | 1.00 |
| 21 | CCA | 1.00 | 0.68 | 1.00 | 0.32 | 1.00 | 0.33 | 0.72 | 1.00 | −0.35 | −0.53 | 0.46 | 0.64 |
| 22 | CCC | 1.00 | 1.00 | 1.00 | 1.00 | 1.00 | 1.00 | 1.00 | 1.00 | 0.88 | 1.00 | 1.00 | 0.73 |
| 23 | CCG | 1.00 | −0.58 | 1.00 | −0.45 | 1.00 | 0.76 | −0.69 | 0.76 | −0.38 | −0.51 | 0.81 | 0.17 |
| 24 | CCT | 1.00 | 0.23 | 1.00 | 1.00 | 1.00 | 1.00 | 0.66 | 0.18 | 0.13 | −0.31 | 0.14 | 0.78 |
| 25 | CGA | 1.00 | 1.00 | 1.00 | 1.00 | 1.00 | 1.00 | 0.72 | 1.00 | 1.00 | 0.47 | 1.00 | 1.00 |
| 26 | CGC | 1.00 | 0.28 | 1.00 | −0.34 | 1.00 | 0.79 | −0.02 | 0.79 | −0.05 | −0.13 | 0.63 | 0.22 |
| 27 | CGG | 1.00 | 1.00 | 1.00 | 1.00 | 1.00 | 1.00 | 1.00 | 1.00 | 1.00 | 1.00 | 1.00 | 1.00 |
| 28 | CGT | 1.00 | −0.34 | 1.00 | −0.65 | 1.00 | 0.33 | −0.73 | 0.09 | −0.49 | −0.68 | −0.19 | 0.28 |
| 29 | CTA | 1.00 | 1.00 | 1.00 | 1.00 | 1.00 | 1.00 | 1.00 | 1.00 | 1.00 | 0.47 | 1.00 | 0.68 |
| 30 | CTC | 1.00 | 1.00 | 1.00 | 0.79 | 1.00 | 0.37 | 0.87 | 0.37 | 0.08 | −0.66 | 0.31 | 0.45 |
| 31 | CTG | 1.00 | −0.40 | 1.00 | −0.70 | 1.00 | −0.05 | −0.69 | 0.47 | −0.52 | −0.47 | 0.32 | −0.07 |
| 32 | CTT | 1.00 | 1.00 | 1.00 | 1.00 | 1.00 | 1.00 | 0.73 | 1.00 | 0.61 | −0.41 | −0.28 | 0.67 |
| 33 | GAA | 0.83 | 0.51 | 1.00 | −0.38 | 1.00 | 0.93 | −0.47 | 0.66 | −0.25 | −0.57 | −0.40 | 0.08 |
| 34 | GAC | 1.00 | −0.37 | 1.00 | −0.72 | 1.00 | −0.15 | −0.65 | 0.32 | −0.54 | −0.66 | −0.20 | 0.30 |
| 35 | GAG | 1.00 | −0.25 | 1.00 | −0.56 | 1.00 | 0.85 | −0.47 | 0.70 | 0.97 | 1.00 | 0.93 | 1.00 |
| 36 | GAT | 1.00 | 0.48 | 1.00 | 0.50 | 1.00 | 0.90 | −0.07 | 0.90 | 0.44 | −0.28 | 0.71 | 0.73 |
| 37 | GCA | 1.00 | 0.13 | 1.00 | −0.62 | 1.00 | 0.40 | −0.58 | 1.00 | −0.37 | −0.42 | 0.10 | 0.70 |
| 38 | GCC | 1.00 | 0.63 | 1.00 | 0.67 | 1.00 | 1.00 | 0.41 | 1.00 | 0.54 | −0.05 | 0.95 | 0.77 |
| 39 | GCG | 1.00 | 0.34 | 1.00 | −0.37 | 1.00 | 0.52 | −0.48 | 0.52 | 0.52 | 0.62 | 0.92 | 0.77 |
| 40 | GCT | 0.33 | −0.50 | 1.00 | −0.69 | 1.00 | 1.00 | −0.69 | 0.20 | −0.74 | −0.86 | −0.27 | −0.38 |
| 41 | GGA | 1.00 | 1.00 | 1.00 | 0.65 | 1.00 | 1.00 | 1.00 | 1.00 | 1.00 | 1.00 | 1.00 | 0.90 |
| 42 | GGC | 1.00 | 0.29 | 1.00 | −0.39 | 1.00 | 0.13 | −0.29 | 0.49 | −0.38 | −0.62 | 0.45 | 0.29 |
| 43 | GGG | 1.00 | 1.00 | 1.00 | 1.00 | 1.00 | 1.00 | 0.93 | 1.00 | 0.94 | 1.00 | 0.88 | 0.86 |
| 44 | GGT | 1.00 | 0.10 | 1.00 | −0.74 | 1.00 | 0.85 | −0.72 | 0.24 | −0.44 | −0.54 | 0.51 | 0.43 |
| 45 | GTA | 1.00 | −0.25 | 1.00 | −0.76 | 1.00 | 0.66 | −0.75 | 0.32 | −0.61 | −0.52 | −0.06 | 0.44 |
| 46 | GTC | 1.00 | 1.00 | 1.00 | 0.60 | 1.00 | 1.00 | 0.75 | 1.00 | 0.76 | 0.33 | 0.92 | 0.92 |
| 47 | GTG | 1.00 | 0.83 | 1.00 | 0.12 | 1.00 | 0.72 | −0.10 | 1.00 | 0.80 | 0.73 | 1.00 | 0.84 |
| 48 | GTT | 0.49 | −0.37 | 1.00 | −0.69 | 1.00 | 0.00 | −0.66 | 0.80 | −0.65 | −0.77 | −0.01 | −0.41 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.26 | −0.38 | 1.00 | −0.70 | 1.00 | −0.31 | −0.65 | 0.26 | −0.45 | −0.61 | −0.01 | 0.00 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 1.00 | 0.91 | 1.00 | 0.35 | 1.00 | 0.17 | 0.19 | 0.72 | 0.41 | 0.10 | 0.45 | 0.64 |
| 53 | TCA | 1.00 | 1.00 | 1.00 | 1.00 | 1.00 | 1.00 | 0.87 | 1.00 | 0.61 | 0.74 | 1.00 | 1.00 |
| 54 | TCC | 1.00 | 0.26 | 1.00 | −0.76 | 1.00 | 0.50 | −0.64 | 1.00 | 0.05 | −0.60 | −0.39 | 0.50 |
| 55 | TCG | 1.00 | 1.00 | 1.00 | 1.00 | 1.00 | 1.00 | 0.09 | 1.00 | 1.00 | 1.00 | 1.00 | 1.00 |
| 56 | TCT | 1.00 | −0.22 | 1.00 | −0.72 | 1.00 | 1.00 | −0.81 | 0.47 | −0.76 | −0.86 | −0.48 | −0.40 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 1.00 | 0.26 | 1.00 | −0.75 | 1.00 | −0.19 | −0.61 | 1.00 | −0.36 | −0.41 | 0.42 | 1.00 |
| 59 | TGG | 1.00 | 0.17 | 1.00 | −0.43 | 1.00 | 0.40 | −0.43 | 1.00 | −0.26 | −0.35 | 0.77 | 0.32 |
| 60 | TGT | 1.00 | 1.00 | 1.00 | 1.00 | 1.00 | 1.00 | 1.00 | 0.36 | −0.36 | 0.35 | −0.65 | 0.27 | 0.37 |

TABLE C.6-continued

CPW matrix *Escherichi coli* K12 highly expressed sequences (left codon indicated in column 2, right codon indicated in row 2). Host cell: *E. coli*; Sequence data: full *E. coli* genome; Highly expressed group: 100 seqs.

|    |     |      |       |      |       |      |       |      |       |      |       |      |      |
|----|-----|------|-------|------|-------|------|-------|------|-------|------|-------|------|------|
| 61 | TTA | 1.00 | 0.84  | 1.00 | 0.83  | 1.00 | 1.00  | 1.00 | 1.00  | 1.00 | 0.70  | 1.00 | 0.82 |
| 62 | TTC | 1.00 | −0.45 | 1.00 | −0.75 | 1.00 | −0.62 | −0.73 | −0.35 | −0.40 | −0.64 | −0.09 | 0.02 |
| 63 | TTG | 1.00 | 0.84  | 1.00 | 1.00  | 1.00 | 1.00  | 0.78 | 0.48  | 0.94 | 0.55  | 0.86 | 0.91 |
| 64 | TTT | 1.00 | 1.00  | 1.00 | 0.80  | 1.00 | 1.00  | 0.94 | 1.00  | 0.23 | −0.05 | 0.67 | 0.82 |

|    |     | CGA<br>25 | CGC<br>26 | CGG<br>27 | CGT<br>28 | CTA<br>29 | CTC<br>30 | CTG<br>31 | CTT<br>32 | GAA<br>33 | GAC<br>34 | GAG<br>35 | GAT<br>36 |
|----|-----|---|---|---|---|---|---|---|---|---|---|---|---|

|    |     | 37<br>GCA | 38<br>GCC | 39<br>GCG | 40<br>GCT | 41<br>GGA | 42<br>GGC | 43<br>GGG | 44<br>GGT | 45<br>GTA | 46<br>GTC | 47<br>GTG | 48<br>GTT |
|----|-----|-------|-------|-------|-------|-------|-------|-------|-------|-------|-------|-------|-------|
| 1  | AAA | −0.28 | 0.55  | −0.19 | −0.59 | 1.00  | −0.35 | 0.79  | −0.41 | −0.36 | 0.58  | −0.03 | −0.51 |
| 2  | AAC | −0.49 | −0.44 | 0.30  | −0.56 | 1.00  | −0.43 | 1.00  | −0.61 | −0.69 | 0.33  | −0.07 | −0.59 |
| 3  | AAG | 0.82  | 1.00  | 0.84  | 0.40  | 1.00  | 0.68  | 1.00  | 0.62  | 0.64  | 0.75  | 0.93  | 0.79  |
| 4  | AAT | 0.61  | 0.92  | 0.66  | 0.11  | 1.00  | 0.62  | 1.00  | 0.59  | 0.85  | 1.00  | 0.94  | 0.48  |
| 5  | ACA | 0.75  | 0.61  | 1.00  | 0.34  | 1.00  | 1.00  | 1.00  | 0.47  | 0.59  | 1.00  | 1.00  | 0.75  |
| 6  | ACC | −0.24 | 0.66  | 0.48  | −0.59 | 0.75  | 0.35  | 0.91  | −0.65 | −0.70 | 0.91  | 0.50  | −0.73 |
| 7  | ACG | 0.76  | 0.91  | 0.86  | 0.84  | 1.00  | 0.95  | 1.00  | 0.94  | 0.80  | 1.00  | 0.92  | 0.88  |
| 8  | ACT | −0.80 | −0.45 | −0.33 | −0.84 | 1.00  | −0.68 | 1.00  | −0.72 | −0.61 | 0.77  | 0.60  | −0.67 |
| 9  | AGA | 1.00  | 1.00  | 1.00  | 1.00  | 1.00  | 1.00  | 1.00  | 1.00  | 1.00  | 1.00  | 1.00  | 1.00  |
| 10 | AGC | 0.59  | 0.47  | 0.51  | 0.64  | 1.00  | 0.45  | 1.00  | −0.06 | 0.79  | 0.54  | 0.38  | −0.22 |
| 11 | AGG | 1.00  | 1.00  | 1.00  | 1.00  | 1.00  | 1.00  | 1.00  | 1.00  | 1.00  | 1.00  | 1.00  | 1.00  |
| 12 | AGT | 0.75  | 0.80  | 0.55  | 1.00  | 1.00  | 0.87  | 1.00  | 0.85  | 1.00  | 1.00  | 1.00  | 1.00  |
| 13 | ATA | 1.00  | 1.00  | 1.00  | 1.00  | 1.00  | 1.00  | 1.00  | 1.00  | 1.00  | 1.00  | 1.00  | 1.00  |
| 14 | ATC | −0.18 | 0.01  | −0.20 | −0.79 | 0.82  | −0.28 | 0.87  | −0.74 | −0.34 | −0.13 | 0.19  | −0.78 |
| 15 | ATG | 0.08  | 0.70  | 0.05  | −0.59 | 1.00  | −0.08 | 0.90  | −0.38 | −0.28 | 0.51  | 0.52  | −0.48 |
| 16 | ATT | 0.40  | 0.50  | 0.84  | −0.25 | 1.00  | 0.44  | 1.00  | 0.52  | 0.82  | 0.62  | 1.00  | 0.09  |
| 17 | CAA | 0.85  | 0.65  | 0.74  | 0.22  | 1.00  | 0.39  | 1.00  | 0.51  | 0.73  | 1.00  | 0.78  | 0.52  |
| 18 | CAC | 0.25  | −0.36 | −0.44 | −0.75 | 1.00  | −0.41 | 1.00  | −0.72 | −0.75 | −0.11 | 0.83  | −0.80 |
| 19 | CAG | −0.28 | 0.76  | −0.05 | −0.74 | 1.00  | −0.36 | 1.00  | −0.50 | −0.50 | 0.30  | 0.30  | −0.62 |
| 20 | CAT | 0.62  | 0.71  | 0.78  | 0.26  | 1.00  | 0.65  | 1.00  | 0.49  | 1.00  | 1.00  | 0.88  | 0.82  |
| 21 | CCA | 0.29  | 0.82  | 0.44  | −0.36 | 0.44  | 0.41  | 1.00  | −0.19 | −0.44 | 1.00  | 1.00  | −0.05 |
| 22 | CCC | 0.64  | 1.00  | 1.00  | 1.00  | 0.53  | 1.00  | 1.00  | 1.00  | 1.00  | 1.00  | 1.00  | 0.68  |
| 23 | CCG | −0.58 | 0.80  | 0.45  | −0.68 | 0.80  | −0.47 | 0.43  | −0.36 | −0.73 | 0.55  | 0.58  | −0.68 |
| 24 | CCT | −0.41 | 0.78  | −0.34 | −0.46 | 1.00  | −0.37 | 1.00  | 0.58  | 0.57  | 1.00  | 1.00  | 0.75  |
| 25 | CGA | 1.00  | 1.00  | 1.00  | 0.30  | 1.00  | 1.00  | 1.00  | 1.00  | 0.25  | 1.00  | 1.00  | 1.00  |
| 26 | CGC | −0.20 | 0.68  | 0.85  | −0.57 | 1.00  | 0.10  | 0.87  | −0.17 | −0.66 | 0.83  | 0.42  | −0.63 |
| 27 | CGG | 1.00  | 1.00  | 1.00  | 1.00  | 1.00  | 1.00  | 1.00  | 1.00  | 1.00  | 1.00  | 1.00  | 1.00  |
| 28 | CGT | −0.37 | 0.45  | −0.34 | −0.79 | 1.00  | −0.41 | 0.86  | −0.69 | −0.58 | 0.82  | 0.54  | −0.53 |
| 29 | CTA | 1.00  | 1.00  | 1.00  | 1.00  | 1.00  | 1.00  | 1.00  | 1.00  | 1.00  | 1.00  | 1.00  | 0.37  |
| 30 | CTC | 0.64  | 0.72  | 0.57  | 1.00  | 1.00  | −0.10 | 1.00  | −0.53 | 0.27  | 1.00  | 1.00  | 0.35  |
| 31 | CTG | −0.54 | 0.71  | −0.23 | −0.79 | 1.00  | −0.37 | 0.87  | −0.62 | −0.70 | 0.19  | 0.02  | −0.68 |
| 32 | CTT | 1.00  | 0.57  | 0.78  | −0.17 | 1.00  | −0.26 | 0.70  | 0.60  | 1.00  | 1.00  | 1.00  | 0.78  |
| 33 | GAA | −0.34 | 0.40  | −0.27 | −0.65 | 0.93  | −0.39 | 0.79  | −0.52 | −0.20 | 0.37  | −0.06 | −0.63 |
| 34 | GAC | −0.54 | 0.43  | −0.08 | −0.73 | 1.00  | −0.52 | 0.79  | −0.66 | −0.75 | 0.64  | −0.02 | −0.73 |
| 35 | GAG | 0.93  | 1.00  | 1.00  | 0.91  | 1.00  | 0.96  | 1.00  | 0.74  | 1.00  | 0.83  | 0.95  | 0.93  |
| 36 | GAT | 0.06  | 0.75  | 0.63  | −0.35 | 0.91  | 0.54  | 1.00  | 0.17  | 0.51  | 0.78  | 0.67  | 0.46  |
| 37 | GCA | −0.31 | 0.73  | 0.23  | −0.68 | 1.00  | −0.29 | 0.74  | −0.51 | −0.70 | 0.61  | 0.38  | −0.32 |
| 38 | GCC | 0.25  | 0.96  | 0.97  | −0.41 | 1.00  | 0.96  | 0.90  | −0.05 | 0.36  | 0.92  | 0.87  | −0.21 |
| 39 | GCG | 0.19  | 0.94  | 0.73  | 0.09  | 1.00  | 0.36  | 0.92  | −0.04 | −0.49 | 0.71  | 0.70  | −0.17 |
| 40 | GCT | −0.75 | 0.15  | −0.43 | −0.87 | 1.00  | −0.73 | 0.65  | −0.64 | −0.65 | 0.49  | 0.25  | −0.79 |
| 41 | GGA | 1.00  | 1.00  | 1.00  | 1.00  | 1.00  | 1.00  | 1.00  | 1.00  | 1.00  | 1.00  | 1.00  | 1.00  |
| 42 | GGC | −0.39 | 0.88  | −0.01 | −0.58 | 1.00  | −0.32 | 1.00  | −0.53 | −0.61 | 0.67  | 0.03  | −0.65 |
| 43 | GGG | 0.86  | 1.00  | 0.91  | 0.81  | 1.00  | 1.00  | 1.00  | 0.91  | 1.00  | 1.00  | 1.00  | 0.87  |
| 44 | GGT | −0.44 | 0.55  | −0.29 | −0.72 | 1.00  | 0.18  | 1.00  | −0.68 | −0.37 | 0.87  | 0.46  | −0.57 |
| 45 | GTA | −0.41 | 0.23  | −0.25 | −0.46 | 1.00  | 0.53  | 1.00  | −0.65 | −0.54 | 1.00  | 0.55  | −0.49 |
| 46 | GTC | 0.80  | 0.92  | 0.76  | −0.24 | 0.75  | 0.40  | 1.00  | −0.34 | 0.38  | 1.00  | 0.74  | 0.27  |
| 47 | GTG | 0.65  | 0.91  | 0.83  | 0.39  | 1.00  | 0.84  | 1.00  | −0.11 | 0.19  | 0.74  | 0.66  | −0.51 |
| 48 | GTT | −0.46 | 0.09  | −0.12 | −0.88 | 1.00  | −0.47 | 1.00  | −0.70 | −0.36 | 0.27  | 0.25  | −0.76 |
| 49 | TAA | 0.00  | 0.00  | 0.00  | 0.00  | 0.00  | 0.00  | 0.00  | 0.00  | 0.00  | 0.00  | 0.00  | 0.00  |
| 50 | TAC | −0.56 | 0.53  | 0.28  | −0.67 | 1.00  | −0.56 | 1.00  | −0.64 | −0.35 | −0.08 | 0.47  | −0.53 |
| 51 | TAG | 0.00  | 0.00  | 0.00  | 0.00  | 0.00  | 0.00  | 0.00  | 0.00  | 0.00  | 0.00  | 0.00  | 0.00  |
| 52 | TAT | 0.19  | 0.73  | 0.38  | −0.40 | 1.00  | 0.74  | 1.00  | 0.31  | 0.61  | 0.32  | 0.68  | −0.49 |
| 53 | TCA | 0.69  | 1.00  | 0.81  | 0.17  | 1.00  | 1.00  | 0.58  | 1.00  | 0.81  | 1.00  | 0.80  | 1.00  |
| 54 | TCC | −0.77 | 0.80  | −0.17 | −0.79 | 0.52  | −0.44 | 1.00  | −0.79 | −0.83 | −0.11 | −0.14 | −0.75 |
| 55 | TCG | 1.00  | 1.00  | 1.00  | 0.35  | 1.00  | 1.00  | 1.00  | 0.85  | 1.00  | 0.73  | 1.00  | 0.77  |
| 56 | TCT | −0.78 | −0.19 | −0.62 | −0.83 | 1.00  | −0.52 | 1.00  | −0.84 | −0.87 | −0.14 | 0.32  | −0.74 |
| 57 | TGA | 0.00  | 0.00  | 0.00  | 0.00  | 0.00  | 0.00  | 0.00  | 0.00  | 0.00  | 0.00  | 0.00  | 0.00  |
| 58 | TGC | −0.67 | 0.47  | 0.40  | 0.55  | 1.00  | 0.41  | 1.00  | −0.60 | −0.44 | 0.36  | 0.25  | −0.07 |
| 59 | TGG | −0.46 | 0.80  | 0.07  | −0.28 | 1.00  | −0.26 | 1.00  | −0.26 | −0.28 | 0.67  | 0.42  | −0.48 |
| 60 | TGT | 0.57  | 0.67  | −0.21 | −0.41 | 0.30  | 0.07  | 1.00  | −0.25 | −0.70 | 1.00  | 0.06  | 0.33  |

TABLE C.6-continued

CPW matrix *Escherichi coli* K12 highly expressed sequences (left codon indicated in column 2, right codon indicated in row 2). Host cell: *E. coli*; Sequence data: full *E. coli* genome; Highly expressed group: 100 seqs.

| | | | | | | | | | | | | |
|---|---|---|---|---|---|---|---|---|---|---|---|---|
| 61 | TTA | 0.71 | 0.77 | 1.00 | 0.42 | 1.00 | 0.91 | 0.76 | 0.68 | 0.41 | 1.00 | 1.00 | 0.82 |
| 62 | TTC | −0.37 | 0.11 | 0.19 | −0.63 | 0.18 | −0.19 | 0.71 | −0.72 | −0.70 | 0.72 | 0.43 | −0.71 |
| 63 | TTG | 1.00 | 0.88 | 0.91 | 0.80 | 1.00 | 1.00 | 1.00 | 0.89 | 0.70 | 1.00 | 1.00 | 0.82 |
| 64 | TTT | 0.57 | 0.54 | 0.44 | −0.55 | 1.00 | 0.80 | 0.89 | 0.23 | 0.26 | 0.79 | 0.69 | 0.12 |

| | | GCA 37 | GCC 38 | GCG 39 | GCT 40 | GGA 41 | GGC 42 | GGG 43 | GGT 44 | GTA 45 | GTC 46 | GTG 47 | GTT 48 |
|---|---|---|---|---|---|---|---|---|---|---|---|---|---|

| | | 49 TAA | 50 TAC | 51 TAG | 52 TAT | 53 TCA | 54 TCC | 55 TCG | 56 TCT | 57 TGA | 58 TGC | 59 TGG | 60 TGT |
|---|---|---|---|---|---|---|---|---|---|---|---|---|---|
| 1 | AAA | 0.00 | −0.31 | 0.00 | 0.21 | 1.00 | −0.35 | 0.66 | −0.65 | 0.00 | −0.06 | 0.02 | 0.20 |
| 2 | AAC | 0.00 | −0.71 | 0.00 | 0.40 | 1.00 | −0.74 | 0.81 | −0.71 | 0.00 | −0.62 | −0.45 | 0.18 |
| 3 | AAG | 0.00 | 0.14 | 0.00 | 0.35 | 1.00 | 0.21 | 0.24 | −0.81 | 0.00 | −0.29 | −0.07 | 0.11 |
| 4 | AAT | 0.00 | 1.00 | 0.00 | 1.00 | 1.00 | 0.51 | 1.00 | 1.00 | 0.00 | 1.00 | 1.00 | 1.00 |
| 5 | ACA | 0.00 | 1.00 | 0.00 | 1.00 | 1.00 | 1.00 | 1.00 | 0.31 | 0.00 | 1.00 | 0.40 | 1.00 |
| 6 | ACC | 0.00 | −0.60 | 0.00 | 0.38 | 1.00 | −0.15 | 0.81 | −0.69 | 0.00 | −0.27 | −0.53 | −0.61 |
| 7 | ACG | 0.00 | 1.00 | 0.00 | 0.85 | 1.00 | 1.00 | 1.00 | 0.67 | 0.00 | 1.00 | 1.00 | 1.00 |
| 8 | ACT | 0.00 | −0.77 | 0.00 | 0.53 | 0.36 | −0.88 | 0.00 | −0.88 | 0.00 | −0.45 | 1.00 | 1.00 |
| 9 | AGA | 0.00 | 1.00 | 0.00 | 1.00 | 1.00 | 1.00 | 1.00 | 1.00 | 0.00 | 1.00 | 1.00 | 1.00 |
| 10 | AGC | 0.00 | −0.40 | 0.00 | 0.49 | 1.00 | −0.54 | 1.00 | −0.47 | 0.00 | −0.28 | 0.70 | 0.42 |
| 11 | AGG | 0.00 | 1.00 | 0.00 | 1.00 | 1.00 | 1.00 | 1.00 | 1.00 | 0.00 | 1.00 | 1.00 | 1.00 |
| 12 | AGT | 0.00 | 0.69 | 0.00 | 1.00 | 1.00 | 0.32 | 1.00 | 0.30 | 0.00 | 1.00 | 1.00 | 1.00 |
| 13 | ATA | 0.00 | 1.00 | 0.00 | 1.00 | 1.00 | 1.00 | 1.00 | 1.00 | 0.00 | 1.00 | 1.00 | 1.00 |
| 14 | ATC | 0.00 | −0.69 | 0.00 | 0.28 | 1.00 | −0.84 | 0.84 | −0.64 | 0.00 | −0.41 | −0.58 | −0.53 |
| 15 | ATG | 0.00 | −0.43 | 0.00 | 0.56 | 1.00 | −0.60 | 0.80 | −0.42 | 0.00 | 0.40 | 0.00 | −0.33 |
| 16 | ATT | 0.00 | 0.30 | 0.00 | 0.70 | 1.00 | 0.03 | 0.87 | −0.53 | 0.00 | 0.53 | 1.00 | 0.70 |
| 17 | CAA | 0.00 | 0.40 | 0.00 | 0.89 | 1.00 | 0.54 | 1.00 | 1.00 | 0.00 | 1.00 | 0.64 | 1.00 |
| 18 | CAC | 0.00 | −0.77 | 0.00 | 0.61 | −0.27 | −0.40 | 1.00 | −0.83 | 0.00 | −0.60 | −0.57 | −0.05 |
| 19 | CAG | 0.00 | −0.53 | 0.00 | 0.23 | 1.00 | −0.31 | 0.77 | −0.80 | 0.00 | −0.51 | −0.25 | 0.14 |
| 20 | CAT | 0.00 | 1.00 | 0.00 | 0.71 | 1.00 | 1.00 | 1.00 | 1.00 | 0.00 | 0.37 | 1.00 | 1.00 |
| 21 | CCA | 0.00 | 0.34 | 0.00 | 0.75 | 1.00 | −0.22 | 1.00 | 0.34 | 0.00 | −0.74 | 0.47 | 1.00 |
| 22 | CCC | 0.00 | 1.00 | 0.00 | 1.00 | 1.00 | 1.00 | 1.00 | 1.00 | 0.00 | 1.00 | 1.00 | 1.00 |
| 23 | CCG | 0.00 | −0.44 | 0.00 | 0.37 | 0.44 | −0.52 | 1.00 | −0.78 | 0.00 | 0.32 | −0.41 | −0.41 |
| 24 | CCT | 0.00 | −0.77 | 0.00 | 0.70 | 0.05 | −0.68 | 1.00 | −0.58 | 0.00 | 1.00 | 1.00 | 1.00 |
| 25 | CGA | 0.00 | 1.00 | 0.00 | 1.00 | 1.00 | 1.00 | 1.00 | 1.00 | 0.00 | 1.00 | 1.00 | 1.00 |
| 26 | CGC | 0.00 | 0.01 | 0.00 | 0.50 | 1.00 | −0.11 | 1.00 | −0.14 | 0.00 | 0.36 | −0.52 | 1.00 |
| 27 | CGG | 0.00 | 1.00 | 0.00 | 1.00 | 1.00 | 1.00 | 1.00 | 1.00 | 0.00 | 1.00 | 1.00 | 1.00 |
| 28 | CGT | 0.00 | −0.64 | 0.00 | −0.16 | 0.13 | −0.75 | 0.77 | −0.87 | 0.00 | −0.70 | 0.56 | 0.15 |
| 29 | CTA | 0.00 | 1.00 | 0.00 | 1.00 | 1.00 | 1.00 | 1.00 | 1.00 | 0.00 | 1.00 | 1.00 | 1.00 |
| 30 | CTC | 0.00 | −0.31 | 0.00 | 1.00 | 1.00 | −0.50 | 1.00 | −0.36 | 0.00 | 1.00 | 1.00 | 1.00 |
| 31 | CTG | 0.00 | −0.67 | 0.00 | 0.24 | 0.74 | −0.60 | 0.70 | −0.80 | 0.00 | −0.48 | −0.44 | −0.42 |
| 32 | CTT | 0.00 | 0.02 | 0.00 | 1.00 | 1.00 | −0.35 | 1.00 | −0.52 | 0.00 | −0.25 | 1.00 | 1.00 |
| 33 | GAA | 0.00 | −0.54 | 0.00 | 0.64 | 1.00 | −0.56 | 0.77 | −0.57 | 0.00 | 0.40 | 0.28 | −0.34 |
| 34 | GAC | 0.00 | −0.66 | 0.00 | 0.37 | 0.71 | −0.80 | 0.54 | −0.49 | 0.00 | −0.62 | −0.61 | 0.40 |
| 35 | GAG | 0.00 | −0.07 | 0.00 | 0.65 | 1.00 | −0.53 | 1.00 | −0.60 | 0.00 | −0.25 | −0.38 | 0.44 |
| 36 | GAT | 0.00 | −0.18 | 0.00 | 0.83 | 0.83 | −0.41 | 1.00 | −0.15 | 0.00 | 0.43 | 0.94 | 0.46 |
| 37 | GCA | 0.00 | −0.42 | 0.00 | 0.68 | 0.69 | −0.43 | 0.76 | −0.70 | 0.00 | 0.50 | −0.62 | −0.47 |
| 38 | GCC | 0.00 | 0.44 | 0.00 | 0.08 | 1.00 | 0.42 | 1.00 | −0.38 | 0.00 | 0.22 | −0.02 | 0.02 |
| 39 | GCG | 0.00 | 0.41 | 0.00 | 1.00 | 1.00 | 0.11 | 0.72 | −0.61 | 0.00 | 0.41 | 0.69 | −0.10 |
| 40 | GCT | 0.00 | −0.83 | 0.00 | 0.00 | 1.00 | −0.81 | 0.37 | −0.89 | 0.00 | −0.62 | 0.65 | 1.00 |
| 41 | GGA | 0.00 | 0.73 | 0.00 | 1.00 | 0.46 | 1.00 | 1.00 | 1.00 | 0.00 | 1.00 | 1.00 | 1.00 |
| 42 | GGC | 0.00 | −0.36 | 0.00 | 0.57 | 1.00 | −0.33 | 1.00 | 0.40 | 0.00 | 0.32 | −0.50 | −0.07 |
| 43 | GGG | 0.00 | 1.00 | 0.00 | 1.00 | 1.00 | 1.00 | 1.00 | 0.36 | 0.00 | 1.00 | 1.00 | 1.00 |
| 44 | GGT | 0.00 | −0.68 | 0.00 | 0.16 | 0.15 | −0.79 | 0.87 | −0.87 | 0.00 | −0.62 | 0.44 | −0.03 |
| 45 | GTA | 0.00 | −0.40 | 0.00 | 0.64 | 1.00 | −0.82 | 1.00 | −0.84 | 0.00 | −0.46 | −0.71 | −0.68 |
| 46 | GTC | 0.00 | −0.02 | 0.00 | 0.87 | 1.00 | 0.72 | 1.00 | 0.71 | 0.00 | 1.00 | 0.65 | 1.00 |
| 47 | GTG | 0.00 | 0.11 | 0.00 | 0.77 | 1.00 | 0.35 | 1.00 | 0.33 | 0.00 | −0.02 | 0.17 | 1.00 |
| 48 | GTT | 0.00 | −0.71 | 0.00 | −0.16 | 1.00 | −0.81 | 1.00 | −0.85 | 0.00 | −0.61 | 0.70 | 0.54 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.00 | −0.78 | 0.00 | 0.61 | 1.00 | −0.76 | 0.67 | −0.77 | 0.00 | −0.71 | −0.57 | 1.00 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.00 | 0.81 | 0.00 | 1.00 | 1.00 | 0.22 | 1.00 | 1.00 | 0.00 | 1.00 | 1.00 | 0.34 |
| 53 | TCA | 0.00 | 0.24 | 0.00 | 1.00 | 1.00 | 1.00 | 1.00 | 0.14 | 0.00 | 1.00 | 0.32 | 1.00 |
| 54 | TCC | 0.00 | −0.68 | 0.00 | 0.53 | 1.00 | −0.63 | 0.35 | −0.52 | 0.00 | −0.71 | −0.80 | −0.54 |
| 55 | TCG | 0.00 | 1.00 | 0.00 | 1.00 | 1.00 | 1.00 | 1.00 | −0.26 | 0.00 | 1.00 | 1.00 | 1.00 |
| 56 | TCT | 0.00 | −0.82 | 0.00 | 0.03 | 0.14 | −0.84 | −0.63 | −0.88 | 0.00 | −0.44 | 0.43 | −0.55 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.00 | −0.76 | 0.00 | 1.00 | 1.00 | −0.58 | 0.23 | −0.76 | 0.00 | −0.54 | −0.44 | −0.26 |
| 59 | TGG | 0.00 | −0.41 | 0.00 | 0.52 | 1.00 | −0.50 | 1.00 | −0.71 | 0.00 | 1.00 | 0.00 | −0.56 |
| 60 | TGT | 0.00 | 1.00 | 0.00 | 1.00 | 1.00 | −0.01 | 1.00 | −0.04 | 0.00 | 1.00 | 1.00 | 1.00 |

TABLE C.6-continued

CPW matrix *Escherichi coli* K12 highly expressed sequences (left codon indicated in column 2, right codon indicated in row 2). Host cell: *E. coli*; Sequence data: full *E. coli* genome; Highly expressed group: 100 seqs.

| | | | | | | | | | | | | | |
|---|---|---|---|---|---|---|---|---|---|---|---|---|---|
| 61 | TTA | 0.00 | 0.61 | 0.00 | 1.00 | 1.00 | 1.00 | 1.00 | 1.00 | 0.00 | 1.00 | 1.00 | 1.00 |
| 62 | TTC | 0.00 | −0.74 | 0.00 | 0.11 | 1.00 | −0.79 | 0.72 | −0.86 | 0.00 | −0.69 | −0.57 | −0.15 |
| 63 | TTG | 0.00 | 1.00 | 0.00 | 1.00 | 1.00 | 1.00 | 1.00 | 0.15 | 0.00 | 1.00 | 0.17 | 1.00 |
| 64 | TTT | 0.00 | 0.82 | 0.00 | 0.87 | 1.00 | 0.56 | 1.00 | 1.00 | 0.00 | 1.00 | 1.00 | 1.00 |

| | | TAA 49 | TAC 50 | TAG 51 | TAT 52 | TCA 53 | TCC 54 | TCG 55 | TCT 56 | TGA 57 | TGC 58 | TGG 59 | TGT 60 |
|---|---|---|---|---|---|---|---|---|---|---|---|---|---|

| | | 61 TTA | 62 TTC | 63 TTG | 64 TTT |
|---|---|---|---|---|---|
| 1 | AAA | 0.87 | −0.43 | 0.87 | 0.69 |
| 2 | AAC | 1.00 | −0.72 | 0.83 | 0.57 |
| 3 | AAG | 0.78 | −0.53 | 0.78 | 0.42 |
| 4 | AAT | 0.80 | 1.00 | 1.00 | 0.93 |
| 5 | ACA | 1.00 | 1.00 | 1.00 | 1.00 |
| 6 | ACC | 0.84 | −0.59 | 1.00 | 0.28 |
| 7 | ACG | 0.75 | 0.43 | 0.74 | 0.79 |
| 8 | ACT | 1.00 | −0.64 | 0.58 | 0.31 |
| 9 | AGA | 1.00 | 1.00 | 1.00 | 1.00 |
| 10 | AGC | 1.00 | −0.48 | 0.56 | 0.88 |
| 11 | AGG | 1.00 | 1.00 | 1.00 | 1.00 |
| 12 | AGT | 1.00 | 0.40 | 0.59 | 1.00 |
| 13 | ATA | 1.00 | 1.00 | 1.00 | 1.00 |
| 14 | ATC | 1.00 | −0.69 | 1.00 | 0.29 |
| 15 | ATG | 0.76 | −0.52 | 0.76 | 0.81 |
| 16 | ATT | 1.00 | 0.05 | 0.85 | 0.88 |
| 17 | CAA | 1.00 | 1.00 | 1.00 | 0.88 |
| 18 | CAC | 1.00 | −0.77 | 0.56 | 0.49 |
| 19 | CAG | 1.00 | −0.66 | 0.75 | 0.58 |
| 20 | CAT | 1.00 | 0.74 | 0.67 | 1.00 |
| 21 | CCA | 1.00 | 1.00 | 1.00 | 1.00 |
| 22 | CCC | 1.00 | 1.00 | 1.00 | 1.00 |
| 23 | CCG | 0.80 | −0.70 | 0.41 | 0.40 |
| 24 | CCT | 1.00 | 0.66 | 1.00 | 0.50 |
| 25 | CGA | 1.00 | 1.00 | 1.00 | 1.00 |
| 26 | CGC | 1.00 | −0.48 | 1.00 | 0.36 |
| 27 | CGG | 1.00 | 1.00 | 1.00 | 1.00 |
| 28 | CGT | 1.00 | −0.61 | 1.00 | 0.51 |
| 29 | CTA | 1.00 | 1.00 | 1.00 | 1.00 |
| 30 | CTC | 1.00 | 1.00 | 1.00 | 0.73 |
| 31 | CTG | 0.57 | −0.72 | 0.46 | 0.44 |
| 32 | CTT | 1.00 | 0.27 | 1.00 | 1.00 |
| 33 | GAA | 0.95 | −0.35 | 0.95 | 0.76 |
| 34 | GAC | 0.86 | −0.74 | 0.58 | 0.40 |
| 35 | GAG | 0.88 | −0.63 | 1.00 | 0.46 |
| 36 | GAT | 0.84 | 0.22 | 0.84 | 0.87 |
| 37 | GCA | 1.00 | −0.70 | 0.83 | 0.29 |
| 38 | GCC | 1.00 | −0.06 | 1.00 | 0.84 |
| 39 | GCG | 1.00 | −0.44 | 1.00 | 0.76 |
| 40 | GCT | 0.78 | −0.44 | 1.00 | 0.73 |
| 41 | GGA | 1.00 | 1.00 | 1.00 | 1.00 |
| 42 | GGC | 1.00 | −0.60 | 0.90 | 0.33 |
| 43 | GGG | 1.00 | 0.84 | 1.00 | 1.00 |
| 44 | GGT | 0.76 | −0.48 | 0.88 | 0.36 |
| 45 | GTA | 1.00 | −0.63 | 0.45 | 0.00 |
| 46 | GTC | 1.00 | −0.43 | 1.00 | 0.76 |
| 47 | GTG | 1.00 | −0.55 | 0.77 | 0.72 |
| 48 | GTT | 1.00 | −0.06 | 0.84 | 0.90 |
| 49 | TAA | 0.00 | 0.00 | 0.00 | 0.00 |
| 50 | TAC | 1.00 | −0.75 | 1.00 | 0.42 |
| 51 | TAG | 0.00 | 0.00 | 0.00 | 0.00 |
| 52 | TAT | 1.00 | 0.65 | 1.00 | 0.91 |
| 53 | TCA | 1.00 | 1.00 | 1.00 | 1.00 |
| 54 | TCC | 0.59 | −0.79 | 0.59 | 0.33 |
| 55 | TCG | 1.00 | 0.42 | 1.00 | 0.78 |
| 56 | TCT | 0.58 | −0.73 | 0.57 | 0.30 |
| 57 | TGA | 0.00 | 0.00 | 0.00 | 0.00 |
| 58 | TGC | 1.00 | 0.16 | 1.00 | −0.47 |
| 59 | TGG | 0.51 | −0.45 | 1.00 | 0.61 |

TABLE C.6-continued

CPW matrix *Escherichi coli* K12 highly expressed sequences (left codon indicated in column 2, right codon indicated in row 2). Host cell: *E. coli*; Sequence data: full *E. coli* genome; Highly expressed group: 100 seqs.

| | | | | | |
|---|---|---|---|---|---|
| 60 | TGT | 1.00 | −0.05 | 1.00 | 1.00 |
| 61 | TTA | 1.00 | 1.00 | 1.00 | 1.00 |
| 62 | TTC | 1.00 | −0.76 | 1.00 | 0.16 |
| 63 | TTG | 1.00 | 0.70 | 0.58 | 1.00 |
| 64 | TTT | 1.00 | 1.00 | 1.00 | 0.92 |
| | | TTA | TTC | TTG | TTT |
| | | 61 | 62 | 63 | 64 |

TABLE C.7

CPW matrix *Bacillus amyloliquefaciens* full genome (left codon indicated in column 2, right codon indicated in row 2). Host cell: *B. amyloliqueaciens*; Sequence data: full *B. amyloliqueaciens* genome.

| | | 1<br>AAA | 2<br>AAC | 3<br>AAG | 4<br>AAT | 5<br>ACA | 6<br>ACC | 7<br>ACG | 8<br>ACT | 9<br>AGA | 10<br>AGC | 11<br>AGG | 12<br>AGT |
|---|---|---|---|---|---|---|---|---|---|---|---|---|---|
| 1 | AAA | −0.05 | −0.25 | −0.09 | 0.00 | −0.34 | −0.02 | −0.08 | 0.42 | −0.33 | −0.40 | −0.31 | −0.19 |
| 2 | AAC | 0.05 | −0.11 | 0.11 | −0.07 | 0.21 | 0.18 | 0.08 | 0.18 | −0.48 | −0.61 | −0.54 | −0.58 |
| 3 | AAG | 0.12 | 0.35 | 0.23 | 0.38 | 0.32 | 0.34 | 0.20 | 0.37 | 0.18 | 0.20 | 0.04 | 0.21 |
| 4 | AAT | −0.12 | 0.07 | 0.10 | 0.12 | −0.23 | 0.05 | −0.15 | 0.00 | 0.53 | 0.79 | 0.64 | 0.32 |
| 5 | ACA | −0.43 | −0.44 | −0.32 | −0.32 | −0.20 | −0.29 | 0.02 | −0.27 | −0.63 | −0.38 | −0.68 | −0.44 |
| 6 | ACC | 0.60 | 0.33 | 0.56 | −0.01 | 0.50 | 0.32 | 0.64 | −0.08 | −0.05 | 0.34 | 0.45 | 0.31 |
| 7 | ACG | 0.05 | 0.24 | −0.10 | 0.11 | −0.16 | −0.09 | −0.28 | −0.16 | −0.46 | 0.00 | −0.37 | 0.27 |
| 8 | ACT | 0.48 | 0.67 | 0.64 | 0.51 | 0.44 | 0.50 | 0.71 | 0.08 | 0.46 | 0.90 | 0.22 | 0.53 |
| 9 | AGA | −0.60 | −0.52 | −0.64 | −0.44 | −0.42 | −0.32 | −0.41 | −0.29 | −0.32 | −0.48 | −0.38 | −0.35 |
| 10 | AGC | −0.01 | 0.19 | 0.08 | 0.01 | 0.01 | −0.14 | −0.10 | −0.08 | −0.38 | −0.30 | −0.60 | −0.25 |
| 11 | AGG | −0.06 | 0.17 | −0.24 | −0.08 | −0.09 | 0.29 | −0.11 | 0.09 | 0.23 | 0.19 | 0.13 | −0.28 |
| 12 | AGT | −0.08 | 0.61 | 0.16 | 0.12 | 0.26 | 0.48 | 0.32 | 0.24 | 0.60 | 0.89 | 0.56 | 0.62 |
| 13 | ATA | −0.54 | −0.26 | −0.35 | −0.19 | −0.27 | 0.05 | 0.19 | −0.15 | −0.45 | 0.23 | −0.40 | −0.16 |
| 14 | ATC | 0.24 | −0.06 | 0.16 | −0.15 | 0.16 | −0.20 | 0.25 | −0.04 | −0.60 | −0.45 | −0.59 | −0.44 |
| 15 | ATG | 0.04 | 0.06 | −0.07 | −0.05 | 0.08 | 0.05 | −0.08 | 0.04 | −0.46 | −0.19 | −0.37 | −0.17 |
| 16 | ATT | −0.02 | 0.25 | 0.18 | 0.16 | −0.20 | 0.01 | −0.05 | 0.01 | 0.63 | 0.91 | 0.74 | 0.70 |
| 17 | CAA | −0.39 | −0.46 | −0.41 | −0.29 | 0.15 | −0.28 | −0.02 | 0.19 | −0.22 | −0.43 | −0.26 | −0.23 |
| 18 | CAC | 0.34 | 0.06 | 0.17 | −0.05 | 0.29 | −0.02 | 0.27 | 0.31 | 0.02 | −0.46 | −0.21 | −0.33 |
| 19 | CAG | 0.48 | 0.39 | 0.33 | 0.43 | 0.11 | 0.07 | −0.08 | 0.05 | 0.67 | 0.53 | 0.54 | 0.54 |
| 20 | CAT | −0.20 | 0.02 | −0.13 | −0.01 | −0.22 | −0.06 | −0.15 | −0.02 | 0.79 | 0.82 | 0.76 | 0.61 |
| 21 | CCA | −0.26 | −0.45 | −0.25 | −0.20 | −0.29 | −0.42 | 0.14 | −0.66 | −0.47 | −0.44 | −0.53 | −0.47 |
| 22 | CCC | 0.72 | 0.58 | 0.53 | 0.35 | 0.65 | 0.27 | 0.53 | 0.36 | 0.61 | 0.67 | 0.75 | 0.50 |
| 23 | CCG | −0.14 | −0.13 | −0.29 | −0.20 | −0.14 | −0.18 | −0.13 | −0.43 | 0.02 | 0.05 | 0.37 | 0.18 |
| 24 | CCT | 0.30 | 0.42 | 0.46 | 0.56 | 0.39 | 0.60 | 0.74 | −0.04 | 0.75 | 0.77 | 0.71 | 0.58 |
| 25 | CGA | −0.18 | −0.22 | −0.11 | −0.15 | 0.04 | −0.14 | 0.01 | −0.32 | 0.48 | −0.55 | −0.33 | −0.56 |
| 26 | CGC | 0.56 | 0.00 | 0.00 | 0.26 | 0.48 | −0.06 | −0.18 | 0.45 | 0.72 | −0.07 | 0.43 | 0.22 |
| 27 | CGG | 0.08 | 0.17 | 0.19 | −0.09 | 0.24 | 0.38 | −0.19 | 0.01 | 0.70 | 0.48 | 0.66 | 0.60 |
| 28 | CGT | 0.42 | 0.71 | 0.48 | 0.48 | 0.37 | 0.53 | 0.29 | −0.03 | 0.97 | 0.82 | 0.84 | 0.74 |
| 29 | CTA | −0.19 | 0.20 | −0.21 | −0.03 | 0.04 | 0.07 | 0.48 | −0.36 | −0.48 | 0.14 | −0.52 | −0.41 |
| 30 | CTC | 0.63 | 0.54 | 0.39 | 0.29 | 0.51 | 0.13 | 0.40 | 0.23 | −0.37 | −0.14 | −0.34 | −0.30 |
| 31 | CTG | −0.15 | −0.18 | −0.30 | −0.15 | −0.24 | −0.26 | −0.24 | −0.29 | 0.01 | 0.28 | 0.02 | 0.33 |
| 32 | CTT | 0.64 | 0.59 | 0.75 | 0.59 | 0.49 | 0.42 | 0.70 | 0.16 | 0.70 | 0.87 | 0.56 | 0.64 |
| 33 | GAA | −0.16 | −0.24 | −0.03 | 0.00 | −0.27 | −0.18 | −0.07 | 0.34 | −0.05 | −0.35 | 0.17 | −0.22 |
| 34 | GAC | 0.13 | −0.07 | −0.17 | −0.09 | 0.32 | 0.00 | 0.04 | 0.18 | −0.36 | −0.58 | −0.49 | −0.51 |
| 35 | GAG | 0.29 | 0.29 | 0.21 | 0.30 | 0.39 | 0.44 | 0.04 | 0.45 | 0.39 | 0.21 | 0.46 | 0.12 |
| 36 | GAT | −0.09 | 0.09 | 0.16 | 0.06 | −0.13 | 0.10 | −0.17 | 0.01 | 0.73 | 0.83 | 0.72 | 0.66 |
| 37 | GCA | −0.48 | −0.50 | −0.48 | −0.37 | −0.34 | −0.43 | −0.06 | −0.53 | −0.25 | −0.51 | −0.41 | −0.50 |
| 38 | GCC | 0.25 | 0.27 | 0.27 | −0.15 | 0.32 | 0.14 | 0.50 | 0.06 | 0.11 | 0.38 | 0.49 | 0.17 |
| 39 | GCG | 0.14 | −0.08 | −0.21 | 0.21 | −0.13 | −0.02 | −0.31 | −0.08 | 0.30 | 0.06 | 0.33 | 0.45 |
| 40 | GCT | 0.40 | 0.55 | 0.61 | 0.55 | 0.32 | 0.45 | 0.63 | 0.33 | 0.89 | 0.91 | 0.88 | 0.84 |
| 41 | GGA | −0.46 | −0.41 | −0.25 | −0.38 | −0.33 | −0.21 | −0.37 | −0.15 | −0.35 | −0.48 | −0.26 | −0.30 |
| 42 | GGC | 0.43 | 0.07 | −0.05 | 0.15 | 0.19 | −0.02 | −0.09 | 0.09 | −0.13 | −0.31 | −0.23 | −0.18 |
| 43 | GGG | −0.04 | 0.37 | 0.20 | 0.00 | 0.22 | 0.65 | 0.24 | 0.27 | 0.23 | 0.37 | 0.44 | 0.34 |
| 44 | GGT | 0.23 | 0.64 | 0.50 | 0.40 | 0.22 | 0.60 | 0.13 | 0.19 | 0.85 | 0.92 | 0.75 | 0.44 |
| 45 | GTA | −0.45 | −0.39 | −0.35 | −0.25 | −0.19 | −0.18 | −0.22 | −0.22 | −0.34 | 0.04 | −0.37 | −0.18 |
| 46 | GTC | 0.21 | 0.06 | 0.38 | −0.16 | 0.13 | −0.18 | 0.11 | −0.07 | −0.44 | −0.39 | −0.31 | −0.45 |
| 47 | GTG | −0.17 | 0.00 | −0.28 | −0.10 | −0.10 | −0.01 | −0.32 | 0.19 | 0.20 | 0.31 | 0.22 | 0.49 |
| 48 | GTT | 0.40 | 0.64 | 0.52 | 0.40 | 0.34 | 0.40 | 0.48 | 0.23 | 0.67 | 0.94 | 0.71 | 0.65 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.12 | −0.16 | −0.06 | −0.17 | 0.13 | 0.05 | −0.14 | 0.14 | −0.59 | −0.55 | −0.61 | −0.57 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | −0.14 | 0.14 | 0.23 | 0.14 | −0.15 | 0.28 | −0.03 | 0.08 | 0.50 | 0.82 | 0.59 | 0.70 |
| 53 | TCA | −0.38 | −0.39 | −0.19 | −0.39 | −0.28 | −0.36 | 0.06 | −0.58 | −0.50 | −0.30 | −0.42 | −0.26 |
| 54 | TCC | 0.29 | 0.35 | 0.46 | −0.18 | 0.25 | 0.11 | 0.54 | −0.33 | −0.44 | 0.35 | 0.37 | −0.08 |
| 55 | TCG | 0.35 | −0.06 | −0.14 | 0.22 | 0.18 | −0.26 | −0.31 | −0.24 | 0.09 | 0.00 | 0.16 | 0.41 |

TABLE C.7-continued

CPW matrix *Bacillus amyloliquefaciens* full genome (left codon indicated in column 2, right codon indicated in row 2). Host cell: *B. amyloliqueaciens*; Sequence data: full *B. amyloliqueaciens* genome.

| | | | | | | | | | | | | |
|---|---|---|---|---|---|---|---|---|---|---|---|---|
| 56 TCT | −0.04 | 0.40 | 0.33 | 0.24 | 0.20 | 0.49 | 0.63 | −0.01 | 0.76 | 0.91 | 0.75 | 0.74 |
| 57 TGA | 0.00 | 0.00 | 0.00 | 0.00 | 0.00 | 0.00 | 0.00 | 0.00 | 0.00 | 0.00 | 0.00 | 0.00 |
| 58 TGC | 0.21 | −0.16 | −0.17 | 0.09 | 0.27 | −0.15 | −0.10 | 0.38 | 0.10 | −0.27 | −0.39 | −0.22 |
| 59 TGG | 0.05 | 0.18 | −0.10 | −0.15 | 0.16 | 0.21 | −0.21 | 0.15 | −0.32 | −0.09 | 0.01 | −0.27 |
| 60 TGT | −0.18 | 0.46 | 0.00 | −0.22 | −0.11 | 0.46 | −0.23 | 0.00 | 0.77 | 0.91 | 0.74 | 0.59 |
| 61 TTA | −0.47 | −0.45 | −0.45 | −0.43 | −0.25 | −0.32 | −0.19 | −0.34 | −0.52 | −0.18 | −0.30 | −0.33 |
| 62 TTC | 0.19 | −0.01 | 0.06 | 0.04 | 0.25 | −0.20 | 0.20 | −0.25 | −0.62 | −0.45 | −0.63 | −0.41 |
| 63 TTG | −0.25 | −0.09 | −0.16 | −0.28 | −0.22 | −0.19 | −0.13 | −0.35 | −0.27 | 0.35 | −0.20 | 0.13 |
| 64 TTT | −0.18 | 0.06 | 0.13 | −0.08 | −0.15 | −0.06 | 0.06 | −0.04 | 0.58 | 0.93 | 0.67 | 0.66 |

| | AAA 1 | AAC 2 | AAG 3 | AAT 4 | ACA 5 | ACC 6 | ACG 7 | ACT 8 | AGA 9 | AGC 10 | AGG 11 | AGT 12 |
|---|---|---|---|---|---|---|---|---|---|---|---|---|
| | 13 ATA | 14 ATC | 15 ATG | 16 ATT | 17 CAA | 18 CAC | 19 CAG | 20 CAT | 21 CCA | 22 CCC | 23 CCG | 24 CCT |
| 1 AAA | −0.41 | −0.20 | −0.08 | 0.26 | −0.09 | 0.32 | 0.26 | 0.20 | 0.18 | 0.45 | 0.26 | 0.34 |
| 2 AAC | 0.24 | 0.09 | 0.09 | 0.15 | 0.17 | 0.25 | 0.32 | 0.10 | 0.19 | 0.40 | 0.24 | 0.13 |
| 3 AAG | 0.14 | 0.18 | 0.20 | 0.20 | 0.00 | −0.28 | −0.30 | −0.40 | −0.30 | −0.28 | −0.43 | −0.37 |
| 4 AAT | −0.31 | −0.08 | −0.08 | −0.08 | −0.34 | −0.06 | −0.07 | −0.18 | −0.11 | −0.12 | −0.22 | −0.18 |
| 5 ACA | −0.12 | 0.34 | 0.06 | 0.35 | −0.15 | 0.14 | 0.05 | 0.17 | 0.23 | 0.11 | 0.08 | 0.07 |
| 6 ACC | −0.09 | −0.04 | 0.43 | −0.39 | 0.15 | 0.24 | 0.30 | −0.10 | 0.22 | 0.38 | 0.58 | 0.29 |
| 7 ACG | −0.01 | −0.13 | −0.30 | −0.21 | 0.25 | −0.13 | −0.12 | 0.17 | 0.03 | −0.23 | −0.27 | −0.16 |
| 8 ACT | 0.03 | 0.74 | 0.57 | 0.46 | −0.53 | −0.29 | 0.02 | −0.41 | −0.03 | 0.05 | 0.14 | −0.42 |
| 9 AGA | −0.40 | −0.21 | −0.37 | −0.15 | −0.10 | 0.47 | −0.27 | 0.35 | 0.38 | 0.49 | 0.40 | 0.29 |
| 10 AGC | 0.12 | −0.01 | −0.12 | −0.11 | −0.03 | 0.10 | −0.12 | −0.16 | 0.50 | 0.16 | 0.11 | 0.44 |
| 11 AGG | −0.35 | 0.37 | 0.01 | −0.11 | 0.00 | −0.24 | −0.37 | −0.25 | −0.13 | −0.31 | −0.24 | 0.21 |
| 12 AGT | −0.21 | 0.23 | −0.14 | −0.06 | −0.25 | 0.38 | −0.06 | −0.26 | −0.29 | −0.01 | −0.03 | −0.07 |
| 13 ATA | −0.24 | 0.59 | 0.42 | 0.61 | −0.37 | −0.04 | −0.13 | −0.12 | −0.20 | 0.12 | 0.03 | −0.20 |
| 14 ATC | 0.15 | −0.11 | −0.03 | −0.16 | 0.49 | 0.49 | 0.50 | 0.36 | 0.38 | 0.41 | 0.39 | 0.39 |
| 15 ATG | 0.13 | 0.07 | 0.00 | −0.10 | 0.43 | −0.15 | −0.22 | 0.14 | 0.49 | 0.13 | −0.09 | −0.04 |
| 16 ATT | −0.09 | 0.02 | −0.08 | −0.01 | −0.36 | −0.23 | −0.25 | −0.33 | −0.19 | −0.35 | −0.30 | −0.23 |
| 17 CAA | −0.31 | −0.10 | −0.21 | 0.00 | 0.55 | 0.69 | 0.70 | 0.72 | 0.53 | 0.60 | 0.82 | 0.54 |
| 18 CAC | 0.20 | 0.15 | 0.24 | 0.19 | 0.42 | 0.34 | 0.43 | 0.15 | 0.18 | 0.39 | 0.28 | 0.24 |
| 19 CAG | 0.22 | 0.00 | 0.17 | 0.10 | 0.07 | −0.37 | −0.42 | −0.27 | −0.18 | −0.30 | −0.32 | −0.37 |
| 20 CAT | −0.17 | −0.05 | −0.15 | −0.16 | −0.20 | −0.19 | −0.27 | −0.11 | −0.24 | −0.17 | −0.17 | −0.16 |
| 21 CCA | 0.00 | 0.27 | 0.04 | 0.39 | 0.19 | 0.04 | 0.36 | 0.38 | −0.39 | 0.20 | 0.54 | −0.04 |
| 22 CCC | 0.30 | 0.50 | 0.53 | 0.30 | 0.47 | 0.40 | 0.62 | 0.23 | −0.28 | 0.53 | 0.69 | 0.27 |
| 23 CCG | 0.17 | −0.25 | −0.26 | −0.32 | −0.18 | −0.23 | −0.12 | 0.07 | −0.25 | −0.39 | −0.13 | −0.07 |
| 24 CCT | 0.24 | 0.65 | 0.60 | 0.43 | −0.22 | −0.01 | 0.02 | −0.12 | 0.21 | −0.06 | 0.33 | −0.15 |
| 25 CGA | −0.50 | −0.20 | −0.04 | 0.31 | 0.12 | −0.38 | 0.09 | 0.01 | −0.45 | 0.31 | 0.41 | 0.02 |
| 26 CGC | 0.31 | 0.01 | 0.30 | 0.47 | 0.56 | 0.33 | 0.39 | 0.40 | 0.07 | 0.22 | 0.33 | 0.55 |
| 27 CGG | −0.33 | −0.31 | −0.30 | −0.27 | −0.23 | −0.43 | −0.39 | −0.27 | −0.48 | −0.48 | −0.37 | −0.40 |
| 28 CGT | 0.12 | 0.31 | 0.42 | 0.38 | −0.02 | −0.23 | −0.09 | 0.05 | −0.40 | −0.24 | −0.07 | −0.15 |
| 29 CTA | −0.38 | 0.32 | 0.38 | 0.47 | −0.29 | −0.01 | 0.66 | −0.21 | −0.57 | −0.09 | 0.37 | −0.44 |
| 30 CTC | 0.28 | 0.20 | 0.39 | 0.11 | 0.60 | 0.67 | 0.68 | 0.38 | 0.49 | 0.53 | 0.56 | 0.31 |
| 31 CTG | 0.27 | −0.29 | −0.30 | −0.17 | −0.25 | −0.27 | −0.14 | −0.01 | 0.28 | −0.34 | −0.38 | −0.12 |
| 32 CTT | 0.45 | 0.55 | 0.51 | 0.42 | −0.27 | −0.36 | −0.24 | −0.34 | −0.03 | −0.23 | −0.15 | −0.40 |
| 33 GAA | −0.12 | −0.18 | −0.09 | 0.16 | 0.12 | 0.34 | 0.23 | 0.34 | 0.26 | 0.44 | 0.33 | 0.38 |
| 34 GAC | 0.17 | −0.04 | 0.04 | 0.08 | 0.31 | 0.35 | 0.38 | 0.23 | 0.27 | 0.45 | 0.28 | 0.29 |
| 35 GAG | 0.13 | 0.05 | 0.19 | 0.12 | 0.10 | −0.40 | −0.39 | −0.39 | −0.42 | −0.40 | −0.40 | −0.39 |
| 36 GAT | −0.10 | 0.14 | −0.03 | −0.16 | −0.23 | −0.25 | −0.22 | −0.13 | −0.10 | 0.00 | −0.28 | −0.12 |
| 37 GCA | −0.03 | 0.11 | −0.06 | 0.21 | 0.10 | 0.29 | 0.19 | 0.45 | −0.03 | 0.15 | 0.37 | 0.34 |
| 38 GCC | 0.13 | −0.02 | 0.11 | −0.25 | 0.27 | 0.42 | 0.52 | 0.17 | 0.43 | 0.39 | 0.70 | 0.60 |
| 39 GCG | 0.19 | −0.26 | −0.24 | −0.10 | −0.15 | −0.39 | −0.28 | 0.01 | −0.30 | −0.49 | −0.38 | −0.08 |
| 40 GCT | 0.40 | 0.63 | 0.60 | 0.40 | −0.33 | −0.21 | 0.11 | −0.13 | −0.28 | 0.02 | 0.18 | −0.25 |
| 41 GGA | −0.05 | −0.08 | −0.22 | 0.00 | −0.30 | 0.16 | −0.23 | −0.01 | 0.17 | 0.51 | 0.18 | 0.10 |
| 42 GGC | 0.21 | −0.12 | 0.07 | −0.11 | 0.44 | 0.19 | 0.27 | 0.07 | 0.08 | 0.26 | 0.23 | 0.40 |
| 43 GGG | −0.05 | 0.34 | 0.04 | 0.05 | −0.09 | −0.12 | −0.35 | −0.35 | −0.27 | −0.27 | −0.43 | −0.44 |
| 44 GGT | 0.07 | 0.26 | 0.19 | −0.04 | 0.08 | 0.09 | 0.09 | −0.01 | −0.60 | −0.18 | −0.07 | 0.12 |
| 45 GTA | 0.26 | 0.43 | 0.26 | 0.67 | 0.23 | 0.14 | −0.11 | 0.17 | −0.14 | 0.56 | 0.38 | 0.08 |
| 46 GTC | 0.11 | −0.26 | −0.12 | −0.37 | 0.54 | 0.57 | 0.66 | 0.34 | 0.56 | 0.61 | 0.68 | 0.54 |
| 47 GTG | 0.24 | −0.12 | −0.20 | 0.12 | 0.18 | −0.03 | −0.34 | −0.04 | 0.23 | −0.25 | −0.47 | −0.29 |
| 48 GTT | 0.26 | 0.29 | 0.35 | 0.21 | −0.46 | −0.35 | −0.36 | −0.47 | −0.21 | −0.46 | −0.19 | −0.43 |
| 49 TAA | 0.00 | 0.00 | 0.00 | 0.00 | 0.00 | 0.00 | 0.00 | 0.00 | 0.00 | 0.00 | 0.00 | 0.00 |
| 50 TAC | −0.25 | 0.17 | 0.11 | 0.14 | 0.29 | 0.29 | 0.49 | 0.25 | 0.48 | 0.58 | 0.28 | 0.37 |
| 51 TAG | 0.00 | 0.00 | 0.00 | 0.00 | 0.00 | 0.00 | 0.00 | 0.00 | 0.00 | 0.00 | 0.00 | 0.00 |
| 52 TAT | −0.36 | 0.00 | −0.07 | 0.00 | −0.31 | −0.06 | −0.17 | −0.22 | −0.02 | −0.14 | −0.29 | −0.05 |
| 53 TCA | 0.03 | 0.27 | −0.05 | 0.11 | −0.10 | 0.35 | 0.23 | 0.33 | −0.04 | 0.15 | 0.24 | −0.19 |
| 54 TCC | 0.17 | −0.15 | −0.02 | −0.41 | 0.28 | 0.27 | 0.58 | −0.06 | 0.47 | 0.43 | 0.63 | 0.38 |
| 55 TCG | 0.15 | −0.12 | −0.03 | 0.02 | −0.04 | −0.21 | −0.16 | 0.05 | −0.34 | −0.46 | −0.41 | −0.37 |
| 56 TCT | 0.08 | 0.38 | 0.44 | 0.12 | −0.45 | −0.14 | 0.15 | −0.30 | −0.38 | −0.35 | 0.03 | −0.38 |
| 57 TGA | 0.00 | 0.00 | 0.00 | 0.00 | 0.00 | 0.00 | 0.00 | 0.00 | 0.00 | 0.00 | 0.00 | 0.00 |
| 58 TGC | 0.07 | 0.05 | 0.11 | 0.38 | 0.00 | −0.09 | 0.12 | 0.11 | −0.03 | 0.24 | 0.02 | 0.32 |
| 59 TGG | −0.15 | 0.16 | 0.00 | −0.10 | 0.40 | −0.03 | −0.21 | 0.02 | 0.53 | 0.15 | −0.16 | 0.18 |
| 60 TGT | −0.52 | −0.23 | −0.17 | −0.18 | −0.18 | 0.10 | −0.06 | −0.13 | −0.02 | −0.13 | −0.14 | −0.29 |

TABLE C.7-continued

CPW matrix *Bacillus amyloliquefaciens* full genome (left codon indicated in column 2, right codon indicated in row 2). Host cell: *B. amyloliqueaciens*; Sequence data: full *B. amyloliqueaciens* genome.

| | | | | | | | | | | | | |
|---|---|---|---|---|---|---|---|---|---|---|---|---|
| 61 | TTA | −0.31 | −0.18 | −0.32 | −0.22 | 0.14 | 0.50 | 0.32 | 0.17 | 0.28 | 0.63 | 0.81 | 0.46 |
| 62 | TTC | 0.34 | 0.19 | 0.23 | 0.21 | 0.19 | 0.24 | 0.34 | 0.27 | 0.16 | 0.38 | 0.04 | −0.15 |
| 63 | TTG | 0.13 | −0.10 | 0.04 | −0.33 | 0.00 | 0.13 | −0.25 | 0.24 | 0.08 | 0.01 | −0.06 | 0.04 |
| 64 | TTT | −0.15 | −0.16 | −0.15 | −0.11 | −0.31 | 0.01 | −0.05 | −0.26 | −0.10 | −0.17 | −0.03 | 0.07 |

| | | ATA 13 | ATC 14 | ATG 15 | ATT 16 | CAA 17 | CAC 18 | CAG 19 | CAT 20 | CCA 21 | CCC 22 | CCG 23 | CCT 24 |
|---|---|---|---|---|---|---|---|---|---|---|---|---|---|

| | | 25 CGA | 26 CGC | 27 CGG | 28 CGT | 29 CTA | 30 CTC | 31 CTG | 32 CTT | 33 GAA | 34 GAC | 35 GAG | 36 GAT |
|---|---|---|---|---|---|---|---|---|---|---|---|---|---|
| 1 | AAA | 0.32 | 0.37 | −0.15 | 0.38 | −0.15 | 0.56 | 0.31 | 0.57 | −0.16 | −0.17 | 0.08 | 0.11 |
| 2 | AAC | 0.16 | −0.23 | −0.23 | −0.38 | −0.21 | 0.25 | −0.05 | 0.07 | 0.32 | 0.21 | 0.35 | 0.24 |
| 3 | AAG | 0.21 | −0.16 | −0.47 | −0.07 | −0.08 | −0.47 | −0.61 | −0.59 | 0.14 | 0.17 | 0.36 | 0.00 |
| 4 | AAT | 0.10 | 0.54 | 0.34 | 0.23 | −0.25 | −0.01 | −0.10 | 0.12 | −0.32 | −0.11 | −0.02 | −0.23 |
| 5 | ACA | 0.45 | 0.48 | 0.42 | 0.10 | −0.19 | 0.40 | 0.37 | 0.27 | −0.12 | −0.03 | 0.07 | 0.08 |
| 6 | ACC | 0.27 | 0.16 | 0.07 | −0.26 | 0.58 | 0.44 | 0.56 | 0.16 | 0.17 | −0.20 | −0.18 | −0.11 |
| 7 | ACG | 0.32 | −0.16 | 0.07 | 0.25 | 0.19 | −0.42 | −0.33 | −0.28 | 0.14 | 0.38 | 0.28 | 0.11 |
| 8 | ACT | 0.22 | 0.46 | 0.57 | −0.19 | −0.46 | 0.38 | 0.58 | −0.23 | −0.40 | −0.29 | −0.32 | −0.43 |
| 9 | AGA | 0.62 | 0.78 | 0.39 | 0.64 | 0.04 | 0.44 | 0.27 | 0.44 | −0.27 | 0.12 | −0.19 | 0.13 |
| 10 | AGC | −0.02 | −0.13 | −0.35 | −0.24 | 0.38 | 0.29 | −0.09 | 0.11 | 0.35 | 0.24 | 0.11 | 0.24 |
| 11 | AGG | 0.39 | 0.43 | −0.11 | 0.42 | 0.03 | −0.40 | −0.64 | −0.52 | −0.22 | 0.28 | −0.09 | 0.05 |
| 12 | AGT | −0.20 | 0.72 | 0.56 | 0.64 | −0.24 | −0.13 | −0.28 | −0.25 | −0.56 | −0.31 | −0.36 | −0.53 |
| 13 | ATA | −0.13 | 0.30 | 0.08 | −0.02 | −0.41 | 0.22 | 0.28 | 0.11 | −0.23 | −0.02 | −0.02 | −0.04 |
| 14 | ATC | 0.34 | −0.34 | −0.14 | −0.33 | 0.35 | 0.39 | 0.41 | 0.44 | 0.37 | 0.06 | 0.15 | 0.38 |
| 15 | ATG | 0.61 | 0.10 | 0.04 | 0.18 | 0.28 | −0.13 | −0.30 | −0.17 | 0.02 | 0.03 | −0.04 | −0.02 |
| 16 | ATT | 0.46 | 0.61 | 0.51 | 0.40 | 0.00 | −0.14 | 0.07 | 0.00 | −0.29 | −0.05 | 0.04 | −0.28 |
| 17 | CAA | 0.24 | 0.57 | 0.56 | 0.56 | −0.18 | 0.75 | 0.64 | 0.76 | 0.16 | 0.09 | 0.10 | 0.18 |
| 18 | CAC | −0.20 | −0.32 | −0.14 | −0.19 | 0.39 | 0.20 | 0.23 | 0.18 | 0.24 | −0.11 | −0.23 | 0.00 |
| 19 | CAG | 0.01 | −0.34 | −0.31 | −0.35 | 0.02 | −0.38 | −0.34 | −0.46 | −0.14 | 0.05 | 0.05 | −0.17 |
| 20 | CAT | −0.14 | 0.22 | 0.11 | −0.07 | −0.19 | 0.01 | −0.08 | 0.14 | −0.07 | 0.11 | 0.03 | −0.01 |
| 21 | CCA | −0.14 | −0.12 | −0.07 | −0.21 | −0.49 | 0.44 | 0.69 | 0.54 | 0.30 | 0.26 | 0.23 | 0.35 |
| 22 | CCC | −0.26 | 0.04 | 0.08 | −0.16 | 0.27 | 0.48 | 0.66 | 0.38 | 0.05 | −0.36 | −0.36 | −0.17 |
| 23 | CCG | −0.05 | −0.22 | 0.14 | 0.01 | −0.20 | −0.43 | −0.18 | −0.38 | 0.20 | 0.27 | 0.32 | 0.27 |
| 24 | CCT | −0.27 | 0.20 | 0.34 | −0.05 | −0.34 | 0.38 | 0.51 | 0.10 | −0.44 | −0.31 | −0.38 | −0.45 |
| 25 | CGA | −0.61 | −0.33 | −0.22 | −0.24 | −0.53 | 0.67 | 0.59 | 0.55 | 0.51 | 0.38 | 0.55 | 0.25 |
| 26 | CGC | −0.20 | −0.11 | 0.25 | 0.24 | 0.41 | 0.09 | 0.16 | 0.42 | 0.31 | −0.35 | −0.46 | −0.03 |
| 27 | CGG | −0.36 | −0.34 | −0.22 | −0.28 | −0.62 | −0.54 | −0.45 | −0.39 | 0.23 | 0.46 | 0.28 | 0.23 |
| 28 | CGT | −0.55 | −0.14 | 0.08 | −0.28 | −0.42 | −0.29 | −0.19 | −0.19 | −0.12 | −0.27 | −0.25 | −0.14 |
| 29 | CTA | −0.64 | −0.16 | −0.16 | −0.37 | −0.70 | 0.74 | 0.68 | 0.32 | 0.37 | 0.59 | 0.49 | 0.26 |
| 30 | CTC | 0.50 | 0.35 | 0.26 | −0.10 | 0.32 | 0.56 | 0.71 | 0.49 | 0.28 | −0.46 | −0.30 | −0.16 |
| 31 | CTG | 0.45 | −0.39 | −0.10 | −0.04 | 0.18 | −0.40 | −0.36 | −0.28 | 0.31 | 0.49 | 0.35 | 0.42 |
| 32 | CTT | −0.11 | −0.03 | 0.16 | −0.25 | −0.08 | −0.08 | 0.20 | −0.02 | −0.42 | −0.17 | −0.06 | −0.45 |
| 33 | GAA | 0.29 | 0.48 | 0.02 | 0.37 | 0.33 | 0.60 | 0.27 | 0.51 | −0.13 | −0.06 | −0.06 | −0.02 |
| 34 | GAC | −0.01 | −0.07 | −0.20 | −0.27 | 0.36 | 0.38 | 0.32 | 0.23 | 0.30 | −0.07 | −0.13 | 0.03 |
| 35 | GAG | −0.11 | −0.43 | −0.52 | −0.36 | −0.23 | −0.32 | −0.54 | −0.58 | 0.22 | 0.20 | 0.27 | −0.03 |
| 36 | GAT | −0.26 | 0.15 | 0.28 | 0.09 | −0.25 | −0.07 | −0.12 | 0.04 | −0.19 | 0.04 | 0.08 | −0.01 |
| 37 | GCA | 0.32 | 0.47 | 0.45 | 0.52 | −0.06 | 0.41 | 0.46 | 0.47 | 0.11 | 0.09 | 0.15 | 0.17 |
| 38 | GCC | 0.07 | 0.07 | 0.26 | 0.01 | 0.44 | 0.56 | 0.61 | 0.44 | 0.11 | −0.26 | −0.41 | −0.20 |
| 39 | GCG | −0.24 | −0.34 | −0.05 | 0.04 | −0.21 | −0.57 | −0.37 | −0.36 | 0.22 | 0.37 | 0.35 | 0.32 |
| 40 | GCT | −0.56 | −0.14 | −0.05 | −0.28 | −0.32 | 0.22 | 0.45 | −0.18 | −0.39 | −0.19 | −0.11 | −0.39 |
| 41 | GGA | 0.19 | 0.44 | 0.08 | 0.27 | 0.09 | 0.41 | 0.12 | 0.04 | −0.24 | −0.04 | 0.02 | 0.07 |
| 42 | GGC | 0.06 | −0.10 | −0.12 | −0.05 | 0.62 | 0.31 | 0.24 | 0.34 | 0.32 | −0.15 | −0.23 | 0.03 |
| 43 | GGG | −0.28 | −0.20 | −0.32 | −0.23 | −0.04 | −0.39 | −0.45 | −0.53 | 0.27 | 0.52 | 0.42 | 0.41 |
| 44 | GGT | −0.12 | 0.39 | 0.31 | 0.15 | 0.02 | 0.04 | −0.07 | −0.39 | −0.32 | −0.29 | −0.21 | −0.34 |
| 45 | GTA | −0.06 | 0.35 | 0.15 | 0.17 | 0.17 | 0.46 | 0.38 | 0.55 | 0.13 | 0.15 | 0.13 | 0.32 |
| 46 | GTC | 0.45 | 0.19 | 0.10 | 0.16 | 0.62 | 0.66 | 0.58 | 0.57 | 0.29 | −0.30 | −0.35 | −0.11 |
| 47 | GTG | 0.44 | −0.36 | −0.15 | 0.13 | 0.39 | −0.52 | −0.57 | −0.43 | 0.18 | 0.52 | 0.33 | 0.35 |
| 48 | GTT | −0.37 | 0.05 | 0.07 | −0.20 | −0.13 | −0.11 | 0.18 | −0.14 | −0.35 | −0.17 | −0.12 | −0.27 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.20 | −0.20 | −0.43 | −0.44 | 0.32 | 0.46 | 0.24 | 0.47 | 0.32 | 0.05 | 0.14 | 0.16 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.39 | 0.54 | 0.24 | 0.41 | −0.23 | 0.05 | 0.07 | 0.29 | −0.24 | −0.06 | 0.06 | −0.09 |
| 53 | TCA | 0.45 | 0.43 | 0.43 | 0.42 | −0.09 | 0.33 | 0.37 | 0.20 | −0.10 | −0.01 | 0.00 | 0.15 |
| 54 | TCC | 0.17 | 0.02 | 0.07 | −0.19 | 0.50 | 0.51 | 0.58 | 0.32 | 0.34 | 0.06 | 0.14 | 0.04 |
| 55 | TCG | −0.24 | −0.45 | −0.13 | 0.11 | −0.28 | −0.50 | −0.29 | −0.26 | 0.40 | 0.36 | 0.36 | 0.41 |
| 56 | TCT | 0.12 | 0.50 | 0.47 | 0.22 | −0.17 | −0.04 | 0.38 | −0.23 | −0.38 | −0.32 | −0.15 | −0.34 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | −0.24 | −0.27 | −0.19 | −0.02 | 0.67 | 0.09 | 0.10 | 0.21 | 0.47 | −0.07 | −0.04 | 0.27 |
| 59 | TGG | 0.41 | 0.06 | −0.04 | −0.02 | 0.01 | −0.23 | −0.28 | 0.02 | 0.06 | 0.04 | −0.11 | −0.03 |
| 60 | TGT | −0.10 | 0.49 | 0.53 | 0.34 | −0.04 | −0.21 | −0.33 | −0.14 | −0.42 | −0.24 | −0.15 | −0.12 |

TABLE C.7-continued

CPW matrix *Bacillus amyloliquefaciens* full genome (left codon indicated in column 2, right codon indicated in row 2). Host cell: *B. amyloliqueaciens*; Sequence data: full *B. amyloliqueaciens* genome.

| | | | | | | | | | | | | |
|---|---|---|---|---|---|---|---|---|---|---|---|---|
| 61 | TTA | 0.63 | 0.77 | 0.44 | 0.60 | 0.29 | 0.66 | 0.63 | 0.61 | −0.02 | 0.31 | 0.17 | 0.12 |
| 62 | TTC | 0.09 | −0.30 | −0.24 | −0.44 | 0.37 | 0.37 | 0.36 | 0.44 | 0.46 | 0.11 | −0.05 | 0.37 |
| 63 | TTG | 0.26 | −0.14 | −0.13 | −0.15 | −0.19 | −0.05 | −0.18 | −0.26 | 0.10 | 0.43 | 0.25 | 0.09 |
| 64 | TTT | 0.38 | 0.47 | 0.42 | 0.34 | −0.27 | −0.04 | 0.24 | 0.16 | −0.28 | −0.12 | 0.14 | −0.18 |

| | | CGA 25 | CGC 26 | CGG 27 | CGT 28 | CTA 29 | CTC 30 | CTG 31 | CTT 32 | GAA 33 | GAC 34 | GAG 35 | GAT 36 |
|---|---|---|---|---|---|---|---|---|---|---|---|---|---|
| | | 37 GCA | 38 GCC | 39 GCG | 40 GCT | 41 GGA | 42 GGC | 43 GGG | 44 GGT | 45 GTA | 46 GTC | 47 GTG | 48 GTT |
| 1 | AAA | −0.23 | 0.06 | −0.16 | 0.28 | −0.29 | −0.04 | −0.22 | 0.28 | −0.26 | 0.18 | −0.19 | 0.44 |
| 2 | AAC | −0.06 | −0.08 | −0.12 | 0.17 | −0.45 | −0.44 | −0.12 | −0.35 | 0.03 | 0.05 | 0.09 | 0.32 |
| 3 | AAG | 0.10 | 0.45 | −0.09 | 0.19 | 0.21 | 0.28 | 0.27 | 0.47 | −0.08 | 0.14 | −0.32 | 0.07 |
| 4 | AAT | −0.07 | −0.06 | 0.13 | 0.20 | 0.52 | 0.71 | 0.60 | 0.46 | −0.34 | −0.02 | −0.12 | 0.07 |
| 5 | ACA | 0.05 | 0.23 | 0.50 | 0.15 | −0.06 | 0.20 | 0.28 | −0.09 | 0.37 | 0.49 | 0.52 | 0.43 |
| 6 | ACC | −0.24 | −0.12 | −0.17 | −0.28 | −0.52 | −0.30 | −0.12 | −0.43 | −0.30 | −0.41 | −0.18 | −0.55 |
| 7 | ACG | −0.25 | 0.08 | −0.01 | −0.22 | −0.10 | 0.21 | 0.26 | 0.07 | 0.14 | 0.20 | −0.02 | −0.08 |
| 8 | ACT | −0.12 | 0.03 | 0.27 | −0.24 | −0.10 | 0.65 | 0.63 | −0.05 | −0.41 | 0.04 | 0.19 | −0.40 |
| 9 | AGA | 0.39 | 0.47 | 0.35 | 0.53 | −0.21 | 0.24 | −0.05 | 0.24 | 0.32 | 0.36 | 0.03 | 0.47 |
| 10 | AGC | 0.05 | −0.16 | 0.00 | 0.16 | −0.39 | −0.34 | −0.06 | −0.26 | 0.18 | 0.13 | 0.16 | 0.36 |
| 11 | AGG | 0.33 | 0.59 | 0.34 | 0.29 | −0.08 | 0.51 | −0.28 | 0.44 | 0.24 | 0.40 | −0.20 | 0.08 |
| 12 | AGT | 0.04 | 0.49 | 0.34 | 0.11 | 0.73 | 0.88 | 0.77 | 0.45 | −0.41 | −0.01 | −0.14 | −0.18 |
| 13 | ATA | 0.27 | 0.26 | 0.45 | 0.35 | 0.32 | 0.57 | 0.42 | 0.43 | 0.49 | 0.77 | 0.66 | 0.52 |
| 14 | ATC | −0.18 | −0.38 | −0.10 | −0.10 | −0.41 | −0.54 | −0.30 | −0.49 | −0.18 | −0.37 | −0.16 | −0.17 |
| 15 | ATG | 0.16 | 0.23 | −0.13 | −0.15 | −0.13 | 0.10 | −0.09 | 0.08 | 0.24 | 0.06 | −0.21 | 0.09 |
| 16 | ATT | 0.23 | −0.10 | 0.35 | 0.20 | 0.77 | 0.89 | 0.79 | 0.58 | 0.09 | 0.06 | 0.29 | 0.24 |
| 17 | CAA | 0.04 | 0.22 | 0.29 | 0.04 | −0.20 | −0.16 | −0.32 | −0.36 | −0.23 | −0.02 | −0.23 | 0.22 |
| 18 | CAC | 0.06 | −0.28 | −0.25 | −0.23 | −0.25 | −0.54 | −0.40 | −0.46 | −0.19 | −0.16 | −0.08 | −0.07 |
| 19 | CAG | 0.01 | 0.11 | −0.26 | −0.07 | 0.03 | 0.23 | 0.10 | 0.52 | 0.15 | 0.18 | −0.18 | 0.15 |
| 20 | CAT | 0.30 | 0.14 | 0.22 | 0.21 | 0.53 | 0.70 | 0.66 | 0.50 | 0.17 | 0.02 | 0.10 | 0.20 |
| 21 | CCA | 0.17 | −0.08 | 0.48 | −0.06 | 0.51 | 0.30 | 0.13 | −0.35 | −0.27 | 0.32 | 0.55 | 0.15 |
| 22 | CCC | −0.31 | −0.54 | −0.38 | −0.48 | −0.45 | −0.66 | −0.35 | −0.58 | −0.23 | −0.52 | −0.31 | −0.57 |
| 23 | CCG | 0.09 | 0.19 | 0.29 | −0.06 | 0.04 | 0.08 | 0.22 | 0.20 | 0.39 | 0.36 | 0.32 | 0.06 |
| 24 | CCT | −0.01 | 0.03 | 0.30 | −0.32 | 0.63 | 0.72 | 0.60 | 0.38 | −0.33 | −0.24 | 0.18 | −0.42 |
| 25 | CGA | −0.20 | 0.15 | 0.12 | −0.06 | 0.14 | 0.14 | 0.51 | 0.03 | 0.37 | 0.75 | 0.60 | 0.40 |
| 26 | CGC | −0.14 | −0.33 | −0.36 | −0.29 | 0.04 | −0.55 | −0.32 | −0.42 | −0.03 | −0.33 | −0.35 | −0.12 |
| 27 | CGG | 0.36 | 0.45 | 0.27 | 0.18 | 0.50 | 0.59 | 0.23 | 0.53 | 0.39 | 0.38 | 0.10 | 0.26 |
| 28 | CGT | 0.24 | 0.06 | 0.13 | −0.20 | 0.67 | 0.71 | 0.70 | 0.41 | −0.24 | −0.31 | 0.01 | −0.30 |
| 29 | CTA | 0.41 | 0.52 | 0.84 | 0.37 | 0.54 | 0.52 | 0.44 | 0.03 | 0.27 | 0.72 | 0.30 | 0.36 |
| 30 | CTC | 0.00 | −0.53 | −0.52 | −0.12 | −0.50 | −0.73 | −0.47 | −0.67 | −0.27 | −0.62 | −0.44 | −0.38 |
| 31 | CTG | 0.31 | 0.38 | 0.34 | 0.19 | 0.60 | 0.60 | 0.53 | 0.66 | 0.65 | 0.54 | 0.56 | 0.50 |
| 32 | CTT | −0.11 | −0.39 | −0.01 | −0.11 | 0.42 | 0.47 | 0.61 | 0.27 | −0.22 | −0.41 | −0.25 | −0.28 |
| 33 | GAA | −0.16 | 0.02 | −0.19 | 0.12 | −0.28 | −0.18 | −0.10 | 0.07 | −0.14 | 0.05 | −0.31 | 0.24 |
| 34 | GAC | −0.01 | −0.14 | −0.22 | 0.04 | −0.43 | −0.52 | −0.34 | −0.39 | 0.09 | 0.08 | −0.13 | 0.12 |
| 35 | GAG | 0.29 | 0.35 | −0.01 | 0.25 | 0.43 | 0.38 | 0.27 | 0.47 | 0.29 | 0.37 | −0.12 | 0.10 |
| 36 | GAT | 0.16 | 0.07 | 0.09 | 0.24 | 0.64 | 0.81 | 0.65 | 0.45 | −0.15 | 0.00 | −0.07 | 0.13 |
| 37 | GCA | 0.08 | 0.15 | 0.43 | 0.16 | −0.01 | 0.04 | 0.11 | −0.15 | 0.34 | 0.35 | 0.51 | 0.30 |
| 38 | GCC | −0.19 | −0.28 | −0.18 | −0.25 | −0.41 | −0.41 | −0.25 | −0.46 | −0.25 | −0.37 | −0.13 | −0.49 |
| 39 | GCG | 0.10 | 0.18 | 0.01 | 0.05 | 0.08 | 0.10 | 0.21 | 0.24 | 0.34 | 0.36 | 0.06 | 0.17 |
| 40 | GCT | −0.08 | −0.02 | 0.23 | −0.18 | 0.70 | 0.79 | 0.69 | 0.44 | −0.18 | −0.03 | 0.29 | −0.41 |
| 41 | GGA | 0.01 | 0.21 | 0.14 | 0.28 | 0.37 | 0.56 | 0.65 | 0.66 | −0.06 | 0.53 | 0.39 | 0.49 |
| 42 | GGC | 0.01 | 0.03 | −0.31 | −0.19 | −0.18 | −0.25 | 0.05 | −0.13 | −0.07 | −0.21 | −0.23 | −0.12 |
| 43 | GGG | −0.09 | 0.63 | 0.29 | 0.14 | 0.54 | 0.51 | −0.87 | 0.81 | 0.33 | 0.62 | 0.42 | 0.16 |
| 44 | GGT | −0.14 | 0.10 | 0.03 | −0.30 | 0.73 | 0.83 | 0.79 | 0.64 | −0.45 | −0.30 | −0.26 | −0.48 |
| 45 | GTA | 0.35 | 0.13 | 0.35 | 0.25 | 0.30 | 0.45 | 0.34 | −0.01 | 0.23 | 0.52 | 0.54 | 0.61 |
| 46 | GTC | 0.07 | −0.32 | −0.34 | −0.09 | −0.39 | −0.59 | −0.35 | −0.62 | −0.32 | −0.44 | −0.28 | −0.30 |
| 47 | GTG | 0.22 | 0.37 | 0.19 | 0.16 | 0.61 | 0.67 | 0.51 | 0.62 | 0.70 | 0.57 | 0.43 | 0.51 |
| 48 | GTT | 0.02 | −0.15 | 0.14 | 0.03 | 0.75 | 0.80 | 0.73 | 0.48 | −0.18 | −0.24 | 0.03 | −0.16 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | −0.14 | −0.04 | −0.16 | 0.11 | −0.58 | −0.50 | −0.36 | −0.42 | 0.23 | 0.07 | −0.07 | 0.40 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | −0.08 | 0.06 | 0.06 | 0.23 | 0.60 | 0.80 | 0.72 | 0.57 | −0.22 | −0.03 | −0.19 | 0.13 |
| 53 | TCA | −0.21 | 0.01 | 0.36 | −0.05 | −0.17 | −0.04 | 0.16 | −0.08 | 0.35 | 0.41 | 0.50 | 0.16 |
| 54 | TCC | −0.28 | −0.27 | 0.12 | −0.44 | −0.46 | −0.41 | 0.01 | −0.49 | −0.40 | −0.37 | 0.12 | −0.55 |
| 55 | TCG | −0.28 | 0.10 | −0.12 | −0.03 | 0.27 | 0.12 | 0.22 | 0.40 | 0.47 | 0.07 | 0.05 | 0.08 |
| 56 | TCT | −0.14 | 0.05 | 0.50 | −0.25 | 0.66 | 0.83 | 0.75 | 0.53 | −0.37 | −0.23 | 0.33 | −0.42 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.21 | −0.20 | −0.27 | 0.03 | −0.28 | −0.34 | −0.22 | −0.33 | 0.23 | −0.07 | −0.01 | 0.37 |
| 59 | TGG | 0.05 | 0.29 | −0.20 | 0.07 | −0.18 | 0.04 | −0.08 | 0.36 | 0.27 | 0.26 | −0.37 | 0.16 |

TABLE C.7-continued

CPW matrix *Bacillus amyloliquefaciens* full genome (left codon indicated in column 2, right codon indicated in row 2). Host cell: *B. amyloliqueaciens*; Sequence data: full *B. amyloliqueaciens* genome.

| | | GCA 37 | GCC 38 | GCG 39 | GCT 40 | GGA 41 | GGC 42 | GGG 43 | GGT 44 | GTA 45 | GTC 46 | GTG 47 | GTT 48 |
|---|---|---|---|---|---|---|---|---|---|---|---|---|---|
| 60 | TGT | 0.12 | 0.42 | 0.31 | 0.40 | 0.78 | 0.87 | 0.84 | 0.67 | −0.13 | −0.10 | −0.17 | −0.17 |
| 61 | TTA | 0.37 | 0.41 | 0.56 | 0.29 | −0.07 | 0.26 | 0.05 | 0.14 | 0.28 | 0.49 | 0.55 | 0.41 |
| 62 | TTC | 0.17 | −0.26 | −0.14 | −0.05 | −0.45 | −0.55 | −0.32 | −0.54 | 0.31 | −0.23 | 0.20 | 0.10 |
| 63 | TTG | −0.15 | 0.22 | 0.09 | −0.05 | 0.16 | 0.49 | 0.27 | 0.27 | 0.28 | 0.43 | 0.25 | 0.13 |
| 64 | TTT | −0.04 | −0.01 | 0.23 | 0.14 | 0.67 | 0.77 | 0.77 | 0.57 | −0.04 | −0.16 | 0.16 | 0.05 |

| | | 49 TAA | 50 TAC | 51 TAG | 52 TAT | 53 TCA | 54 TCC | 55 TCG | 56 TCT | 57 TGA | 58 TGC | 59 TGG | 60 TGT |
|---|---|---|---|---|---|---|---|---|---|---|---|---|---|
| 1 | AAA | 0.00 | −0.10 | 0.00 | −0.03 | −0.26 | 0.15 | 0.23 | 0.38 | 0.00 | 0.00 | −0.07 | −0.13 |
| 2 | AAC | 0.00 | 0.10 | 0.00 | 0.03 | 0.38 | 0.41 | 0.39 | 0.27 | 0.00 | −0.21 | −0.17 | −0.05 |
| 3 | AAG | 0.00 | 0.12 | 0.00 | 0.17 | 0.26 | 0.44 | 0.17 | 0.32 | 0.00 | 0.16 | 0.16 | 0.02 |
| 4 | AAT | 0.00 | 0.03 | 0.00 | −0.11 | −0.11 | −0.05 | 0.21 | 0.05 | 0.00 | 0.33 | 0.19 | −0.06 |
| 5 | ACA | 0.00 | −0.20 | 0.00 | −0.13 | −0.17 | −0.18 | −0.06 | −0.19 | 0.00 | −0.15 | −0.38 | −0.12 |
| 6 | ACC | 0.00 | 0.25 | 0.00 | 0.05 | 0.37 | 0.26 | 0.19 | 0.08 | 0.00 | −0.15 | 0.36 | −0.29 |
| 7 | ACG | 0.00 | 0.22 | 0.00 | 0.13 | 0.26 | 0.30 | 0.02 | 0.32 | 0.00 | 0.36 | 0.33 | 0.48 |
| 8 | ACT | 0.00 | −0.28 | 0.00 | −0.26 | −0.50 | −0.40 | −0.26 | −0.58 | 0.00 | −0.13 | −0.27 | −0.58 |
| 9 | AGA | 0.00 | −0.13 | 0.00 | −0.19 | −0.03 | 0.11 | −0.06 | 0.49 | 0.00 | 0.34 | −0.40 | 0.08 |
| 10 | AGC | 0.00 | 0.02 | 0.00 | −0.10 | 0.35 | 0.35 | 0.23 | 0.40 | 0.00 | −0.03 | −0.36 | −0.09 |
| 11 | AGG | 0.00 | 0.49 | 0.00 | 0.39 | 0.01 | 0.64 | 0.10 | 0.19 | 0.00 | 0.48 | −0.30 | 0.15 |
| 12 | AGT | 0.00 | 0.25 | 0.00 | −0.12 | −0.35 | 0.10 | −0.10 | −0.18 | 0.00 | 0.22 | 0.71 | 0.38 |
| 13 | ATA | 0.00 | −0.29 | 0.00 | −0.06 | −0.21 | −0.34 | −0.17 | −0.13 | 0.00 | −0.16 | −0.47 | −0.47 |
| 14 | ATC | 0.00 | 0.39 | 0.00 | 0.36 | 0.46 | 0.34 | 0.36 | 0.56 | 0.00 | −0.07 | 0.08 | 0.15 |
| 15 | ATG | 0.00 | −0.03 | 0.00 | 0.03 | 0.16 | 0.09 | −0.01 | 0.18 | 0.00 | 0.00 | 0.00 | 0.00 |
| 16 | ATT | 0.00 | −0.18 | 0.00 | −0.30 | −0.29 | −0.35 | 0.14 | −0.44 | 0.00 | 0.35 | 0.17 | −0.24 |
| 17 | CAA | 0.00 | −0.37 | 0.00 | −0.35 | −0.39 | −0.41 | −0.35 | −0.28 | 0.00 | −0.31 | −0.42 | −0.26 |
| 18 | CAC | 0.00 | 0.27 | 0.00 | 0.33 | 0.41 | 0.21 | 0.28 | 0.35 | 0.00 | 0.06 | 0.08 | 0.06 |
| 19 | CAG | 0.00 | 0.25 | 0.00 | 0.45 | 0.31 | 0.40 | 0.19 | 0.37 | 0.00 | 0.20 | 0.48 | 0.41 |
| 20 | CAT | 0.00 | −0.21 | 0.00 | −0.17 | −0.30 | −0.32 | −0.23 | −0.07 | 0.00 | 0.05 | −0.06 | −0.18 |
| 21 | CCA | 0.00 | −0.32 | 0.00 | −0.28 | −0.27 | −0.54 | 0.01 | −0.54 | 0.00 | −0.57 | −0.41 | −0.45 |
| 22 | CCC | 0.00 | 0.56 | 0.00 | 0.41 | 0.49 | 0.42 | 0.49 | 0.46 | 0.00 | 0.18 | 0.49 | 0.19 |
| 23 | CCG | 0.00 | 0.17 | 0.00 | 0.15 | 0.08 | 0.06 | −0.11 | 0.05 | 0.00 | 0.19 | 0.06 | 0.49 |
| 24 | CCT | 0.00 | −0.32 | 0.00 | −0.44 | −0.41 | −0.40 | 0.02 | −0.54 | 0.00 | −0.22 | −0.18 | −0.41 |
| 25 | CGA | 0.00 | −0.16 | 0.00 | 0.22 | −0.18 | −0.58 | −0.49 | −0.50 | 0.00 | −0.68 | 0.38 | −0.37 |
| 26 | CGC | 0.00 | −0.17 | 0.00 | 0.11 | 0.47 | 0.33 | −0.19 | 0.52 | 0.00 | −0.08 | −0.31 | 0.26 |
| 27 | CGG | 0.00 | 0.35 | 0.00 | 0.11 | 0.40 | 0.62 | 0.22 | 0.44 | 0.00 | 0.36 | 0.64 | 0.51 |
| 28 | CGT | 0.00 | −0.15 | 0.00 | −0.26 | −0.40 | −0.30 | −0.46 | −0.44 | 0.00 | 0.08 | 0.54 | 0.53 |
| 29 | CTA | 0.00 | −0.41 | 0.00 | −0.44 | −0.41 | −0.54 | −0.48 | −0.62 | 0.00 | −0.72 | −0.56 | −0.68 |
| 30 | CTC | 0.00 | 0.49 | 0.00 | 0.45 | 0.58 | 0.48 | 0.55 | 0.60 | 0.00 | 0.24 | 0.40 | 0.35 |
| 31 | CTG | 0.00 | −0.10 | 0.00 | 0.14 | −0.07 | −0.01 | −0.29 | 0.00 | 0.00 | 0.04 | 0.07 | 0.52 |
| 32 | CTT | 0.00 | −0.09 | 0.00 | −0.21 | −0.16 | −0.35 | 0.07 | −0.53 | 0.00 | 0.02 | 0.22 | −0.37 |
| 33 | GAA | 0.00 | −0.20 | 0.00 | 0.00 | −0.09 | −0.09 | −0.17 | 0.27 | 0.00 | 0.01 | −0.11 | −0.23 |
| 34 | GAC | 0.00 | 0.35 | 0.00 | 0.29 | 0.52 | 0.53 | 0.54 | 0.45 | 0.00 | −0.10 | −0.13 | 0.04 |
| 35 | GAG | 0.00 | 0.21 | 0.00 | 0.21 | 0.43 | 0.50 | 0.31 | 0.39 | 0.00 | 0.18 | 0.23 | 0.21 |
| 36 | GAT | 0.00 | −0.21 | 0.00 | −0.20 | −0.22 | −0.28 | −0.22 | −0.15 | 0.00 | 0.06 | 0.13 | 0.03 |
| 37 | GCA | 0.00 | −0.35 | 0.00 | −0.07 | −0.35 | −0.41 | −0.40 | −0.38 | 0.00 | −0.32 | −0.48 | −0.14 |
| 38 | GCC | 0.00 | 0.38 | 0.00 | 0.15 | 0.43 | 0.36 | 0.33 | 0.46 | 0.00 | −0.24 | 0.28 | −0.13 |
| 39 | GCG | 0.00 | 0.21 | 0.00 | 0.40 | 0.48 | 0.37 | −0.19 | 0.35 | 0.00 | 0.27 | 0.22 | 0.55 |
| 40 | GCT | 0.00 | −0.45 | 0.00 | −0.47 | −0.50 | −0.54 | −0.33 | −0.53 | 0.00 | −0.05 | −0.06 | −0.11 |
| 41 | GGA | 0.00 | 0.04 | 0.00 | −0.09 | −0.26 | 0.79 | 0.04 | 0.06 | 0.00 | −0.06 | 0.16 | 0.16 |
| 42 | GGC | 0.00 | −0.11 | 0.00 | 0.00 | 0.24 | 0.35 | −0.10 | 0.36 | 0.00 | −0.28 | −0.35 | −0.33 |
| 43 | GGG | 0.00 | 0.38 | 0.00 | 0.29 | 0.41 | 0.66 | 0.59 | 0.53 | 0.00 | 0.56 | 0.55 | 0.42 |
| 44 | GGT | 0.00 | 0.01 | 0.00 | −0.26 | −0.60 | −0.28 | −0.43 | −0.50 | 0.00 | 0.49 | 0.55 | 0.63 |
| 45 | GTA | 0.00 | −0.40 | 0.00 | −0.28 | −0.42 | −0.47 | −0.40 | −0.42 | 0.00 | −0.35 | −0.43 | −0.35 |
| 46 | GTC | 0.00 | 0.44 | 0.00 | 0.23 | 0.55 | 0.45 | 0.49 | 0.48 | 0.00 | −0.08 | 0.17 | 0.03 |
| 47 | GTG | 0.00 | 0.03 | 0.00 | 0.12 | 0.27 | 0.18 | −0.23 | 0.34 | 0.00 | 0.21 | 0.10 | 0.51 |
| 48 | GTT | 0.00 | −0.14 | 0.00 | −0.24 | −0.24 | −0.47 | −0.02 | −0.47 | 0.00 | 0.26 | 0.12 | −0.27 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.00 | 0.23 | 0.00 | 0.34 | 0.35 | 0.38 | 0.35 | 0.28 | 0.00 | −0.14 | −0.08 | −0.06 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.00 | −0.19 | 0.00 | −0.17 | −0.25 | −0.24 | −0.01 | −0.08 | 0.00 | 0.15 | 0.06 | −0.02 |
| 53 | TCA | 0.00 | 0.18 | 0.00 | 0.25 | −0.15 | −0.22 | 0.21 | −0.21 | 0.00 | 0.11 | −0.13 | 0.09 |
| 54 | TCC | 0.00 | 0.36 | 0.00 | −0.10 | 0.31 | −0.10 | 0.45 | −0.01 | 0.00 | −0.29 | 0.25 | −0.21 |
| 55 | TCG | 0.00 | 0.14 | 0.00 | 0.45 | 0.32 | 0.24 | −0.39 | 0.35 | 0.00 | −0.08 | 0.11 | 0.58 |
| 56 | TCT | 0.00 | −0.28 | 0.00 | −0.47 | −0.41 | −0.50 | −0.02 | −0.55 | 0.00 | 0.14 | 0.27 | −0.19 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.00 | −0.05 | 0.00 | 0.30 | 0.46 | 0.29 | −0.25 | 0.26 | 0.00 | −0.08 | −0.30 | −0.31 |
| 59 | TGG | 0.00 | 0.01 | 0.00 | −0.01 | 0.16 | 0.33 | −0.21 | 0.10 | 0.00 | −0.03 | 0.00 | 0.06 |

TABLE C.7-continued

CPW matrix *Bacillus amyloliquefaciens* full genome (left codon indicated in column 2, right codon indicated in row 2). Host cell: *B. amyloliqueaciens*; Sequence data: full *B. amyloliqueaciens* genome.

|    |     |      |       |      |       |       |       |       |       |      |      |       |       |
|----|-----|------|-------|------|-------|-------|-------|-------|-------|------|------|-------|-------|
| 60 | TGT | 0.00 | 0.02  | 0.00 | −0.34 | −0.32 | −0.17 | −0.29 | −0.35 | 0.00 | 0.50 | 0.82  | 0.26  |
| 61 | TTA | 0.00 | −0.26 | 0.00 | −0.27 | −0.38 | −0.23 | 0.00  | −0.21 | 0.00 | −0.04 | −0.44 | −0.38 |
| 62 | TTC | 0.00 | 0.31  | 0.00 | 0.42  | 0.20  | 0.07  | 0.06  | 0.29  | 0.00 | −0.18 | −0.05 | −0.13 |
| 63 | TTG | 0.00 | 0.26  | 0.00 | 0.06  | 0.10  | −0.14 | 0.11  | 0.02  | 0.00 | 0.17 | 0.08  | 0.41  |
| 64 | TTT | 0.00 | −0.18 | 0.00 | −0.24 | −0.26 | −0.23 | 0.18  | −0.34 | 0.00 | 0.27 | 0.04  | −0.08 |

| TAA | TAC | TAG | TAT | TCA | TCC | TCG | TCT | TGA | TGC | TGG | TGT |
|-----|-----|-----|-----|-----|-----|-----|-----|-----|-----|-----|-----|
| 49  | 50  | 51  | 52  | 53  | 54  | 55  | 56  | 57  | 58  | 59  | 60  |

|    |     | 61<br>TTA | 62<br>TTC | 63<br>TTG | 64<br>TTT |
|----|-----|-------|-------|-------|-------|
| 1  | AAA | 0.10  | −0.15 | 0.17  | 0.24  |
| 2  | AAC | 0.19  | −0.08 | 0.38  | 0.11  |
| 3  | AAG | 0.63  | −0.11 | 0.69  | −0.14 |
| 4  | AAT | −0.37 | −0.07 | −0.02 | 0.01  |
| 5  | ACA | −0.23 | −0.16 | −0.52 | −0.12 |
| 6  | ACC | 0.46  | 0.17  | 0.16  | 0.07  |
| 7  | ACG | 0.44  | 0.03  | 0.66  | 0.26  |
| 8  | ACT | −0.45 | −0.10 | −0.45 | −0.38 |
| 9  | AGA | 0.17  | 0.30  | −0.20 | 0.34  |
| 10 | AGC | 0.36  | 0.15  | 0.25  | 0.19  |
| 11 | AGG | 0.18  | 0.19  | 0.52  | 0.01  |
| 12 | AGT | −0.40 | 0.06  | −0.23 | −0.28 |
| 13 | ATA | −0.48 | −0.32 | −0.61 | −0.22 |
| 14 | ATC | 0.37  | 0.30  | 0.55  | 0.40  |
| 15 | ATG | 0.66  | 0.10  | 0.81  | −0.07 |
| 16 | ATT | −0.62 | −0.26 | −0.52 | −0.18 |
| 17 | CAA | −0.14 | −0.27 | −0.25 | −0.32 |
| 18 | CAC | 0.36  | 0.12  | 0.20  | 0.40  |
| 19 | CAG | 0.76  | 0.19  | 0.49  | 0.34  |
| 20 | CAT | −0.36 | −0.14 | −0.43 | −0.19 |
| 21 | CCA | −0.29 | −0.19 | −0.42 | −0.19 |
| 22 | CCC | 0.65  | 0.56  | 0.43  | 0.48  |
| 23 | CCG | 0.43  | 0.07  | 0.62  | −0.13 |
| 24 | CCT | −0.39 | 0.12  | −0.29 | −0.23 |
| 25 | CGA | 0.12  | −0.28 | −0.18 | 0.04  |
| 26 | CGC | 0.68  | −0.14 | 0.46  | 0.39  |
| 27 | CGG | 0.64  | 0.17  | 0.64  | 0.01  |
| 28 | CGT | −0.10 | −0.42 | −0.23 | −0.38 |
| 29 | CTA | −0.63 | −0.25 | −0.66 | −0.33 |
| 30 | CTC | 0.58  | 0.53  | 0.30  | 0.46  |
| 31 | CTG | 0.16  | −0.16 | 0.45  | −0.20 |
| 32 | CTT | −0.41 | 0.24  | −0.55 | 0.27  |
| 33 | GAA | 0.11  | −0.02 | −0.19 | −0.04 |
| 34 | GAC | 0.27  | 0.29  | 0.11  | 0.39  |
| 35 | GAG | 0.65  | 0.11  | 0.61  | 0.03  |
| 36 | GAT | −0.42 | −0.24 | −0.34 | −0.21 |
| 37 | GCA | −0.26 | −0.31 | −0.38 | −0.24 |
| 38 | GCC | 0.50  | 0.35  | 0.44  | 0.28  |
| 39 | GCG | 0.59  | 0.02  | 0.57  | 0.23  |
| 40 | GCT | −0.39 | −0.14 | −0.47 | −0.40 |
| 41 | GGA | −0.02 | 0.17  | −0.34 | −0.22 |
| 42 | GGC | 0.45  | 0.01  | 0.33  | 0.22  |
| 43 | GGG | 0.45  | 0.53  | 0.54  | 0.13  |
| 44 | GGT | −0.49 | −0.27 | −0.48 | −0.45 |
| 45 | GTA | −0.40 | −0.37 | −0.50 | −0.38 |
| 46 | GTC | 0.62  | 0.54  | 0.70  | 0.39  |
| 47 | GTG | 0.39  | −0.13 | 0.55  | −0.02 |
| 48 | GTT | −0.41 | −0.12 | −0.49 | −0.18 |
| 49 | TAA | 0.00  | 0.00  | 0.00  | 0.00  |
| 50 | TAC | −0.05 | 0.14  | 0.15  | 0.31  |
| 51 | TAG | 0.00  | 0.00  | 0.00  | 0.00  |
| 52 | TAT | −0.52 | −0.22 | −0.50 | −0.08 |
| 53 | TCA | −0.36 | −0.01 | −0.37 | −0.13 |
| 54 | TCC | 0.16  | 0.22  | 0.27  | −0.06 |
| 55 | TCG | 0.35  | 0.09  | 0.44  | 0.16  |
| 56 | TCT | −0.54 | −0.08 | −0.33 | −0.26 |
| 57 | TGA | 0.00  | 0.00  | 0.00  | 0.00  |
| 58 | TGC | 0.37  | 0.12  | 0.43  | 0.37  |

TABLE C.7-continued

CPW matrix *Bacillus amyloliquefaciens* full genome (left codon indicated in column 2, right codon indicated in row 2). Host cell: *B. amyloliqueaciens*; Sequence data: full *B. amyloliqueaciens* genome.

| | | | | | |
|---|---|---|---|---|---|
| 59 | TGG | 0.54 | 0.11 | 0.76 | −0.07 |
| 60 | TGT | −0.43 | −0.19 | −0.31 | −0.41 |
| 61 | TTA | −0.36 | −0.12 | −0.40 | −0.34 |
| 62 | TTC | 0.04 | 0.02 | 0.43 | 0.11 |
| 63 | TTG | 0.14 | 0.22 | 0.51 | −0.27 |
| 64 | TTT | −0.61 | −0.21 | −0.47 | 0.10 |
| | | TTA | TTC | TTG | TTT |
| | | 61 | 62 | 63 | 64 |

TABLE C.8

CPW matrix *Bacillus amyloliqueaciens* K12 highly expressed sequences (left codon indicated in column 2, right codon indicated in row 2). Host cell: *B. amyloliqueaciens*; Sequence data: full *B. amyloliqueaciens* genome; Highly expressed group: 236 seqs.

| | | 1<br>AAA | 2<br>AAC | 3<br>AAG | 4<br>AAT | 5<br>ACA | 6<br>ACC | 7<br>ACG | 8<br>ACT | 9<br>AGA | 10<br>AGC | 11<br>AGG | 12<br>AGT |
|---|---|---|---|---|---|---|---|---|---|---|---|---|---|
| 1 | AAA | 0.01 | −0.27 | −0.03 | 0.08 | −0.25 | −0.11 | −0.16 | 0.63 | −0.32 | −0.14 | 0.09 | 0.42 |
| 2 | AAC | 0.20 | −0.38 | 0.36 | 0.17 | 0.35 | −0.26 | 0.01 | 0.50 | −0.36 | −0.55 | 0.59 | −0.73 |
| 3 | AAG | 0.01 | 0.40 | −0.01 | 0.62 | 0.31 | 0.37 | 0.03 | 0.65 | 0.50 | −0.01 | 0.57 | 0.35 |
| 4 | AAT | −0.29 | 0.42 | −0.02 | 0.26 | −0.26 | 0.24 | −0.26 | 0.16 | 1.00 | 1.00 | 0.48 | 0.48 |
| 5 | ACA | −0.41 | −0.51 | −0.36 | −0.40 | −0.15 | −0.08 | 0.18 | −0.17 | −0.60 | −0.54 | −0.76 | −0.21 |
| 6 | ACC | 0.52 | 0.06 | 0.23 | 0.32 | 1.00 | −0.17 | 0.81 | −0.25 | −0.49 | 0.00 | −0.10 | 1.00 |
| 7 | ACG | 0.01 | 0.37 | 0.19 | 0.19 | −0.19 | −0.47 | −0.41 | −0.20 | −0.19 | −0.03 | −0.62 | 0.18 |
| 8 | ACT | 0.70 | 0.85 | 0.79 | 1.00 | 0.76 | 1.00 | 0.37 | 1.00 | 1.00 | 1.00 | 1.00 | 1.00 |
| 9 | AGA | −0.47 | −0.20 | −0.39 | −0.18 | −0.20 | −0.03 | −0.17 | −0.41 | −0.21 | −0.34 | −0.65 | 1.00 |
| 10 | AGC | −0.12 | 0.39 | −0.24 | −0.04 | −0.11 | 0.22 | −0.09 | 0.43 | −0.51 | −0.40 | −0.53 | −0.11 |
| 11 | AGG | 0.10 | 0.67 | 0.49 | 0.17 | 1.00 | 1.00 | 0.59 | 1.00 | −0.30 | 1.00 | 1.00 | 1.00 |
| 12 | AGT | −0.02 | 0.41 | 0.36 | 0.62 | 0.59 | −0.34 | −0.44 | 0.17 | 1.00 | 1.00 | 1.00 | 1.00 |
| 13 | ATA | −0.51 | 0.31 | −0.27 | 0.71 | 0.23 | 0.53 | −0.10 | −0.36 | −0.22 | 0.16 | −0.77 | 1.00 |
| 14 | ATC | 0.09 | −0.10 | 0.44 | −0.13 | 0.19 | −0.36 | 0.22 | −0.14 | −0.30 | −0.31 | −0.08 | −0.59 |
| 15 | ATG | 0.17 | 0.21 | −0.32 | −0.21 | −0.15 | −0.04 | 0.20 | −0.05 | −0.39 | 0.17 | −0.35 | −0.17 |
| 16 | ATT | 0.01 | 0.08 | −0.09 | 0.00 | 0.18 | −0.18 | −0.16 | 0.17 | 0.83 | 0.94 | 1.00 | 0.84 |
| 17 | CAA | −0.34 | −0.46 | −0.46 | −0.23 | 0.11 | −0.27 | 0.36 | 0.24 | 0.45 | 0.17 | −0.47 | −0.38 |
| 18 | CAC | −0.04 | 0.45 | 0.27 | −0.39 | 0.28 | 0.73 | 0.12 | 0.12 | 0.61 | −0.53 | −0.75 | −0.61 |
| 19 | CAG | 0.42 | 0.40 | 0.51 | 0.47 | −0.02 | −0.16 | −0.24 | 0.34 | 0.80 | 0.70 | 0.66 | 0.42 |
| 20 | CAT | −0.13 | −0.23 | 0.31 | 0.45 | −0.12 | 0.79 | −0.37 | −0.39 | 0.69 | 0.86 | 1.00 | 1.00 |
| 21 | CCA | 0.44 | −0.39 | −0.68 | −0.05 | 1.00 | −0.06 | 0.50 | −0.57 | 0.00 | −0.74 | 1.00 | −0.76 |
| 22 | CCC | 0.85 | 0.10 | 1.00 | 0.71 | 1.00 | 1.00 | 0.59 | 1.00 | 1.00 | 0.61 | 1.00 | −0.12 |
| 23 | CCG | −0.02 | −0.11 | −0.40 | −0.31 | −0.37 | −0.23 | −0.12 | −0.57 | 0.24 | 0.05 | 0.48 | 0.15 |
| 24 | CCT | 0.14 | 0.89 | 0.20 | 0.33 | 0.34 | 0.59 | 1.00 | 1.00 | 1.00 | 0.45 | −0.62 | −0.06 |
| 25 | CGA | −0.18 | −0.62 | 0.32 | −0.11 | −0.22 | 1.00 | 0.44 | 1.00 | −0.66 | −0.29 | −0.70 | 1.00 |
| 26 | CGC | 0.41 | −0.22 | −0.05 | −0.04 | 0.21 | −0.21 | −0.35 | 0.40 | 0.41 | −0.51 | 1.00 | −0.36 |
| 27 | CGG | 0.35 | 0.21 | 0.18 | −0.41 | −0.35 | 0.65 | −0.50 | 0.61 | 0.42 | 0.37 | −0.66 | 1.00 |
| 28 | CGT | 0.03 | 0.90 | 0.54 | 0.50 | 0.29 | 0.48 | 0.51 | −0.14 | 1.00 | 1.00 | 1.00 | 0.55 |
| 29 | CTA | −0.44 | −0.21 | 1.00 | 0.20 | −0.20 | −0.13 | 1.00 | 1.00 | −0.33 | 0.17 | 1.00 | −0.58 |
| 30 | CTC | 0.60 | 0.75 | 0.53 | 0.06 | 0.84 | −0.16 | 0.58 | 0.01 | −0.26 | −0.22 | −0.24 | −0.47 |
| 31 | CTG | −0.19 | −0.21 | −0.18 | −0.20 | −0.40 | −0.09 | −0.36 | −0.33 | 0.12 | 0.26 | −0.33 | 0.11 |
| 32 | CTT | 0.59 | 0.54 | 0.65 | 0.80 | 0.50 | 0.35 | 0.74 | −0.03 | 0.40 | 0.66 | 1.00 | 1.00 |
| 33 | GAA | −0.04 | −0.22 | 0.03 | −0.05 | −0.33 | −0.21 | 0.05 | 0.46 | −0.04 | −0.43 | 0.60 | −0.10 |
| 34 | GAC | −0.12 | −0.07 | −0.19 | 0.14 | 0.54 | −0.12 | 0.07 | −0.20 | −0.43 | −0.64 | −0.67 | −0.63 |
| 35 | GAG | 0.13 | 0.41 | −0.10 | 0.48 | 0.47 | 0.39 | 0.26 | −0.17 | 0.71 | 0.76 | 0.35 | 0.66 |
| 36 | GAT | 0.21 | −0.02 | −0.08 | −0.01 | −0.03 | 0.53 | −0.34 | −0.05 | 0.92 | 1.00 | 1.00 | 0.62 |
| 37 | GCA | −0.48 | −0.16 | −0.42 | −0.49 | 0.02 | −0.22 | 0.27 | −0.41 | −0.16 | −0.49 | −0.67 | −0.63 |
| 38 | GCC | 0.66 | 0.17 | 0.56 | −0.17 | 0.06 | 0.13 | 0.49 | 0.28 | −0.39 | 0.56 | −0.54 | −0.57 |
| 39 | GCG | −0.15 | 0.18 | −0.12 | −0.13 | −0.49 | −0.05 | 0.01 | −0.25 | −0.05 | 0.39 | −0.16 | 0.82 |
| 40 | GCT | 0.32 | 0.24 | 0.63 | 0.74 | 0.04 | 0.49 | 0.52 | 0.44 | 0.85 | 1.00 | 1.00 | 1.00 |
| 41 | GGA | −0.35 | −0.39 | −0.13 | −0.23 | −0.33 | −0.38 | −0.15 | −0.19 | −0.31 | −0.44 | −0.12 | 0.55 |
| 42 | GGC | 0.45 | 0.13 | −0.25 | 0.26 | 0.14 | 0.03 | −0.20 | 0.41 | 0.05 | −0.48 | −0.07 | −0.11 |
| 43 | GGG | 0.08 | 0.19 | 0.07 | −0.17 | 0.46 | 1.00 | 0.19 | 1.00 | 0.34 | 0.54 | 1.00 | 1.00 |
| 44 | GGT | −0.13 | 0.10 | 0.74 | 0.71 | 0.33 | 0.59 | −0.14 | −0.26 | 0.82 | 1.00 | 1.00 | 1.00 |
| 45 | GTA | −0.43 | −0.45 | −0.33 | −0.33 | −0.23 | −0.16 | −0.35 | 0.01 | −0.62 | 0.14 | 1.00 | 0.06 |
| 46 | GTC | 0.25 | 0.10 | 0.15 | −0.18 | 0.07 | 0.01 | −0.02 | −0.09 | −0.54 | −0.45 | −0.26 | −0.24 |
| 47 | GTG | −0.26 | 0.11 | −0.19 | 0.01 | −0.27 | 0.16 | −0.30 | 0.19 | 0.19 | −0.06 | 0.22 | 0.56 |
| 48 | GTT | 0.49 | 0.60 | 0.75 | 0.28 | 0.42 | 0.36 | 0.65 | 0.17 | 0.77 | 1.00 | 0.60 | 0.78 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.06 | 0.51 | 0.23 | −0.25 | −0.10 | −0.12 | −0.15 | −0.01 | −0.19 | −0.34 | −0.17 | −0.67 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | −0.22 | 0.07 | 0.42 | −0.27 | −0.17 | 0.00 | 0.24 | 0.55 | 0.84 | 0.90 | 1.00 | 0.70 |
| 53 | TCA | −0.10 | −0.49 | −0.25 | −0.05 | 0.15 | 0.21 | −0.33 | −0.31 | −0.43 | −0.45 | −0.08 | −0.74 |
| 54 | TCC | 0.33 | 0.65 | 0.25 | −0.55 | 0.76 | 0.12 | −0.04 | 0.02 | −0.47 | −0.09 | 1.00 | −0.22 |

TABLE C.8-continued

CPW matrix Bacillus amyloliqueaciens K12 highly expressed sequences (left codon indicated in column 2, right codon indicated in row 2). Host cell: *B. amyloliqueaciens*; Sequence data: full *B. amyloliqueaciens* genome; Highly expressed group: 236 seqs.

| | | | | | | | | | | | | |
|---|---|---|---|---|---|---|---|---|---|---|---|---|
| 55 | TCG | 0.10 | 0.41 | 0.58 | 0.00 | 0.19 | 0.50 | −0.15 | −0.39 | 0.09 | 0.75 | −0.51 | 1.00 |
| 56 | TCT | −0.02 | 0.11 | 0.18 | 0.35 | −0.37 | 0.03 | 0.70 | −0.07 | 1.00 | 1.00 | 1.00 | 1.00 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.75 | −0.40 | 0.28 | −0.22 | 1.00 | −0.56 | −0.44 | 1.00 | 0.22 | −0.41 | −0.63 | −0.19 |
| 59 | TGG | 0.11 | −0.22 | −0.24 | 0.35 | −0.01 | 0.73 | −0.12 | −0.32 | −0.35 | 0.11 | −0.05 | −0.61 |
| 60 | TGT | −0.55 | 1.00 | −0.04 | 0.38 | 0.40 | 1.00 | −0.36 | −0.18 | 1.00 | 1.00 | 1.00 | 1.00 |
| 61 | TTA | −0.38 | −0.24 | −0.46 | −0.47 | 0.15 | −0.12 | −0.35 | −0.65 | 0.08 | −0.25 | 0.37 | −0.16 |
| 62 | TTC | −0.06 | −0.08 | 0.13 | 0.42 | 0.22 | −0.21 | 0.55 | −0.53 | −0.58 | −0.44 | −0.59 | −0.42 |
| 63 | TTG | −0.27 | −0.35 | −0.47 | −0.36 | 0.59 | −0.33 | 0.30 | −0.39 | −0.17 | 0.46 | 1.00 | 0.61 |
| 64 | TTT | −0.01 | −0.02 | 0.05 | −0.18 | −0.23 | 0.04 | 0.10 | 0.07 | 0.64 | 0.77 | 1.00 | 1.00 |

| | | AAA 1 | AAC 2 | AAG 3 | AAT 4 | ACA 5 | ACC 6 | ACG 7 | ACT 8 | AGA 9 | AGC 10 | AGG 11 | AGT 12 |
|---|---|---|---|---|---|---|---|---|---|---|---|---|---|
| | | 13 ATA | 14 ATC | 15 ATG | 16 ATT | 17 CAA | 18 CAC | 19 CAG | 20 CAT | 21 CCA | 22 CCC | 23 CCG | 24 CCT |
| 1 | AAA | −0.14 | −0.34 | −0.02 | 0.51 | −0.07 | 0.15 | 0.45 | 0.25 | −0.28 | 0.09 | 0.43 | 0.31 |
| 2 | AAC | 0.43 | 0.18 | −0.04 | −0.03 | −0.10 | −0.05 | 0.39 | 0.05 | 0.02 | 0.19 | 0.35 | 0.50 |
| 3 | AAG | 0.11 | 0.06 | 0.06 | 0.11 | 0.20 | −0.52 | −0.56 | −0.15 | 0.22 | −0.38 | −0.46 | −0.56 |
| 4 | AAT | −0.59 | 0.05 | 0.05 | −0.07 | −0.20 | 0.43 | −0.18 | −0.26 | −0.40 | −0.42 | −0.42 | 0.52 |
| 5 | ACA | 0.51 | 0.27 | −0.22 | 0.61 | −0.42 | 0.06 | −0.11 | 0.50 | 0.12 | 0.28 | −0.17 | 0.50 |
| 6 | ACC | −0.45 | −0.09 | 0.56 | −0.45 | 0.68 | 0.42 | 0.08 | 0.32 | 0.20 | 1.00 | 0.75 | 0.38 |
| 7 | ACG | −0.33 | −0.24 | −0.28 | −0.35 | 0.40 | −0.08 | 0.24 | −0.22 | −0.12 | −0.20 | −0.40 | 0.27 |
| 8 | ACT | 0.50 | 0.81 | 0.84 | 0.50 | 0.30 | −0.22 | −0.44 | −0.43 | 0.11 | 0.27 | 0.32 | −0.41 |
| 9 | AGA | −0.19 | −0.13 | 0.01 | −0.13 | 0.46 | 0.73 | −0.07 | −0.22 | 1.00 | 1.00 | −0.24 | 0.63 |
| 10 | AGC | −0.01 | 0.00 | 0.10 | −0.13 | 0.23 | 0.21 | −0.28 | −0.49 | 0.46 | −0.44 | 0.42 | 1.00 |
| 11 | AGG | −0.64 | 0.48 | 0.33 | 0.16 | 0.08 | −0.64 | 0.67 | 0.28 | 1.00 | −0.63 | −0.33 | 1.00 |
| 12 | AGT | 0.02 | −0.09 | 0.76 | 0.02 | 0.63 | 0.62 | −0.07 | 0.70 | −0.84 | −0.23 | −0.31 | −0.17 |
| 13 | ATA | 0.32 | 0.50 | 1.00 | 0.86 | −0.67 | 0.10 | −0.17 | −0.07 | 0.05 | −0.57 | −0.47 | 0.64 |
| 14 | ATC | 0.24 | −0.28 | −0.03 | −0.03 | 0.64 | 0.24 | 0.33 | 0.47 | 0.30 | 0.57 | 0.57 | 0.19 |
| 15 | ATG | 0.14 | −0.06 | 0.00 | 0.03 | 0.47 | −0.23 | −0.25 | 0.23 | 0.14 | 0.29 | 0.05 | −0.24 |
| 16 | ATT | −0.18 | −0.06 | −0.14 | 0.24 | −0.43 | −0.31 | 0.04 | −0.26 | −0.59 | −0.41 | −0.21 | −0.14 |
| 17 | CAA | 0.15 | −0.10 | −0.25 | −0.03 | 0.67 | 1.00 | 0.60 | 0.73 | 0.37 | 1.00 | 0.00 | 0.76 |
| 18 | CAC | −0.42 | 0.28 | −0.07 | −0.11 | 0.05 | 0.29 | 0.54 | −0.11 | 0.55 | 1.00 | 0.10 | −0.18 |
| 19 | CAG | 0.59 | 0.12 | 0.25 | −0.14 | 0.11 | −0.52 | −0.46 | −0.20 | 0.09 | 1.00 | −0.45 | −0.56 |
| 20 | CAT | 0.32 | −0.07 | 0.06 | −0.02 | −0.11 | 0.21 | −0.27 | −0.20 | −0.30 | −0.15 | −0.17 | 0.18 |
| 21 | CCA | 1.00 | 0.36 | −0.21 | −0.52 | 0.46 | 0.02 | 1.00 | 1.00 | 1.00 | 1.00 | 1.00 | 1.00 |
| 22 | CCC | 1.00 | 1.00 | 1.00 | 0.72 | 0.11 | 0.20 | 0.68 | 0.05 | 1.00 | 1.00 | 1.00 | −0.12 |
| 23 | CCG | 0.47 | −0.32 | −0.33 | −0.24 | −0.19 | −0.36 | 0.16 | 0.06 | −0.09 | −0.45 | −0.20 | −0.21 |
| 24 | CCT | 1.00 | 0.38 | 0.88 | 0.47 | −0.52 | 0.44 | −0.05 | 0.12 | 1.00 | −0.71 | 0.37 | −0.06 |
| 25 | CGA | 1.00 | −0.43 | −0.63 | −0.56 | 0.38 | 1.00 | 0.55 | 0.02 | 1.00 | 1.00 | 1.00 | 1.00 |
| 26 | CGC | 0.71 | 0.03 | 0.03 | 0.01 | 0.15 | 0.05 | −0.03 | −0.17 | 1.00 | 1.00 | 0.18 | 0.48 |
| 27 | CGG | −0.56 | −0.14 | −0.18 | −0.20 | 0.26 | −0.10 | −0.32 | 0.12 | −0.24 | −0.77 | 0.20 | −0.34 |
| 28 | CGT | 0.58 | 0.61 | 0.39 | 0.16 | −0.39 | 0.17 | −0.09 | −0.08 | 1.00 | 0.19 | −0.49 | −0.47 |
| 29 | CTA | 1.00 | −0.62 | −0.27 | 1.00 | 1.00 | 1.00 | 1.00 | 1.00 | 1.00 | 1.00 | 0.41 | 1.00 |
| 30 | CTC | −0.61 | 0.10 | 0.02 | −0.04 | 0.74 | 0.43 | 0.54 | 0.40 | 1.00 | 1.00 | 0.46 | 0.42 |
| 31 | CTG | −0.48 | −0.25 | −0.24 | −0.19 | −0.02 | −0.17 | 0.10 | 0.22 | −0.42 | −0.29 | −0.31 | −0.09 |
| 32 | CTT | 0.54 | 0.48 | 0.28 | 0.77 | −0.30 | −0.30 | −0.33 | −0.38 | −0.21 | −0.61 | −0.23 | −0.41 |
| 33 | GAA | −0.01 | −0.12 | −0.13 | 0.04 | 0.11 | 0.35 | 0.19 | 0.27 | 0.21 | 0.22 | 0.23 | 0.64 |
| 34 | GAC | 0.38 | 0.12 | 0.21 | 0.13 | 0.35 | 0.66 | 0.29 | 0.12 | 0.11 | 0.51 | 0.14 | 0.43 |
| 35 | GAG | −0.20 | 0.30 | 0.38 | 0.00 | −0.25 | −0.38 | −0.30 | −0.47 | −0.58 | −0.48 | −0.44 | −0.34 |
| 36 | GAT | −0.32 | 0.12 | −0.15 | −0.24 | −0.39 | −0.18 | 0.01 | −0.26 | 0.00 | 0.39 | −0.31 | 0.04 |
| 37 | GCA | 0.20 | −0.08 | −0.03 | 0.36 | 0.08 | 0.82 | 0.04 | 0.58 | −0.50 | 0.17 | 0.54 | 0.42 |
| 38 | GCC | −0.45 | −0.01 | −0.27 | −0.35 | −0.28 | 0.40 | 0.25 | 0.06 | 1.00 | 0.30 | 0.74 | 0.35 |
| 39 | GCG | 0.53 | −0.16 | −0.17 | −0.20 | 0.22 | −0.12 | −0.23 | 0.02 | −0.15 | 0.03 | −0.15 | −0.48 |
| 40 | GCT | 0.21 | 0.56 | 0.81 | 0.47 | −0.10 | −0.48 | 0.27 | −0.44 | 0.01 | −0.51 | −0.22 | −0.52 |
| 41 | GGA | 0.15 | 0.08 | −0.12 | −0.06 | −0.44 | −0.21 | 0.02 | −0.09 | 1.00 | 0.59 | 0.02 | −0.41 |
| 42 | GGC | 0.27 | −0.10 | 0.02 | −0.19 | 0.46 | 0.18 | 0.13 | 0.22 | 0.30 | 0.13 | 0.36 | 0.60 |
| 43 | GGG | −0.02 | 0.68 | −0.24 | −0.13 | 0.66 | 0.08 | −0.41 | −0.45 | 1.00 | −0.38 | −0.49 | −0.34 |
| 44 | GGT | 0.16 | 0.27 | 0.45 | −0.15 | −0.49 | 0.05 | 0.70 | 0.25 | 0.19 | 0.33 | −0.19 | −0.54 |
| 45 | GTA | 0.74 | 0.51 | 0.30 | 0.69 | 0.52 | 0.57 | −0.17 | −0.17 | 0.53 | 0.62 | 0.64 | −0.07 |
| 46 | GTC | 0.21 | −0.38 | −0.32 | −0.17 | 0.35 | 0.60 | 0.74 | 0.38 | 0.72 | 0.53 | 0.70 | 0.78 |
| 47 | GTG | −0.09 | 0.01 | 0.01 | −0.09 | 0.08 | 0.69 | −0.43 | −0.17 | 0.01 | −0.47 | −0.53 | −0.43 |
| 48 | GTT | 0.06 | −0.08 | 0.33 | 0.17 | −0.39 | −0.51 | −0.10 | −0.42 | 0.66 | 0.17 | −0.25 | −0.35 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | −0.62 | 0.22 | 0.38 | −0.12 | 0.06 | 0.52 | 0.23 | −0.13 | −0.40 | 0.66 | 0.23 | 0.36 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | −0.40 | 0.19 | −0.25 | 0.13 | −0.13 | 0.15 | −0.12 | −0.26 | 1.00 | 0.39 | −0.41 | 0.29 |
| 53 | TCA | −0.27 | 0.49 | −0.13 | 0.32 | −0.30 | −0.06 | −0.03 | 0.79 | 0.45 | 1.00 | 0.41 | −0.05 |
| 54 | TCC | −0.13 | −0.33 | −0.10 | −0.54 | 0.78 | 0.32 | 0.68 | 1.00 | 0.07 | 0.24 | 0.29 | 0.64 |
| 55 | TCG | 0.35 | −0.08 | 0.06 | 0.09 | 0.51 | −0.60 | −0.20 | 0.00 | −0.04 | −0.42 | −0.21 | −0.58 |
| 56 | TCT | 0.16 | 0.14 | −0.18 | 0.33 | −0.37 | −0.45 | −0.04 | 0.09 | −0.70 | 0.44 | −0.12 | −0.57 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 1.00 | −0.44 | 0.44 | 0.57 | −0.09 | −0.37 | −0.25 | −0.21 | −0.01 | 1.00 | 0.23 | 1.00 |
| 59 | TGG | 0.48 | 0.33 | 0.00 | −0.31 | 0.63 | −0.23 | −0.31 | 0.23 | 1.00 | −0.71 | 0.13 | 0.45 |

TABLE C.8-continued

CPW matrix *Bacillus amyloliqueaciens* K12 highly expressed sequences (left codon indicated in column 2, right codon indicated in row 2). Host cell: *B. amyloliqueaciens*; Sequence data: full *B. amyloliqueaciens* genome; Highly expressed group: 236 seqs.

| | | | | | | | | | | | | |
|---|---|---|---|---|---|---|---|---|---|---|---|---|
| 60 | TGT | −0.35 | 0.14 | −0.39 | 0.07 | −0.05 | 0.54 | 0.62 | 0.64 | −0.66 | −0.58 | 0.55 | −0.75 |
| 61 | TTA | −0.43 | −0.10 | −0.16 | −0.06 | 0.51 | 0.64 | 0.03 | 0.43 | 0.04 | 0.61 | 0.56 | 0.63 |
| 62 | TTC | 1.00 | −0.16 | 0.15 | 0.13 | 0.75 | −0.08 | −0.20 | −0.18 | 1.00 | 1.00 | 0.03 | −0.09 |
| 63 | TTG | 0.53 | 0.05 | 0.44 | −0.28 | −0.22 | −0.17 | −0.34 | −0.34 | 1.00 | −0.36 | 0.61 | 0.03 |
| 64 | TTT | 0.34 | 0.06 | −0.10 | −0.19 | 0.16 | −0.22 | −0.26 | 0.45 | −0.23 | −0.65 | 0.01 | 0.33 |

| | | ATA 13 | ATC 14 | ATG 15 | ATT 16 | CAA 17 | CAC 18 | CAG 19 | CAT 20 | CCA 21 | CCC 22 | CCG 23 | CCT 24 |
|---|---|---|---|---|---|---|---|---|---|---|---|---|---|
| | | 25 CGA | 26 CGC | 27 CGG | 28 CGT | 29 CTA | 30 CTC | 31 CTG | 32 CTT | 33 GAA | 34 GAC | 35 GAG | 36 GAT |
| 1 | AAA | −0.56 | 0.18 | −0.22 | 0.32 | −0.17 | 0.49 | 0.31 | 0.39 | −0.17 | −0.29 | 0.14 | 0.27 |
| 2 | AAC | −0.40 | −0.26 | −0.39 | −0.09 | 1.00 | 0.00 | −0.17 | 0.13 | 0.20 | 0.50 | −0.07 | 0.33 |
| 3 | AAG | 1.00 | −0.13 | −0.03 | 0.36 | 0.15 | −0.52 | −0.63 | −0.64 | 0.24 | 0.01 | 0.48 | 0.17 |
| 4 | AAT | −0.64 | 0.57 | 0.58 | 0.06 | 1.00 | −0.35 | −0.47 | 0.04 | −0.18 | −0.37 | −0.01 | −0.31 |
| 5 | ACA | 0.18 | 0.50 | 0.76 | −0.09 | 0.21 | 0.59 | 0.18 | 0.10 | 0.24 | 0.10 | −0.11 | 0.20 |
| 6 | ACC | 1.00 | 0.77 | 1.00 | −0.25 | 1.00 | 0.24 | 0.14 | −0.06 | 0.39 | −0.31 | 0.03 | 0.22 |
| 7 | ACG | 0.29 | 0.67 | −0.21 | 1.00 | 1.00 | −0.14 | −0.21 | −0.42 | 0.00 | 0.61 | 0.15 | −0.06 |
| 8 | ACT | 1.00 | −0.22 | 0.50 | −0.70 | −0.79 | 0.37 | 0.64 | −0.24 | −0.38 | −0.21 | −0.50 | −0.55 |
| 9 | AGA | 0.03 | −0.16 | 0.42 | 0.14 | −0.58 | 0.85 | 0.56 | 0.71 | −0.20 | 0.02 | −0.22 | 0.18 |
| 10 | AGC | −0.31 | −0.36 | −0.34 | 0.19 | 1.00 | 0.62 | −0.07 | −0.15 | 0.61 | 0.26 | 0.47 | 0.57 |
| 11 | AGG | 1.00 | −0.01 | −0.75 | 1.00 | 1.00 | −0.36 | −0.82 | −0.56 | −0.43 | 0.63 | −0.54 | 0.38 |
| 12 | AGT | 1.00 | 0.68 | 1.00 | 1.00 | 1.00 | −0.45 | −0.20 | 0.09 | −0.44 | −0.53 | −0.65 | −0.60 |
| 13 | ATA | −0.49 | 0.40 | −0.43 | 0.56 | 1.00 | 0.63 | −0.21 | 1.00 | −0.29 | 0.57 | 0.42 | −0.08 |
| 14 | ATC | −0.32 | −0.59 | 0.67 | −0.12 | −0.37 | 0.17 | 0.57 | 0.22 | 0.23 | 0.16 | 0.31 | 0.37 |
| 15 | ATG | 0.16 | 0.36 | 0.13 | 0.16 | 0.46 | −0.04 | −0.37 | −0.23 | 0.00 | 0.05 | −0.01 | −0.04 |
| 16 | ATT | −0.16 | 0.58 | 0.41 | 0.39 | 0.43 | −0.21 | −0.06 | 0.17 | −0.28 | −0.02 | 0.15 | −0.38 |
| 17 | CAA | 0.37 | 0.61 | 0.43 | 0.15 | 0.13 | 1.00 | 0.87 | 0.86 | 0.21 | −0.19 | −0.05 | 0.18 |
| 18 | CAC | −0.72 | −0.27 | 0.47 | −0.50 | −0.40 | 0.78 | 0.01 | 0.46 | 0.11 | 0.45 | 0.19 | 0.38 |
| 19 | CAG | −0.46 | −0.45 | −0.39 | −0.25 | 0.37 | −0.36 | −0.54 | −0.47 | −0.10 | 0.04 | −0.06 | −0.02 |
| 20 | CAT | −0.29 | −0.23 | 0.58 | 0.69 | −0.24 | 0.14 | 0.31 | 0.25 | −0.13 | −0.37 | −0.01 | −0.09 |
| 21 | CCA | 1.00 | −0.29 | −0.27 | 1.00 | 1.00 | 1.00 | 0.24 | 0.26 | 0.21 | −0.46 | 1.00 |
| 22 | CCC | 1.00 | −0.65 | −0.70 | 1.00 | 1.00 | 0.00 | 0.43 | 0.37 | 0.39 | −0.42 | −0.34 | 0.10 |
| 23 | CCG | −0.64 | −0.22 | −0.04 | 0.38 | 0.28 | −0.46 | 0.10 | 0.19 | 0.13 | 0.36 | 0.36 | 0.19 |
| 24 | CCT | 1.00 | −0.07 | 0.48 | −0.15 | 1.00 | 0.53 | 0.47 | −0.32 | −0.33 | −0.24 | −0.38 | −0.54 |
| 25 | CGA | 1.00 | 0.32 | −0.25 | 1.00 | 1.00 | 0.29 | 0.19 | 0.56 | 0.80 | −0.34 | 1.00 | 0.16 |
| 26 | CGC | 0.32 | −0.44 | −0.18 | −0.53 | 0.17 | 0.24 | 0.14 | 0.26 | 0.48 | 0.23 | 0.25 | 0.35 |
| 27 | CGG | 1.00 | 0.59 | −0.37 | 1.00 | 1.00 | −0.66 | −0.31 | −0.16 | 0.17 | 0.40 | −0.15 | 0.25 |
| 28 | CGT | 1.00 | 0.70 | 0.70 | −0.35 | 1.00 | 0.84 | 0.01 | −0.49 | −0.13 | −0.63 | −0.43 | −0.18 |
| 29 | CTA | 1.00 | 1.00 | 1.00 | 1.00 | 1.00 | 1.00 | 1.00 | 0.35 | 1.00 | 1.00 | −0.21 | −0.20 |
| 30 | CTC | −0.44 | 0.05 | 0.73 | −0.28 | 1.00 | 0.32 | 0.69 | 0.41 | 0.41 | −0.19 | 0.27 | −0.08 |
| 31 | CTG | −0.01 | −0.41 | −0.27 | 0.10 | 0.40 | −0.52 | −0.46 | −0.29 | 0.27 | 0.41 | 0.11 | 0.44 |
| 32 | CTT | 1.00 | 0.15 | 0.67 | −0.42 | 0.35 | 0.49 | 0.23 | −0.10 | −0.39 | −0.31 | −0.46 | −0.46 |
| 33 | GAA | 0.29 | 0.45 | −0.22 | 0.41 | 0.57 | 0.50 | 0.38 | 0.56 | −0.06 | 0.02 | −0.16 | 0.08 |
| 34 | GAC | −0.63 | −0.34 | −0.59 | −0.47 | −0.02 | 0.14 | 0.36 | 0.01 | 0.25 | 0.14 | 0.03 | 0.21 |
| 35 | GAG | −0.25 | −0.59 | −0.46 | −0.40 | −0.38 | −0.42 | −0.55 | −0.64 | 0.25 | 0.13 | 0.24 | −0.26 |
| 36 | GAT | 0.25 | 0.88 | 0.78 | 0.58 | 0.15 | −0.14 | −0.10 | 0.38 | −0.24 | 0.09 | 0.26 | −0.26 |
| 37 | GCA | 1.00 | 0.47 | 0.79 | −0.07 | 0.24 | 0.12 | 0.61 | 0.57 | 0.28 | 0.01 | 0.06 | −0.04 |
| 38 | GCC | 0.42 | −0.20 | −0.28 | −0.30 | 1.00 | 0.50 | 0.48 | 0.53 | 0.34 | 0.05 | 0.01 | 0.06 |
| 39 | GCG | 0.19 | −0.23 | −0.36 | 0.46 | 0.56 | −0.58 | −0.29 | −0.40 | −0.07 | 0.42 | 0.12 | 0.28 |
| 40 | GCT | 1.00 | 1.00 | 1.00 | −0.53 | −0.66 | 0.71 | 0.50 | −0.17 | −0.40 | −0.28 | 0.01 | −0.45 |
| 41 | GGA | 0.49 | 0.22 | 0.24 | −0.20 | 1.00 | 0.42 | 0.20 | 0.28 | −0.25 | −0.04 | −0.19 | 0.25 |
| 42 | GGC | 1.00 | −0.33 | −0.16 | −0.23 | −0.44 | 0.01 | 0.30 | 0.34 | 0.27 | −0.17 | 0.16 | 0.26 |
| 43 | GGG | −0.01 | 0.22 | −0.63 | 0.32 | 1.00 | −0.49 | −0.49 | −0.65 | 0.39 | 0.60 | 0.30 | 0.01 |
| 44 | GGT | 0.16 | 0.49 | 0.50 | 0.07 | −0.52 | 0.19 | 0.30 | −0.41 | −0.22 | −0.51 | −0.36 | −0.09 |
| 45 | GTA | 1.00 | 0.54 | 0.55 | 0.33 | −0.67 | 0.61 | 0.33 | 0.35 | 0.03 | 0.14 | −0.10 | 0.28 |
| 46 | GTC | 0.54 | −0.04 | 0.18 | −0.24 | −0.17 | 0.76 | 0.51 | 0.71 | 0.48 | 0.05 | −0.19 | −0.14 |
| 47 | GTG | 0.47 | −0.46 | −0.37 | 0.53 | −0.29 | −0.56 | −0.55 | −0.47 | 0.16 | 0.40 | 0.54 | 0.41 |
| 48 | GTT | −0.38 | 0.50 | 0.52 | 0.28 | −0.30 | −0.40 | 0.31 | −0.09 | −0.39 | −0.33 | −0.34 | −0.33 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | −0.38 | 0.01 | −0.41 | −0.72 | 1.00 | 0.28 | 0.10 | 0.46 | 0.27 | 0.36 | 0.31 | 0.02 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | −0.54 | 0.56 | 0.79 | 0.84 | −0.49 | 0.11 | −0.08 | 0.45 | −0.26 | −0.26 | 0.01 | 0.00 |
| 53 | TCA | 1.00 | −0.31 | 1.00 | 0.51 | 0.02 | 0.49 | 0.42 | 0.37 | 0.06 | −0.04 | −0.26 | −0.06 |
| 54 | TCC | 1.00 | −0.12 | 0.26 | −0.09 | −0.39 | −0.07 | 0.51 | 0.20 | 0.14 | 0.37 | 0.09 | −0.14 |
| 55 | TCG | 1.00 | −0.06 | −0.60 | −0.19 | −0.73 | −0.58 | −0.27 | −0.17 | 0.38 | 0.57 | −0.16 | 0.17 |
| 56 | TCT | 1.00 | 0.17 | 1.00 | 0.00 | −0.58 | −0.09 | 0.64 | −0.32 | −0.25 | −0.16 | −0.36 | −0.14 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | −0.45 | −0.60 | −0.07 | −0.38 | 1.00 | −0.13 | −0.08 | 0.28 | 0.65 | 0.35 | 0.35 | 0.59 |
| 59 | TGG | 1.00 | 0.56 | −0.21 | −0.21 | −0.49 | 0.24 | −0.51 | 0.05 | −0.01 | 0.10 | 0.03 | −0.08 |

TABLE C.8-continued

CPW matrix Bacillus amyloliqueaciens K12 highly expressed sequences (left codon indicated in column 2, right codon indicated in row 2). Host cell: B. amyloliqueaciens; Sequence data: full B. amyloliqueaciens genome; Highly expressed group: 236 seqs.

| | | | | | | | | | | | | |
|---|---|---|---|---|---|---|---|---|---|---|---|---|
| 60 | TGT | 1.00 | 1.00 | 1.00 | 1.00 | 1.00 | 0.45 | 0.05 | −0.52 | −0.39 | −0.46 | −0.55 | −0.36 |
| 61 | TTA | 0.15 | 0.48 | 0.24 | 0.81 | 1.00 | 0.61 | 0.71 | 0.76 | 0.03 | 0.38 | 0.30 | 0.12 |
| 62 | TTC | −0.70 | −0.26 | 0.34 | −0.59 | 1.00 | 0.32 | 0.54 | 0.43 | 0.48 | 0.22 | 0.04 | 0.55 |
| 63 | TTG | 1.00 | −0.27 | −0.62 | −0.19 | −0.24 | −0.16 | −0.43 | −0.28 | 0.34 | 0.59 | −0.11 | −0.02 |
| 64 | TTT | 1.00 | 0.75 | 0.50 | 0.45 | −0.50 | −0.39 | −0.07 | 0.57 | −0.30 | −0.35 | 0.15 | −0.09 |

| | | CGA 25 | CGC 26 | CGG 27 | CGT 28 | CTA 29 | CTC 30 | CTG 31 | CTT 32 | GAA 33 | GAC 34 | GAG 35 | GAT 36 |
|---|---|---|---|---|---|---|---|---|---|---|---|---|---|

| | | 37 GCA | 38 GCC | 39 GCG | 40 GCT | 41 GGA | 42 GGC | 43 GGG | 44 GGT | 45 GTA | 46 GTC | 47 GTG | 48 GTT |
|---|---|---|---|---|---|---|---|---|---|---|---|---|---|
| 1 | AAA | −0.13 | 0.01 | −0.16 | 0.14 | −0.21 | −0.21 | −0.13 | 0.28 | −0.22 | 0.40 | −0.34 | 0.39 |
| 2 | AAC | 0.30 | 0.41 | −0.38 | −0.15 | −0.35 | −0.39 | −0.26 | −0.36 | 0.14 | −0.22 | 0.34 | 0.21 |
| 3 | AAG | 0.30 | 0.52 | −0.14 | 0.24 | 0.42 | 0.40 | 0.10 | 0.79 | −0.28 | 0.03 | −0.35 | 0.43 |
| 4 | AAT | −0.14 | −0.26 | 0.21 | 0.74 | 0.83 | 0.79 | 0.65 | 0.43 | −0.17 | −0.28 | 0.01 | 0.21 |
| 5 | ACA | 0.17 | −0.23 | 0.35 | −0.09 | 0.62 | −0.14 | 0.13 | 0.28 | 0.31 | 0.48 | 0.57 | 0.50 |
| 6 | ACC | −0.13 | 0.03 | −0.11 | −0.39 | −0.28 | −0.28 | 0.08 | −0.52 | −0.61 | −0.60 | −0.11 | −0.37 |
| 7 | ACG | 0.04 | 0.49 | 0.05 | −0.30 | −0.12 | 0.04 | 0.03 | −0.14 | 0.03 | 0.41 | 0.00 | −0.07 |
| 8 | ACT | 0.01 | −0.07 | 0.17 | −0.28 | 0.11 | 0.73 | 0.49 | −0.47 | −0.56 | 0.04 | 0.13 | −0.12 |
| 9 | AGA | 0.33 | 0.15 | −0.27 | 0.84 | 0.22 | −0.16 | −0.22 | −0.22 | 0.20 | −0.17 | 0.16 | 0.71 |
| 10 | AGC | 0.35 | −0.16 | −0.18 | 0.14 | −0.51 | −0.21 | −0.30 | −0.49 | −0.38 | 0.51 | 0.19 | 0.34 |
| 11 | AGG | 0.43 | 0.52 | 1.00 | −0.40 | −0.24 | 1.00 | 1.00 | 1.00 | 1.00 | 0.18 | −0.65 | −0.59 |
| 12 | AGT | 0.37 | 0.20 | 0.26 | 0.38 | 0.81 | 1.00 | 0.24 | 1.00 | −0.50 | 0.19 | −0.39 | 0.04 |
| 13 | ATA | 1.00 | −0.28 | −0.08 | 0.39 | 0.62 | 0.33 | 0.63 | 0.07 | 1.00 | 0.46 | 0.79 | 0.79 |
| 14 | ATC | −0.16 | −0.25 | −0.09 | −0.22 | −0.32 | −0.54 | −0.50 | −0.40 | −0.30 | −0.29 | −0.11 | −0.13 |
| 15 | ATG | 0.23 | 0.09 | 0.01 | −0.26 | 0.20 | −0.09 | 0.15 | −0.19 | −0.12 | 0.19 | −0.24 | 0.19 |
| 16 | ATT | 0.26 | −0.15 | 0.30 | 0.39 | 0.85 | 0.95 | 0.63 | 0.75 | 0.23 | −0.07 | 0.21 | 0.28 |
| 17 | CAA | 0.18 | 0.23 | 0.46 | −0.14 | −0.24 | −0.33 | −0.05 | −0.43 | 0.08 | −0.17 | −0.38 | 0.45 |
| 18 | CAC | 0.02 | −0.10 | 0.33 | 0.20 | −0.23 | −0.53 | −0.32 | −0.35 | −0.13 | 0.03 | −0.12 | −0.33 |
| 19 | CAG | 0.14 | 0.11 | −0.22 | −0.36 | 0.17 | 0.27 | 0.37 | 0.58 | 0.22 | 0.26 | −0.36 | 0.36 |
| 20 | CAT | −0.22 | −0.46 | 0.17 | 0.49 | 0.34 | 0.74 | 0.42 | 0.52 | 0.28 | 0.34 | −0.13 | 0.09 |
| 21 | CCA | −0.01 | 0.14 | 0.70 | −0.33 | 0.05 | 0.32 | 1.00 | −0.68 | 0.53 | 0.71 | 0.67 | −0.02 |
| 22 | CCC | −0.70 | 0.30 | −0.42 | −0.19 | −0.23 | −0.73 | −0.68 | 0.14 | −0.35 | −0.57 | 0.18 | −0.78 |
| 23 | CCG | 0.38 | −0.27 | 0.59 | −0.12 | −0.14 | 0.21 | 0.13 | −0.22 | 0.43 | 0.43 | 0.29 | −0.03 |
| 24 | CCT | −0.36 | −0.24 | 0.43 | −0.35 | 0.51 | 0.83 | 1.00 | 0.40 | −0.38 | −0.30 | 0.49 | −0.36 |
| 25 | CGA | 1.00 | 1.00 | 1.00 | 0.24 | −0.16 | −0.21 | 1.00 | 0.02 | −0.46 | 0.44 | 0.35 | −0.49 |
| 26 | CGC | −0.06 | −0.33 | −0.28 | 0.19 | −0.27 | −0.36 | −0.31 | −0.26 | 0.30 | −0.10 | −0.22 | −0.24 |
| 27 | CGG | 0.54 | 0.61 | −0.47 | −0.26 | −0.20 | 0.24 | −0.53 | 0.12 | 0.73 | 0.00 | 0.42 | 0.02 |
| 28 | CGT | −0.27 | 0.13 | −0.09 | 0.16 | 0.47 | 0.91 | 0.16 | 0.13 | −0.46 | 0.14 | 0.42 | 0.12 |
| 29 | CTA | 0.24 | −0.48 | 0.11 | 0.26 | 0.38 | −0.43 | 1.00 | −0.51 | −0.56 | 0.30 | 0.19 | 0.18 |
| 30 | CTC | 0.12 | −0.57 | −0.31 | 0.32 | −0.41 | −0.74 | −0.63 | −0.67 | −0.33 | −0.60 | −0.21 | −0.28 |
| 31 | CTG | 0.38 | 0.15 | 0.24 | 0.28 | 0.72 | 0.48 | 0.36 | 0.77 | 0.91 | 0.23 | 0.58 | 0.76 |
| 32 | CTT | −0.35 | −0.26 | −0.21 | −0.08 | 0.45 | 0.25 | 0.90 | −0.14 | 0.07 | −0.34 | −0.10 | −0.40 |
| 33 | GAA | −0.12 | −0.09 | −0.22 | 0.07 | −0.04 | −0.16 | −0.18 | 0.06 | −0.08 | −0.08 | −0.38 | 0.22 |
| 34 | GAC | −0.14 | 0.19 | −0.03 | 0.06 | −0.53 | −0.49 | −0.20 | −0.45 | 0.12 | 0.29 | 0.12 | 0.31 |
| 35 | GAG | 0.16 | 0.39 | 0.19 | 0.71 | 0.55 | 0.16 | −0.01 | 0.35 | 0.60 | 0.52 | 0.16 | 0.20 |
| 36 | GAT | 0.02 | 0.25 | −0.20 | 0.04 | 0.67 | 0.88 | 0.61 | 0.62 | −0.35 | −0.08 | −0.28 | 0.16 |
| 37 | GCA | −0.05 | 0.01 | 0.35 | −0.22 | 0.10 | 0.28 | 0.17 | 0.01 | 0.59 | 0.50 | 0.37 | 0.47 |
| 38 | GCC | −0.32 | −0.10 | 0.08 | −0.41 | −0.54 | −0.37 | −0.29 | −0.43 | 0.17 | −0.39 | 0.02 | −0.53 |
| 39 | GCG | 0.13 | 0.32 | 0.10 | −0.04 | −0.16 | 0.20 | 0.02 | 0.07 | −0.01 | 0.07 | −0.05 | −0.07 |
| 40 | GCT | 0.09 | 0.07 | 0.21 | −0.33 | 0.82 | 0.62 | 0.88 | 0.22 | 0.36 | 0.07 | 0.38 | −0.31 |
| 41 | GGA | 0.07 | 0.01 | −0.17 | 0.39 | 0.47 | 0.48 | 0.28 | 0.35 | 0.18 | 0.51 | 0.42 | 0.31 |
| 42 | GGC | 0.21 | −0.13 | 0.05 | −0.23 | −0.46 | −0.25 | 0.02 | −0.24 | 0.05 | −0.25 | −0.16 | −0.15 |
| 43 | GGG | −0.26 | 0.79 | −0.01 | 0.03 | 0.15 | 0.35 | −0.88 | 0.68 | 0.56 | 0.29 | 0.17 | 0.37 |
| 44 | GGT | −0.11 | 0.31 | −0.27 | 0.10 | 0.84 | 0.92 | 1.00 | 0.91 | −0.42 | −0.32 | −0.11 | −0.37 |
| 45 | GTA | 0.42 | 0.12 | 0.32 | 0.54 | −0.12 | −0.10 | 0.59 | −0.35 | 0.50 | 0.54 | 0.47 | 0.64 |
| 46 | GTC | 0.09 | −0.27 | −0.22 | −0.34 | −0.50 | −0.59 | −0.11 | −0.49 | −0.27 | −0.20 | −0.44 | −0.55 |
| 47 | GTG | −0.36 | 0.52 | 0.38 | 0.28 | 0.71 | 0.64 | 0.27 | 1.00 | 0.82 | 0.78 | 0.37 | 0.49 |
| 48 | GTT | −0.20 | 0.08 | −0.24 | 0.10 | 0.55 | 0.73 | 0.70 | 0.51 | 0.37 | −0.21 | −0.17 | −0.38 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.17 | 0.03 | −0.22 | 0.07 | −0.49 | −0.42 | −0.42 | −0.57 | 0.84 | 0.21 | 0.54 | 0.18 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.26 | −0.15 | −0.08 | 0.27 | 0.79 | 0.85 | 0.86 | 0.66 | −0.31 | −0.37 | −0.39 | 0.27 |
| 53 | TCA | 0.23 | −0.37 | 0.22 | 0.35 | −0.16 | −0.24 | 0.34 | 0.45 | −0.04 | 0.30 | 0.51 | −0.14 |
| 54 | TCC | −0.23 | 0.06 | 0.24 | −0.50 | −0.51 | −0.10 | −0.10 | −0.40 | −0.27 | −0.44 | 0.31 | −0.49 |
| 55 | TCG | −0.40 | −0.43 | −0.09 | −0.03 | 0.37 | −0.07 | 1.00 | 0.58 | 0.78 | −0.25 | 0.69 | −0.30 |
| 56 | TCT | −0.26 | 0.31 | 0.52 | 0.07 | 0.67 | 0.65 | 0.84 | 0.33 | −0.22 | 0.22 | 0.50 | −0.43 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | −0.50 | 0.16 | 0.03 | 0.02 | −0.46 | −0.54 | 0.47 | −0.08 | 0.20 | 0.27 | 0.72 | 1.00 |
| 59 | TGG | −0.48 | 0.10 | 0.25 | 0.37 | −0.19 | 0.26 | −0.51 | 0.66 | −0.19 | 0.25 | −0.18 | 0.11 |
| 60 | TGT | 1.00 | 0.59 | −0.41 | 0.53 | 0.81 | 1.00 | 1.00 | 1.00 | −0.66 | −0.43 | −0.51 | 0.17 |

TABLE C.8-continued

CPW matrix *Bacillus amyloliqueaciens* K12 highly expressed sequences (left codon indicated in column 2, right codon indicated in row 2). Host cell: *B. amyloliqueaciens*; Sequence data: full *B. amyloliqueaciens* genome; Highly expressed group: 236 seqs.

|    |     |       |       |       |       |       |       |       |       |       |       |       |
|----|-----|-------|-------|-------|-------|-------|-------|-------|-------|-------|-------|-------|
| 61 | TTA | 0.16  | 0.60  | 0.56  | 0.36  | −0.07 | 0.02  | −0.06 | −0.21 | −0.36 | 0.31  | 0.50  | −0.11 |
| 62 | TTC | 0.58  | −0.06 | 0.39  | −0.03 | −0.59 | −0.53 | 0.06  | −0.50 | −0.18 | 0.20  | 0.22  | 0.37  |
| 63 | TTG | −0.19 | 0.17  | 0.06  | −0.25 | 0.80  | 0.71  | 0.00  | 0.50  | 0.81  | 0.21  | 0.21  | −0.17 |
| 64 | TTT | 0.21  | −0.32 | −0.20 | −0.08 | 0.85  | 0.71  | 1.00  | 0.58  | 0.00  | −0.45 | 0.18  | 0.28  |

|     | GCA | GCC | GCG | GCT | GGA | GGC | GGG | GGT | GTA | GTC | GTG | GTT |
|-----|-----|-----|-----|-----|-----|-----|-----|-----|-----|-----|-----|-----|
|     | 37  | 38  | 39  | 40  | 41  | 42  | 43  | 44  | 45  | 46  | 47  | 48  |

|    |     | 49    | 50    | 51    | 52    | 53    | 54    | 55    | 56    | 57    | 58    | 59    | 60    |
|----|-----|-------|-------|-------|-------|-------|-------|-------|-------|-------|-------|-------|-------|
|    |     | TAA   | TAC   | TAG   | TAT   | TCA   | TCC   | TCG   | TCT   | TGA   | TGC   | TGG   | TGT   |
| 1  | AAA | 0.00  | −0.26 | 0.00  | 0.06  | −0.31 | −0.02 | 0.08  | 0.35  | 0.00  | 0.02  | 0.17  | 0.05  |
| 2  | AAC | 0.00  | −0.14 | 0.00  | 0.18  | 0.72  | 0.76  | −0.26 | 0.30  | 0.00  | 0.07  | −0.13 | −0.40 |
| 3  | AAG | 0.00  | 0.40  | 0.00  | 0.36  | 0.09  | 0.62  | −0.34 | 0.16  | 0.00  | 0.08  | −0.32 | −0.25 |
| 4  | AAT | 0.00  | −0.08 | 0.00  | 0.04  | 0.10  | −0.59 | 0.31  | 0.78  | 0.00  | 0.41  | 0.20  | 0.14  |
| 5  | ACA | 0.00  | −0.16 | 0.00  | −0.05 | 0.02  | −0.10 | −0.31 | 0.06  | 0.00  | −0.26 | 0.15  | 0.03  |
| 6  | ACC | 0.00  | −0.09 | 0.00  | 0.17  | 0.60  | 1.00  | 0.24  | 0.26  | 0.00  | −0.19 | 0.61  | 1.00  |
| 7  | ACG | 0.00  | 0.26  | 0.00  | 0.41  | 0.34  | 0.36  | 0.28  | −0.14 | 0.00  | −0.14 | −0.22 | 0.16  |
| 8  | ACT | 0.00  | −0.42 | 0.00  | −0.35 | −0.10 | 0.25  | −0.21 | −0.67 | 0.00  | −0.27 | −0.23 | 1.00  |
| 9  | AGA | 0.00  | 1.00  | 0.00  | 0.22  | −0.19 | −0.23 | −0.15 | −0.12 | 0.00  | 0.22  | 0.01  | −0.41 |
| 10 | AGC | 0.00  | −0.15 | 0.00  | 0.07  | 0.35  | 0.78  | −0.19 | 0.20  | 0.00  | 0.43  | 0.02  | 0.59  |
| 11 | AGG | 0.00  | 1.00  | 0.00  | 0.34  | 0.48  | 1.00  | 0.00  | 0.35  | 0.00  | 1.00  | −0.56 | 1.00  |
| 12 | AGT | 0.00  | 0.32  | 0.00  | 0.09  | −0.34 | −0.22 | −0.65 | −0.28 | 0.00  | 1.00  | 0.05  | 1.00  |
| 13 | ATA | 0.00  | −0.60 | 0.00  | −0.37 | −0.11 | −0.30 | 1.00  | −0.04 | 0.00  | −0.38 | −0.52 | 1.00  |
| 14 | ATC | 0.00  | 0.46  | 0.00  | 0.40  | 0.37  | 0.11  | 0.50  | 0.55  | 0.00  | −0.04 | −0.13 | 0.35  |
| 15 | ATG | 0.00  | 0.18  | 0.00  | −0.14 | −0.43 | 0.72  | 0.52  | −0.04 | 0.00  | 0.58  | 0.00  | −0.45 |
| 16 | ATT | 0.00  | −0.19 | 0.00  | −0.22 | −0.23 | −0.54 | 0.04  | −0.42 | 0.00  | 0.20  | 0.38  | −0.38 |
| 17 | CAA | 0.00  | −0.32 | 0.00  | −0.47 | −0.21 | −0.47 | −0.58 | 0.14  | 0.00  | −0.17 | −0.42 | −0.43 |
| 18 | CAC | 0.00  | 0.46  | 0.00  | −0.30 | 0.46  | 0.70  | −0.02 | 0.11  | 0.00  | −0.11 | 0.18  | −0.23 |
| 19 | CAG | 0.00  | 0.59  | 0.00  | 0.42  | −0.18 | 0.32  | 0.42  | 0.00  | 0.00  | −0.14 | 0.53  | 1.00  |
| 20 | CAT | 0.00  | 0.47  | 0.00  | −0.29 | −0.50 | −0.31 | 0.46  | 0.47  | 0.00  | 0.11  | −0.12 | 0.23  |
| 21 | CCA | 0.00  | −0.33 | 0.00  | −0.43 | 0.03  | 1.00  | −0.46 | −0.58 | 0.00  | −0.17 | 0.05  | −0.43 |
| 22 | CCC | 0.00  | 0.19  | 0.00  | 0.64  | 0.21  | 0.33  | 1.00  | 0.51  | 0.00  | 0.01  | 1.00  | 1.00  |
| 23 | CCG | 0.00  | 0.09  | 0.00  | 0.07  | −0.03 | 0.50  | 0.44  | 0.36  | 0.00  | 0.45  | −0.31 | −0.25 |
| 24 | CCT | 0.00  | −0.25 | 0.00  | −0.01 | −0.46 | −0.36 | −0.05 | −0.37 | 0.00  | 1.00  | 0.64  | −0.70 |
| 25 | CGA | 0.00  | −0.51 | 0.00  | −0.44 | 0.29  | −0.17 | 1.00  | 0.13  | 0.00  | −0.45 | 1.00  | 1.00  |
| 26 | CGC | 0.00  | −0.35 | 0.00  | 0.04  | 0.78  | 0.82  | 0.18  | −0.32 | 0.00  | −0.40 | −0.46 | −0.64 |
| 27 | CGG | 0.00  | 0.40  | 0.00  | 0.20  | 0.58  | 1.00  | 0.60  | 0.48  | 0.00  | 0.46  | 0.55  | 1.00  |
| 28 | CGT | 0.00  | −0.44 | 0.00  | −0.16 | −0.42 | 0.20  | −0.58 | −0.68 | 0.00  | 1.00  | 1.00  | 1.00  |
| 29 | CTA | 0.00  | 1.00  | 0.00  | −0.78 | −0.60 | −0.29 | −0.69 | −0.03 | 0.00  | 1.00  | −0.79 | −0.82 |
| 30 | CTC | 0.00  | 0.17  | 0.00  | 0.56  | 0.24  | 0.63  | −0.19 | 0.73  | 0.00  | 0.49  | 0.37  | −0.32 |
| 31 | CTG | 0.00  | −0.12 | 0.00  | −0.21 | −0.05 | 0.16  | −0.35 | 0.01  | 0.00  | 0.42  | −0.08 | 0.58  |
| 32 | CTT | 0.00  | −0.13 | 0.00  | 0.45  | −0.26 | 0.31  | −0.03 | −0.50 | 0.00  | 0.04  | 0.60  | −0.57 |
| 33 | GAA | 0.00  | −0.08 | 0.00  | −0.06 | −0.01 | −0.18 | 0.09  | 0.29  | 0.00  | −0.11 | 0.08  | 0.10  |
| 34 | GAC | 0.00  | 0.32  | 0.00  | 0.51  | 0.76  | 0.60  | 0.40  | 0.32  | 0.00  | −0.34 | −0.09 | −0.18 |
| 35 | GAG | 0.00  | 0.04  | 0.00  | 0.32  | 0.76  | −0.29 | −0.12 | 0.26  | 0.00  | −0.19 | −0.17 | 0.55  |
| 36 | GAT | 0.00  | −0.35 | 0.00  | −0.16 | −0.11 | −0.47 | 0.12  | 0.10  | 0.00  | 0.58  | 0.08  | −0.02 |
| 37 | GCA | 0.00  | −0.22 | 0.00  | −0.02 | −0.13 | −0.06 | −0.16 | −0.23 | 0.00  | 0.28  | −0.39 | 0.48  |
| 38 | GCC | 0.00  | 0.71  | 0.00  | 0.05  | 0.64  | 0.55  | 0.49  | 0.12  | 0.00  | −0.53 | −0.07 | −0.55 |
| 39 | GCG | 0.00  | 0.52  | 0.00  | 0.34  | 0.07  | 0.58  | 0.06  | 0.39  | 0.00  | 0.36  | 0.47  | 0.69  |
| 40 | GCT | 0.00  | −0.49 | 0.00  | −0.51 | −0.19 | −0.75 | −0.15 | −0.61 | 0.00  | 0.29  | −0.07 | −0.03 |
| 41 | GGA | 0.00  | −0.06 | 0.00  | −0.29 | 0.45  | 1.00  | 0.11  | 0.13  | 0.00  | 0.40  | 0.41  | 0.71  |
| 42 | GGC | 0.00  | −0.02 | 0.00  | 0.29  | 0.05  | −0.04 | −0.21 | 0.52  | 0.00  | −0.45 | −0.50 | −0.39 |
| 43 | GGG | 0.00  | 0.70  | 0.00  | −0.16 | 0.06  | 1.00  | 0.11  | 0.42  | 0.00  | −0.37 | 1.00  | 1.00  |
| 44 | GGT | 0.00  | −0.11 | 0.00  | −0.09 | −0.36 | 0.34  | −0.49 | −0.65 | 0.00  | 0.67  | 0.81  | 1.00  |
| 45 | GTA | 0.00  | −0.47 | 0.00  | −0.30 | −0.39 | −0.58 | −0.03 | −0.42 | 0.00  | −0.13 | −0.45 | −0.20 |
| 46 | GTC | 0.00  | 0.59  | 0.00  | 0.27  | 0.41  | 0.67  | 0.50  | 0.68  | 0.00  | −0.37 | 0.31  | 0.49  |
| 47 | GTG | 0.00  | −0.25 | 0.00  | 0.16  | 0.39  | −0.03 | −0.14 | 0.62  | 0.00  | 0.80  | 0.04  | 0.71  |
| 48 | GTT | 0.00  | 0.22  | 0.00  | −0.11 | −0.14 | −0.52 | −0.15 | −0.48 | 0.00  | 0.17  | 0.18  | −0.58 |
| 49 | TAA | 0.00  | 0.00  | 0.00  | 0.00  | 0.00  | 0.00  | 0.00  | 0.00  | 0.00  | 0.00  | 0.00  | 0.00  |
| 50 | TAC | 0.00  | 0.12  | 0.00  | 0.22  | 0.64  | 0.20  | 1.00  | 0.12  | 0.00  | 0.02  | 0.20  | −0.47 |
| 51 | TAG | 0.00  | 0.00  | 0.00  | 0.00  | 0.00  | 0.00  | 0.00  | 0.00  | 0.00  | 0.00  | 0.00  | 0.00  |
| 52 | TAT | 0.00  | −0.10 | 0.00  | −0.16 | −0.32 | −0.19 | −0.37 | −0.30 | 0.00  | 0.71  | −0.15 | −0.20 |
| 53 | TCA | 0.00  | 0.17  | 0.00  | 0.27  | 0.21  | 0.33  | −0.33 | 0.84  | 0.00  | 0.42  | −0.49 | 0.58  |
| 54 | TCC | 0.00  | 0.20  | 0.00  | −0.29 | 0.78  | −0.33 | 0.16  | 0.73  | 0.00  | −0.59 | 1.00  | −0.29 |
| 55 | TCG | 0.00  | 0.10  | 0.00  | 0.20  | 0.00  | 1.00  | −0.30 | −0.19 | 0.00  | −0.77 | −0.20 | 1.00  |
| 56 | TCT | 0.00  | 0.12  | 0.00  | −0.41 | −0.31 | −0.59 | 0.08  | −0.28 | 0.00  | −0.07 | 0.59  | 0.48  |
| 57 | TGA | 0.00  | 0.00  | 0.00  | 0.00  | 0.00  | 0.00  | 0.00  | 0.00  | 0.00  | 0.00  | 0.00  | 0.00  |
| 58 | TGC | 0.00  | −0.51 | 0.00  | 0.09  | 1.00  | −0.54 | −0.59 | 1.00  | 0.00  | −0.30 | 1.00  | −0.52 |
| 59 | TGG | 0.00  | 0.36  | 0.00  | −0.24 | 0.32  | 1.00  | −0.53 | 0.17  | 0.00  | −0.32 | 0.00  | 0.69  |

TABLE C.8-continued

CPW matrix *Bacillus amyloliqueaciens* K12 highly expressed sequences (left codon indicated in column 2, right codon indicated in row 2). Host cell: *B. amyloliqueaciens*; Sequence data: full *B. amyloliqueaciens* genome; Highly expressed group: 236 seqs.

| | | TAA 49 | TAC 50 | TAG 51 | TAT 52 | TCA 53 | TCC 54 | TCG 55 | TCT 56 | TGA 57 | TGC 58 | TGG 59 | TGT 60 |
|---|---|---|---|---|---|---|---|---|---|---|---|---|---|
| 60 | TGT | 0.00 | 0.26 | 0.00 | 1.00 | −0.46 | 1.00 | −0.57 | 0.24 | 0.00 | 1.00 | −0.59 | 1.00 |
| 61 | TTA | 0.00 | 0.37 | 0.00 | −0.29 | −0.46 | 0.48 | 0.02 | −0.02 | 0.00 | −0.49 | −0.29 | 0.30 |
| 62 | TTC | 0.00 | 0.10 | 0.00 | 0.20 | −0.17 | −0.16 | 0.24 | 0.01 | 0.00 | −0.30 | −0.39 | 0.48 |
| 63 | TTG | 0.00 | −0.20 | 0.00 | 0.08 | 0.18 | −0.38 | 0.74 | 0.16 | 0.00 | 1.00 | −0.24 | 0.08 |
| 64 | TTT | 0.00 | −0.22 | 0.00 | 0.02 | −0.27 | −0.29 | 0.42 | 0.25 | 0.00 | −0.07 | 0.47 | 0.22 |

| | | 61 TTA | 62 TTC | 63 TTG | 64 TTT |
|---|---|---|---|---|---|
| 1 | AAA | 0.29 | −0.39 | 0.07 | 0.62 |
| 2 | AAC | 0.24 | −0.36 | 0.75 | 0.37 |
| 3 | AAG | 0.68 | −0.10 | 0.72 | −0.24 |
| 4 | AAT | 0.39 | −0.29 | 0.52 | 0.38 |
| 5 | ACA | −0.15 | −0.31 | −0.52 | 0.20 |
| 6 | ACC | 0.82 | 0.47 | 0.52 | −0.38 |
| 7 | ACG | 0.41 | 0.17 | 0.89 | 0.06 |
| 8 | ACT | 0.00 | −0.15 | −0.62 | 0.26 |
| 9 | AGA | 0.27 | 0.69 | 0.61 | 0.65 |
| 10 | AGC | 0.28 | 0.25 | −0.09 | 0.03 |
| 11 | AGG | 1.00 | 0.48 | 1.00 | 0.21 |
| 12 | AGT | −0.28 | −0.20 | 0.08 | 0.53 |
| 13 | ATA | −0.72 | −0.46 | −0.69 | −0.29 |
| 14 | ATC | 0.47 | 0.36 | 0.48 | 0.48 |
| 15 | ATG | 0.80 | −0.14 | 0.83 | 0.12 |
| 16 | ATT | −0.60 | −0.27 | −0.33 | −0.24 |
| 17 | CAA | −0.16 | −0.33 | 0.29 | −0.23 |
| 18 | CAC | −0.20 | −0.10 | −0.39 | 0.27 |
| 19 | CAG | 0.77 | 0.33 | 0.38 | 0.24 |
| 20 | CAT | −0.49 | −0.09 | −0.42 | −0.07 |
| 21 | CCA | −0.43 | −0.32 | −0.35 | 0.17 |
| 22 | CCC | 1.00 | 0.40 | −0.21 | 0.09 |
| 23 | CCG | −0.25 | 0.16 | 0.77 | −0.21 |
| 24 | CCT | −0.63 | 0.72 | −0.43 | −0.22 |
| 25 | CGA | 0.33 | −0.65 | −0.72 | −0.07 |
| 26 | CGC | 0.28 | 0.13 | 0.05 | 0.35 |
| 27 | CGG | 1.00 | 0.37 | −0.06 | −0.48 |
| 28 | CGT | −0.26 | −0.42 | −0.37 | −0.40 |
| 29 | CTA | −0.50 | 1.00 | −0.24 | −0.75 |
| 30 | CTC | 0.48 | 0.73 | −0.02 | 0.59 |
| 31 | CTG | 0.78 | 0.07 | 0.32 | −0.29 |
| 32 | CTT | −0.27 | 0.06 | −0.48 | 0.68 |
| 33 | GAA | 0.18 | 0.01 | −0.32 | 0.03 |
| 34 | GAC | 0.43 | 0.33 | 0.17 | 0.37 |
| 35 | GAG | 0.41 | −0.26 | 0.74 | 0.17 |
| 36 | GAT | −0.35 | −0.41 | −0.52 | 0.01 |
| 37 | GCA | −0.46 | −0.33 | −0.10 | −0.26 |
| 38 | GCC | 0.21 | 0.66 | 0.17 | 0.24 |
| 39 | GCG | 0.29 | 0.30 | 0.78 | 0.17 |
| 40 | GCT | −0.32 | −0.32 | −0.59 | −0.32 |
| 41 | GGA | −0.09 | 0.30 | −0.39 | −0.18 |
| 42 | GGC | 0.44 | 0.39 | 0.49 | 0.31 |
| 43 | GGG | 0.53 | 0.68 | 0.18 | −0.05 |
| 44 | GGT | −0.14 | −0.46 | −0.51 | −0.53 |
| 45 | GTA | −0.10 | −0.23 | 0.03 | −0.40 |
| 46 | GTC | 0.48 | 0.69 | 0.80 | 0.53 |
| 47 | GTG | 0.04 | 0.36 | 0.43 | −0.24 |
| 48 | GTT | −0.29 | −0.37 | −0.22 | −0.11 |
| 49 | TAA | 0.00 | 0.00 | 0.00 | 0.00 |
| 50 | TAC | −0.39 | 0.31 | 0.28 | 0.27 |
| 51 | TAG | 0.00 | 0.00 | 0.00 | 0.00 |
| 52 | TAT | −0.36 | −0.09 | −0.48 | −0.27 |
| 53 | TCA | −0.17 | −0.08 | −0.30 | −0.28 |
| 54 | TCC | 0.39 | 0.82 | 0.19 | 0.45 |
| 55 | TCG | 0.54 | 0.59 | 1.00 | −0.36 |
| 56 | TCT | −0.66 | −0.42 | 0.02 | −0.01 |
| 57 | TGA | 0.00 | 0.00 | 0.00 | 0.00 |
| 58 | TGC | −0.31 | −0.05 | 1.00 | 0.80 |
| 59 | TGG | 0.76 | 0.37 | 1.00 | −0.22 |

TABLE C.8-continued

CPW matrix *Bacillus amyloliqueaciens* K12 highly expressed sequences (left codon indicated in column 2, right codon indicated in row 2). Host cell: *B. amyloliqueaciens*; Sequence data: full *B. amyloliqueaciens* genome; Highly expressed group: 236 seqs.

| | | | | | |
|---|---|---|---|---|---|
| 60 | TGT | −0.05 | −0.12 | 0.31 | −0.50 |
| 61 | TTA | −0.42 | −0.04 | −0.23 | −0.40 |
| 62 | TTC | −0.08 | −0.01 | 0.43 | −0.10 |
| 63 | TTG | 0.68 | −0.03 | −0.06 | −0.45 |
| 64 | TTT | −0.59 | −0.15 | −0.23 | 0.22 |
| | | TTA | TTC | TTG | TTT |
| | | 61 | 62 | 63 | 64 |

TABLE C.9

CPW matrix *Saccharomyces cerevisiae* full genome (left codon indicated in column 2, right codon indicated in row 2). Host cell: *S. cerevisiae*; Sequence data: full *S. cerevisiae* genome.

| | | 1<br>AAA | 2<br>AAC | 3<br>AAG | 4<br>AAT | 5<br>ACA | 6<br>ACC | 7<br>ACG | 8<br>ACT | 9<br>AGA | 10<br>AGC | 11<br>AGG | 12<br>AGT |
|---|---|---|---|---|---|---|---|---|---|---|---|---|---|
| 1 | AAA | 0.18 | 0.05 | 0.13 | −0.05 | −0.12 | 0.12 | 0.00 | 0.05 | −0.09 | −0.24 | −0.17 | −0.23 |
| 2 | AAC | −0.12 | −0.14 | −0.19 | −0.03 | −0.06 | −0.12 | 0.03 | −0.11 | −0.16 | −0.28 | −0.14 | −0.17 |
| 3 | AAG | −0.17 | −0.05 | −0.20 | 0.05 | −0.06 | 0.02 | −0.08 | 0.09 | −0.04 | −0.05 | −0.03 | 0.02 |
| 4 | AAT | 0.06 | 0.09 | 0.21 | 0.04 | 0.01 | 0.07 | 0.04 | 0.10 | 0.14 | −0.04 | 0.02 | −0.07 |
| 5 | ACA | 0.00 | −0.06 | −0.10 | −0.13 | −0.11 | 0.16 | 0.06 | 0.20 | −0.33 | −0.01 | −0.30 | −0.11 |
| 6 | ACC | −0.23 | −0.27 | −0.33 | −0.11 | −0.11 | −0.31 | −0.16 | −0.28 | −0.09 | −0.05 | 0.05 | 0.02 |
| 7 | ACG | −0.10 | 0.06 | 0.00 | 0.01 | 0.15 | 0.33 | 0.19 | 0.38 | −0.09 | 0.01 | −0.19 | 0.13 |
| 8 | ACT | 0.30 | 0.31 | 0.29 | 0.17 | 0.12 | −0.10 | 0.12 | −0.07 | 0.26 | 0.30 | 0.36 | 0.12 |
| 9 | AGA | 0.04 | −0.16 | −0.10 | −0.10 | −0.11 | 0.00 | 0.01 | −0.06 | −0.25 | −0.13 | −0.17 | −0.13 |
| 10 | AGC | −0.13 | −0.21 | 0.04 | −0.19 | −0.08 | −0.25 | −0.21 | −0.14 | 0.01 | −0.31 | −0.16 | −0.22 |
| 11 | AGG | −0.24 | 0.09 | −0.06 | 0.16 | −0.07 | 0.12 | −0.03 | 0.05 | 0.11 | 0.02 | 0.11 | 0.14 |
| 12 | AGT | −0.02 | 0.05 | 0.28 | −0.03 | 0.02 | −0.01 | 0.00 | 0.18 | 0.27 | 0.00 | 0.15 | 0.00 |
| 13 | ATA | −0.05 | −0.08 | 0.04 | −0.12 | −0.14 | 0.19 | −0.16 | 0.06 | −0.12 | −0.01 | −0.17 | 0.07 |
| 14 | ATC | −0.35 | −0.34 | −0.35 | −0.24 | −0.11 | −0.27 | −0.05 | −0.25 | −0.22 | −0.04 | −0.12 | −0.19 |
| 15 | ATG | −0.05 | 0.00 | 0.08 | 0.00 | −0.13 | −0.01 | −0.09 | 0.18 | −0.09 | −0.17 | −0.03 | −0.14 |
| 16 | ATT | 0.30 | 0.31 | 0.34 | 0.29 | 0.22 | 0.12 | 0.23 | 0.06 | 0.25 | 0.39 | 0.28 | 0.31 |
| 17 | CAA | 0.05 | 0.01 | −0.08 | −0.06 | −0.11 | 0.06 | −0.15 | −0.09 | −0.07 | −0.14 | −0.10 | −0.28 |
| 18 | CAC | −0.17 | −0.22 | −0.27 | −0.16 | −0.22 | −0.09 | −0.10 | −0.16 | −0.09 | −0.06 | 0.16 | 0.08 |
| 19 | CAG | −0.05 | 0.16 | 0.11 | 0.01 | −0.02 | 0.31 | 0.04 | 0.33 | 0.28 | −0.01 | 0.10 | 0.09 |
| 20 | CAT | 0.11 | 0.17 | 0.22 | 0.10 | 0.05 | 0.16 | 0.19 | 0.09 | 0.24 | 0.29 | 0.27 | 0.28 |
| 21 | CCA | 0.01 | −0.04 | −0.18 | −0.08 | −0.04 | 0.01 | 0.07 | −0.13 | −0.28 | 0.09 | −0.17 | 0.01 |
| 22 | CCC | −0.25 | −0.12 | −0.28 | −0.18 | −0.24 | −0.25 | −0.22 | −0.15 | 0.05 | −0.15 | 0.09 | −0.11 |
| 23 | CCG | 0.09 | 0.02 | 0.05 | 0.08 | 0.00 | 0.53 | 0.17 | 0.37 | 0.20 | 0.31 | 0.11 | 0.28 |
| 24 | CCT | 0.21 | 0.22 | 0.34 | 0.12 | 0.13 | −0.06 | 0.05 | 0.19 | 0.44 | 0.45 | 0.41 | 0.32 |
| 25 | CGA | 0.12 | −0.08 | 0.30 | −0.14 | 0.02 | −0.07 | −0.24 | 0.19 | 0.06 | −0.03 | −0.03 | −0.26 |
| 26 | CGC | 0.05 | 0.07 | 0.05 | 0.07 | −0.22 | −0.14 | −0.08 | 0.17 | 0.31 | −0.49 | 0.16 | −0.30 |
| 27 | CGG | −0.10 | 0.21 | 0.04 | −0.15 | −0.07 | 0.40 | 0.11 | 0.52 | 0.44 | 0.27 | −0.05 | −0.06 |
| 28 | CGT | 0.27 | 0.40 | 0.29 | 0.26 | 0.24 | −0.08 | 0.18 | 0.12 | 0.47 | 0.38 | 0.45 | 0.15 |
| 29 | CTA | 0.12 | 0.05 | 0.11 | −0.02 | −0.08 | 0.11 | 0.05 | 0.14 | −0.06 | −0.05 | −0.06 | −0.01 |
| 30 | CTC | −0.02 | −0.09 | −0.01 | −0.15 | −0.07 | −0.35 | −0.21 | −0.19 | 0.32 | −0.22 | 0.19 | −0.27 |
| 31 | CTG | −0.11 | −0.08 | 0.00 | −0.01 | 0.15 | 0.20 | −0.10 | 0.21 | 0.22 | 0.02 | 0.06 | 0.16 |
| 32 | CTT | 0.53 | 0.39 | 0.59 | 0.46 | 0.33 | 0.24 | 0.19 | 0.18 | 0.54 | 0.48 | 0.61 | 0.53 |
| 33 | GAA | 0.05 | 0.00 | −0.05 | −0.05 | −0.07 | 0.05 | −0.11 | −0.08 | −0.10 | −0.24 | −0.06 | −0.31 |
| 34 | GAC | −0.11 | −0.18 | −0.24 | −0.05 | −0.03 | −0.17 | 0.06 | −0.19 | −0.11 | −0.11 | −0.11 | −0.10 |
| 35 | GAG | −0.04 | 0.06 | 0.02 | 0.10 | 0.08 | 0.19 | 0.05 | 0.21 | 0.18 | −0.14 | 0.09 | −0.10 |
| 36 | GAT | 0.04 | 0.14 | 0.22 | 0.02 | 0.06 | 0.07 | 0.06 | 0.08 | 0.15 | 0.12 | 0.18 | 0.12 |
| 37 | GCA | 0.05 | −0.05 | 0.03 | −0.11 | 0.05 | 0.31 | 0.15 | 0.21 | −0.34 | −0.10 | −0.29 | −0.06 |
| 38 | GCC | −0.18 | −0.18 | −0.41 | −0.19 | −0.10 | −0.34 | −0.19 | −0.32 | 0.06 | −0.08 | −0.07 | −0.08 |
| 39 | GCG | 0.07 | 0.01 | −0.06 | 0.17 | 0.18 | 0.45 | 0.08 | 0.25 | 0.21 | 0.25 | 0.20 | 0.28 |
| 40 | GCT | 0.22 | 0.14 | 0.20 | 0.21 | 0.15 | −0.04 | 0.20 | −0.19 | 0.21 | 0.30 | 0.33 | 0.27 |
| 41 | GGA | −0.12 | −0.15 | −0.02 | −0.26 | −0.16 | 0.14 | −0.29 | 0.05 | −0.26 | −0.22 | −0.24 | −0.30 |
| 42 | GGC | 0.10 | 0.04 | 0.05 | −0.03 | 0.01 | 0.03 | 0.11 | −0.03 | 0.04 | −0.24 | −0.04 | −0.27 |
| 43 | GGG | −0.19 | 0.02 | −0.13 | 0.13 | −0.01 | 0.24 | −0.06 | 0.23 | 0.06 | −0.01 | 0.01 | 0.21 |
| 44 | GGT | 0.10 | 0.02 | 0.02 | 0.18 | 0.12 | −0.13 | 0.16 | −0.09 | 0.00 | 0.12 | 0.40 | 0.27 |
| 45 | GTA | −0.05 | −0.02 | 0.09 | −0.10 | −0.05 | 0.14 | −0.18 | 0.11 | −0.09 | −0.01 | −0.16 | 0.12 |
| 46 | GTC | −0.19 | −0.25 | −0.36 | −0.16 | −0.14 | −0.40 | 0.06 | −0.29 | −0.11 | −0.10 | −0.07 | −0.16 |
| 47 | GTG | −0.13 | −0.07 | −0.13 | 0.07 | 0.02 | 0.07 | 0.03 | 0.21 | −0.01 | 0.01 | −0.02 | 0.14 |
| 48 | GTT | 0.26 | 0.16 | 0.29 | 0.17 | 0.27 | 0.01 | 0.29 | −0.04 | 0.26 | 0.26 | 0.40 | 0.28 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | −0.13 | −0.18 | −0.23 | −0.10 | −0.14 | −0.04 | −0.09 | −0.10 | −0.02 | 0.11 | −0.15 | 0.04 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.12 | 0.15 | 0.22 | 0.10 | 0.06 | 0.13 | −0.14 | 0.17 | 0.21 | 0.30 | 0.07 | 0.26 |
| 53 | TCA | 0.03 | 0.04 | 0.07 | −0.05 | 0.16 | 0.30 | 0.06 | 0.12 | −0.27 | 0.03 | −0.27 | 0.10 |
| 54 | TCC | −0.28 | −0.17 | −0.31 | −0.13 | −0.16 | −0.22 | −0.12 | −0.34 | −0.05 | −0.14 | −0.02 | −0.14 |
| 55 | TCG | −0.15 | 0.03 | −0.14 | −0.04 | 0.12 | 0.33 | 0.02 | 0.30 | −0.15 | 0.07 | −0.21 | 0.21 |

TABLE C.9-continued

CPW matrix *Saccharomyces cerevisiae* full genome (left codon indicated in column 2, right codon indicated in row 2). Host cell: *S. cerevisiae*; Sequence data: full *S. cerevisiae* genome.

| | | | | | | | | | | | | |
|---|---|---|---|---|---|---|---|---|---|---|---|---|
| 56 | TCT | 0.21 | 0.28 | 0.27 | 0.19 | 0.05 | 0.03 | 0.11 | −0.07 | 0.35 | 0.33 | 0.24 | 0.30 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | −0.12 | −0.03 | −0.14 | −0.10 | −0.04 | −0.11 | 0.04 | −0.02 | 0.09 | −0.15 | −0.17 | 0.00 |
| 59 | TGG | −0.04 | 0.02 | 0.06 | −0.01 | −0.03 | −0.02 | −0.11 | 0.09 | −0.17 | 0.15 | −0.15 | 0.18 |
| 60 | TGT | 0.00 | 0.00 | 0.21 | 0.08 | 0.13 | −0.06 | −0.05 | 0.02 | 0.30 | 0.27 | 0.16 | 0.36 |
| 61 | TTA | 0.14 | 0.05 | 0.06 | 0.10 | −0.12 | −0.07 | −0.10 | −0.06 | −0.08 | −0.03 | −0.09 | −0.07 |
| 62 | TTC | −0.35 | −0.32 | −0.34 | −0.28 | 0.03 | −0.28 | −0.07 | −0.19 | −0.18 | −0.17 | −0.17 | −0.16 |
| 63 | TTG | −0.28 | −0.25 | −0.29 | −0.15 | 0.07 | −0.18 | −0.06 | −0.05 | −0.13 | −0.10 | −0.09 | −0.07 |
| 64 | TTT | 0.30 | 0.28 | 0.44 | 0.29 | 0.26 | −0.06 | 0.07 | 0.11 | 0.14 | 0.13 | 0.15 | 0.18 |

| | | AAA 1 | AAC 2 | AAG 3 | AAT 4 | ACA 5 | ACC 6 | ACG 7 | ACT 8 | AGA 9 | AGC 10 | AGG 11 | AGT 12 |
|---|---|---|---|---|---|---|---|---|---|---|---|---|---|

| | | 13 ATA | 14 ATC | 15 ATG | 16 ATT | 17 CAA | 18 CAC | 19 CAG | 20 CAT | 21 CCA | 22 CCC | 23 CCG | 24 CCT |
|---|---|---|---|---|---|---|---|---|---|---|---|---|---|
| 1 | AAA | −0.16 | 0.00 | −0.10 | −0.06 | 0.10 | 0.18 | 0.05 | 0.13 | 0.00 | 0.10 | −0.08 | −0.01 |
| 2 | AAC | 0.06 | −0.05 | 0.00 | 0.01 | −0.15 | −0.07 | −0.12 | −0.07 | 0.01 | 0.06 | 0.18 | −0.02 |
| 3 | AAG | 0.11 | 0.10 | 0.15 | 0.13 | −0.12 | −0.21 | −0.10 | −0.15 | −0.07 | 0.03 | 0.11 | 0.04 |
| 4 | AAT | 0.05 | 0.01 | 0.00 | −0.05 | 0.06 | 0.11 | 0.23 | 0.01 | 0.03 | 0.15 | −0.15 | −0.10 |
| 5 | ACA | −0.10 | 0.27 | −0.13 | 0.07 | 0.09 | −0.02 | −0.05 | −0.13 | −0.05 | 0.04 | 0.04 | −0.17 |
| 6 | ACC | −0.19 | −0.33 | −0.15 | −0.24 | 0.04 | 0.07 | 0.20 | 0.21 | 0.14 | 0.21 | 0.35 | 0.36 |
| 7 | ACG | −0.16 | 0.25 | −0.05 | 0.30 | −0.12 | −0.19 | −0.26 | −0.23 | 0.02 | −0.28 | −0.35 | −0.24 |
| 8 | ACT | 0.13 | 0.04 | 0.26 | 0.09 | −0.07 | 0.13 | 0.11 | 0.09 | −0.11 | 0.13 | 0.05 | 0.09 |
| 9 | AGA | −0.14 | 0.03 | −0.06 | −0.01 | 0.10 | 0.05 | 0.10 | 0.12 | 0.04 | 0.23 | 0.08 | 0.04 |
| 10 | AGC | −0.21 | −0.02 | 0.09 | −0.02 | 0.10 | 0.05 | 0.21 | 0.04 | 0.36 | 0.14 | 0.39 | 0.23 |
| 11 | AGG | −0.21 | 0.27 | 0.10 | 0.14 | −0.09 | 0.14 | −0.18 | −0.02 | −0.18 | −0.29 | −0.32 | −0.19 |
| 12 | AGT | −0.15 | 0.14 | 0.24 | 0.04 | 0.25 | 0.21 | 0.47 | 0.18 | 0.42 | 0.28 | 0.33 | 0.30 |
| 13 | ATA | −0.19 | 0.17 | −0.08 | 0.18 | 0.20 | −0.08 | 0.06 | 0.09 | 0.05 | −0.03 | −0.39 | 0.09 |
| 14 | ATC | −0.06 | −0.30 | −0.22 | −0.14 | 0.07 | 0.18 | 0.02 | 0.04 | 0.10 | 0.24 | 0.29 | 0.30 |
| 15 | ATG | 0.01 | 0.08 | 0.00 | −0.05 | −0.07 | 0.07 | 0.16 | −0.04 | 0.07 | −0.21 | 0.07 | 0.02 |
| 16 | ATT | 0.18 | 0.01 | 0.21 | 0.06 | −0.14 | −0.08 | −0.04 | −0.06 | −0.07 | 0.01 | −0.19 | −0.10 |
| 17 | CAA | −0.13 | 0.04 | −0.09 | −0.01 | 0.19 | 0.16 | −0.06 | 0.08 | 0.00 | 0.31 | −0.21 | −0.01 |
| 18 | CAC | 0.03 | −0.05 | −0.07 | −0.06 | −0.07 | −0.09 | −0.09 | 0.10 | 0.05 | 0.19 | 0.23 | 0.33 |
| 19 | CAG | −0.05 | 0.10 | 0.22 | 0.16 | −0.05 | −0.15 | −0.40 | −0.22 | 0.06 | −0.03 | −0.27 | 0.01 |
| 20 | CAT | 0.08 | −0.09 | 0.04 | 0.04 | 0.02 | −0.01 | 0.11 | −0.02 | −0.04 | 0.17 | −0.29 | −0.16 |
| 21 | CCA | −0.06 | 0.14 | −0.03 | 0.03 | 0.18 | 0.09 | −0.11 | 0.12 | −0.18 | 0.36 | −0.17 | 0.00 |
| 22 | CCC | −0.28 | −0.29 | −0.25 | −0.21 | 0.34 | 0.26 | 0.31 | 0.02 | 0.33 | 0.49 | 0.55 | 0.38 |
| 23 | CCG | −0.18 | 0.13 | 0.03 | 0.07 | −0.10 | −0.11 | −0.45 | −0.15 | −0.08 | −0.07 | 0.05 | 0.00 |
| 24 | CCT | 0.17 | 0.09 | 0.21 | 0.13 | −0.18 | −0.10 | 0.02 | −0.13 | −0.18 | 0.00 | −0.09 | −0.04 |
| 25 | CGA | −0.32 | 0.13 | −0.24 | 0.07 | 0.11 | 0.25 | −0.20 | −0.23 | 0.16 | 0.12 | 0.53 | 0.01 |
| 26 | CGC | −0.21 | 0.03 | 0.05 | 0.18 | −0.09 | −0.33 | −0.13 | −0.30 | 0.02 | −0.25 | −0.13 | 0.04 |
| 27 | CGG | 0.02 | 0.27 | −0.02 | 0.26 | 0.10 | −0.09 | −0.41 | 0.12 | 0.09 | −0.47 | −0.29 | −0.11 |
| 28 | CGT | 0.16 | 0.01 | 0.20 | −0.08 | −0.02 | −0.08 | −0.01 | −0.14 | 0.24 | 0.05 | 0.11 | 0.19 |
| 29 | CTA | −0.10 | 0.10 | −0.01 | 0.19 | −0.02 | 0.00 | −0.10 | −0.03 | −0.07 | −0.08 | −0.25 | −0.06 |
| 30 | CTC | −0.26 | −0.24 | 0.03 | −0.16 | 0.42 | 0.08 | 0.25 | 0.09 | 0.19 | −0.06 | 0.36 | 0.19 |
| 31 | CTG | −0.22 | 0.03 | 0.03 | 0.08 | 0.01 | −0.11 | −0.15 | −0.05 | 0.22 | −0.28 | −0.06 | 0.19 |
| 32 | CTT | 0.30 | 0.21 | 0.42 | 0.13 | 0.11 | −0.05 | 0.25 | −0.13 | −0.09 | −0.15 | −0.18 | −0.08 |
| 33 | GAA | −0.09 | 0.03 | −0.07 | −0.08 | 0.10 | 0.10 | 0.07 | 0.14 | 0.14 | 0.17 | 0.04 | 0.03 |
| 34 | GAC | 0.05 | −0.05 | −0.02 | 0.03 | −0.17 | −0.17 | −0.22 | −0.16 | −0.01 | −0.05 | 0.10 | −0.10 |
| 35 | GAG | 0.15 | 0.16 | 0.18 | 0.12 | −0.16 | −0.19 | −0.21 | −0.25 | −0.17 | −0.27 | 0.10 | −0.25 |
| 36 | GAT | 0.09 | −0.07 | 0.01 | −0.03 | 0.11 | 0.11 | 0.16 | 0.10 | 0.10 | 0.15 | −0.11 | −0.09 |
| 37 | GCA | 0.14 | 0.15 | −0.09 | 0.16 | 0.03 | 0.12 | 0.01 | −0.08 | −0.06 | 0.01 | 0.31 | −0.16 |
| 38 | GCC | −0.05 | −0.38 | −0.22 | −0.38 | 0.10 | 0.23 | 0.27 | 0.13 | 0.10 | 0.18 | 0.54 | 0.34 |
| 39 | GCG | 0.19 | 0.33 | 0.13 | 0.26 | −0.15 | −0.12 | −0.29 | −0.26 | −0.15 | −0.28 | 0.00 | −0.13 |
| 40 | GCT | 0.32 | 0.02 | 0.21 | −0.04 | −0.11 | −0.11 | 0.18 | 0.07 | −0.13 | −0.13 | 0.27 | −0.01 |
| 41 | GGA | −0.10 | 0.25 | −0.07 | 0.11 | −0.03 | −0.17 | −0.07 | 0.14 | 0.20 | −0.13 | 0.14 | −0.07 |
| 42 | GGC | −0.06 | 0.14 | 0.17 | 0.13 | −0.27 | −0.31 | −0.33 | −0.27 | −0.10 | −0.30 | 0.38 | −0.11 |
| 43 | GGG | 0.10 | 0.29 | 0.10 | 0.33 | −0.03 | −0.11 | −0.10 | −0.02 | −0.26 | −0.52 | −0.48 | −0.36 |
| 44 | GGT | 0.07 | −0.18 | −0.06 | −0.19 | 0.09 | 0.12 | 0.49 | 0.22 | 0.13 | 0.21 | 0.45 | 0.15 |
| 45 | GTA | −0.11 | 0.28 | −0.04 | 0.24 | 0.03 | 0.22 | −0.17 | −0.03 | −0.10 | −0.09 | −0.26 | −0.04 |
| 46 | GTC | 0.04 | −0.35 | −0.18 | −0.32 | 0.08 | −0.13 | 0.21 | −0.05 | 0.13 | 0.15 | 0.53 | 0.27 |
| 47 | GTG | −0.01 | 0.23 | −0.03 | 0.21 | −0.04 | 0.16 | −0.15 | 0.13 | 0.14 | −0.13 | −0.03 | 0.15 |
| 48 | GTT | 0.19 | −0.03 | 0.15 | −0.05 | −0.06 | −0.05 | 0.15 | −0.06 | −0.11 | −0.02 | 0.13 | −0.15 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.13 | −0.24 | −0.09 | 0.05 | −0.11 | −0.17 | −0.06 | −0.01 | −0.01 | 0.27 | 0.36 | 0.29 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.15 | −0.06 | 0.07 | −0.02 | 0.02 | 0.10 | 0.21 | 0.03 | −0.14 | 0.09 | −0.21 | −0.13 |
| 53 | TCA | −0.05 | 0.25 | −0.08 | 0.20 | −0.01 | 0.15 | −0.18 | −0.03 | −0.17 | −0.15 | −0.09 | −0.27 |
| 54 | TCC | −0.19 | −0.34 | −0.24 | −0.26 | 0.10 | 0.01 | 0.17 | 0.18 | 0.32 | 0.21 | 0.46 | 0.30 |
| 55 | TCG | −0.15 | 0.15 | −0.15 | 0.20 | −0.17 | −0.36 | −0.27 | −0.26 | −0.16 | −0.32 | −0.30 | −0.17 |
| 56 | TCT | 0.19 | 0.05 | 0.14 | 0.08 | −0.20 | −0.01 | 0.03 | −0.10 | −0.24 | −0.23 | −0.11 | −0.11 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | −0.17 | 0.02 | −0.16 | −0.02 | −0.20 | −0.13 | −0.13 | −0.07 | 0.21 | −0.17 | 0.16 | 0.15 |
| 59 | TGG | −0.12 | 0.11 | 0.00 | 0.02 | −0.04 | −0.13 | 0.09 | 0.09 | −0.02 | −0.19 | 0.14 | 0.10 |
| 60 | TGT | 0.11 | −0.04 | 0.12 | 0.04 | 0.08 | −0.03 | 0.25 | 0.11 | 0.14 | −0.33 | 0.14 | −0.18 |

TABLE C.9-continued

CPW matrix *Saccharomyces cerevisiae* full genome (left codon indicated in column 2, right codon indicated in row 2). Host cell: *S. cerevisiae*; Sequence data: full *S. cerevisiae* genome.

|  |  |  |  |  |  |  |  |  |  |  |  |  |
|---|---|---|---|---|---|---|---|---|---|---|---|---|
| 61 | TTA | 0.00 | 0.06 | −0.07 | 0.06 | −0.15 | 0.00 | −0.14 | 0.07 | −0.09 | 0.08 | −0.25 | −0.02 |
| 62 | TTC | 0.09 | −0.26 | −0.18 | −0.16 | −0.15 | −0.20 | −0.16 | −0.15 | −0.06 | −0.37 | 0.21 | −0.04 |
| 63 | TTG | −0.07 | −0.07 | −0.12 | −0.14 | 0.05 | 0.02 | 0.09 | 0.04 | 0.12 | −0.10 | 0.21 | 0.20 |
| 64 | TTT | 0.27 | 0.07 | 0.15 | 0.02 | 0.10 | 0.14 | 0.19 | 0.14 | 0.18 | −0.16 | 0.06 | 0.06 |

|  |  | ATA 13 | ATC 14 | ATG 15 | ATT 16 | CAA 17 | CAC 18 | CAG 19 | CAT 20 | CCA 21 | CCC 22 | CCG 23 | CCT 24 |
|---|---|---|---|---|---|---|---|---|---|---|---|---|---|
|  |  | 25 CGA | 26 CGC | 27 CGG | 28 CGT | 29 CTA | 30 CTC | 31 CTG | 32 CTT | 33 GAA | 34 GAC | 35 GAG | 36 GAT |
| 1 | AAA | 0.08 | 0.33 | 0.01 | 0.25 | −0.27 | 0.09 | −0.20 | −0.05 | 0.08 | 0.08 | 0.00 | 0.04 |
| 2 | AAC | 0.26 | −0.17 | 0.09 | −0.13 | 0.08 | −0.11 | 0.06 | −0.06 | 0.15 | 0.12 | 0.20 | 0.11 |
| 3 | AAG | 0.28 | 0.22 | 0.12 | 0.20 | −0.11 | 0.06 | −0.11 | 0.04 | −0.07 | −0.14 | −0.08 | −0.03 |
| 4 | AAT | −0.02 | 0.06 | 0.15 | 0.09 | 0.08 | −0.04 | 0.12 | 0.10 | −0.10 | −0.11 | −0.11 | −0.05 |
| 5 | ACA | 0.00 | 0.04 | −0.06 | 0.12 | 0.08 | 0.16 | 0.13 | 0.14 | −0.05 | 0.05 | −0.06 | −0.05 |
| 6 | ACC | 0.46 | 0.31 | 0.36 | 0.14 | 0.34 | 0.31 | 0.23 | 0.05 | 0.24 | 0.19 | 0.20 | 0.13 |
| 7 | ACG | −0.22 | 0.12 | −0.11 | 0.34 | −0.22 | −0.11 | −0.31 | −0.17 | 0.02 | −0.07 | −0.13 | −0.06 |
| 8 | ACT | 0.32 | 0.23 | 0.16 | 0.21 | 0.10 | 0.14 | 0.23 | 0.15 | −0.11 | 0.03 | 0.02 | −0.08 |
| 9 | AGA | 0.35 | 0.34 | 0.23 | 0.29 | 0.01 | 0.32 | 0.06 | 0.29 | −0.04 | 0.03 | 0.00 | −0.04 |
| 10 | AGC | −0.07 | −0.24 | −0.12 | 0.23 | 0.38 | 0.25 | 0.35 | 0.22 | −0.03 | −0.13 | −0.11 | −0.15 |
| 11 | AGG | −0.14 | −0.02 | −0.30 | 0.08 | −0.27 | −0.20 | −0.17 | −0.17 | 0.03 | 0.01 | −0.03 | 0.11 |
| 12 | AGT | 0.10 | 0.06 | 0.13 | 0.28 | 0.44 | 0.22 | 0.31 | 0.15 | −0.29 | −0.28 | −0.25 | −0.31 |
| 13 | ATA | −0.46 | 0.02 | −0.53 | 0.15 | −0.12 | 0.19 | −0.18 | −0.04 | 0.15 | 0.09 | 0.01 | 0.12 |
| 14 | ATC | 0.22 | −0.08 | 0.23 | 0.16 | 0.09 | −0.15 | 0.15 | 0.08 | 0.15 | 0.06 | 0.02 | 0.09 |
| 15 | ATG | 0.26 | 0.26 | 0.03 | 0.11 | −0.18 | −0.08 | −0.29 | −0.30 | −0.02 | −0.07 | 0.06 | 0.04 |
| 16 | ATT | 0.08 | 0.05 | 0.17 | −0.05 | 0.08 | 0.00 | 0.12 | −0.20 | −0.15 | −0.10 | −0.01 | −0.10 |
| 17 | CAA | −0.03 | 0.22 | −0.01 | 0.12 | −0.03 | 0.26 | −0.14 | 0.22 | −0.04 | 0.11 | −0.05 | −0.03 |
| 18 | CAC | 0.12 | −0.20 | −0.15 | −0.32 | 0.41 | −0.06 | 0.18 | 0.02 | 0.06 | −0.04 | 0.08 | 0.01 |
| 19 | CAG | −0.13 | −0.26 | −0.35 | −0.19 | −0.13 | −0.11 | −0.19 | −0.04 | 0.14 | −0.10 | 0.02 | 0.00 |
| 20 | CAT | −0.48 | −0.19 | −0.04 | −0.20 | 0.08 | −0.01 | 0.16 | 0.01 | −0.05 | 0.00 | 0.00 | 0.01 |
| 21 | CCA | 0.16 | 0.06 | 0.01 | 0.09 | 0.10 | 0.20 | 0.12 | 0.18 | −0.02 | 0.16 | −0.09 | 0.04 |
| 22 | CCC | 0.24 | −0.01 | 0.32 | 0.09 | 0.19 | −0.11 | 0.29 | 0.17 | 0.27 | 0.19 | 0.30 | 0.20 |
| 23 | CCG | −0.14 | −0.22 | −0.34 | 0.18 | −0.45 | −0.03 | −0.41 | −0.17 | 0.01 | −0.08 | −0.13 | −0.04 |
| 24 | CCT | −0.38 | −0.21 | 0.06 | −0.29 | 0.20 | 0.09 | 0.01 | 0.01 | −0.06 | −0.09 | −0.08 | −0.19 |
| 25 | CGA | 0.30 | 0.08 | 0.04 | 0.36 | −0.38 | 0.07 | 0.03 | −0.07 | 0.07 | −0.16 | −0.09 | 0.00 |
| 26 | CGC | −0.03 | −0.47 | −0.49 | −0.38 | 0.15 | −0.23 | −0.10 | −0.01 | 0.33 | 0.21 | −0.16 | 0.01 |
| 27 | CGG | 0.16 | −0.22 | −0.54 | 0.29 | −0.31 | −0.42 | −0.43 | −0.36 | 0.13 | 0.14 | −0.01 | 0.22 |
| 28 | CGT | 0.01 | −0.32 | 0.05 | −0.48 | 0.04 | −0.11 | 0.22 | 0.01 | −0.05 | −0.11 | 0.07 | −0.09 |
| 29 | CTA | −0.29 | 0.10 | −0.10 | −0.10 | −0.20 | −0.13 | −0.27 | 0.06 | −0.03 | 0.10 | −0.02 | 0.08 |
| 30 | CTC | −0.25 | −0.22 | 0.18 | 0.21 | 0.19 | −0.11 | 0.15 | 0.05 | 0.29 | 0.09 | 0.08 | −0.08 |
| 31 | CTG | −0.42 | −0.19 | −0.39 | 0.16 | −0.16 | −0.11 | −0.22 | −0.01 | −0.08 | −0.18 | −0.14 | −0.04 |
| 32 | CTT | −0.49 | 0.05 | −0.29 | −0.04 | −0.11 | −0.36 | −0.03 | −0.27 | 0.15 | 0.00 | 0.28 | −0.03 |
| 33 | GAA | 0.01 | 0.21 | −0.14 | 0.08 | −0.13 | 0.11 | −0.06 | 0.11 | 0.00 | 0.02 | 0.01 | −0.02 |
| 34 | GAC | 0.05 | −0.30 | −0.02 | −0.42 | 0.18 | 0.01 | 0.06 | −0.03 | 0.11 | 0.11 | 0.17 | 0.13 |
| 35 | GAG | 0.20 | −0.16 | −0.03 | 0.07 | −0.20 | −0.24 | −0.30 | −0.13 | 0.04 | −0.03 | −0.11 | 0.03 |
| 36 | GAT | 0.07 | 0.01 | 0.35 | −0.11 | 0.23 | 0.01 | 0.22 | 0.02 | −0.06 | −0.05 | −0.07 | −0.07 |
| 37 | GCA | 0.18 | −0.07 | 0.27 | 0.03 | 0.01 | 0.02 | 0.05 | 0.19 | −0.15 | −0.10 | −0.09 | −0.13 |
| 38 | GCC | 0.57 | 0.16 | 0.43 | −0.16 | 0.13 | −0.05 | 0.21 | −0.09 | 0.33 | 0.33 | 0.43 | 0.30 |
| 39 | GCG | 0.41 | −0.19 | −0.08 | 0.18 | −0.37 | −0.30 | −0.36 | −0.24 | −0.01 | −0.15 | −0.11 | −0.05 |
| 40 | GCT | 0.24 | 0.02 | −0.10 | −0.13 | 0.14 | 0.12 | 0.31 | −0.09 | −0.12 | 0.00 | 0.05 | −0.07 |
| 41 | GGA | 0.11 | −0.17 | −0.05 | 0.16 | −0.03 | 0.01 | −0.10 | 0.02 | 0.05 | 0.15 | −0.03 | 0.13 |
| 42 | GGC | 0.29 | −0.33 | 0.03 | −0.38 | 0.05 | −0.20 | −0.02 | −0.05 | 0.08 | 0.04 | 0.11 | 0.08 |
| 43 | GGG | −0.16 | −0.10 | −0.10 | −0.17 | −0.39 | −0.43 | −0.42 | −0.39 | 0.18 | 0.23 | 0.03 | 0.33 |
| 44 | GGT | 0.51 | 0.26 | 0.63 | −0.08 | 0.04 | 0.07 | 0.41 | 0.08 | −0.13 | −0.21 | 0.05 | −0.11 |
| 45 | GTA | −0.51 | −0.18 | −0.29 | −0.27 | 0.01 | −0.12 | −0.14 | −0.09 | 0.02 | 0.02 | −0.17 | −0.07 |
| 46 | GTC | 0.49 | −0.07 | 0.37 | −0.07 | 0.26 | −0.04 | 0.17 | −0.20 | 0.23 | 0.04 | 0.32 | 0.23 |
| 47 | GTG | 0.13 | −0.09 | −0.36 | 0.16 | −0.10 | −0.13 | −0.16 | −0.11 | −0.26 | −0.14 | −0.32 | −0.10 |
| 48 | GTT | 0.23 | −0.11 | 0.20 | −0.31 | 0.19 | −0.17 | 0.18 | −0.25 | 0.06 | 0.02 | 0.15 | 0.00 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.23 | −0.19 | −0.05 | −0.27 | 0.06 | 0.00 | −0.05 | 0.18 | 0.06 | 0.02 | 0.07 | 0.08 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | −0.04 | −0.02 | −0.03 | −0.18 | 0.14 | −0.02 | 0.06 | 0.01 | −0.05 | −0.10 | −0.04 | −0.01 |
| 53 | TCA | −0.37 | 0.02 | −0.01 | 0.27 | −0.11 | 0.14 | −0.11 | −0.04 | 0.02 | 0.15 | 0.05 | 0.05 |
| 54 | TCC | −0.11 | 0.02 | 0.32 | −0.05 | 0.14 | 0.18 | 0.17 | 0.13 | 0.33 | 0.36 | 0.21 | 0.30 |
| 55 | TCG | −0.02 | −0.22 | 0.06 | 0.23 | −0.32 | −0.10 | −0.34 | −0.11 | 0.19 | 0.27 | 0.01 | 0.15 |
| 56 | TCT | −0.17 | −0.30 | 0.20 | −0.18 | 0.06 | 0.04 | 0.13 | 0.01 | −0.01 | 0.09 | 0.07 | −0.05 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | −0.26 | −0.19 | −0.46 | −0.41 | 0.16 | −0.27 | 0.01 | −0.11 | 0.23 | 0.14 | 0.15 | 0.17 |
| 59 | TGG | 0.17 | 0.51 | 0.36 | 0.52 | −0.09 | −0.09 | −0.18 | 0.05 | 0.04 | −0.10 | −0.08 | 0.06 |

TABLE C.9-continued

CPW matrix *Saccharomyces cerevisiae* full genome (left codon indicated in column 2, right codon indicated in row 2). Host cell: *S. cerevisiae*; Sequence data: full *S. cerevisiae* genome.

| | | | | | | | | | | | | |
|---|---|---|---|---|---|---|---|---|---|---|---|---|
| 60 | TGT | −0.17 | −0.15 | 0.05 | −0.23 | 0.08 | −0.19 | 0.03 | −0.03 | −0.07 | −0.09 | −0.20 | −0.09 |
| 61 | TTA | −0.22 | −0.19 | −0.15 | 0.01 | −0.19 | −0.08 | −0.19 | −0.05 | −0.02 | 0.03 | −0.02 | 0.04 |
| 62 | TTC | −0.08 | −0.22 | −0.01 | −0.25 | 0.09 | −0.14 | 0.15 | 0.06 | 0.27 | 0.23 | 0.28 | 0.23 |
| 63 | TTG | 0.12 | 0.08 | 0.13 | 0.11 | 0.14 | 0.27 | 0.15 | 0.27 | −0.06 | −0.03 | −0.04 | −0.02 |
| 64 | TTT | −0.05 | 0.13 | −0.20 | 0.38 | 0.21 | −0.03 | 0.19 | 0.04 | −0.19 | −0.14 | −0.07 | −0.13 |

| | CGA 25 | CGC 26 | CGG 27 | CGT 28 | CTA 29 | CTC 30 | CTG 31 | CTT 32 | GAA 33 | GAC 34 | GAG 35 | GAT 36 |
|---|---|---|---|---|---|---|---|---|---|---|---|---|

| | | 37 GCA | 38 GCC | 39 GCG | 40 GCT | 41 GGA | 42 GGC | 43 GGG | 44 GGT | 45 GTA | 46 GTC | 47 GTG | 48 GTT |
|---|---|---|---|---|---|---|---|---|---|---|---|---|---|
| 1 | AAA | 0.09 | 0.22 | 0.20 | 0.10 | 0.01 | 0.10 | 0.01 | 0.11 | −0.04 | −0.01 | −0.10 | −0.08 |
| 2 | AAC | 0.24 | 0.19 | 0.35 | 0.15 | 0.19 | 0.14 | 0.17 | 0.18 | 0.14 | −0.14 | 0.22 | 0.01 |
| 3 | AAG | −0.10 | −0.13 | −0.17 | −0.21 | −0.07 | −0.26 | 0.10 | −0.06 | 0.14 | 0.01 | 0.21 | 0.05 |
| 4 | AAT | −0.12 | −0.15 | −0.21 | −0.08 | −0.15 | −0.21 | −0.27 | 0.05 | 0.02 | −0.08 | 0.10 | −0.09 |
| 5 | ACA | −0.06 | 0.25 | −0.06 | 0.30 | −0.12 | 0.06 | −0.04 | 0.13 | −0.18 | 0.24 | −0.03 | 0.24 |
| 6 | ACC | 0.16 | 0.08 | 0.21 | 0.08 | 0.28 | 0.27 | 0.30 | −0.08 | 0.06 | −0.09 | 0.08 | 0.04 |
| 7 | ACG | −0.12 | 0.26 | −0.27 | 0.23 | −0.12 | −0.09 | −0.21 | 0.24 | −0.25 | 0.12 | −0.22 | 0.22 |
| 8 | ACT | −0.20 | −0.21 | −0.10 | −0.18 | 0.03 | 0.08 | −0.12 | −0.21 | −0.07 | −0.03 | −0.08 | −0.11 |
| 9 | AGA | 0.00 | −0.01 | 0.11 | −0.02 | −0.03 | −0.04 | 0.23 | −0.13 | −0.08 | 0.08 | 0.13 | 0.02 |
| 10 | AGC | 0.12 | −0.16 | 0.28 | 0.05 | −0.13 | −0.21 | −0.16 | 0.03 | −0.10 | 0.14 | 0.02 | 0.14 |
| 11 | AGG | −0.13 | −0.02 | −0.18 | −0.10 | 0.19 | 0.15 | 0.42 | 0.39 | −0.11 | 0.12 | −0.13 | 0.22 |
| 12 | AGT | −0.23 | −0.22 | −0.29 | −0.19 | −0.32 | −0.22 | −0.33 | −0.20 | −0.16 | −0.14 | −0.04 | −0.08 |
| 13 | ATA | 0.11 | 0.25 | −0.09 | 0.31 | 0.14 | 0.17 | 0.11 | 0.40 | 0.06 | 0.30 | 0.00 | 0.33 |
| 14 | ATC | 0.35 | 0.26 | 0.29 | 0.31 | 0.21 | 0.06 | 0.03 | 0.07 | 0.30 | 0.07 | 0.24 | 0.21 |
| 15 | ATG | −0.05 | −0.01 | −0.09 | 0.08 | −0.04 | −0.03 | −0.12 | 0.07 | 0.02 | −0.01 | 0.02 | −0.02 |
| 16 | ATT | −0.17 | −0.30 | −0.22 | −0.22 | −0.11 | −0.09 | −0.23 | −0.09 | −0.26 | −0.19 | −0.21 | |
| 17 | CAA | 0.05 | 0.04 | −0.05 | −0.04 | 0.06 | −0.04 | −0.02 | −0.05 | −0.10 | 0.05 | −0.17 | 0.04 |
| 18 | CAC | 0.21 | 0.15 | 0.29 | 0.22 | 0.23 | 0.10 | 0.09 | 0.06 | 0.10 | −0.01 | 0.15 | −0.09 |
| 19 | CAG | −0.03 | 0.00 | −0.26 | 0.12 | −0.18 | −0.18 | 0.10 | 0.29 | −0.05 | 0.17 | −0.09 | 0.21 |
| 20 | CAT | −0.03 | −0.19 | −0.20 | −0.07 | −0.10 | 0.02 | −0.17 | −0.03 | 0.06 | 0.00 | 0.02 | −0.05 |
| 21 | CCA | −0.02 | 0.27 | 0.16 | 0.13 | 0.12 | 0.00 | 0.20 | −0.06 | 0.01 | 0.26 | 0.15 | 0.18 |
| 22 | CCC | 0.21 | 0.25 | 0.41 | 0.09 | 0.22 | 0.14 | 0.42 | 0.20 | −0.29 | 0.07 | −0.11 | 0.04 |
| 23 | CCG | −0.11 | 0.29 | 0.05 | 0.16 | −0.24 | −0.26 | −0.17 | 0.47 | −0.28 | 0.17 | −0.03 | 0.15 |
| 24 | CCT | −0.22 | −0.10 | −0.24 | −0.30 | −0.12 | −0.11 | −0.30 | −0.10 | −0.25 | 0.01 | −0.15 | −0.11 |
| 25 | CGA | −0.15 | 0.28 | 0.25 | 0.30 | −0.23 | −0.02 | 0.17 | 0.47 | −0.16 | 0.28 | −0.04 | 0.17 |
| 26 | CGC | 0.00 | 0.40 | 0.52 | 0.32 | −0.03 | −0.12 | −0.11 | 0.31 | 0.26 | 0.40 | 0.15 | 0.00 |
| 27 | CGG | 0.33 | 0.12 | 0.00 | 0.35 | 0.04 | 0.30 | 0.39 | 0.62 | −0.07 | 0.28 | 0.10 | 0.36 |
| 28 | CGT | −0.04 | −0.18 | −0.05 | −0.08 | −0.16 | −0.36 | −0.27 | −0.40 | −0.25 | −0.27 | −0.18 | −0.29 |
| 29 | CTA | −0.03 | 0.20 | 0.01 | 0.06 | −0.04 | 0.09 | 0.12 | 0.18 | 0.00 | 0.11 | −0.02 | 0.22 |
| 30 | CTC | 0.34 | 0.21 | 0.29 | 0.30 | 0.20 | 0.10 | 0.06 | −0.13 | 0.02 | 0.05 | 0.09 | 0.14 |
| 31 | CTG | −0.18 | −0.17 | −0.32 | 0.17 | −0.21 | −0.17 | −0.05 | 0.09 | −0.28 | −0.08 | −0.22 | 0.13 |
| 32 | CTT | 0.00 | −0.08 | −0.17 | −0.04 | −0.26 | −0.16 | −0.15 | −0.09 | 0.02 | −0.04 | −0.16 | −0.06 |
| 33 | GAA | 0.08 | 0.11 | 0.06 | −0.02 | 0.01 | 0.03 | −0.01 | −0.07 | −0.01 | 0.02 | −0.04 | −0.06 |
| 34 | GAC | 0.24 | 0.13 | 0.38 | 0.13 | 0.25 | 0.08 | 0.17 | 0.08 | 0.11 | 0.18 | 0.15 | 0.02 |
| 35 | GAG | −0.25 | −0.03 | −0.16 | 0.05 | −0.13 | −0.12 | 0.04 | 0.26 | 0.03 | 0.14 | −0.03 | 0.11 |
| 36 | GAT | −0.02 | −0.06 | −0.08 | −0.16 | −0.04 | −0.06 | −0.13 | −0.06 | 0.08 | −0.12 | −0.02 | −0.09 |
| 37 | GCA | 0.00 | 0.30 | 0.26 | 0.22 | −0.08 | −0.03 | 0.16 | 0.04 | −0.11 | 0.27 | 0.11 | 0.26 |
| 38 | GCC | 0.29 | 0.04 | 0.49 | −0.06 | 0.43 | 0.31 | 0.48 | −0.06 | 0.25 | 0.03 | 0.19 | −0.04 |
| 39 | GCG | −0.05 | 0.14 | −0.03 | 0.13 | −0.14 | −0.19 | 0.16 | 0.31 | −0.28 | 0.25 | −0.08 | 0.21 |
| 40 | GCT | −0.01 | −0.22 | 0.05 | −0.33 | 0.10 | −0.04 | 0.23 | −0.30 | 0.01 | −0.19 | −0.13 | −0.21 |
| 41 | GGA | 0.11 | 0.36 | 0.22 | 0.33 | −0.08 | 0.18 | 0.08 | 0.38 | 0.22 | 0.42 | 0.28 | 0.37 |
| 42 | GGC | 0.14 | −0.05 | 0.39 | −0.06 | 0.09 | −0.05 | 0.20 | 0.12 | 0.18 | 0.18 | 0.20 | 0.12 |
| 43 | GGG | 0.11 | 0.17 | 0.16 | 0.34 | 0.32 | 0.21 | 0.33 | 0.56 | 0.15 | 0.46 | 0.20 | 0.38 |
| 44 | GGT | 0.05 | −0.29 | 0.03 | −0.27 | 0.11 | −0.02 | −0.06 | −0.37 | −0.04 | −0.37 | −0.09 | −0.31 |
| 45 | GTA | −0.11 | 0.26 | −0.16 | 0.27 | −0.03 | 0.09 | −0.08 | 0.32 | 0.04 | 0.26 | −0.10 | 0.21 |
| 46 | GTC | 0.13 | 0.18 | 0.43 | 0.16 | 0.13 | 0.19 | 0.13 | −0.03 | 0.28 | 0.09 | 0.32 | 0.07 |
| 47 | GTG | −0.21 | −0.18 | −0.13 | 0.08 | −0.11 | −0.01 | −0.30 | −0.23 | −0.31 | 0.00 | −0.28 | 0.07 |
| 48 | GTT | 0.02 | −0.16 | 0.04 | −0.15 | −0.20 | 0.06 | 0.02 | −0.17 | 0.18 | −0.21 | 0.11 | −0.19 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.30 | 0.10 | 0.27 | 0.12 | 0.21 | 0.20 | 0.15 | 0.03 | 0.19 | −0.11 | 0.06 | 0.02 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | −0.12 | −0.11 | −0.18 | −0.12 | −0.09 | 0.02 | −0.14 | −0.10 | 0.26 | −0.14 | −0.13 | −0.06 |
| 53 | TCA | −0.01 | 0.42 | 0.01 | 0.20 | −0.15 | 0.07 | 0.03 | 0.22 | −0.11 | 0.40 | 0.05 | 0.27 |
| 54 | TCC | 0.26 | 0.24 | 0.35 | 0.22 | 0.25 | 0.29 | 0.33 | 0.13 | 0.07 | 0.07 | 0.12 | 0.03 |
| 55 | TCG | 0.09 | 0.43 | −0.04 | 0.44 | 0.24 | 0.23 | 0.26 | 0.48 | −0.14 | 0.39 | −0.01 | 0.20 |
| 56 | TCT | −0.17 | −0.17 | −0.20 | −0.21 | −0.03 | 0.02 | −0.04 | −0.13 | −0.08 | −0.14 | −0.24 | −0.14 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.26 | 0.20 | 0.20 | 0.33 | 0.30 | 0.24 | 0.00 | 0.23 | −0.03 | 0.23 | 0.25 | 0.17 |
| 59 | TGG | 0.01 | 0.04 | −0.12 | 0.01 | 0.18 | −0.02 | −0.24 | 0.01 | −0.08 | 0.03 | 0.21 | −0.07 |

TABLE C.9-continued

CPW matrix *Saccharomyces cerevisiae* full genome (left codon indicated in column 2, right codon indicated in row 2). Host cell: *S. cerevisiae*; Sequence data: full *S. cerevisiae* genome.

|  |  | GCA | GCC | GCG | GCT | GGA | GGC | GGG | GGT | GTA | GTC | GTG | GTT |
|---|---|---|---|---|---|---|---|---|---|---|---|---|---|
| 60 | TGT | −0.03 | −0.13 | −0.19 | −0.20 | 0.07 | −0.14 | −0.18 | −0.16 | 0.08 | −0.21 | 0.05 | −0.15 |
| 61 | TTA | 0.06 | 0.12 | −0.04 | 0.22 | −0.02 | 0.14 | 0.03 | 0.08 | 0.09 | 0.11 | −0.03 | 0.17 |
| 62 | TTC | 0.45 | 0.36 | 0.52 | 0.46 | 0.44 | 0.36 | 0.47 | 0.17 | 0.43 | 0.16 | 0.40 | 0.26 |
| 63 | TTG | −0.10 | −0.17 | −0.12 | −0.12 | 0.08 | 0.05 | 0.07 | −0.08 | −0.05 | −0.11 | −0.13 | −0.08 |
| 64 | TTT | −0.17 | −0.36 | −0.21 | −0.19 | −0.16 | −0.19 | −0.09 | −0.19 | −0.06 | −0.21 | 0.01 | −0.27 |

|  |  | GCA | GCC | GCG | GCT | GGA | GGC | GGG | GGT | GTA | GTC | GTG | GTT |
|---|---|---|---|---|---|---|---|---|---|---|---|---|---|
|  |  | 37 | 38 | 39 | 40 | 41 | 42 | 43 | 44 | 45 | 46 | 47 | 48 |
|  |  | 49 | 50 | 51 | 52 | 53 | 54 | 55 | 56 | 57 | 58 | 59 | 60 |
|  |  | TAA | TAC | TAG | TAT | TCA | TCC | TCG | TCT | TGA | TGC | TGG | TGT |
| 1 | AAA | 0.00 | −0.03 | 0.00 | −0.09 | −0.17 | 0.08 | −0.13 | 0.01 | 0.00 | −0.08 | −0.15 | −0.14 |
| 2 | AAC | 0.00 | −0.14 | 0.00 | −0.06 | 0.15 | −0.03 | 0.10 | 0.00 | 0.00 | 0.00 | −0.14 | −0.12 |
| 3 | AAG | 0.00 | 0.01 | 0.00 | 0.16 | 0.22 | 0.28 | 0.16 | 0.30 | 0.00 | 0.12 | 0.26 | 0.23 |
| 4 | AAT | 0.00 | 0.09 | 0.00 | 0.06 | −0.01 | 0.12 | 0.03 | 0.09 | 0.00 | 0.07 | 0.11 | 0.05 |
| 5 | ACA | 0.00 | 0.07 | 0.00 | −0.11 | −0.05 | 0.07 | 0.07 | 0.04 | 0.00 | −0.17 | −0.07 | −0.08 |
| 6 | ACC | 0.00 | −0.01 | 0.00 | 0.12 | 0.06 | 0.12 | 0.20 | 0.01 | 0.00 | 0.13 | 0.04 | 0.00 |
| 7 | ACG | 0.00 | −0.05 | 0.00 | −0.16 | −0.05 | 0.21 | 0.07 | 0.28 | 0.00 | −0.21 | 0.04 | 0.05 |
| 8 | ACT | 0.00 | 0.04 | 0.00 | 0.06 | −0.16 | −0.14 | 0.01 | −0.20 | 0.00 | 0.21 | 0.03 | 0.07 |
| 9 | AGA | 0.00 | 0.18 | 0.00 | 0.13 | −0.04 | 0.27 | −0.01 | 0.17 | 0.00 | 0.27 | 0.08 | 0.12 |
| 10 | AGC | 0.00 | 0.09 | 0.00 | −0.08 | 0.16 | 0.19 | 0.12 | 0.05 | 0.00 | −0.08 | 0.03 | 0.00 |
| 11 | AGG | 0.00 | 0.06 | 0.00 | 0.14 | −0.09 | 0.20 | −0.18 | 0.11 | 0.00 | 0.09 | 0.13 | 0.35 |
| 12 | AGT | 0.00 | 0.10 | 0.00 | 0.01 | 0.02 | 0.23 | 0.18 | 0.18 | 0.00 | −0.17 | 0.01 | −0.16 |
| 13 | ATA | 0.00 | −0.20 | 0.00 | −0.24 | −0.28 | −0.12 | −0.29 | −0.14 | 0.00 | −0.13 | −0.18 | −0.09 |
| 14 | ATC | 0.00 | 0.11 | 0.00 | 0.27 | 0.27 | 0.02 | 0.29 | 0.22 | 0.00 | 0.06 | 0.19 | 0.13 |
| 15 | ATG | 0.00 | −0.04 | 0.00 | 0.03 | 0.05 | 0.05 | −0.03 | 0.13 | 0.00 | −0.07 | 0.00 | 0.05 |
| 16 | ATT | 0.00 | 0.08 | 0.00 | 0.04 | 0.00 | −0.13 | 0.10 | −0.11 | 0.00 | −0.07 | 0.03 | 0.07 |
| 17 | CAA | 0.00 | 0.10 | 0.00 | 0.08 | 0.04 | 0.16 | −0.02 | 0.01 | 0.00 | 0.21 | −0.06 | −0.08 |
| 18 | CAC | 0.00 | 0.02 | 0.00 | −0.08 | −0.03 | −0.04 | 0.15 | 0.02 | 0.00 | −0.04 | −0.01 | 0.04 |
| 19 | CAG | 0.00 | −0.23 | 0.00 | −0.11 | −0.01 | 0.25 | −0.09 | 0.24 | 0.00 | −0.23 | 0.13 | 0.09 |
| 20 | CAT | 0.00 | 0.17 | 0.00 | −0.08 | −0.08 | −0.05 | −0.13 | −0.14 | 0.00 | 0.14 | 0.01 | −0.08 |
| 21 | CCA | 0.00 | 0.07 | 0.00 | −0.07 | −0.08 | 0.14 | 0.04 | −0.07 | 0.00 | −0.19 | −0.17 | 0.08 |
| 22 | CCC | 0.00 | 0.13 | 0.00 | 0.20 | −0.03 | −0.12 | −0.02 | −0.26 | 0.00 | −0.03 | 0.17 | −0.05 |
| 23 | CCG | 0.00 | −0.25 | 0.00 | −0.14 | 0.07 | 0.23 | 0.20 | 0.28 | 0.00 | 0.15 | 0.20 | 0.30 |
| 24 | CCT | 0.00 | 0.11 | 0.00 | −0.04 | −0.15 | −0.13 | −0.13 | −0.11 | 0.00 | 0.00 | 0.10 | −0.03 |
| 25 | CGA | 0.00 | −0.28 | 0.00 | −0.12 | 0.03 | 0.32 | −0.06 | 0.06 | 0.00 | −0.45 | 0.04 | −0.09 |
| 26 | CGC | 0.00 | −0.45 | 0.00 | −0.17 | −0.06 | 0.03 | −0.10 | −0.16 | 0.00 | −0.41 | −0.34 | −0.18 |
| 27 | CGG | 0.00 | −0.22 | 0.00 | −0.27 | −0.20 | −0.11 | −0.51 | −0.12 | 0.00 | −0.37 | 0.24 | 0.04 |
| 28 | CGT | 0.00 | −0.23 | 0.00 | −0.16 | −0.06 | −0.22 | 0.00 | −0.08 | 0.00 | −0.30 | −0.25 | −0.38 |
| 29 | CTA | 0.00 | −0.05 | 0.00 | −0.06 | −0.09 | −0.22 | −0.23 | −0.01 | 0.00 | 0.03 | −0.22 | −0.10 |
| 30 | CTC | 0.00 | −0.05 | 0.00 | −0.15 | 0.01 | −0.19 | −0.19 | −0.13 | 0.00 | −0.35 | 0.00 | −0.30 |
| 31 | CTG | 0.00 | −0.04 | 0.00 | 0.10 | 0.13 | 0.25 | −0.01 | 0.34 | 0.00 | 0.01 | 0.19 | 0.20 |
| 32 | CTT | 0.00 | −0.29 | 0.00 | −0.36 | −0.29 | −0.43 | −0.30 | −0.33 | 0.00 | −0.31 | −0.25 | −0.34 |
| 33 | GAA | 0.00 | 0.06 | 0.00 | 0.02 | 0.10 | 0.14 | 0.11 | 0.06 | 0.00 | 0.11 | −0.05 | −0.09 |
| 34 | GAC | 0.00 | −0.13 | 0.00 | −0.06 | 0.23 | −0.01 | 0.01 | −0.10 | 0.00 | −0.07 | −0.05 | −0.19 |
| 35 | GAG | 0.00 | −0.14 | 0.00 | −0.04 | 0.13 | 0.30 | −0.06 | 0.21 | 0.00 | −0.11 | 0.13 | 0.14 |
| 36 | GAT | 0.00 | 0.16 | 0.00 | −0.03 | 0.02 | −0.03 | −0.01 | −0.07 | 0.00 | 0.20 | 0.03 | 0.03 |
| 37 | GCA | 0.00 | −0.04 | 0.00 | −0.10 | 0.04 | 0.03 | −0.04 | 0.01 | 0.00 | −0.31 | −0.05 | −0.05 |
| 38 | GCC | 0.00 | 0.18 | 0.00 | 0.11 | 0.28 | −0.01 | 0.23 | −0.07 | 0.00 | 0.17 | 0.17 | −0.14 |
| 39 | GCG | 0.00 | −0.19 | 0.00 | −0.23 | −0.01 | 0.10 | 0.01 | 0.12 | 0.00 | −0.09 | −0.10 | 0.18 |
| 40 | GCT | 0.00 | 0.04 | 0.00 | 0.09 | −0.03 | −0.30 | −0.02 | −0.16 | 0.00 | 0.35 | −0.02 | 0.05 |
| 41 | GGA | 0.00 | 0.11 | 0.00 | −0.15 | 0.11 | 0.08 | −0.08 | 0.02 | 0.00 | 0.01 | −0.08 | −0.03 |
| 42 | GGC | 0.00 | −0.17 | 0.00 | −0.12 | −0.09 | −0.20 | 0.11 | −0.12 | 0.00 | −0.07 | −0.19 | −0.27 |
| 43 | GGG | 0.00 | −0.02 | 0.00 | 0.15 | 0.17 | −0.11 | 0.07 | −0.02 | 0.00 | 0.08 | 0.22 | 0.23 |
| 44 | GGT | 0.00 | 0.00 | 0.00 | 0.14 | 0.11 | 0.01 | 0.23 | −0.02 | 0.00 | 0.08 | 0.08 | 0.07 |
| 45 | GTA | 0.00 | 0.00 | 0.00 | −0.09 | −0.11 | −0.18 | −0.14 | 0.03 | 0.00 | −0.11 | −0.06 | 0.14 |
| 46 | GTC | 0.00 | −0.04 | 0.00 | 0.30 | 0.28 | −0.06 | 0.28 | 0.07 | 0.00 | 0.12 | 0.10 | 0.03 |
| 47 | GTG | 0.00 | 0.15 | 0.00 | 0.17 | 0.23 | 0.18 | 0.06 | 0.31 | 0.00 | 0.01 | 0.16 | 0.23 |
| 48 | GTT | 0.00 | −0.12 | 0.00 | −0.10 | −0.13 | −0.24 | 0.00 | −0.25 | 0.00 | −0.12 | −0.09 | −0.11 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.00 | −0.14 | 0.00 | 0.00 | 0.10 | −0.01 | 0.15 | −0.03 | 0.00 | 0.12 | −0.10 | −0.12 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.00 | 0.16 | 0.00 | −0.02 | −0.05 | −0.15 | −0.13 | −0.18 | 0.00 | 0.07 | 0.09 | 0.01 |
| 53 | TCA | 0.00 | −0.04 | 0.00 | −0.19 | −0.18 | 0.02 | −0.17 | 0.06 | 0.00 | −0.19 | −0.13 | −0.07 |
| 54 | TCC | 0.00 | 0.15 | 0.00 | 0.21 | 0.07 | −0.02 | −0.03 | −0.02 | 0.00 | 0.14 | 0.15 | 0.17 |
| 55 | TCG | 0.00 | −0.26 | 0.00 | −0.18 | 0.05 | 0.01 | −0.17 | 0.26 | 0.00 | 0.00 | −0.20 | 0.08 |
| 56 | TCT | 0.00 | 0.11 | 0.00 | 0.08 | −0.14 | −0.15 | −0.10 | −0.20 | 0.00 | 0.14 | 0.11 | 0.13 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.00 | −0.12 | 0.00 | −0.16 | 0.00 | −0.20 | 0.05 | −0.10 | 0.00 | −0.13 | −0.06 | −0.14 |
| 59 | TGG | 0.00 | −0.11 | 0.00 | 0.09 | −0.15 | 0.05 | −0.08 | −0.02 | 0.00 | 0.01 | 0.00 | −0.01 |

TABLE C.9-continued

CPW matrix *Saccharomyces cerevisiae* full genome (left codon indicated in column 2, right codon indicated in row 2). Host cell: *S. cerevisiae*; Sequence data: full *S. cerevisiae* genome.

| | | TAA 49 | TAC 50 | TAG 51 | TAT 52 | TCA 53 | TCC 54 | TCG 55 | TCT 56 | TGA 57 | TGC 58 | TGG 59 | TGT 60 |
|---|---|---|---|---|---|---|---|---|---|---|---|---|---|
| 60 | TGT | 0.00 | 0.17 | 0.00 | 0.05 | −0.05 | −0.04 | −0.04 | −0.05 | 0.00 | 0.09 | 0.04 | 0.11 |
| 61 | TTA | 0.00 | 0.09 | 0.00 | 0.08 | −0.11 | −0.05 | −0.15 | −0.02 | 0.00 | 0.04 | −0.16 | −0.03 |
| 62 | TTC | 0.00 | 0.01 | 0.00 | 0.22 | 0.27 | 0.07 | 0.23 | 0.21 | 0.00 | 0.02 | 0.09 | 0.10 |
| 63 | TTG | 0.00 | 0.17 | 0.00 | 0.22 | 0.30 | 0.23 | 0.37 | 0.35 | 0.00 | 0.27 | 0.42 | 0.35 |
| 64 | TTT | 0.00 | −0.15 | 0.00 | −0.02 | −0.10 | −0.15 | −0.09 | −0.15 | 0.00 | −0.10 | −0.06 | 0.00 |

| | | 61 TTA | 62 TTC | 63 TTG | 64 TTT |
|---|---|---|---|---|---|
| 1 | AAA | −0.03 | 0.00 | 0.10 | −0.08 |
| 2 | AAC | 0.10 | −0.01 | −0.07 | 0.03 |
| 3 | AAG | 0.24 | 0.12 | 0.16 | 0.04 |
| 4 | AAT | −0.07 | −0.02 | −0.07 | 0.00 |
| 5 | ACA | 0.00 | 0.22 | 0.22 | −0.09 |
| 6 | ACC | 0.08 | 0.05 | 0.20 | 0.23 |
| 7 | ACG | 0.05 | 0.11 | 0.03 | −0.02 |
| 8 | ACT | −0.30 | −0.17 | −0.31 | −0.09 |
| 9 | AGA | −0.03 | 0.14 | 0.09 | −0.09 |
| 10 | AGC | 0.28 | 0.15 | 0.31 | 0.11 |
| 11 | AGG | 0.00 | 0.01 | 0.13 | −0.21 |
| 12 | AGT | −0.05 | −0.08 | −0.02 | 0.02 |
| 13 | ATA | −0.05 | −0.04 | 0.10 | −0.17 |
| 14 | ATC | 0.21 | 0.07 | 0.16 | 0.24 |
| 15 | ATG | 0.22 | 0.11 | 0.29 | −0.07 |
| 16 | ATT | −0.13 | −0.12 | −0.03 | 0.07 |
| 17 | CAA | 0.02 | 0.10 | −0.01 | 0.09 |
| 18 | CAC | 0.25 | −0.06 | 0.04 | 0.22 |
| 19 | CAG | 0.02 | −0.07 | 0.00 | −0.23 |
| 20 | CAT | −0.20 | −0.09 | −0.15 | −0.03 |
| 21 | CCA | −0.06 | 0.08 | −0.01 | −0.12 |
| 22 | CCC | −0.07 | −0.10 | 0.11 | −0.12 |
| 23 | CCG | −0.27 | 0.08 | 0.05 | 0.02 |
| 24 | CCT | −0.06 | 0.01 | 0.02 | 0.19 |
| 25 | CGA | −0.12 | 0.14 | 0.12 | −0.12 |
| 26 | CGC | 0.05 | 0.17 | 0.30 | 0.25 |
| 27 | CGG | −0.12 | −0.14 | −0.17 | −0.34 |
| 28 | CGT | −0.08 | 0.17 | −0.13 | 0.34 |
| 29 | CTA | −0.10 | 0.09 | 0.04 | 0.03 |
| 30 | CTC | 0.15 | −0.29 | 0.08 | −0.18 |
| 31 | CTG | 0.21 | 0.01 | 0.13 | 0.11 |
| 32 | CTT | −0.34 | −0.49 | −0.32 | −0.17 |
| 33 | GAA | 0.10 | 0.20 | 0.05 | −0.02 |
| 34 | GAC | 0.12 | 0.05 | −0.06 | 0.13 |
| 35 | GAG | 0.06 | 0.02 | 0.08 | −0.23 |
| 36 | GAT | −0.11 | −0.05 | −0.16 | −0.05 |
| 37 | GCA | −0.01 | 0.01 | 0.04 | −0.20 |
| 38 | GCC | 0.21 | 0.00 | 0.13 | 0.01 |
| 39 | GCG | −0.08 | −0.11 | −0.07 | −0.21 |
| 40 | GCT | −0.04 | 0.12 | −0.18 | 0.22 |
| 41 | GGA | −0.06 | −0.03 | 0.11 | −0.33 |
| 42 | GGC | 0.16 | 0.24 | 0.22 | 0.18 |
| 43 | GGG | −0.19 | −0.45 | −0.27 | −0.50 |
| 44 | GGT | 0.05 | 0.15 | 0.03 | 0.44 |
| 45 | GTA | 0.19 | 0.09 | 0.08 | −0.14 |
| 46 | GTC | 0.20 | 0.00 | −0.01 | 0.10 |
| 47 | GTG | 0.31 | 0.21 | 0.17 | 0.05 |
| 48 | GTT | −0.11 | −0.22 | −0.16 | 0.10 |
| 49 | TAA | 0.00 | 0.00 | 0.00 | 0.00 |
| 50 | TAC | 0.19 | 0.01 | −0.06 | 0.15 |
| 51 | TAG | 0.00 | 0.00 | 0.00 | 0.00 |
| 52 | TAT | −0.06 | −0.12 | −0.16 | −0.02 |
| 53 | TCA | −0.18 | −0.01 | −0.03 | −0.15 |
| 54 | TCC | 0.05 | 0.02 | 0.09 | −0.03 |
| 55 | TCG | −0.14 | −0.06 | −0.09 | −0.14 |
| 56 | TCT | −0.17 | 0.07 | −0.19 | 0.13 |
| 57 | TGA | 0.00 | 0.00 | 0.00 | 0.00 |
| 58 | TGC | 0.07 | 0.04 | 0.18 | −0.18 |
| 59 | TGG | 0.02 | 0.00 | 0.11 | 0.00 |

TABLE C.9-continued

CPW matrix *Saccharomyces cerevisiae* full genome (left codon indicated in column 2, right codon indicated in row 2). Host cell: *S. cerevisiae*; Sequence data: full *S. cerevisiae* genome.

| | | | | | |
|---|---|---|---|---|---|
| 60 | TGT | 0.00 | 0.04 | −0.09 | 0.08 |
| 61 | TTA | −0.01 | 0.06 | 0.06 | 0.00 |
| 62 | TTC | 0.09 | −0.09 | −0.02 | 0.16 |
| 63 | TTG | 0.34 | 0.27 | 0.26 | 0.21 |
| 64 | TTT | −0.13 | −0.20 | −0.15 | 0.11 |
| | | TTA | TTC | TTG | TTT |
| | | 61 | 62 | 63 | 64 |

TABLE C.10

CPW matrix *Saccaromyces. cerevisiae* highly expressed sequences (left codon indicated in column 2, right codon indicated in row 2). Host cell: *S. cerevisiae*; Sequence data: full *S. cerevisiae* genome; Highly expressed group: 300 seqs.

| | | 1 AAA | 2 AAC | 3 AAG | 4 AAT | 5 ACA | 6 ACC | 7 ACG | 8 ACT | 9 AGA | 10 AGC | 11 AGG | 12 AGT |
|---|---|---|---|---|---|---|---|---|---|---|---|---|---|
| 1 | AAA | 0.67 | 0.35 | 0.49 | 0.42 | 0.66 | 0.30 | 0.47 | 0.24 | 0.43 | 0.44 | 0.51 | 0.55 |
| 2 | AAC | −0.05 | −0.62 | −0.63 | 0.07 | 0.12 | −0.62 | −0.11 | −0.52 | −0.53 | −0.26 | −0.04 | −0.25 |
| 3 | AAG | −0.10 | −0.61 | −0.65 | 0.12 | 0.21 | −0.59 | 0.26 | −0.53 | −0.59 | −0.16 | 0.20 | 0.11 |
| 4 | AAT | 0.61 | 0.16 | 0.35 | 0.58 | 0.63 | 0.28 | 0.62 | 0.40 | 0.42 | 0.44 | 0.38 | 0.44 |
| 5 | ACA | 0.49 | 0.22 | 0.13 | 0.28 | 0.52 | 0.49 | 0.78 | 0.49 | −0.19 | 0.62 | −0.07 | 0.38 |
| 6 | ACC | −0.13 | −0.71 | −0.71 | −0.18 | −0.15 | −0.67 | 0.00 | −0.56 | −0.54 | −0.15 | 0.12 | 0.14 |
| 7 | ACG | 0.50 | 0.37 | 0.29 | 0.53 | 0.57 | 0.56 | 0.62 | 0.61 | 0.07 | 0.89 | 0.17 | 0.49 |
| 8 | ACT | 0.31 | −0.16 | 0.07 | 0.61 | 0.19 | −0.34 | 0.49 | −0.34 | −0.27 | 0.48 | 0.83 | 0.53 |
| 9 | AGA | 0.25 | −0.53 | −0.59 | 0.10 | 0.03 | −0.59 | 0.27 | −0.38 | −0.53 | 0.19 | 0.24 | −0.01 |
| 10 | AGC | 0.54 | −0.04 | 0.21 | 0.55 | 0.59 | 0.17 | 1.00 | 0.19 | 0.38 | −0.02 | 0.31 | 0.46 |
| 11 | AGG | 0.42 | 0.44 | 0.45 | 0.47 | 0.68 | 0.33 | 0.69 | 0.71 | 0.29 | 0.66 | 0.56 | 0.84 |
| 12 | AGT | 0.49 | 0.04 | 0.48 | 0.46 | 0.72 | 0.47 | 0.69 | 0.31 | 0.70 | 0.57 | 0.39 | 0.52 |
| 13 | ATA | 0.56 | 0.50 | 0.64 | 0.67 | 0.53 | 0.32 | 0.63 | 0.47 | 0.58 | 0.75 | 0.58 | 0.59 |
| 14 | ATC | −0.31 | −0.66 | −0.68 | −0.28 | −0.11 | −0.55 | 0.04 | −0.63 | −0.67 | 0.30 | 0.14 | −0.10 |
| 15 | ATG | 0.23 | −0.30 | −0.25 | 0.29 | 0.39 | −0.12 | 0.56 | −0.33 | −0.30 | 0.47 | 0.16 | 0.20 |
| 16 | ATT | 0.49 | −0.20 | 0.02 | 0.50 | 0.55 | −0.15 | 0.49 | 0.01 | −0.07 | 0.67 | 0.48 | 0.64 |
| 17 | CAA | 0.22 | −0.40 | −0.43 | 0.25 | 0.26 | −0.48 | 0.50 | −0.29 | −0.36 | 0.00 | 0.23 | −0.16 |
| 18 | CAC | 0.10 | −0.55 | −0.67 | 0.07 | 0.12 | −0.62 | 0.44 | −0.53 | −0.59 | 0.31 | 0.61 | −0.02 |
| 19 | CAG | 0.54 | 0.40 | 0.20 | 0.16 | 0.43 | 0.35 | −0.08 | 0.60 | 0.19 | 0.11 | 0.62 | 0.39 |
| 20 | CAT | 0.54 | −0.09 | 0.31 | 0.50 | 0.51 | 0.07 | 0.45 | 0.36 | 0.46 | 0.74 | 0.62 | 0.87 |
| 21 | CCA | 0.20 | −0.52 | −0.64 | −0.15 | 0.12 | −0.54 | 0.45 | −0.53 | −0.61 | 0.13 | −0.09 | −0.11 |
| 22 | CCC | 0.41 | −0.03 | −0.07 | 0.27 | 0.58 | 0.09 | 0.18 | −0.08 | 0.21 | 0.63 | 0.65 | 0.49 |
| 23 | CCG | 0.84 | 0.75 | 0.63 | 0.75 | 0.80 | 1.00 | 0.85 | 0.94 | 0.73 | 0.53 | 1.00 | 0.89 |
| 24 | CCT | 0.45 | 0.10 | 0.28 | 0.51 | 0.71 | −0.20 | 0.22 | 0.10 | 0.54 | 0.81 | 0.64 | 0.61 |
| 25 | CGA | 0.83 | 0.56 | 0.92 | 0.70 | 0.87 | 0.80 | 0.40 | 0.88 | 0.83 | 0.67 | 1.00 | 0.09 |
| 26 | CGC | 0.46 | 0.34 | 0.33 | 0.65 | 0.52 | −0.14 | 0.29 | 0.42 | 0.80 | 1.00 | 1.00 | 0.19 |
| 27 | CGG | 0.71 | 0.44 | 0.73 | 0.62 | 0.54 | 1.00 | 0.49 | 1.00 | 0.86 | 0.43 | 0.68 | 1.00 |
| 28 | CGT | 0.19 | −0.25 | −0.18 | 0.13 | 0.32 | −0.44 | 0.39 | −0.23 | 0.07 | 0.66 | 0.53 | −0.04 |
| 29 | CTA | 0.39 | 0.19 | 0.24 | 0.47 | 0.47 | 0.61 | 0.41 | 0.22 | −0.39 | 0.74 | 0.34 | 0.41 |
| 30 | CTC | 0.67 | 0.17 | 0.03 | 0.40 | 0.68 | −0.21 | −0.29 | 0.57 | 0.65 | 0.69 | 0.74 | 0.68 |
| 31 | CTG | 0.42 | 0.38 | 0.29 | 0.35 | 0.62 | 0.33 | 0.72 | 0.54 | 0.78 | 0.50 | 0.79 | 0.66 |
| 32 | CTT | 0.78 | 0.60 | 0.61 | 0.71 | 0.89 | 0.54 | 0.61 | 0.55 | 0.76 | 0.72 | 1.00 | 0.81 |
| 33 | GAA | 0.22 | −0.35 | −0.37 | 0.24 | 0.28 | −0.40 | 0.28 | −0.31 | −0.39 | −0.03 | 0.50 | 0.13 |
| 34 | GAC | −0.04 | −0.57 | −0.62 | −0.07 | 0.20 | −0.62 | 0.44 | −0.50 | −0.44 | 0.17 | 0.22 | 0.02 |
| 35 | GAG | 0.49 | −0.03 | −0.03 | 0.30 | 0.46 | 0.38 | 0.47 | 0.30 | 0.32 | 0.19 | 0.53 | 0.41 |
| 36 | GAT | 0.44 | 0.19 | 0.27 | 0.40 | 0.68 | −0.05 | 0.42 | 0.12 | 0.34 | 0.55 | 0.53 | 0.78 |
| 37 | GCA | 0.58 | 0.37 | 0.27 | 0.62 | 0.51 | 0.40 | 0.60 | 0.61 | −0.07 | 0.56 | 0.22 | 0.45 |
| 38 | GCC | −0.02 | −0.58 | −0.62 | −0.07 | 0.10 | −0.57 | 0.41 | −0.53 | −0.51 | 0.51 | 0.48 | 0.70 |
| 39 | GCG | 0.83 | 0.45 | 0.26 | 0.56 | 0.79 | 0.50 | 0.71 | 0.65 | 0.67 | 0.81 | 0.82 | 0.67 |
| 40 | GCT | 0.26 | −0.46 | −0.40 | 0.21 | 0.35 | −0.55 | 0.38 | −0.37 | −0.28 | 0.56 | 0.52 | 0.43 |
| 41 | GGA | 0.64 | 0.46 | 0.46 | 0.58 | 0.69 | 0.39 | 0.63 | 0.50 | 0.43 | 0.72 | 0.89 | 0.74 |
| 42 | GGC | 0.55 | 0.00 | 0.27 | 0.49 | 0.68 | 0.49 | 0.79 | 0.02 | 0.37 | 0.24 | 0.67 | 0.44 |
| 43 | GGG | 0.62 | 0.55 | 0.40 | 0.73 | 0.49 | 0.48 | 0.43 | 0.30 | 0.39 | 0.39 | 0.61 | 0.86 |
| 44 | GGT | 0.03 | −0.61 | −0.60 | 0.08 | 0.32 | −0.56 | 0.41 | −0.58 | −0.55 | 0.53 | 0.52 | 0.55 |
| 45 | GTA | 0.66 | 0.37 | 0.47 | 0.42 | 0.59 | 0.53 | 0.58 | 0.26 | 0.54 | 0.72 | 0.34 | 0.69 |
| 46 | GTC | −0.17 | −0.63 | −0.70 | −0.17 | 0.27 | −0.65 | 0.67 | −0.60 | −0.56 | −0.36 | 0.74 | 0.21 |
| 47 | GTG | 0.51 | 0.10 | 0.07 | 0.64 | 0.54 | 0.25 | 0.52 | 0.48 | −0.20 | 0.50 | 0.66 | 0.57 |
| 48 | GTT | 0.31 | −0.27 | −0.21 | 0.21 | 0.59 | −0.45 | 0.66 | −0.37 | −0.17 | 0.56 | 0.52 | 0.67 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | −0.09 | −0.58 | −0.61 | 0.08 | 0.04 | −0.56 | 0.42 | −0.57 | −0.57 | 0.30 | 0.52 | −0.09 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.60 | 0.06 | 0.43 | 0.61 | 0.67 | 0.42 | 0.66 | 0.30 | 0.59 | 0.52 | 0.64 | 0.64 |
| 53 | TCA | 0.69 | 0.22 | 0.07 | 0.48 | 0.37 | 0.20 | 0.29 | 0.52 | −0.29 | 0.19 | 0.03 | 0.39 |
| 54 | TCC | 0.04 | −0.68 | −0.74 | −0.25 | −0.17 | −0.66 | −0.13 | −0.59 | −0.60 | −0.09 | 0.10 | −0.02 |
| 55 | TCG | −0.01 | 0.17 | −0.05 | 0.38 | 0.68 | 0.80 | 0.59 | 0.12 | −0.23 | 0.65 | 0.22 | 0.21 |

TABLE C.10-continued

CPW matrix Saccaromyces. cerevisiae highly expressed sequences (left codon indicated in column 2, right codon indicated in row 2). Host cell: S. cerevisiae; Sequence data: full S. cerevisiae genome; Highly expressed group: 300 seqs.

| | | | | | | | | | | | | |
|---|---|---|---|---|---|---|---|---|---|---|---|---|
| 56 | TCT | 0.21 | −0.45 | −0.36 | 0.38 | 0.29 | −0.54 | 0.11 | −0.44 | 0.06 | 0.67 | 0.50 | 0.41 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.26 | 0.62 | 0.12 | 0.42 | 0.11 | 0.02 | 0.50 | 0.70 | 0.34 | 0.29 | 0.76 | 0.51 |
| 59 | TGG | 0.15 | −0.17 | −0.17 | 0.14 | 0.59 | −0.25 | 0.16 | −0.28 | −0.33 | 0.35 | 0.17 | 0.33 |
| 60 | TGT | 0.09 | −0.43 | −0.30 | 0.00 | 0.45 | −0.52 | 0.23 | −0.30 | −0.26 | 0.13 | 0.40 | 0.70 |
| 61 | TTA | 0.57 | −0.21 | 0.06 | 0.61 | 0.25 | −0.38 | 0.58 | −0.14 | −0.19 | 0.16 | 0.18 | 0.35 |
| 62 | TTC | −0.20 | −0.61 | −0.64 | −0.13 | 0.26 | −0.60 | 0.42 | −0.51 | −0.58 | −0.10 | 0.44 | −0.07 |
| 63 | TTG | −0.27 | −0.64 | −0.68 | −0.28 | 0.17 | −0.65 | 0.43 | −0.59 | −0.62 | −0.04 | 0.21 | −0.06 |
| 64 | TTT | 0.68 | 0.33 | 0.47 | 0.61 | 0.54 | 0.07 | 0.47 | 0.34 | 0.32 | 0.39 | 0.43 | 0.53 |

| | | AAA 1 | AAC 2 | AAG 3 | AAT 4 | ACA 5 | ACC 6 | ACG 7 | ACT 8 | AGA 9 | AGC 10 | AGG 11 | AGT 12 |
|---|---|---|---|---|---|---|---|---|---|---|---|---|---|
| | | 13 ATA | 14 ATC | 15 ATG | 16 ATT | 17 CAA | 18 CAC | 19 CAG | 20 CAT | 21 CCA | 22 CCC | 23 CCG | 24 CCT |
| 1 | AAA | 0.52 | 0.14 | 0.16 | 0.15 | 0.22 | 0.25 | 0.34 | 0.54 | 0.04 | 0.54 | 0.59 | 0.32 |
| 2 | AAC | 0.53 | −0.61 | −0.24 | −0.41 | −0.45 | −0.53 | 0.05 | −0.33 | −0.50 | 0.40 | 0.18 | −0.19 |
| 3 | AAG | 0.62 | −0.56 | −0.18 | −0.31 | −0.41 | −0.55 | 0.35 | −0.21 | −0.51 | 0.16 | 0.57 | −0.16 |
| 4 | AAT | 0.71 | 0.03 | 0.22 | 0.39 | 0.26 | 0.44 | 0.63 | 0.52 | 0.20 | 0.09 | 0.44 | 0.36 |
| 5 | ACA | 0.68 | 0.51 | 0.29 | 0.41 | 0.60 | 0.33 | 0.41 | 0.22 | 0.01 | 0.50 | 0.94 | 0.52 |
| 6 | ACC | 0.44 | −0.61 | −0.54 | −0.59 | −0.26 | −0.49 | 0.33 | 0.08 | −0.40 | 0.13 | 0.45 | 0.30 |
| 7 | ACG | 0.54 | 0.12 | 0.18 | 0.63 | 0.14 | 0.43 | 0.34 | 0.42 | 0.09 | 0.00 | 0.44 | 0.55 |
| 8 | ACT | 0.38 | −0.30 | 0.41 | −0.12 | −0.48 | −0.44 | 0.43 | 0.08 | −0.54 | 0.46 | 0.60 | −0.12 |
| 9 | AGA | 0.47 | −0.48 | −0.21 | −0.32 | −0.26 | −0.41 | 0.21 | 0.06 | −0.54 | 0.44 | 0.44 | −0.11 |
| 10 | AGC | 0.36 | 0.02 | 0.59 | 0.54 | 0.09 | 0.13 | 0.39 | 0.51 | 0.54 | 0.56 | 1.00 | 0.10 |
| 11 | AGG | 0.50 | 0.46 | 0.28 | 0.27 | 0.51 | 0.25 | 0.39 | 0.39 | 0.19 | 0.58 | 0.47 | 0.50 |
| 12 | AGT | 0.63 | 0.52 | 0.54 | 0.19 | 0.52 | 0.63 | 0.79 | 0.42 | 0.61 | 0.90 | 0.62 | 0.48 |
| 13 | ATA | 0.66 | 0.51 | 0.37 | 0.68 | 0.79 | 0.78 | 0.68 | 0.49 | 0.53 | 0.59 | 0.77 | 0.65 |
| 14 | ATC | 0.41 | −0.64 | −0.47 | −0.46 | −0.44 | −0.39 | 0.38 | 0.09 | −0.39 | 0.35 | 0.43 | −0.02 |
| 15 | ATG | 0.71 | −0.25 | 0.00 | −0.19 | −0.05 | −0.19 | 0.11 | 0.13 | −0.33 | 0.27 | 0.59 | 0.26 |
| 16 | ATT | 0.62 | −0.24 | 0.28 | −0.13 | −0.30 | −0.51 | 0.21 | 0.17 | −0.48 | 0.30 | 0.39 | −0.02 |
| 17 | CAA | 0.54 | −0.50 | −0.22 | −0.16 | −0.19 | −0.17 | 0.26 | −0.08 | −0.37 | 0.36 | 0.42 | −0.05 |
| 18 | CAC | 0.69 | −0.52 | −0.45 | −0.46 | −0.27 | −0.61 | −0.17 | 0.28 | −0.21 | 0.78 | 0.32 | 0.12 |
| 19 | CAG | 0.85 | 0.27 | 0.60 | 0.29 | 0.22 | 0.37 | 0.07 | 0.23 | 0.45 | 0.60 | 0.37 | −0.02 |
| 20 | CAT | 0.48 | 0.09 | 0.46 | 0.23 | 0.07 | 0.13 | 0.41 | 0.26 | −0.27 | 0.58 | 0.62 | −0.19 |
| 21 | CCA | 0.53 | −0.52 | −0.38 | −0.42 | −0.12 | −0.21 | 0.02 | 0.36 | −0.47 | 0.53 | 0.74 | −0.22 |
| 22 | CCC | 0.58 | −0.36 | 0.36 | 0.19 | 0.35 | 0.12 | 0.09 | 0.67 | 0.06 | 0.65 | 1.00 | 0.29 |
| 23 | CCG | 0.69 | 0.42 | 0.43 | 0.62 | 0.59 | 0.26 | 0.49 | 0.79 | 0.40 | −0.09 | 0.72 | 0.78 |
| 24 | CCT | 0.78 | 0.13 | 0.45 | 0.13 | −0.33 | −0.54 | 0.28 | −0.28 | −0.22 | 0.21 | 0.10 | 0.14 |
| 25 | CGA | 0.33 | 0.76 | 0.70 | 0.79 | 0.90 | 0.51 | 0.78 | 1.00 | 0.68 | 1.00 | 1.00 | 1.00 |
| 26 | CGC | 0.47 | −0.01 | 0.10 | 0.75 | −0.10 | −0.43 | −0.38 | 0.35 | 0.43 | 0.51 | 1.00 | 0.01 |
| 27 | CGG | 1.00 | 0.79 | 1.00 | 0.53 | 0.82 | 1.00 | 0.62 | 1.00 | 1.00 | 0.30 | 1.00 | 1.00 |
| 28 | CGT | 0.43 | −0.35 | −0.18 | −0.32 | −0.56 | −0.60 | 0.54 | 0.03 | −0.38 | −0.03 | 0.47 | 0.05 |
| 29 | CTA | 0.61 | 0.58 | 0.45 | 0.31 | 0.12 | −0.23 | 0.04 | −0.10 | −0.28 | −0.12 | 0.90 | 0.14 |
| 30 | CTC | 0.58 | 0.46 | 0.47 | 0.33 | 0.74 | 0.59 | 0.66 | 0.89 | 0.65 | 0.82 | 0.77 | 0.72 |
| 31 | CTG | 0.60 | −0.10 | 0.35 | 0.12 | 0.16 | −0.17 | 0.27 | −0.04 | 0.25 | −0.20 | 0.88 | 0.46 |
| 32 | CTT | 0.85 | 0.63 | 0.53 | 0.54 | 0.30 | 0.26 | 0.69 | 0.59 | 0.46 | 0.27 | 0.59 | 0.34 |
| 33 | GAA | 0.60 | −0.32 | −0.19 | −0.29 | −0.19 | −0.31 | 0.33 | 0.34 | −0.26 | 0.53 | 0.56 | −0.11 |
| 34 | GAC | 0.61 | −0.40 | −0.31 | −0.24 | −0.47 | −0.41 | −0.19 | −0.21 | −0.41 | 0.43 | 0.61 | −0.23 |
| 35 | GAG | 0.64 | 0.12 | 0.54 | 0.23 | 0.03 | 0.15 | 0.37 | −0.22 | 0.14 | 0.42 | 0.26 | −0.24 |
| 36 | GAT | 0.69 | −0.29 | 0.24 | −0.02 | 0.27 | 0.24 | 0.60 | 0.22 | −0.12 | 0.36 | 0.58 | 0.16 |
| 37 | GCA | 0.82 | 0.45 | 0.44 | 0.58 | 0.39 | 0.29 | 0.69 | 0.49 | 0.27 | 0.76 | 0.82 | 0.51 |
| 38 | GCC | 0.40 | −0.58 | −0.41 | −0.58 | −0.22 | 0.11 | 0.51 | 0.12 | −0.44 | 0.36 | 0.76 | 0.31 |
| 39 | GCG | 0.81 | 0.59 | 0.78 | 0.57 | 0.46 | 0.34 | 0.12 | 0.41 | 0.27 | 0.50 | 0.84 | 0.74 |
| 40 | GCT | 0.75 | −0.42 | −0.15 | −0.30 | −0.48 | −0.59 | 0.46 | −0.03 | −0.61 | 0.46 | 0.66 | −0.10 |
| 41 | GGA | 0.74 | 0.69 | 0.63 | 0.52 | 0.41 | 0.48 | 0.65 | 0.60 | 0.52 | 0.39 | 0.89 | 0.33 |
| 42 | GGC | 0.82 | 0.42 | 0.52 | 0.47 | −0.32 | −0.32 | 0.14 | −0.03 | −0.18 | 0.30 | 0.87 | −0.07 |
| 43 | GGG | 0.81 | 0.33 | 0.64 | 0.79 | 0.66 | 0.53 | 0.51 | 0.73 | 0.31 | −0.11 | 0.59 | 0.01 |
| 44 | GGT | 0.49 | −0.62 | −0.42 | −0.50 | −0.41 | −0.52 | 0.60 | 0.03 | −0.53 | 0.34 | 0.78 | 0.01 |
| 45 | GTA | 0.72 | 0.63 | 0.67 | 0.68 | 0.43 | 0.48 | 0.65 | 0.34 | 0.27 | 0.74 | 0.75 | 0.54 |
| 46 | GTC | 0.60 | −0.70 | −0.32 | −0.54 | −0.46 | −0.64 | 0.57 | −0.28 | −0.43 | 0.16 | 0.91 | 0.32 |
| 47 | GTG | 0.72 | 0.40 | 0.20 | 0.49 | 0.16 | 0.09 | 0.22 | 0.54 | 0.26 | −0.19 | 0.72 | 0.41 |
| 48 | GTT | 0.76 | −0.42 | −0.19 | −0.26 | −0.32 | −0.18 | 0.50 | 0.20 | −0.54 | 0.34 | 0.44 | −0.06 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.30 | −0.57 | −0.26 | −0.19 | −0.27 | −0.27 | −0.12 | −0.32 | −0.53 | 0.48 | 0.72 | −0.09 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.59 | 0.26 | 0.26 | 0.10 | 0.10 | 0.18 | 0.49 | 0.42 | 0.01 | 0.66 | 0.50 | 0.25 |
| 53 | TCA | 0.61 | 0.55 | 0.04 | 0.56 | 0.38 | 0.38 | 0.25 | 0.31 | −0.16 | 0.09 | 0.61 | 0.22 |
| 54 | TCC | 0.29 | −0.71 | −0.59 | −0.56 | −0.14 | −0.52 | 0.25 | 0.14 | −0.27 | 0.48 | 0.61 | 0.31 |
| 55 | TCG | 0.52 | −0.19 | 0.01 | 0.41 | −0.16 | −0.19 | −0.17 | 0.04 | −0.19 | 0.01 | 1.00 | 0.15 |
| 56 | TCT | 0.55 | −0.49 | 0.24 | −0.29 | −0.50 | −0.50 | 0.16 | −0.22 | −0.62 | −0.15 | −0.02 | −0.10 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.32 | 0.26 | 0.19 | 0.32 | −0.27 | −0.49 | 0.84 | 0.11 | −0.25 | 0.21 | 1.00 | 0.60 |
| 59 | TGG | 0.70 | −0.33 | 0.00 | −0.13 | −0.16 | −0.36 | 0.42 | 0.31 | −0.28 | 0.40 | 0.34 | 0.16 |
| 60 | TGT | 0.43 | −0.48 | −0.11 | −0.13 | −0.02 | −0.25 | 0.03 | 0.46 | −0.37 | 0.35 | 0.39 | 0.01 |

TABLE C.10-continued

CPW matrix *Saccaromyces. cerevisiae* highly expressed sequences (left codon indicated in column 2, right codon indicated in row 2). Host cell: *S. cerevisiae*; Sequence data: full *S. cerevisiae* genome; Highly expressed group: 300 seqs.

| | | | | | | | | | | | | |
|---|---|---|---|---|---|---|---|---|---|---|---|---|
| 61 | TTA | 0.62 | −0.27 | 0.07 | 0.16 | −0.20 | −0.25 | 0.14 | 0.26 | −0.14 | 0.41 | 0.50 | 0.00 |
| 62 | TTC | 0.54 | −0.55 | −0.23 | −0.32 | −0.55 | −0.62 | 0.04 | −0.19 | −0.62 | −0.37 | 0.83 | −0.35 |
| 63 | TTG | 0.39 | −0.58 | −0.44 | −0.58 | −0.34 | −0.55 | 0.00 | 0.19 | −0.56 | −0.24 | 0.65 | −0.10 |
| 64 | TTT | 0.79 | −0.01 | 0.21 | 0.09 | 0.52 | 0.32 | 0.67 | 0.60 | 0.54 | 0.28 | 0.83 | 0.59 |

| | ATA 13 | ATC 14 | ATG 15 | ATT 16 | CAA 17 | CAC 18 | CAG 19 | CAT 20 | CCA 21 | CCC 22 | CCG 23 | CCT 24 |
|---|---|---|---|---|---|---|---|---|---|---|---|---|

| | | 25 CGA | 26 CGC | 27 CGG | 28 CGT | 29 CTA | 30 CTC | 31 CTG | 32 CTT | 33 GAA | 34 GAC | 35 GAG | 36 GAT |
|---|---|---|---|---|---|---|---|---|---|---|---|---|---|
| 1 | AAA | 0.64 | 0.63 | 0.82 | 0.24 | 0.21 | 0.83 | 0.06 | 0.62 | 0.33 | 0.42 | 0.39 | 0.33 |
| 2 | AAC | 0.87 | −0.17 | −0.08 | −0.53 | 0.28 | −0.23 | −0.17 | 0.20 | −0.30 | −0.27 | 0.03 | −0.04 |
| 3 | AAG | 0.85 | 0.30 | 0.75 | −0.49 | −0.12 | 0.52 | −0.02 | 0.31 | −0.40 | −0.54 | −0.05 | −0.14 |
| 4 | AAT | 0.66 | 0.49 | 0.85 | 0.35 | 0.22 | 0.56 | 0.44 | 0.56 | 0.15 | −0.10 | 0.30 | 0.22 |
| 5 | ACA | 0.73 | 0.35 | 0.30 | 0.38 | 0.69 | 0.42 | 0.57 | 0.64 | 0.34 | 0.27 | 0.29 | 0.45 |
| 6 | ACC | 0.80 | 1.00 | 0.32 | −0.01 | 0.28 | 0.36 | 0.77 | 0.43 | −0.23 | −0.20 | 0.25 | −0.18 |
| 7 | ACG | 1.00 | 0.27 | 1.00 | 0.38 | 0.59 | 0.51 | −0.11 | 0.05 | 0.47 | 0.38 | 0.35 | 0.56 |
| 8 | ACT | 1.00 | 0.70 | 0.79 | −0.12 | −0.06 | 0.80 | 0.44 | 0.08 | −0.36 | −0.42 | −0.02 | −0.20 |
| 9 | AGA | 0.75 | 0.51 | 0.29 | −0.24 | 0.06 | 0.63 | 0.21 | 0.31 | −0.31 | −0.38 | 0.11 | −0.14 |
| 10 | AGC | 0.71 | −0.27 | 0.51 | 0.41 | 0.59 | 0.36 | 0.91 | 0.64 | 0.14 | 0.33 | 0.28 | 0.17 |
| 11 | AGG | 0.45 | 0.78 | 0.05 | 0.53 | 0.42 | 0.45 | 0.20 | 0.63 | 0.38 | 0.33 | 0.43 | 0.55 |
| 12 | AGT | 1.00 | 0.29 | 0.66 | 0.30 | 0.72 | 0.56 | 0.76 | 0.90 | 0.05 | −0.09 | 0.00 | −0.04 |
| 13 | ATA | 0.86 | 1.00 | 0.30 | 0.86 | 0.46 | 0.82 | 0.46 | 0.71 | 0.69 | 0.71 | 0.55 | 0.65 |
| 14 | ATC | 1.00 | 0.29 | 0.24 | −0.49 | 0.49 | 0.50 | −0.01 | 0.24 | −0.15 | −0.26 | 0.07 | −0.08 |
| 15 | ATG | 1.00 | 0.58 | 0.80 | 0.17 | 0.15 | 0.50 | −0.14 | −0.05 | −0.17 | −0.31 | 0.49 | 0.24 |
| 16 | ATT | 0.83 | 0.60 | 0.71 | −0.27 | 0.02 | 0.26 | 0.24 | −0.23 | −0.34 | −0.44 | 0.07 | −0.05 |
| 17 | CAA | 0.91 | 0.49 | 0.85 | −0.16 | 0.18 | 0.51 | 0.11 | 0.56 | −0.21 | −0.10 | 0.10 | −0.09 |
| 18 | CAC | 1.00 | 1.00 | 0.51 | −0.54 | 0.57 | 0.66 | 0.46 | 0.24 | −0.27 | −0.42 | −0.03 | 0.01 |
| 19 | CAG | 0.44 | −0.11 | 0.04 | −0.05 | 0.24 | 0.47 | 0.37 | 0.71 | 0.26 | −0.07 | 0.48 | 0.39 |
| 20 | CAT | 0.68 | −0.42 | 0.72 | −0.32 | 0.32 | 0.53 | 0.19 | 0.32 | 0.13 | −0.17 | 0.20 | 0.32 |
| 21 | CCA | 0.73 | 0.36 | 0.54 | −0.13 | −0.08 | 0.52 | 0.31 | 0.31 | −0.43 | −0.24 | 0.07 | −0.10 |
| 22 | CCC | 1.00 | −0.39 | 0.42 | 0.65 | 0.22 | 0.59 | 0.56 | 0.72 | 0.67 | 0.29 | 0.68 | 0.52 |
| 23 | CCG | 0.57 | 1.00 | 0.26 | 1.00 | 0.56 | −0.04 | −0.10 | 0.18 | 0.41 | 0.26 | 0.43 | 0.04 |
| 24 | CCT | 0.82 | −0.04 | 0.70 | −0.41 | −0.10 | 0.47 | 0.44 | 0.81 | 0.03 | 0.04 | 0.45 | −0.07 |
| 25 | CGA | 1.00 | 1.00 | 1.00 | 1.00 | 0.83 | 0.19 | 1.00 | 0.64 | 0.73 | 0.88 | 0.74 | 0.80 |
| 26 | CGC | 1.00 | 0.23 | −0.09 | −0.49 | −0.01 | 0.52 | 0.49 | 1.00 | 0.67 | 0.71 | 0.85 | 0.22 |
| 27 | CGG | −0.46 | 1.00 | 1.00 | 1.00 | 0.42 | −0.27 | −0.09 | 0.69 | 0.81 | 0.58 | 1.00 | 0.89 |
| 28 | CGT | 1.00 | 1.00 | 1.00 | −0.75 | −0.11 | 0.80 | −0.39 | 0.08 | −0.48 | −0.40 | 0.15 | −0.25 |
| 29 | CTA | 0.84 | 1.00 | 0.72 | −0.53 | −0.05 | 0.76 | −0.07 | 0.36 | 0.13 | 0.03 | 0.29 | 0.11 |
| 30 | CTC | 0.62 | 0.08 | 1.00 | 0.80 | 0.76 | 1.00 | 0.85 | 0.75 | 0.69 | 0.04 | 0.85 | 0.72 |
| 31 | CTG | 0.38 | 0.51 | 0.30 | 0.27 | 0.05 | −0.17 | −0.27 | 0.39 | 0.13 | −0.26 | 0.30 | 0.17 |
| 32 | CTT | 0.83 | 0.79 | −0.32 | 0.39 | 0.09 | 0.24 | 0.12 | 0.49 | 0.42 | 0.10 | 0.70 | 0.50 |
| 33 | GAA | 0.76 | 0.71 | 0.42 | −0.31 | −0.18 | 0.61 | 0.16 | 0.50 | −0.20 | −0.18 | 0.18 | −0.05 |
| 34 | GAC | 0.57 | −0.02 | 0.51 | −0.70 | 0.42 | 0.63 | 0.27 | 0.55 | −0.12 | −0.21 | 0.11 | 0.15 |
| 35 | GAG | 0.77 | −0.08 | 0.61 | 0.02 | −0.07 | 0.15 | 0.21 | 0.30 | 0.30 | 0.16 | 0.27 | 0.32 |
| 36 | GAT | 0.92 | 0.63 | 0.87 | −0.39 | 0.27 | 0.53 | 0.43 | 0.40 | −0.09 | −0.21 | 0.33 | 0.14 |
| 37 | GCA | 0.79 | 0.51 | 0.12 | 0.00 | 0.64 | 0.82 | 0.67 | 0.48 | 0.44 | 0.18 | 0.41 | 0.50 |
| 38 | GCC | 1.00 | 0.50 | 0.76 | −0.38 | 0.17 | 0.34 | 0.56 | −0.03 | 0.14 | −0.12 | 0.47 | 0.18 |
| 39 | GCG | 1.00 | 0.36 | 1.00 | 0.18 | 0.33 | −0.10 | 0.23 | 0.43 | 0.57 | 0.14 | 0.10 | 0.45 |
| 40 | GCT | 0.83 | 0.50 | 0.86 | −0.49 | 0.02 | 0.46 | 0.18 | 0.20 | −0.48 | −0.46 | 0.08 | −0.20 |
| 41 | GGA | 0.69 | 0.82 | 1.00 | 0.45 | 0.57 | 0.63 | 0.55 | 0.71 | 0.58 | 0.63 | 0.60 | 0.57 |
| 42 | GGC | 0.82 | −0.21 | 1.00 | −0.50 | 0.46 | 0.36 | 0.37 | 0.42 | 0.36 | 0.45 | 0.41 | 0.27 |
| 43 | GGG | 0.43 | 0.66 | 0.51 | 0.28 | −0.08 | −0.03 | 0.08 | 0.23 | 0.78 | 0.74 | 0.58 | 0.78 |
| 44 | GGT | 0.84 | 0.81 | 0.87 | −0.57 | −0.27 | 0.49 | 0.30 | 0.14 | −0.48 | −0.54 | −0.05 | −0.27 |
| 45 | GTA | 0.82 | 0.58 | 0.70 | 0.02 | 0.61 | 0.54 | 0.56 | 0.34 | 0.29 | 0.36 | 0.19 | 0.46 |
| 46 | GTC | 0.81 | 0.09 | 1.00 | −0.59 | 0.33 | 0.60 | 0.15 | −0.03 | −0.22 | −0.44 | 0.36 | 0.04 |
| 47 | GTG | 0.80 | 0.06 | 1.00 | 0.30 | 0.26 | 0.59 | 0.17 | 0.16 | −0.02 | −0.09 | 0.04 | 0.28 |
| 48 | GTT | 1.00 | 0.05 | 0.83 | −0.56 | 0.25 | 0.27 | 0.50 | 0.04 | −0.24 | −0.41 | 0.41 | 0.09 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.29 | 0.16 | 0.70 | −0.66 | 0.25 | 0.25 | 0.05 | 0.37 | −0.21 | −0.33 | −0.03 | −0.08 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.87 | 0.84 | 0.54 | −0.02 | 0.40 | 0.50 | 0.24 | 0.55 | 0.10 | −0.11 | 0.26 | 0.34 |
| 53 | TCA | 1.00 | 0.64 | 0.23 | 0.24 | 0.23 | 0.50 | 0.33 | 0.59 | 0.32 | 0.52 | 0.48 | 0.36 |
| 54 | TCC | 0.80 | 0.03 | 1.00 | −0.60 | 0.19 | 0.43 | 0.52 | 0.29 | −0.20 | −0.29 | −0.06 | −0.01 |
| 55 | TCG | 1.00 | 0.22 | 1.00 | 0.34 | 0.08 | 0.64 | −0.31 | 0.43 | 0.54 | 0.07 | 0.31 | 0.28 |
| 56 | TCT | 0.63 | −0.02 | 1.00 | −0.63 | −0.29 | 0.32 | 0.31 | 0.29 | −0.45 | −0.48 | 0.34 | −0.09 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 1.00 | −0.41 | 1.00 | 0.28 | 0.58 | 0.34 | 0.47 | −0.04 | 0.05 | 0.06 | 0.70 | 0.94 |
| 59 | TGG | 1.00 | 0.42 | 0.58 | 0.51 | 0.23 | 0.54 | −0.18 | 0.79 | −0.15 | −0.29 | 0.41 | 0.21 |
| 60 | TGT | 1.00 | −0.36 | 1.00 | −0.65 | 0.14 | −0.02 | −0.29 | 0.36 | −0.20 | −0.19 | 0.09 | −0.32 |

TABLE C.10-continued

CPW matrix *Saccaromyces. cerevisiae* highly expressed sequences (left codon indicated in column 2, right codon indicated in row 2). Host cell: *S. cerevisiae*; Sequence data: full *S. cerevisiae* genome; Highly expressed group: 300 seqs.

| | | | | | | | | | | | | |
|---|---|---|---|---|---|---|---|---|---|---|---|---|
| 61 | TTA | 0.75 | 0.70 | 0.86 | 0.07 | 0.02 | 0.82 | 0.28 | 0.26 | 0.15 | 0.25 | 0.38 | 0.28 |
| 62 | TTC | 0.67 | 0.03 | 1.00 | -0.57 | 0.08 | -0.01 | 0.28 | 0.21 | -0.10 | -0.22 | 0.20 | 0.03 |
| 63 | TTG | 0.83 | 0.70 | 0.72 | -0.39 | -0.29 | 0.64 | 0.19 | 0.59 | -0.52 | -0.49 | -0.08 | -0.28 |
| 64 | TTT | 0.89 | 0.20 | 0.81 | 0.60 | 0.59 | 0.83 | 0.60 | 0.72 | -0.10 | -0.17 | 0.29 | 0.19 |

| | CGA 25 | CGC 26 | CGG 27 | CGT 28 | CTA 29 | CTC 30 | CTG 31 | CTT 32 | GAA 33 | GAC 34 | GAG 35 | GAT 36 |
|---|---|---|---|---|---|---|---|---|---|---|---|---|

| | | 37 GCA | 38 GCC | 39 GCG | 40 GCT | 41 GGA | 42 GGC | 43 GGG | 44 GGT | 45 GTA | 46 GTC | 47 GTG | 48 GTT |
|---|---|---|---|---|---|---|---|---|---|---|---|---|---|
| 1 | AAA | 0.64 | 0.29 | 0.72 | 0.30 | 0.68 | 0.54 | 0.46 | 0.09 | 0.57 | 0.10 | 0.31 | 0.24 |
| 2 | AAC | 0.43 | -0.37 | 0.73 | -0.33 | 0.52 | 0.27 | 0.16 | -0.46 | 0.50 | -0.49 | 0.32 | -0.43 |
| 3 | AAG | 0.24 | -0.51 | 0.33 | -0.58 | 0.39 | -0.28 | 0.41 | -0.56 | 0.65 | -0.58 | 0.38 | -0.48 |
| 4 | AAT | 0.45 | -0.09 | 0.14 | -0.14 | 0.48 | 0.26 | 0.20 | -0.11 | 0.69 | 0.00 | 0.27 | 0.03 |
| 5 | ACA | 0.60 | 0.51 | 0.70 | 0.41 | 0.44 | 0.61 | 0.60 | 0.32 | 0.64 | 0.50 | 0.40 | 0.57 |
| 6 | ACC | 0.40 | -0.38 | 0.62 | -0.44 | 0.72 | 0.27 | 0.61 | -0.57 | 0.50 | -0.60 | 0.12 | -0.39 |
| 7 | ACG | 0.63 | 0.55 | 0.42 | 0.31 | 0.62 | 0.26 | 0.50 | 0.54 | 0.19 | 0.36 | 0.15 | 0.63 |
| 8 | ACT | 0.25 | -0.45 | -0.12 | -0.52 | 0.67 | 0.47 | 0.47 | -0.61 | 0.27 | -0.49 | 0.16 | -0.42 |
| 9 | AGA | 0.51 | -0.33 | 0.34 | -0.48 | 0.62 | 0.11 | 0.63 | -0.57 | 0.55 | -0.43 | 0.25 | -0.35 |
| 10 | AGC | 0.54 | -0.15 | 0.89 | 0.29 | 0.33 | 0.23 | 0.66 | 0.33 | 0.26 | 0.35 | 0.77 | 0.43 |
| 11 | AGG | 0.51 | 0.24 | 0.72 | -0.05 | 0.72 | 0.17 | 0.80 | 0.44 | 0.58 | 0.30 | 0.33 | 0.63 |
| 12 | AGT | 0.40 | 0.19 | 0.62 | 0.28 | 0.46 | 0.38 | 0.54 | -0.16 | 0.58 | 0.10 | 0.17 | 0.27 |
| 13 | ATA | 0.70 | 0.90 | 0.86 | 0.75 | 0.69 | 0.62 | 0.64 | 0.75 | 0.78 | 0.58 | 0.68 | 0.68 |
| 14 | ATC | 0.58 | -0.09 | 0.42 | 0.09 | 0.70 | 0.27 | 0.22 | -0.49 | 0.60 | -0.10 | 0.08 | -0.18 |
| 15 | ATG | 0.40 | -0.23 | 0.60 | -0.25 | 0.38 | 0.35 | 0.36 | -0.31 | 0.55 | -0.17 | 0.30 | -0.26 |
| 16 | ATT | 0.18 | -0.55 | 0.32 | -0.54 | 0.37 | 0.04 | 0.21 | -0.49 | 0.28 | -0.59 | 0.17 | -0.38 |
| 17 | CAA | 0.44 | -0.07 | 0.63 | -0.51 | 0.58 | 0.09 | 0.43 | -0.52 | 0.39 | -0.41 | -0.03 | -0.28 |
| 18 | CAC | 0.39 | -0.29 | 0.56 | -0.36 | 0.80 | 0.14 | 0.75 | -0.58 | 0.59 | -0.48 | 0.23 | -0.32 |
| 19 | CAG | 0.45 | 0.59 | 0.36 | 0.31 | 0.81 | 0.45 | 0.82 | 0.52 | 0.43 | 0.57 | 0.50 | 0.40 |
| 20 | CAT | 0.53 | -0.11 | -0.12 | -0.11 | 0.66 | 0.43 | 0.37 | -0.18 | 0.47 | -0.13 | 0.23 | -0.02 |
| 21 | CCA | 0.22 | -0.30 | 0.59 | -0.52 | 0.52 | 0.05 | 0.30 | -0.59 | 0.43 | -0.31 | 0.36 | -0.30 |
| 22 | CCC | 0.40 | 0.40 | 0.74 | 0.32 | 0.67 | 0.26 | 1.00 | 0.39 | 0.43 | -0.22 | 0.58 | 0.50 |
| 23 | CCG | 0.68 | 0.75 | 0.67 | 0.69 | 0.79 | 0.17 | 0.81 | 0.85 | 0.52 | 0.23 | 0.46 | 0.55 |
| 24 | CCT | 0.31 | -0.11 | 0.20 | -0.22 | 0.67 | -0.09 | 0.69 | -0.23 | 0.04 | -0.42 | 0.20 | -0.26 |
| 25 | CGA | 1.00 | 0.86 | 1.00 | 0.92 | 1.00 | 0.81 | 1.00 | 1.00 | 0.83 | 0.81 | 1.00 | 0.70 |
| 26 | CGC | 0.63 | 0.34 | 0.68 | 0.50 | 0.42 | 0.55 | -0.07 | 0.22 | 0.79 | 0.55 | 0.53 | 0.41 |
| 27 | CGG | 1.00 | 0.76 | 1.00 | 0.71 | 0.16 | 1.00 | -0.35 | 0.72 | 0.40 | 0.68 | 0.66 | 0.66 |
| 28 | CGT | 0.37 | -0.51 | 0.59 | -0.54 | 0.67 | -0.19 | 0.08 | -0.50 | 0.12 | -0.75 | -0.28 | -0.41 |
| 29 | CTA | 0.57 | 0.32 | 0.65 | 0.16 | 0.47 | 0.14 | 0.65 | -0.13 | 0.60 | 0.30 | 0.23 | 0.22 |
| 30 | CTC | 0.81 | 0.32 | 0.83 | 0.64 | 0.73 | 0.80 | 0.18 | 0.28 | 0.71 | 0.79 | 0.46 | 0.51 |
| 31 | CTG | 0.39 | -0.08 | 0.47 | 0.26 | 0.09 | 0.29 | 0.56 | 0.00 | 0.18 | -0.10 | 0.25 | 0.24 |
| 32 | CTT | 0.72 | 0.05 | 0.55 | 0.40 | 0.64 | 0.45 | 0.63 | 0.07 | 0.87 | 0.30 | 0.32 | 0.22 |
| 33 | GAA | 0.49 | -0.25 | 0.50 | -0.38 | 0.57 | 0.31 | 0.52 | -0.49 | 0.54 | -0.36 | 0.13 | -0.38 |
| 34 | GAC | 0.72 | -0.19 | 0.35 | -0.19 | 0.67 | 0.51 | 0.30 | -0.30 | 0.51 | -0.11 | 0.32 | 0.02 |
| 35 | GAG | 0.26 | 0.14 | 0.22 | 0.25 | 0.58 | 0.34 | 0.83 | 0.24 | 0.74 | 0.40 | 0.62 | 0.30 |
| 36 | GAT | 0.52 | -0.22 | 0.43 | -0.36 | 0.46 | 0.50 | 0.05 | -0.36 | 0.58 | -0.38 | 0.24 | -0.26 |
| 37 | GCA | 0.53 | 0.63 | 0.79 | 0.53 | 0.58 | 0.45 | 0.67 | 0.19 | 0.63 | 0.53 | 0.60 | 0.56 |
| 38 | GCC | 0.42 | -0.31 | 0.79 | -0.37 | 0.68 | 0.45 | 0.90 | -0.55 | 0.41 | -0.53 | 0.17 | -0.20 |
| 39 | GCG | 0.71 | 0.50 | 0.45 | 0.51 | 0.64 | 0.29 | 0.52 | 0.48 | 0.60 | 0.01 | 0.55 | 0.51 |
| 40 | GCT | 0.31 | -0.47 | 0.68 | -0.60 | 0.74 | 0.19 | 0.59 | -0.58 | 0.40 | -0.60 | 0.08 | -0.42 |
| 41 | GGA | 0.77 | 0.53 | 0.95 | 0.67 | 0.77 | 0.61 | 0.64 | 0.65 | 0.78 | 0.76 | 0.75 | 0.84 |
| 42 | GGC | 0.62 | 0.14 | 0.75 | 0.10 | 0.84 | 0.67 | 0.64 | 0.27 | 0.78 | 0.31 | 0.57 | 0.47 |
| 43 | GGG | 0.85 | 0.59 | 0.80 | 0.63 | 0.84 | 0.82 | 0.90 | 0.66 | 0.85 | 0.89 | 0.88 | 0.71 |
| 44 | GGT | 0.39 | -0.54 | 0.40 | -0.62 | 0.53 | 0.12 | 0.17 | -0.67 | 0.37 | -0.67 | 0.35 | -0.60 |
| 45 | GTA | 0.66 | 0.55 | 0.74 | 0.58 | 0.70 | 0.58 | 0.69 | 0.60 | 0.71 | 0.63 | 0.68 | 0.69 |
| 46 | GTC | 0.49 | -0.27 | 0.44 | -0.30 | 0.42 | -0.04 | 0.53 | -0.64 | 0.60 | -0.41 | 0.41 | -0.39 |
| 47 | GTG | 0.40 | -0.12 | 0.77 | 0.28 | 0.51 | 0.65 | 0.65 | 0.30 | 0.29 | -0.01 | 0.20 | 0.41 |
| 48 | GTT | 0.28 | -0.48 | 0.47 | -0.52 | 0.45 | 0.28 | 0.61 | -0.51 | 0.56 | -0.60 | 0.52 | -0.47 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.58 | -0.34 | 0.65 | -0.45 | 0.62 | 0.14 | 0.41 | -0.50 | 0.28 | -0.44 | 0.37 | -0.39 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.45 | -0.01 | 0.47 | -0.13 | 0.72 | 0.37 | 0.44 | -0.19 | 0.68 | -0.17 | 0.36 | 0.07 |
| 53 | TCA | 0.70 | 0.51 | 0.60 | 0.32 | 0.24 | 0.53 | 0.53 | 0.35 | 0.41 | 0.25 | 0.33 | 0.52 |
| 54 | TCC | 0.50 | -0.41 | 0.54 | -0.48 | 0.36 | 0.16 | 0.53 | -0.59 | 0.05 | -0.63 | -0.19 | -0.40 |
| 55 | TCG | 0.67 | 0.43 | 0.14 | 0.66 | 0.72 | 0.53 | 0.37 | 0.41 | 0.62 | 0.34 | 0.74 | 0.66 |
| 56 | TCT | 0.15 | -0.61 | 0.21 | -0.59 | 0.59 | 0.35 | 0.43 | -0.61 | 0.34 | -0.56 | -0.29 | -0.41 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.75 | 0.20 | 0.56 | 0.59 | 0.90 | 0.33 | -0.07 | 0.22 | 1.00 | 0.87 | 1.00 | 0.39 |
| 59 | TGG | 0.46 | -0.20 | 0.44 | -0.26 | 0.62 | 0.48 | -0.21 | -0.31 | 0.58 | -0.06 | 0.53 | -0.36 |

TABLE C.10-continued

CPW matrix *Saccaromyces. cerevisiae* highly expressed sequences (left codon indicated in column 2, right codon indicated in row 2). Host cell: *S. cerevisiae*; Sequence data: full *S. cerevisiae* genome; Highly expressed group: 300 seqs.

| | | GCA | GCC | GCG | GCT | GGA | GGC | GGG | GGT | GTA | GTC | GTG | GTT |
|---|---|---|---|---|---|---|---|---|---|---|---|---|---|
| 60 | TGT | 0.63 | −0.47 | −0.48 | −0.38 | 0.76 | −0.03 | 0.23 | −0.48 | 0.19 | −0.45 | 0.01 | −0.46 |
| 61 | TTA | 0.49 | 0.16 | 0.36 | −0.05 | 0.48 | 0.29 | 0.54 | −0.25 | 0.52 | −0.22 | 0.04 | 0.03 |
| 62 | TTC | 0.47 | 0.03 | 0.50 | 0.20 | 0.70 | 0.18 | 0.63 | −0.51 | 0.73 | −0.44 | 0.17 | −0.01 |
| 63 | TTG | 0.18 | −0.58 | 0.08 | −0.62 | 0.48 | 0.05 | 0.50 | −0.59 | 0.32 | −0.58 | −0.16 | −0.50 |
| 64 | TTT | 0.20 | −0.40 | 0.25 | −0.26 | 0.73 | 0.24 | 0.47 | −0.23 | 0.53 | −0.29 | 0.34 | −0.23 |

| | | GCA | GCC | GCG | GCT | GGA | GGC | GGG | GGT | GTA | GTC | GTG | GTT |
|---|---|---|---|---|---|---|---|---|---|---|---|---|---|
| | | 37 | 38 | 39 | 40 | 41 | 42 | 43 | 44 | 45 | 46 | 47 | 48 |

| | | TAA | TAC | TAG | TAT | TCA | TCC | TCG | TCT | TGA | TGC | TGG | TGT |
|---|---|---|---|---|---|---|---|---|---|---|---|---|---|
| | | 49 | 50 | 51 | 52 | 53 | 54 | 55 | 56 | 57 | 58 | 59 | 60 |
| 1 | AAA | 0.00 | −0.14 | 0.00 | 0.31 | 0.10 | 0.12 | 0.26 | −0.18 | 0.00 | 0.34 | −0.03 | 0.01 |
| 2 | AAC | 0.00 | −0.53 | 0.00 | −0.15 | −0.03 | −0.48 | −0.17 | −0.40 | 0.00 | 0.25 | −0.43 | −0.57 |
| 3 | AAG | 0.00 | −0.43 | 0.00 | 0.32 | 0.35 | −0.37 | 0.07 | −0.42 | 0.00 | 0.24 | 0.05 | −0.31 |
| 4 | AAT | 0.00 | 0.34 | 0.00 | 0.44 | 0.46 | 0.08 | 0.34 | 0.11 | 0.00 | 0.60 | 0.51 | 0.41 |
| 5 | ACA | 0.00 | 0.31 | 0.00 | 0.63 | 0.41 | 0.16 | 0.46 | 0.19 | 0.00 | 0.66 | 0.27 | −0.16 |
| 6 | ACC | 0.00 | −0.54 | 0.00 | 0.24 | 0.25 | −0.45 | −0.15 | −0.44 | 0.00 | −0.33 | −0.39 | −0.42 |
| 7 | ACG | 0.00 | −0.02 | 0.00 | 0.66 | 0.56 | 0.70 | 0.52 | 0.46 | 0.00 | 0.75 | 0.57 | 0.53 |
| 8 | ACT | 0.00 | −0.50 | 0.00 | 0.11 | −0.11 | −0.49 | −0.11 | −0.54 | 0.00 | 0.90 | −0.08 | −0.34 |
| 9 | AGA | 0.00 | −0.31 | 0.00 | 0.43 | 0.05 | −0.44 | 0.37 | −0.41 | 0.00 | 0.46 | −0.17 | −0.34 |
| 10 | AGC | 0.00 | 0.23 | 0.00 | 0.60 | 0.39 | 0.01 | 0.56 | 0.17 | 0.00 | 0.20 | 0.10 | 0.51 |
| 11 | AGG | 0.00 | 0.23 | 0.00 | 0.54 | 0.00 | 0.12 | 0.49 | 0.19 | 0.00 | 1.00 | 0.61 | 0.71 |
| 12 | AGT | 0.00 | 0.14 | 0.00 | 0.63 | 0.41 | 0.51 | 0.57 | 0.47 | 0.00 | 0.45 | 0.44 | 0.49 |
| 13 | ATA | 0.00 | 0.25 | 0.00 | 0.56 | 0.43 | 0.37 | 0.44 | 0.50 | 0.00 | 0.71 | 0.76 | 0.53 |
| 14 | ATC | 0.00 | −0.49 | 0.00 | −0.06 | −0.06 | −0.57 | 0.03 | −0.53 | 0.00 | 0.37 | −0.44 | −0.46 |
| 15 | ATG | 0.00 | −0.24 | 0.00 | 0.23 | 0.31 | −0.33 | 0.28 | −0.27 | 0.00 | 0.29 | 0.00 | −0.15 |
| 16 | ATT | 0.00 | −0.21 | 0.00 | 0.18 | 0.34 | −0.45 | 0.14 | −0.39 | 0.00 | −0.06 | −0.02 | −0.17 |
| 17 | CAA | 0.00 | −0.27 | 0.00 | 0.20 | 0.36 | −0.27 | 0.59 | −0.33 | 0.00 | 0.44 | −0.20 | −0.30 |
| 18 | CAC | 0.00 | −0.31 | 0.00 | −0.09 | 0.52 | −0.60 | −0.14 | −0.60 | 0.00 | 0.45 | −0.31 | −0.32 |
| 19 | CAG | 0.00 | −0.21 | 0.00 | 0.35 | 0.13 | 0.16 | 0.33 | 0.08 | 0.00 | 0.19 | 0.55 | 0.25 |
| 20 | CAT | 0.00 | −0.06 | 0.00 | 0.29 | 0.30 | 0.05 | 0.42 | −0.16 | 0.00 | 0.08 | 0.25 | 0.06 |
| 21 | CCA | 0.00 | −0.45 | 0.00 | 0.26 | 0.15 | −0.39 | 0.24 | −0.58 | 0.00 | 0.16 | −0.48 | −0.45 |
| 22 | CCC | 0.00 | 0.47 | 0.00 | 0.14 | 0.36 | 0.04 | 0.30 | −0.09 | 0.00 | 0.28 | 0.90 | 0.12 |
| 23 | CCG | 0.00 | 0.52 | 0.00 | 0.56 | 0.76 | 0.78 | 0.82 | 0.80 | 0.00 | 0.54 | 0.88 | 0.44 |
| 24 | CCT | 0.00 | −0.36 | 0.00 | 0.24 | 0.34 | −0.39 | −0.18 | −0.09 | 0.00 | −0.09 | 0.40 | 0.55 |
| 25 | CGA | 0.00 | 0.84 | 0.00 | 0.63 | 1.00 | 1.00 | 0.63 | 0.72 | 0.00 | 1.00 | 0.81 | 1.00 |
| 26 | CGC | 0.00 | 0.03 | 0.00 | 0.41 | 1.00 | −0.28 | −0.25 | 0.16 | 0.00 | 0.17 | 0.54 | 1.00 |
| 27 | CGG | 0.00 | 0.44 | 0.00 | 0.58 | −0.15 | 0.60 | 1.00 | 0.76 | 0.00 | 1.00 | 0.67 | 0.26 |
| 28 | CGT | 0.00 | −0.68 | 0.00 | −0.47 | 0.30 | −0.53 | −0.25 | −0.50 | 0.00 | −0.44 | −0.51 | −0.69 |
| 29 | CTA | 0.00 | −0.18 | 0.00 | 0.08 | 0.32 | 0.03 | 0.04 | −0.05 | 0.00 | 0.31 | −0.38 | −0.30 |
| 30 | CTC | 0.00 | 0.01 | 0.00 | 0.55 | 0.60 | −0.35 | 0.82 | 0.21 | 0.00 | 0.67 | 0.59 | 0.00 |
| 31 | CTG | 0.00 | 0.10 | 0.00 | 0.52 | 0.48 | 0.41 | 0.34 | 0.26 | 0.00 | 0.31 | 0.42 | −0.22 |
| 32 | CTT | 0.00 | −0.25 | 0.00 | 0.15 | 0.17 | −0.39 | −0.10 | −0.25 | 0.00 | 0.56 | 0.39 | −0.07 |
| 33 | GAA | 0.00 | −0.26 | 0.00 | 0.23 | 0.55 | −0.44 | 0.53 | −0.38 | 0.00 | 0.30 | −0.12 | −0.26 |
| 34 | GAC | 0.00 | −0.48 | 0.00 | 0.07 | 0.31 | −0.57 | 0.00 | −0.58 | 0.00 | −0.01 | −0.25 | −0.56 |
| 35 | GAG | 0.00 | −0.17 | 0.00 | 0.22 | 0.58 | −0.06 | 0.03 | 0.13 | 0.00 | 0.37 | 0.32 | 0.15 |
| 36 | GAT | 0.00 | 0.09 | 0.00 | 0.28 | 0.39 | 0.02 | −0.11 | 0.00 | 0.00 | 0.70 | 0.18 | 0.24 |
| 37 | GCA | 0.00 | 0.24 | 0.00 | 0.59 | 0.32 | −0.12 | 0.21 | 0.07 | 0.00 | 0.61 | 0.35 | 0.33 |
| 38 | GCC | 0.00 | −0.24 | 0.00 | 0.45 | 0.06 | −0.56 | −0.10 | −0.40 | 0.00 | 0.68 | 0.08 | −0.26 |
| 39 | GCG | 0.00 | 0.00 | 0.00 | 0.34 | 0.60 | 0.39 | 0.57 | 0.51 | 0.00 | 0.39 | −0.02 | 0.75 |
| 40 | GCT | 0.00 | −0.55 | 0.00 | 0.07 | 0.29 | −0.56 | 0.30 | −0.50 | 0.00 | 0.43 | −0.24 | −0.54 |
| 41 | GGA | 0.00 | 0.55 | 0.00 | 0.53 | 0.54 | 0.53 | 0.88 | 0.32 | 0.00 | 0.72 | 0.17 | 0.20 |
| 42 | GGC | 0.00 | −0.34 | 0.00 | 0.40 | 0.31 | −0.46 | 0.36 | −0.33 | 0.00 | 0.14 | −0.24 | 0.01 |
| 43 | GGG | 0.00 | 0.61 | 0.00 | 0.58 | 0.68 | 0.00 | 0.54 | −0.07 | 0.00 | 0.31 | 0.47 | 0.47 |
| 44 | GGT | 0.00 | −0.55 | 0.00 | 0.14 | 0.24 | −0.59 | 0.22 | −0.57 | 0.00 | 0.25 | −0.07 | −0.41 |
| 45 | GTA | 0.00 | 0.37 | 0.00 | 0.55 | 0.62 | 0.25 | 0.43 | 0.10 | 0.00 | −0.18 | 0.54 | 0.48 |
| 46 | GTC | 0.00 | −0.44 | 0.00 | 0.10 | 0.47 | −0.60 | 0.46 | −0.49 | 0.00 | 0.21 | −0.42 | −0.44 |
| 47 | GTG | 0.00 | 0.15 | 0.00 | 0.46 | 0.71 | 0.11 | 0.72 | 0.31 | 0.00 | 0.59 | 0.43 | 0.24 |
| 48 | GTT | 0.00 | −0.41 | 0.00 | 0.02 | 0.06 | −0.61 | 0.39 | −0.50 | 0.00 | −0.03 | −0.12 | −0.13 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.00 | −0.54 | 0.00 | 0.15 | 0.11 | −0.49 | 0.14 | −0.40 | 0.00 | 0.14 | −0.39 | −0.47 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.00 | 0.29 | 0.00 | 0.35 | 0.48 | −0.05 | 0.24 | −0.21 | 0.00 | 0.71 | 0.48 | 0.16 |
| 53 | TCA | 0.00 | −0.07 | 0.00 | 0.21 | 0.20 | 0.26 | 0.54 | 0.07 | 0.00 | −0.20 | 0.03 | −0.13 |
| 54 | TCC | 0.00 | −0.32 | 0.00 | 0.11 | 0.31 | −0.45 | −0.06 | −0.49 | 0.00 | 0.29 | −0.38 | −0.28 |
| 55 | TCG | 0.00 | −0.29 | 0.00 | 0.14 | 0.50 | 0.31 | −0.17 | 0.36 | 0.00 | −0.37 | −0.01 | 0.30 |
| 56 | TCT | 0.00 | −0.51 | 0.00 | 0.10 | −0.15 | −0.64 | 0.21 | −0.59 | 0.00 | 0.32 | 0.03 | −0.34 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.00 | −0.27 | 0.00 | 0.26 | 0.72 | −0.20 | 0.40 | 0.10 | 0.00 | −0.25 | −0.02 | 0.32 |

TABLE C.10-continued

CPW matrix *Saccaromyces. cerevisiae* highly expressed sequences (left codon indicated in column 2, right codon indicated in row 2). Host cell: *S. cerevisiae*; Sequence data: full *S. cerevisiae* genome; Highly expressed group: 300 seqs.

| | | | | | | | | | | | | |
|---|---|---|---|---|---|---|---|---|---|---|---|---|
| 59 | TGG | 0.00 | −0.33 | 0.00 | 0.37 | 0.46 | −0.30 | 0.09 | −0.34 | 0.00 | 0.47 | 0.00 | −0.23 |
| 60 | TGT | 0.00 | −0.21 | 0.00 | 0.22 | 0.38 | −0.57 | 0.51 | −0.47 | 0.00 | 0.59 | 0.01 | −0.30 |
| 61 | TTA | 0.00 | −0.09 | 0.00 | 0.37 | 0.42 | −0.20 | 0.24 | −0.26 | 0.00 | 0.65 | −0.36 | −0.15 |
| 62 | TTC | 0.00 | −0.48 | 0.00 | 0.08 | 0.22 | −0.64 | −0.20 | −0.40 | 0.00 | 0.37 | −0.22 | −0.40 |
| 63 | TTG | 0.00 | −0.50 | 0.00 | 0.19 | 0.20 | −0.60 | 0.39 | −0.51 | 0.00 | 0.23 | 0.38 | −0.30 |
| 64 | TTT | 0.00 | 0.05 | 0.00 | 0.39 | 0.27 | −0.02 | 0.36 | 0.34 | 0.00 | −0.06 | 0.19 | 0.34 |

| TAA | TAC | TAG | TAT | TCA | TCC | TCG | TCT | TGA | TGC | TGG | TGT |
|---|---|---|---|---|---|---|---|---|---|---|---|
| 49 | 50 | 51 | 52 | 53 | 54 | 55 | 56 | 57 | 58 | 59 | 60 |

| | | 61 TTA | 62 TTC | 63 TTG | 64 TTT |
|---|---|---|---|---|---|
| 1 | AAA | 0.15 | −0.20 | −0.19 | 0.40 |
| 2 | AAC | −0.11 | −0.53 | −0.59 | −0.02 |
| 3 | AAG | 0.20 | −0.44 | −0.53 | 0.20 |
| 4 | AAT | 0.28 | 0.16 | 0.04 | 0.42 |
| 5 | ACA | 0.42 | 0.47 | 0.26 | 0.34 |
| 6 | ACC | −0.11 | −0.42 | −0.42 | 0.07 |
| 7 | ACG | 0.54 | 0.52 | 0.30 | 0.67 |
| 8 | ACT | −0.29 | −0.52 | −0.65 | −0.03 |
| 9 | AGA | −0.21 | −0.44 | −0.57 | 0.06 |
| 10 | AGC | 0.65 | 0.53 | 0.31 | 0.46 |
| 11 | AGG | 0.55 | 0.28 | 0.26 | 0.26 |
| 12 | AGT | 0.50 | 0.28 | −0.12 | 0.48 |
| 13 | ATA | 0.42 | 0.34 | 0.38 | 0.47 |
| 14 | ATC | −0.13 | −0.38 | −0.60 | −0.05 |
| 15 | ATG | 0.24 | −0.17 | −0.25 | 0.14 |
| 16 | ATT | 0.18 | −0.35 | −0.37 | 0.21 |
| 17 | CAA | −0.16 | −0.21 | −0.48 | 0.06 |
| 18 | CAC | 0.34 | −0.52 | −0.51 | 0.34 |
| 19 | CAG | 0.40 | −0.24 | 0.17 | 0.47 |
| 20 | CAT | 0.10 | −0.27 | −0.39 | 0.48 |
| 21 | CCA | −0.31 | −0.42 | −0.60 | −0.19 |
| 22 | CCC | 0.15 | −0.31 | 0.29 | 0.63 |
| 23 | CCG | 0.38 | 0.62 | 0.61 | 0.63 |
| 24 | CCT | 0.34 | −0.23 | 0.00 | 0.58 |
| 25 | CGA | 1.00 | 0.60 | 0.83 | 0.46 |
| 26 | CGC | 0.79 | 0.37 | 0.48 | 0.79 |
| 27 | CGG | 0.55 | 0.10 | 0.26 | 0.08 |
| 28 | CGT | −0.06 | −0.38 | −0.45 | 0.41 |
| 29 | CTA | −0.14 | 0.20 | −0.19 | 0.19 |
| 30 | CTC | 0.57 | −0.23 | 0.03 | 0.32 |
| 31 | CTG | 0.45 | −0.09 | 0.03 | 0.39 |
| 32 | CTT | 0.18 | −0.54 | −0.36 | 0.41 |
| 33 | GAA | 0.11 | −0.22 | −0.37 | 0.17 |
| 34 | GAC | 0.11 | −0.40 | −0.52 | 0.27 |
| 35 | GAG | 0.40 | −0.11 | −0.18 | 0.15 |
| 36 | GAT | 0.10 | −0.23 | −0.37 | 0.31 |
| 37 | GCA | 0.60 | 0.62 | 0.32 | 0.36 |
| 38 | GCC | −0.03 | −0.47 | −0.24 | −0.19 |
| 39 | GCG | 0.59 | −0.05 | 0.45 | 0.39 |
| 40 | GCT | −0.21 | −0.48 | −0.67 | 0.39 |
| 41 | GGA | 0.52 | 0.19 | 0.46 | 0.31 |
| 42 | GGC | 0.49 | 0.65 | 0.26 | 0.50 |
| 43 | GGG | −0.16 | −0.58 | −0.48 | −0.25 |
| 44 | GGT | −0.08 | −0.53 | −0.57 | 0.48 |
| 45 | GTA | 0.56 | 0.54 | 0.54 | 0.43 |
| 46 | GTC | −0.18 | −0.52 | −0.65 | −0.01 |
| 47 | GTG | 0.39 | −0.06 | −0.07 | 0.32 |
| 48 | GTT | 0.08 | −0.43 | −0.51 | 0.31 |
| 49 | TAA | 0.00 | 0.00 | 0.00 | 0.00 |
| 50 | TAC | 0.15 | −0.32 | −0.57 | −0.14 |
| 51 | TAG | 0.00 | 0.00 | 0.00 | 0.00 |
| 52 | TAT | 0.22 | −0.13 | −0.21 | 0.48 |
| 53 | TCA | 0.13 | −0.18 | 0.03 | 0.24 |
| 54 | TCC | −0.05 | −0.44 | −0.51 | 0.04 |
| 55 | TCG | 0.02 | −0.11 | 0.14 | 0.39 |
| 56 | TCT | −0.29 | −0.60 | −0.67 | 0.35 |
| 57 | TGA | 0.00 | 0.00 | 0.00 | 0.00 |
| 58 | TGC | 0.21 | 0.60 | 0.57 | 0.24 |

TABLE C.10-continued

CPW matrix Saccaromyces. cerevisiae highly expressed sequences (left codon indicated in column 2, right codon indicated in row 2). Host cell: S. cerevisiae; Sequence data: full S. cerevisiae genome; Highly expressed group: 300 seqs.

| | | | | | |
|---|---|---|---|---|---|
| 59 | TGG | −0.24 | −0.25 | −0.17 | 0.23 |
| 60 | TGT | 0.08 | −0.43 | −0.49 | 0.11 |
| 61 | TTA | 0.27 | −0.20 | −0.16 | 0.23 |
| 62 | TTC | −0.11 | −0.54 | −0.65 | 0.03 |
| 63 | TTG | 0.05 | −0.27 | −0.58 | 0.06 |
| 64 | TTT | 0.28 | 0.11 | −0.16 | 0.46 |
| | | TTA | TTC | TTG | TTT |
| | | 61 | 62 | 63 | 64 |

TABLE C.11

CPW matrix Streptomyces coelicolor A3(2) full genome (left codon indicated in column 2, right codon indicated in row 2). Host cell: S. coelicolor; Sequence data: full S. coelicolor genome.

| | | 1 AAA | 2 AAC | 3 AAG | 4 AAT | 5 ACA | 6 ACC | 7 ACG | 8 ACT | 9 AGA | 10 AGC | 11 AGG | 12 AGT |
|---|---|---|---|---|---|---|---|---|---|---|---|---|---|
| 1 | AAA | 0.00 | 0.79 | 0.70 | −0.65 | −0.60 | 0.28 | 0.48 | −0.48 | −0.86 | 0.24 | −0.66 | −0.69 |
| 2 | AAC | 0.44 | −0.05 | −0.06 | 0.30 | 0.52 | −0.13 | 0.15 | 0.32 | 0.10 | −0.27 | 0.09 | 0.36 |
| 3 | AAG | 0.58 | −0.05 | −0.06 | 0.45 | −0.01 | 0.03 | −0.10 | 0.15 | 0.08 | −0.03 | 0.21 | 0.52 |
| 4 | AAT | −0.02 | 0.89 | 0.87 | 1.00 | 0.22 | 0.80 | 0.57 | −0.63 | 1.00 | 0.77 | 0.62 | 0.60 |
| 5 | ACA | 1.00 | 0.83 | 0.74 | −0.23 | −0.60 | 0.71 | 0.50 | −0.58 | −0.75 | 0.30 | −0.40 | −0.15 |
| 6 | ACC | 0.08 | −0.16 | −0.11 | −0.18 | −0.05 | −0.03 | −0.02 | −0.26 | 0.15 | −0.17 | −0.34 | −0.29 |
| 7 | ACG | 0.19 | 0.31 | 0.12 | −0.08 | −0.39 | 0.22 | −0.30 | −0.22 | −0.32 | 0.22 | 0.00 | −0.14 |
| 8 | ACT | 1.00 | 0.85 | 0.87 | 0.40 | −0.37 | 0.69 | 0.63 | −0.61 | −0.26 | 0.88 | −0.06 | −0.38 |
| 9 | AGA | −0.47 | 0.37 | 0.44 | −0.82 | −0.80 | 0.35 | −0.03 | −0.66 | −0.88 | −0.26 | −0.72 | −0.60 |
| 10 | AGC | −0.23 | −0.11 | −0.14 | −0.47 | −0.35 | 0.05 | −0.03 | −0.32 | −0.62 | −0.34 | −0.60 | −0.58 |
| 11 | AGG | −0.64 | −0.13 | −0.27 | −0.58 | −0.62 | 0.06 | −0.27 | −0.35 | −0.60 | −0.22 | −0.22 | −0.51 |
| 12 | AGT | −0.64 | 0.74 | 0.87 | 0.14 | 0.19 | 0.51 | −0.40 | −0.67 | 0.55 | 0.74 | 0.91 | −0.47 |
| 13 | ATA | −0.12 | 0.91 | 0.74 | 0.32 | 1.00 | 0.84 | 0.41 | 0.02 | −0.69 | 0.46 | −0.20 | 0.14 |
| 14 | ATC | −0.02 | −0.04 | −0.03 | 0.07 | 0.32 | −0.11 | 0.15 | −0.07 | −0.05 | −0.22 | −0.31 | −0.19 |
| 15 | ATG | 0.07 | −0.01 | 0.00 | 0.24 | 0.01 | 0.08 | −0.14 | 0.01 | 0.54 | −0.17 | 0.43 | −0.02 |
| 16 | ATT | 0.39 | 0.85 | 0.78 | −0.54 | −0.48 | 0.77 | 0.67 | −0.36 | −0.12 | 0.95 | 0.55 | −0.27 |
| 17 | CAA | 0.12 | 0.80 | 0.62 | −0.22 | −0.65 | 0.62 | 0.59 | −0.06 | −0.42 | 0.58 | −0.01 | 0.31 |
| 18 | CAC | 0.05 | −0.06 | −0.07 | 0.01 | 0.08 | −0.15 | 0.19 | −0.10 | 0.51 | −0.23 | 0.54 | 0.00 |
| 19 | CAG | −0.01 | −0.05 | −0.03 | 0.38 | −0.15 | −0.03 | −0.01 | 0.13 | 0.49 | −0.07 | 0.66 | 0.47 |
| 20 | CAT | 0.66 | 0.90 | 0.89 | −0.37 | 0.31 | 0.90 | 0.61 | −0.39 | 0.39 | 0.75 | 0.82 | 0.61 |
| 21 | CCA | −0.34 | 0.53 | 0.55 | −0.66 | −0.65 | 0.63 | 0.36 | −0.54 | −0.75 | 0.55 | −0.41 | −0.42 |
| 22 | CCC | −0.10 | −0.11 | −0.09 | −0.13 | −0.13 | −0.18 | 0.05 | −0.28 | 0.23 | 0.03 | −0.38 | −0.17 |
| 23 | CCG | 0.00 | 0.05 | 0.03 | 0.15 | −0.20 | 0.20 | −0.16 | −0.23 | −0.12 | 0.23 | −0.22 | 0.10 |
| 24 | CCT | −0.40 | 0.81 | 0.81 | −0.51 | −0.27 | 0.71 | 0.32 | −0.64 | 0.50 | 0.83 | 0.51 | 1.00 |
| 25 | CGA | 0.07 | 0.27 | 0.20 | −0.63 | −0.43 | 0.54 | 0.42 | −0.12 | −0.79 | −0.06 | −0.33 | −0.41 |
| 26 | CGC | −0.46 | −0.34 | −0.34 | −0.51 | −0.08 | −0.28 | 0.01 | −0.23 | −0.56 | −0.35 | −0.58 | −0.42 |
| 27 | CGG | 0.21 | 0.56 | 0.57 | −0.10 | −0.11 | 0.45 | 0.22 | 0.29 | 0.36 | 0.51 | 0.54 | 0.41 |
| 28 | CGT | 0.18 | 0.79 | 0.75 | −0.36 | −0.28 | 0.01 | −0.57 | −0.57 | 0.45 | 0.75 | 0.75 | 0.62 |
| 29 | CTA | −0.22 | 0.52 | 0.67 | 1.00 | 0.27 | 0.81 | 0.49 | −0.83 | −0.70 | 0.81 | 0.34 | −0.70 |
| 30 | CTC | −0.30 | −0.30 | −0.23 | −0.13 | 0.29 | −0.38 | 0.28 | −0.14 | 0.04 | −0.15 | −0.31 | −0.03 |
| 31 | CTG | 0.15 | 0.20 | 0.17 | 0.55 | 0.36 | 0.10 | 0.23 | 0.53 | 0.31 | 0.19 | 0.29 | 0.43 |
| 32 | CTT | 0.44 | 0.95 | 0.94 | 0.16 | 0.84 | 0.79 | 0.67 | −0.62 | 0.63 | 0.92 | 0.78 | 0.27 |
| 33 | GAA | 0.57 | 0.82 | 0.78 | 0.19 | −0.35 | 0.57 | 0.46 | 0.05 | −0.06 | 0.47 | 0.28 | 0.52 |
| 34 | GAC | 0.12 | −0.05 | −0.05 | 0.18 | 0.28 | −0.09 | 0.07 | 0.09 | 0.34 | −0.17 | 0.40 | 0.03 |
| 35 | GAG | 0.29 | −0.14 | −0.14 | 0.31 | −0.14 | 0.01 | −0.24 | 0.21 | 0.57 | −0.10 | 0.49 | 0.36 |
| 36 | GAT | 0.71 | 0.91 | 0.89 | −0.23 | 0.19 | 0.76 | 0.54 | −0.28 | 0.42 | 0.80 | 0.85 | 0.54 |
| 37 | GCA | −0.09 | 0.84 | 0.75 | 0.17 | −0.50 | 0.68 | 0.49 | −0.20 | −0.20 | 0.48 | −0.06 | −0.10 |
| 38 | GCC | 0.14 | −0.18 | −0.10 | −0.22 | 0.14 | −0.12 | 0.07 | −0.01 | 0.06 | 0.41 | −0.24 | −0.02 |
| 39 | GCG | −0.05 | 0.20 | 0.04 | 0.27 | −0.18 | 0.15 | −0.21 | 0.10 | 0.17 | −0.08 | 0.20 | −0.02 |
| 40 | GCT | 0.29 | 0.86 | 0.93 | 0.50 | −0.24 | 0.72 | 0.53 | −0.52 | 0.59 | 0.87 | 0.72 | 0.78 |
| 41 | GGA | −0.40 | 0.40 | 0.48 | −0.16 | −0.49 | 0.47 | 0.11 | −0.08 | −0.61 | 0.10 | −0.28 | −0.35 |
| 42 | GGC | −0.11 | −0.20 | −0.20 | −0.31 | −0.05 | −0.14 | −0.12 | −0.03 | −0.36 | −0.26 | −0.42 | −0.34 |
| 43 | GGG | −0.27 | 0.28 | 0.24 | −0.20 | −0.21 | 0.45 | −0.20 | 0.04 | −0.33 | 0.28 | 0.15 | −0.08 |
| 44 | GGT | 0.66 | 0.91 | 0.88 | 0.64 | 0.34 | 0.60 | −0.17 | 0.35 | 0.44 | 0.90 | 0.83 | 0.58 |
| 45 | GTA | 0.18 | 0.91 | 0.90 | 0.20 | 0.33 | 0.92 | 0.88 | 0.21 | −0.20 | 0.86 | −0.02 | 0.24 |
| 46 | GTC | −0.16 | −0.19 | −0.03 | −0.28 | 0.27 | −0.25 | 0.19 | 0.06 | 0.17 | −0.13 | 0.10 | 0.12 |
| 47 | GTG | −0.09 | 0.22 | −0.04 | 0.35 | 0.11 | 0.23 | −0.14 | 0.31 | 0.38 | 0.06 | 0.42 | 0.22 |
| 48 | GTT | 0.39 | 0.97 | 0.87 | 1.00 | 0.28 | 0.87 | 0.71 | 0.26 | 0.61 | 0.88 | 0.69 | 0.59 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.47 | −0.08 | −0.07 | 0.83 | 0.20 | 0.00 | −0.16 | 0.92 | 0.75 | −0.20 | 0.79 | 0.70 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 1.00 | 0.91 | 0.90 | 1.00 | 0.39 | 0.82 | 0.71 | 1.00 | 0.44 | 0.74 | 0.67 | 0.03 |
| 53 | TCA | 0.12 | 0.89 | 0.70 | 0.38 | −0.57 | 0.73 | 0.29 | −0.50 | 0.35 | 0.13 | −0.14 | −0.54 |
| 54 | TCC | 0.30 | −0.17 | −0.02 | 0.28 | 0.01 | −0.07 | −0.12 | −0.28 | 0.05 | −0.04 | −0.04 | −0.03 |

TABLE C.11-continued

CPW matrix Streptomyces coelicolor A3(2) full genome (left codon indicated in column 2, right codon indicated in row 2). Host cell: *S. coelicolor*; Sequence data: full *S. coelicilor* genome.

| | | | | | | | | | | | | |
|---|---|---|---|---|---|---|---|---|---|---|---|---|
| 55 | TCG | 0.03 | 0.24 | 0.00 | 0.21 | −0.24 | 0.32 | −0.30 | 0.27 | 0.21 | 0.49 | 0.38 | 0.20 |
| 56 | TCT | 1.00 | 0.91 | 1.00 | −0.05 | −0.32 | 0.62 | 0.46 | 1.00 | −0.55 | 0.58 | 0.78 | 1.00 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | −0.10 | −0.07 | −0.07 | −0.26 | −0.21 | 0.02 | −0.12 | 0.40 | 0.04 | 0.29 | 0.42 | −0.09 |
| 59 | TGG | −0.36 | −0.01 | 0.03 | 0.34 | −0.20 | 0.15 | −0.23 | −0.20 | 0.47 | −0.02 | 0.51 | 0.00 |
| 60 | TGT | −0.46 | 0.97 | 0.81 | −0.56 | 1.00 | 0.51 | −0.10 | −0.50 | 0.12 | 0.92 | 0.31 | 0.64 |
| 61 | TTA | 1.00 | 1.00 | 1.00 | 1.00 | −0.76 | 0.84 | 0.67 | 1.00 | −0.90 | 0.46 | 1.00 | 1.00 |
| 62 | TTC | −0.20 | −0.02 | 0.00 | 0.19 | 0.58 | −0.13 | 0.22 | 0.28 | 0.21 | −0.01 | 0.33 | 0.20 |
| 63 | TTG | −0.70 | 0.24 | −0.23 | −0.60 | 0.04 | 0.35 | −0.20 | −0.32 | −0.71 | −0.22 | −0.49 | −0.54 |
| 64 | TTT | −0.05 | 0.95 | 0.73 | 1.00 | −0.07 | 0.72 | 0.62 | −0.55 | −0.41 | 0.61 | 0.00 | 1.00 |

| | | AAA 1 | AAC 2 | AAG 3 | AAT 4 | ACA 5 | ACC 6 | ACG 7 | ACT 8 | AGA 9 | AGC 10 | AGG 11 | AGT 12 |
|---|---|---|---|---|---|---|---|---|---|---|---|---|---|
| | | 13 ATA | 14 ATC | 15 ATG | 16 ATT | 17 CAA | 18 CAC | 19 CAG | 20 CAT | 21 CCA | 22 CCC | 23 CCG | 24 CCT |
| 1 | AAA | −0.50 | 0.74 | 0.22 | −0.69 | −0.42 | −0.21 | −0.24 | −0.69 | −0.67 | −0.47 | −0.58 | −0.57 |
| 2 | AAC | 0.58 | −0.05 | −0.03 | 0.21 | 0.37 | −0.02 | 0.00 | 0.47 | 0.55 | 0.23 | −0.03 | 0.22 |
| 3 | AAG | 0.46 | −0.05 | −0.01 | 0.23 | 0.50 | −0.01 | −0.01 | 0.37 | 0.36 | 0.06 | 0.04 | 0.33 |
| 4 | AAT | 1.00 | 0.75 | 0.83 | −0.39 | −0.74 | −0.10 | −0.18 | −0.74 | −0.82 | −0.62 | −0.72 | −0.70 |
| 5 | ACA | 1.00 | 0.85 | 0.68 | −0.07 | −0.67 | −0.24 | −0.44 | −0.76 | −0.89 | −0.73 | −0.75 | −0.80 |
| 6 | ACC | 0.59 | 0.11 | 0.16 | −0.10 | 0.15 | 0.09 | 0.04 | −0.21 | 0.40 | 0.38 | 0.18 | 0.15 |
| 7 | ACG | 0.18 | −0.26 | −0.30 | −0.35 | −0.15 | −0.05 | 0.02 | −0.27 | 0.05 | −0.15 | −0.10 | −0.29 |
| 8 | ACT | 0.31 | 0.82 | 0.86 | −0.32 | −0.70 | 0.13 | −0.37 | −0.78 | −0.87 | −0.75 | −0.75 | −0.90 |
| 9 | AGA | −0.30 | 0.39 | 0.37 | −0.67 | −0.74 | −0.13 | −0.13 | −0.17 | −0.86 | −0.19 | −0.28 | −0.79 |
| 10 | AGC | 1.00 | 0.13 | 0.30 | −0.17 | 0.12 | −0.12 | −0.07 | −0.48 | 0.04 | 0.08 | 0.12 | −0.37 |
| 11 | AGG | 0.72 | 0.00 | 0.06 | −0.45 | −0.64 | 0.20 | −0.02 | −0.30 | −0.62 | −0.23 | −0.10 | −0.18 |
| 12 | AGT | 0.51 | 0.70 | 0.85 | −0.52 | −0.33 | −0.22 | −0.20 | −0.69 | −0.65 | −0.30 | −0.37 | −0.79 |
| 13 | ATA | 1.00 | 0.87 | 0.91 | −0.57 | 0.43 | 0.12 | 0.06 | −0.25 | 0.44 | −0.67 | −0.65 | −0.66 |
| 14 | ATC | 0.82 | −0.05 | −0.04 | −0.12 | 0.44 | 0.00 | −0.01 | 0.18 | 0.50 | 0.18 | 0.08 | 0.43 |
| 15 | ATG | 0.97 | −0.03 | 0.00 | 0.17 | 0.15 | −0.01 | −0.01 | 0.17 | 0.09 | 0.07 | −0.06 | 0.07 |
| 16 | ATT | 1.00 | 0.73 | 0.80 | −0.19 | −0.83 | −0.44 | −0.24 | −0.58 | −0.91 | −0.79 | −0.81 | −0.91 |
| 17 | CAA | 0.63 | 0.80 | 0.77 | −0.17 | −0.32 | 0.22 | 0.02 | 0.45 | −0.19 | −0.25 | −0.19 | −0.72 |
| 18 | CAC | −0.25 | −0.06 | −0.05 | 0.37 | 0.20 | 0.01 | 0.00 | 0.04 | 0.28 | 0.03 | 0.20 | 0.14 |
| 19 | CAG | −0.18 | −0.04 | −0.04 | 0.07 | 0.01 | −0.02 | 0.00 | 0.12 | −0.24 | −0.05 | 0.09 | −0.02 |
| 20 | CAT | 0.19 | 0.79 | 0.65 | 0.57 | −0.68 | −0.08 | −0.06 | −0.37 | −0.59 | −0.60 | −0.65 | −0.67 |
| 21 | CCA | −0.58 | 0.96 | 0.69 | −0.83 | −0.70 | 0.03 | −0.37 | −0.42 | −0.93 | −0.67 | −0.73 | −0.87 |
| 22 | CCC | −0.18 | 0.30 | 0.25 | −0.28 | 0.32 | 0.56 | 0.44 | 0.21 | 0.29 | 0.82 | 0.48 | 0.07 |
| 23 | CCG | −0.29 | −0.21 | −0.20 | −0.18 | −0.18 | −0.30 | −0.23 | 0.07 | −0.35 | −0.28 | −0.18 | −0.16 |
| 24 | CCT | 0.30 | 0.84 | 0.75 | −0.78 | −0.70 | −0.08 | −0.23 | −0.65 | −0.84 | −0.60 | −0.55 | −0.84 |
| 25 | CGA | −0.60 | 0.63 | 0.64 | −0.59 | −0.60 | 0.34 | −0.18 | −0.58 | −0.78 | −0.06 | −0.34 | −0.65 |
| 26 | CGC | −0.09 | 0.03 | 0.08 | 0.05 | 0.13 | 0.31 | 0.24 | −0.05 | 0.28 | 0.05 | 0.34 | 0.39 |
| 27 | CGG | −0.37 | −0.12 | −0.21 | −0.26 | −0.27 | −0.29 | −0.18 | −0.22 | −0.01 | −0.15 | 0.08 | −0.06 |
| 28 | CGT | 0.35 | 0.47 | 0.61 | 0.11 | −0.61 | 0.21 | −0.04 | −0.56 | −0.67 | −0.49 | −0.46 | −0.71 |
| 29 | CTA | −0.44 | 0.75 | 0.83 | −0.48 | −0.80 | 0.14 | −0.34 | −0.67 | −0.88 | −0.54 | −0.47 | −0.82 |
| 30 | CTC | 0.07 | 0.23 | 0.30 | −0.01 | −0.23 | 0.54 | −0.38 | 0.52 | 0.56 | 0.41 | 0.57 | 0.54 |
| 31 | CTG | 0.16 | −0.14 | −0.17 | 0.28 | −0.48 | −0.27 | 0.56 | 0.32 | 0.25 | −0.32 | −0.07 | 0.19 |
| 32 | CTT | 0.60 | 0.89 | 0.85 | −0.21 | −0.69 | 0.08 | −0.72 | −0.39 | −0.86 | −0.75 | −0.64 | −0.82 |
| 33 | GAA | 0.50 | 0.80 | 0.71 | 0.40 | −0.35 | −0.15 | −0.15 | 0.20 | −0.64 | −0.38 | −0.48 | −0.43 |
| 34 | GAC | −0.06 | −0.05 | −0.04 | 0.36 | 0.34 | 0.04 | 0.01 | 0.01 | 0.46 | 0.24 | 0.00 | 0.37 |
| 35 | GAG | −0.17 | −0.13 | −0.11 | 0.20 | 0.22 | 0.01 | 0.03 | 0.32 | 0.26 | 0.21 | 0.08 | 0.42 |
| 36 | GAT | 0.16 | 0.86 | 0.75 | −0.44 | −0.68 | −0.36 | −0.27 | −0.68 | −0.80 | −0.66 | −0.72 | −0.74 |
| 37 | GCA | 0.26 | 0.83 | 0.81 | −0.42 | −0.69 | −0.33 | −0.47 | −0.58 | −0.84 | −0.70 | −0.72 | −0.78 |
| 38 | GCC | −0.04 | 0.22 | 0.17 | 0.22 | 0.20 | 0.14 | 0.11 | −0.09 | 0.44 | 0.33 | 0.30 | 0.25 |
| 39 | GCG | −0.49 | −0.32 | −0.29 | −0.18 | 0.12 | −0.11 | −0.03 | 0.08 | 0.05 | −0.13 | 0.01 | 0.08 |
| 40 | GCT | 0.47 | 0.86 | 0.85 | −0.12 | −0.75 | −0.03 | −0.42 | −0.80 | −0.85 | −0.77 | −0.70 | −0.86 |
| 41 | GGA | −0.15 | 0.54 | 0.40 | −0.49 | −0.57 | −0.37 | −0.32 | −0.41 | −0.73 | −0.33 | −0.51 | −0.57 |
| 42 | GGC | −0.13 | −0.16 | −0.12 | 0.15 | 0.41 | 0.26 | 0.26 | 0.25 | 0.36 | 0.24 | 0.29 | 0.36 |
| 43 | GGG | −0.22 | 0.13 | −0.02 | −0.28 | −0.47 | −0.36 | −0.41 | −0.51 | −0.38 | −0.16 | −0.27 | −0.42 |
| 44 | GGT | 0.72 | 0.62 | 0.68 | 0.16 | −0.06 | −0.04 | 0.01 | −0.46 | −0.38 | −0.30 | −0.38 | −0.52 |
| 45 | GTA | 0.11 | 0.88 | 0.85 | −0.40 | −0.67 | 0.21 | −0.34 | −0.32 | −0.47 | −0.50 | −0.68 | −0.53 |
| 46 | GTC | 0.10 | 0.05 | 0.15 | 0.19 | 0.43 | 0.25 | 0.14 | 0.11 | 0.71 | 0.33 | 0.37 | 0.54 |
| 47 | GTG | 0.35 | −0.16 | −0.23 | 0.21 | 0.28 | −0.27 | −0.14 | 0.27 | 0.04 | −0.18 | −0.25 | 0.30 |
| 48 | GTT | 0.58 | 0.81 | 0.70 | −0.44 | −0.55 | −0.17 | −0.39 | −0.77 | −0.86 | −0.75 | −0.72 | −0.85 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.27 | −0.05 | −0.04 | 0.40 | 0.24 | −0.05 | 0.00 | 0.79 | 0.33 | 0.35 | 0.00 | 0.63 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.13 | 0.75 | 0.80 | −0.46 | −0.60 | −0.22 | −0.18 | 1.00 | −0.81 | −0.69 | −0.80 | −0.65 |
| 53 | TCA | −0.29 | 0.82 | 0.87 | −0.74 | −0.53 | 0.13 | −0.40 | −0.56 | −0.87 | −0.65 | −0.74 | −0.83 |
| 54 | TCC | −0.12 | 0.09 | 0.11 | 0.12 | 0.34 | 0.23 | 0.14 | 0.31 | 0.28 | 0.28 | 0.18 | 0.20 |
| 55 | TCG | −0.43 | −0.28 | −0.38 | −0.31 | 0.19 | −0.12 | −0.07 | 0.13 | 0.04 | −0.10 | −0.05 | 0.09 |
| 56 | TCT | −0.72 | 0.80 | 0.87 | −0.22 | 0.40 | −0.25 | −0.35 | −0.79 | −0.37 | −0.70 | −0.62 | −0.90 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.22 | −0.07 | −0.04 | −0.45 | 0.02 | 0.02 | 0.00 | −0.11 | −0.06 | 0.10 | 0.04 | 0.18 |
| 59 | TGG | −0.18 | 0.01 | 0.00 | −0.01 | 0.27 | −0.02 | −0.01 | 0.20 | 0.04 | 0.00 | −0.01 | 0.19 |

TABLE C.11-continued

CPW matrix Streptomyces coelicolor A3(2) full genome (left codon indicated in column 2, right codon indicated in row 2). Host cell: *S. coelicolor*; Sequence data: full *S. coelicilor* genome.

|  |  |  |  |  |  |  |  |  |  |  |  |  |
|---|---|---|---|---|---|---|---|---|---|---|---|---|
| 60 | TGT | 1.00 | 0.91 | 0.41 | −0.29 | −0.42 | 0.02 | 0.01 | −0.69 | −0.67 | −0.31 | −0.44 | −0.46 |
| 61 | TTA | 1.00 | 1.00 | 1.00 | −0.91 | −0.86 | 1.00 | −0.31 | −0.88 | −0.91 | −0.36 | −0.61 | 1.00 |
| 62 | TTC | 0.41 | −0.02 | −0.01 | 0.20 | 0.47 | −0.01 | −0.02 | 0.35 | 0.70 | 0.05 | 0.03 | 0.33 |
| 63 | TTG | 0.21 | −0.05 | −0.19 | −0.68 | −0.44 | 0.05 | −0.60 | −0.30 | −0.68 | −0.01 | −0.16 | −0.43 |
| 64 | TTT | 1.00 | 0.72 | 0.85 | −0.84 | −0.79 | −0.34 | −0.21 | −0.84 | −0.89 | −0.83 | −0.71 | −0.94 |

|  |  | ATA 13 | ATC 14 | ATG 15 | ATT 16 | CAA 17 | CAC 18 | CAG 19 | CAT 20 | CCA 21 | CCC 22 | CCG 23 | CCT 24 |
|---|---|---|---|---|---|---|---|---|---|---|---|---|---|

|  |  | 25 CGA | 26 CGC | 27 CGG | 28 CGT | 29 CTA | 30 CTC | 31 CTG | 32 CTT | 33 GAA | 34 GAC | 35 GAG | 36 GAT |
|---|---|---|---|---|---|---|---|---|---|---|---|---|---|
| 1 | AAA | −0.82 | −0.59 | −0.56 | −0.28 | −0.85 | −0.65 | −0.45 | −0.58 | 0.20 | 0.67 | 0.50 | 0.10 |
| 2 | AAC | 0.02 | −0.01 | −0.05 | 0.31 | 0.60 | −0.17 | 0.15 | 0.08 | 0.14 | −0.03 | −0.04 | 0.27 |
| 3 | AAG | 0.19 | 0.12 | −0.05 | 0.34 | 0.37 | −0.07 | 0.13 | 0.29 | −0.10 | −0.05 | −0.01 | 0.38 |
| 4 | AAT | −0.68 | 0.03 | 0.24 | −0.43 | −0.74 | −0.56 | −0.38 | −0.80 | −0.44 | 0.48 | 0.46 | −0.65 |
| 5 | ACA | −0.80 | −0.08 | −0.34 | −0.69 | −0.63 | −0.35 | −0.36 | −0.68 | −0.09 | 0.57 | 0.55 | −0.07 |
| 6 | ACC | 0.07 | −0.09 | −0.12 | −0.21 | 0.80 | 0.00 | 0.25 | 0.02 | −0.07 | −0.05 | −0.12 | −0.29 |
| 7 | ACG | 0.08 | 0.43 | 0.35 | 0.02 | 0.44 | −0.16 | −0.23 | −0.27 | 0.22 | 0.10 | 0.20 | −0.16 |
| 8 | ACT | −0.58 | −0.18 | −0.05 | −0.40 | −0.59 | −0.44 | −0.08 | −0.86 | −0.16 | 0.50 | 0.49 | −0.49 |
| 9 | AGA | −0.76 | −0.08 | −0.12 | −0.22 | −0.37 | −0.39 | −0.17 | −0.78 | −0.40 | 0.56 | 0.47 | −0.35 |
| 10 | AGC | −0.41 | −0.16 | −0.11 | −0.42 | 0.89 | 0.12 | 0.23 | −0.36 | −0.20 | −0.13 | −0.25 | −0.49 |
| 11 | AGG | −0.44 | 0.28 | 0.10 | −0.11 | −0.21 | −0.13 | 0.01 | −0.42 | −0.48 | 0.19 | 0.23 | −0.41 |
| 12 | AGT | −0.42 | 0.47 | 0.53 | −0.51 | −0.45 | 0.11 | 0.02 | −0.62 | −0.50 | −0.03 | −0.12 | −0.71 |
| 13 | ATA | −0.75 | −0.53 | −0.60 | −0.72 | −0.59 | −0.39 | −0.15 | −0.37 | 0.21 | 0.52 | 0.28 | 0.28 |
| 14 | ATC | 0.47 | −0.06 | 0.19 | 0.08 | 0.66 | −0.22 | 0.18 | −0.18 | 0.22 | −0.03 | −0.06 | 0.18 |
| 15 | ATG | 0.10 | −0.08 | 0.02 | 0.16 | 0.75 | −0.13 | 0.05 | 0.28 | 0.15 | −0.01 | −0.03 | 0.23 |
| 16 | ATT | −0.77 | −0.30 | 0.12 | −0.66 | 1.00 | −0.50 | −0.38 | −0.91 | 0.36 | 0.56 | 0.51 | −0.73 |
| 17 | CAA | −0.73 | −0.38 | −0.40 | −0.36 | −0.91 | −0.63 | −0.67 | −0.68 | −0.26 | 0.61 | 0.49 | −0.07 |
| 18 | CAC | 0.09 | −0.07 | −0.05 | 0.04 | −0.53 | −0.02 | 0.12 | 0.16 | 0.00 | −0.04 | −0.04 | −0.01 |
| 19 | CAG | 0.04 | −0.06 | 0.05 | 0.18 | −0.19 | −0.13 | 0.36 | 0.11 | −0.09 | −0.04 | 0.00 | 0.17 |
| 20 | CAT | −0.44 | 0.20 | 0.52 | 0.05 | −0.76 | −0.45 | −0.51 | −0.71 | 0.30 | 0.43 | 0.47 | −0.54 |
| 21 | CCA | −0.85 | −0.47 | −0.48 | −0.72 | −0.78 | −0.12 | −0.44 | −0.60 | −0.07 | 0.73 | 0.60 | −0.27 |
| 22 | CCC | −0.08 | 0.06 | 0.13 | −0.05 | 0.17 | 0.44 | 0.48 | 0.32 | −0.18 | −0.15 | −0.25 | −0.22 |
| 23 | CCG | −0.01 | −0.14 | 0.28 | 0.08 | −0.26 | −0.09 | −0.29 | −0.06 | 0.25 | 0.10 | 0.20 | 0.18 |
| 24 | CCT | −0.76 | −0.22 | −0.11 | −0.67 | −0.74 | −0.10 | 0.32 | −0.82 | −0.33 | 0.27 | 0.40 | −0.74 |
| 25 | CGA | −0.78 | −0.31 | −0.38 | −0.50 | −0.69 | −0.20 | −0.32 | −0.74 | 0.02 | 0.57 | 0.45 | −0.57 |
| 26 | CGC | −0.15 | −0.07 | 0.06 | −0.26 | 0.38 | 0.29 | 0.42 | 0.26 | −0.01 | −0.04 | −0.11 | −0.05 |
| 27 | CGG | 0.10 | 0.09 | 0.13 | 0.10 | −0.32 | −0.25 | −0.33 | 0.00 | 0.07 | 0.00 | 0.12 | 0.18 |
| 28 | CGT | −0.36 | 0.37 | 0.36 | −0.39 | −0.40 | 0.14 | 0.27 | −0.65 | −0.38 | −0.02 | −0.08 | −0.61 |
| 29 | CTA | −0.94 | −0.57 | −0.67 | −0.78 | −0.92 | −0.43 | −0.37 | −0.87 | −0.18 | 0.59 | 0.31 | −0.09 |
| 30 | CTC | 0.72 | 0.65 | 0.70 | 0.56 | 0.34 | 0.26 | 0.57 | 0.36 | −0.43 | −0.28 | 0.65 | −0.22 |
| 31 | CTG | 0.15 | −0.41 | −0.06 | −0.06 | 0.38 | −0.28 | −0.17 | 0.29 | −0.08 | 0.18 | −0.22 | 0.50 |
| 32 | CTT | −0.71 | −0.01 | 0.15 | −0.26 | −0.77 | −0.32 | 0.03 | −0.77 | −0.37 | 0.52 | −0.04 | −0.66 |
| 33 | GAA | −0.58 | −0.45 | −0.40 | 0.02 | −0.75 | −0.61 | −0.56 | −0.53 | 0.12 | 0.60 | 0.44 | 0.10 |
| 34 | GAC | 0.30 | 0.11 | −0.21 | 0.05 | 0.22 | 0.05 | 0.02 | 0.17 | 0.11 | −0.03 | −0.05 | 0.07 |
| 35 | GAG | 0.25 | 0.22 | −0.10 | 0.40 | 0.23 | 0.79 | −0.04 | 0.30 | −0.06 | −0.10 | −0.07 | 0.16 |
| 36 | GAT | −0.50 | 0.38 | 0.55 | −0.24 | −0.87 | −0.50 | −0.45 | −0.77 | 0.09 | 0.50 | 0.55 | −0.39 |
| 37 | GCA | −0.72 | −0.38 | −0.54 | −0.50 | −0.66 | −0.38 | −0.47 | −0.59 | 0.24 | 0.64 | 0.68 | −0.23 |
| 38 | GCC | 0.16 | −0.15 | −0.04 | −0.16 | 0.09 | 0.24 | 0.21 | 0.17 | −0.20 | −0.15 | −0.18 | −0.27 |
| 39 | GCG | −0.05 | 0.41 | 0.16 | 0.26 | 0.11 | −0.08 | −0.24 | 0.25 | 0.23 | 0.21 | 0.26 | 0.22 |
| 40 | GCT | −0.58 | 0.17 | 0.10 | −0.49 | −0.80 | −0.34 | −0.22 | −0.74 | −0.05 | 0.53 | 0.57 | −0.61 |
| 41 | GGA | −0.67 | −0.31 | −0.37 | −0.39 | −0.70 | −0.40 | −0.40 | −0.58 | 0.20 | 0.49 | 0.53 | −0.06 |
| 42 | GGC | 0.11 | 0.10 | 0.03 | −0.09 | 0.25 | 0.31 | 0.23 | 0.22 | 0.14 | −0.06 | −0.07 | 0.12 |
| 43 | GGG | −0.05 | 0.05 | −0.32 | −0.21 | −0.39 | −0.24 | −0.37 | −0.27 | 0.12 | 0.14 | 0.10 | 0.11 |
| 44 | GGT | 0.25 | 0.67 | 0.66 | 0.06 | −0.43 | −0.20 | −0.25 | −0.59 | −0.32 | −0.18 | −0.19 | −0.58 |
| 45 | GTA | −0.80 | −0.69 | −0.83 | −0.60 | −0.51 | −0.45 | −0.56 | −0.50 | 0.62 | 0.88 | 0.76 | 0.63 |
| 46 | GTC | 0.46 | 0.17 | 0.34 | 0.22 | 0.45 | 0.07 | 0.28 | 0.22 | −0.01 | −0.15 | −0.13 | −0.12 |
| 47 | GTG | 0.23 | −0.13 | −0.14 | 0.19 | 0.50 | −0.13 | −0.20 | 0.29 | 0.28 | 0.15 | 0.07 | 0.25 |
| 48 | GTT | −0.73 | 0.00 | 0.03 | −0.49 | −0.78 | −0.49 | −0.22 | −0.83 | 0.04 | 0.56 | 0.48 | −0.58 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.15 | 0.00 | −0.18 | 0.37 | 0.57 | 0.01 | 0.11 | 0.32 | 0.26 | −0.06 | −0.07 | 0.71 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | −0.59 | 0.44 | 0.34 | −0.07 | −0.87 | −0.59 | −0.69 | −0.67 | 0.46 | 0.64 | 0.63 | 0.55 |
| 53 | TCA | −0.75 | −0.31 | −0.49 | −0.55 | −0.90 | −0.43 | −0.55 | −0.57 | 0.35 | 0.65 | 0.77 | −0.20 |
| 54 | TCC | 0.09 | −0.05 | −0.01 | −0.05 | 0.11 | 0.15 | 0.17 | 0.24 | −0.07 | −0.06 | −0.03 | 0.03 |
| 55 | TCG | 0.39 | 0.31 | 0.32 | 0.25 | −0.10 | −0.11 | −0.30 | 0.02 | 0.39 | 0.22 | 0.28 | 0.24 |
| 56 | TCT | −0.81 | 0.16 | 0.08 | −0.67 | −0.78 | −0.19 | 0.08 | −0.86 | −0.22 | 0.42 | 0.59 | −0.66 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | −0.27 | 0.03 | −0.10 | −0.31 | 0.46 | 0.24 | −0.04 | 0.16 | 0.02 | −0.03 | −0.04 | 0.15 |
| 59 | TGG | 0.01 | 0.12 | −0.19 | 0.13 | −0.45 | 0.16 | −0.09 | 0.34 | 0.18 | −0.02 | −0.03 | 0.39 |
| 60 | TGT | −0.03 | 0.53 | 0.66 | −0.32 | −0.45 | −0.20 | −0.53 | −0.69 | −0.11 | 0.37 | 0.40 | −0.63 |

TABLE C.11-continued

CPW matrix Streptomyces coelicolor A3(2) full genome (left codon indicated in column 2, right codon indicated in row 2). Host cell: *S. coelicolor*; Sequence data: full *S. coelicilor* genome.

|    |     |       |       |       |       |       |       |       |       |       |       |       |
|----|-----|-------|-------|-------|-------|-------|-------|-------|-------|-------|-------|-------|
| 61 | TTA | −0.88 | −0.58 | −0.70 | −0.87 | 1.00  | −0.16 | −0.48 | 1.00  | 0.00  | 0.68  | 0.64  | 1.00  |
| 62 | TTC | 0.37  | −0.05 | 0.01  | 0.03  | 0.56  | −0.11 | 0.06  | 0.30  | 0.15  | −0.03 | −0.03 | 0.39  |
| 63 | TTG | −0.34 | −0.23 | −0.36 | −0.46 | −0.47 | −0.03 | −0.21 | −0.58 | −0.20 | 0.50  | −0.11 | −0.19 |
| 64 | TTT | −0.83 | −0.33 | −0.08 | −0.62 | −0.84 | −0.42 | −0.31 | −0.50 | 0.03  | 0.57  | 0.52  | −0.72 |

|     |     | CGA | CGC | CGG | CGT | CTA | CTC | CTG | CTT | GAA | GAC | GAG | GAT |
|-----|-----|-----|-----|-----|-----|-----|-----|-----|-----|-----|-----|-----|-----|
|     |     | 25  | 26  | 27  | 28  | 29  | 30  | 31  | 32  | 33  | 34  | 35  | 36  |

|    |     | 37    | 38    | 39    | 40    | 41    | 42    | 43    | 44    | 45    | 46    | 47    | 48    |
|----|-----|-------|-------|-------|-------|-------|-------|-------|-------|-------|-------|-------|-------|
|    |     | GCA   | GCC   | GCG   | GCT   | GGA   | GGC   | GGG   | GGT   | GTA   | GTC   | GTG   | GTT   |
| 1  | AAA | −0.31 | 0.44  | 0.43  | −0.27 | −0.23 | 0.43  | 0.30  | 0.30  | 0.09  | 0.66  | 0.57  | −0.12 |
| 2  | AAC | 0.40  | −0.05 | 0.01  | 0.22  | 0.21  | −0.15 | 0.25  | 0.31  | 0.33  | −0.10 | 0.13  | 0.26  |
| 3  | AAG | −0.13 | 0.10  | −0.17 | 0.12  | 0.29  | −0.16 | 0.23  | 0.39  | 0.58  | −0.10 | 0.02  | 0.23  |
| 4  | AAT | −0.23 | 0.13  | 0.26  | −0.48 | 0.25  | 0.67  | 0.45  | 0.19  | 0.51  | −0.05 | 0.02  | −0.69 |
| 5  | ACA | −0.61 | 0.39  | 0.32  | −0.62 | −0.29 | 0.62  | 0.21  | 0.20  | 0.29  | 0.68  | 0.56  | −0.50 |
| 6  | ACC | −0.14 | 0.08  | 0.07  | −0.21 | −0.20 | −0.15 | −0.12 | −0.27 | 0.38  | 0.02  | 0.20  | −0.12 |
| 7  | ACG | −0.46 | 0.05  | −0.28 | −0.33 | 0.18  | 0.40  | 0.21  | 0.35  | 0.43  | −0.16 | −0.32 | 0.01  |
| 8  | ACT | −0.05 | 0.38  | 0.16  | −0.79 | −0.07 | 0.68  | 0.52  | 0.18  | 0.39  | 0.49  | 0.45  | −0.51 |
| 9  | AGA | −0.55 | 0.21  | 0.13  | −0.47 | −0.62 | 0.47  | −0.26 | −0.25 | 0.75  | 0.35  | 0.36  | −0.58 |
| 10 | AGC | 0.13  | 0.14  | 0.03  | −0.08 | −0.14 | −0.07 | −0.14 | −0.26 | 0.71  | 0.13  | 0.15  | −0.31 |
| 11 | AGG | −0.42 | 0.09  | −0.11 | −0.38 | −0.14 | 0.28  | 0.28  | 0.42  | 0.60  | 0.07  | −0.12 | −0.62 |
| 12 | AGT | 0.02  | −0.09 | −0.15 | −0.72 | −0.27 | 0.41  | −0.05 | −0.22 | 0.68  | 0.16  | −0.15 | −0.50 |
| 13 | ATA | 0.36  | −0.16 | −0.14 | 0.81  | 0.04  | 0.27  | −0.10 | 0.66  | 1.00  | 0.54  | 0.58  | −0.42 |
| 14 | ATC | 0.45  | −0.12 | 0.14  | 0.30  | 0.37  | −0.13 | 0.21  | 0.10  | 0.85  | −0.14 | 0.09  | 0.03  |
| 15 | ATG | 0.12  | 0.03  | −0.06 | 0.07  | 0.33  | −0.12 | 0.21  | 0.24  | 0.93  | −0.01 | −0.06 | 0.04  |
| 16 | ATT | −0.02 | 0.50  | 0.49  | −0.59 | 0.29  | 0.74  | 0.33  | 0.76  | 0.75  | 0.60  | 0.64  | −0.82 |
| 17 | CAA | −0.49 | 0.35  | 0.40  | −0.48 | −0.62 | 0.40  | −0.43 | 0.00  | 0.08  | 0.55  | 0.51  | −0.23 |
| 18 | CAC | 0.24  | −0.05 | 0.05  | 0.37  | 0.08  | −0.09 | 0.00  | 0.09  | −0.11 | −0.04 | 0.18  | 0.00  |
| 19 | CAG | −0.29 | 0.02  | −0.02 | −0.06 | 0.10  | −0.09 | 0.14  | 0.34  | 0.12  | −0.02 | −0.04 | −0.12 |
| 20 | CAT | −0.36 | −0.06 | 0.15  | −0.63 | 0.26  | 0.74  | 0.61  | 0.22  | −0.52 | −0.25 | −0.46 | −0.74 |
| 21 | CCA | −0.49 | 0.50  | 0.42  | −0.60 | −0.59 | 0.47  | 0.00  | −0.19 | 0.19  | 0.68  | 0.44  | −0.49 |
| 22 | CCC | −0.36 | −0.14 | −0.02 | −0.40 | −0.29 | −0.30 | −0.14 | −0.33 | −0.37 | 0.09  | 0.24  | −0.13 |
| 23 | CCG | −0.10 | 0.11  | 0.12  | −0.09 | 0.18  | 0.30  | 0.17  | 0.34  | 0.09  | 0.00  | −0.24 | −0.12 |
| 24 | CCT | −0.17 | −0.10 | 0.14  | −0.82 | −0.33 | 0.52  | 0.15  | −0.40 | −0.34 | 0.35  | 0.51  | −0.76 |
| 25 | CGA | −0.59 | 0.16  | 0.14  | −0.56 | −0.61 | 0.15  | −0.35 | −0.36 | −0.53 | 0.53  | 0.20  | −0.60 |
| 26 | CGC | 0.20  | 0.03  | 0.22  | 0.24  | −0.18 | −0.22 | −0.21 | −0.28 | 0.18  | 0.10  | 0.41  | 0.09  |
| 27 | CGG | −0.13 | −0.05 | −0.14 | 0.04  | 0.27  | 0.24  | 0.30  | 0.42  | −0.17 | −0.10 | −0.40 | −0.09 |
| 28 | CGT | −0.01 | −0.24 | −0.15 | −0.49 | 0.19  | 0.48  | 0.26  | −0.23 | 0.15  | 0.16  | 0.38  | −0.32 |
| 29 | CTA | 0.18  | 0.47  | 0.80  | −0.32 | −0.07 | 0.67  | 0.38  | 0.03  | 0.56  | 0.78  | 0.49  | −0.76 |
| 30 | CTC | 0.24  | −0.39 | 0.05  | 0.10  | 0.05  | −0.48 | −0.16 | −0.37 | 0.01  | −0.17 | 0.39  | 0.06  |
| 31 | CTG | 0.40  | 0.09  | 0.31  | 0.45  | 0.52  | 0.29  | 0.51  | 0.57  | 0.54  | −0.07 | −0.08 | 0.47  |
| 32 | CTT | −0.15 | −0.12 | 0.36  | −0.57 | 0.29  | 0.61  | 0.27  | 0.00  | 0.41  | 0.35  | 0.43  | −0.73 |
| 33 | GAA | −0.24 | 0.37  | 0.23  | −0.07 | −0.36 | 0.32  | −0.23 | 0.44  | −0.13 | 0.52  | 0.45  | 0.42  |
| 34 | GAC | 0.33  | 0.01  | −0.07 | 0.36  | 0.01  | −0.06 | −0.06 | 0.15  | −0.34 | 0.05  | −0.03 | 0.33  |
| 35 | GAG | −0.19 | 0.11  | −0.23 | 0.16  | 0.14  | −0.12 | 0.06  | 0.39  | 0.28  | −0.06 | −0.13 | 0.11  |
| 36 | GAT | 0.04  | −0.03 | 0.21  | −0.65 | 0.31  | 0.76  | 0.60  | 0.57  | −0.47 | −0.06 | −0.08 | −0.70 |
| 37 | GCA | −0.51 | 0.41  | 0.42  | −0.36 | −0.35 | 0.49  | 0.05  | 0.16  | 0.36  | 0.71  | 0.53  | −0.44 |
| 38 | GCC | −0.09 | −0.04 | 0.08  | −0.12 | −0.41 | 0.33  | −0.42 | −0.45 | −0.50 | 0.03  | 0.01  | −0.04 |
| 39 | GCG | −0.23 | 0.07  | −0.16 | 0.04  | 0.08  | 0.01  | 0.00  | 0.15  | −0.05 | 0.08  | −0.30 | 0.12  |
| 40 | GCT | −0.01 | 0.07  | 0.14  | −0.76 | 0.05  | 0.71  | 0.35  | −0.14 | −0.19 | 0.37  | 0.48  | −0.74 |
| 41 | GGA | −0.52 | 0.22  | −0.05 | 0.17  | 0.01  | 0.52  | 0.28  | 0.39  | −0.32 | 0.38  | 0.09  | −0.10 |
| 42 | GGC | 0.26  | 0.05  | 0.01  | 0.27  | −0.15 | −0.21 | −0.19 | −0.30 | −0.20 | 0.02  | 0.14  | 0.02  |
| 43 | GGG | −0.19 | 0.34  | −0.27 | −0.10 | 0.18  | 0.59  | 0.79  | 0.54  | 0.33  | 0.22  | −0.34 | −0.12 |
| 44 | GGT | 0.17  | −0.29 | −0.34 | −0.62 | 0.09  | 0.39  | 0.30  | −0.29 | 0.07  | −0.27 | −0.35 | −0.55 |
| 45 | GTA | 0.45  | 0.73  | 0.74  | 0.06  | 0.38  | 0.73  | 0.50  | 0.54  | 0.64  | 0.85  | 0.80  | 0.13  |
| 46 | GTC | 0.35  | −0.21 | 0.14  | 0.21  | 0.06  | −0.30 | 0.01  | −0.14 | −0.27 | −0.23 | 0.23  | 0.29  |
| 47 | GTG | 0.20  | 0.11  | −0.05 | 0.23  | 0.37  | 0.31  | 0.27  | 0.45  | 0.53  | 0.11  | −0.12 | 0.39  |
| 48 | GTT | −0.17 | 0.11  | 0.39  | −0.68 | 0.60  | 0.57  | 0.57  | 0.15  | 0.03  | 0.40  | 0.47  | −0.58 |
| 49 | TAA | 0.00  | 0.00  | 0.00  | 0.00  | 0.00  | 0.00  | 0.00  | 0.00  | 0.00  | 0.00  | 0.00  | 0.00  |
| 50 | TAC | 0.37  | 0.01  | −0.10 | 0.59  | 0.16  | −0.13 | −0.02 | 0.55  | 0.11  | −0.12 | 0.19  | 0.28  |
| 51 | TAG | 0.00  | 0.00  | 0.00  | 0.00  | 0.00  | 0.00  | 0.00  | 0.00  | 0.00  | 0.00  | 0.00  | 0.00  |
| 52 | TAT | 0.30  | 0.24  | 0.17  | 0.16  | 0.18  | 0.76  | 0.72  | 0.72  | −0.58 | 0.03  | −0.34 | 0.37  |
| 53 | TCA | −0.39 | 0.45  | 0.34  | −0.29 | −0.43 | 0.63  | 0.33  | −0.05 | 0.38  | 0.78  | 0.57  | −0.51 |
| 54 | TCC | −0.14 | 0.08  | 0.04  | −0.15 | −0.15 | −0.11 | −0.17 | −0.22 | −0.29 | 0.11  | 0.16  | −0.05 |
| 55 | TCG | −0.31 | 0.07  | −0.34 | −0.23 | 0.22  | 0.31  | 0.15  | 0.39  | −0.09 | −0.09 | −0.43 | −0.18 |
| 56 | TCT | −0.37 | 0.12  | 0.02  | −0.87 | −0.48 | 0.66  | 0.20  | −0.32 | −0.05 | 0.24  | 0.56  | −0.71 |
| 57 | TGA | 0.00  | 0.00  | 0.00  | 0.00  | 0.00  | 0.00  | 0.00  | 0.00  | 0.00  | 0.00  | 0.00  | 0.00  |
| 58 | TGC | 0.19  | 0.12  | −0.10 | 0.06  | −0.13 | 0.05  | −0.23 | −0.19 | −0.06 | 0.14  | −0.04 | −0.01 |
| 59 | TGG | −0.03 | 0.14  | −0.19 | 0.30  | 0.05  | −0.09 | 0.20  | 0.21  | 0.26  | 0.16  | −0.20 | 0.24  |

TABLE C.11-continued

CPW matrix Streptomyces coelicolor A3(2) full genome (left codon indicated in column 2, right codon indicated in row 2). Host cell: *S. coelicolor*; Sequence data: full *S. coelicilor* genome.

| | | | | | | | | | | | | |
|---|---|---|---|---|---|---|---|---|---|---|---|---|
| 60 | TGT | −0.10 | −0.23 | −0.32 | −0.50 | 0.05 | 0.71 | 0.56 | 0.37 | −0.08 | −0.23 | −0.49 | −0.69 |
| 61 | TTA | 1.00 | 0.92 | 0.24 | −0.84 | −0.51 | 0.88 | −0.16 | 1.00 | −0.61 | 0.58 | 0.03 | 1.00 |
| 62 | TTC | 0.39 | −0.09 | 0.09 | 0.41 | 0.31 | −0.07 | 0.08 | 0.05 | 0.25 | −0.09 | 0.09 | 0.16 |
| 63 | TTG | −0.34 | 0.43 | 0.21 | −0.36 | 0.13 | 0.57 | 0.28 | 0.15 | 0.48 | 0.48 | 0.18 | −0.18 |
| 64 | TTT | 0.28 | 0.24 | 0.48 | −0.76 | −0.07 | 0.63 | 0.68 | 0.36 | −0.32 | 0.47 | 0.49 | −0.71 |

| | | GCA 37 | GCC 38 | GCG 39 | GCT 40 | GGA 41 | GGC 42 | GGG 43 | GGT 44 | GTA 45 | GTC 46 | GTG 47 | GTT 48 |
|---|---|---|---|---|---|---|---|---|---|---|---|---|---|

| | | 49 TAA | 50 TAC | 51 TAG | 52 TAT | 53 TCA | 54 TCC | 55 TCG | 56 TCT | 57 TGA | 58 TGC | 59 TGG | 60 TGT |
|---|---|---|---|---|---|---|---|---|---|---|---|---|---|
| 1 | AAA | 0.00 | 0.20 | 0.00 | −0.13 | −0.48 | 0.26 | 0.57 | −0.48 | 0.00 | 0.33 | −0.35 | −0.40 |
| 2 | AAC | 0.00 | −0.04 | 0.00 | 0.45 | 0.41 | 0.02 | 0.22 | 0.08 | 0.00 | −0.06 | −0.03 | 0.46 |
| 3 | AAG | 0.00 | −0.04 | 0.00 | 0.62 | 0.27 | 0.01 | −0.10 | 0.26 | 0.00 | −0.05 | 0.03 | 0.39 |
| 4 | AAT | 0.00 | 0.46 | 0.00 | 1.00 | −0.43 | −0.07 | −0.07 | −0.75 | 0.00 | 0.58 | 0.75 | −0.53 |
| 5 | ACA | 0.00 | 0.57 | 0.00 | −0.37 | −0.64 | 0.13 | −0.02 | −0.79 | 0.00 | 0.15 | 0.17 | −0.59 |
| 6 | ACC | 0.00 | 0.12 | 0.00 | −0.28 | −0.20 | 0.13 | −0.12 | −0.17 | 0.00 | −0.17 | −0.22 | −0.39 |
| 7 | ACG | 0.00 | −0.20 | 0.00 | −0.50 | −0.16 | 0.18 | 0.05 | −0.34 | 0.00 | 0.55 | 0.56 | −0.07 |
| 8 | ACT | 0.00 | 0.68 | 0.00 | −0.08 | −0.76 | −0.22 | −0.45 | −0.90 | 0.00 | 0.39 | 0.16 | 1.00 |
| 9 | AGA | 0.00 | 0.74 | 0.00 | −0.42 | −0.86 | 0.16 | −0.31 | −0.80 | 0.00 | 0.04 | 0.11 | 0.12 |
| 10 | AGC | 0.00 | 0.22 | 0.00 | −0.54 | 0.35 | 0.43 | 0.42 | −0.17 | 0.00 | 0.05 | −0.07 | −0.27 |
| 11 | AGG | 0.00 | 0.39 | 0.00 | −0.37 | −0.62 | 0.15 | −0.29 | −0.58 | 0.00 | 0.24 | 0.48 | −0.18 |
| 12 | AGT | 0.00 | 0.12 | 0.00 | −0.51 | −0.59 | −0.27 | −0.56 | −0.78 | 0.00 | −0.27 | 0.08 | −0.51 |
| 13 | ATA | 0.00 | 0.51 | 0.00 | 0.18 | 0.38 | −0.38 | −0.43 | −0.76 | 0.00 | 0.37 | 0.22 | 0.21 |
| 14 | ATC | 0.00 | −0.03 | 0.00 | 0.18 | 0.49 | 0.01 | 0.24 | 0.29 | 0.00 | −0.05 | −0.01 | 0.31 |
| 15 | ATG | 0.00 | −0.02 | 0.00 | 0.39 | 0.34 | 0.11 | −0.01 | −0.03 | 0.00 | −0.03 | 0.00 | 0.36 |
| 16 | ATT | 0.00 | 0.30 | 0.00 | −0.43 | −0.75 | −0.24 | 0.02 | −0.70 | 0.00 | 0.83 | 0.45 | −0.41 |
| 17 | CAA | 0.00 | 0.80 | 0.00 | −0.13 | −0.39 | 0.47 | 0.49 | 1.00 | 0.00 | 0.58 | 0.11 | 1.00 |
| 18 | CAC | 0.00 | −0.05 | 0.00 | −0.05 | 0.07 | −0.02 | 0.21 | 0.42 | 0.00 | −0.08 | −0.06 | 0.27 |
| 19 | CAG | 0.00 | −0.07 | 0.00 | 0.63 | 0.09 | −0.02 | −0.06 | 0.39 | 0.00 | −0.07 | −0.01 | 0.40 |
| 20 | CAT | 0.00 | 0.64 | 0.00 | 0.26 | 0.15 | −0.06 | 0.24 | −0.48 | 0.00 | 0.66 | 0.79 | 0.69 |
| 21 | CCA | 0.00 | 0.72 | 0.00 | 0.41 | −0.75 | 0.43 | 0.34 | −0.81 | 0.00 | 0.11 | 0.15 | −0.72 |
| 22 | CCC | 0.00 | 0.12 | 0.00 | −0.15 | −0.17 | 0.00 | −0.11 | −0.51 | 0.00 | −0.29 | −0.25 | −0.42 |
| 23 | CCG | 0.00 | −0.11 | 0.00 | −0.09 | −0.08 | −0.01 | −0.01 | 0.17 | 0.00 | 0.33 | 0.23 | 0.40 |
| 24 | CCT | 0.00 | 0.58 | 0.00 | −0.61 | −0.83 | −0.53 | −0.50 | −0.86 | 0.00 | 0.13 | 0.45 | −0.76 |
| 25 | CGA | 0.00 | 0.41 | 0.00 | −0.46 | −0.72 | 0.24 | 0.14 | −0.72 | 0.00 | −0.17 | −0.05 | −0.65 |
| 26 | CGC | 0.00 | −0.19 | 0.00 | −0.43 | −0.18 | −0.11 | 0.06 | 0.05 | 0.00 | −0.21 | −0.31 | −0.38 |
| 27 | CGG | 0.00 | 0.19 | 0.00 | −0.02 | 0.02 | 0.32 | 0.17 | 0.32 | 0.00 | 0.33 | 0.41 | 0.11 |
| 28 | CGT | 0.00 | 0.34 | 0.00 | −0.11 | −0.66 | −0.42 | −0.42 | −0.64 | 0.00 | 0.38 | 0.58 | −0.42 |
| 29 | CTA | 0.00 | 0.59 | 0.00 | −0.76 | −0.72 | 0.71 | 0.49 | −0.50 | 0.00 | 0.68 | −0.10 | −0.68 |
| 30 | CTC | 0.00 | −0.16 | 0.00 | 0.04 | 0.52 | −0.23 | 0.42 | 0.31 | 0.00 | 0.40 | 0.43 | 0.37 |
| 31 | CTG | 0.00 | 0.08 | 0.00 | 0.37 | 0.43 | −0.11 | 0.05 | 0.52 | 0.00 | −0.23 | −0.20 | 0.27 |
| 32 | CTT | 0.00 | 0.58 | 0.00 | −0.53 | −0.62 | −0.37 | −0.18 | −0.83 | 0.00 | 0.72 | 0.75 | 0.30 |
| 33 | GAA | 0.00 | 0.65 | 0.00 | 0.45 | −0.35 | 0.44 | 0.42 | 0.01 | 0.00 | 0.21 | 0.16 | 0.75 |
| 34 | GAC | 0.00 | −0.05 | 0.00 | 0.39 | 0.33 | 0.02 | 0.09 | 0.51 | 0.00 | −0.06 | −0.04 | 0.27 |
| 35 | GAG | 0.00 | −0.13 | 0.00 | 0.56 | 0.15 | −0.02 | −0.17 | 0.57 | 0.00 | −0.09 | −0.03 | 0.45 |
| 36 | GAT | 0.00 | 0.60 | 0.00 | 0.37 | −0.78 | −0.08 | −0.17 | −0.68 | 0.00 | 0.64 | 0.88 | 0.59 |
| 37 | GCA | 0.00 | 0.56 | 0.00 | 0.28 | −0.53 | 0.13 | −0.10 | −0.68 | 0.00 | 0.32 | 0.05 | −0.32 |
| 38 | GCC | 0.00 | 0.00 | 0.00 | −0.16 | −0.04 | −0.12 | −0.11 | −0.09 | 0.00 | −0.18 | −0.19 | −0.41 |
| 39 | GCG | 0.00 | −0.07 | 0.00 | −0.10 | 0.05 | 0.06 | 0.03 | 0.05 | 0.00 | 0.38 | 0.33 | 0.24 |
| 40 | GCT | 0.00 | 0.59 | 0.00 | 0.00 | −0.75 | −0.53 | −0.52 | −0.87 | 0.00 | 0.44 | 0.52 | −0.52 |
| 41 | GGA | 0.00 | −0.01 | 0.00 | −0.29 | −0.47 | 0.32 | −0.09 | 0.20 | 0.00 | 0.22 | 0.23 | −0.46 |
| 42 | GGC | 0.00 | 0.01 | 0.00 | −0.32 | 0.13 | 0.12 | 0.04 | 0.24 | 0.00 | −0.11 | −0.21 | −0.32 |
| 43 | GGG | 0.00 | −0.07 | 0.00 | −0.06 | −0.07 | 0.33 | 0.00 | 0.15 | 0.00 | 0.25 | 0.38 | −0.12 |
| 44 | GGT | 0.00 | 0.23 | 0.00 | 0.26 | −0.56 | −0.26 | −0.49 | −0.70 | 0.00 | 0.57 | 0.80 | 0.01 |
| 45 | GTA | 0.00 | 0.88 | 0.00 | 0.47 | 0.38 | 0.55 | 0.46 | −0.46 | 0.00 | 0.75 | 0.35 | −0.13 |
| 46 | GTC | 0.00 | −0.10 | 0.00 | −0.07 | 0.40 | −0.22 | 0.16 | 0.17 | 0.00 | −0.04 | 0.14 | 0.21 |
| 47 | GTG | 0.00 | 0.05 | 0.00 | 0.21 | 0.27 | 0.19 | −0.03 | 0.47 | 0.00 | −0.07 | −0.20 | 0.24 |
| 48 | GTT | 0.00 | 0.64 | 0.00 | −0.24 | −0.83 | −0.22 | −0.33 | −0.49 | 0.00 | 0.68 | 0.81 | 0.28 |
| 49 | TAA | 0.00 | 0.00 | 0.00 | 0.00 | 0.00 | 0.00 | 0.00 | 0.00 | 0.00 | 0.00 | 0.00 | 0.00 |
| 50 | TAC | 0.00 | −0.08 | 0.00 | 0.94 | 0.26 | 0.10 | −0.11 | 0.80 | 0.00 | −0.09 | −0.03 | 0.62 |
| 51 | TAG | 0.00 | 0.00 | 0.00 | 0.00 | 0.00 | 0.00 | 0.00 | 0.00 | 0.00 | 0.00 | 0.00 | 0.00 |
| 52 | TAT | 0.00 | 0.73 | 0.00 | 0.61 | −0.46 | 0.57 | 0.04 | 1.00 | 0.00 | 0.62 | 0.64 | 0.45 |
| 53 | TCA | 0.00 | 0.78 | 0.00 | 1.00 | −0.63 | 0.38 | −0.12 | −0.85 | 0.00 | 0.18 | 0.07 | 0.41 |
| 54 | TCC | 0.00 | −0.01 | 0.00 | 0.28 | 0.10 | −0.07 | −0.24 | −0.02 | 0.00 | −0.25 | −0.22 | −0.05 |
| 55 | TCG | 0.00 | −0.21 | 0.00 | 0.22 | 0.01 | 0.10 | −0.07 | 0.07 | 0.00 | 0.45 | 0.45 | 0.42 |
| 56 | TCT | 0.00 | 0.76 | 0.00 | −0.46 | −0.62 | −0.52 | −0.55 | −0.90 | 0.00 | 0.41 | 0.48 | 1.00 |
| 57 | TGA | 0.00 | 0.00 | 0.00 | 0.00 | 0.00 | 0.00 | 0.00 | 0.00 | 0.00 | 0.00 | 0.00 | 0.00 |
| 58 | TGC | 0.00 | −0.02 | 0.00 | −0.25 | 0.03 | 0.06 | −0.20 | −0.03 | 0.00 | −0.03 | −0.07 | −0.08 |
| 59 | TGG | 0.00 | −0.01 | 0.00 | 0.15 | −0.14 | 0.15 | −0.17 | 0.39 | 0.00 | −0.03 | 0.00 | 0.27 |

TABLE C.11-continued

CPW matrix Streptomyces coelicolor A3(2) full genome (left codon indicated in column 2, right codon indicated in row 2). Host cell: *S. coelicolor*; Sequence data: full *S. coelicilor* genome.

| | | | | | | | | | | | | |
|---|---|---|---|---|---|---|---|---|---|---|---|---|
| 60 | TGT | 0.00 | 0.43 | 0.00 | −0.26 | −0.72 | −0.31 | −0.45 | −0.84 | 0.00 | 0.43 | 0.76 | −0.42 |
| 61 | TTA | 0.00 | 1.00 | 0.00 | −0.94 | −0.85 | 0.67 | 0.52 | −0.91 | 0.00 | −0.45 | −0.69 | 1.00 |
| 62 | TTC | 0.00 | −0.02 | 0.00 | 0.38 | 0.40 | −0.12 | 0.14 | 0.40 | 0.00 | −0.03 | −0.01 | 0.29 |
| 63 | TTG | 0.00 | 0.08 | 0.00 | −0.55 | −0.73 | −0.10 | −0.27 | −0.57 | 0.00 | 0.01 | −0.44 | −0.52 |
| 64 | TTT | 0.00 | 0.47 | 0.00 | −0.48 | −0.48 | −0.02 | 0.11 | −0.69 | 0.00 | 0.57 | 0.62 | −0.69 |

| | TAA 49 | TAC 50 | TAG 51 | TAT 52 | TCA 53 | TCC 54 | TCG 55 | TCT 56 | TGA 57 | TGC 58 | TGG 59 | TGT 60 |
|---|---|---|---|---|---|---|---|---|---|---|---|---|

| | | 61 TTA | 62 TTC | 63 TTG | 64 TTT |
|---|---|---|---|---|---|
| 1 | AAA | 1.00 | 0.43 | −0.28 | −0.73 |
| 2 | AAC | 0.08 | −0.02 | 0.78 | 0.57 |
| 3 | AAG | 1.00 | −0.02 | 0.27 | −0.02 |
| 4 | AAT | 1.00 | 0.35 | 0.44 | −0.65 |
| 5 | ACA | 1.00 | 0.65 | −0.14 | −0.51 |
| 6 | ACC | 0.62 | −0.12 | 0.28 | 0.01 |
| 7 | ACG | −0.37 | 0.22 | −0.25 | −0.01 |
| 8 | ACT | −0.93 | 0.25 | −0.57 | −0.82 |
| 9 | AGA | 1.00 | 0.48 | −0.14 | −0.76 |
| 10 | AGC | 1.00 | 0.18 | 0.51 | −0.41 |
| 11 | AGG | −0.44 | 0.13 | −0.48 | 0.20 |
| 12 | AGT | 1.00 | 0.15 | 0.60 | −0.80 |
| 13 | ATA | 1.00 | 0.41 | −0.05 | −0.43 |
| 14 | ATC | 1.00 | −0.01 | 0.76 | 0.18 |
| 15 | ATG | 1.00 | −0.01 | 0.63 | 0.38 |
| 16 | ATT | 1.00 | 0.25 | −0.70 | −0.91 |
| 17 | CAA | −0.90 | 0.77 | −0.69 | −0.85 |
| 18 | CAC | −0.19 | −0.04 | 0.49 | 0.16 |
| 19 | CAG | −0.46 | −0.04 | −0.74 | 0.39 |
| 20 | CAT | 1.00 | 0.50 | −0.31 | 1.00 |
| 21 | CCA | −0.84 | 0.71 | −0.64 | −0.59 |
| 22 | CCC | −0.37 | −0.15 | −0.07 | −0.15 |
| 23 | CCG | 0.04 | 0.09 | −0.58 | −0.07 |
| 24 | CCT | 1.00 | 0.34 | −0.41 | −0.65 |
| 25 | CGA | −0.88 | 0.41 | −0.39 | −0.69 |
| 26 | CGC | 0.51 | −0.09 | 0.64 | −0.30 |
| 27 | CGG | −0.43 | 0.09 | −0.51 | 0.21 |
| 28 | CGT | −0.72 | −0.05 | 0.03 | −0.56 |
| 29 | CTA | −0.95 | 0.56 | −0.70 | −0.67 |
| 30 | CTC | 0.32 | −0.09 | 0.71 | 0.04 |
| 31 | CTG | 0.29 | 0.04 | 0.02 | 0.54 |
| 32 | CTT | −0.94 | 0.36 | −0.56 | −0.79 |
| 33 | GAA | −0.29 | 0.65 | 0.19 | 0.00 |
| 34 | GAC | 1.00 | −0.03 | 0.62 | 0.38 |
| 35 | GAG | −0.12 | −0.11 | −0.52 | 0.26 |
| 36 | GAT | −0.57 | 0.40 | −0.39 | 0.37 |
| 37 | GCA | −0.59 | 0.68 | −0.52 | −0.55 |
| 38 | GCC | 0.26 | −0.10 | 0.47 | −0.12 |
| 39 | GCG | −0.52 | 0.09 | −0.43 | −0.20 |
| 40 | GCT | −0.85 | 0.36 | −0.53 | −0.70 |
| 41 | GGA | −0.50 | 0.19 | 0.08 | −0.33 |
| 42 | GGC | 0.65 | −0.04 | 0.63 | −0.12 |
| 43 | GGG | −0.48 | 0.05 | −0.43 | −0.19 |
| 44 | GGT | −0.35 | 0.05 | 0.31 | −0.58 |
| 45 | GTA | 1.00 | 0.82 | −0.21 | 0.65 |
| 46 | GTC | 0.61 | −0.18 | 0.84 | 0.57 |
| 47 | GTG | 0.64 | 0.20 | 0.32 | 0.41 |
| 48 | GTT | 1.00 | 0.26 | −0.53 | −0.24 |
| 49 | TAA | 0.00 | 0.00 | 0.00 | 0.00 |
| 50 | TAC | 0.65 | −0.02 | 0.60 | 0.37 |
| 51 | TAG | 0.00 | 0.00 | 0.00 | 0.00 |
| 52 | TAT | −0.86 | 0.37 | −0.31 | −0.41 |
| 53 | TCA | −0.87 | 0.65 | −0.42 | −0.81 |
| 54 | TCC | 0.27 | −0.24 | 0.12 | −0.10 |
| 55 | TCG | −0.06 | 0.25 | −0.52 | 0.25 |
| 56 | TCT | −0.92 | 0.33 | −0.72 | −0.67 |
| 57 | TGA | 0.00 | 0.00 | 0.00 | 0.00 |
| 58 | TGC | −0.52 | −0.02 | 0.50 | −0.21 |
| 59 | TGG | −0.17 | 0.00 | −0.01 | −0.11 |
| 60 | TGT | 1.00 | 0.31 | −0.25 | −0.22 |
| 61 | TTA | 1.00 | 0.72 | −0.82 | 1.00 |
| 62 | TTC | 0.16 | −0.02 | 0.63 | 0.51 |
| 63 | TTG | 1.00 | 0.20 | −0.74 | −0.55 |
| 64 | TTT | 1.00 | 0.45 | −0.86 | −0.47 |

TABLE C.11-continued

CPW matrix Streptomyces coelicolor A3(2) full genome (left codon indicated in column 2, right codon indicated in row 2). Host cell: *S. coelicolor*; Sequence data: full *S. coelicilor* genome.

| | TTA | TTC | TTG | TTT |
|---|---|---|---|---|
| | 61 | 62 | 63 | 64 |

The invention claimed is:

1. A computerized method of optimizing a nucleotide coding sequence coding for a predetermined amino acid sequence for expression in a predetermined host cell, the method comprising:
(a) generating, using a suitably programmed computer, at least one coding sequence that codes for the predetermined amino acid sequence;
(b) generating, using the suitably programmed computer, at least one newly generated coding sequence from at least one coding sequence by replacing in at least one coding sequence at least one codon by a synonymous codon;
(c) determining, using the suitably programmed computer, a fitness value of said at least one coding sequence and a fitness value of said at least one newly generated coding sequence while using a fitness function that determines at least one of single codon fitness and codon pair fitness for the predetermined host cell;
(d) choosing, using the suitably programmed computer, at least one selected coding sequence amongst said at least one coding sequence and said at least one newly generated coding sequence in accordance with a predetermined selection criterion such that the higher is said fitness value, the higher is a chance of being chosen;
(e) repeating (b) through (d), using the suitably programmed computer, while treating said at least one selected coding sequence as at least one coding sequence in (b) through (d) until a predetermined iteration stop criterion is fulfilled,
wherein said fitness function defines single codon fitness by:

$$fit_c(g) = 100 - \frac{1}{|g|} \cdot \sum_{k=1}^{|g|} |r_c^{target}(c(k)) - r_c^g(c(k))| \cdot 100$$

wherein g symbolizes a coding sequence, |g| its length, g(k) its k-th codon, $r_c^{target}(c(k))$ is a desired ratio of codon c(k) and $r_c^g(c(k))$ an actual ratio in the nucleotide coding sequence g.

2. A method according to claim 1, wherein said predetermined selection criterion is such that said at least one selected coding sequence have a best fitness value according to a predetermined criterion.

3. A method according to claim 1, wherein said method comprises, after (e):
(f) selecting a best individual coding sequence amongst said at least one selected coding sequences where said best individual coding sequence has a better fitness value than other selected coding sequences.

4. A method according to claim 1, wherein said predetermined iteration stop criterion is at least one of the following:
(a) testing whether at least one of said selected coding sequences have a best fitness value above a predetermined threshold value; or
(b) testing whether none of said selected coding sequences has a best fitness value below said predetermined threshold value; or
(c) testing whether at least one of said selected coding sequences has at least 30% of the codon pairs with associated positive codon pair weights for the predetermined host cell in said coding sequence being transformed into codon pairs with associated negative weights; or
(d) testing whether at least one of said selected coding sequences has at least 30% of the codon pairs with associated positive weights above 0 for the predetermined host cell in said coding sequence being transformed into codon pairs with associated weights below 0.

5. A method according to claim 1, where said coding nucleotide sequence coding for a predetermined amino acid sequence is selected from the group consisting of:
(a) a wild-type nucleotide sequence coding for said predetermined amino acid sequence;
(b) a reverse translation of the predetermined amino acid sequence whereby a codon for an amino acid position in the predetermined amino acid sequence is randomly chosen from the synonymous codons coding for the amino acid; and
(c) a reverse translation of the predetermined amino acid sequence whereby a codon for an amino acid position in the predetermined amino acid sequence is chosen in accordance with a single-codon bias for the predetermined host cell or a species related to the host cell.

6. A method according to claim 1, wherein said predetermined host cell is a cell of a microorganism of a genus selected from the group consisting of: *Bacillus, Actinomycetis, Escherichia, Streptomyces, Aspergillus, Penicillium, Kluyveromyces*, and *Saccharomyces*.

7. A method according to claim 1, wherein said predetermined host cell is a cell of an animal or plant, preferably a cell of a cell line selected from the group consisting of CHO, BHK, NS0, COS, Vero, PER.C6™, HEK-293, *Drosophila* S2, *Spodoptera* Sf9, and *Spodoptera* S f21.

8. A computer for optimizing a nucleotide coding sequence coding for a predetermined amino acid sequence for expression in a predetermined host cell, comprising:
a processor and memory, wherein the processor is arranged to read from said memory and write into said memory, and wherein the memory comprises data and instructions arranged such that said processor is suitably programmed to perform the method according to claim 1.

9. A computer program product comprising data and instructions encoded on a non-transitory computer readable medium, wherein the data and instructions are executable by a computer to cause the computer and a processor to carry out the method according to claim 1.

10. A method according to claim 1, wherein cpi is between $10^{-4}$ and 0.5.

11. A method according to claim 1, wherein said codon pair weights w are taken from a 61×61 codon pair matrix without stop codons, or a 61×64 codon pair matrix that includes stop-codons, and wherein said codon pair weights w are calculated on the basis of a computer-based method, using as input at least one of the following:
(a) a group of nucleotide sequences consisting of at least 200 coding sequences of a predetermined host; or
(b) a group of nucleotide sequences consisting of at least 200 coding sequences of the species to which the predetermined host belongs; or
(c) a group of nucleotide sequences consisting of at least 5% of the protein encoding nucleotide sequences in a genome sequence of the predetermined host; or
(d) a group of nucleotide sequences consisting of at least 5% of the protein encoding nucleotide sequences in a genome sequence of a genus related to the predetermined host.

12. A method according to claim 1, wherein said codon pair weights w are determined for at least 50% of the possible 61×64 codon pairs including the termination signal as stop codon.

13. A computerized method of optimizing a nucleotide coding sequence coding for a predetermined amino acid sequence, for expression in a predetermined host cell, the method comprising:
(a) generating, using a suitably programmed computer, at least one coding sequence that codes for the predetermined amino acid sequence;
(b) generating, using the suitably programmed computer, at least one newly generated coding sequence from at least one coding sequence by replacing in at least one coding sequence at least one codons by a synonymous codon;
(c) determining, using the suitably programmed computer, a fitness value of said at least one coding sequence and a fitness value of said at least one newly generated coding sequence while using a fitness function that determines at least one of single codon fitness and codon pair fitness for the predetermined host cell;
(d) choosing, using the suitably programmed computer, at least one selected coding sequence amongst said at least one coding sequence and said at least one newly generated coding sequence in accordance with a predetermined selection criterion such that the higher is said fitness value, the higher is a chance of being chosen;
(e) repeating (b) through (d), using the suitably programmed computer, while treating said at least one selected coding sequence as at least one coding sequence in (b) through (d) until a predetermined iteration stop criterion is fulfilled,
wherein said fitness function defines codon pair fitness:

$$fit_{cp}(g) = \frac{1}{|g|-1} \cdot \sum_{k=1}^{|g|-1} w((c(k), c(k+1))$$

wherein w((c(k), c(k+1)) is a weight of a codon pair in a coding sequence g, |g| is length of said nucleotide coding sequence and c(k) is k-th codon in said coding sequence.

14. A method according to claim 13, wherein said codon pair weights w are taken from a 61×61 codon pair matrix without stop codons, or a 61×64 codon pair matrix that includes stop-codons, and wherein said codon pair weights w are calculated on the basis of a computer-based method, using as input at least one of the following:
  (a) a group of nucleotide sequences consisting of at least 200 coding sequences of a predetermined host; or
  (b) a group of nucleotide sequences consisting of at least 200 coding sequences of the species to which the predetermined host belongs; or
  (c) a group of nucleotide sequences consisting of at least 5% of the protein encoding nucleotide sequences in a genome sequence of the predetermined host; or
  (d) a group of nucleotide sequences consisting of at least 5% of the protein encoding nucleotide sequences in a genome sequence of a genus related to the predetermined host.

15. A method according to claim 14, wherein said codon pair weights w are determined for at least 50% of the possible 61×64 codon pairs including the termination signal as stop codon.

16. A method according to claim 13, wherein said codon pair weights w are taken from a 61×61 codon pair matrix without stop codons, or a 61×64 codon pair matrix that includes stop-codons, and wherein said codon pair weights w are defined by:

$$w((c_i, c_j)) = \frac{n_{exp}^{combi}((c_i, c_j)) - n_{obs}^{high}((c_i, c_j))}{\max(n_{obs}^{high}((c_i, c_j)), n_{exp}^{combi}((c_i, c_j)))}$$

wherein the combined expected values $n_{exp}^{combi}((c_i,c_j))$ are defined by:

$$n_{exp}^{combi}((c_i, c_j)) = r_{sc}^{all}(c_i) \cdot r_{sc}^{all}(c_j) \cdot \sum_{\substack{c_k \in syn(c_i) \\ c_l \in syn(c_j)}} n_{obs}^{high}((c_k, c_l))$$

wherein $r_{sc}^{all}(c_k)$ denote the single codon ratio of $c_k$ in the whole genome data set and $n_{obs}^{high}((c_i,c_j))$ the occurrences of a pair $(c_i,c_j)$ in the highly expressed group, and wherein the highly expressed group are the genes whose mRNA's can be detected at a level of at least 20 copies per cell.

17. A method according to claim 13, wherein said predetermined selection criterion is such that said at least one selected coding sequence have a best fitness value according to a predetermined criterion.

18. A method according to claim 13, wherein said method comprises, after (e):
  (f) selecting a best individual coding sequence amongst said at least one selected coding sequences where said best individual coding sequence has a better fitness value than other selected coding sequences.

19. A method according to claim 13, wherein said predetermined iteration stop criterion is at least one of the following:
  (a) testing whether at least one of said selected coding sequences have a best fitness value above a predetermined threshold value; or
  (b) testing whether none of said selected coding sequences has a best fitness value below said predetermined threshold value; or
  (c) testing whether at least one of said selected coding sequences has at least 30% of the codon pairs with associated positive codon pair weights for the predetermined host cell in said coding sequence being transformed into codon pairs with associated negative weights; or
  (d) testing whether at least one of said selected coding sequences has at least 30% of the codon pairs with associated positive weights above 0 for the predetermined host cell in said coding sequence being transformed into codon pairs with associated weights below 0.

20. A method according to claim 13, wherein cpi is between $10^{-4}$ and 0.5.

21. A method according to claim 13, where said coding nucleotide sequence coding for a predetermined amino acid sequence is selected from the group consisting of:
  (a) a wild-type nucleotide sequence coding for said predetermined amino acid sequence;
  (b) a reverse translation of the predetermined amino acid sequence whereby a codon for an amino acid position in the predetermined amino acid sequence is randomly chosen from the synonymous codons coding for the amino acid; and
  (c) a reverse translation of the predetermined amino acid sequence whereby a codon for an amino acid position in the predetermined amino acid sequence is chosen in accordance with a single-codon bias for the predetermined host cell or a species related to the host cell.

22. A method according to claim 13, wherein said predetermined host cell is a cell of a microorganism of a genus selected from the group consisting of: *Bacillus, Actinomycetis, Escherichia, Streptomyces, Aspergillus, Penicillium, Kluyveromyces*, and *Saccharomyces*.

23. A method according to claim 13, wherein said predetermined host cell is a cell of an animal or plant, preferably a cell of a cell line selected from the group consisting of CHO, BHK, NS0, COS, Vero, PER.C6™, HEK-293, *Drosophila* S2, *Spodoptera* Sf9, and *Spodoptera* Sf21.

24. A computer for optimizing a nucleotide coding sequence coding for a predetermined amino acid sequence for expression in a predetermined host cell, comprising:
  a processor and memory, wherein the processor is arranged to read from said memory and write into said memory, and wherein the memory comprises data and instructions arranged such that said processor is suitably programmed to perform the method according to claim 13.

25. A computerized method of optimizing a nucleotide coding sequence coding for a predetermined amino acid sequence, for expression in a predetermined host cell, the method comprising:
  (a) generating, using a suitably programmed computer, at least one coding sequence that codes for the predetermined amino acid sequence;
  (b) generating, using the suitably programmed computer, at least one newly generated coding sequence from at least one coding sequence by replacing in at least one coding sequence at least one codons by a synonymous codon;
  (c) determining, using the suitably programmed computer, a fitness value of said at least one coding sequence and a fitness value of said at least one newly generated coding sequence while using a fitness function that determines at least one of single codon fitness and codon pair fitness for the predetermined host cell;
  (d) choosing, using the suitably programmed computer, at least one selected coding sequence amongst said at least one coding sequence and said at least one newly generated coding sequence in accordance with a predetermined selection criterion such that the higher is said fitness value, the higher is a chance of being chosen;

(e) repeating (b) through (d), using the suitably programmed computer, while treating said at least one selected coding sequence as at least one coding sequence in (b) through (d) until a predetermined iteration stop criterion is fulfilled, wherein said fitness function is defined by:

$$fit_{combi}(g) = \frac{fit_{cp}(g)}{cpi + fit_{sc}(g)}$$

wherein $$fit_{cp}(g) = \frac{1}{|g|-1} \cdot \sum_{k=1}^{|g|-1} w((c(k)), c(k+1))$$

$$fit_{sc}(g) = \frac{1}{|g|} \cdot \sum_{k=1}^{|g|} |r_{sc}^{target}(c(k)) - r_{sc}^{g}(c(k))|$$

cpi is a real value greater than zero, $fit_{cp}(g)$ is codon pair fitness function, $fit_{sc}(g)$ is a single codon fitness function, w((c(k), c(k+1))) is a weight of a codon pair in a coding sequence g, |g| is length of said coding sequence, c(k) is k-th codon in said sequence of codons, $r_{sc}^{target}$ (c(k)) is a desired ratio of codon c(k) and $r_{sc}^{g}$ (c(k)) an actual ratio in the coding sequence g.

26. A method according to claim 25, wherein cpi is between $10^{-4}$ and 0.5.

27. A method according to claim 25, wherein said predetermined selection criterion is such that said at least one selected coding sequence have a best fitness value according to a predetermined criterion.

28. A method according to claim 25, wherein said method comprises, after (e):
(f) selecting a best individual coding sequence amongst said at least one selected coding sequences where said best individual coding sequence has a better fitness value than other selected coding sequences.

29. A method according to claim 25, wherein said predetermined iteration stop criterion is at least one of the following:
(a) testing whether at least one of said selected coding sequences have a best fitness value above a predetermined threshold value; or
(b) testing whether none of said selected coding sequences has a best fitness value below said predetermined threshold value; or
(c) testing whether at least one of said selected coding sequences has at least 30% of the codon pairs with associated positive codon pair weights for the predetermined host cell in said coding sequence being transformed into codon pairs with associated negative weights; or
(d) testing whether at least one of said selected coding sequences has at least 30% of the codon pairs with associated positive weights above 0 for the predetermined host cell in said coding sequence being transformed into codon pairs with associated weights below 0.

30. A method according to claim 25, where said coding nucleotide sequence coding for a predetermined amino acid sequence is selected from the group consisting of:
(a) a wild-type nucleotide sequence coding for said predetermined amino acid sequence;
(b) a reverse translation of the predetermined amino acid sequence whereby a codon for an amino acid position in the predetermined amino acid sequence is randomly chosen from the synonymous codons coding for the amino acid; and
(c) a reverse translation of the predetermined amino acid sequence whereby a codon for an amino acid position in the predetermined amino acid sequence is chosen in accordance with a single-codon bias for the predetermined host cell or a species related to the host cell.

31. A method according to claim 25, wherein said predetermined host cell is a cell of a microorganism of a genus selected from the group consisting of: *Bacillus, Actinomycetis, Escherichia, Streptomyces, Aspergillus, Penicillium, Kluyveromyces*, and *Saccharomyces*.

32. A method according to claim 25, wherein said predetermined host cell is a cell of an animal or plant, preferably a cell of a cell line selected from the group consisting of CHO, BHK, NS0, COS, Vero, PER.C6™, HEK-293, *Drosophila* S2, *Spodoptera* Sf9, and *Spodoptera* Sf21.

33. A computer program product comprising data and instructions encoded on a non-transitory computer readable medium, wherein the data and instructions are executable by a computer to cause the computer and a processor to carry out the method according to claim 13.

34. A method according to claim 25, wherein said codon pair weights w are taken from a 61×61 codon pair matrix without stop codons, or a 61×64 codon pair matrix that includes stop-codons, and wherein said codon pair weights w are calculated on the basis of a computer-based method, using as input at least one of the following:
(a) a group of nucleotide sequences consisting of at least 200 coding sequences of a predetermined host; or
(b) a group of nucleotide sequences consisting of at least 200 coding sequences of the species to which the predetermined host belongs; or
(c) a group of nucleotide sequences consisting of at least 5% of the protein encoding nucleotide sequences in a genome sequence of the predetermined host; or
(d) a group of nucleotide sequences consisting of at least 5% of the protein encoding nucleotide sequences in a genome sequence of a genus related to the predetermined host.

35. A method according to claim 25, wherein said codon pair weights w are determined for at least 50% of the possible 61×64 codon pairs including the termination signal as stop codon.

36. A computer for optimizing a nucleotide coding sequence coding for a predetermined amino acid sequence for expression in a predetermined host cell, comprising:
a processor and memory, wherein the processor is arranged to read from said memory and write into said memory, and wherein the memory comprises data and instructions arranged such that said processor is suitably programmed to perform the method according to claim 25.

37. A computer program product comprising data and instructions encoded on a non-transitory computer readable medium, wherein the data and instructions are executable by a computer to cause the computer and a processor to carry out the method according to claim 25.

* * * * *